(12) United States Patent
Muthuppalaniappan et al.

(10) Patent No.: US 8,912,331 B2
(45) Date of Patent: *Dec. 16, 2014

(54) 3,5-DISUBSTITUTED-3H-IMIDAZO[4,5-B] PYRIDINE AND 3,5-DISUBSTITUTED-3H-[1,2,3]TRIAZOLO[4,5-B] PYRIDINE COMPOUNDS AS MODULATORS OF PROTEIN KINASES

(71) Applicants: Incozen Therapeutics Pvt. Ltd., Hyderabad (IN); Rhizen Pharmaceuticals SA, La Chaux-de-Fonds (CH)

(72) Inventors: Meyyappan Muthuppalaniappan, Hyderabad (IN); Srikant Viswanadha, Hyderabad (IN); Govindarajulu Babu, Hyderabad (IN); Swaroop Kumar V. S. Vakkalanka, La Chaux-de-Fonds (CH)

(73) Assignees: Rhizen Pharmaceuticals SA, La Chaux-de-Fonds (CH); Incozen Therapeutics Pvt. Ltd., Hyderabad (IN)

( * ) Notice: Subject to any disclaimer, the term of this patent is extended or adjusted under 35 U.S.C. 154(b) by 0 days.

This patent is subject to a terminal disclaimer.

(21) Appl. No.: 13/891,961

(22) Filed: May 10, 2013

(65) Prior Publication Data
US 2013/0261116 A1   Oct. 3, 2013

Related U.S. Application Data

(63) Continuation of application No. 13/108,642, filed on May 16, 2011, now Pat. No. 8,481,739.

(30) Foreign Application Priority Data

May 17, 2010 (IN) .......................... 1377/CHE/2010

(51) Int. Cl.
| | | |
|---|---|---|
| C07D 513/02 | (2006.01) | |
| A61K 31/4709 | (2006.01) | |
| A61K 31/506 | (2006.01) | |
| C07D 471/04 | (2006.01) | |
| A61K 45/06 | (2006.01) | |
| A61K 31/437 | (2006.01) | |
| A61K 31/5377 | (2006.01) | |

(52) U.S. Cl.
CPC .......... *C07D 471/04* (2013.01); *A61K 31/4709* (2013.01); *A61K 31/506* (2013.01); *A61K 45/06* (2013.01); *A61K 31/437* (2013.01); *A61K 31/5377* (2013.01)
USPC ........................................................ 546/117

(58) Field of Classification Search
USPC ................................................. 546/117, 118
See application file for complete search history.

(56) References Cited

U.S. PATENT DOCUMENTS

| | | |
|---|---|---|
| 7,169,800 B2 | 1/2007 | Aronov et al. |
| 7,173,031 B2 | 2/2007 | Borzilleri et al. |
| 7,314,885 B2 | 1/2008 | Aronov et al. |
| 7,348,325 B2 | 3/2008 | Cai et al. |
| 7,432,373 B2 | 10/2008 | Crispino et al. |
| 7,439,246 B2 | 10/2008 | Borzilleri et al. |
| 7,446,199 B2 | 11/2008 | Aronov et al. |
| 7,459,562 B2 | 12/2008 | Borzilleri et al. |
| 7,470,693 B2 | 12/2008 | Borzilleri et al. |
| 8,481,739 B2 * | 7/2013 | Muthuppalaniappan et al. ............... 546/117 |
| 2005/0101650 A1 | 5/2005 | Aronov et al. |
| 2005/0137201 A1 | 6/2005 | Aronov et al. |
| 2005/0148574 A1 | 7/2005 | Aronov et al. |
| 2006/0135537 A1 | 6/2006 | Knegtel et al. |
| 2006/0173055 A1 | 8/2006 | Aronov et al. |
| 2007/0054928 A1 | 3/2007 | Bannen et al. |
| 2007/0179130 A1 | 8/2007 | Bannen |
| 2007/0191369 A1 | 8/2007 | Lauffer et al. |
| 2007/0225307 A1 | 9/2007 | Bannen et al. |
| 2007/0244116 A1 | 10/2007 | Bannen et al. |
| 2007/0254868 A1 | 11/2007 | Lauffer et al. |
| 2008/0119496 A1 | 5/2008 | Ohlmeyer et al. |
| 2008/0161305 A1 | 7/2008 | Forsyth et al. |
| 2008/0312232 A1 | 12/2008 | Kim et al. |
| 2009/0012076 A1 | 1/2009 | Dinsmore et al. |
| 2010/0105656 A1 | 4/2010 | Cheng et al. |

FOREIGN PATENT DOCUMENTS

| | | |
|---|---|---|
| EP | 0400974 A2 | 12/1990 |
| EP | 0470543 A1 | 2/1992 |
| WO | WO-8304254 A1 | 12/1983 |
| WO | WO-2005004607 A1 | 1/2005 |
| WO | WO-2005007891 A2 | 1/2005 |
| WO | WO-2005016920 A1 | 2/2005 |
| WO | WO-2005028475 A2 | 3/2005 |
| WO | WO-2005030140 A2 | 4/2005 |
| WO | WO-2005040345 A2 | 5/2005 |
| WO | WO-2005075478 A1 | 8/2005 |
| WO | WO-2006014325 A2 | 2/2006 |

(Continued)

OTHER PUBLICATIONS

Annex to Form PCT/IS/206 issued in PCT/IB2011/052120 dated Aug. 12, 2011.

(Continued)

*Primary Examiner* — Nizal Chandrakumar
(74) *Attorney, Agent, or Firm* — Blank Rome LLP

(57) ABSTRACT

The present invention provides, inter alia, compounds of formula I as protein kinase modulators, methods of preparing them, pharmaceutical compositions containing them and methods of treatment, prevention and/or amelioration of kinase mediated diseases or disorders with them.

28 Claims, No Drawings

(56) References Cited

FOREIGN PATENT DOCUMENTS

| | | |
|---|---|---|
| WO | WO-2006021881 A2 | 3/2006 |
| WO | WO-2006021884 A2 | 3/2006 |
| WO | WO-2006021886 A1 | 3/2006 |
| WO | WO-2006052913 A1 | 5/2006 |
| WO | WO-2006108059 A1 | 10/2006 |
| WO | WO-2006128692 A2 | 12/2006 |
| WO | WO-2007064797 A2 | 6/2007 |
| WO | WO-2007111904 A2 | 10/2007 |
| WO | WO-2007132308 A1 | 11/2007 |
| WO | WO-2008036272 A1 | 3/2008 |
| WO | WO-2008051805 A2 | 5/2008 |
| WO | WO-2008054702 A1 | 5/2008 |
| WO | WO-2008060866 A1 | 5/2008 |
| WO | WO-2008078085 A1 | 7/2008 |
| WO | WO-2008088881 A1 | 7/2008 |
| WO | WO-2008102870 A1 | 8/2008 |
| WO | WO-2008145839 A1 | 12/2008 |
| WO | WO-2008145843 A1 | 12/2008 |
| WO | WO-2009002806 A1 | 12/2008 |
| WO | WO-2009058728 A1 | 5/2009 |
| WO | WO-2009058729 A2 | 5/2009 |
| WO | WO-2009058730 A1 | 5/2009 |
| WO | WO-2009058739 A1 | 5/2009 |
| WO | WO-2010017870 A1 | 2/2010 |
| WO | WO-2011018454 A1 | 2/2011 |
| WO | WO-2011020861 A1 | 2/2011 |
| WO | WO-2011079804 A1 | 7/2011 |

OTHER PUBLICATIONS

Booth, et al., Synthesis of 1-Substituted 5-Aminoimidazole-4-carbaldehydes and 8-Amino-1-(2-fluorobenzyl)imidazo[4'5':5,6]pyrido[2,3-*d*]pyrimidine, Synthesis, No. 16, 2393-2396, 2001.

* cited by examiner

US 8,912,331 B2

3,5-DISUBSTITUTED-3H-IMIDAZO[4,5-B] PYRIDINE AND 3,5-DISUBSTITUTED-3H-[1,2,3]TRIAZOLO[4,5-B] PYRIDINE COMPOUNDS AS MODULATORS OF PROTEIN KINASES

This application is a continuation application of U.S. application Ser. No. 13/108,642, filed May 16, 2011.

This application claims the benefit of Indian Provisional Patent Application No. 1377/CHE/2010 dated 17 May 2010 which is hereby incorporated by reference.

FIELD OF THE INVENTION

The present invention provides, inter alia, compounds of formula I as protein kinase modulators, methods of preparing them, pharmaceutical compositions containing them and methods of treatment, prevention and/or amelioration of kinase mediated diseases or disorders with them.

BACKGROUND OF THE INVENTION

In the recent past immense research has been dedicated to the discovery and understanding of the structure and functions of enzymes and bio-molecules associated with various diseases. One such important class of enzymes that has been the subject of extensive research is Protein Kinase.

In general, protein kinases represent a set of structurally related pbosphoryl transferases, having conserved structures and catalytic functions. These enzymes modify proteins by chemically adding phosphate groups (phosphorylation). Phosphorylation involves the removal of a phosphate group from ATP and covalently attaching it to amino acids that have a free hydroxyl group such as serine, threonine or tyrosine. Phosphorylation usually results in a functional change of the target protein (substrate) by altering enzyme activity, cellular localization or association with other proteins. Up to 30% of all proteins may be modified by kinase activity.

This class of proteins are classified into subsets depending upon the substrate they act upon such as tyrosine kinase, serine/theronine kinase, histidine kinase and the like. These proteins can also be classified based on their localization into receptor tyrosine kinases (RTKs) or non-receptor tyrosine kinases.

Receptor tyrosine kinases (RTKs) have an extracellular portion, a transmembrane domain, and an intracellular portion, while non-receptor tyrosine kinases are entirely intracellular. Receptor tyrosine kinase mediated signal transduction is typically initialed by an extracellular interaction with a specific growth factor (ligand), followed by receptor dimerization, stimulation of the intrinsic protein tyrosine kinase activity, and phosphorylation of amino acid residues. The ensuing conformational change leads to the formation of complexes with a spectrum of cytoplasmic signalling molecules and facilitates a myriad of responses such as cell division, differentiation, metabolic effects, and changes in the extracellular microenvironment.

At present, at least twenty (20) distinct RTK subfamilies have been identified. One subfamily of the RTKs is designated as the Met subfamily (c-Met, Ron and Sea). For a detailed discussion of protein kinases, see, Plowman et al., DN&P 7(6): 334-339, 1994, Blume-Jensen, P. et al, Nature 2001, 411(6835):355-365 and Manning, G. et al., Science. 2002, 298(5600): 1912-1934.

Kinases have also been classified either based on the pathway or the diseases in which they are involved (visit:www.reactionbiology.com/pages/kinase.htm), c-Met has been identified as involved in oncogenesis.

Protein kinases exert their physiological functions through phosphorylation of proteins (or substrates) thereby modulating the cellular activities of the substrate in various biological contexts. Protein kinases are known to control a wide variety of biological processes such as cell growth, survival and differentiation, organ formation and morphogenesis, neovascularization, tissue repair and regeneration. In addition to their functions in normal tissues/organs, many protein kinases also play specialized roles in a host of human diseases including cancer. A subset of protein kinases (also referred to as oncogenic protein kinases), when dysregulated, can cause tumor formation and growth and contribute to tumor maintenance and progression (Blume-Jensen P et al. Nature 2001, 411(6835):355-365). Thus far, oncogenic protein kinases represent one of the largest and most attractive groups of protein targets for therapeutic intervention and drug development.

Both receptor and non-receptor protein kinases have been found to be attractive targets for small molecule drug discovery due to their impact on cell physiology and signalling. Dysregulation of protein kinase activity thus leads to altered cellular responses including uncontrolled cell growth associated with cancer. In addition to oncological indications, altered kinase signalling is implicated in numerous other pathological diseases. These include, but are not limited to immunological disorders, cardiovascular diseases, inflammatory diseases, and degenerative diseases.

A significant number of tyrosine kinases (both receptor and nonreceptor) are associated with cancer (see Madhusudan S, Ganesan T S. Tyrosine kinase inhibitors in cancer therapy. Clin. Biochem. 2004. 37(7):618-35.). Clinical studies suggest that over expression or dysregulation of tyrosine kinases may also be of prognostic value. For example, members of the HER family of RTKs have been implicated in breast, colorectal, head and neck and lung cancer. Mutation of c-Kit tyrosine kinase is associated with decreased survival in gastrointestinal stromal tumors (GIST). In acute myelogenous leukemia, Flt-3 mutation predicts shorter disease free survival. VEGFR expression, which is important for tumor angiogenesis, is associated with a lower survival rate in lung cancer. Tie-1 kinase expression is inversely correlated to survival in gastric cancer, BCR-AbI expression is an important predictor of response in chronic myelogenous leukemia while Src tyrosine kinase expression is co-related to the stage of colorectal cancer.

Modulation (particularly inhibition) of cell proliferation and angiogenesis, the two key cellular processes needed for tumor growth and survival is an attractive goal for development of small-molecule drugs (Matter A. Drug Disc Technol 2001, 6, 1005-1024). Anti-angiogenic therapy represents a potentially important approach for the treatment of solid tumors and other diseases associated with dysregulated vascularisation including ischemic coronary artery disease, diabetic retinopathy, psoriasis and rheumatoid arthritis. Similarly, cell antiproliferative agents are desirable to slow or inhibit the growth of tumors.

Some of the kinases implicated in cancer are c-Met, RON (recepteur d'origine nantais) receptor, Vascular Endothelial Growth Factor (VEGF) receptor, Epidermal growth factor receptor kinase (EGF-R kinase), Eph receptors, c-Kit, and Flt-3.

A number of small molecule kinase modulators have found their way into the clinic which either act selectively on either one or multiple kinases. These include Gefitinib (AstraZeneca), a EGFR kinase inhibitor; Gleevec (Novartis), a dual c-Kit and Abl kinase inhibitor approved for the treatment of Chronic Myeloid Leukemia (CML) and gastrointestinal stroma cancers; Dasatinib (BMS), a dual BCR/ABL and Src family tyrosine kinases inhibitor, and Sunitinib (Pfizer) a multi kinase inhibitor targeting PDGF-R, VEGF-R, RET, KIT(CD117), CSF-1R and flt-3.

The kinase, c-Met, is the prototypic member of a subfamily of heterodimeric receptor tyrosine kinases (RTKs) which include Met, Ron and Sea (see Birchmeier, C. et al., Nat. Rev. Mol. Cell Biol. 2003, 4(12):915-925; Christensen, J. G. et al. Cancer Lett. 2005, 225(1): 1-26). Expression of c-Met occurs in a wide variety of cell types including epithelial, endothelial and mesenchymal cells where activation of the receptor induces cell migration, invasion, proliferation and other biological activities associated with "invasive cell growth." As such, signal transduction through c-Met receptor activation is responsible for many of the characteristics of tumor cells.

The only high affinity endogenous ligand for c-Met is the hepatocyte growth factor (HGF), also known as scatter factor (SF). Binding of HGF to c-Met induces activation of the receptor via autophosphorylation resulting in an increase of receptor dependent signalling, which promotes cell growth and invasion. Both c-Met and HGF are widely expressed in a variety of organs, but their expression is normally confined to cells of epithelial and mesenchymal origin. Anti-HGF antibodies or HGF antagonists have been shown to inhibit tumor metastasis in vivo (See: Maulik et al Cytokine & Growth Factor Reviews 2002, 13, 41-59). The biological functions of c-Met (or c-Met signalling pathway) in normal tissues and human malignancies such as cancer have been well documented (Christensen, J. G. et al., Cancer Lett. 2005, 225(1): 1-26; Corso, S. et al., Trends in Mol. Med. 2005, 11 (6):284-292).

Tumor growth progression involves the recruitment of new blood vessels into the tumor as well as invasion, adhesion and proliferation of malignant cells. c-Met over expression has been demonstrated on a wide variety of tumor types including breast, colon, renal, lung, squamous cell myeloid leukemia, hemangiomas, melanomas, astrocytomas, and glioblastomas. Additionally activating mutations in the kinase domain of c-Met have been identified in hereditary and sporadic renal papilloma and squamous cell carcinoma. See Maulik et al Cytokine & growth Factor reviews 2002, 13, 41-59; Longati et al Curr Drug Targets 2001, 2, 41-55; Funakoshi et al Clinica Chimica Acta 2003 1-23. Thus modulation of c-Met offers an attractive opportunity to target key oncogenic processes thus limiting cell proliferation, survival and metastasis.

Dysregulated c-Met pathway is linked to tumor formation, growth, maintenance and progression (Birchmeier, C. et al., Nat. Rev. Mol. Cell. Biol, 2003, 4(12):915-925; Boccaccio, C. et al., Nat. Rev. Cancer 2006, 6(8):637-645; Christensen, J. G. et al., Cancer Lett. 2005, 225(1): 1-26). HGF and/or c-Met are over expressed in significant portions of most human cancers, and are often associated with poor clinical outcomes such as more aggressive disease, disease progression, tumor metastasis and shortened patient survival. Further, patients with high levels of HGF/c-Met proteins are more resistant to chemotherapy and radiotherapy. In addition to abnormal HGF/c-Met expression, the c-Met receptor can also be activated in cancer patients through genetic mutations (both germline and somatic) and gene amplification. Although gene amplification and mutations are the most common genetic alterations that have been reported in patients, the receptor can also be activated by deletions, truncations, and gene rearrangement, as well as abnormal receptor processing and defective negative regulatory mechanisms.

The various cancers in which c-Met is implicated include but are not limited to carcinomas (e.g., bladder, breast, cervical, cholangiocarcinoma, colorectal, esophageal, gastric, head and neck, kidney, liver, lung, nasopharyngeal, ovarian, pancreas, prostate, thyroid); musculoskeletal sarcomas (e.g., osteosarcaoma, synovial sarcoma, rhabdomyosarcoma); soft tissue sarcomas (e.g., MFH/fibrosarcoma, leiomyosarcoma, Kaposi's sarcoma); hematopoietic malignancies (e.g., multiple myeloma, lymphomas, adult T cell leukemia, acute myelogenous leukemia, chronic myeloid leukemia); and other neoplasms (e.g., glioblastomas, astrocytomas, melanoma, mesothelioma and Wilm's tumor (www.vai.org/met/; Christensen, J. G, et al., Cancer Lett. 2005, 225(1): 1-26). c-Met inhibitors may also be useful in preventative and adjuvant therapy settings. In addition, certain cancers (e.g., papillary renal cell carcinoma, and some gastric and lung cancers) may be treated with c-Met inhibitors as they are believed to be driven by c-Met mutation/genetic alteration and dependent on c-Met for growth and survival. These cancers are expected to be sensitive to treatment.

The notion that activated c-Met contributes to tumor formation and progression and could therefore be a potential target for effective cancer intervention has been further validated by numerous preclinical studies (Birchmeier, C. et al., Nat. Rev. Mol. Cell Biol. 2003, 4(12):915-925; Christensen, J. G. et al. Cancer Lett. 2005, 225(1): 1-26; Corso, S. et al., Trends in Mol. Med. 2005, 11(6):284-292). For example, studies have demonstrated that the tpr-met fusion gene, over expression of c-Met, and activated c-Met mutations caused oncogenic transformation of various model cell lines and resulted in tumor formation and metastasis in mice. Conversely, significant anti-tumor and anti-metastasis activities have been demonstrated in vitro and in vivo with agents that specifically impair and/or block HGF/c-Met signalling. Those agents include anti-HGF and anti-c-Met antibodies, HGF peptide antagonists, decoy c-Met receptor, c-Met peptide antagonists, dominant negative c-Met mutations, c-Met specific antisense oligonucleotides and ribozymes, and selective small molecule c-Met kinase inhibitors (Christensen, J. G. et al. Cancer Lett. 2005, 225(1): 1-26). In addition to its established role in cancer, abnormal HGF/c-Met signalling is also implicated in atherosclerosis, lung fibrosis, renal fibrosis and regeneration, liver diseases, allergic disorders, inflammatory and autoimmune disorders, cerebrovascular diseases, cardiovascular diseases, and conditions associated with organ transplantation. See Ma, H. et al., Atherosclerosis. 2002, 164 (1):79-87; Crestani, B. et al., Lab. Invest. 2002, 82(8): 1015-1022; Sequra-Flores, A. A. et al. Rev. Gastroenterol. Mex. 2004, 69(4)243-250; Morishita, R. et al., Curr. Gene Ther, 2004, 4(2)199-206; Morishita, R. et al., Endocr. J. 2002, 49(3)273-284; Liu, Y., Curr, Opin. Nephrol. Hypertens. 2002, 11 (1):23-30; Matsumoto, K. et al., Kidney Int. 2001, 59(6): 2023-2038; Balkovetz, D. F. et al., Int. Rev. Cytol. 1999, 186:225-250; Miyazawa, et al., J. Cereb. Blood Flow Metab. 1998, 18(4)345-348; Koch, A. F. et al., Arthritis Rheum. 1996, 39(9): 1566-1575; Futamatsu, H. et al., Circ. Res. 2005, 96(8)823-830; Eguchi, S, et al., Clin. Transplant. 1999, 13(6) 536-544.

c-Met is thus an attractive target from a clinical perspective mainly because of its upstream localisation which aids in early detection and limiting metastasis and implications in the growth and metastases of most types of cancers. These observations suggest that c-Met kinase inhibitors would be an effective treatment for tumors driven by c-Met, and also would prevent disseminated micrometastases from further progression.

A family of novel compounds have been discovered which exhibit c-Met modulating ability and have an ameliorating effect against disorders related to abnormal c-Met activity such as Johnson & Johnson's JNJ-38877605, Amgen's AMG-458, Eisai's E-7050 and Pfizer's PF-04217903. However, to date, none of them have been used in a clinical study.

vated by different mechanisms in cancer cells. Due to a significant homology between the two RTKs, some small molecule kinase inhibitors of c-Met have inhibitory activity on RON suggesting that both receptors might be involved in cancer progression. The review (Dussault et al., supra) discusses the relevance of both c-Met and RON deregulation in human cancers and the progress made in identifying small molecule kinase inhibitors that can block the activity of these targets in vitro and in animal models. One of the compounds discussed in the review, AMG-458, inhibited c-Met and RON with $IC_{50}$s of 4 and 9 nM respectively.

Various research groups around the world such as Amgen, Arquel, AstraZeneca, Bristol-Myers Squibb, Exelixis, Eisai, Incyte, MethylGene, Pfizer, SGX Pharma, SmithKline Beecham, Sobering, Vertex, Xcovery. Novartis and others have been working on targeting either single, dual or multiple kinase targets.

JNJ-38877605

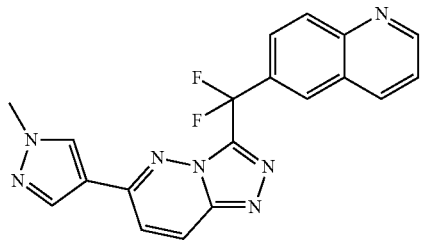

AMG-458

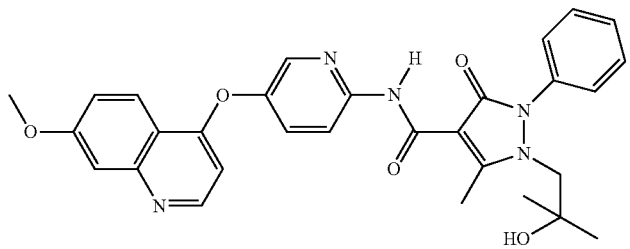

E-7050

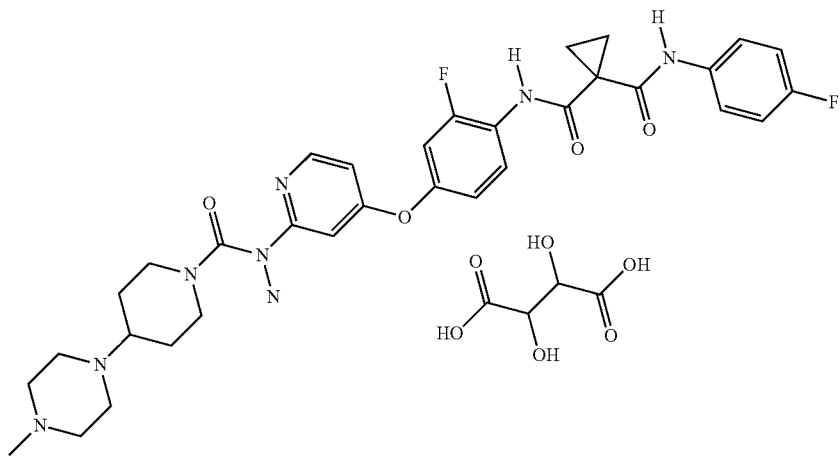

PF-04217903

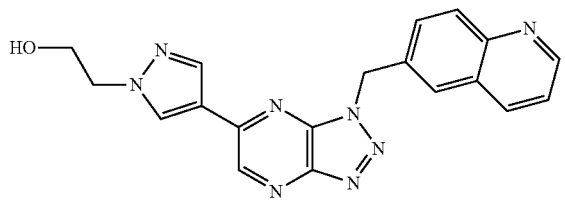

More recently Dussault et. al., Anti-Cancer Agents in Medicinal Chemistry, 2009, 9(2), 221-229, have provided additional insight about a receptor tyrosine kinase namely, RON (recepteur d'origine nantais) which is closely related to c-Met. Both c-MET and RON receptors upon activation can induce cell migration, invasion, proliferation and survival. Moreover, both possess oncogenic activity in vitro and in vivo and are often dysregulated in human cancers.

While c-Met is now a well-accepted target for anti-cancer treatment, less is known about the role of RON in cancer. Despite their common attributes, c-Met and RON are acti- Patent literature belonging to some of these applicants include the following patents and/or patent applications: U.S. Pat. No. 7,446,199; U.S. Pat. No. 7,470,693; U.S. Pat. No. 7,459,562; U.S. Pat. No. 7,439,246; U.S. Pat. No. 7,432,373; U.S. Pat. No. 7,348,325; U.S. Pat. No. 7,173,031; U.S. Pat. No. 7,314,885; U.S. Pat. No. 7,169,800; US20100105656, US20090012076; US20080312232; US20080161305; US20070244116; US20070225307; US20070054928; US20070179130; US20070254868; US20070191369; US20060173055; US20060135537; US20050148574; US20050137201; US20050101650; WO2009002806; WO2008088881; WO2008051805; WO2008102870; WO2008078085; WO2008060866; WO200854702; WO2008036272; WO2007111904; WO2007064797; WO2006052913; WO2006021881; WO2006021886; WO2006021884; WO2006108059; WO006014325; WO2006052913; WO200507891; WO2005030140; WO2005040345; WO2005028475; WO2005016920.

Recent PCT patent applications viz., WO2009058728, WO2009058729, WO2009058730 and WO2009058739 all assigned to Schering corporation disclose a series of thiazole carboxamide compounds as protein kinase inhibitors and more specifically to be inhibiting Aurora, MEK1 and/or CDK2 kinases.

Further review and literature disclosure on protein kinase molecules have been given by Isabelle Dussault (see; Anti-Cancer Agents in Medicinal Chemistry, 2009, 9, 221-229), Ted L. Underiner et. al., (see; Anti-Cancer Agents in Medicinal Chemistry, 2010, 10, 7-27) and Stephen Claridge et. al (see; Bioorganic & Medicinal Chemistry Letters 18 (2008) 2793-2798). All of these patents and/or patent applications and literature disclosures are incorporated herein as reference in their entirety for all purposes.

Despite the advances made in the area of kinases and in particular the role that c-met, RON, EGFR or KDR pathway plays in human diseases, challenges remain in term of the complexities of the target involved, the protein structure of the kinases, specificity issues for various kinase inhibitors, side effects and desired clinical benefits expected form the small molecule inhibitors. Accordingly, there still remains an unmet and dire need for small molecule compounds having specificity towards either one, two or multiple kinase inhibitors in order to regulate and/or modulate transduction of kinases, particularly c-Met, RON, EGFR or KDR for the treatment of diseases and disorders associated with kinases-mediated events.

The c-Met pathway plays an important role in the above described human diseases including cancer. There are no c-Met inhibitors or antagonists that are currently available for treating these human disorders that are characterized by abnormal HGF/c-Met signaling. Therefore, there is a clear unmet medical need for compounds which inhibit c-Met and other kinases. The compounds, compositions, and pharmaceutical methods provided herein help meet this need.

SUMMARY OF THE INVENTION

The present invention is directed to compounds useful as protein kinase modulators and in particular as inhibitors of c-Met.

In one embodiment, the compound of the present invention has the formula I:

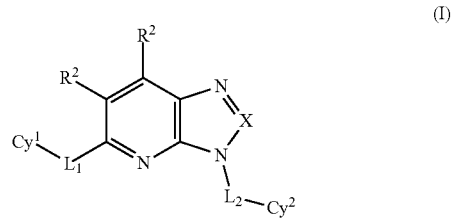

(I)

or a tautomer, stereoisomer, enantiomer, diastereomer, salt (e.g., pharmaceutically acceptable salt), prodrug (e.g., ester), or N-oxide thereof, wherein X is $CR^1$ or N;

$Cy^1$ and $Cy^2$ may be same or different and are independently selected from substituted or unsubstituted cycloalkyl, substituted or unsubstituted heterocyclic group, substituted or unsubstituted aryl, and substituted or unsubstituted heteroaryl;

$L_1$ is absent or selected from —O—, —S(=O)$_q$—, —NR$^a$—, —(CR$^a$R$^b$)$_n$—, —C(=Y)—, —C(=Y)—C(=Y)—, —CR$^a$R$^b$—C(=Y)—CR$^a$R$^b$—, —CR$^a$R$^b$—Y—CR$^a$R$^b$—, —C(=Y)—NR$^a$R$^b$—, —NR$^a$R$^b$—C(=Y)—NR$^a$R$^b$—, —S(=O)$_q$—NR$^a$R$^b$—, —NR$^a$R$^b$—S(=O)$_q$—NR$^a$R$^b$—, —NR$^a$R$^b$—NR$^a$R$^b$—, substituted or unsubstituted alkyl, substituted or unsubstituted alkenyl, substituted or unsubstituted alkynyl, substituted or unsubstituted cycloalkyl, and substituted or unsubstituted heterocyclyl;

$L_2$ is absent or selected from —O—, —S(=O)$_q$—, —NR$^a$—, —(CR$^a$R$^b$)$_n$—, —C(=Y)—, —C(=Y)—C(=Y)—, —CR$^a$R$^b$—C(=Y)—CR$^a$R$^b$—, —CR$^a$R$^b$—Y—CR$^a$R$^b$—, —C(=Y)—NR$^a$R$^b$—, —NR$^a$R$^b$—C(=Y)—NR$^a$R$^b$—, —S(=O)$_q$—NR$^a$R$^b$—, —NR$^a$R$^b$—S(=O)$_q$—NR$^a$R$^b$—, —NR$^a$R$^b$—NR$^a$R$^b$—, substituted or unsubstituted alkyl, substituted or unsubstituted alkenyl, substituted or unsubstituted alkynyl, substituted or unsubstituted cycloalkyl, and substituted or unsubstituted heterocyclyl;

each occurrence of $R^1$ and $R^2$ may be same or different and is independently selected from hydrogen, nitro, hydroxy, cyano, halogen, —OR$^a$, —S(=O)$_q$—R$^a$, —NR$^a$R$^b$, —C(=Y)—R$^a$, —CR$^a$R$^b$—C(=Y)—R$^a$, —CR$^a$R$^b$—Y—CR$^a$R$^b$—, —C(=Y)—NR$^a$R$^b$—, —NR$^a$R$^b$—C(=Y)—NR$^a$R$^b$—, —S(=O)$_q$—NR$^a$R$^b$—, —NR$^a$R$^b$—S(=O)$_q$—NR$^a$R$^b$—, —NR$^a$R$^b$—NR$^a$R$^b$—, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ cycloalkyl, substituted or unsubstituted $C_{3-6}$ cycloalkylalkyl, and substituted or unsubstituted $C_{3-6}$ cycloalkenyl;

each occurrence of $R^a$ and $R^b$ may be same or different and is independently selected from hydrogen, nitro, hydroxy, cyano, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ cycloalkyl, substituted or unsubstituted $C_{3-6}$ cycloalkylalkyl, and substituted or unsubstituted $C_{3-6}$ cycloalkenyl, or when two $R^a$ and/or $R^b$ substituents are directly bound to a common atom, they may be joined to form a substituted or unsubstituted, saturated or unsaturated 3-10 member ring, which may optionally include one or more heteroatoms which may be same or different and are selected from O, $NR^c$ or S;

each occurrence of $R^c$ is independently selected from hydrogen, nitro, hydroxy, cyano, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ cycloalkyl, substituted or unsubstituted $C_{3-6}$ cycloalkylalkyl and substituted or unsubstituted $C_{3-6}$ cycloalkenyl;

each occurrence of Y is independently selected from O, S, and $NR^a$;

each occurrence of n independently represents 0, 1, 2, 3 or 4; and each occurrence of q independently represents 0, 1 or 2.

Another embodiment is a compound of formula (IA):

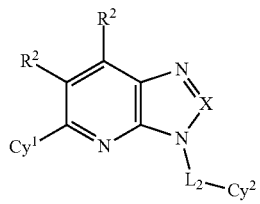

(IA)

or a tautomer, stereoisomer, enantiomer, diastereomer, salt (e.g., pharmaceutically acceptable salt), prodrug (e.g., ester), or N-oxide thereof, wherein each occurrence of $R^2$ is independently hydrogen, nitro, hydroxy, cyano, halogen, $-OR^a$, $-S(=O)_q-R^a$, $-NR^aR^b$, $-C(=O)-R^a$, or $-C(=O)-R^a$, wherein $R^a$ and $R^b$ in the $R^2$ group are independently hydrogen, hydroxy, or substituted or unsubstituted $C_{1-6}$ alkyl;

and all the other variables are the same as described above for compound of formula (I).

Further preferred is a compound of formula (I) and (IA) wherein $Cy^1$ is selected from: (The squiggly lines ($\sim\!\sim\!\sim$) in the structures below represent the point of attachment of the structure to the rest of the compound.)

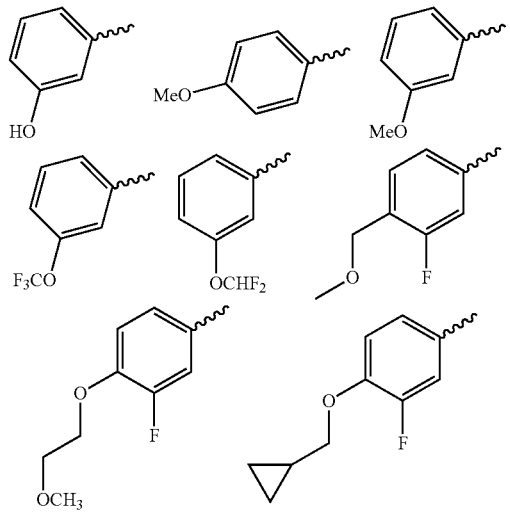

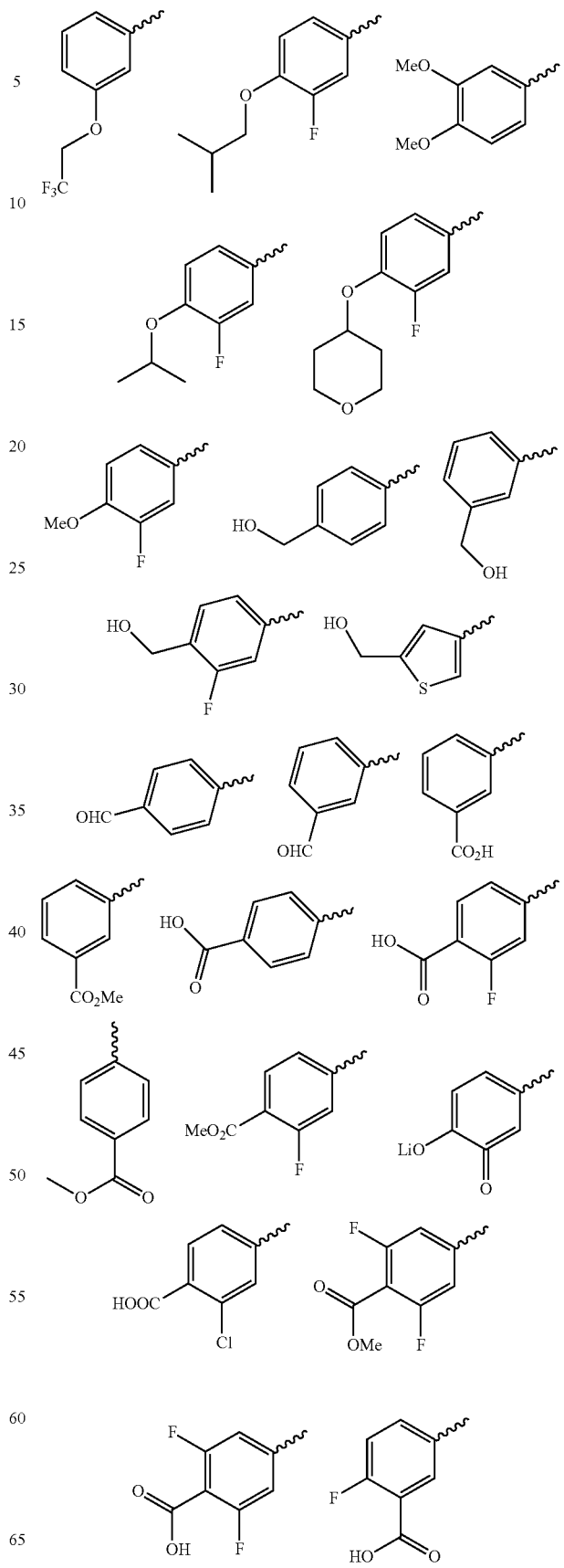

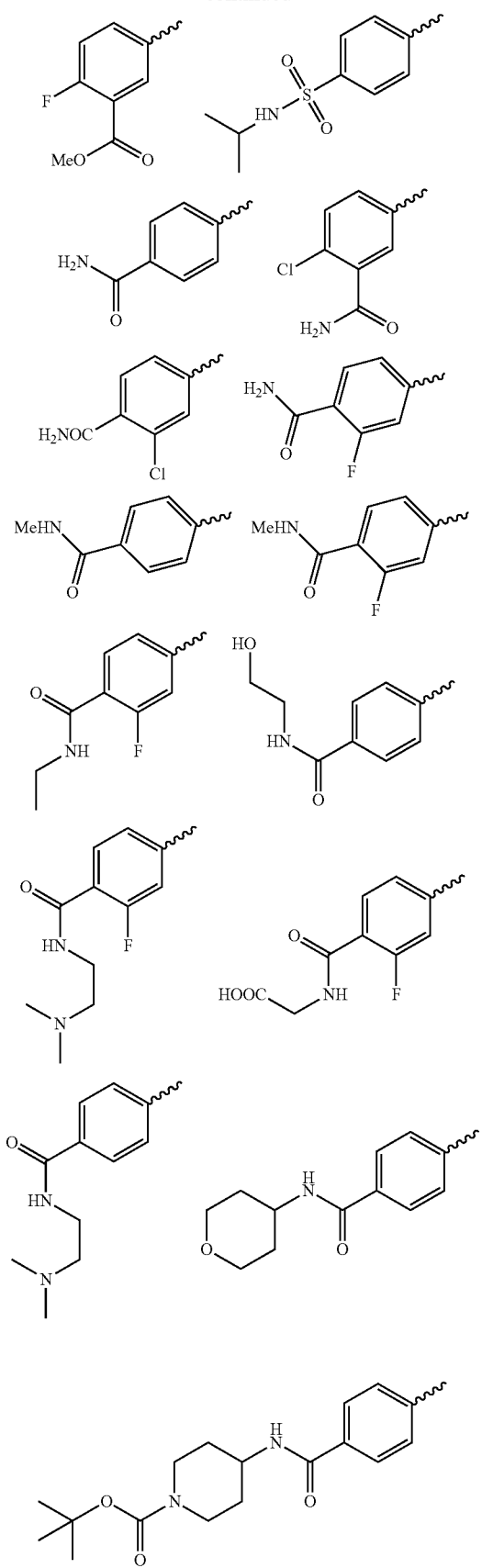
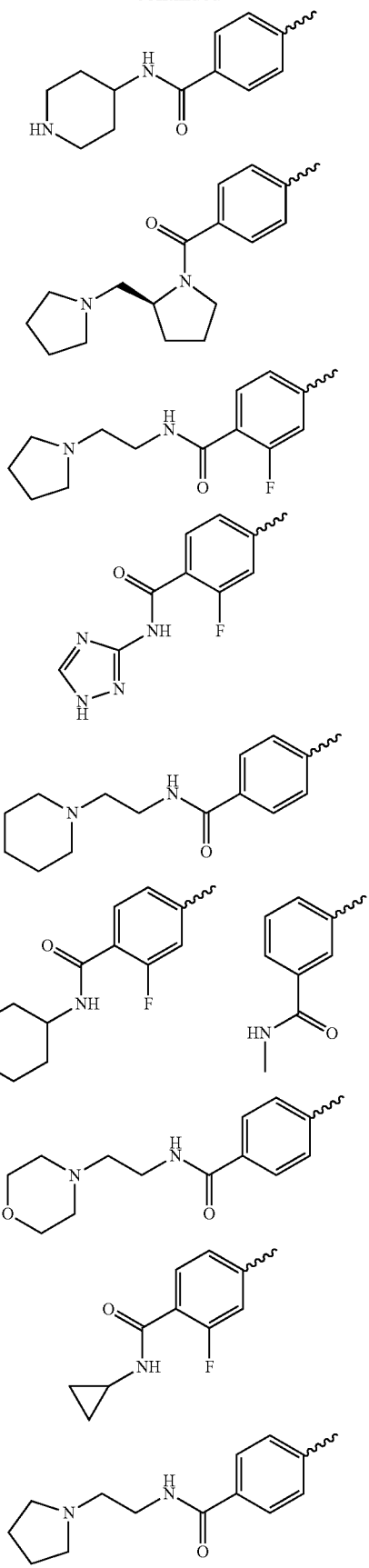

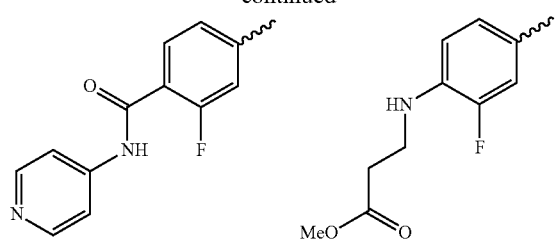
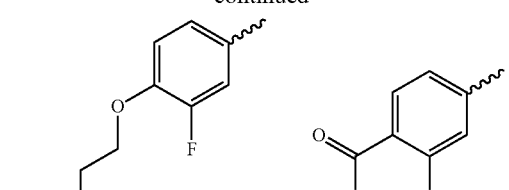
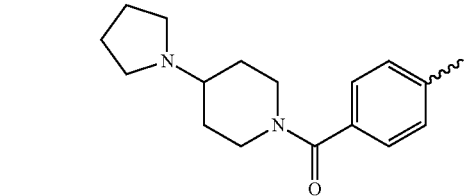
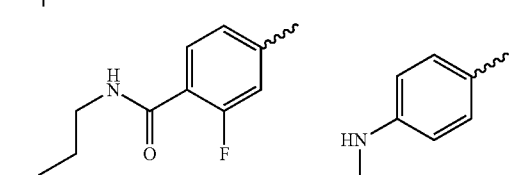
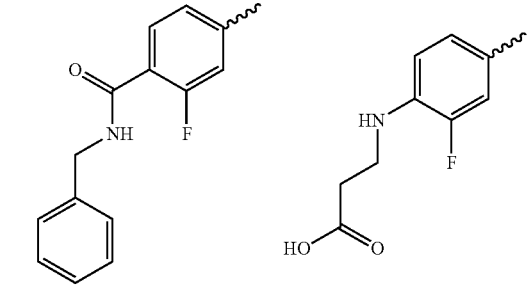
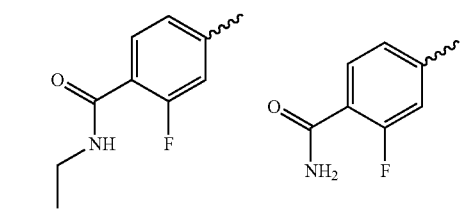
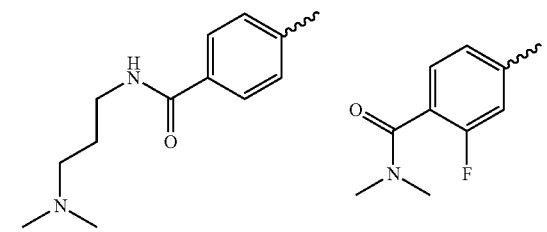
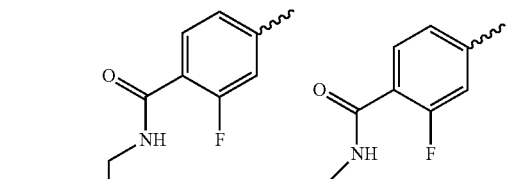
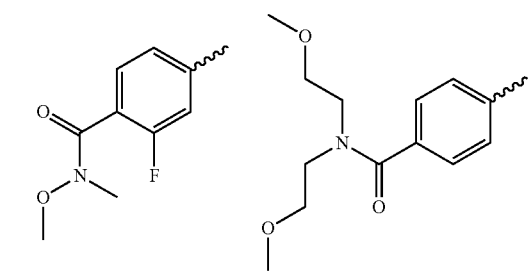
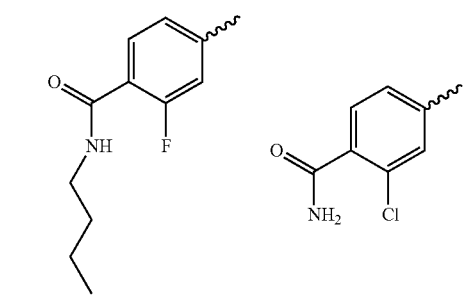
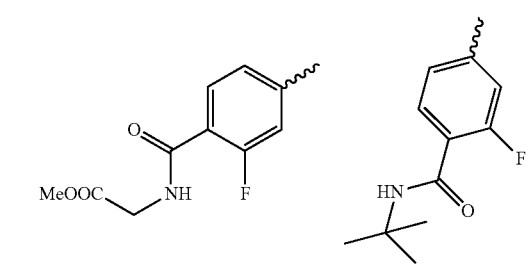
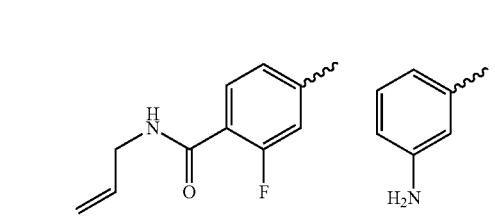
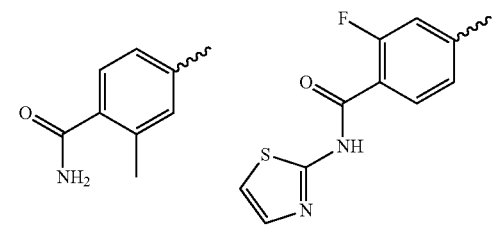

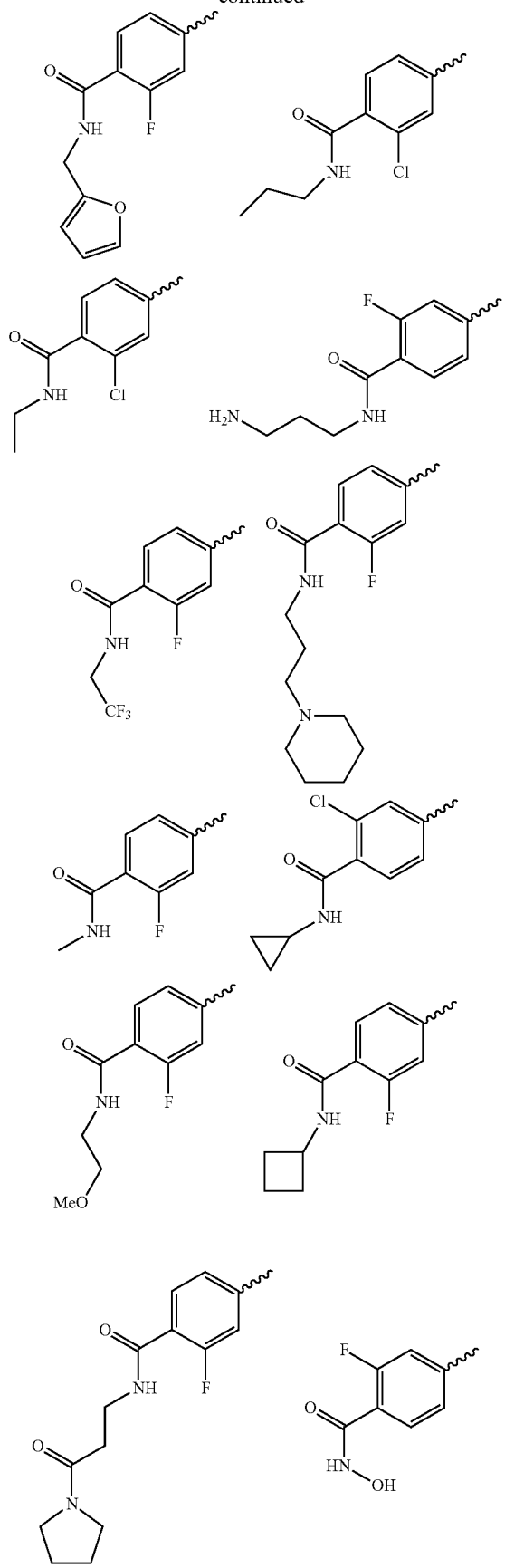
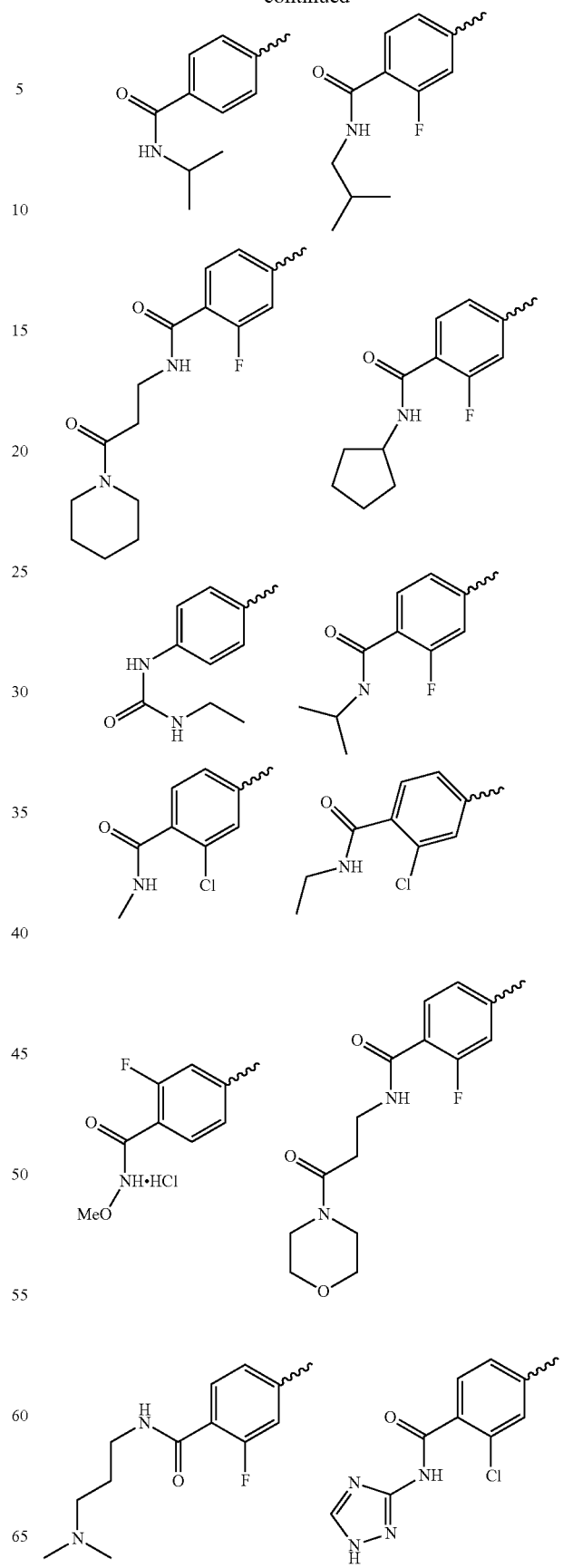

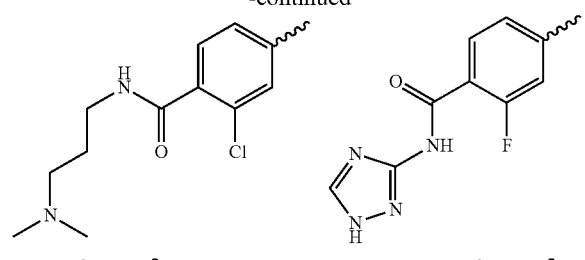
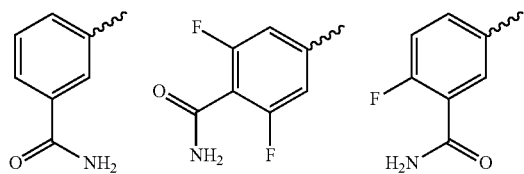
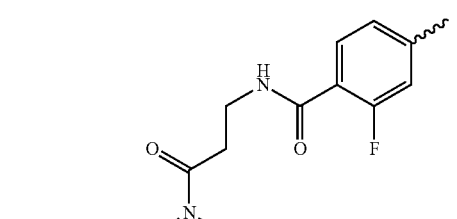
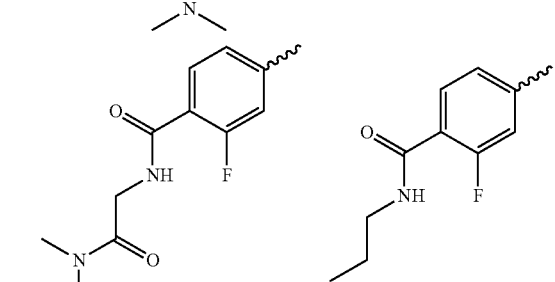
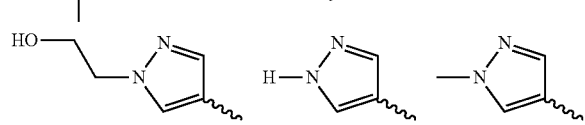
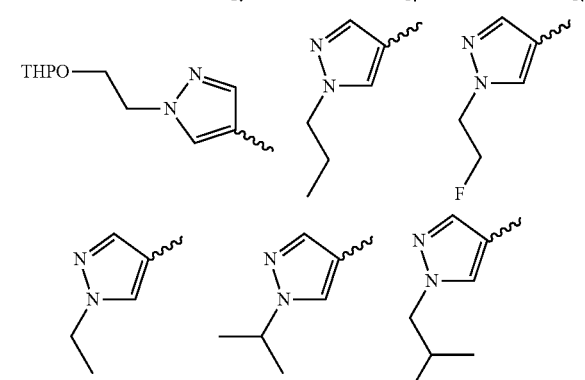
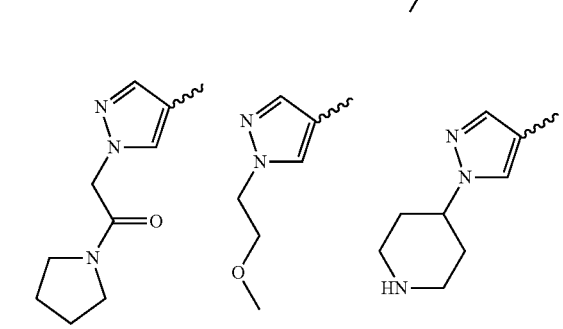
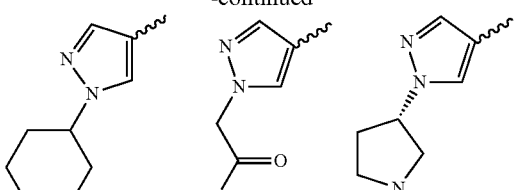
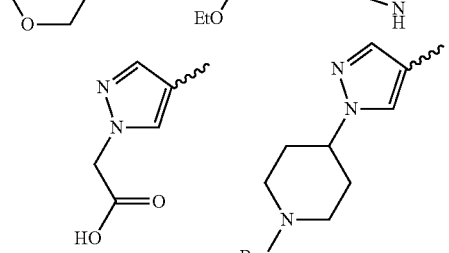
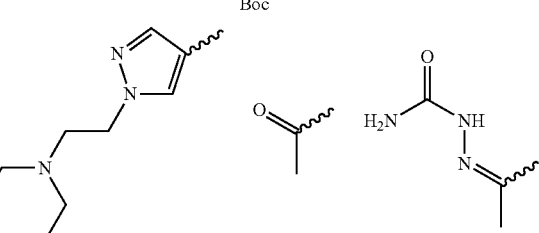
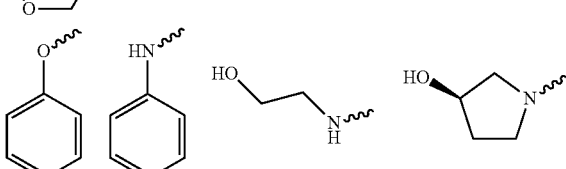
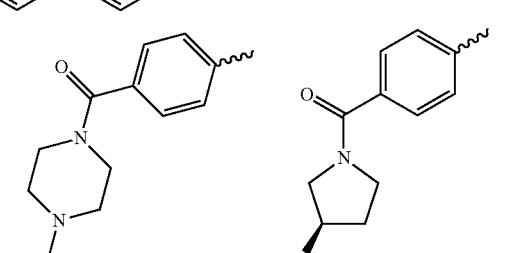
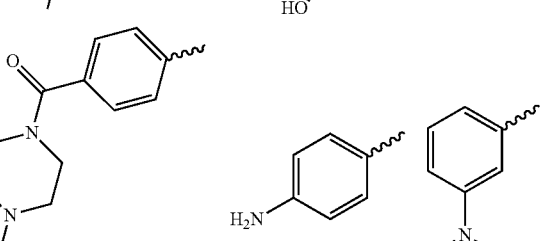
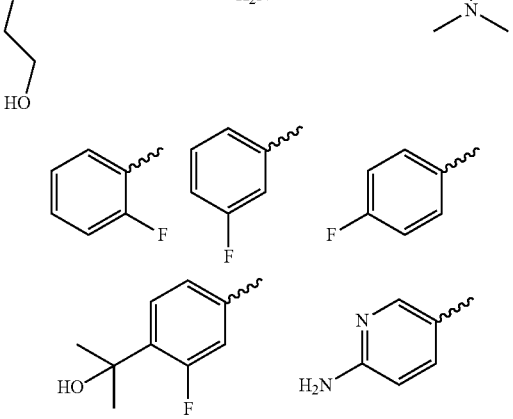

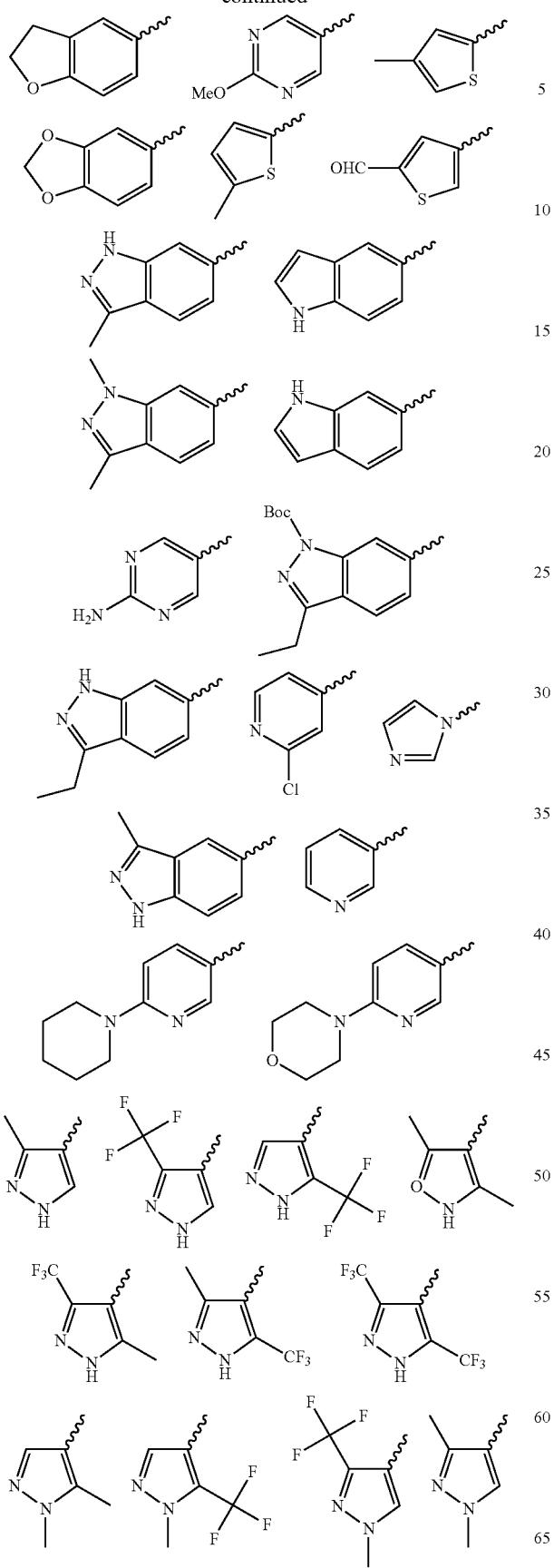
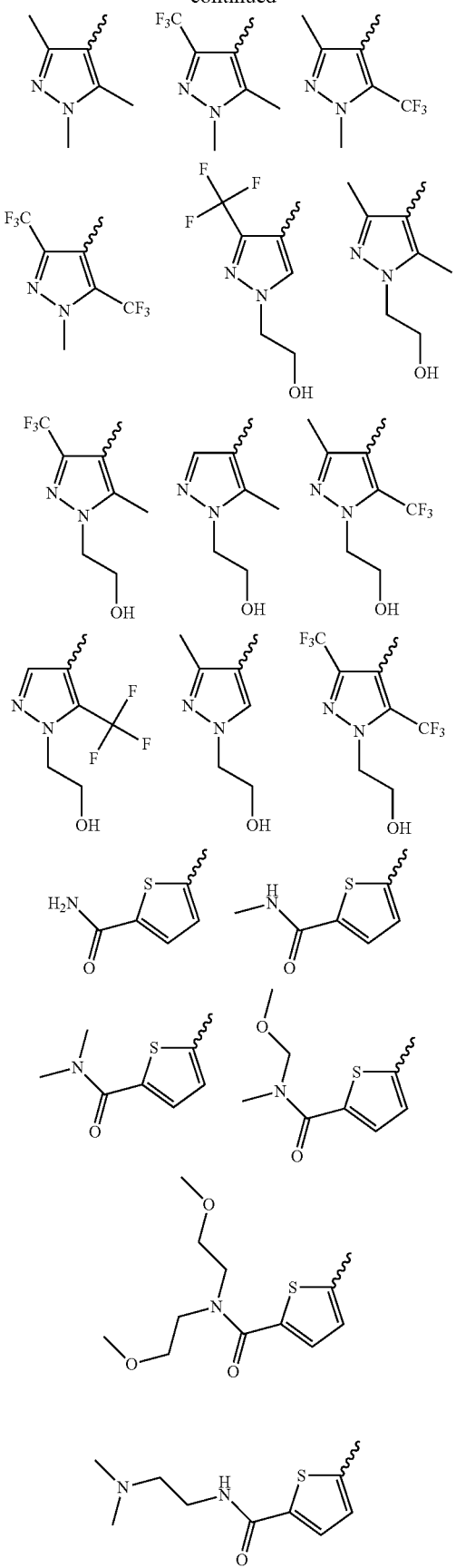

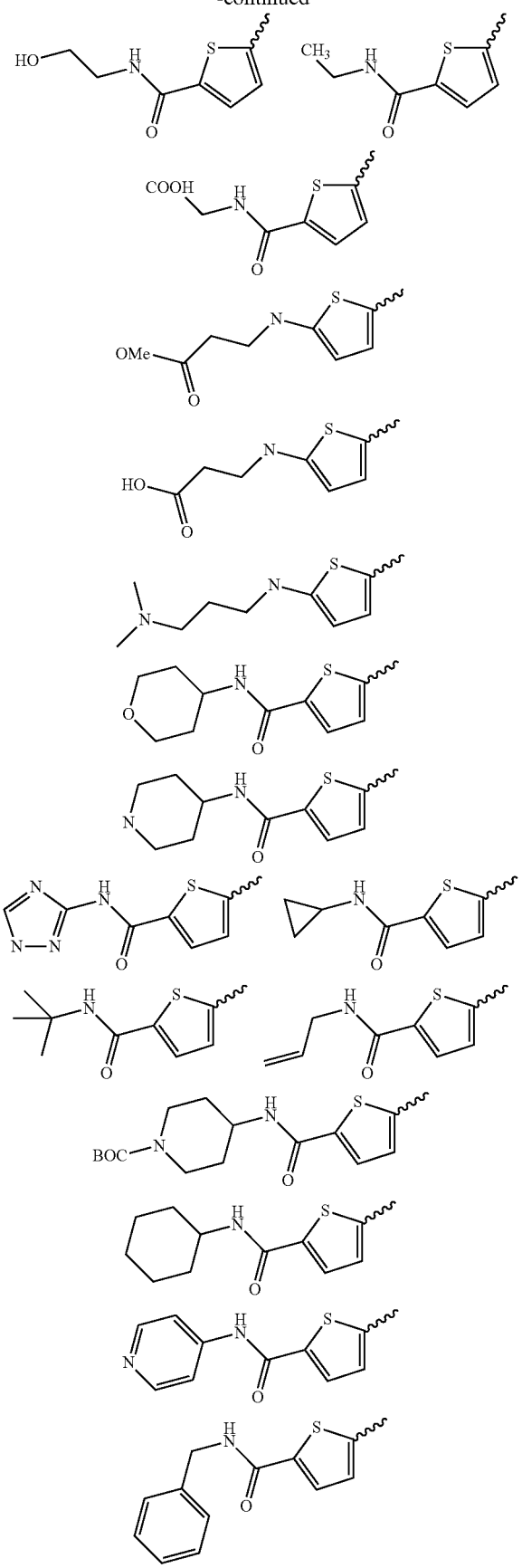
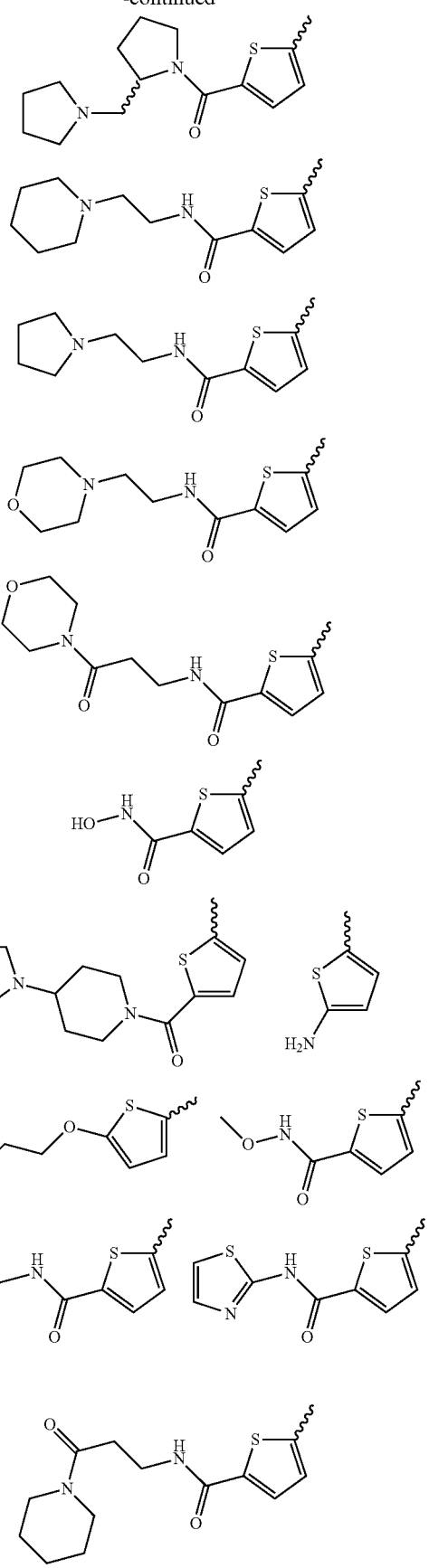

23
-continued
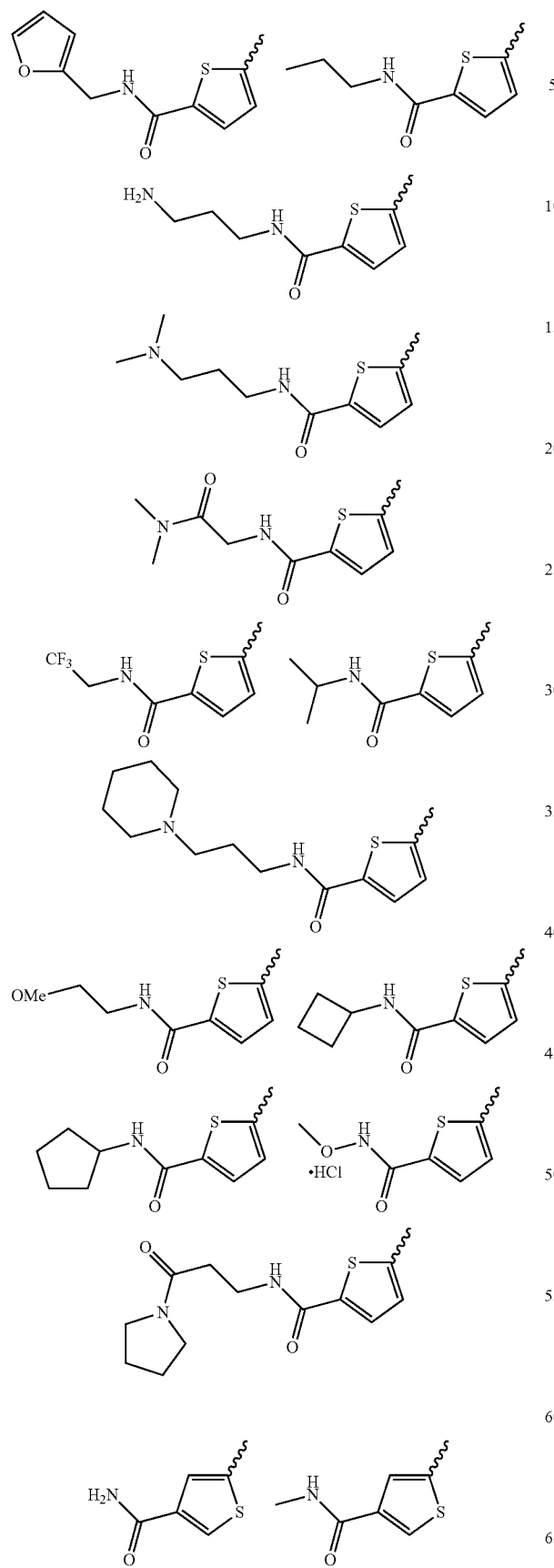
24
-continued
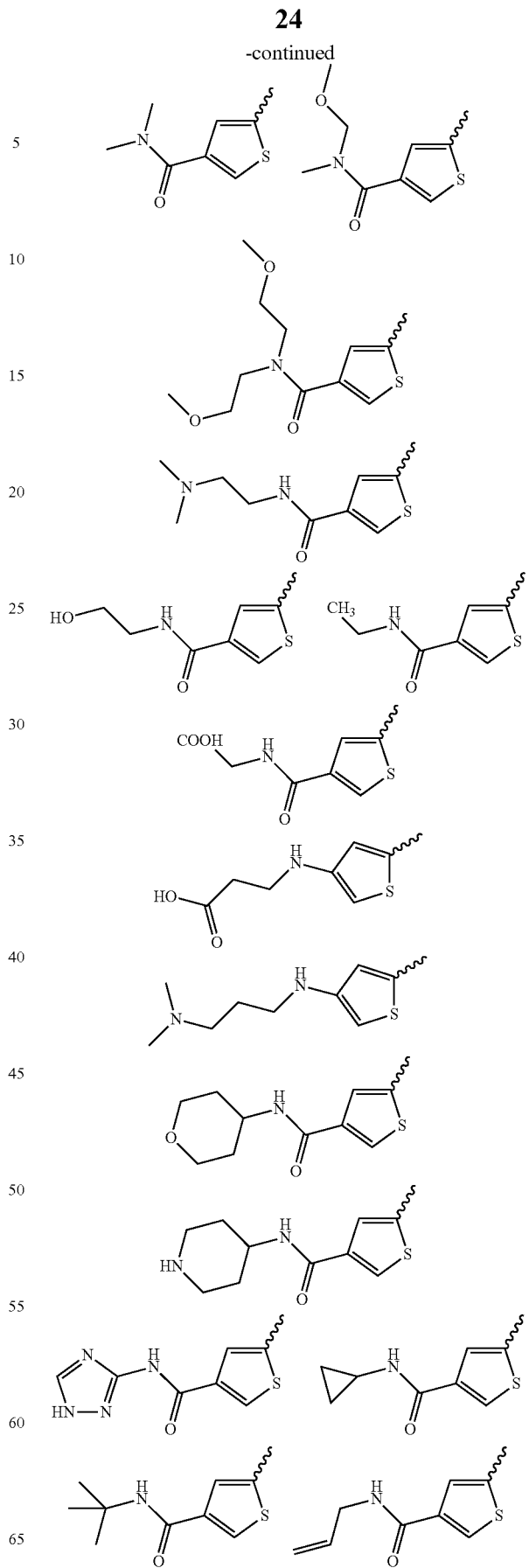

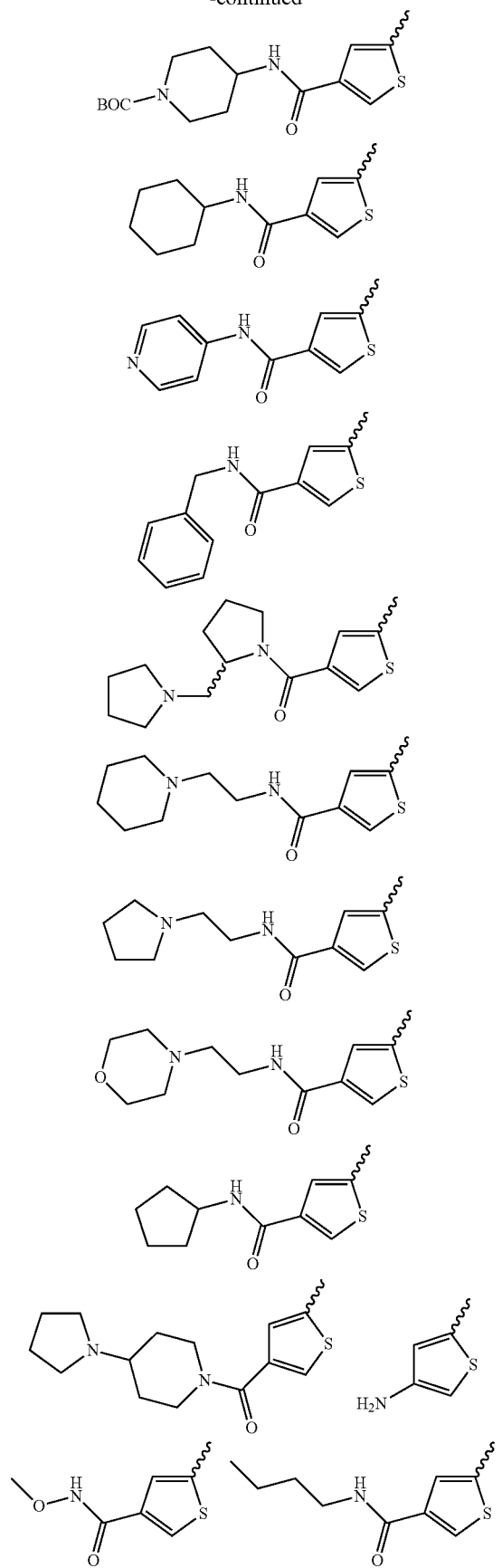
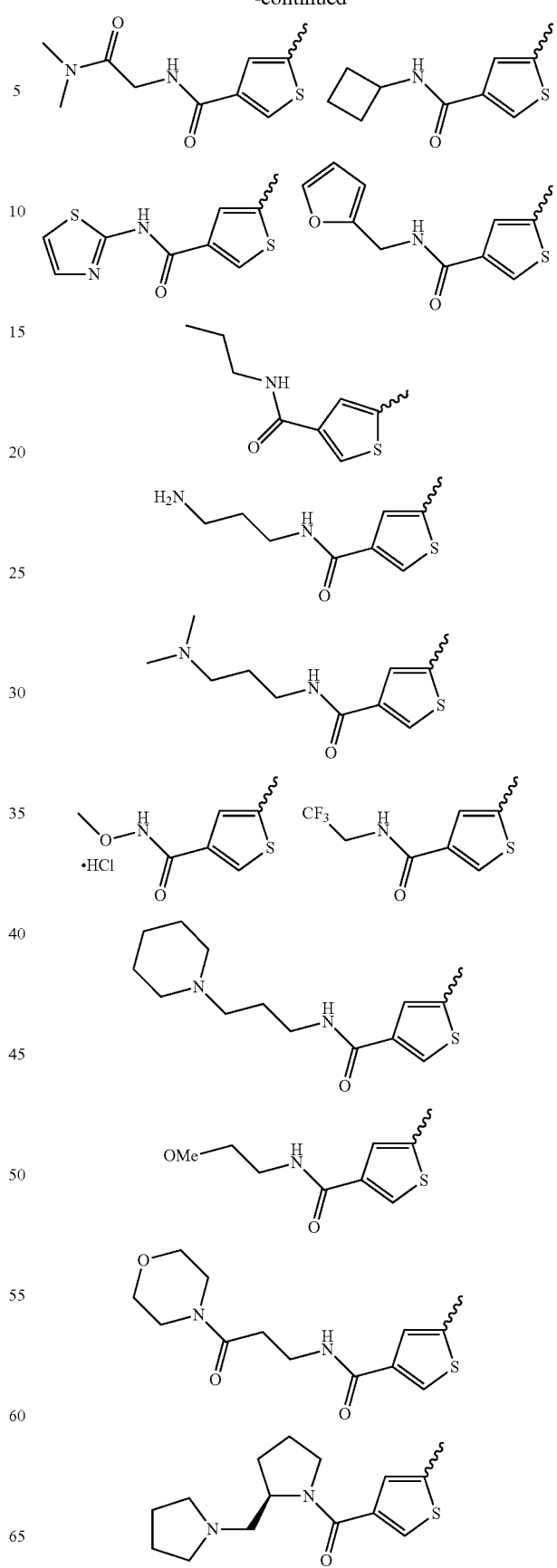

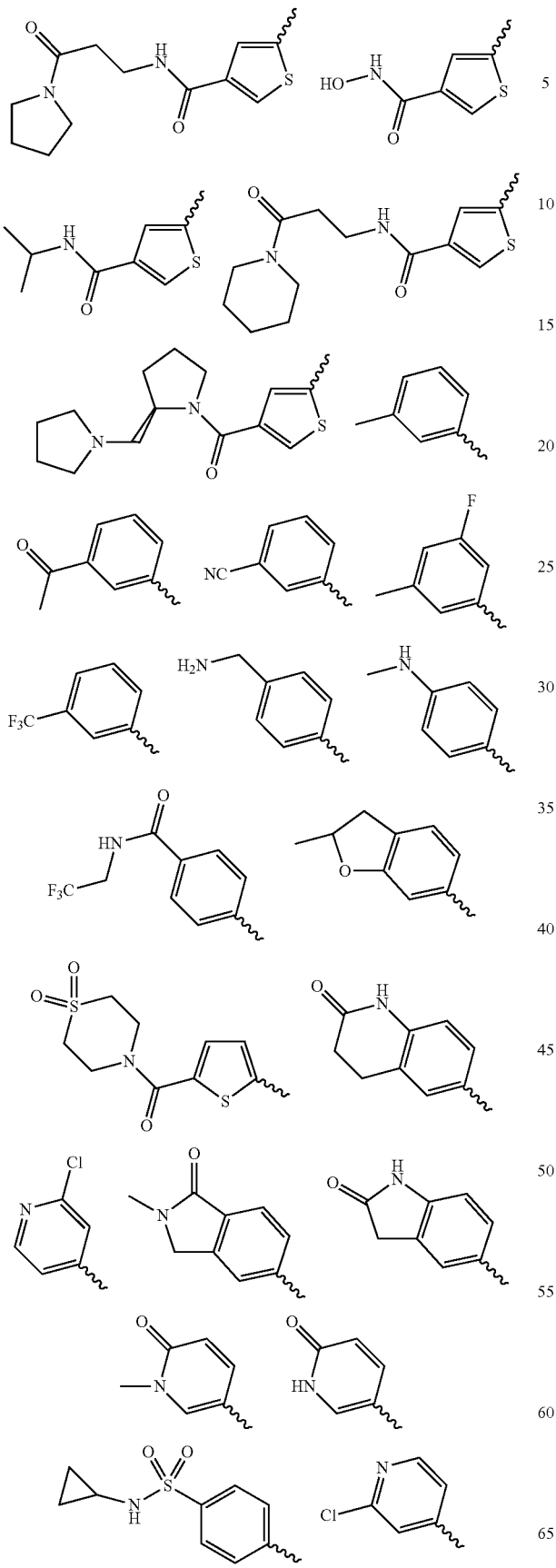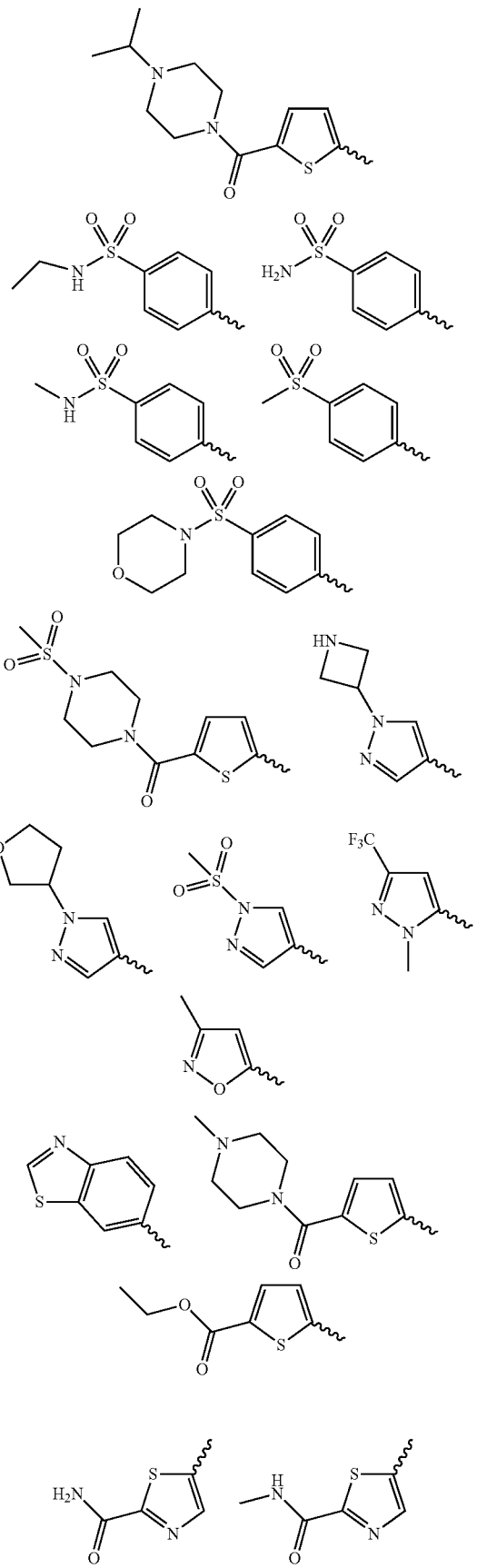

-continued
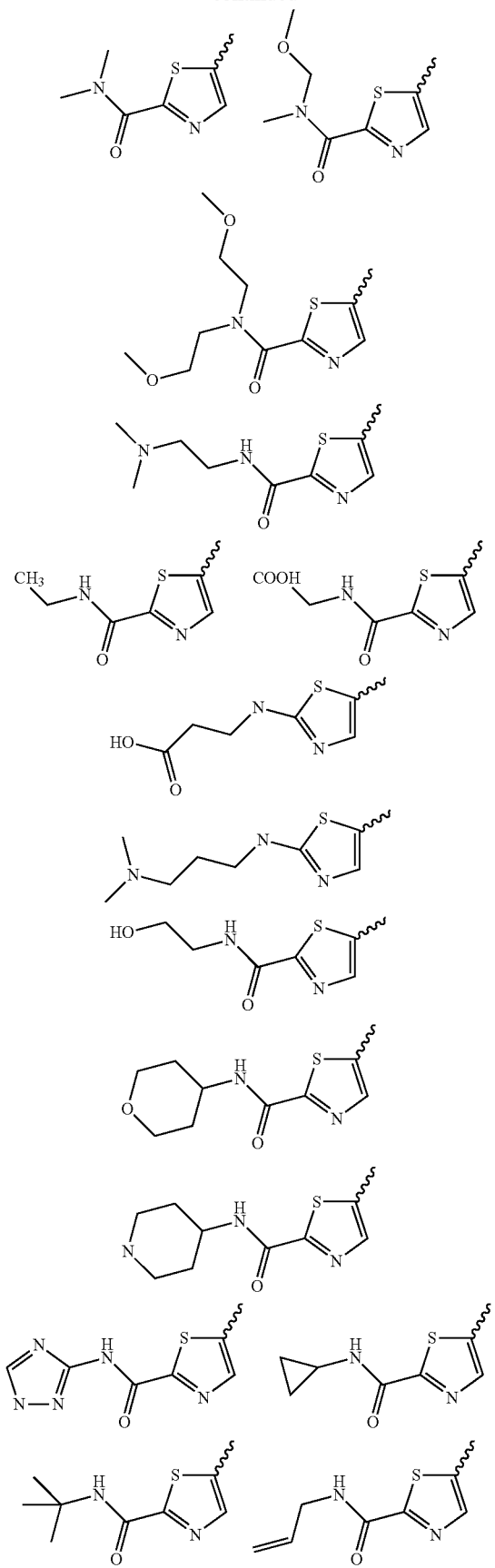
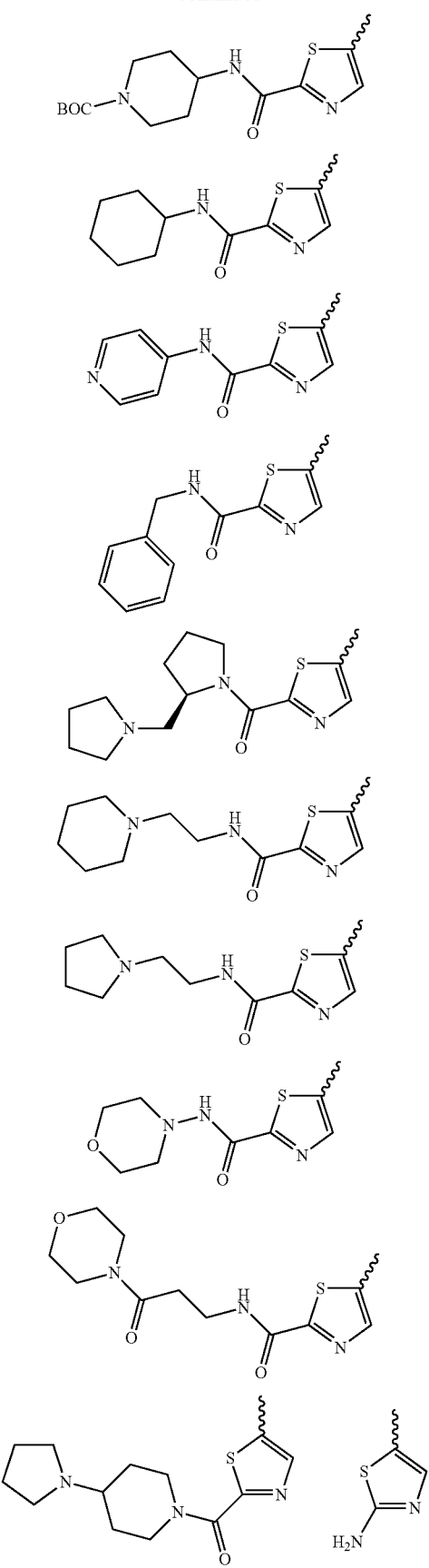

-continued

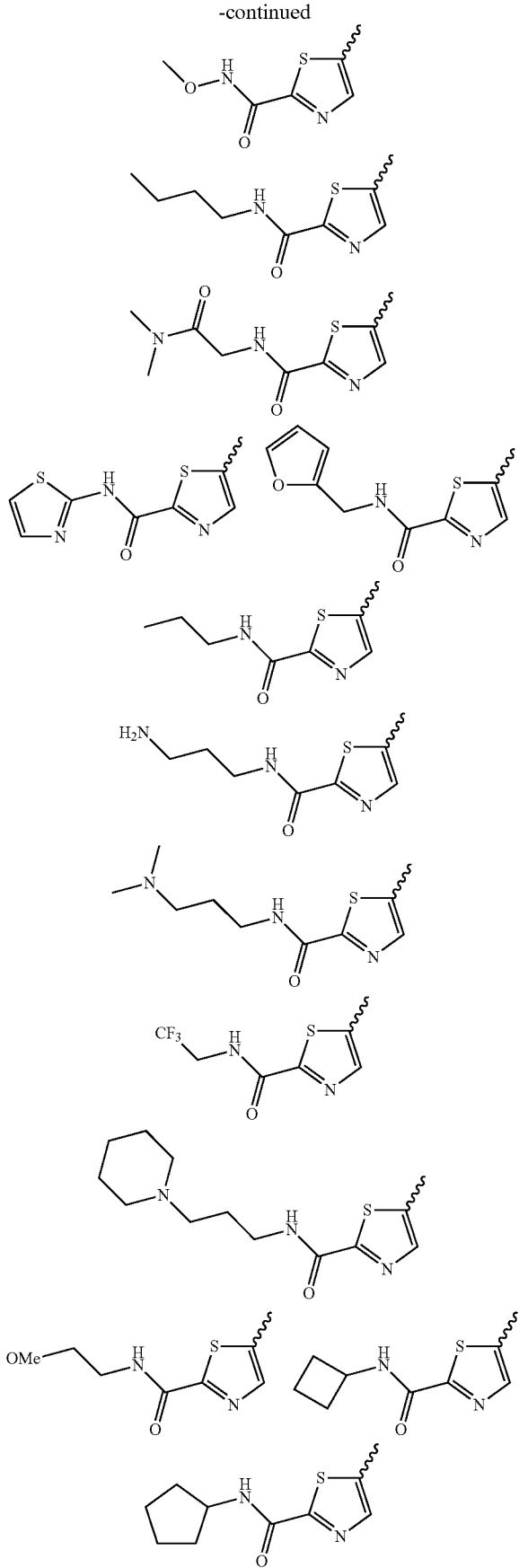

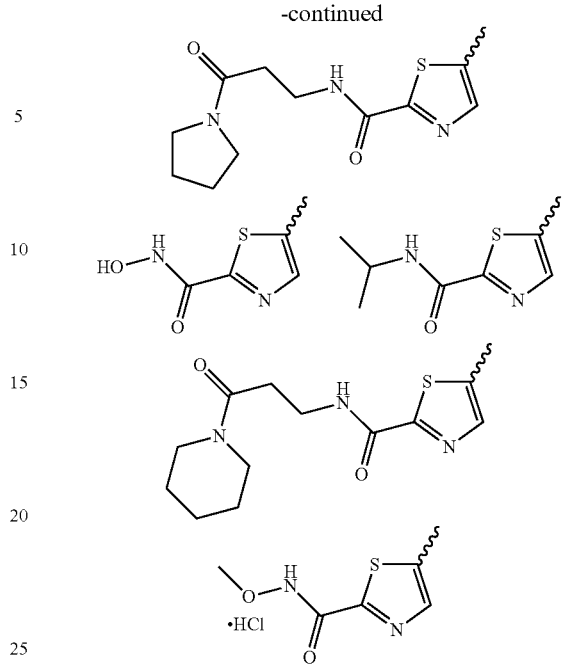

Yet another embodiment is a compound of formula (IA-I):

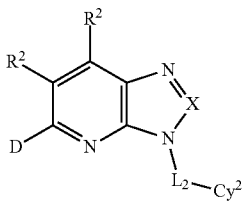

(IA-1)

or a tautomer, stereoisomer, enantiomer, diastereomer, salt (e.g., pharmaceutically acceptable salt), prodrug (e.g., ester), or N-oxide thereof, wherein D is substituted or unsubstituted monocyclic aryl or substituted or unsubstituted monocyclic heteroaryl;

each occurrence of $R^2$ is independently hydrogen, nitro, hydroxy, cyano, halogen, —$OR^a$, —$S(=O)_q$—$R^a$, —$NR^aR^b$, —$C(=O)$—$R^a$, —$C(=O)$—$R^a$, wherein each occurrence of $R^a$ and $R^b$ in group $R^2$ is independently hydrogen, hydroxy, or substituted or unsubstituted $C_{1-6}$ alkyl;

and all other variables are the same as described herein above.

Further preferred is a compound of formula (IA-1) wherein $L_2$ is —$CR^aR^b$—.

Further preferred is a compound of formula (IA-1) wherein D is substituted with one to five substituents selected from halogen, substituted or unsubstituted alkyl, substituted or unsubstituted alkoxy, —$COR^x$, —$CONR^xR^y$, —$S(O)_qNR^xR^y$ or —$NR^xR^y$;

wherein each occurrence of $R^x$ and $R^y$ is independently selected from hydrogen, hydroxy, halogen, carboxyl, cyano, nitro, oxo (=O), thio (=S), substituted or unsubstituted alkyl, substituted or unsubstituted alkoxy, substituted or unsubstituted alkenyl, substituted or unsubstituted alkynyl, substituted or unsubstituted cycloalkyl, substituted or unsubstituted cycloalkenyl, substituted or unsubstituted cycloalkylalkyl, substituted or unsubstituted cycloalkenylalkyl, substituted or unsubstituted heterocycyl, substituted or unsubstituted heterocyclylalkyl, substituted or unsubstituted aryl, substituted or unsubstituted arylalkyl, substituted or unsubstituted heteroaryl, substituted or unsubstituted heteroarylalkyl, —COOR$^z$, —C(O)R$^z$, —C(S)R$^z$, —C(O)NR$^z$R$^z$, —C(O)ONR$^z$R$^z$, —NR$^z$R$^z$, —NR$^z$CONR$^z$R$^z$, —N(R$^z$)SOR$^z$, N(R$^z$)SO$_2$R$^z$, —(=N—N(R$^z$)R$^z$), —NR$^z$C(O)OR$^z$, —NR$^z$C(O)R$^z$—, —NR$^x$C(S)$^y$—NR$^z$C(S)NR$^z$R$^z$, SONR$^z$R$^z$—, —SO$_2$NR$^z$R$^z$—, —OR$^z$, —OR$^z$C(O)NR$^z$R$^z$, —OR$^z$C(O)OR$^z$—, —OC(O)R$^z$, —OC(O)NR$^z$R$^z$, —R$^z$N-R$^z$C(O)R$^z$, —R$^z$OR$^z$, —R$^z$C(O)OR$^z$, —R$^z$C(O)NR$^z$R$^z$, —R$^z$C(O)R$^z$, —R$^z$OC(O)R$^z$, —SR$^z$, —SOR$^z$, —SO$_2$R$^z$, and —ONO$_2$, or any two or R$^x$ and R$^y$ which are directly bound to a common atom may be joined to form (i) a substituted or unsubstituted, saturated or unsaturated 3-14 membered ring, which may optionally include one or more heteroatoms which may be the same or different and are selected from O, NR$^z$ or S, or (ii) an oxo (=O), thio (=S) or imino (=NR$^z$), wherein each occurrence of R$^z$ is independently hydrogen, hydroxy, halogen, carboxyl, cyano, nitro, oxo (=O), thio (=S), substituted or unsubstituted alkyl, substituted or unsubstituted alkoxy, substituted or unsubstituted alkenyl, substituted or unsubstituted alkynyl, substituted or unsubstituted cycloalkyl, substituted or unsubstituted cycloalkenyl, substituted or unsubstituted cycloalkylalkyl, substituted or unsubstituted cycloalkenylalkyl, substituted or unsubstituted heterocycyl, substituted or unsubstituted heterocyclyalkyl, substituted or unsubstituted aryl, substituted or unsubstituted arylalkyl substituted or unsubstituted heteroaryl substituted or unsubstituted heteroarylalkyl, and —ONO$_2$, or any two of R$^z$ which are directly bound to a common atom may be joined to form (i) a substituted or unsubstituted, saturated or unsaturated 3-14 membered ring, which may optionally include one or more heteroatoms which may be the same or different and are selected from O, NR' (where R' is H or alkyl) or S, or (ii) an oxo (=O), thio (=S) or imino (=NR$^z$); and q in the group D is 0, 1 or 2.

Further preferred is a compound of formula (IA-1) wherein D is selected from

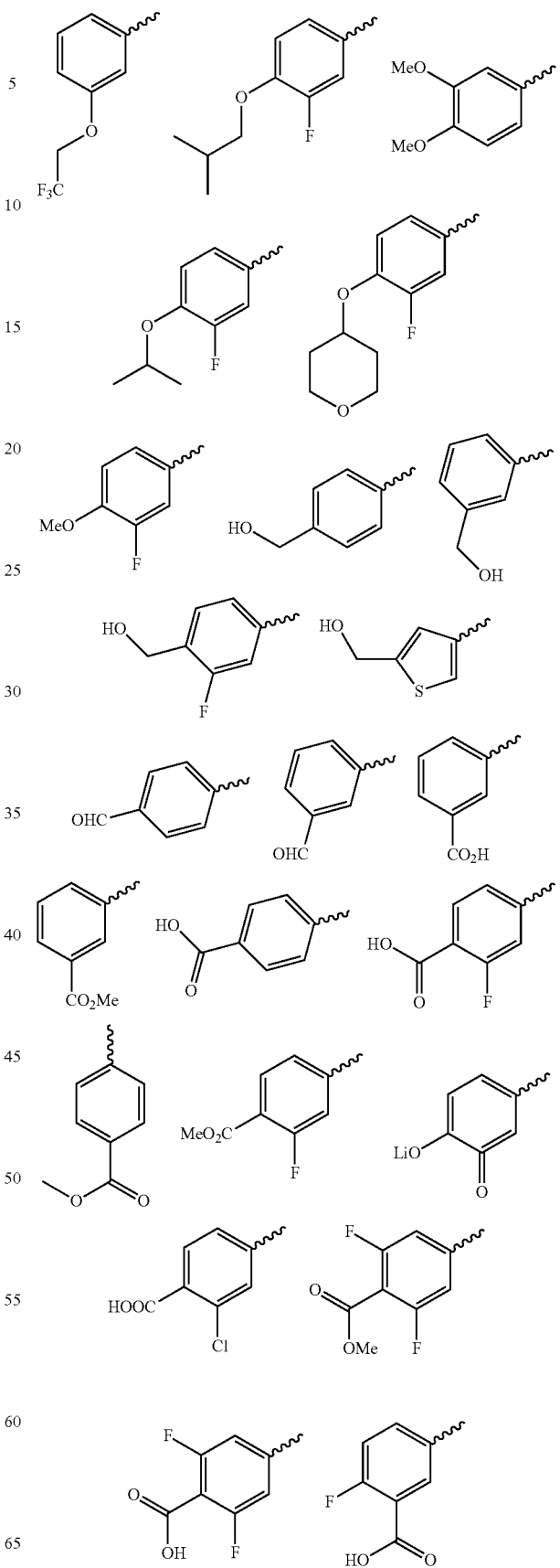

-continued
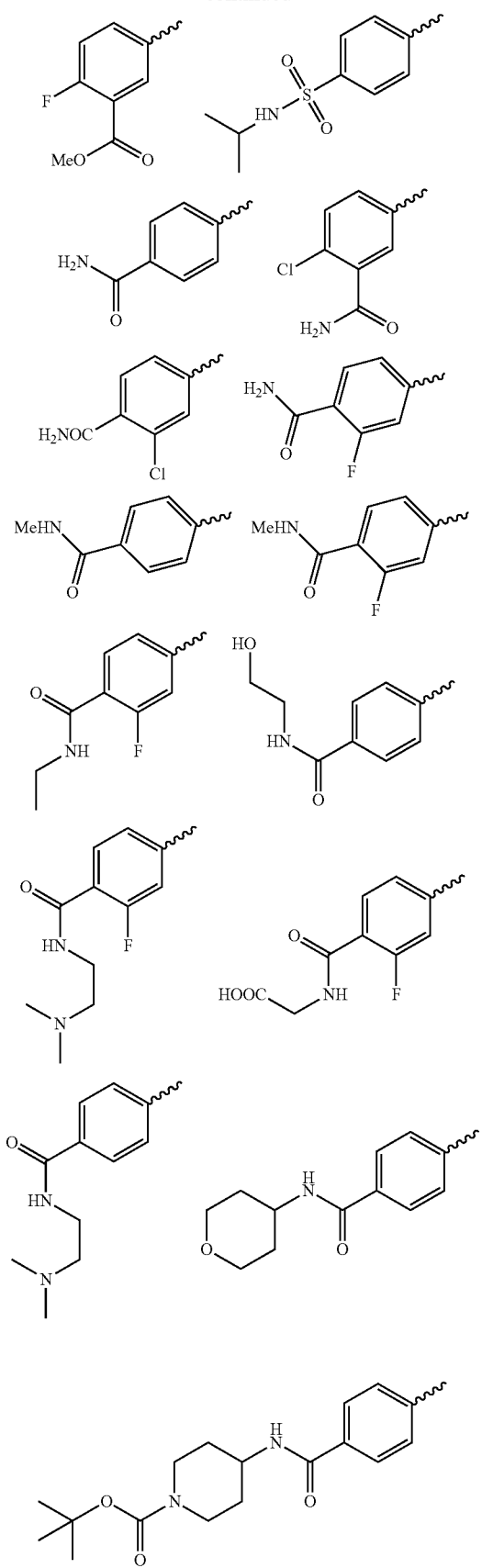
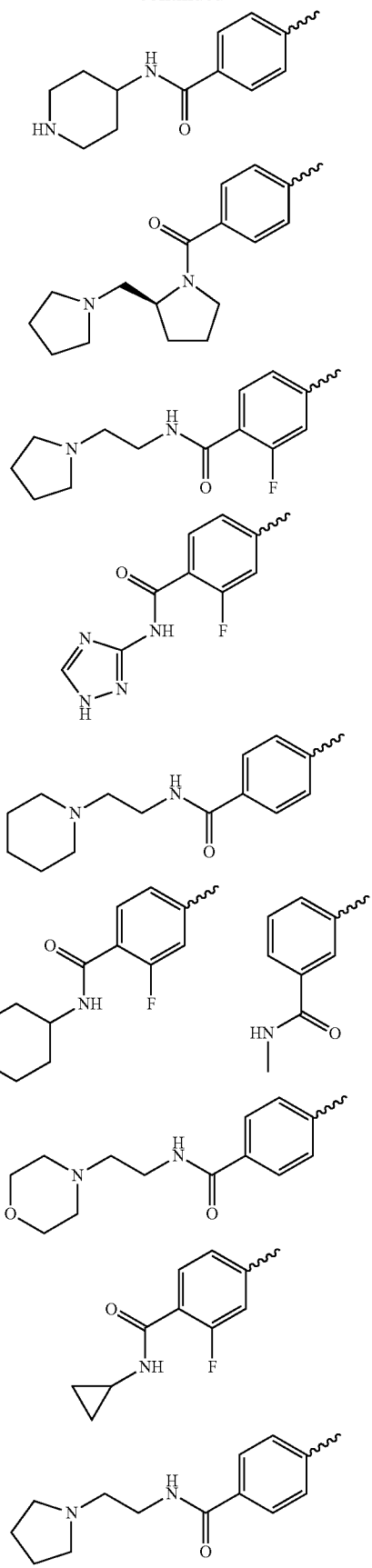

37
-continued
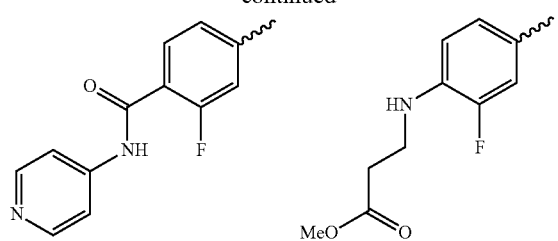
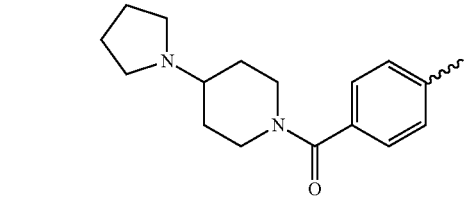
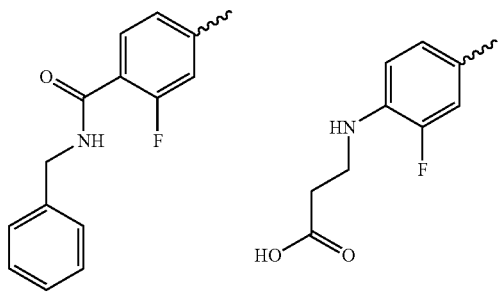
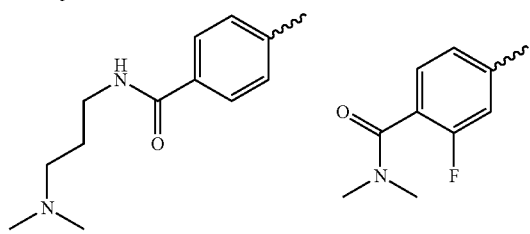
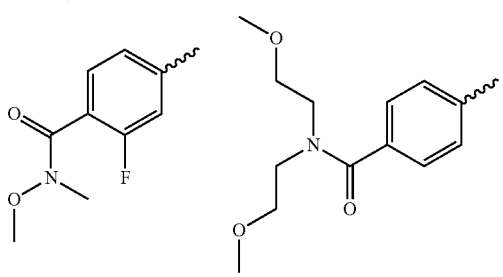
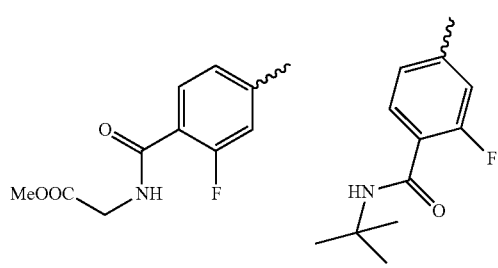
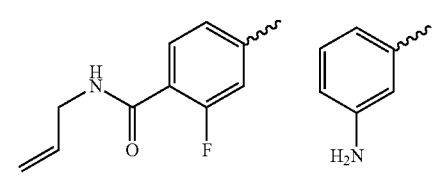
38
-continued
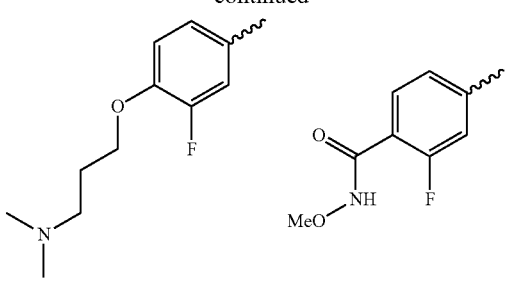
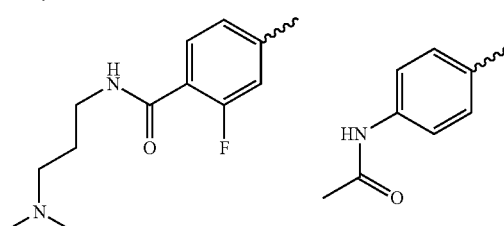
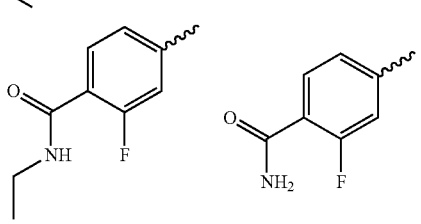
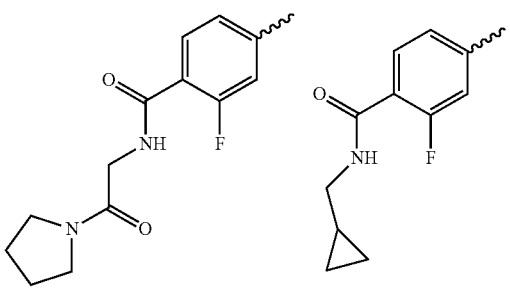
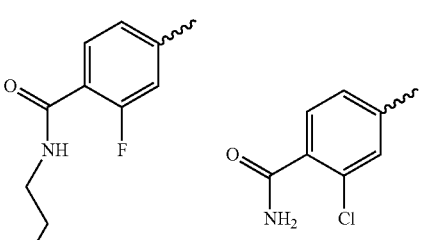
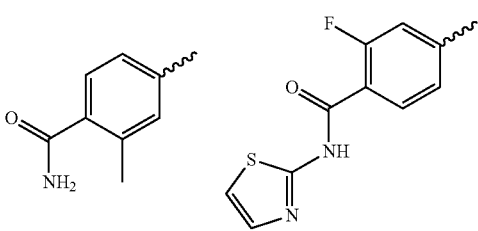

39
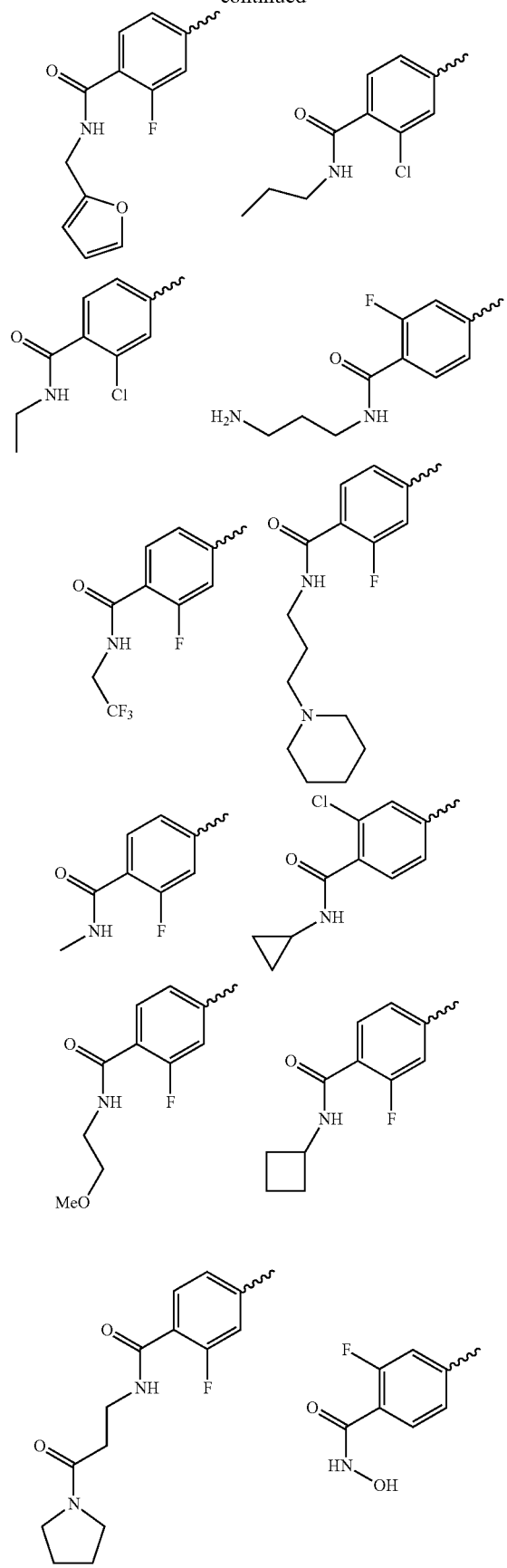
40
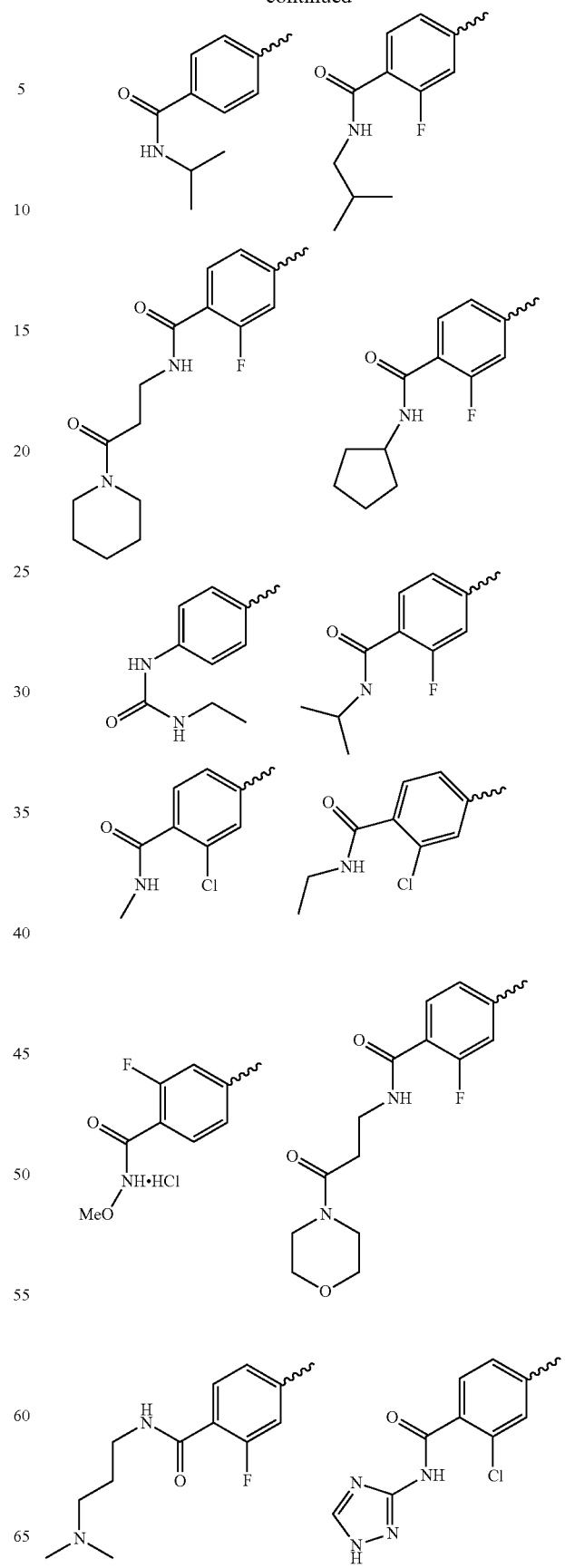

41
-continued
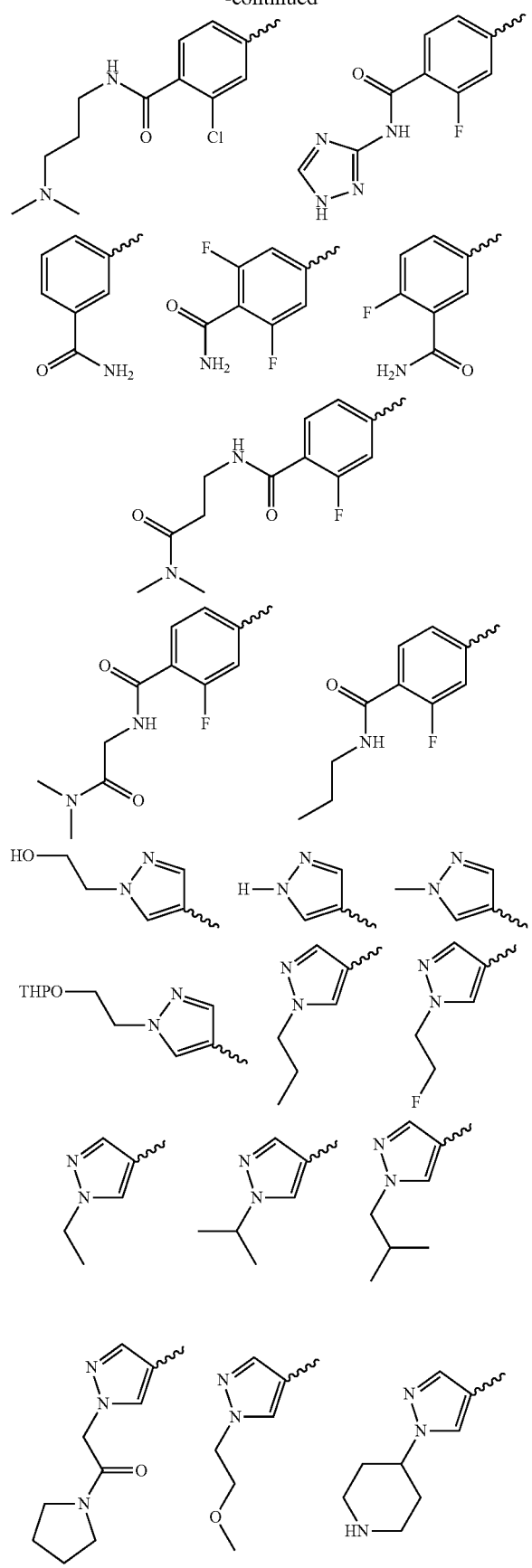
42
-continued
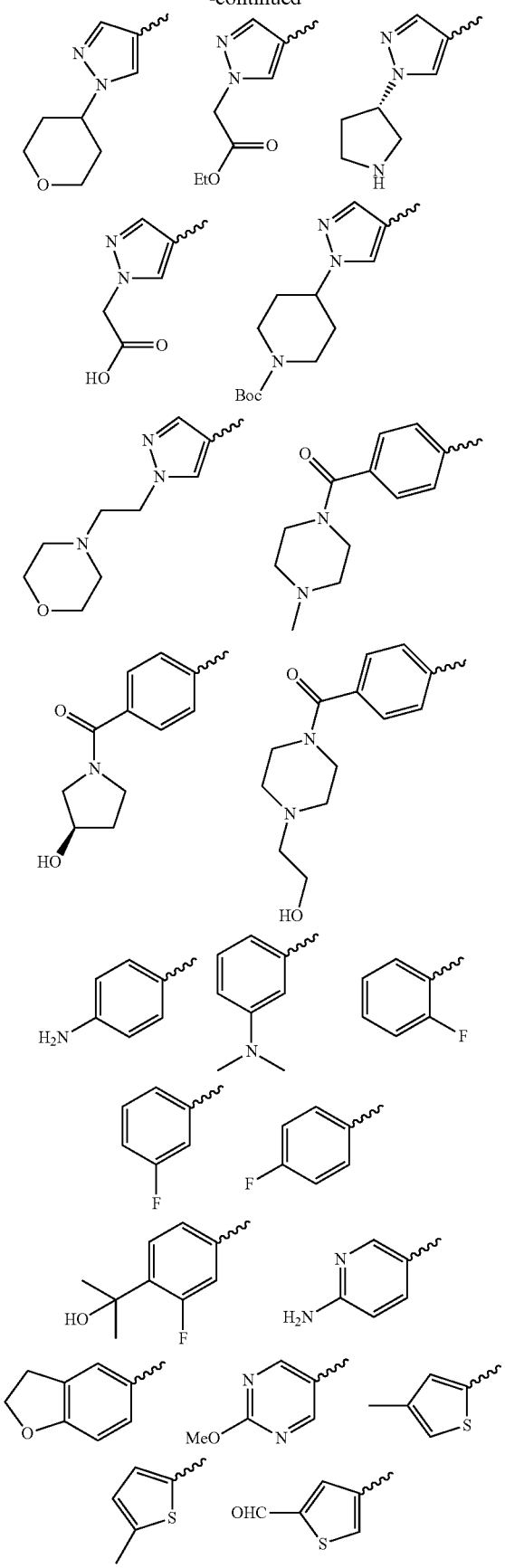

-continued
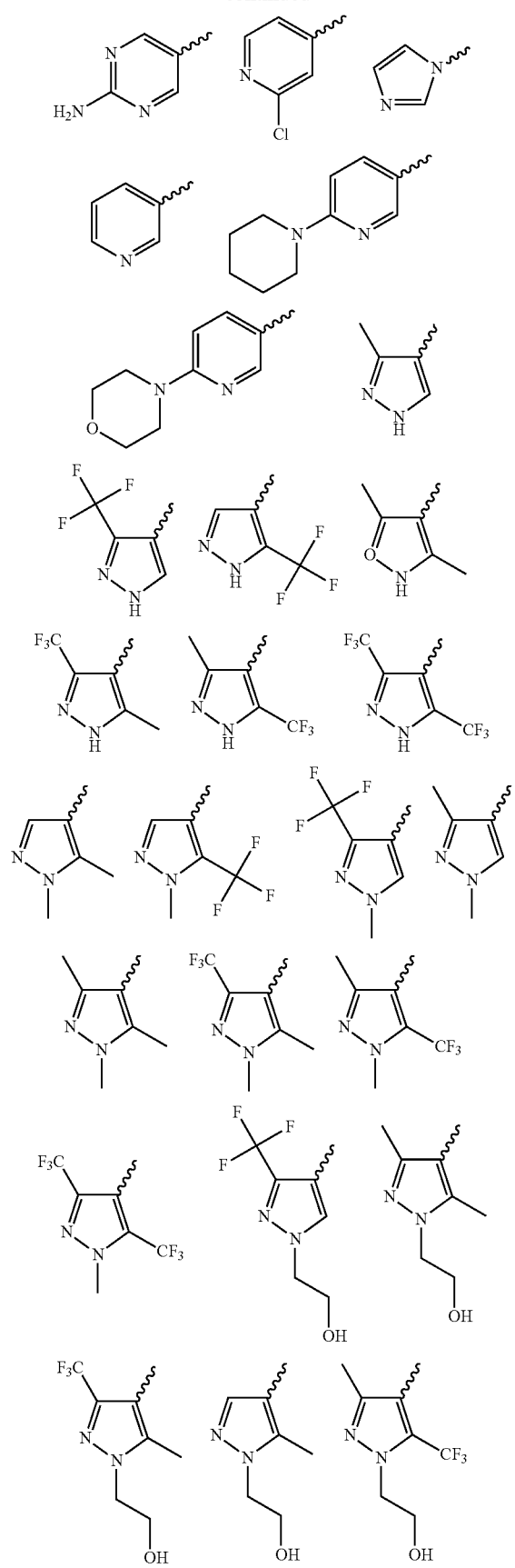
-continued
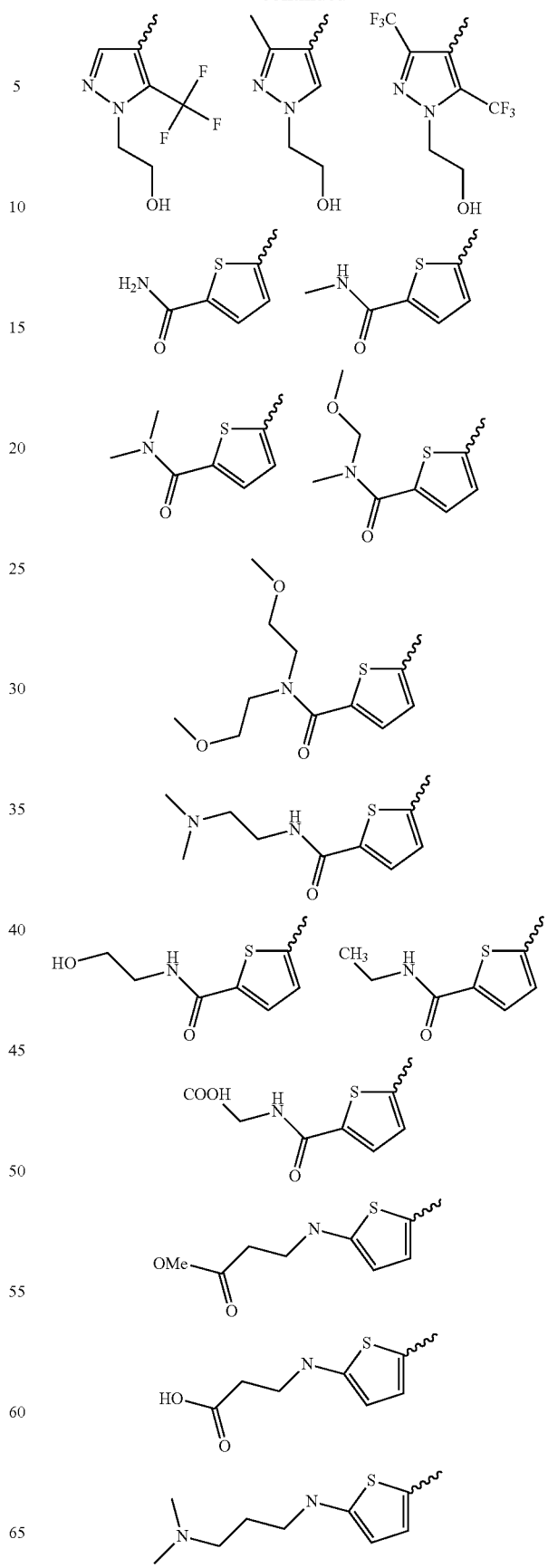

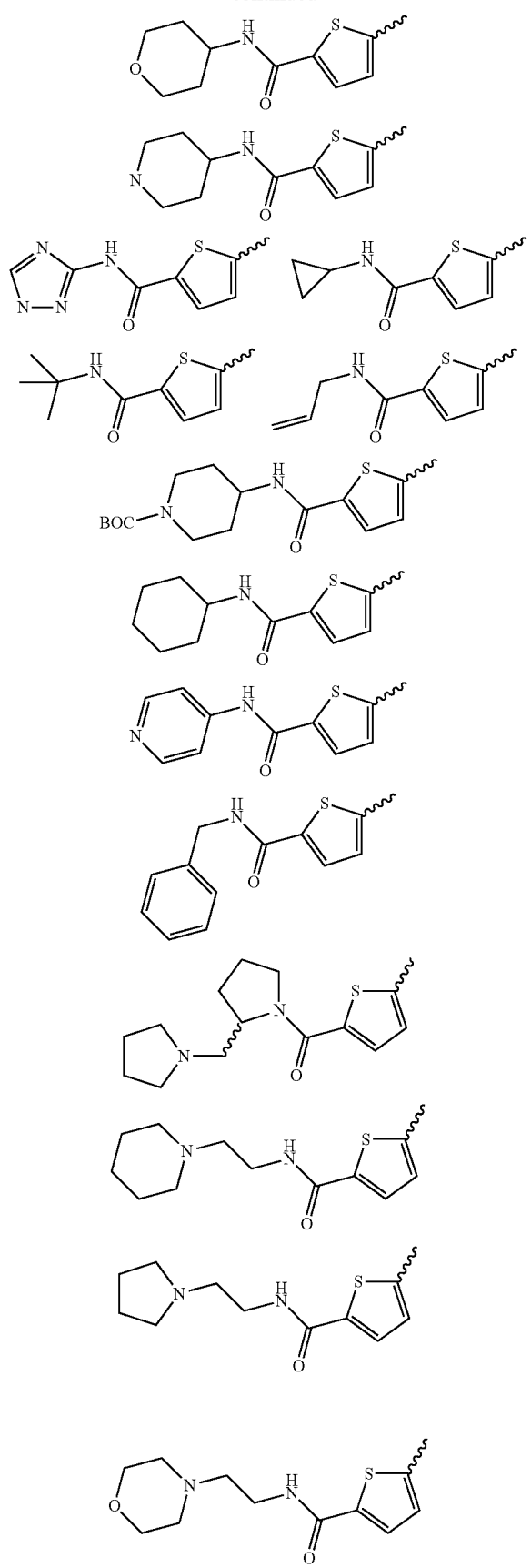
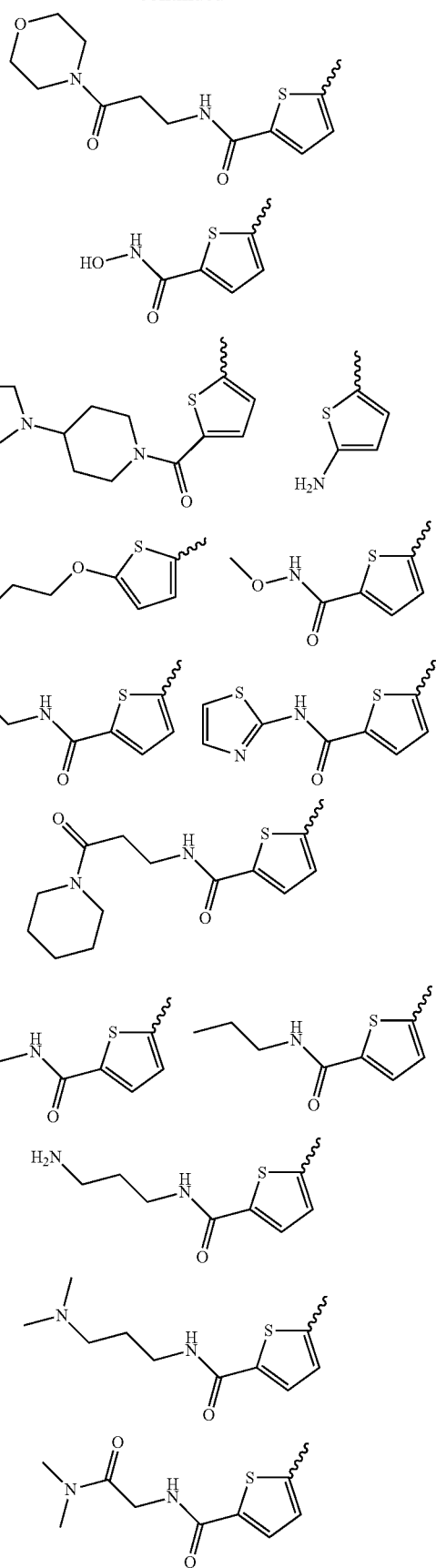

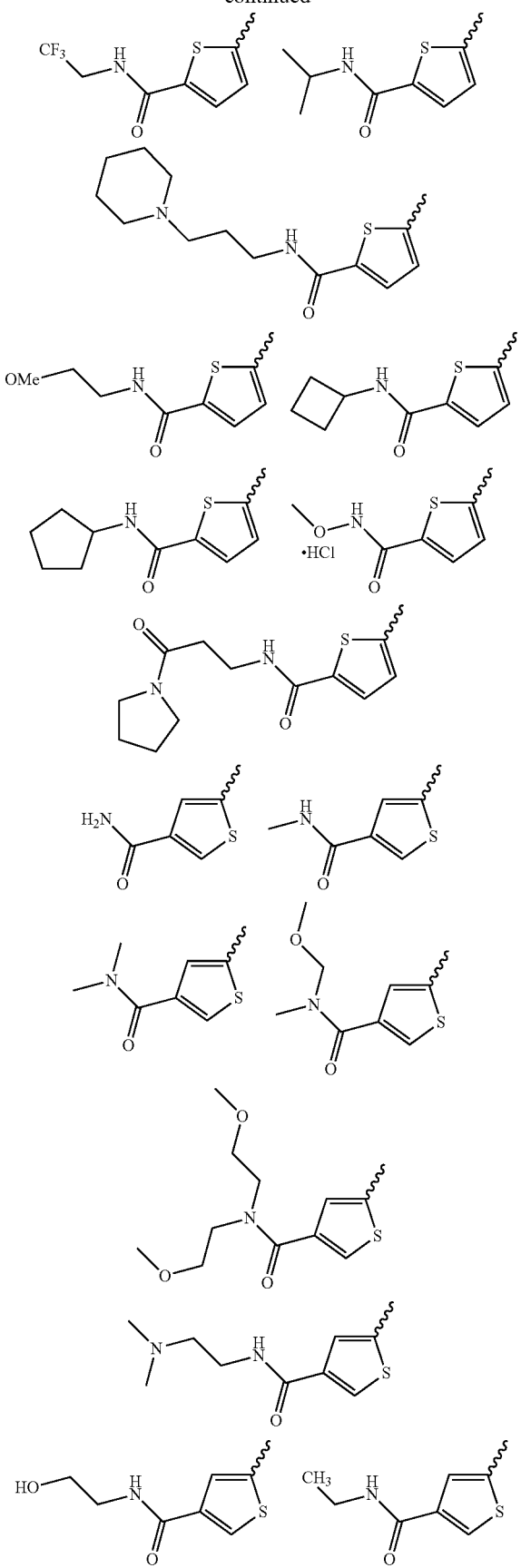
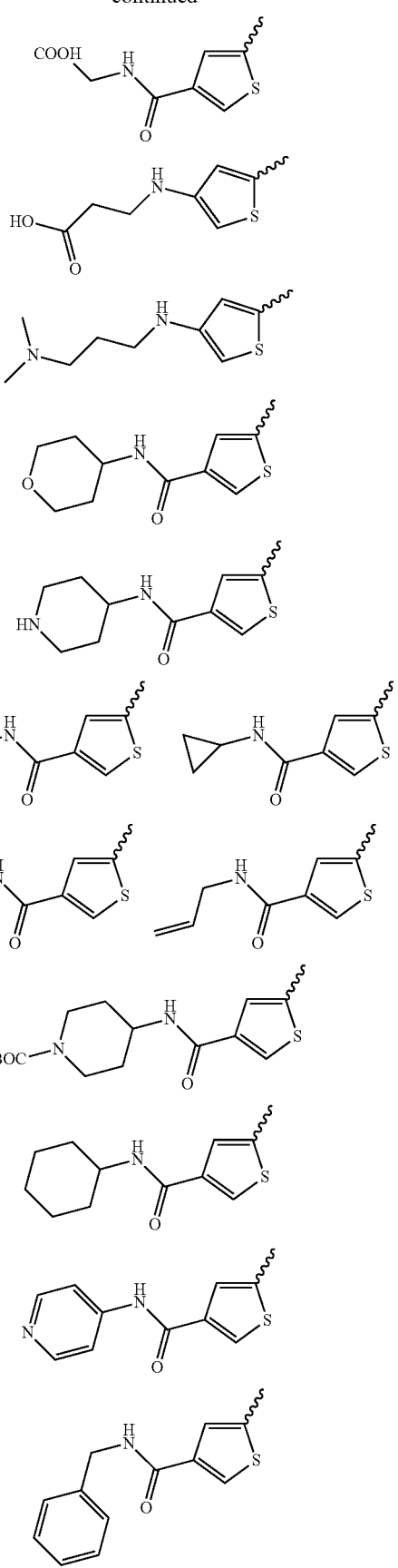

49
-continued
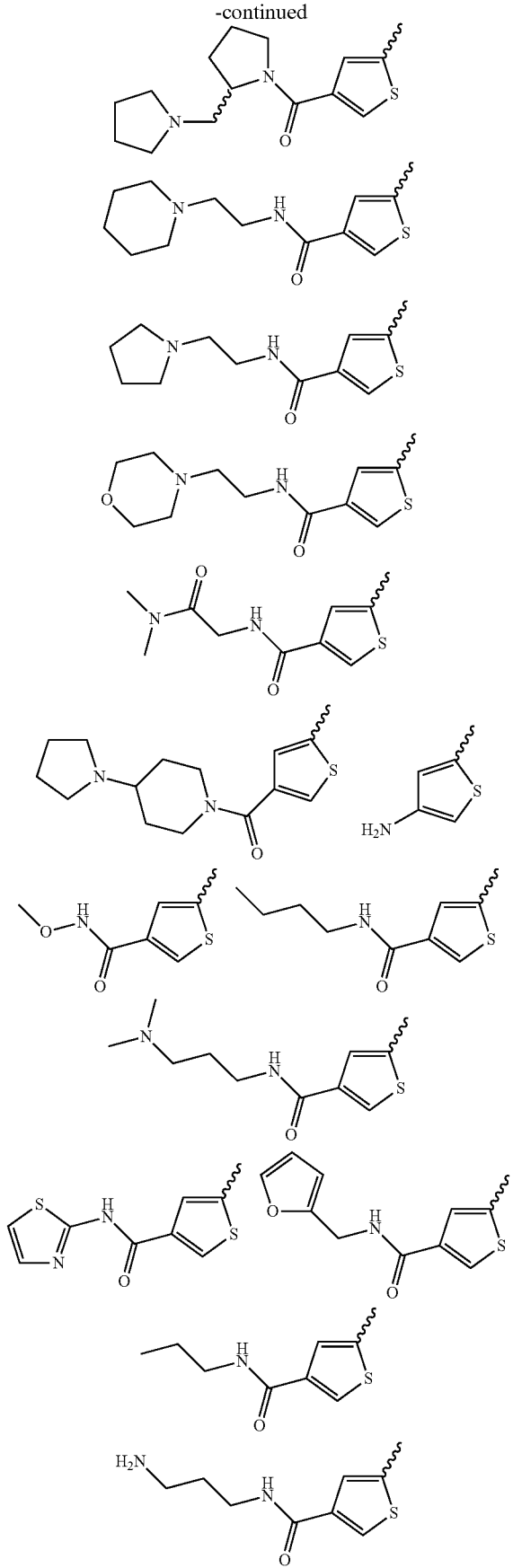
50
-continued
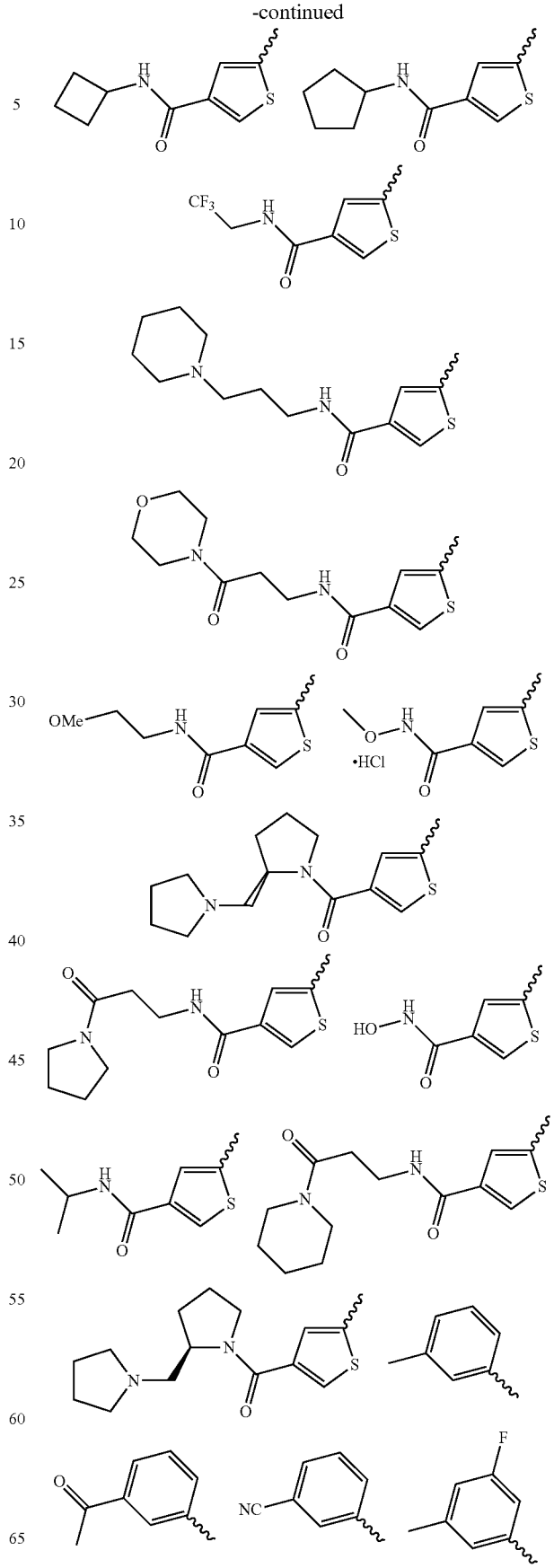

51
-continued
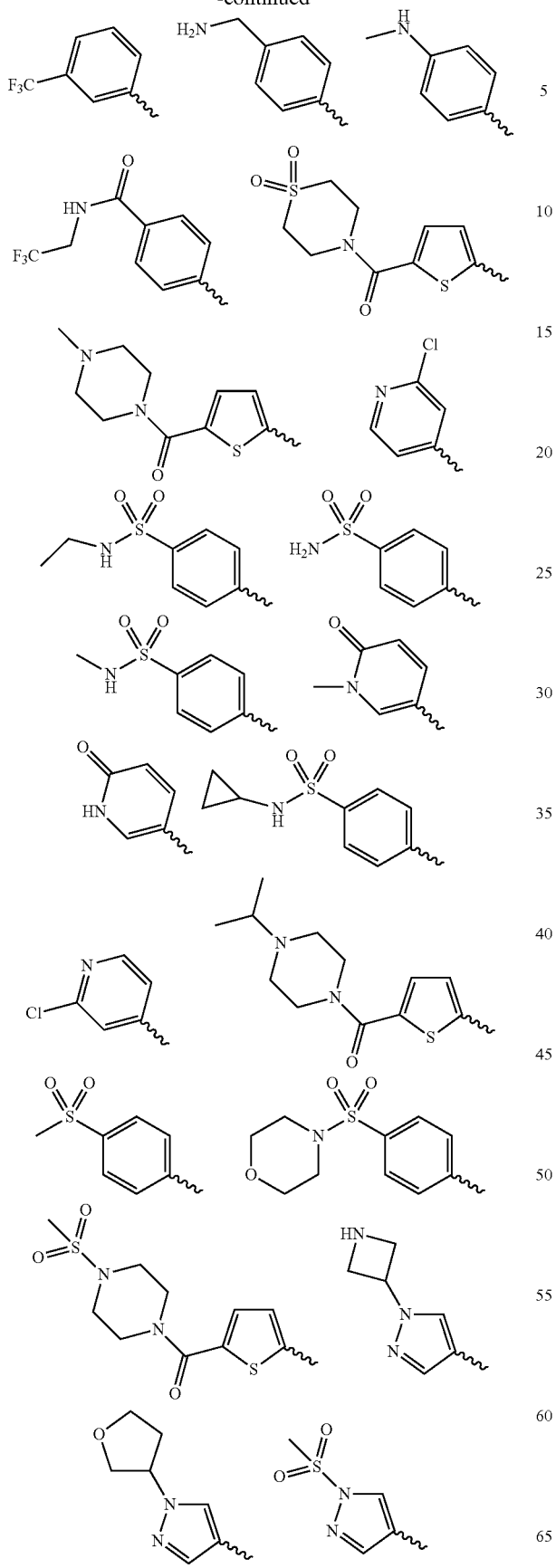
52
-continued
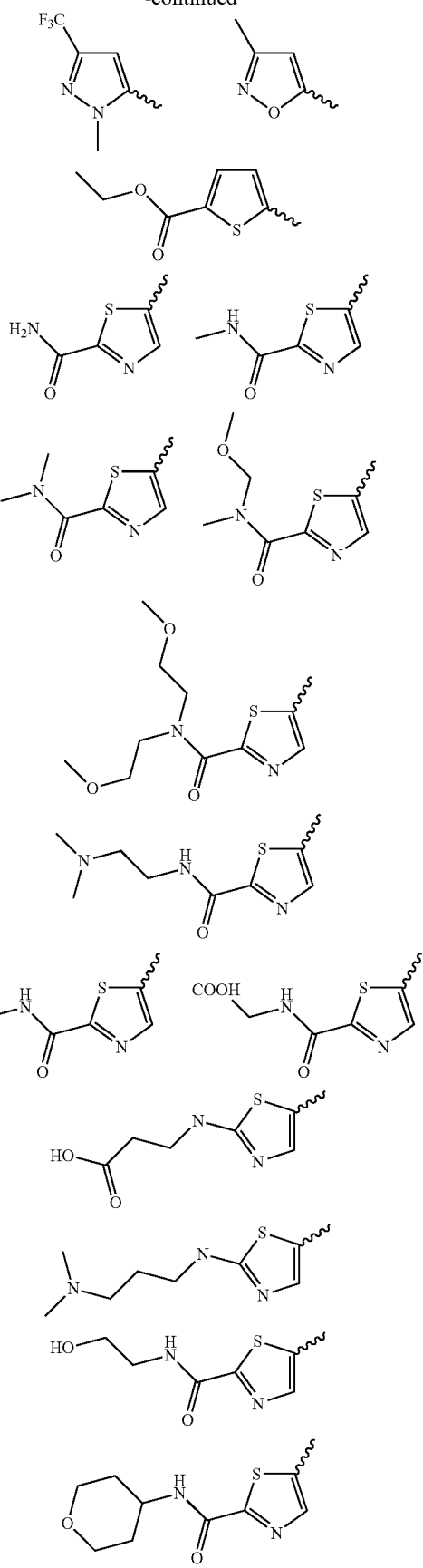

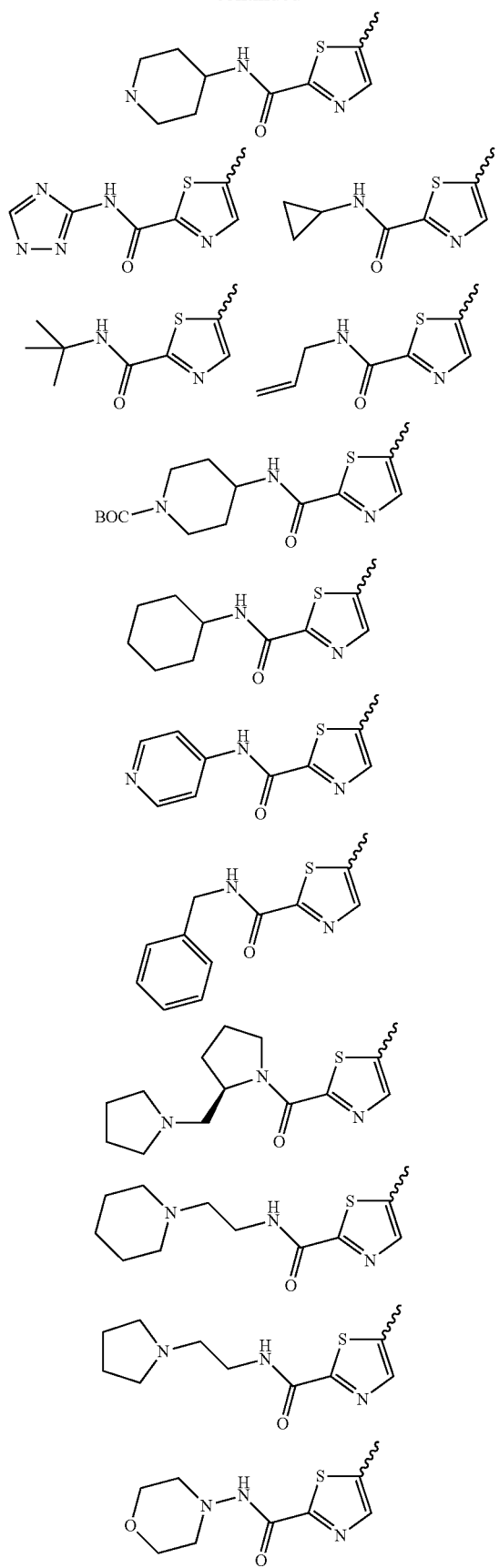
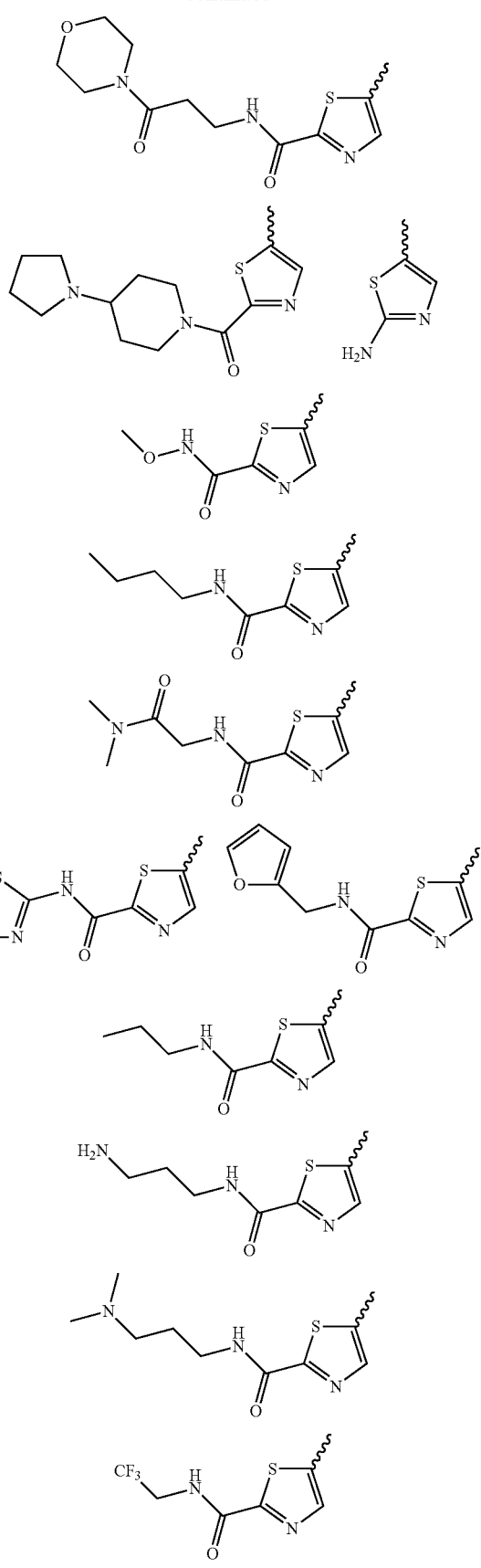

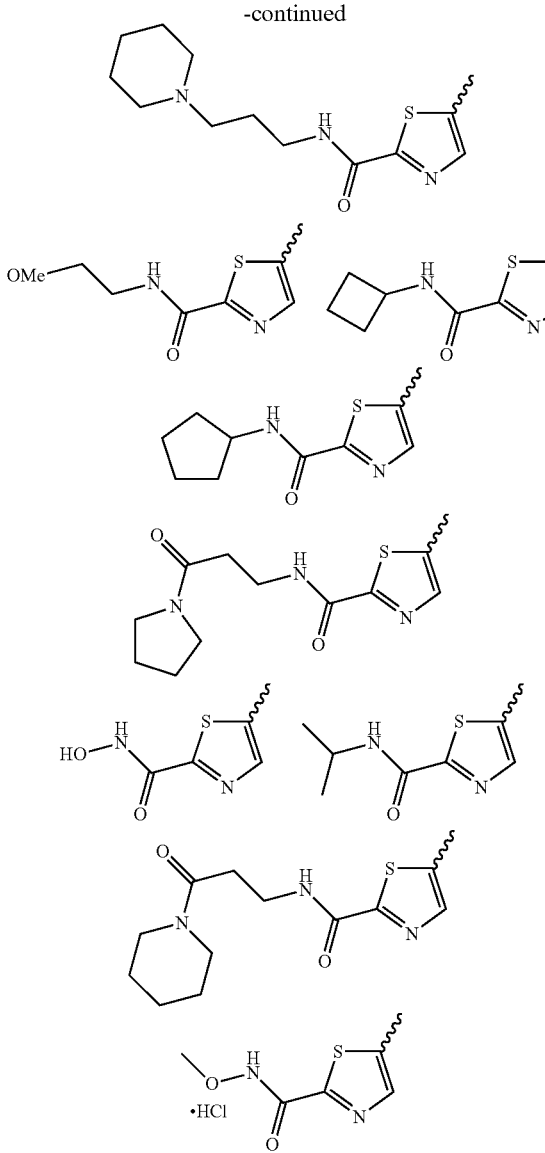

Yet another embodiment is a compound of formula (II):

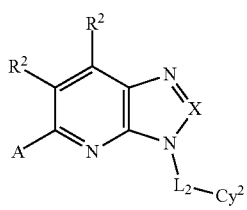

or a tautomer, stereoisomer, enantiomer, diastereomer, salt (e.g., pharmaceutically acceptable salt), prodrug (e.g., ester), or N-oxide thereof, wherein A is selected from halogen, —$OR^c$, —$S(=O)_q$—$R^c$, —$NR^cR^d$, —$(CR^cR^d)_n$—$R^c$, —$C(=Y)$—$R^c$, —$C(=Y)$—$C(=Y)$—$R^c$, —$CR^cR^d$—$C(=Y)$—$CR^cR^d$—$R^e$, —$CR^cR^d$—$Y$—$CR^cR^d$—$R^e$, —$C(=Y)$—$NR^cR^d$, —$NR^c$—$C(=Y)$—$NR^cR^d$, —$S(=O)_q$—$NR^cR^d$, —$NR^c$—$S(=O)_q$—$NR^cR^d$, —$NR^c$—$NR^cR^d$, substituted or unsubstituted alkyl, substituted or unsubstituted alkenyl substituted or unsubstituted alkynyl, substituted or unsubstituted $C_{3-6}$ cycloalkyl, and substituted or unsubstituted $C_{3-6}$ cycloalkenyl; or when two $R^c$ and $R^d$ substituents are directly bound to a common atom, they may be joined to form a substituted or unsubstituted, saturated or unsaturated 3-10 member ring, which may optionally include one or more heteroatoms which may be same or different and are selected from O, $NR^e$ or S;

each occurrence of $R^c$, $R^d$, and $R^e$ are independently selected from hydrogen, hydroxy, halogen, carboxyl, cyano, nitro, oxo (=O), thio (=S), substituted or unsubstituted alkyl, substituted or unsubstituted alkoxy, substituted or unsubstituted alkenyl, substituted or unsubstituted alkynyl, substituted or unsubstituted cycloalkyl, substituted or unsubstituted cycloalkylalkyl, substituted or unsubstituted cycloalkenyl, substituted or unsubstituted cycloalkenyl alkyl, substituted or unsubstituted heterocyclic ring, substituted or unsubstituted heterocycylalkyl ring, substituted or unsubstituted aryl, substituted or unsubstituted arylalkyl, substituted or unsubstituted heteroaryl, substituted or unsubstituted heteroarylalkyl, substituted or unsubstituted guanidine, —$COOR^x$, —$C(O)R^x$, —$C(S)R^x$, —$C(O)NR^xR^y$, —$C(O)ONR^xR^y$, —$NR^yR^z$, —$NR^xCONR^yR^z$, —$N(R^x)SOR^y$, —$N(R^x)SO_2R^y$, —(=N—$N(R^xR^y)$), —$NR^xC(O)OR^y$, —$NR^xR^y$, —$NR^xC(O)R^y$—, —$NR^xC(S)R^y$, —$NR^xC(S)NR^yR^z$, —$SONR^xR^y$—, —$SO_2NR^xR^y$—, —$OR^x$, —$OR^xC(O)NR^yR^z$, —$OR^xC(O)OR^y$—, —$OC(O)R^x$, —$OC(O)NR^xR^y$, —$R^xNR^yC(O)R^z$, —$R^xOR^y$, —$R^xC(O)OR^y$, —$R^xC(O)NR^yR^z$, —$R^xC(O)R^x$, —$R^xOC(O)R^y$, —$SR^x$, —$SOR^x$, —$SO_2R^x$, and —$ONO_2$, wherein each occurrence of $R^x$, $R^y$ and $R^z$ in each of the above groups is independently hydrogen, substituted or unsubstituted amino, substituted or unsubstituted alkyl, substituted or unsubstituted alkoxy, substituted or unsubstituted alkenyl, substituted or unsubstituted alkynyl, substituted or unsubstituted cycloalkyl, substituted or unsubstituted cycloalkylalkyl, substituted or unsubstituted cycloalkenyl, substituted or unsubstituted cycloalkenylalkyl, substituted or unsubstituted heterocyclic ring, substituted or unsubstituted heterocyclylalkyl ring, substituted or unsubstituted aryl, substituted or unsubstituted arylalkyl, substituted or unsubstituted heteroaryl, and substituted or unsubstituted heteroarylalkyl, or any two of $R^x$, $R^y$ and $R^z$ which are directly bound to a common atom may be joined to form (i) an oxo (C=O), thio (C=S) or imino (C=NR') group (where R' is H or alkyl) or (ii) substituted or unsubstituted, saturated or unsaturated 3-10 membered ring, which may optionally include one or more heteroatoms which may be the same or different and are selected from O, NR' (where R' is H or alkyl) or S; and all other variables are the same as described above for compound of formula (I).

Yet another embodiment is a compound of formula (IIA):

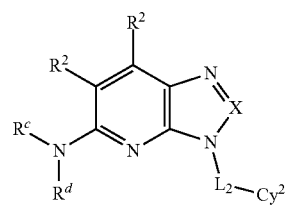

or a tautomer, stereoisomer, enantiomer, diastereomer, salt (e.g., pharmaceutical acceptable salt), prodrug (e.g., ester), or N-oxide thereof, wherein $R^c$ and $R^d$ together with the nitrogen to which they are attached form a substituted or unsubstituted, saturated or unsaturated 3-10 member ring, which may optionally include one or more heteroatoms which may be same or different and are selected from O, $NR^e$ or S; and all other variables are the same as described above for compound of formula (II).

Further preferred is a compound of formula (IIA) wherein $NR^cR^d$ is selected from

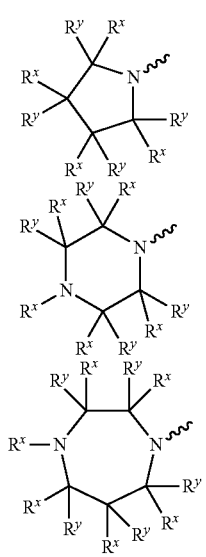

wherein each occurrence of $R^x$ and $R^y$ is independently selected from hydrogen, substituted or unsubstituted alkyl, and substituted or unsubstituted alkoxy, or any two of $R^x$ and $R^y$ which are directly bound to a common atom may be joined to form an oxo (C=O), thio (C=S) or imino (C=NR') group (where R' is H or alkyl) or, any two of $R^x$ and $R^y$ may be joined to form a substituted or unsubstituted, saturated or unsaturated 3-6 membered ring, which may optionally include one or more heteroatoms which may be the same or different and are selected from O, NR' (where R' is H or alkyl) or S.

Further preferred is a compound of formula (IIA) wherein $NR^cR^d$ is selected from

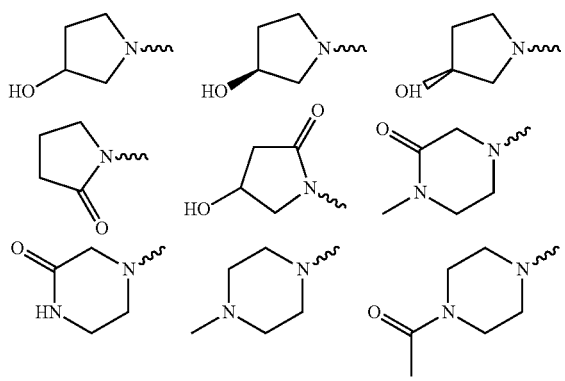

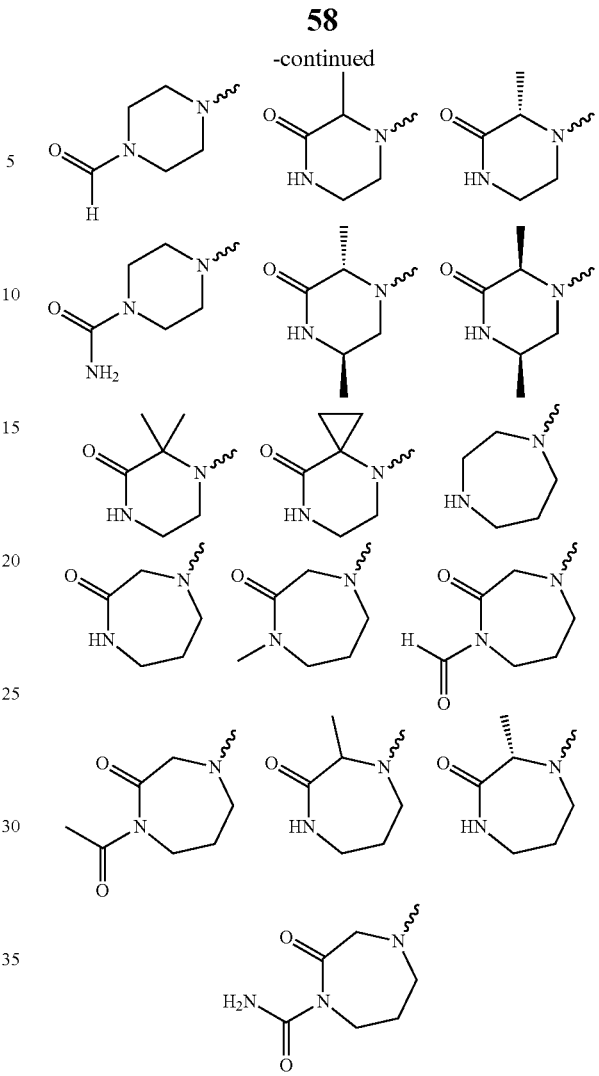

Yet another embodiment is a compound of formula (III):

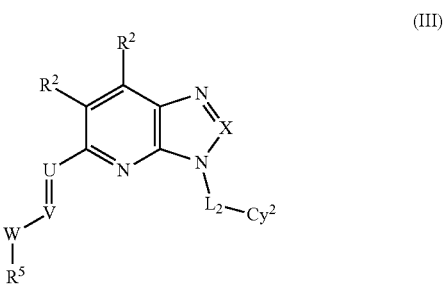

(III)

or a tautomer, stereoisomer, enantiomer, diastereomer, salt (e.g., pharmaceutical acceptable salt), prodrug (e.g., ester), or N-oxide thereof, wherein U and V are each independently selected from $CR^3$ or N;

W is selected from O, S, or $NR^4$;

each occurrence of $R^3$ is independently hydrogen, halogen, cyano (CN), $-OR^c$, $-S(=O)_q-R^c$, $-NR^cR^d$, substituted or unsubstituted alkyl, substituted or unsubstituted alkenyl, substituted or unsubstituted alkynyl, substituted or unsubstituted $C_{3-6}$ cycloalkyl, substituted or unsubstituted $C_{3-6}$cycloalkylalkyl, or substituted or unsubstituted $C_{3-6}$ cycloalkenyl;

R⁴ is selected from hydrogen, hydroxy, carboxyl, cyano, oxo (=O), thio (=S), substituted or unsubstituted alkyl, substituted or unsubstituted alkoxy, substituted or unsubstituted alkenyl, substituted or unsubstituted alkynyl, substituted or unsubstituted C$_{3-6}$ cycloalkyl, substituted or unsubstituted C$_{3-6}$cycloalkylalkyl, and substituted or unsubstituted C$_{3-6}$ cycloalkenyl;

R⁵ is selected front hydrogen, hydroxy, halogen, carboxyl, cyano, nitro, oxo (=O), thio (=S), substituted or unsubstituted alkyl, substituted or unsubstituted alkoxy, substituted or unsubstituted alkenyl, substituted or unsubstituted alkynyl, substituted or unsubstituted cycloalkyl, substituted or unsubstituted cycloalkylalkyl, substituted or unsubstituted cycloalkenyl, substituted or unsubstituted heterocyclic ring, substituted or unsubstituted heterocyclylalkyl, substituted or unsubstituted aryl, substituted or unsubstituted arylalkyl substituted or unsubstituted heteroaryl, substituted or unsubstituted heteroarylalkyl, substituted or unsubstituted guanidine, —COOR$^x$, —C(O)R$^x$, —C(S)R$^x$, —C(O)NR$^x$R$^y$, —C(O)ONR$^x$R$^y$, —NR$^x$R$^z$, —NR$^x$CONR$^y$R$^z$, —N(R)$^x$)SOR$^y$, —N(R$^x$)SO$_2$R$^y$, —(=N—N(R$^x$)R$^y$), —NR$^x$C(O)OR$^y$, —NR$^x$C(O)R$^y$—, —NR$^x$C(S)R$^y$, —NR$^x$C(S)NR$^y$R$^z$, —SONR$^x$R$^y$—, —SO$_2$NR$^x$R$^y$—, —OR$^x$, —OR$^x$C(O) NR$^y$R$^z$, —OR$^x$C(O)OR$^y$—, —OC(O)R$^x$, —OC(O)NR$^x$R$^y$, —R$^x$NR$^y$C(O)R$^z$, —R$^x$OR$^y$, —R$^x$C(O)OR$^y$, —R$^x$C(O) NR$^y$R$^z$, —R$^x$C(O)R$^x$, —R$^x$OC(O)R$^y$, —SR$^x$, —SOR$^x$, —SO$_2$R$^x$, and —ONO$_2$, wherein R$^x$, R$^y$ and R$^z$ in each of the above groups can be hydrogen, substituted or unsubstituted amino, substituted or unsubstituted alkyl, substituted or unsubstituted alkoxy, substituted or unsubstituted alkenyl, substituted or unsubstituted alkynyl, substituted or unsubstituted cycloalkyl, substituted or unsubstituted cycloalkylalkyl, substituted or unsubstituted cycloalkenyl, substituted or unsubstituted heterocyclic ring, substituted or unsubstituted heterocyclylalkyl, substituted or unsubstituted aryl, substituted or unsubstituted arylalkyl, substituted or unsubstituted heteroaryl, substituted or unsubstituted heteroarylalkyl, or any two of R$^x$, R$^y$ and R$^z$ which are directly bound to a common atom may be joined to form an oxo (C=O), thio (C=S) or imino (C=NR') group (where R' is H or alkyl) or substituted or unsubstituted, saturated or unsaturated 3-10 membered ring, which may optionally include one or more heteroatoms which may be the same or different and are selected from O, NR' (where R' is H or alkyl) or S;

or when W is NR⁴, R⁴ and R⁵ together with the nitrogen to which they are attached form a substituted or unsubstituted, saturated or unsaturated 3-10 member ring, which may optionally include one or more heteroatoms which may be same or different and are selected from O, NR$^e$ or S; and all the other variables are the same as described above for compound of formula (I).

Further preferred is a compound of formula (III) wherein U is CR³.

Further preferred is a compound of formula (III) wherein V is N.

Further preferred is a compound of formula (III) wherein W is O or NR⁴.

Further preferred is a compound of formula (III) wherein —U=V—W—R⁵ is

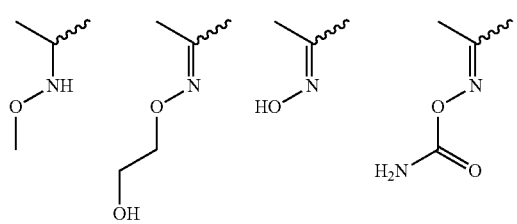

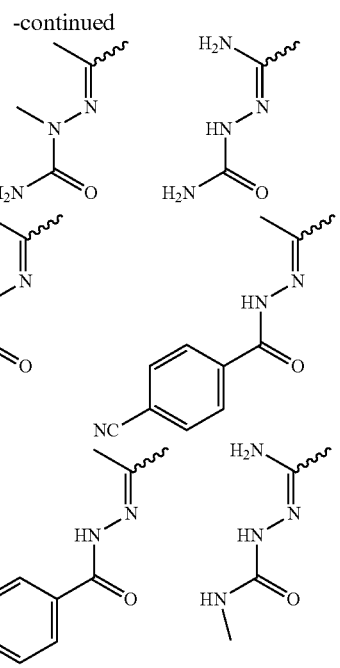

Yet another embodiment is compound of formula (IIIA) or (IIIB):

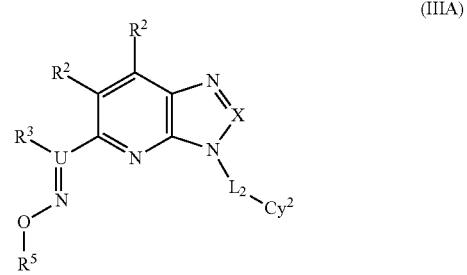

(IIIA)

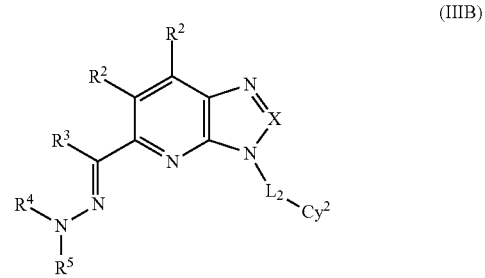

(IIIB)

or a tautomer, stereoisomer, enantiomer, diastereomer, salt (e.g., pharmaceutically acceptable salt), prodrug (e.g., ester), or N-oxide thereof, wherein all the variables are the same as described above for compound of formula (III).

Further preferred is a compound of formula (IIIA) wherein —CR³=N—O—R⁵ is selected from

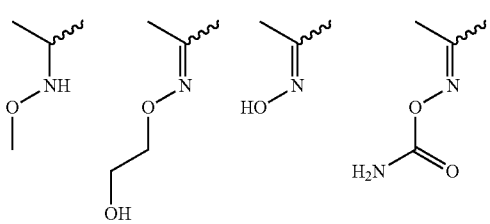

Further preferred is a compound of formula (IIIA) wherein —CR³=N—NR⁴R⁵ is selected from

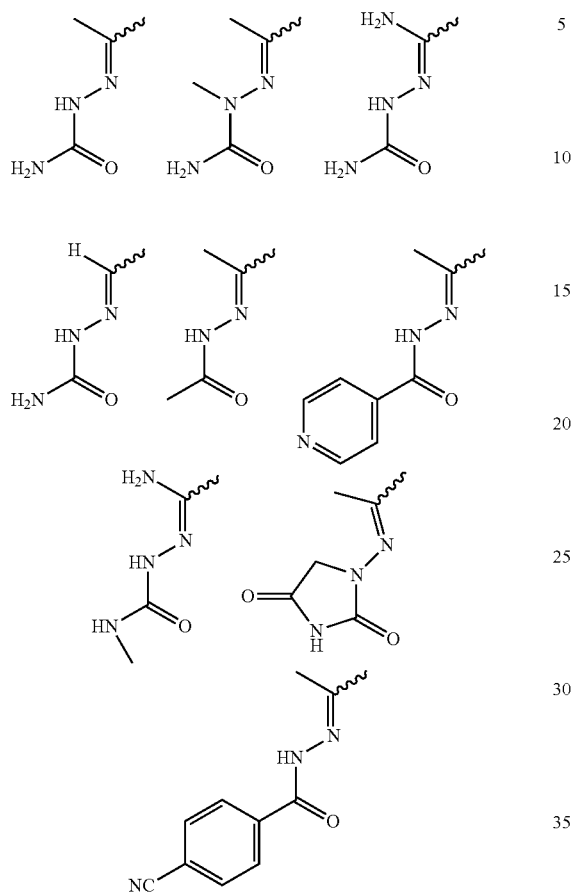

Further preferred is a compound of formula (I), (IA), (IA-1), (II), (IIA), (III), (IIIA) or (IIIB) wherein X is CR¹.

Further preferred is a compound of formula (I), (IA), (IA-1), (II), (IIA), (III), (IIIA) or (IIIB) wherein X is N.

Further preferred is a compound of formula (I), (IA), (IA-1), (II), (IIA), (III), (IIIA) or (IIIB) wherein R¹ is H.

Further preferred is a compound of formula (I), (IA), (IA-1), (II), (IIA), (III), (IIIA) or (IIIB) wherein each of R² is H;

Further preferred is a compound of formula (I), (IA), (IA-1), (II), (IIA), (III), (IIIA) or (IIIB) wherein $L_2$ is —CR$^a$CR$^b$—.

Further preferred is a compound of formula (I), (IA), (IA-1), (II), (IIA), (III), (IIIA) or (IIIB) wherein $L_2$ is —CH$_2$—, —CH(OH)—, —CHF—, —CF$_2$—, —CH(CH$_3$)— or —C(CH$_3$)$_2$—.

Further preferred is a compound of formula (I), (IA), (IA-1), (II), (IIA), (III), (IIIA) or (IIIB) wherein $L_2$ is —CH$_2$— or —CH(CH$_3$)—.

Further preferred is a compound of formula (I), (IA), (IA-1), (II), (IIA), (III), (IIIA) or (IIIB) wherein Cy² is substituted or unsubstituted aryl or substituted or unsubstituted heteroaryl.

Further preferred is a compound of formula (I), (IA), (IA-1), (II), (IIA), (III), (IIIA) or (IIIB) wherein Cy² is selected from

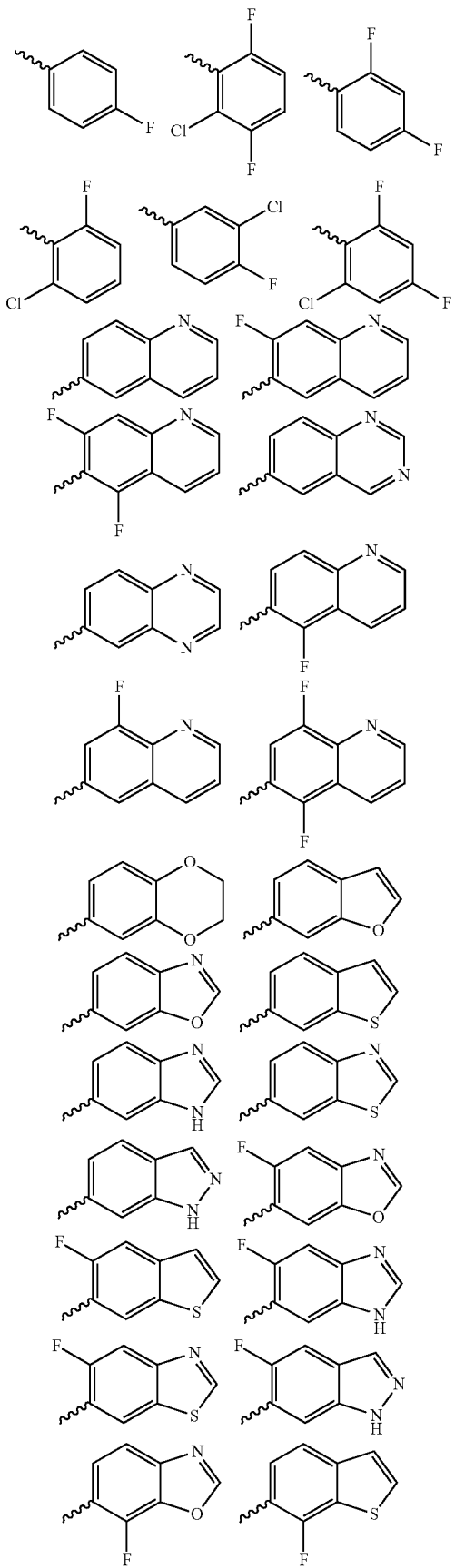

-continued

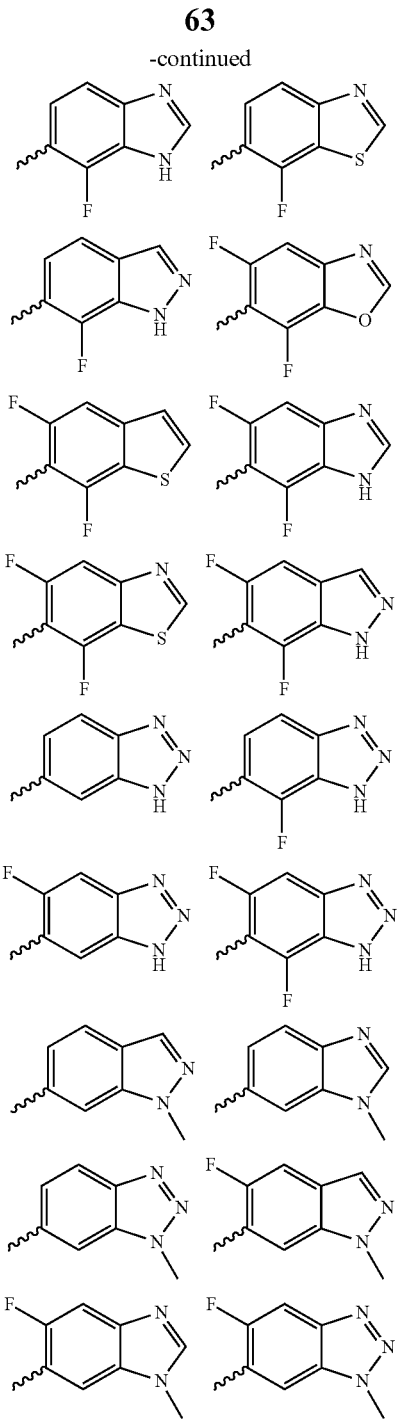

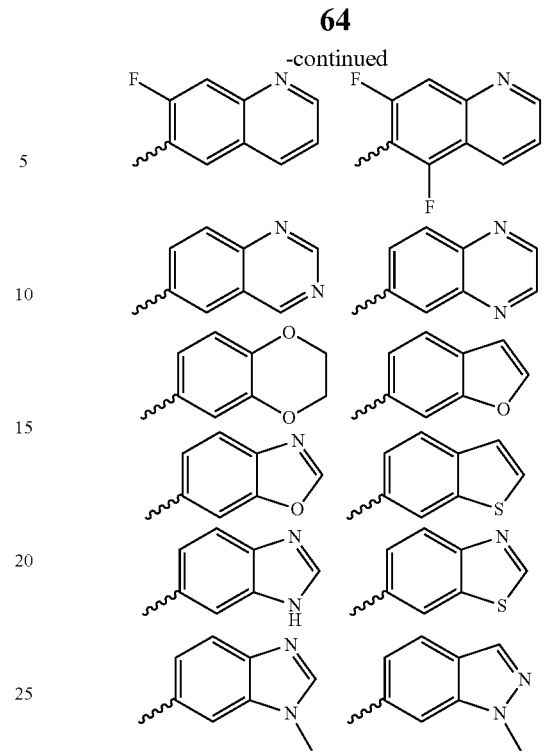

Yet another embodiment is a compound of formula (IV):

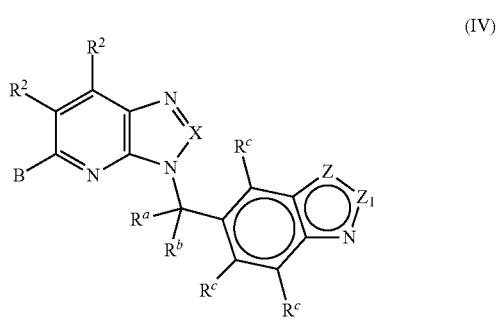

(IV)

or a tautomer, stereoisomer, enantiomer, diastereomer, salt (e.g., pharmaceutically acceptable salt), prodrug (e.g., ester), or N-oxide thereof, wherein
B is selected from $L_1$-$Cy_1$, $Cy_1$, D, A, $NR^cR^d$ and —U=V—W—$R^5$ (e.g., $Cy^1$, D, $NR^cR^d$ or —U=V—W—$R^5$);
$R^a$ and $R^b$, located between the two bicyclic groups, are independently selected from hydrogen, halogen, and substituted or unsubstituted ($C_{1-6}$) alkyl, or both together with the carbon atom to which they are attached form a saturated 3 to 6 member cyclic ring which may optionally include one or more heteroatoms which may be same or different and are selected from O, $NR^e$ and S;
Z is selected from $CR^c$, S, O, $NR^c$, $R^cC$=$CR^c$, —N=$CR^c$—, and —$R^cC$=N—;
$Z_1$ is selected from N, $NR^c$ and $CR^c$;
$R^c$ is absent or selected from hydrogen, hydroxy and halogen; and all other variables are the same as described herein above.
Further preferred is a compound of formula (IV) wherein X is N.
Further preferred is a compound of formula (IV) wherein each occurrence of $R^2$ is H.
Further preferred is a compound of formula (IV) wherein each of $R^a$ and $R^b$ is hydrogen.

Further preferred is a compound of formula (I), (IA), (IA-1), (II), (IIA), (III), (IIIA) or (IIIB) wherein $Cy^2$ is selected from

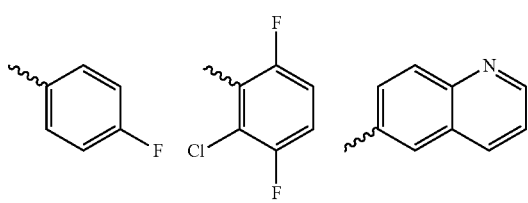

Further preferred is a compound of formula (IV) wherein $R^a$ methyl and $R^b$ is hydrogen.

Further preferred is a compound of formula (IV) wherein $R^a$ is fluoro and $R^b$ is hydrogen.

Further preferred is a compound of formula (IV) wherein $R^a$ and $R^b$ both are fluoro.

Further preferred is a compound of formula (IV) wherein $R^a$ and $R^b$ both are methyl.

Further preferred is a compound of formula (IV) wherein Z is $CR^c$, N, S, O, HC=CH—, or —N=CH—.

Further preferred is a compound of formula (IV) wherein $Z_1$ is CH or N.

Further preferred is a compound of formula (IV) wherein Z is —HC=CH—, —S— or —O— O and $Z_1$ is CH.

Further preferred is a compound of formula (IV) wherein Z is —HC=CH— and $Z_1$ is CH.

Further preferred is a compound of formula (IV) wherein Z is —S— and $Z_1$ is CH.

Further preferred is a compound of formula (IV) wherein Z is —O— and $Z_1$ is CH.

Further preferred is a compound of formula (IV) wherein Z is —CH— and $Z_1$ is NH.

Further preferred is a compound of formula (IV), wherein each occurrence of $R^c$ is hydrogen or fluoro.

Further preferred is a compound of formula (IV) wherein B is $L_1$-$Cy^1$, wherein $L_1$-$Cy^1$ is as described above for the compound of formula (I).

Further preferred is a compound of formula (IV) wherein B is $Cy^1$, wherein $Cy^1$ is as described above for the compound of formula (IA).

Further preferred is a compound of formula (IV) wherein D is as described above for the compound of formula (IA-1).

Further preferred is a compound of formula (IV) wherein A is as described above for the compound of formula (II).

Further preferred is a compound of formula (IV) wherein B is $NR^cR^d$, wherein $NR^cR^d$ is as described above for the compound of formula (IIA).

Further preferred is a compound of formula (IV) wherein B is —U=V—W—$R^5$, wherein U=V—W—$R^5$ is as described above for the compound of formula (III).

Further preferred is a compound of formula (IV) wherein U=V—W—$R^5$ is —$CR^3$=N—O—$R^5$, wherein —$CR^3$=N—O—$R^5$ is as described above for the compound of formula (IIIA).

Further preferred is a compound of formula (IV) wherein U=V—W—$R^5$ is $CR^3$=N—$NR^4R^5$, wherein —$CR^3$=N—$NR^4R^5$ is as described above for the compound of formula (IIIB).

In one embodiment, in the compound of formula (IV), (a) the bicyclic ring containing ring atoms Z and $Z_1$ is quinoline, benzo[d]thiazol-6-yl, or an N-oxide thereof, which is optionally substituted with one or two halogen (e.g., F), (b) $R^a$, $R^b$, and each $R^c$ are hydrogen, (c) each $R^2$ is hydrogen, and (d) B is substituted phenyl, substituted thiophenyl, —$CR^3$=N—O—$R^5$ or —$CR^3$=N—$NR^4R^5$ (where $R^3$, $R^4$, and $R^5$ are as described above for the compounds of formulas (IIIA) and (IIIB)). For example, B may be 4-amidophenyl (i.e., 4-$NH_2$C(O)-Ph) or 4-(R'—NHC(O)-phenyl (where R' is ($C_1$-$C_4$) alkyl), where the phenyl group may optionally be further substituted by one, two, or three substituents selected from halogens (e.g., F or Cl) and fluorinated methyl (e.g., —$CF_3$). In another embodiment, B is thiophenyl substituted with hydroxymethyl, or B is a pyrazolyl group optionally substituted with ($C_1$-$C_6$)alkyl or hydroxy ($C_1$-$C_6$) alkyl.

Yet another embodiment is a compound of formula (IVA) or (IVB):

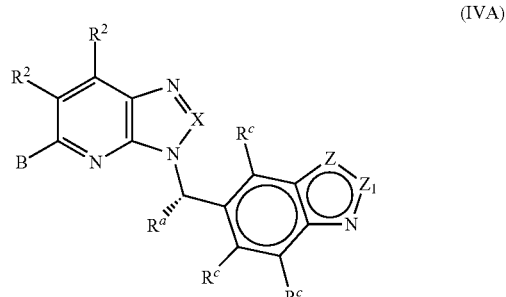

(IVA)

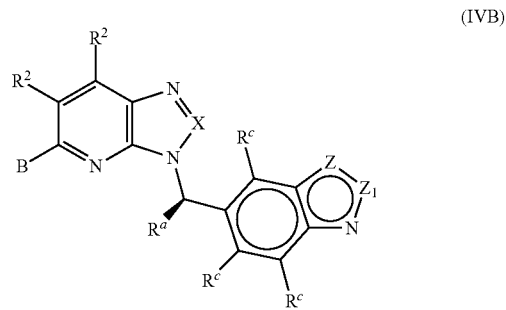

(IVB)

or a tautomer, stereoisomer, enantiomer, diastereomer, salt (e.g., pharmaceutically acceptable salt), prodrug (e.g., ester), or N-oxide thereof, wherein $R^a$ is halogen or substituted or unsubstituted (($C_{1-6}$)alkyl (e.g., methyl);

and all other variables are the same as described herein above.

In one embodiment, the bicyclic ring containing ring atoms Z and $Z_1$ in the compound of formula (IVA) is quinoline or an N-oxide thereof, which is optionally substituted with one or two halogen (e.g., F).

In one embodiment, the bicyclic ring containing ring atoms Z and $Z_1$ in the compound of formula (IVB) is quinoline or an N-oxide thereof, which is optionally substituted with one or two halogen (e.g., F).

In one embodiment, the bicyclic ring containing ring atoms Z and $Z_1$ in the compound of formula (IVA) is benzo[d] thiazol-6-yl or an N-oxide thereof, which is optionally substituted with one or two halogen (e.g., F).

In one embodiment, the bicyclic ring containing ring atoms Z and $Z_1$ in the compound of formula (IVB) is benzo[d] thiazol-6-yl or an N-oxide thereof, which is optionally substituted with one or two halogen (e.g., F).

In a preferred embodiment, B in compound (IVA) or (IVB) is substituted phenyl, substituted thiophenyl, —$CR^3$=N—O—$R^5$ or —$CR^3$=N—$NR^4R^5$ (where $R^3$, $R^4$, and $R^5$ are as described above for the compounds of formulas (IIIA) and (IIIB)). For example, B may be 4-amidophenyl (i.e., 4-$NH_2$C(O)-phenyl) or 4-(R'—NHC(O))-phenyl (where R' is ($C_1$-$C_4$) alkyl), where the phenyl group may optionally be further substituted by one, two, or three substituents selected from halogens (e.g., F or Cl) and fluorinated methyl (e.g., —$CF_3$). In another embodiment, B is thiophenyl substituted with hydroxymethyl, or B is a pyrazolyl group optionally substituted with ($C_1$-$C_6$) alkyl or hydroxy ($C_1$-$C_6$) alkyl.

In a preferred embodiment, each $R^z$ is hydrogen.

Representative compounds of fee present invention include those specified below and pharmaceutically acceptable salts thereof. The present invention should not be construed to be limited to them.

1. 6-((5-(4-Methoxyphenyl)-3H-[1,2,3]triazolo[4,5-b]pyridin-3-yl)methyl)quinoline
2. 6-((5-(3-Methoxyphenyl)-3H-[1,2,3]triazolo[4,5-b]pyridin-3-yl)methyl)quinoline
3. 3-(3-(quinolin-6-ylmethyl)-3H-[1,2,3]triazolo[4,5-b]pyridin-5-yl)benzaldehyde
4. (3-(3-(quinolin-6-ylmethyl)-3H-[1,2,3]triazolo[4,5-b]pyridin-5-yl)phenyl)methanol
5. 4-(3-(quinolin-6-ylmethyl)-3H-[1,2,3]triazolo[4,5-b]pyridin-5-yl)benzaldehyde
6. (4-(3-(quinolin-6-ylmethyl)-3H-[1,2,3]triazolo[4,5-b]pyridin-5-yl)phenyl)methanol
7. Methyl 4-(3-(quinolin-6-ylmethyl)-3H-[1,2,3]triazolo[4,5-b]pyridin-5-yl)benzoate
8. 4-(3-(quinolin-6-ylmethyl)-3H-[1,2,3]triazolo[4,5-b]pyridin-5-yl)benzoic acid
9. N-Methyl-4-(3-(quinolin-6-ylmethyl)-3H-[1,2,3]triazolo[4,5-b]pyridin-5-yl)benzamide
10. 4-(3-(4-Fluorobenzyl)-3H-[1,2,3]triazolo[4,5-b]pyridin-5-yl)benzaldehyde
11. (4-(3-(4-Fluorobenzyl)-3H-[1,2,3]triazolo[4,5-b]pyridin-5-yl)phenyl)methanol
12. Methyl 2-fluoro-4-(3-(quinolin-6-ylmethyl)-3H-[1,2,3]triazolo[4,5-b]pyridin-5-yl)benzoate
13. 2-Fluoro-4-(3-(quinolin-6-ylmethyl)-3H-[1,2,3]triazolo[4,5-b]pyridin-5-yl)benzoate acid
14. 2-Fluoro-N-methyl-4-(3-(quinolin-6-ylmethyl)-3H-[1,2,3]triazolo[4,5-b]pyridin-5-yl)benzamide
15. 2-Fluoro-4-(3-(quinolin-6-ylmethyl)-3H-[1,2,3]triazolo[4,5-b]pyridin-5-yl)benzamide
16. (2-Fluoro-4-(3-(quinolin-6-ylmethyl)-3H-[1,2,3]triazolo[4,5-b]pyridin-5-yl)phenyl)methanol
17. Methyl 4-(3-(2-chloro-3,6-difluorobenzyl)-3H-[1,2,3]triazolo[4,5-b]pyridin-5-yl)-2-fluoro benzoate
18. 4-(3-(2-Chloro-3,6-difluorobenzyl)-3H-[1,2,3]triazolo[4,5-b]pyridin-5-yl)-2-fluoro benzoic acid
19. 4-(3-(2-Chloro-3,6-difluorobenzyl)-3H-[1,2,3]triazolo[4,5-b]pyridin-5-yl)-2-fluoro-N-methyl benzamide
20. N-(2-Hydroxyethyl)-4-(3-(quinolin-6-ylmethyl)-3H-[1,2,3]triazolo[4,5-b]pyridin-5-yl)benzamide
21. 4-(3-(quinolin-6-ylmethyl)-3H-[1,2,3]triazolo[4,5-b]pyridin-5-yl)-2-benzamide
22. Lithium 4-(3-(quinolin-6-ylmethyl)-3H-[1,2,3]triazolo[4,5-b]pyridin-5-yl)-2-benzoate
23. 6-((5-(3-(trifluoromethoxy)phenyl)-3H-[1,2,3]triazolo[4,5-b]pyridin-3-yl)methyl)quinoline
24. 3-(3-(quinolin-6-ylmethyl)-3H-[1,2,3]triazolo[4,5-b]pyridin-5-yl)phenol
25. 6-((5-(3-(difluoromethoxy)phenyl)-3H-[1,2,3]triazolo[4,5-b]pyridin-3-yl)methyl)quinoline
26. (4-Methylpiperazin-1-yl)(4-(3-(quinolin-6-ylmethyl)-3H-[1,2,3]triazolo[4,5-b]pyridin-5-yl)phenyl)methanone
27. N-(2-(dimethylamino)ethyl)-4-(3-(quinolin-6-ylmethyl)-3H-[1,2,3]triazolo[4,5-b]pyridin-5-yl)benzamide
28. 4-(3-(quinolin-6-ylmethyl)-3H-[1,2,3]triazolo[4,5-b]pyridin-5-yl)-N-(tetrahydro-2H-pyran-4-yl)benzamide
29. tert-Butyl 4-(4-(3-(quinolin-6-ylmethyl)-3H-[1,2,3]triazolo[4,5-b]pyridin-5-yl)benzamido)piperidine-1-carboxylate
30. N-(Piperidin-4-yl)-4-(3-(quinolin-6-ylmethyl)-3H-[1,2,3]triazolo[4,5-b]pyridin-5-yl)benzamide hydrochloride
31. N-(2-(dimethylamino)ethyl)-2-fluoro-4-(3-(quinolin-6-ylmethyl)-3H-[1,2,3]triazolo[4,5-b]pyridin-5-yl)benzamide
32. (S)-(2-(pyrrolidin-1-ylmethyl)pyrrolidin-1-yl)(4-(3-(quinolin-6-ylmethyl)-3H-[1,2,3]triazolo[4,5-b]pyridin-5-yl)phenyl)methanone hydrochloride
33. (4-(2-hydroxyethyl)piperazin-1-yl)(4-(3-(quinolin-6-ylmethyl)-3H-[1,2,3]triazolo[4,5-b]pyridin-5-yl)phenyl)methanone
34. (R)-(3-hydroxypyrrolidin-1-yl)(4-(3-(quinolin-6-ylmethyl)-3H-[1,2,3]triazolo[4,5-b]pyridin-5-yl)phenyl)methanone hydrochloride
35. N-(2-(piperidin-1-yl)ethyl)-4-(3-(quinolin-6-ylmethyl)-3H-[1,2,3]triazolo[4,5-b]pyridin-5-yl)benzamide
36. N-(2-morpholinoethyl)-4-(3-(quinolin-6-ylmethyl)-3H-[1,2,3]triazolo[4,5-b]pyridin-5-yl)benzamide
37. N-(2-(piperidin-1-yl)ethyl)-4-(3-(quinolin-6-ylmethyl)-3H-[1,2,3]triazolo[4,5-b]pyridin-5-yl)benzamide
38. (4-(pyrrolidin-1-yl)(4-(3-(quinolin-6-ylmethyl)-3H-[1,2,3]triazolo[4,5-b]pyridin-5-yl)phenyl)methanone
39. N-(3-(dimethylamino)propyl)-4-(3-(quinolin-6-ylmethyl)-3H-[1,2,3]triazolo[4,5-b]pyridin-5-yl)benzamide
40. N,N-Bis(2-methoxyethyl)-4-(3-(quinolin-6-ylmethyl)-3H-[1,2,3]triazolo[4,5-b]pyridin-5-yl)benzamide hydrochloride
41. (2-Fluoro-4-(3-(quinolin-6-ylmethyl)-3H-[1,2,3]triazolo[4,5-b]pyridin-5-yl)phenyl)methanol hydrochloride
42. 6-((5-(3-Fluoro-4-(methoxymethyl)phenyl)-3H-[1,2,3]triazolo[4,5-b]pyridin-3-yl)methyl)quinoline
43. N-ethyl-2-fluoro-4-(3-(quinolin-6-ylmethyl)-3H-[1,2,3]triazolo[4,5-b]pyridin-5-yl)benzamide
44. 2-Fluoro-N-(2-(pyrrolidin-1-yl)ethyl)-4-(3-(quinolin-6-ylmethyl)-3H-[1,2,3]triazolo[4,5-b]pyridin-5-yl)benzamide
45. N-cyclohexyl-2-fluoro-4-(3-(quinolin-6-ylmethyl)-3H-[1,2,3]triazolo[4,5-b]pyridin-5-yl)benzamide
46. N-Cyclopropyl-2-fluoro-4-(3-(quinolin-6-ylmethyl)-3H-[1,2,3]triazolo[4,5-b]pyridin-5-yl)benzamide
47. 2-Fluoro-N-(pyridin-4-yl)-4-(3-(quinolin-6-ylmethyl)-3H-[1,2,3]triazolo[4,5-b]pyridin-5-yl)benzamide
48. N-Benzyl-2-fluoro-4-(3-(quinolin-6-ylmethyl)-3H-[1,2,3]triazolo[4,5-b]pyridin-5-yl)benzamide
49. 2-Fluoro-N,N-dimethyl-4-(3-(quinolin-6-ylmethyl)-3H-[1,2,3]triazolo[4,5-b]pyridin-5-yl)benzamide
50. Methyl 2-(2-fluoro-4-(3-(quinolin-6-ylmethyl)-3H-[1,2,3]triazolo[4,5-b]pyridin-5-yl)benzamido)acetate.
51. 2-(2-Fluoro-4-(3-(quinolin-6-ylmethyl)-3H-[1,2,3]triazolo[4,5-b]pyridin-5-yl)benzamido)acetic acid
52. 2-Fluoro-4-(3-(quinolin-6-ylmethyl)-3H-[1,2,3]triazolo[4,5-b]pyridin-5-yl)-N-(1H-1,2,4-triazol-3-yl)benzamide
53. Methyl 3-(3-(quinolin-6-ylmethyl)-3H-[1,2,3]triazolo[4,5-b]pyridin-5-yl)benzoate
54. 3-(3-(quinolin-6-ylmethyl)-3H-[1,2,3]triazolo[4,5-b]pyridin-5-yl)benzoic acid
55. N-Methyl-3-(3-(quinolin-6-ylmethyl)-3H-[1,2,3]triazolo[4,5-b]pyridin-5-yl)benzamide
56. 6-((5-(3-Fluorophenyl)-3H-[1,2,3]triazolo[4,5-b]pyridin-3-yl)methyl)quinoline
57. Methyl 3-(2-fluoro-4-(3-(quinolin-6-ylmethyl)-3H-[1,2,3]triazolo[4,5-b]pyridin-5-yl)phenyl amino)propanoate
58. 3-(2-Fluoro-4-(3-(quinolin-6-ylmethyl)-3H-[1,2,3]triazolo[4,5-b]pyridin-5-yl)phenylamino)propanoic acid
59. 2-Fluoro-N-methoxy-N-methyl-4-(3-(quinolin-6-ylmethyl)-3H-[1,2,3]triazolo[4,5-b]pyridin-5-yl)benzamide hydrochloride
60. N-tert-Butyl-2-fluoro-4-(3-(quinolin-6-ylmethyl)-3H-[1,2,3]triazolo[4,5-b]pyridin-5-yl)benzamide
61. N-Allyl-2-fluoro-4-(3-(quinolin-6-ylmethyl)-3H-[1,2,3]triazolo[4,5-b]pyridin-5-yl)benzamide
62. 2-Fluoro-N-methoxy-4-(3-(quinolin-6-ylmethyl)-3H-[1,2,3]triazolo[4,5-b]pyridin-5-yl)benzamide
63. N-(4-(3-(quinolin-6-ylmethyl)-3H-[1,2,3]triazolo[4,5-b]pyridin-5-yl)phenyl)acetamide 64. 4-(3-(quinolin-6-ylmethyl)-3H-[1,2,3]triazolo[4,5-b]pyridin-5-yl)aniline
65. 6-((5-(3,4-Dimethoxyphenyl)-3H-[1,2,3]triazolo[4,5-b]pyridin-3-yl)methyl)quinoline
66. 6-((5-(3-Fluoro-4-methoxyphenyl)-3H-[1,2,3]triazolo[4,5-b]pyridin-3-yl)methyl)quinoline.
67. 6-((5-(4-Fluorophenyl)-3H-[1,2,3]triazolo[4,5-b]pyridin-3-yl)methyl)quinoline
68. 6-((5-(2-Fluorophenyl)-3H-[1,2,3]triazolo[4,5-b]pyridin-3-yl)methyl)quinoline
69. N-(3-(3-(quinolin-6-ylmethyl)-3H-[1,2,3]triazolo[4,5-b]pyridin-5-yl)phenyl)acetamide
70. 6-((5-(3-(2,2,2-Trifluoroethoxy)phenyl)-3H-[1,2,3]triazolo[4,5-b]pyridin-3-yl)methyl)quinoline
71. 3-(3-(quinolin-6-ylmethyl)-3H-[1,2,3]triazolo[4,5-b]pyridin-5-yl)aniline
72. N-(3-(dimethylamino)propyl)-2-fluoro-4-(3-(quinolin-6-ylmethyl)-3H-[1,2,3]triazolo[4,5-b]pyridin-5-yl)benzamide
73. N-Ethyl-2-fluoro-4-(3-(quinolin-6-ylmethyl)-3H-[1,2,3]triazolo[4,5-b]pyridin-5-yl)benzamide hydrochloride
74. 2-Fluoro-4-(3-(quinolin-6-ylmethyl)-3H-[1,2,3]triazolo[4,5-b]pyridin-5-yl)benzamide hydrochloride
75. 6-((5-(3-Fluoro-4-isopropoxyphenyl)-3H-[1,2,3]triazolo[4,5-b]pyridin-3-yl)methyl)quinoline
76. N-(3-(dimethylamino)-3-oxopropyl)-2-fluoro-4-(3-(quinolin-6-ylmethyl)-3H-[1,2,3]triazolo[4,5-b]pyridin-5-yl)benzamide
77. N-(2-(dimethylamino)-2-oxoethyl)-2-fluoro-4-(3-(quinolin-6-ylmethyl)-3H-[1,2,3]triazolo[4,5-b]pyridin-5-yl)benzamide
78. 2-Fluoro-N-(2-oxo-2-(pyrrolidin-1-yl)ethyl)-4-(3-(quinolin-6-ylmethyl)-3H-[1,2,3]triazolo[4,5-b]pyridin-5-yl)benzamide
79. 6-((5-(4-(Cyclopropylmethoxy)-3-fluorophenyl)-3H-[1,2,3]triazolo[4,5-b]pyridin-3-yl)methyl)quinoline
80. 6-((5-(3-Fluoro-4-isobutoxyphenyl)-3H-[1,2,3]triazolo[4,5-b]pyridin-3-yl)methyl)quinoline
81. 3-(2-Fluoro-4-(3-(quinolin-6-ylmethyl)-3H-[1,2,3]triazolo[4,5-b]pyridin-5-yl)phenoxy)-N,N-dimethylpropan-1-amine
82. Methyl 2-fluoro-4-(3-(2-(quinolin-6-yl)propan-2-yl)-3H-[1,2,3]triazolo[4,5-b]pyridin-5-yl)benzoate
83. 2-Fluoro-4-(3-(2-(quinolin-6-yl)propan-2-yl)-3H-[1,2,3]triazolo[4,5-b]pyridin-5-yl)benzoic acid
84. 2-Fluoro-4-(3-(2-(quinolin-6-yl)propan-2-yl)-3H-[1,2,3]triazolo[4,5-b]pyridin-5-yl)benzamide
85. 6-((5-(3-Fluoro-4-(tetrahydro-2H-pyran-4-yloxy)phenyl-3H-[1,2,3]triazolo[4,5-b]pyridin-3-yl)methyl)quinoline
86. 6-((5-(3-Fluoro-4-(2-methoxyethoxy)phenyl)-3H-[1,2,3]triazolo[4,5-b]pyridin-3-yl)methyl)quinoline
87. 2-Fluoro-N-propyl-4-(3-(quinolin-6-ylmethyl)-3H-[1,2,3]triazolo[4,5-b]pyridin-5-yl)benzamide
88. 6-((5-(4-(Cyclopropylcarbamoyl)-3-fluorophenyl)-3H-[1,2,3]triazolo[4,5-b]pyridin-3-yl)methyl)quinoline 1-oxide
89. N-Cyclopropyl-2-fluoro-4-(3-(quinolin-6-ylmethyl)-3H-[1,2,3]triazolo[4,5-b]pyridin-5-yl)benzamide hydrochloride
90. N-(Cyclopropylmethyl)-2-fluoro-4-(3-(quinolin-6-ylmethyl)-3H-[1,2,3]triazolo[4,5-b]pyridin-5-yl)benzamide
91. N-Butyl-2-fluoro-4-(3-(quinolin-6-ylmethyl)-3H-[1,2,3]triazolo[4,5-b]pyridin-5-yl)benzamide
92. 2-Fluoro-N-(furan-2-ylmethyl)-4-(3-(quinolin-6-ylmethyl)-3H-[1,2,3]triazolo[4,5-b]pyridin-5-yl)benzamide
93. 2-Fluoro-4-(3-(quinolin-6-ylmethyl)-3H-[1,2,3]triazolo[4,5-b]pyridin-5-yl)-N-(2,2,2-trifluoroethyl)benzamide
94. 2-Fluoro-N-(2-methoxyethyl)-4-(3-(quinolin-6-ylmethyl)-3H-[1,2,3]triazolo[4,5-b]pyridin-5-yl)benzamide
95. N-Isopropyl-4-(3-(quinolin-6-ylmethyl)-3H-[1,2,3]triazolo[4,5-b]pyridin-5-yl)benzenesulfonamide
96. N,N-Dimethyl-3-(3-(quinolin-6-ylmethyl)-3H-[1,2,3]triazolo[4,5-b]pyridin-5-yl)aniline
97. 2-Fluoro-N-isobutyl-4-(3-(quinolin-6-ylmethyl)-3H-[1,2,3]triazolo[4,5-b]pyridin-5-yl)benzamide
98. N-Cyclopentyl-2-fluoro-4-(3-(quinolin-6-ylmethyl)-3H-[1,2,3]triazolo[4,5-b]pyridin-5-yl)benzamide
99. 2-Fluoro-N-isopropyl-4-(3-(quinolin-6-ylmethyl)-3H-[1,2,3]triazolo[4,5-b]pyridin-5-yl)benzamide
100. Methyl 2-chloro-4-(3-(quinolin-6-ylmethyl)-3H-[1,2,3]triazolo[4,5-b]pyridin-5-yl)benzoate
101. 2-Chloro-4-(3-(quinolin-6-ylmethyl)-3H-[1,2,3]triazolo[4,5-b]pyridin-5-yl)benzoic acid
102. 2-Chloro-N-propyl-4-(3-(quinolin-6-ylmethyl)-3H-[1,2,3]triazolo[4,5-b]pyridin-5-yl)benzamide
103. 2-Fluoro-N-methyl-4-(3-(quinolin-6-ylmethyl)-3H-[1,2,3]triazolo[4,5-b]pyridin-5-yl)benzamide
104. N-Cyclobutyl-2-fluoro-4-(3-(quinolin-6-ylmethyl)-3H-[1,2,3]triazolo[4,5-b]pyridin-5-yl)benzamide
105. 2-Fluoro-N-propyl-4-(3-(2-(quinolin-6-yl)propan-2-yl)-3H-[1,2,3]triazolo[4,5-b]pyridin-5-yl)benzamide
106. N-Cyclopropyl-2-fluoro-4-(3-(2-(quinolin-6-yl)propan-2-yl)-3H-[1,2,3]triazolo[4,5-b]pyridin-5-yl)benzamide
107. N-Ethyl-2-fluoro-4-(3-(2-(quinolin-6-yl)propan-2-yl)-3H-[1,2,3]triazolo[4,5-b]pyridin-5-yl)benzamide
108. 2-Chloro-4-(3-(quinolin-6-ylmethyl)-3H-[1,2,3]triazolo[4,5-b]pyridin-5-yl)benzamide
109. 2-Chloro-N-methyl-4-(3-(quinolin-6-ylmethyl)-3H-[1,2,3]triazolo[4,5-b]pyridin-5-yl)benzamide
110. 2-Fluoro-N-methoxy-4-(3-(quinolin-6-ylmethyl)-3H-[1,2,3]triazolo[4,5-b]pyridin-5-yl)benzamide hydrochloride
111. 2-Fluoro-4-(3-(quinolin-6-ylmethyl)-3H-[1,2,3]triazolo[4,5-b]pyridin-5-yl)-N-(thiazol-2-yl)benzamide
112. N-(3-Aminopropyl)-2-fluoro-4-(3-(quinolin-6-ylmethyl)-3H-[1,2,3]triazolo[4,5-b]pyridin-5-yl)benzamide
113. 2-Chloro-N-cyclopropyl-4-(3-(quinolin-6-ylmethyl)-3H-[1,2,3]triazolo[4,5-b]pyridin-5-yl)benzamide
114. 2-Fluoro-N-(3-oxo-3-(pyrrolidin-1-yl)propyl)-4-(3-(quinolin-6-ylmethyl)-3H-[1,2,3]triazolo[4,5-b]pyridin-5-yl)benzamide
115. 2-Fluoro-N-hydroxy-4-(3-(quinolin-6-ylmethyl)-3H-[1,2,3]triazolo[4,5-b]pyridin-5-yl)benzamide
116. N-Isopropyl-4-(3-(quinolin-6-ylmethyl)-3H-[1,2,3]triazolo[4,5-b]pyridin-5-yl)benzamide
117. 2-Fluoro-N-(3-oxo-3-(piperidin-1-yl)propyl)-4-(3-(quinolin-6-ylmethyl)-3H-[1,2,3]triazolo[4,5-b]pyridin-5-yl)benzamide
118. 1-Ethyl-3-(4-(3-(quinolin-6-ylmethyl)-3H-[1,2,3]triazolo[4,5-b]pyridin-5-yl)phenyl)urea
119. 2-Chloro-N-ethyl-4-(3-(quinolin-6-ylmethyl)-3H-[1,2,3]triazolo[4,5-b]pyridin-5-yl)benzamide
120. 2-Fluoro-N-(3-morpholino-3-oxopropyl)-4-(3-(quinolin-6-ylmethyl)-3H-[1,2,3]triazolo[4,5-b]pyridin-5-yl)benzamide
121. N-(3-(dimethylamino)propyl-2-fluoro-4-(3-(quinolin-6-ylmethyl)-3H-[1,2,3]triazolo[4,5-b]pyridin-5-yl)benzamide dihydrochloride
122. 2-chloro-4-(3-(quinolin-6-ylmethyl)-3H-[1,2,3]triazolo[4,5-b]pyridin-5-yl)-N-(1H-1,2,4-triazol-3-yl)benzamide 123. 2-Chloro-4-(3-(quinolin-6-ylmethyl)-3H-[1,2,3]triazolo[4,5-b]pyridin-5-yl)benzamide hydrochloride
124. 2-Fluoro-N-(3-(piperidin-1-yl)propyl)-4-(3-(quinolin-6-ylmethyl)-3H-[1,2,3]triazolo[4,5-b]pyridin-5-yl)benzamide
125. N-(3-Aminopropyl)-2-fluoro-4-(3-(quinolin-6-ylmethyl)-3H-[1,2,3]triazolo[4,5-b]pyridin-5-yl)benzamide dihydrochloride
126. 2-Chloro-N-(3-(dimethylamino)propyl)-4-(3-(quinolin-6-ylmethyl)-3H-[1,2,3]triazolo[4,5-b]pyridin-5-yl)benzamide dihydrochloride
127. 2-Fluoro-4-(3-(quinolin-6-ylmethyl)-3H-[1,2,3]triazolo[4,5-b]pyridin-5-yl)-N-(1H-1,2,4-triazol-3-yl)benzamide hydrochloride
128. Methyl 2,6-difluoro-4-(3-(quinolin-6-ylmethyl)-3H-[1,2,3]triazolo[4,5-b]pyridin-5-yl)benzoate
129. 2,6-Difluoro-4-(3-(quinolin-6-ylmethyl)-3H-[1,2,3]triazolo[4,5-b]pyridin-5-yl)benzoic acid
130. 2,6-Difluoro-4-(3-(quinolin-6-ylmethyl)-3H-[1,2,3]triazolo[4,5-b]pyridin-5-yl)benzamide
131. Methyl 2-chloro-4-(3-((7-fluoroquinolin-6-ylmethyl)-3H-[1,2,3]triazolo[4,5-b]pyridin-5-yl)benzoate
132. 2-Chloro-4-(3-((7-fluoroquinolin-6-ylmethyl)-3H-[1,2,3]triazolo[4,5-b]pyridin-5-yl)benzoic acid
133. 2-Chloro-N-ethyl-4-(3-((7-fluoroquinolin-6-ylmethyl)-3H-[1,2,3]triazolo[4,5-b]pyridin-5-yl)benzamide
134. 2-Chloro-4-(3-((7-fluoroquinolin-6-ylmethyl)-3H-[1,2,3]triazolo[4,5-b]pyridin-5-yl)benzamide
135. Methyl 2-fluoro-4-(3-((7-fluoroquinolin-6-ylmethyl)-3H-[1,2,3]triazolo[4,5-b]pyridin-5-yl)benzoate
136. 2-Fluoro-4-(3-((7-fluoroquinolin-6-ylmethyl)-3H-[1,2,3]triazolo[4,5-b]pyridin-5-yl)benzoic acid
137. 2-Fluoro-4-(3-((7-fluoroquinolin-6-ylmethyl)-3H-[1,2,3]triazolo[4,5-b]pyridin-5-yl)benzamide
138. 3-(3-(Quinolin-6-ylmethyl)-3H-[1,2,3]triazolo[4,5-b]pyridin-5-yl)benzamide
139. 2,6-Difluoro-4-(3-(quinolin-6-ylmethyl)-3H-[1,2,3]triazolo[4,5-b]pyridin-5-yl)benzamide hydrochloride
140. 2-Chloro-4-(3-((7-fluoroquinolin-6-ylmethyl)-3H-[1,2,3]triazolo[4,5-b]pyridin-5-yl)benzamide hydrochloride
141. 2-Fluoro-4-(3-((7-fluoroquinolin-6-ylmethyl)-3H-[1,2,3]triazolo[4,5-b]pyridin-5-yl)benzamide hydrochloride
142. 2-Methyl-4-(3-(quinolin-6-ylmethyl)-3H-[1,2,3]triazolo[4,5-b]pyridin-5-yl)benzamide
143. 6-((5-(1H-Pyrazol-4-yl)-3H-[1,2,3]triazolo[4,5-b]pyridin-3-yl)quinoline
144. 6-((5-(1-Methyl-1H-pyrazol-4-yl)-3H-[1,2,3]triazolo[4,5-b]pyridin-3-yl)methyl)quinoline
145. 6-((5-(1-(2-(Tetrahydro-2H-pyran-2-yloxy)ethyl)-1H-pyrazol-4-yl)-3H-[1,2,3]triazolo[4,5-b]pyridin-3-yl)methyl)quinoline
146. 2-(4-(3-(Quinolin-6-ylmethyl)-3H-[1,2,3]triazolo[4,5-b]pyridin-5-yl)-1H-pyrazol-1-yl)ethanol
147. 6-((5-(1H-Pyrazol-4-yl)-3H-[1,2,3]triazolo[4,5-b]pyridin-3-yl)methyl)quinoline
148. 6-((5-(1-Methyl-1H-pyrazol-4-yl)-3H-[1,2,3]triazolo[4,5-b]pyridin-3-yl)methyl)quinoline
149. 6-((5-(1-(2-(Tetrahydro-2H-pyran-2-yloxy)ethyl)-1H-pyrazol-4-yl)-3H-[1,2,3]triazolo[4,5-b]pyridin-3-yl)methyl)quinoline
150. 2-(4-(3-(Quinolin-6-ylmethyl)-3H-imidazo[4,5-b]pyridin-5-yl)-1H-pyrazol-1-yl)ethanol
151. 2-(3-(Quinolin-6-ylmethyl)-3H-[1,2,3]triazolo[4,5-b]pyridin-5-yl)ethanol
152. 6-((5-(1H-Imidazol-1-yl)-3H-[1,2,3]triazolo[4,5-b]pyridin-3-yl)methyl)quinoline
153. 6-((5-(1-Propyl-1H-pyrazol-4-yl)-3H-[1,2,3]triazolo[4,5-b]pyridin-3-yl)methyl)quinoline
154. Ethyl 2-(4-(3-(quinolin-6-ylmethyl)-3H-[1,2,3]triazolo[4,5-b]pyridin-5-yl)-1H-pyrazol-1-yl)acetate
155. 2-(4-(3-(Quinolin-6-ylmethyl)-3H-[1,2,3]triazolo[4,5-b]pyridin-5-yl)-1H-pyrazol-1-yl) acetic acid
156. tert-Butyl 4-(4-(3-(quinolin-6-ylmethyl)-3H-[1,2,3]triazolo[4,5-b]pyridin-5-yl)-1H-pyrazol-1-yl)piperidine-1-carboxylate
157. 6-((5-(1-Piperidin-4-yl)-1H-pyrazol-4-yl)-3H-[1,2,3]triazolo[4,5-b]pyridin-3-yl)methyl)quinoline
158. (R)-1-(3-(Quinolin-6-ylmethyl)-3H-[1,2,3]triazolo[4,5-b]pyridin-5-yl)pyrrolidin-3-ol
159. 3-(4-Fluorobenzyl)-5-(1H-pyrazol-4-yl)-3H-[1,2,3]triazolo[4,5-b]pyridin-5-yl)pyridine
160. 3-(4-Fluorobenzyl)-5-(1-(2-(tetrahydro-2H-pyran-2-yloxy)ethyl-1H-pyrazol-4-yl)-3H-[1,2,3]triazolo[4,5-b]pyridin
161. 2-(4-(3-(4-Fluorobenzyl)-3H-[1,2,3]triazolo[4,5-b]pyridin-5-yl)-1H-pyrazol-1-yl)ethanol
162. 6-(1-(5-(1H-Pyrazol-4-yl)-3H-[1,2,3]triazolo[4,5-b]pyridin-3-yl)ethyl)quinoline
163. 6-(1-(5-(1-(2-(Tetrahydro-2H-pyran-2-yloxy)ethyl)-1H-pyrazol-4-yl)-3H-[1,2,3]triazolo[4,5-b]pyridin-3-yl)ethyl)quinoline
164. 2-(4-(3-(1-(Quinolin-6-yl)ethyl-3H-[1,2,3]triazolo[4,5-b]pyridin-5-yl)-1H-pyrazol-1-yl)ethanol
165. 2-(4-(3-(2-Chloro-3,6-difluorobenzyl)-3H-[1,2,3]triazolo[4,5-b]pyridin-5-yl)-1H-pyrazol-1-yl)ethanol
166. tert-Butyl 4-(4-(3-(2-chloro-3,6-difluorobenzyl)-3H-[1,2,3]triazolo[4,5-b]pyridin-5-yl)-1H-pyrazol-1-yl)piperidine-1-carboxylate
167. 3-(2-Chloro-3,6-difluorobenzyl)-5-(1-(piperidin-4-yl)-1H-pyrazol-4-yl)-3H-[1,2,3]triazolo[4,5-b]pyridin hydrochloride
168. 6-((5-(3-Methyl-1H-indazol-6-yl)-3H-[1,2,3]triazolo[4,5-b]pyridin-5-yl)methyl)quinoline
169. 6-((5-(1H-Indol-5-yl)-3H-[1,2,3]triazolo[4,5-b]pyridin-3-yl)methyl)quinoline
170. 6-((5-(1H-Indol-6-yl)-3H-[1,2,3]triazolo[4,5-b]pyridin-3-yl)methyl)quinoline
171. 6-((5-(2-Chloropyridin-4-yl)-3H-[1,2,3]triazolo[4,5-b]pyridin-3-yl)quinoline
172. 6-((5-(3-Methyl-1H-indazol-5-yl)-3H-[1,2,3]triazolo[4,5-b]pyridin-5-yl)methyl)quinoline
173. 6-((5-(Pyridin-3-yl)-3H-[1,2,3]triazolo[4,5-b]pyridin-3-yl)methyl)quinoline
174. (S)-6-((5-(1-(Pyrrolidin-3-yl)-1H-pyrazol-4-yl)-3H-[1,2,3]triazolo[4,5-b]pyridin-3-yl)methyl)quinoline hydrochloride
175. (S)-6-((5-(1-(Pyrrolidin-3-yl)-1H-pyrazol-4-yl)-3H-[1,2,3]triazolo[4,5-b]pyridin-3-yl)methyl)quinoline hydrochloride
176. 4-(2-(4-(3-(Quinolin-6-ylmethyl)-3H-[1,2,3]triazolo[4,5-b]pyridin-5-yl)-1H-pyrazol-1-yl)ethyl)morpholine hydrochloride
177. 6-((5-(1-(Tetrahydro-2H-pyran-4-yl)-1H-pyrazol-4-yl)-3H-[1,2,3]triazolo[4,5-b]pyridin-3-yl)methyl)quinoline
178. 6-((5-(1-(2-Hydroxyethyl)-1H-pyrazol-4-yl)-3H-[1,2,3]triazolo[4,5-b]pyridin-3-yl)methyl)quinoline 1-oxide
179. 6-((5-(1,3-Dimethyl-1H-indazol-6-yl)-3H-[1,2,3]triazolo[4,5-b]pyridin-3-yl)methyl)quinoline 180. 5-(3-(Quinolin-6-ylmethyl)-3H-[1,2,3]triazolo[4,5-b]pyridin-5-yl)pyrimidin-2-amine
181. tert-Butyl 3-ethyl-6-(3-(quinolin-6-ylmethyl)-3H-[1,2,3]triazolo[4,5-b]pyridin-5-yl)-1H-indazole-1-carboxylate
182. 4-(Quinolin-6-ylmethyl)-3H-[1,2,3]triazolo[4,5-b]pyridin-5-yl)thiophene-2-carbaldehyde
183. 6-((5-(2-Methoxypyrimidin-5-yl)-3H-[1,2,3]triazolo[4,5-b]pyridin-3-yl)methyl)quinoline
184. 6-((5-(Benzo[d][1,3]dioxol-5-yl)-3H-[1,2,3]triazolo[4,5-b]pyridin-3-yl)methyl)quinoline
185. 6-((5-(2,3-Dihydrobenzofuran-5-yl)-3H-[1,2,3]triazolo[4,5-b]pyridin-3-yl)methyl)quinoline
186. 5-(3-(Quinolin-6-ylmethyl)-3H-[1,2,3]triazolo[4,5-b]pyridin-5-yl)pyridin-2-amine
187. 6-((5-(1-(2-fluoroethyl)-1H-pyrazol-4-yl)-3H-[1,2,3]triazolo[4,5-b]pyridin-3-yl)methyl)quinoline
188. (4-(3-(Quinolin-6-ylmethyl)-3H-[1,2,3]triazolo[4,5-b]pyridin-5-yl)thiophen-2-yl)methanol
189. 6-(2-(5-(1-(2-(Tetrahydro-2H-pyran-2-yloxy)ethyl)-1H-pyrazol-4-yl)-3H-[1,2,3]triazolo[4,5-b]pyridin-3-yl)propan-2-yl)quinoline
190. 2-(4-(3-(2-(Quinolin-6-yl)propan-2-yl)-3H-[1,2,3]triazolo[4,5-b]pyridin-5-yl)-1H-pyrazol-1-yl)ethanol
191. 6-((5-(3-ethyl-1H-indazol-6-yl)-3H-[1,2,3]triazolo[4,5-b]pyridin-3-yl)methyl)quinoline
192. 6-(2-(5-(1H-Pyrazol-4-yl)-3H-[1,2,3]triazolo[4,5-b]pyridin-3-yl)propan-2-yl)quinoline
193. 6-((5-(4-Methylthiophen-2-yl)-3H-[1,2,3]triazolo[4,5-b]pyridin-3-yl)methyl)quinoline
194. 6-((5-(5-Methylthiophen-2-yl)-3H-[1,2,3]triazolo[4,5-b]pyridin-3-yl)methyl)quinoline
195. 4-(5-(3-(Quinolin-6-ylmethyl)-3H-[1,2,3]triazolo[4,5-b]pyridin-5-yl)pyridin-2-yl)morpholine
196. 6-((5-(6-(Piperidin-1-yl)pyridin-3-yl)-3H-[1,2,3]triazolo[4,5-b]pyridin-3-yl)methyl)quinoline
197. 6-((5-(1-Ethyl-1H-pyrazol-4-yl)-3H-[1,2,3]triazolo[4,5-b]pyridin-3-yl)methyl)quinoline
198. 6-((5-(1-Isopropyl-1H-pyrazol-4-yl)-3H-[1,2,3]triazolo[4,5-b]pyridin-3-yl)methyl)quinoline
199. 6-((5-(1-Isobutyl-1H-pyrazol-4-yl)-3H-[1,2,3]triazolo[4,5-b]pyridin-3-yl)methyl)quinoline
200. 1-(Pyrrolidin-1-yl)-2-(4-(3-(quinolin-6-ylmethyl)-3H-[1,2,3]triazolo[4,5-b]pyridin-5-yl)-1H-pyrazol-1-yl)ethanone
201. 6-((5-(1-(2-Methoxyethyl)-1H-pyrazol-4-yl)-3H-[1,2,3]triazolo[4,5-b]pyridin-3-yl)methyl)quinoline
202. N-Phenyl-3-(quinolin-6-ylmethyl)-3H-[1,2,3]triazolo[4,5-b]pyridin-5-amine
203. 6-((5-Phenoxy-3H-[1,2,3]triazolo[4,5-b]pyridin-3-yl)methyl)quinoline
204. Methyl 2-fluoro-5-(3-(quinolin-6-ylmethyl)-3H-[1,2,3]triazolo[4,5-b]pyridin-5-yl)benzoate
205. 2-Fluoro-5-(3-(quinolin-6-ylmethyl)-3H-[1,2,3]triazolo[4,5-b]pyridin-5-yl)benzoic acid
206. 2-Fluoro-5-(3-(quinolin-6-ylmethyl)-3H-[1,2,3]triazolo[4,5-b]pyridin-5-yl)benzamide
207. 2-Chloro-4-(3-((5,7-difluoroquinolin-6-yl)methyl)-3H-[1,2,3]triazolo[4,5-b]pyridin-5-yl)benzamide
208. 1-(3-(Quinolin-6-ylmethyl)-3H-[1,2,3]triazolo[4,5-b]pyridin-5-yl)ethanone
209. 2-(1-(3-(Quinolin-6-ylmethyl)-3H-[1,2,3]triazolo[4,5-b]pyridin-5-yl)ethylidene)hydrazinecarboxamide
210. 4-(3-(Benzo[d]thiazol-6-ylmethyl)-3H-[1,2,3]triazolo[4,5-b]pyridin-5-yl)-2-chloro benzamide
211. 2-(2-Fluoro-4-(3-(quinolin-6-ylmethyl)-3H-[1,2,3]triazolo[4,5-b]pyridin-5-yl)phenyl)propan-2-ol
212. 2-Chloro-5-(3-(quinolin-6-ylmethyl)-3H-[1,2,3]triazolo[4,5-b]pyridin-5-yl)benzamide
213. 3-(2-Chloro-3,6-difluorobenzyl)-5-(1H-pyrazol-4-yl)-3H-[1,2,3]triazolo[4,5-b]pyridin
214. (±)2-Chloro-4-(3-(1-(quinolin-6-yl)ethyl)-3H-[1,2,3]triazolo[4,5-b]pyridin-5-yl)benzamide
215. 2-Chloro-4-(3-(quinolin-6-ylmethyl)-3H-[1,2,3]triazolo[4,5-b]pyridin-5-yl)benzamide
216. 1-(3-(Quinolin-6-ylmethyl)-3H-[1,2,3]triazolo[4,5-b]pyridin-5-yl)ethanone oxime
217. 1-(3-(Quinolin-6-ylmethyl)-3H-[1,2,3]triazolo[4,5-b]pyridin-5-yl)ethanoneO-methyl oxime
218. N'-(1-(3-(quinolin-6-ylmethyl)-3H-[1,2,3]triazolo[4,5-b]pyridin-5-yl)ethylidene)acetohydrazide
219. 6-((5-(4-Methylpiperazin-1-yl)-3H-[1,2,3]triazolo[4,5-b]pyridin-3-yl)methyl)quinoline
220. N'-(1-(3-(quinolin-6-ylmethyl)-3H-[1,2,3]triazolo[4,5-b]pyridin-5-yl)ethylidene)isonicotinohydrazide
221. (−)2-Chloro-4-(3-(1-(quinolin-6-ylmethyl)-3H-[1,2,3]triazolo[4,5-b]pyridin-5-yl)benzamide
222. (+)2-Chloro-4-(3-(1-(quinolin-6-ylmethyl)-3H-[1,2,3]triazolo[4,5-b]pyridin-5-yl)benzamide
223. 4-(3-(quinolin-6-ylmethyl)-3H-[1,2,3]triazolo[4,5-b]pyridin-5-yl)-2-(trifluoromethyl)benzamide
224. 6-((5-(4-carbamoyl-3-chlorophenyl)-3H-[1,2,3]triazolo[4,5-b]pyridin-3-yl)methyl)quinoline 1-oxide
225. 2-chloro-N-ethyl-4-(3-(quinolin-6-ylmethyl)-3H-[1,2,3]triazolo[4,5-b]pyridin-5-yl)benzamide hydrochloride
226. 6-((5-(4-carbamoyl-3-chlorophenyl)-3H-[1,2,3]triazolo[4,5-b]pyridin-3-yl)methyl)quinoline 1 oxide
227. 6-((5-(3-methyl-1H-pyrazol-4-yl)-3H-[1,2,3]triazolo[4,5-b]pyridin-3-yl)methyl)quinoline

| Compound | Structure |
|---|---|
| Ex 1 | 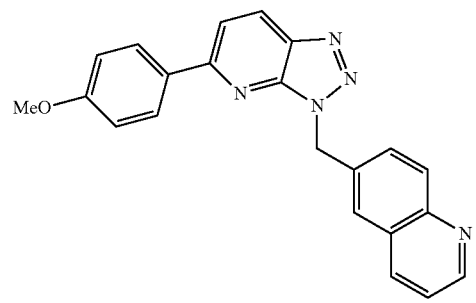 [SMILES: COc1ccc(-c2ccc3nnn(Cc4ccc5ncccc5c4)c3n2)cc1] |

-continued

| Compound | Structure |
|---|---|
| Ex 2 | 5-(3-methoxyphenyl)-3-(quinolin-6-ylmethyl)-3H-[1,2,3]triazolo[4,5-b]pyridine |
| Ex 3 | 3-[3-(quinolin-6-ylmethyl)-3H-[1,2,3]triazolo[4,5-b]pyridin-5-yl]benzaldehyde |
| Ex 4 | {3-[3-(quinolin-6-ylmethyl)-3H-[1,2,3]triazolo[4,5-b]pyridin-5-yl]phenyl}methanol |
| Ex 5 | 4-[3-(quinolin-6-ylmethyl)-3H-[1,2,3]triazolo[4,5-b]pyridin-5-yl]benzaldehyde |
| Ex 6 | {4-[3-(quinolin-6-ylmethyl)-3H-[1,2,3]triazolo[4,5-b]pyridin-5-yl]phenyl}methanol |

-continued
| Compound | Structure |
|---|---|
| Ex 7 | 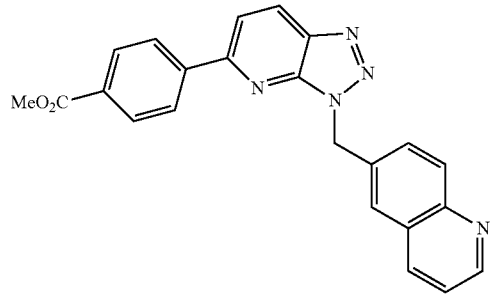 [SMILES: COC(=O)c1ccc(-c2ccc3nnn(Cc4ccc5ncccc5c4)c3n2)cc1] |
| Ex 8 | 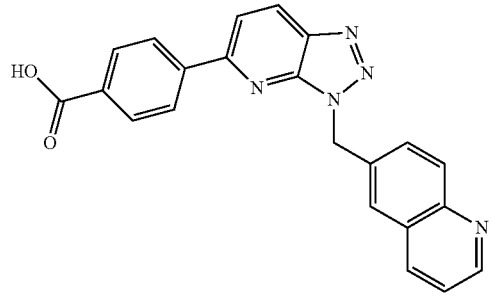 [SMILES: O=C(O)c1ccc(-c2ccc3nnn(Cc4ccc5ncccc5c4)c3n2)cc1] |
| Ex 9 | 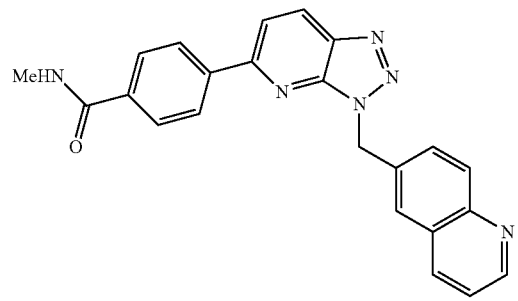 [SMILES: CNC(=O)c1ccc(-c2ccc3nnn(Cc4ccc5ncccc5c4)c3n2)cc1] |
| Ex 10 | 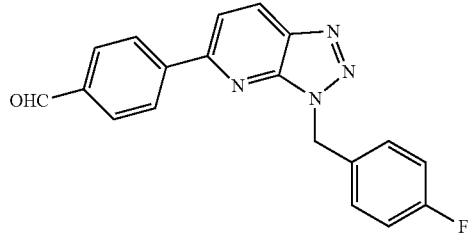 [SMILES: O=Cc1ccc(-c2ccc3nnn(Cc4ccc(F)cc4)c3n2)cc1] |
| Ex 11 | 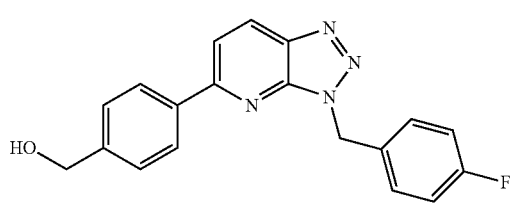 [SMILES: OCc1ccc(-c2ccc3nnn(Cc4ccc(F)cc4)c3n2)cc1] |

-continued

| Compound | Structure |
|---|---|
| Ex 12 | 4-(methyl ester, fluoro-phenyl)-triazolopyridine-CH2-quinoline |
| Ex 13 | 4-(carboxylic acid, fluoro-phenyl)-triazolopyridine-CH2-quinoline |
| Ex 14 | 4-(N-methylamide, fluoro-phenyl)-triazolopyridine-CH2-quinoline |
| Ex 15 | 4-(amide, fluoro-phenyl)-triazolopyridine-CH2-quinoline |
| Ex 16 | 4-(hydroxymethyl, fluoro-phenyl)-triazolopyridine-CH2-quinoline |

| Compound | Structure |
|---|---|
| Ex 17 | 5-(4-(methoxycarbonyl)-3-fluorophenyl)-3-(2-chloro-6-fluoro-3-fluorobenzyl)-3H-[1,2,3]triazolo[4,5-b]pyridine |
| Ex 18 | 5-(4-carboxy-3-fluorophenyl)-3-(2-chloro-6-fluoro-3-fluorobenzyl)-3H-[1,2,3]triazolo[4,5-b]pyridine |
| Ex 19 | 5-(4-(methylcarbamoyl)-3-fluorophenyl)-3-(2-chloro-6-fluoro-3-fluorobenzyl)-3H-[1,2,3]triazolo[4,5-b]pyridine |
| Ex 20 | 5-(4-((2-hydroxyethyl)carbamoyl)phenyl)-3-(quinolin-6-ylmethyl)-3H-[1,2,3]triazolo[4,5-b]pyridine |
| Ex 21 | 5-(4-carbamoylphenyl)-3-(quinolin-6-ylmethyl)-3H-[1,2,3]triazolo[4,5-b]pyridine |
| Ex 22 | lithium 4-(3-(quinolin-6-ylmethyl)-3H-[1,2,3]triazolo[4,5-b]pyridin-5-yl)benzoate |

| Compound | Structure |
|---|---|
| Ex 23 | 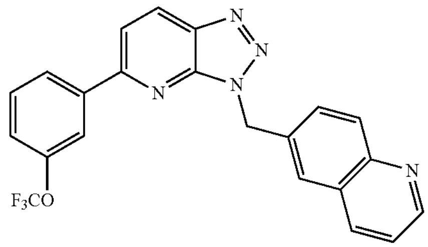 [SMILES: FC(F)(F)Oc1cccc(-c2ccc3nnn(Cc4ccc5ncccc5c4)c3n2)c1] |
| Ex 24 | 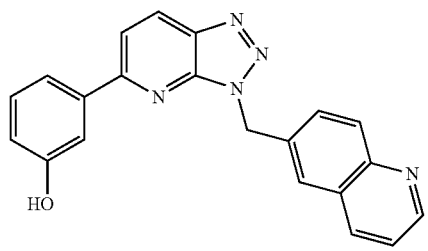 [SMILES: Oc1cccc(-c2ccc3nnn(Cc4ccc5ncccc5c4)c3n2)c1] |
| Ex 25 | 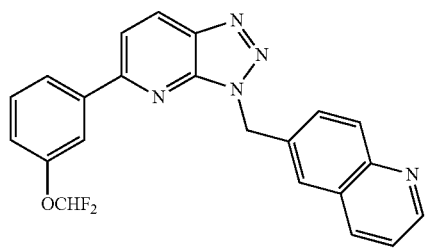 [SMILES: FC(F)Oc1cccc(-c2ccc3nnn(Cc4ccc5ncccc5c4)c3n2)c1] |
| Ex 26 | 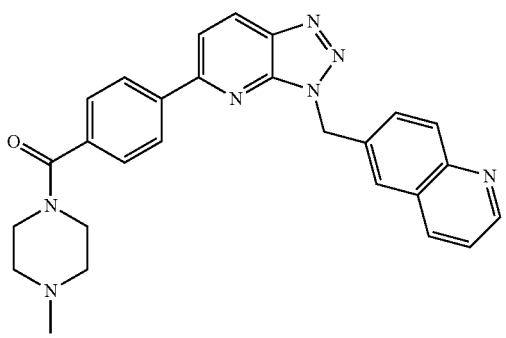 [SMILES: CN1CCN(C(=O)c2ccc(-c3ccc4nnn(Cc5ccc6ncccc6c5)c4n3)cc2)CC1] |
| Ex 27 | 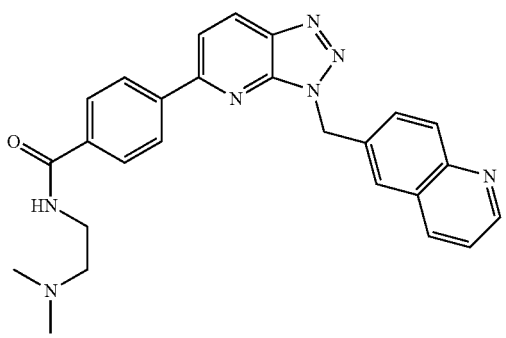 [SMILES: CN(C)CCNC(=O)c1ccc(-c2ccc3nnn(Cc4ccc5ncccc5c4)c3n2)cc1] |

-continued
| Compound | Structure |
|---|---|
| Ex 28 | 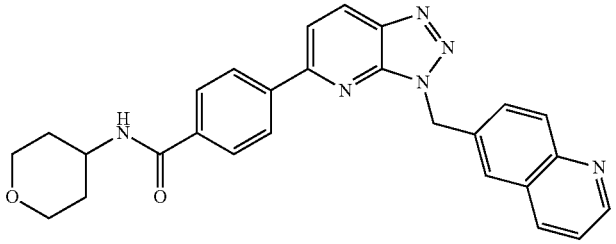 [SMILES: O=C(NC1CCOCC1)c1ccc(-c2ccc3nnn(Cc4ccc5ncccc5c4)c3n2)cc1] |
| Ex 29 | 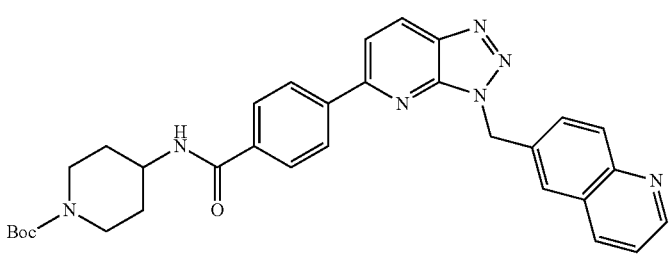 [SMILES: CC(C)(C)OC(=O)N1CCC(NC(=O)c2ccc(-c3ccc4nnn(Cc5ccc6ncccc6c5)c4n3)cc2)CC1] |
| Ex 30 | 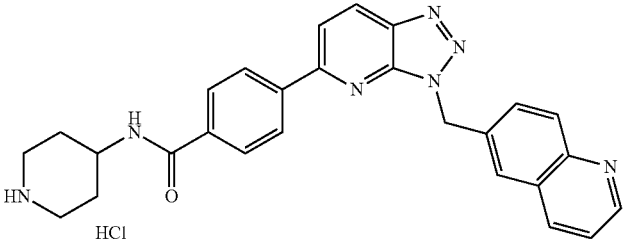 [SMILES: O=C(NC1CCNCC1)c1ccc(-c2ccc3nnn(Cc4ccc5ncccc5c4)c3n2)cc1 ; Cl] |
| Ex 31 | 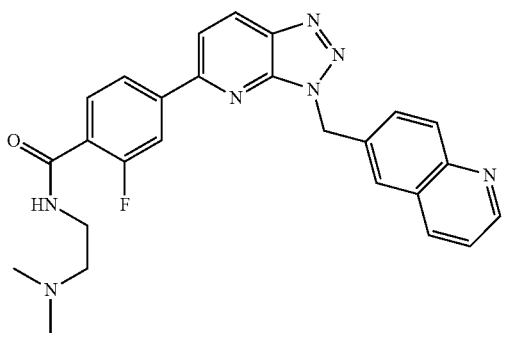 [SMILES: CN(C)CCNC(=O)c1ccc(-c2ccc3nnn(Cc4ccc5ncccc5c4)c3n2)cc1F] |
| Ex 32 | 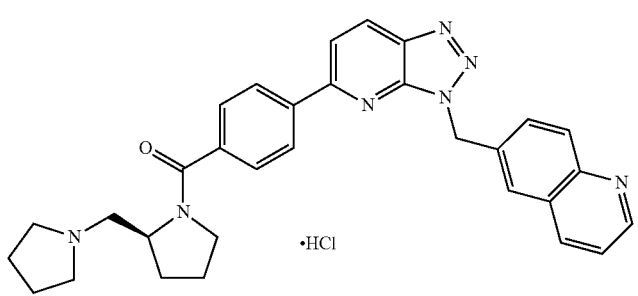 [SMILES: O=C(c1ccc(-c2ccc3nnn(Cc4ccc5ncccc5c4)c3n2)cc1)N1CCC[C@H]1CN1CCCC1 ; Cl] |

| Compound | Structure |
|---|---|
| Ex 33 | 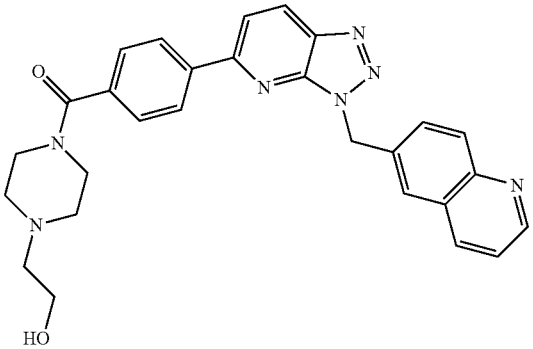 [SMILES: O=C(c1ccc(-c2ccc3nnn(Cc4ccc5ncccc5c4)c3n2)cc1)N1CCN(CCO)CC1] |
| Ex 34 | 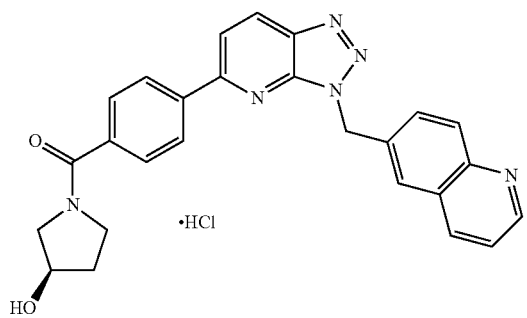 [SMILES: O=C(c1ccc(-c2ccc3nnn(Cc4ccc5ncccc5c4)c3n2)cc1)N1CC[C@@H](O)C1 ; Cl] •HCl |
| Ex 35 | 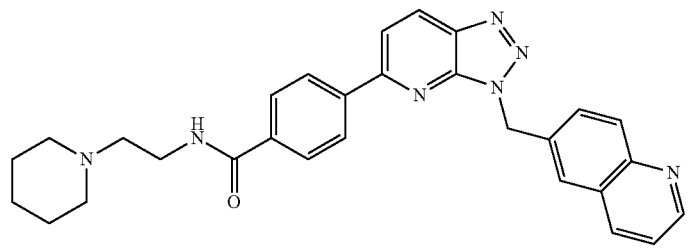 [SMILES: O=C(NCCN1CCCCC1)c1ccc(-c2ccc3nnn(Cc4ccc5ncccc5c4)c3n2)cc1] |
| Ex 36 | 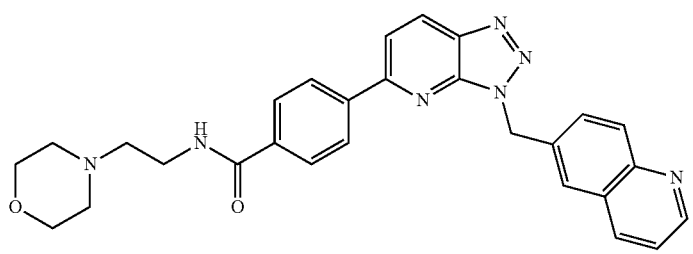 [SMILES: O=C(NCCN1CCOCC1)c1ccc(-c2ccc3nnn(Cc4ccc5ncccc5c4)c3n2)cc1] |
| Ex 37 | 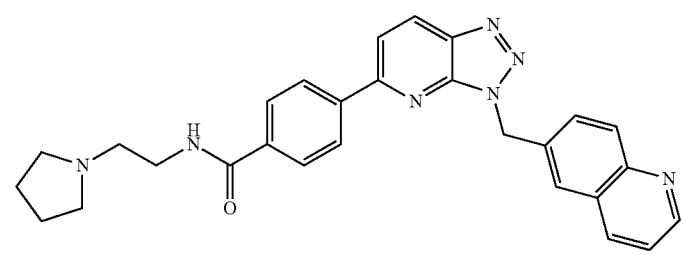 [SMILES: O=C(NCCN1CCCC1)c1ccc(-c2ccc3nnn(Cc4ccc5ncccc5c4)c3n2)cc1] |

| Compound | Structure |
|---|---|
| Ex 38 | 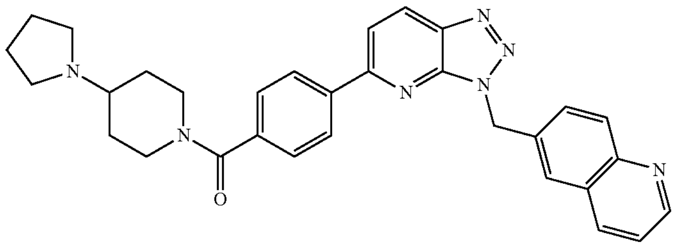 [SMILES: O=C(c1ccc(-c2ccc3nnn(Cc4ccc5ncccc5c4)c3n2)cc1)N1CCC(N2CCCC2)CC1] |
| Ex 39 | 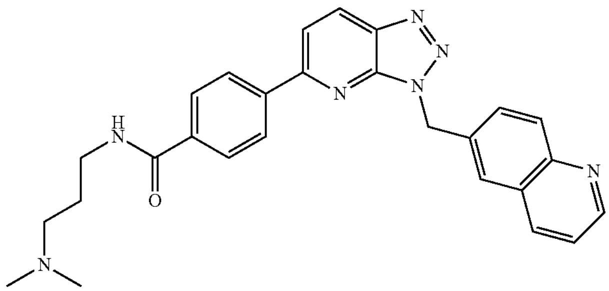 [SMILES: CN(C)CCCNC(=O)c1ccc(-c2ccc3nnn(Cc4ccc5ncccc5c4)c3n2)cc1] |
| Ex 40 | ·HCl |
| Ex 41 | ·HCl |
| Ex 42 | 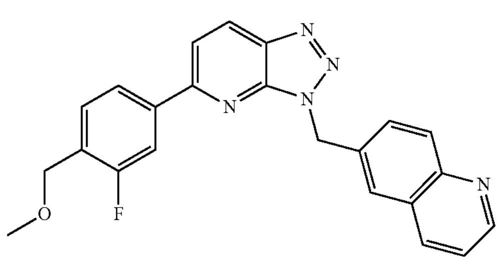 [SMILES: COCc1ccc(-c2ccc3nnn(Cc4ccc5ncccc5c4)c3n2)cc1F] |

-continued

| Compound | Structure |
|---|---|
| Ex 43 | 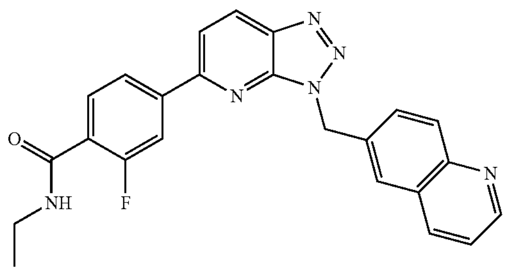 [SMILES: CCNC(=O)c1ccc(-c2ccc3nnn(Cc4ccc5ncccc5c4)c3n2)cc1F] |
| Ex 44 | 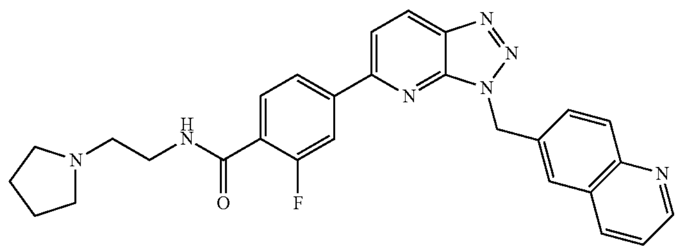 [SMILES: O=C(NCCN1CCCC1)c1ccc(-c2ccc3nnn(Cc4ccc5ncccc5c4)c3n2)cc1F] |
| Ex 45 | 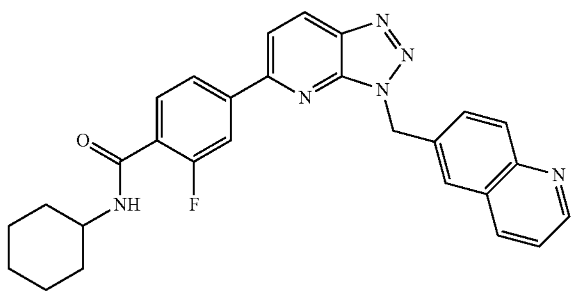 [SMILES: O=C(NC1CCCCC1)c1ccc(-c2ccc3nnn(Cc4ccc5ncccc5c4)c3n2)cc1F] |
| Ex 46 | 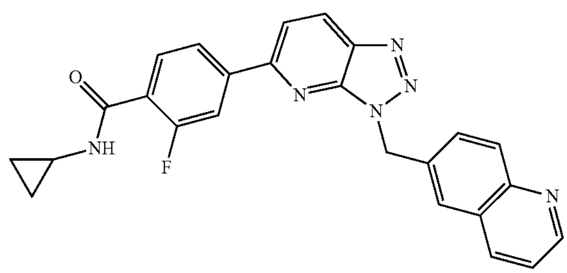 [SMILES: O=C(NC1CC1)c1ccc(-c2ccc3nnn(Cc4ccc5ncccc5c4)c3n2)cc1F] |
| Ex 47 | 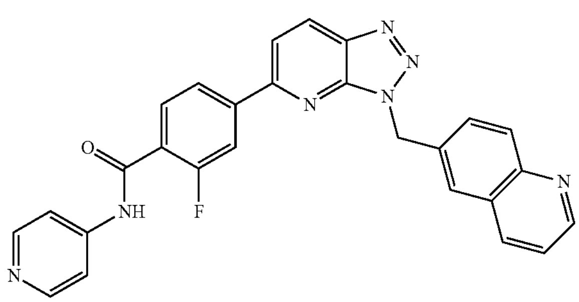 [SMILES: O=C(Nc1ccncc1)c1ccc(-c2ccc3nnn(Cc4ccc5ncccc5c4)c3n2)cc1F] |

-continued

| Compound | Structure |
|---|---|
| Ex 48 | *(structure: N-benzyl 2-fluoro-4-[3-(quinolin-6-ylmethyl)-3H-[1,2,3]triazolo[4,5-b]pyridin-5-yl]benzamide)* |
| Ex 49 | *(structure: N,N-dimethyl 2-fluoro-4-[3-(quinolin-6-ylmethyl)-3H-[1,2,3]triazolo[4,5-b]pyridin-5-yl]benzamide)* |
| Ex 50 | *(structure: methyl 2-({2-fluoro-4-[3-(quinolin-6-ylmethyl)-3H-[1,2,3]triazolo[4,5-b]pyridin-5-yl]benzoyl}amino)acetate)* |
| Ex 51 | *(structure: 2-({2-fluoro-4-[3-(quinolin-6-ylmethyl)-3H-[1,2,3]triazolo[4,5-b]pyridin-5-yl]benzoyl}amino)acetic acid)* |
| Ex 52 | *(structure: 2-fluoro-N-(1H-1,2,4-triazol-3-yl)-4-[3-(quinolin-6-ylmethyl)-3H-[1,2,3]triazolo[4,5-b]pyridin-5-yl]benzamide)* |

-continued

| Compound | Structure |
|---|---|
| Ex 53 | 5-(3-(methoxycarbonyl)phenyl)-3-(quinolin-6-ylmethyl)-3H-[1,2,3]triazolo[4,5-b]pyridine |
| Ex 54 | 3-(3-(quinolin-6-ylmethyl)-3H-[1,2,3]triazolo[4,5-b]pyridin-5-yl)benzoic acid |
| Ex 55 | N-methyl-3-(3-(quinolin-6-ylmethyl)-3H-[1,2,3]triazolo[4,5-b]pyridin-5-yl)benzamide |
| Ex 56 | 5-(3-fluorophenyl)-3-(quinolin-6-ylmethyl)-3H-[1,2,3]triazolo[4,5-b]pyridine |
| Ex 57 | methyl 3-((2-fluoro-4-(3-(quinolin-6-ylmethyl)-3H-[1,2,3]triazolo[4,5-b]pyridin-5-yl)phenyl)amino)propanoate |

-continued
| Compound | Structure |
|---|---|
| Ex 58 | 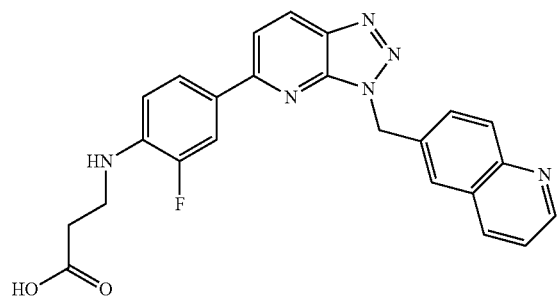 [SMILES: O=C(O)CCNc1ccc(-c2ccc3nnn(Cc4ccc5ncccc5c4)c3n2)cc1F] |
| Ex 59 | 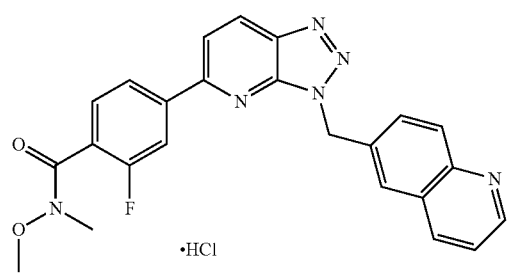 [SMILES: CON(C)C(=O)c1ccc(-c2ccc3nnn(Cc4ccc5ncccc5c4)c3n2)cc1F ; Cl] •HCl |
| Ex 60 | 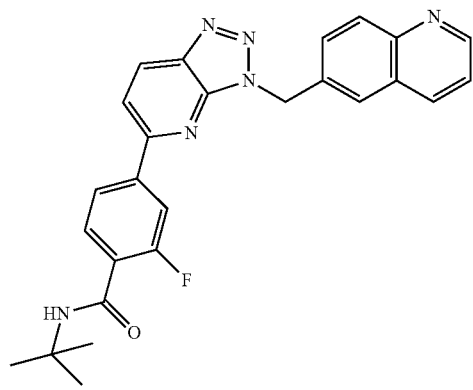 [SMILES: CC(C)(C)NC(=O)c1ccc(-c2ccc3nnn(Cc4ccc5ncccc5c4)c3n2)cc1F] |
| Ex 61 | 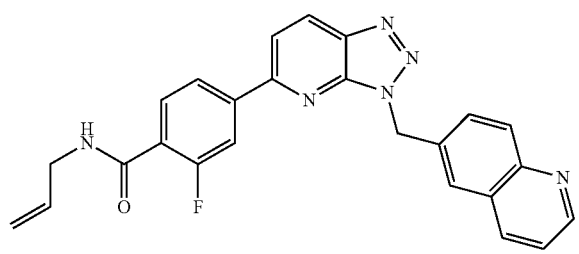 [SMILES: C=CCNC(=O)c1ccc(-c2ccc3nnn(Cc4ccc5ncccc5c4)c3n2)cc1F] |
| Ex 62 | 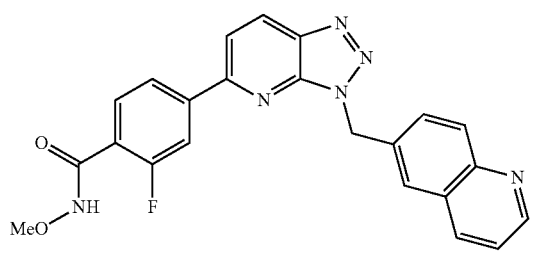 [SMILES: CONC(=O)c1ccc(-c2ccc3nnn(Cc4ccc5ncccc5c4)c3n2)cc1F] |

-continued
| Compound | Structure |
|---|---|
| Ex 63 | 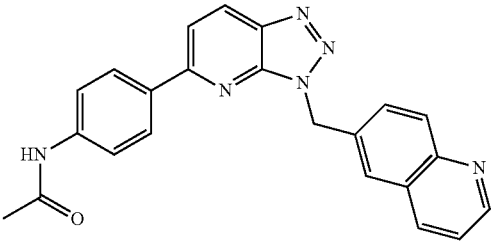 [SMILES: CC(=O)Nc1ccc(-c2ccc3nnn(Cc4ccc5ncccc5c4)c3n2)cc1] |
| Ex 64 | 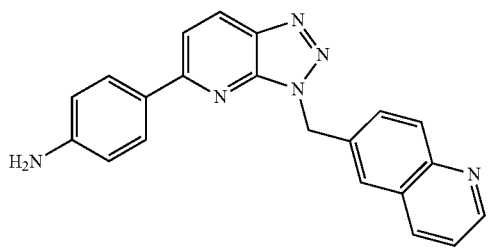 |
| Ex 65 | 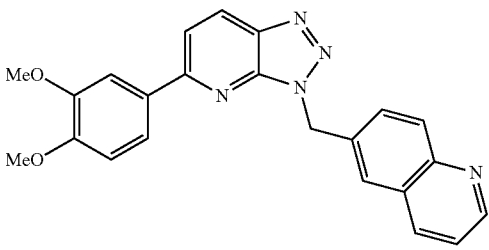 [SMILES: COc1ccc(-c2ccc3nnn(Cc4ccc5ncccc5c4)c3n2)cc1OC] |
| Ex 66 | 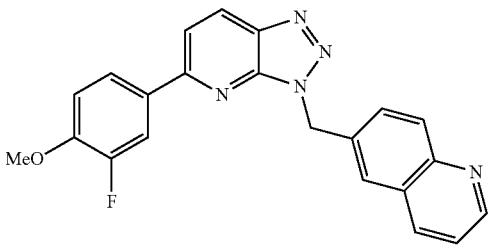 [SMILES: COc1ccc(-c2ccc3nnn(Cc4ccc5ncccc5c4)c3n2)cc1F] |
| Ex 67 | 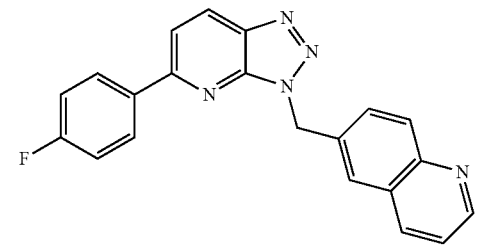 [SMILES: Fc1ccc(-c2ccc3nnn(Cc4ccc5ncccc5c4)c3n2)cc1] |
| Ex 68 | 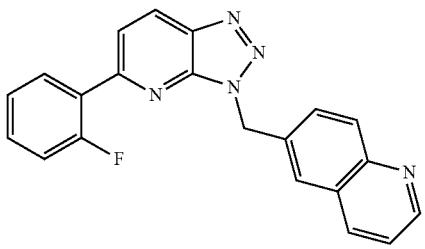 [SMILES: Fc1ccccc1-c1ccc2nnn(Cc3ccc4ncccc4c3)c2n1] |

-continued

| Compound | Structure |
|---|---|
| Ex 69 | 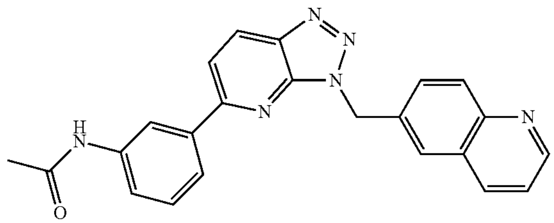 [SMILES: CC(=O)Nc1cccc(-c2ccc3nnn(Cc4ccc5ncccc5c4)c3n2)c1] |
| Ex 70 | 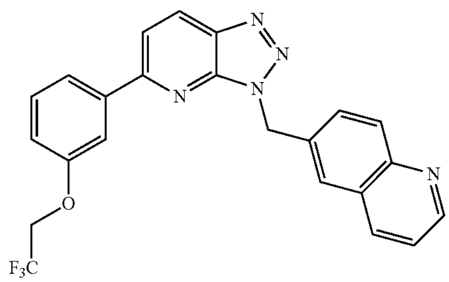 [SMILES: FC(F)(F)COc1cccc(-c2ccc3nnn(Cc4ccc5ncccc5c4)c3n2)c1] |
| Ex 71 | 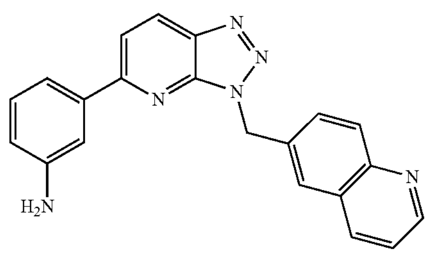 |
| Ex 72 | 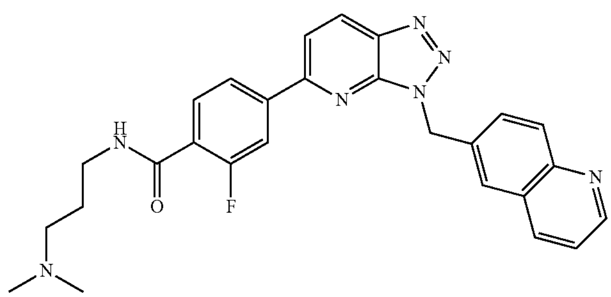 [SMILES: CN(C)CCCNC(=O)c1ccc(-c2ccc3nnn(Cc4ccc5ncccc5c4)c3n2)cc1F] |
| Ex 73 | 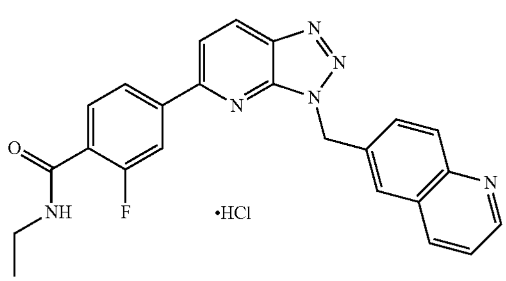 [SMILES: CCNC(=O)c1ccc(-c2ccc3nnn(Cc4ccc5ncccc5c4)c3n2)cc1F ; Cl] |
| Ex 74 | 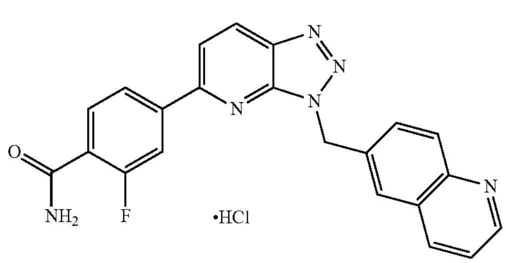 [SMILES: NC(=O)c1ccc(-c2ccc3nnn(Cc4ccc5ncccc5c4)c3n2)cc1F ; Cl] |

-continued

| Compound | Structure |
|---|---|
| Ex 75 | 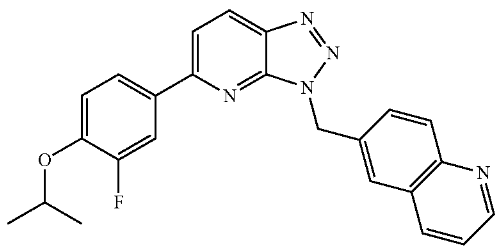 [SMILES: CC(C)Oc1ccc(-c2ccc3nnn(Cc4ccc5ncccc5c4)c3n2)cc1F] |
| Ex 76 | 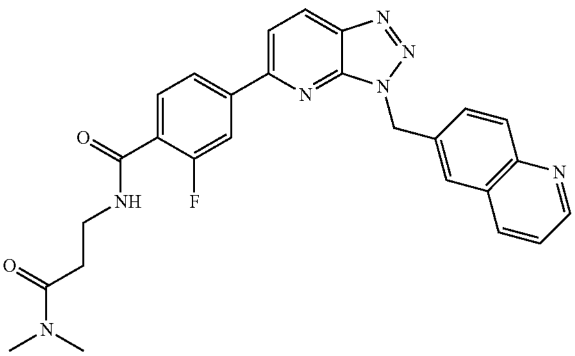 [SMILES: CN(C)C(=O)CCNC(=O)c1ccc(-c2ccc3nnn(Cc4ccc5ncccc5c4)c3n2)cc1F] |
| Ex 77 | 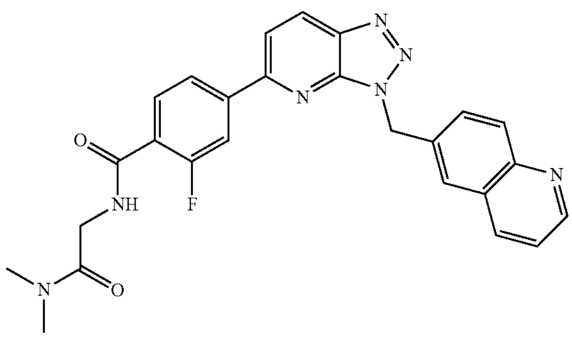 [SMILES: CN(C)C(=O)CNC(=O)c1ccc(-c2ccc3nnn(Cc4ccc5ncccc5c4)c3n2)cc1F] |
| Ex 78 | 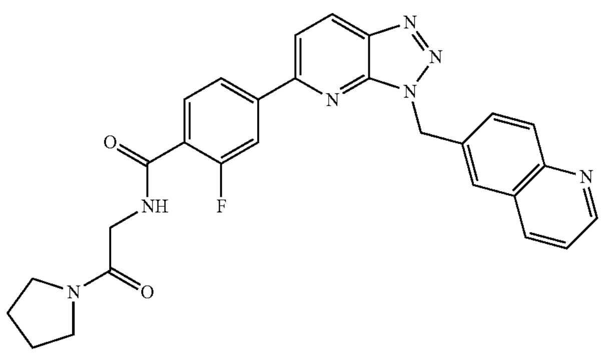 [SMILES: O=C(NCC(=O)N1CCCC1)c1ccc(-c2ccc3nnn(Cc4ccc5ncccc5c4)c3n2)cc1F] |
| Ex 79 | 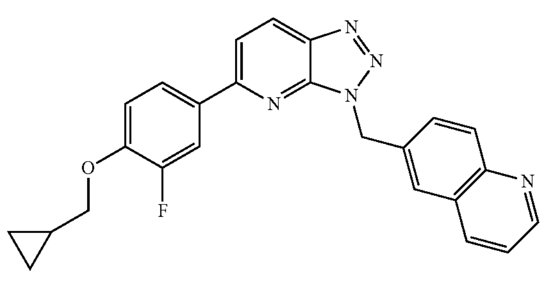 [SMILES: Fc1cc(-c2ccc3nnn(Cc4ccc5ncccc5c4)c3n2)ccc1OCC1CC1] |

-continued

| Compound | Structure |
|---|---|
| Ex 80 | 5-[3-fluoro-4-isobutoxyphenyl]-3-(quinolin-6-ylmethyl)-3H-[1,2,3]triazolo[4,5-b]pyridine |
| Ex 81 | 5-{3-fluoro-4-[3-(dimethylamino)propoxy]phenyl}-3-(quinolin-6-ylmethyl)-3H-[1,2,3]triazolo[4,5-b]pyridine |
| Ex 82 | methyl 2-fluoro-4-{3-[2-(quinolin-6-yl)propan-2-yl]-3H-[1,2,3]triazolo[4,5-b]pyridin-5-yl}benzoate |
| Ex 83 | 2-fluoro-4-{3-[2-(quinolin-6-yl)propan-2-yl]-3H-[1,2,3]triazolo[4,5-b]pyridin-5-yl}benzoic acid |
| Ex 84 | 2-fluoro-4-{3-[2-(quinolin-6-yl)propan-2-yl]-3H-[1,2,3]triazolo[4,5-b]pyridin-5-yl}benzamide |

| Compound | Structure |
|---|---|
| Ex 85 | 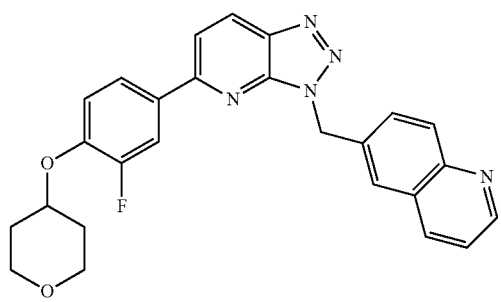 [SMILES: Fc1cc(-c2ccc3nnn(Cc4ccc5ncccc5c4)c3n2)ccc1OC1CCOCC1] |
| Ex 86 | 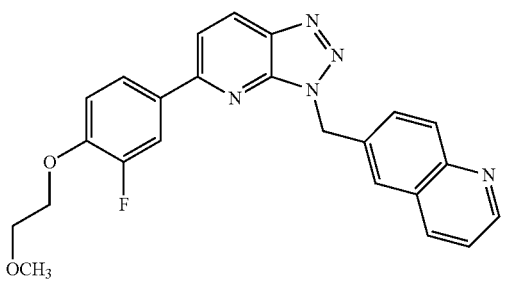 [SMILES: COCCOc1ccc(-c2ccc3nnn(Cc4ccc5ncccc5c4)c3n2)cc1F] |
| Ex 87 | 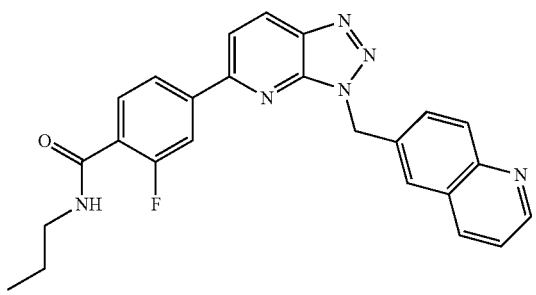 [SMILES: CCCNC(=O)c1ccc(-c2ccc3nnn(Cc4ccc5ncccc5c4)c3n2)cc1F] |
| Ex 88 | 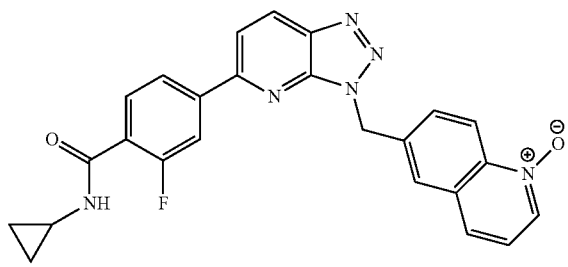 [SMILES: O=C(NC1CC1)c1ccc(-c2ccc3nnn(Cc4ccc5c(ccc[n+]5[O-])c4)c3n2)cc1F] |
| Ex 89 | 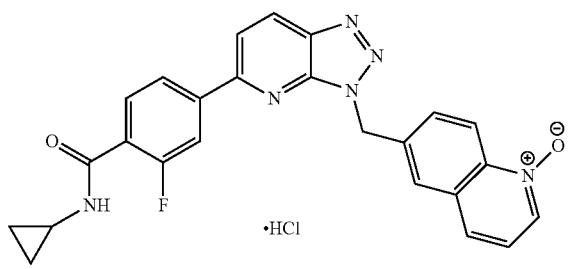 [SMILES: O=C(NC1CC1)c1ccc(-c2ccc3nnn(Cc4ccc5c(ccc[n+]5[O-])c4)c3n2)cc1F ; Cl] |

-continued
| Compound | Structure |
|---|---|
| Ex 90 | 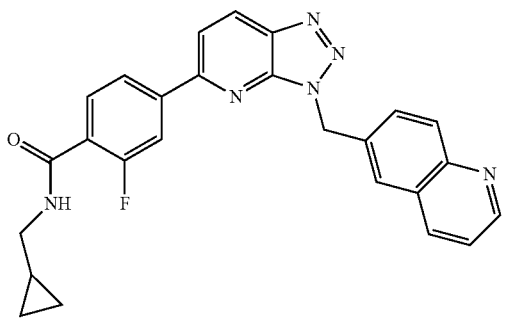 [SMILES: O=C(NCC1CC1)c1ccc(-c2ccc3nnn(Cc4ccc5ncccc5c4)c3n2)cc1F] |
| Ex 91 | 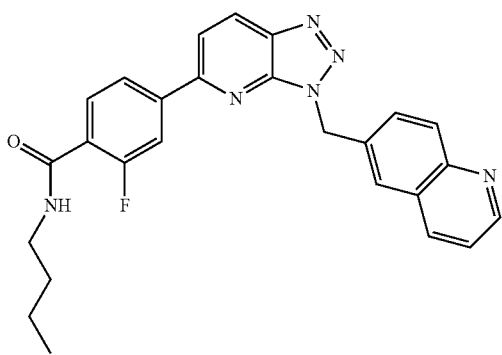 [SMILES: CCCCNC(=O)c1ccc(-c2ccc3nnn(Cc4ccc5ncccc5c4)c3n2)cc1F] |
| Ex 92 | 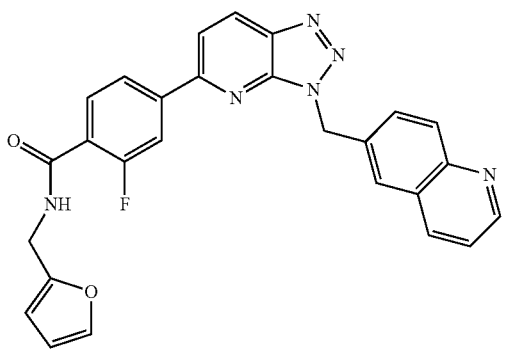 [SMILES: O=C(NCc1ccco1)c1ccc(-c2ccc3nnn(Cc4ccc5ncccc5c4)c3n2)cc1F] |
| Ex 93 | 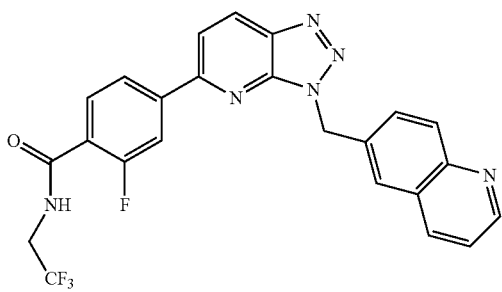 [SMILES: O=C(NCC(F)(F)F)c1ccc(-c2ccc3nnn(Cc4ccc5ncccc5c4)c3n2)cc1F] |

-continued
| Compound | Structure |
|---|---|
| Ex 94 | 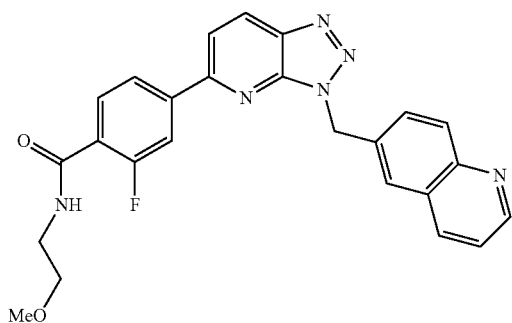 [SMILES: COCCNC(=O)c1ccc(-c2ccc3nnn(Cc4ccc5ncccc5c4)c3n2)cc1F] |
| Ex 95 | 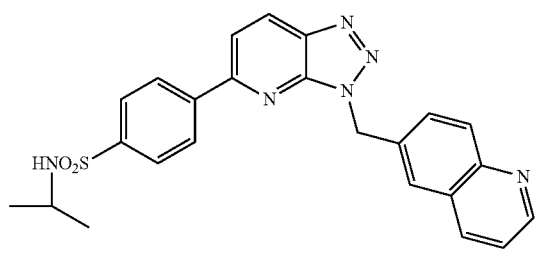 |
| Ex 96 | 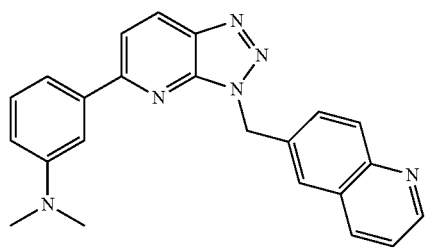 [SMILES: CN(C)c1cccc(-c2ccc3nnn(Cc4ccc5ncccc5c4)c3n2)c1] |
| Ex 97 | 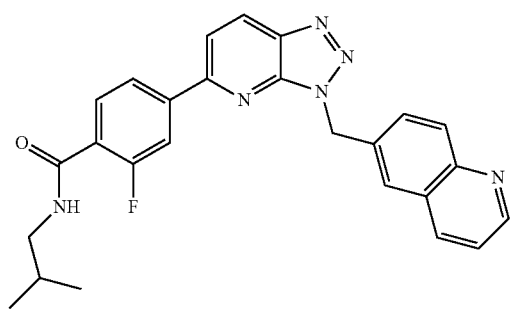 [SMILES: CC(C)CNC(=O)c1ccc(-c2ccc3nnn(Cc4ccc5ncccc5c4)c3n2)cc1F] |
| Ex 98 | 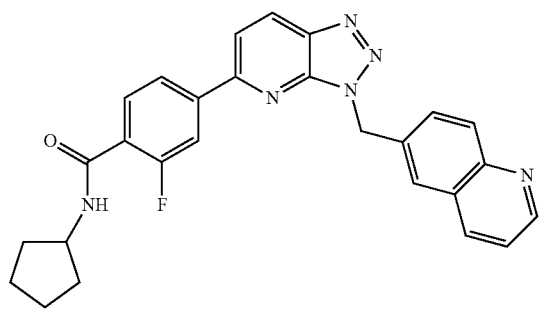 [SMILES: O=C(NC1CCCC1)c1ccc(-c2ccc3nnn(Cc4ccc5ncccc5c4)c3n2)cc1F] |

-continued

| Compound | Structure |
|---|---|
| Ex 99 | 4-[3-(quinolin-6-ylmethyl)-3H-[1,2,3]triazolo[4,5-b]pyridin-5-yl]-2-fluoro-N-isopropylbenzamide |
| Ex 100 | methyl 4-[3-(quinolin-6-ylmethyl)-3H-[1,2,3]triazolo[4,5-b]pyridin-5-yl]-2-chlorobenzoate |
| Ex 101 | 4-[3-(quinolin-6-ylmethyl)-3H-[1,2,3]triazolo[4,5-b]pyridin-5-yl]-2-chlorobenzoic acid |
| Ex 102 | 4-[3-(quinolin-6-ylmethyl)-3H-[1,2,3]triazolo[4,5-b]pyridin-5-yl]-2-chloro-N-propylbenzamide |
| Ex 103 | 4-{3-[1-(quinolin-6-yl)-1-methylethyl]-3H-[1,2,3]triazolo[4,5-b]pyridin-5-yl}-2-fluoro-N-methylbenzamide |
| Ex 104 | 4-[3-(quinolin-6-ylmethyl)-3H-[1,2,3]triazolo[4,5-b]pyridin-5-yl]-2-fluoro-N-cyclobutylbenzamide |

| Compound | Structure |
|---|---|
| Ex 105 | (4-(1-(2-(quinolin-6-yl)propan-2-yl)-1H-[1,2,3]triazolo[4,5-b]pyridin-5-yl)-2-fluoro-N-propylbenzamide) |
| Ex 106 | (4-(1-(2-(quinolin-6-yl)propan-2-yl)-1H-[1,2,3]triazolo[4,5-b]pyridin-5-yl)-N-cyclopropyl-2-fluorobenzamide) |
| Ex 107 | (4-(1-(2-(quinolin-6-yl)propan-2-yl)-1H-[1,2,3]triazolo[4,5-b]pyridin-5-yl)-N-ethyl-2-fluorobenzamide) |
| Ex 108 | (4-(1-(quinolin-6-ylmethyl)-1H-[1,2,3]triazolo[4,5-b]pyridin-5-yl)-2-chlorobenzamide) |
| Ex 109 | (4-(1-(quinolin-6-ylmethyl)-1H-[1,2,3]triazolo[4,5-b]pyridin-5-yl)-2-chloro-N-methylbenzamide) |

-continued

| Compound | Structure |
|---|---|
| Ex 110 | (2-fluoro-4-(3-(quinolin-6-ylmethyl)-3H-[1,2,3]triazolo[4,5-b]pyridin-5-yl)-N-methoxybenzamide·HCl) |
| Ex 111 | (2-fluoro-4-(3-(quinolin-6-ylmethyl)-3H-[1,2,3]triazolo[4,5-b]pyridin-5-yl)-N-(thiazol-2-yl)benzamide) |
| Ex 112 | (N-(3-aminopropyl)-2-fluoro-4-(3-(quinolin-6-ylmethyl)-3H-[1,2,3]triazolo[4,5-b]pyridin-5-yl)benzamide) |
| Ex 113 | (2-chloro-N-cyclopropyl-4-(3-(quinolin-6-ylmethyl)-3H-[1,2,3]triazolo[4,5-b]pyridin-5-yl)benzamide) |
| Ex 114 | (2-fluoro-N-(3-oxo-3-(pyrrolidin-1-yl)propyl)-4-(3-(quinolin-6-ylmethyl)-3H-[1,2,3]triazolo[4,5-b]pyridin-5-yl)benzamide) |

-continued
| Compound | Structure |
|---|---|
| Ex 115 | 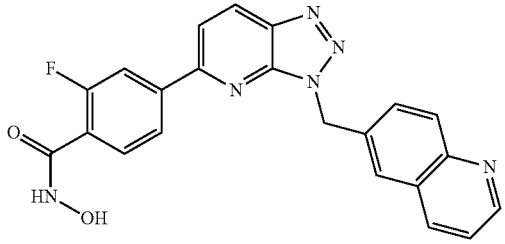 [SMILES: O=C(NO)c1ccc(-c2ccc3nnn(Cc4ccc5ncccc5c4)c3n2)cc1F] |
| Ex 116 | 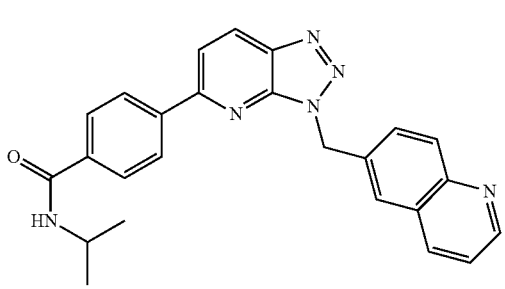 [SMILES: CC(C)NC(=O)c1ccc(-c2ccc3nnn(Cc4ccc5ncccc5c4)c3n2)cc1] |
| Ex 117 | 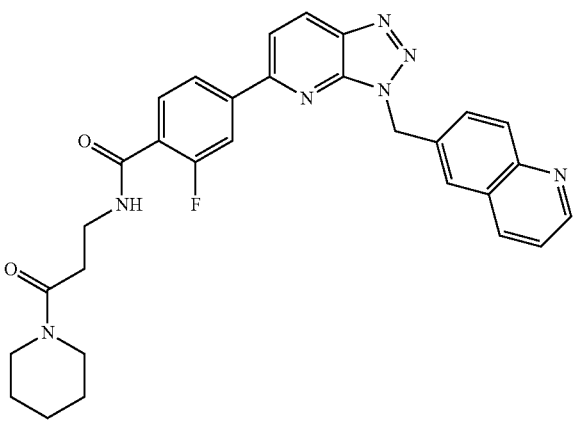 [SMILES: O=C(NCCC(=O)N1CCCCC1)c1ccc(-c2ccc3nnn(Cc4ccc5ncccc5c4)c3n2)cc1F] |
| Ex 118 | 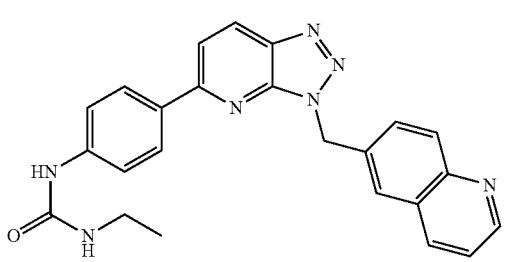 [SMILES: CCNC(=O)Nc1ccc(-c2ccc3nnn(Cc4ccc5ncccc5c4)c3n2)cc1] |
| Ex 119 | 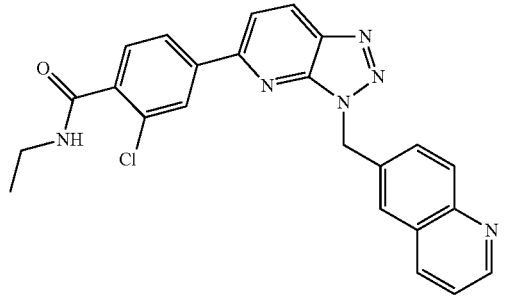 [SMILES: CCNC(=O)c1ccc(-c2ccc3nnn(Cc4ccc5ncccc5c4)c3n2)cc1Cl] |

-continued

| Compound | Structure |
|---|---|
| Ex 120 | (chemical structure: 4-[triazolopyridinyl-quinolinylmethyl]-2-fluoro-N-[3-oxo-3-morpholinopropyl]benzamide) |
| Ex 121 | (chemical structure: N-[3-(dimethylamino)propyl]-2-fluoro-4-[triazolopyridinyl-quinolinylmethyl]benzamide, 2HCl) |
| Ex 122 | (chemical structure: 2-chloro-4-[triazolopyridinyl-quinolinylmethyl]-N-(1H-1,2,4-triazol-3-yl)benzamide) |
| Ex 123 | (chemical structure: 2-chloro-4-[triazolopyridinyl-quinolinylmethyl]benzamide, HCl) |

-continued
| Compound | Structure |
|---|---|
| Ex 124 | 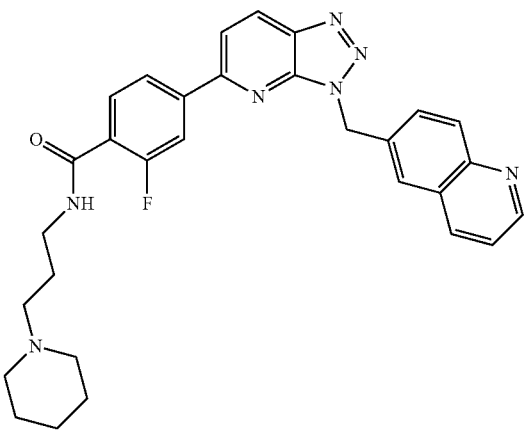 [SMILES: O=C(NCCCN1CCCCC1)c1ccc(-c2ccc3nnn(Cc4ccc5ncccc5c4)c3n2)cc1F] |
| Ex 125 | 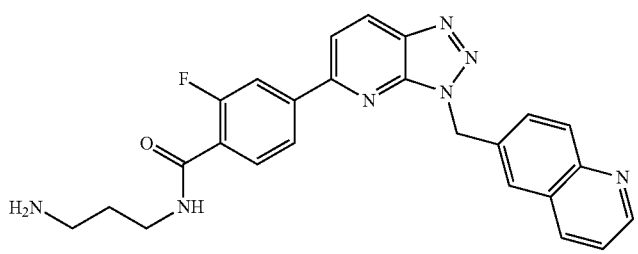 •2HCl |
| Ex 126 | 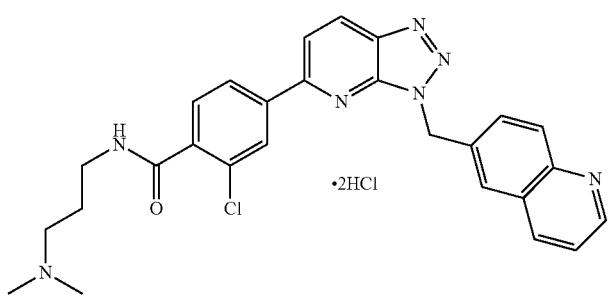 [SMILES: CN(C)CCCNC(=O)c1ccc(-c2ccc3nnn(Cc4ccc5ncccc5c4)c3n2)cc1Cl] •2HCl |
| Ex 127 | 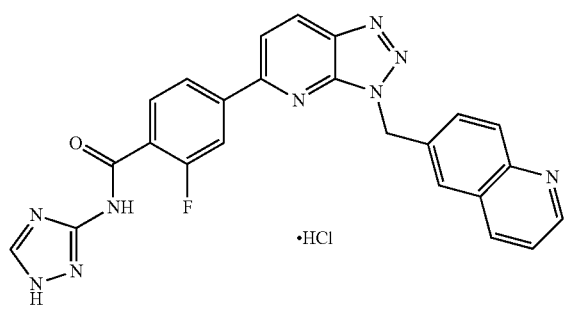 [SMILES: O=C(Nc1nc[nH]n1)c1ccc(-c2ccc3nnn(Cc4ccc5ncccc5c4)c3n2)cc1F ; Cl] •HCl |
| Ex 128 | 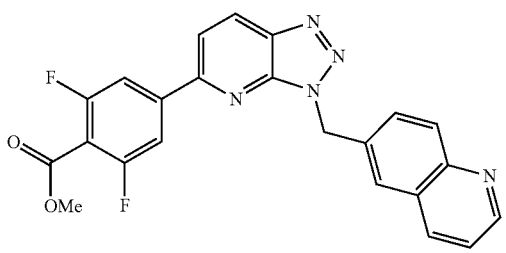 [SMILES: COC(=O)c1c(F)cc(-c2ccc3nnn(Cc4ccc5ncccc5c4)c3n2)cc1F] |

-continued

| Compound | Structure |
|---|---|
| Ex 129 | 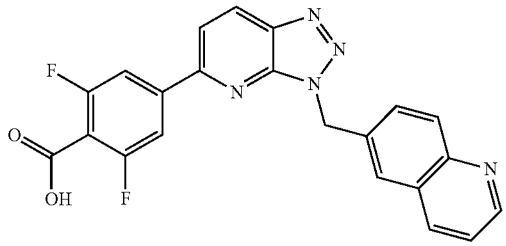 [SMILES: O=C(O)c1c(F)cc(-c2ccc3nnn(Cc4ccc5ncccc5c4)c3n2)cc1F] |
| Ex 130 | 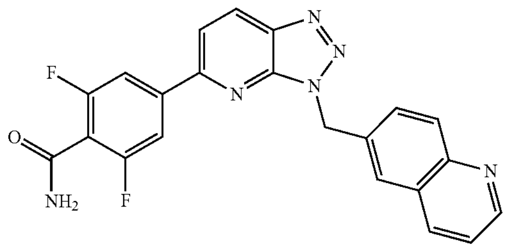 [SMILES: NC(=O)c1c(F)cc(-c2ccc3nnn(Cc4ccc5ncccc5c4)c3n2)cc1F] |
| Ex 131 | 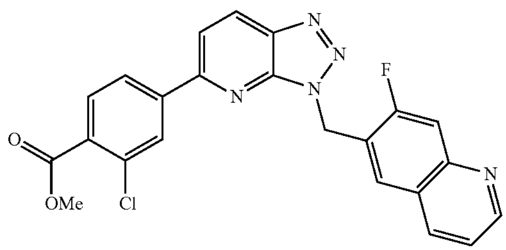 |
| Ex 132 | 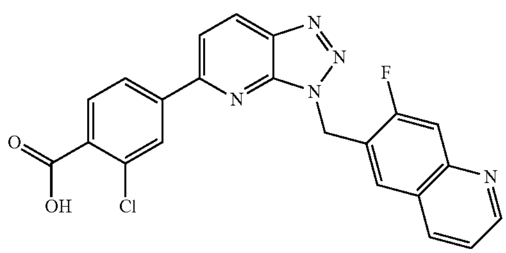 [SMILES: O=C(O)c1ccc(-c2ccc3nnn(Cc4cc5cccnc5cc4F)c3n2)cc1Cl] |
| Ex 133 | 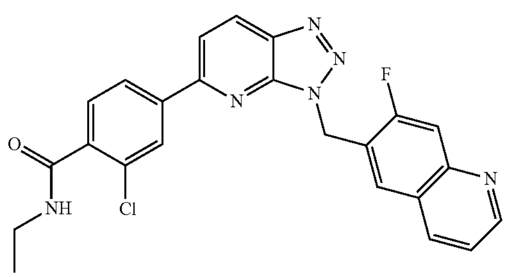 [SMILES: CCNC(=O)c1ccc(-c2ccc3nnn(Cc4cc5cccnc5cc4F)c3n2)cc1Cl] |
| Ex 134 | 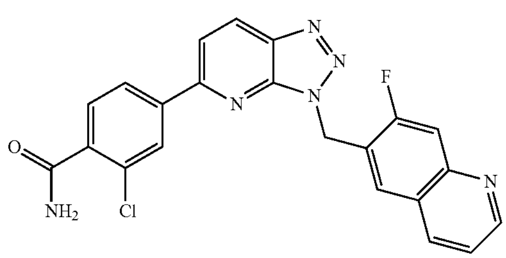 [SMILES: NC(=O)c1ccc(-c2ccc3nnn(Cc4cc5cccnc5cc4F)c3n2)cc1Cl] |

| Compound | Structure |
|---|---|
| Ex 135 | 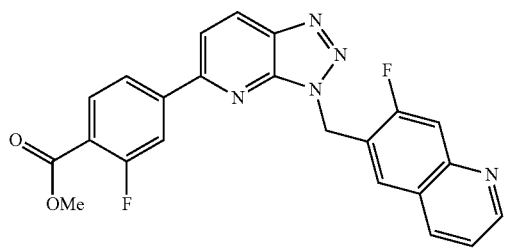 [SMILES: COC(=O)c1ccc(-c2ccc3nnn(Cc4cc5cccnc5cc4F)c3n2)cc1F] |
| Ex 136 | 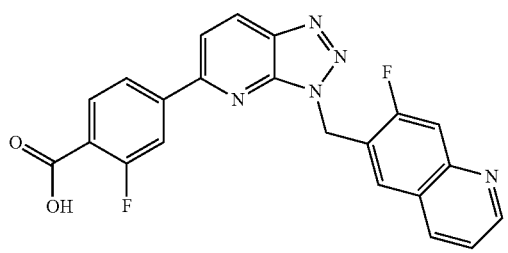 [SMILES: O=C(O)c1ccc(-c2ccc3nnn(Cc4cc5cccnc5cc4F)c3n2)cc1F] |
| Ex 137 | 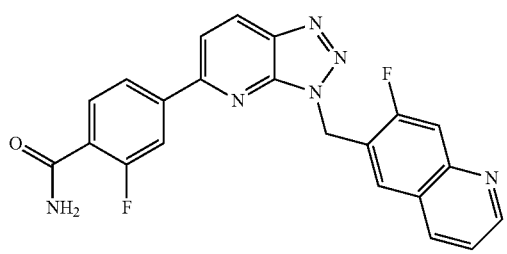 [SMILES: NC(=O)c1ccc(-c2ccc3nnn(Cc4cc5cccnc5cc4F)c3n2)cc1F] |
| Ex 138 | 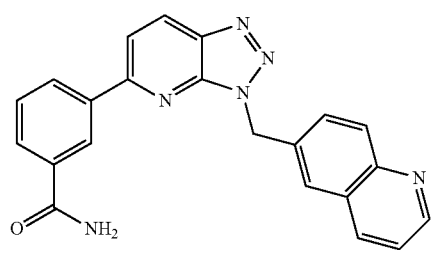 [SMILES: NC(=O)c1cccc(-c2ccc3nnn(Cc4ccc5ncccc5c4)c3n2)c1] |
| Ex 139 | 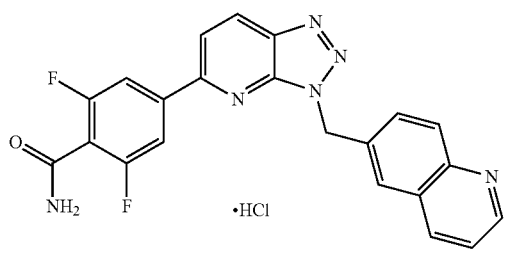 [SMILES: NC(=O)c1c(F)cc(-c2ccc3nnn(Cc4ccc5ncccc5c4)c3n2)cc1F ; Cl] |
| Ex 140 | 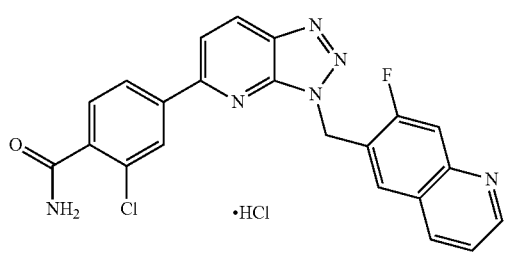 [SMILES: NC(=O)c1ccc(-c2ccc3nnn(Cc4cc5cccnc5cc4F)c3n2)cc1Cl ; Cl] |

| Compound | Structure |
|---|---|
| Ex 141 | 4-(3-((3-fluoroquinolin-6-yl)methyl)-3H-[1,2,3]triazolo[4,5-b]pyridin-5-yl)-2-fluorobenzamide hydrochloride |
| Ex 142 | 4-(3-(quinolin-6-ylmethyl)-3H-[1,2,3]triazolo[4,5-b]pyridin-5-yl)-2-methylbenzamide |
| Ex 143 | 5-(1H-pyrazol-4-yl)-3-(quinolin-6-ylmethyl)-3H-[1,2,3]triazolo[4,5-b]pyridine |
| Ex 144 | 5-(1-methyl-1H-pyrazol-4-yl)-3-(quinolin-6-ylmethyl)-3H-[1,2,3]triazolo[4,5-b]pyridine |
| Ex 145 | THPO-ethyl-pyrazolyl triazolopyridine quinoline derivative |
| Ex 146 | 2-(4-(3-(quinolin-6-ylmethyl)-3H-[1,2,3]triazolo[4,5-b]pyridin-5-yl)-1H-pyrazol-1-yl)ethanol |
| Ex 147 | 6-(1H-pyrazol-4-yl)-3-(quinolin-6-ylmethyl)-3H-[1,2,3]triazolo[4,5-b]pyridine isomer |

-continued
| Compound | Structure |
|---|---|
| Ex 148 | 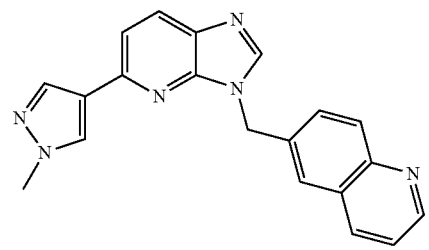 [SMILES: Cn1cc(-c2ccc3ncn(Cc4ccc5ncccc5c4)c3n2)cn1] |
| Ex 149 | 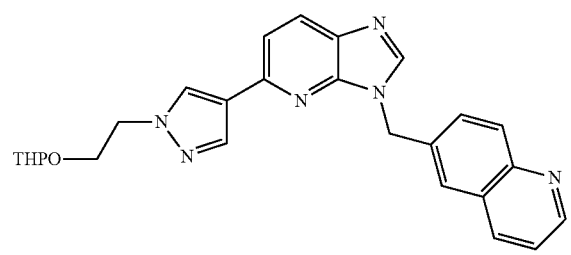 |
| Ex 150 | 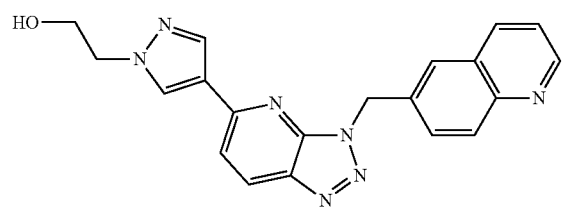 [SMILES: OCCn1cc(-c2ccc3nnn(Cc4ccc5ncccc5c4)c3n2)cn1] |
| Ex 151 | 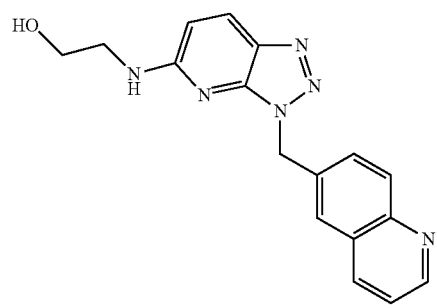 [SMILES: OCCNc1ccc2nnn(Cc3ccc4ncccc4c3)c2n1] |
| Ex 152 | 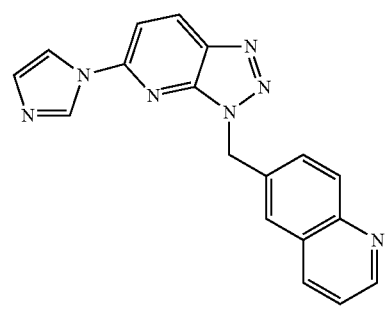 [SMILES: c1cnc2ccc(Cn3nnc4ccc(-n5ccnc5)nc43)cc2c1] |

-continued

| Compound | Structure |
|---|---|
| Ex 153 | 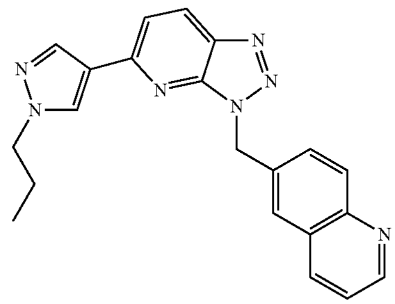 [SMILES: CCCn1cc(-c2ccc3nnn(Cc4ccc5ncccc5c4)c3n2)cn1] |
| Ex 154 | 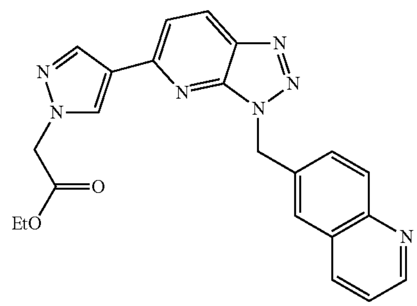 [SMILES: CCOC(=O)Cn1cc(-c2ccc3nnn(Cc4ccc5ncccc5c4)c3n2)cn1] |
| Ex 155 | 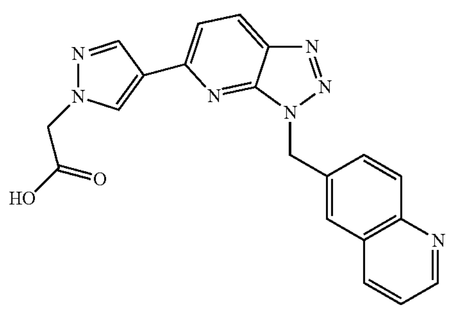 [SMILES: O=C(O)Cn1cc(-c2ccc3nnn(Cc4ccc5ncccc5c4)c3n2)cn1] |
| Ex 156 | 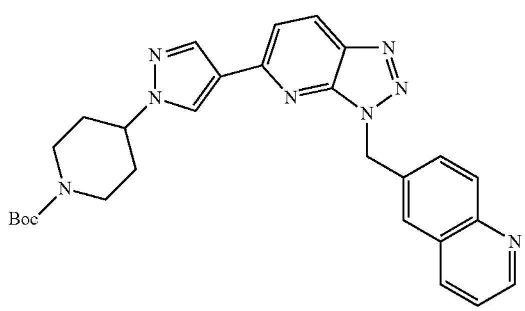 [SMILES: CC(C)(C)OC(=O)N1CCC(n2cc(-c3ccc4nnn(Cc5ccc6ncccc6c5)c4n3)cn2)CC1] |
| Ex 157 | 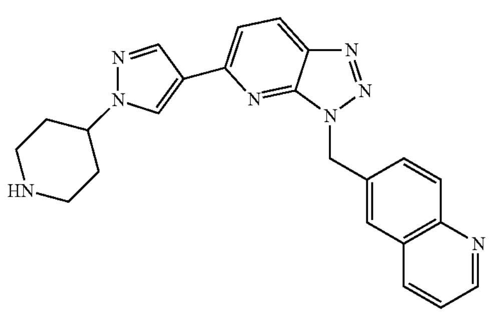 [SMILES: c1cnc2ccc(Cn3nnc4ccc(-c5cnn(C6CCNCC6)c5)nc43)cc2c1] |

-continued

| Compound | Structure |
|---|---|
| Ex 158 | 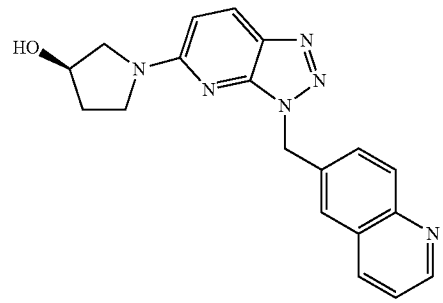 [SMILES: O[C@@H]1CCN(c2ccc3nnn(Cc4ccc5ncccc5c4)c3n2)C1] |
| Ex 159 | 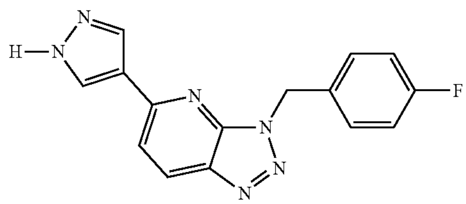 [SMILES: Fc1ccc(Cn2nnc3ccc(-c4cn[nH]c4)nc32)cc1] |
| Ex 160 | 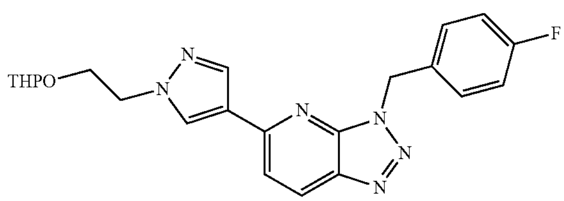 |
| Ex 161 | 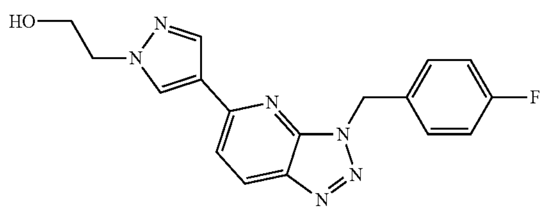 [SMILES: OCCn1cc(-c2ccc3nnn(Cc4ccc(F)cc4)c3n2)cn1] |
| Ex 162 | 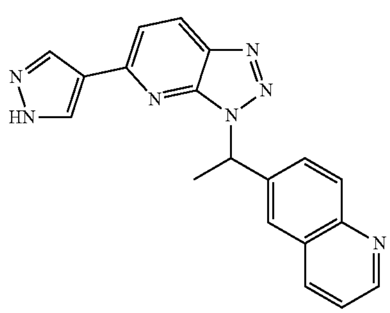 [SMILES: CC(c1ccc2ncccc2c1)n1nnc2ccc(-c3cn[nH]c3)nc21] |
| Ex 163 | 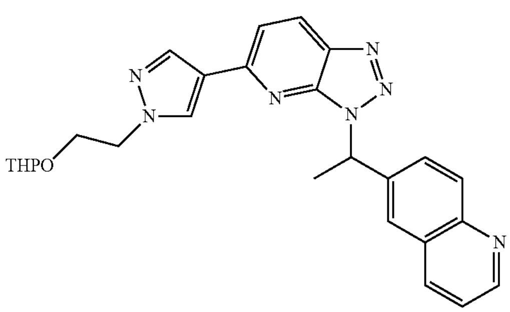 |

-continued
| Compound | Structure |
|---|---|
| Ex 164 | 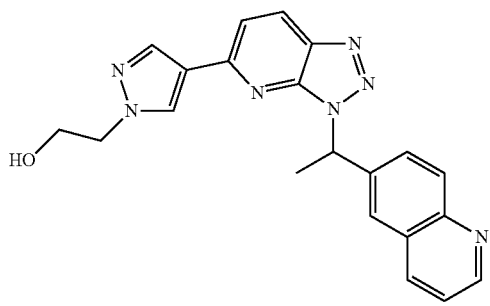 [SMILES: CC(c1ccc2ncccc2c1)n1nnc2ccc(-c3cnn(CCO)c3)nc21] |
| Ex 165 | 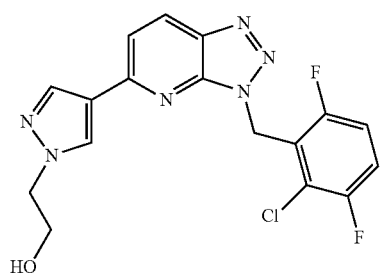 [SMILES: OCCn1cc(-c2ccc3nnn(Cc4c(F)ccc(F)c4Cl)c3n2)cn1] |
| Ex 166 | 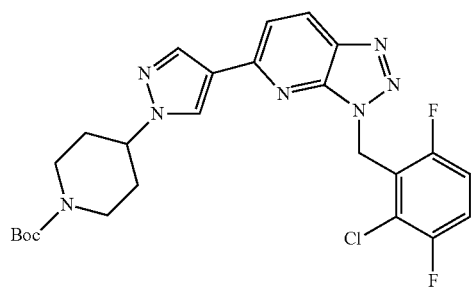 [SMILES: CC(C)(C)OC(=O)N1CCC(n2cc(-c3ccc4nnn(Cc5c(F)ccc(F)c5Cl)c4n3)cn2)CC1] |
| Ex 167 | 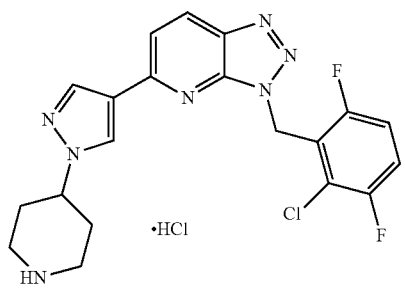 [SMILES: Fc1ccc(F)c(Cn2nnc3ccc(-c4cnn(C5CCNCC5)c4)nc32)c1Cl ; Cl] |
| Ex 168 | 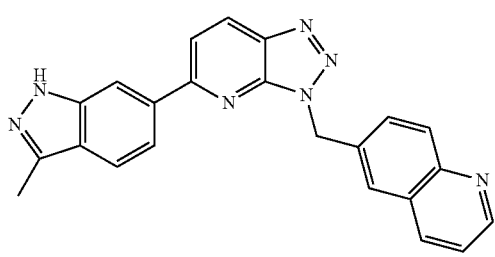 [SMILES: Cc1n[nH]c2cc(-c3ccc4nnn(Cc5ccc6ncccc6c5)c4n3)ccc12] |

-continued
| Compound | Structure |
|---|---|
| Ex 169 | 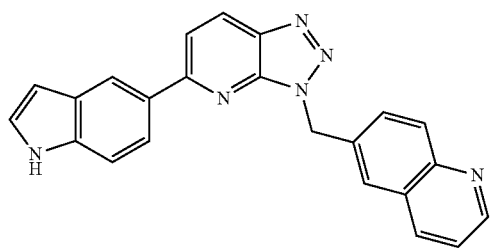 [SMILES: c1cnc2ccc(Cn3nnc4ccc(-c5ccc6[nH]ccc6c5)nc43)cc2c1] |
| Ex 170 | 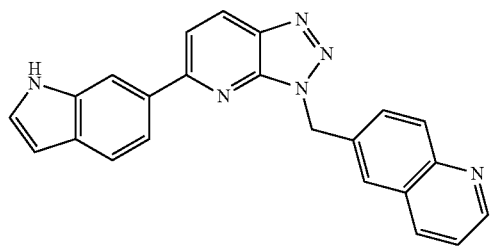 [SMILES: c1cnc2ccc(Cn3nnc4ccc(-c5ccc6cc[nH]c6c5)nc43)cc2c1] |
| Ex 171 | 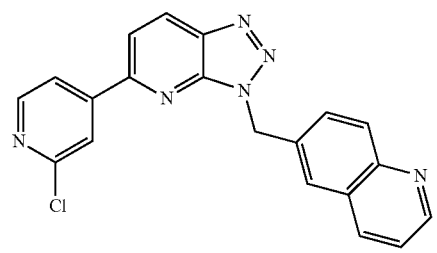 [SMILES: Clc1cc(-c2ccc3nnn(Cc4ccc5ncccc5c4)c3n2)ccn1] |
| Ex 172 | 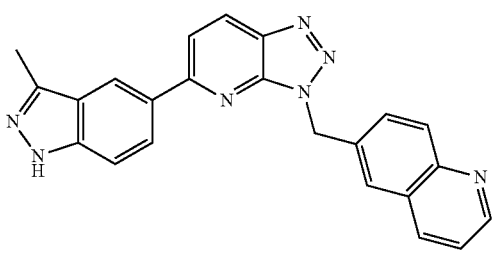 [SMILES: Cc1n[nH]c2ccc(-c3ccc4nnn(Cc5ccc6ncccc6c5)c4n3)cc12] |
| Ex 173 | 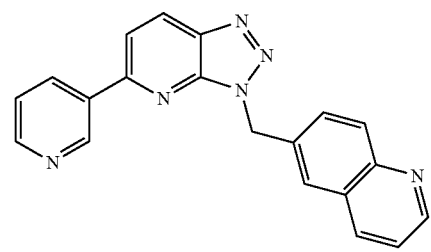 [SMILES: c1cncc(-c2ccc3nnn(Cc4ccc5ncccc5c4)c3n2)c1] |
| Ex 174 | 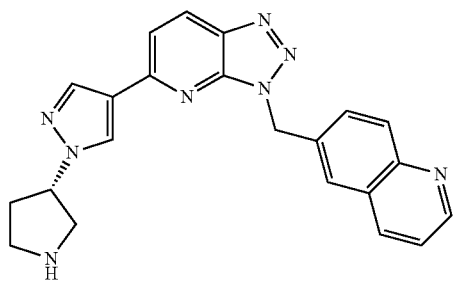 [SMILES: c1cnc2ccc(Cn3nnc4ccc(-c5cnn([C@H]6CCNC6)c5)nc43)cc2c1] |

-continued
| Compound | Structure |
|---|---|
| Ex 175 | 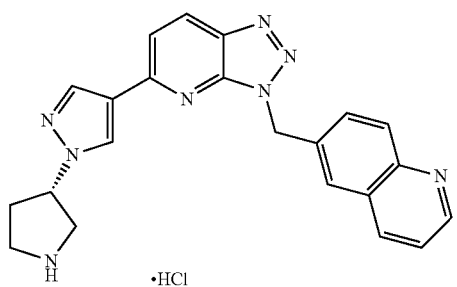 [SMILES: c1cnc2ccc(Cn3nnc4ccc(-c5cnn([C@H]6CCNC6)c5)nc43)cc2c1 ; Cl] ·HCl |
| Ex 176 | 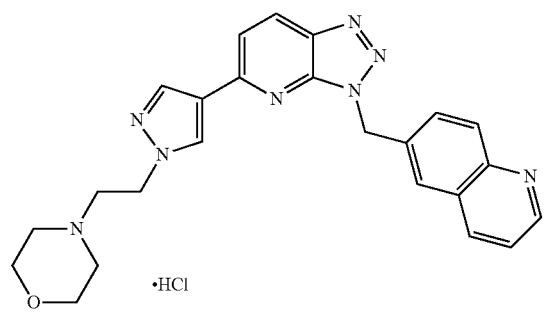 [SMILES: c1cnc2ccc(Cn3nnc4ccc(-c5cnn(CCN6CCOCC6)c5)nc43)cc2c1 ; Cl] ·HCl |
| Ex 177 | 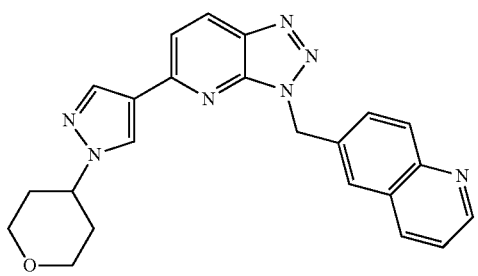 [SMILES: c1cnc2ccc(Cn3nnc4ccc(-c5cnn(C6CCOCC6)c5)nc43)cc2c1] |
| Ex 178 | 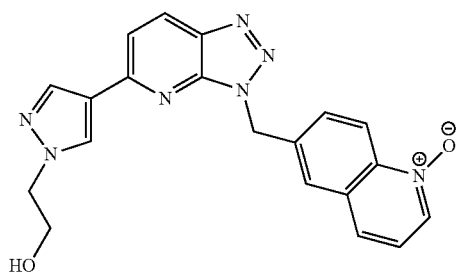 [SMILES: [O-][n+]1cccc2cc(Cn3nnc4ccc(-c5cnn(CCO)c5)nc43)ccc21] |
| Ex 179 | 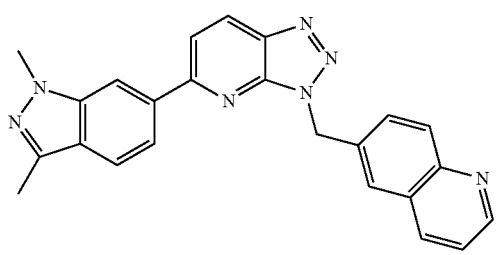 [SMILES: Cc1nn(C)c2cc(-c3ccc4nnn(Cc5ccc6ncccc6c5)c4n3)ccc12] |

-continued

| Compound | Structure |
|---|---|
| Ex 180 | 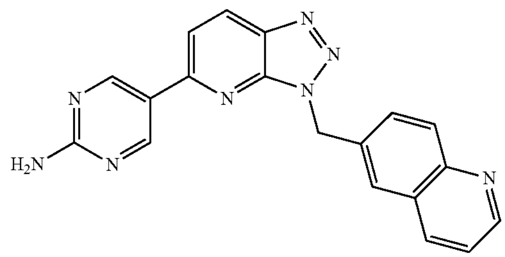 [SMILES: Nc1ncc(-c2ccc3nnn(Cc4ccc5ncccc5c4)c3n2)cn1] |
| Ex 181 | 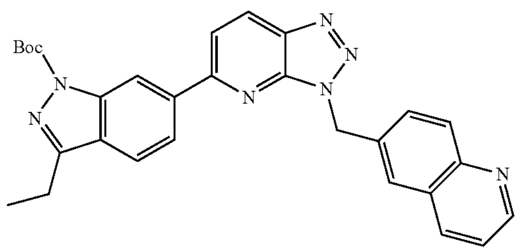 [SMILES: CCc1nn(C(=O)OC(C)(C)C)c2cc(-c3ccc4nnn(Cc5ccc6ncccc6c5)c4n3)ccc12] |
| Ex 182 | 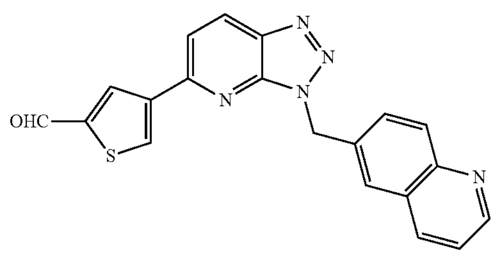 [SMILES: O=Cc1cc(-c2ccc3nnn(Cc4ccc5ncccc5c4)c3n2)cs1] |
| Ex 183 | 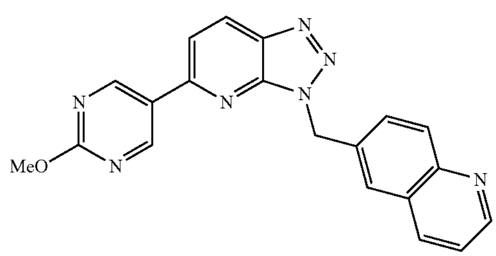 [SMILES: COc1ncc(-c2ccc3nnn(Cc4ccc5ncccc5c4)c3n2)cn1] |
| Ex 184 | 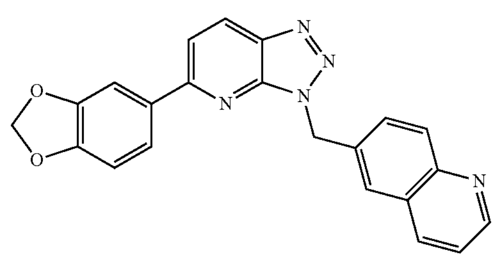 [SMILES: c1cnc2ccc(Cn3nnc4ccc(-c5ccc6c(c5)OCO6)nc43)cc2c1] |
| Ex 185 | 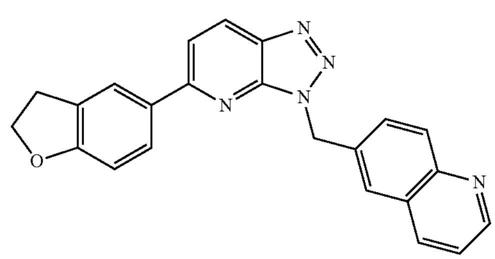 [SMILES: c1cnc2ccc(Cn3nnc4ccc(-c5ccc6c(c5)CCO6)nc43)cc2c1] |

| Compound | Structure |
|---|---|
| Ex 186 | 5-(6-aminopyridin-3-yl) triazolopyridine with quinolin-6-ylmethyl substituent |
| Ex 187 | 5-[1-(2-fluoroethyl)pyrazol-4-yl] triazolopyridine with quinolin-6-ylmethyl substituent |
| Ex 188 | 5-[5-(hydroxymethyl)thiophen-3-yl] triazolopyridine with quinolin-6-ylmethyl substituent |
| Ex 189 | 5-(pyrazol-4-yl) triazolopyridine with 2-(quinolin-6-yl)propan-2-yl substituent; pyrazole N-CH$_2$CH$_2$-OTHP |
| Ex 190 | 5-(pyrazol-4-yl) triazolopyridine with 2-(quinolin-6-yl)propan-2-yl substituent; pyrazole N-CH$_2$CH$_2$-OH |

-continued

| Compound | Structure |
|---|---|
| Ex 191 | 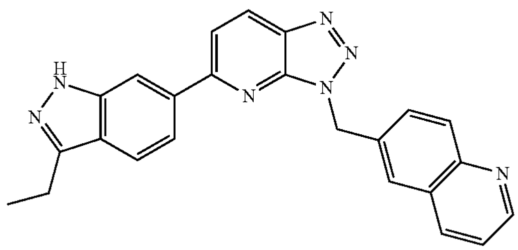 [SMILES: CCc1n[nH]c2cc(-c3ccc4nnn(Cc5ccc6ncccc6c5)c4n3)ccc12] |
| Ex 192 | 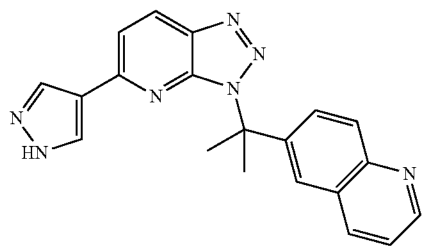 [SMILES: CC(C)(c1ccc2ncccc2c1)n1nnc2ccc(-c3cn[nH]c3)nc21] |
| Ex 193 | 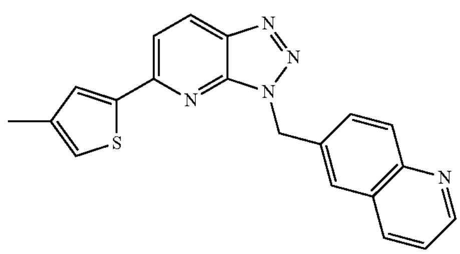 [SMILES: Cc1csc(-c2ccc3nnn(Cc4ccc5ncccc5c4)c3n2)c1] |
| Ex 194 | 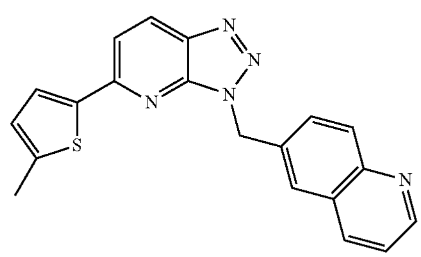 [SMILES: Cc1ccc(-c2ccc3nnn(Cc4ccc5ncccc5c4)c3n2)s1] |
| Ex 195 | 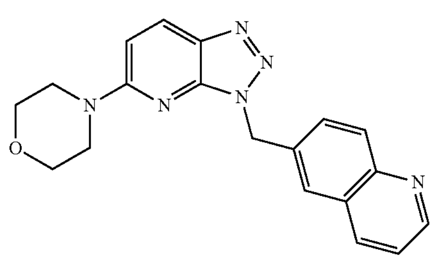 [SMILES: c1cnc2ccc(Cn3nnc4ccc(N5CCOCC5)nc43)cc2c1] |
| Ex 196 | 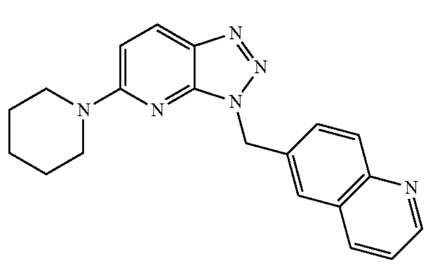 [SMILES: c1cnc2ccc(Cn3nnc4ccc(N5CCCCC5)nc43)cc2c1] |

-continued
| Compound | Structure |
|---|---|
| Ex 197 | 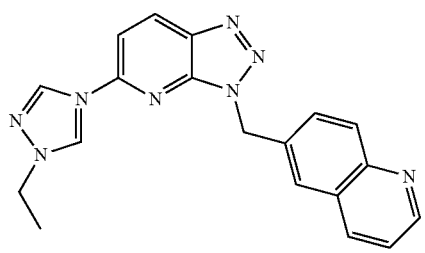 |
| Ex 198 | 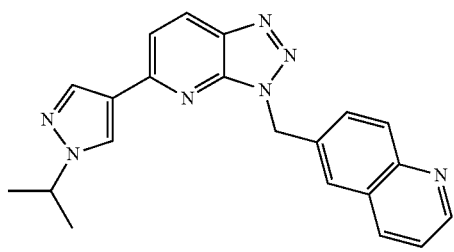 [SMILES: CC(C)n1cc(-c2ccc3nnn(Cc4ccc5ncccc5c4)c3n2)cn1] |
| Ex 199 | 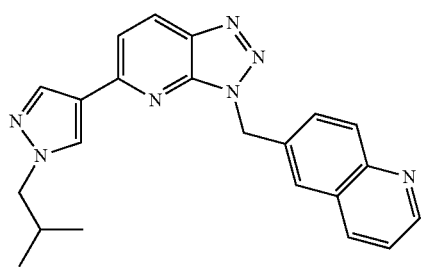 [SMILES: CC(C)Cn1cc(-c2ccc3nnn(Cc4ccc5ncccc5c4)c3n2)cn1] |
| Ex 200 | 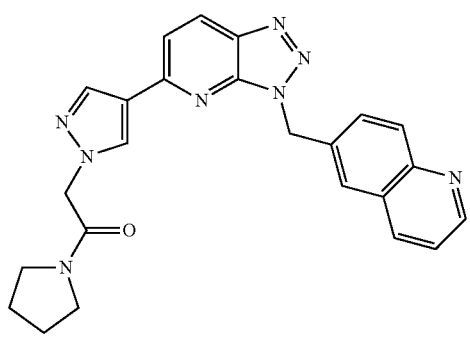 [SMILES: O=C(Cn1cc(-c2ccc3nnn(Cc4ccc5ncccc5c4)c3n2)cn1)N1CCCC1] |
| Ex 201 | 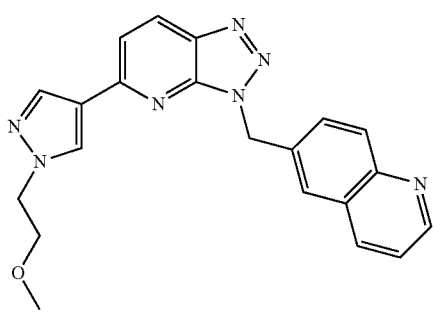 [SMILES: COCCn1cc(-c2ccc3nnn(Cc4ccc5ncccc5c4)c3n2)cn1] |

-continued
| Compound | Structure |
|---|---|
| Ex 202 | 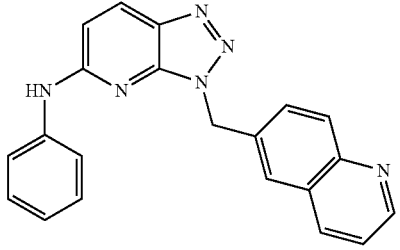 [SMILES: c1ccc(Nc2ccc3nnn(Cc4ccc5ncccc5c4)c3n2)cc1] |
| Ex 203 | 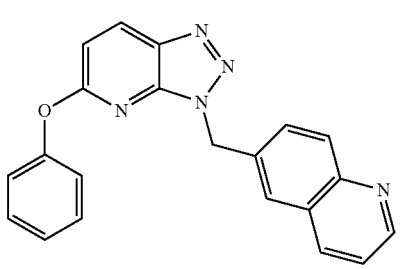 [SMILES: c1ccc(Oc2ccc3nnn(Cc4ccc5ncccc5c4)c3n2)cc1] |
| Ex 204 | 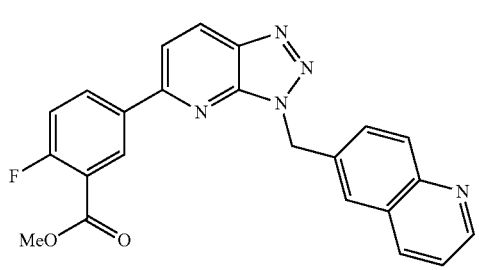 [SMILES: COC(=O)c1cc(-c2ccc3nnn(Cc4ccc5ncccc5c4)c3n2)ccc1F] |
| Ex 205 | 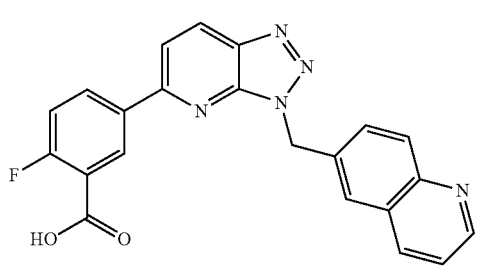 [SMILES: O=C(O)c1cc(-c2ccc3nnn(Cc4ccc5ncccc5c4)c3n2)ccc1F] |
| Ex 206 | 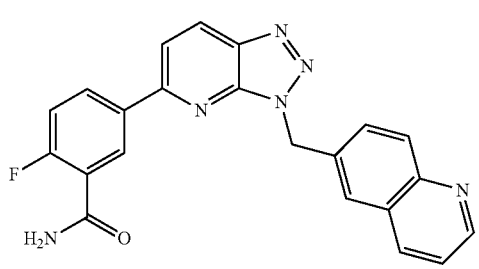 [SMILES: NC(=O)c1cc(-c2ccc3nnn(Cc4ccc5ncccc5c4)c3n2)ccc1F] |
| Ex 207 | 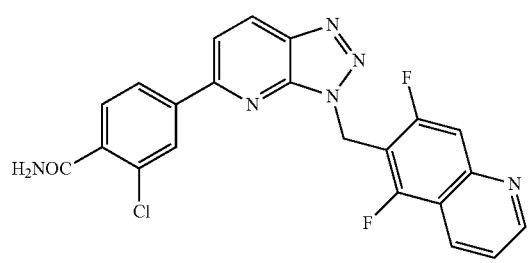 [SMILES: NC(=O)c1ccc(-c2ccc3nnn(Cc4c(F)cc5ncccc5c4F)c3n2)cc1Cl] |

-continued

| Compound | Structure |
|---|---|
| Ex 208 | 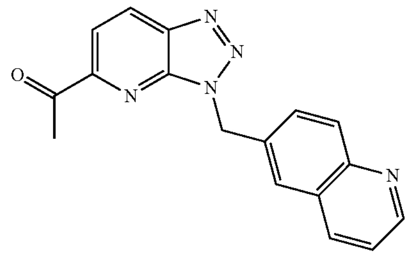 [SMILES: CC(=O)c1ccc2nnn(Cc3ccc4ncccc4c3)c2n1] |
| Ex 209 | 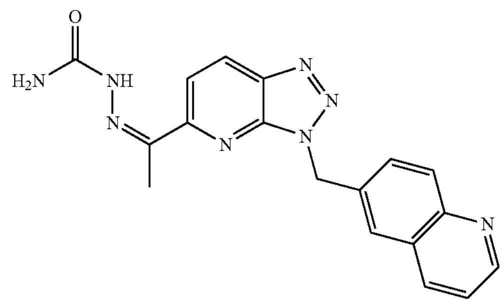 [SMILES: C/C(=N/NC(N)=O)c1ccc2nnn(Cc3ccc4ncccc4c3)c2n1] |
| Ex 210 | 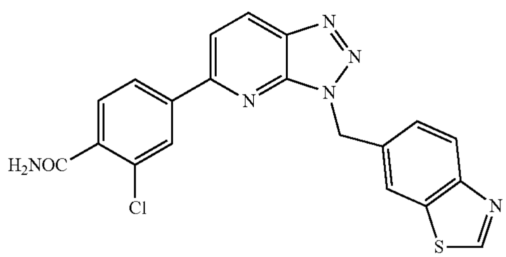 [SMILES: NC(=O)c1ccc(-c2ccc3nnn(Cc4ccc5ncsc5c4)c3n2)cc1Cl] |
| Ex 211 | 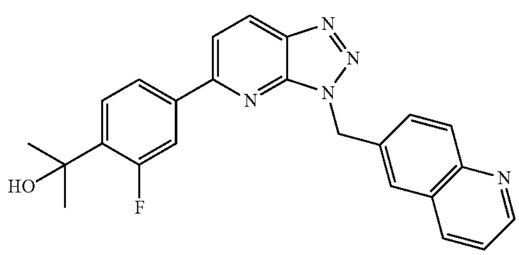 [SMILES: CC(C)(O)c1ccc(-c2ccc3nnn(Cc4ccc5ncccc5c4)c3n2)cc1F] |
| Ex 212 | 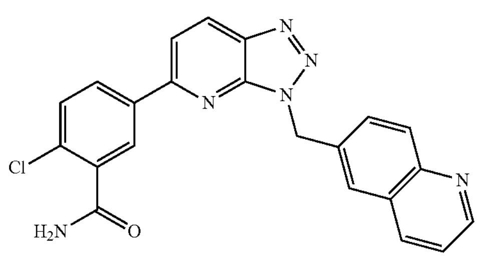 [SMILES: NC(=O)c1cc(-c2ccc3nnn(Cc4ccc5ncccc5c4)c3n2)ccc1Cl] |
| Ex 213 | 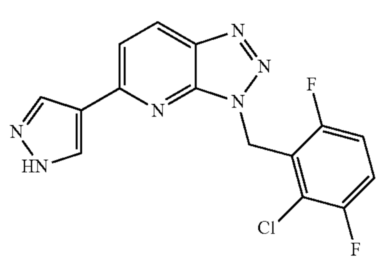 [SMILES: Fc1ccc(F)c(Cn2nnc3ccc(-c4cn[nH]c4)nc32)c1Cl] |

-continued
| Compound | Structure |
|---|---|
| Ex 214 | 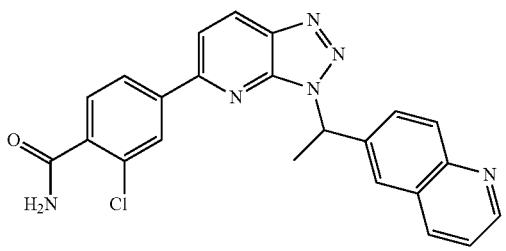 [SMILES: CC(c1ccc2ncccc2c1)n1nnc2ccc(-c3ccc(C(N)=O)c(Cl)c3)nc21] |
| Ex 215 | 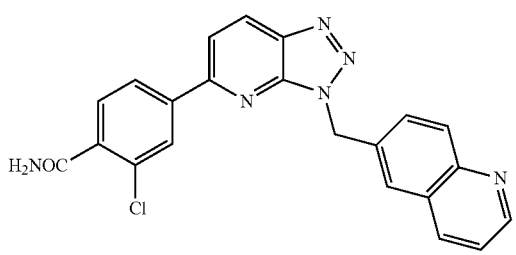 |
| Ex 216 | 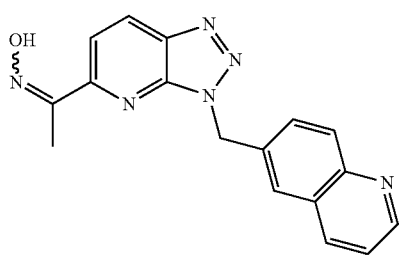 [SMILES: CC(=NO)c1ccc2nnn(Cc3ccc4ncccc4c3)c2n1] |
| Ex 217 | 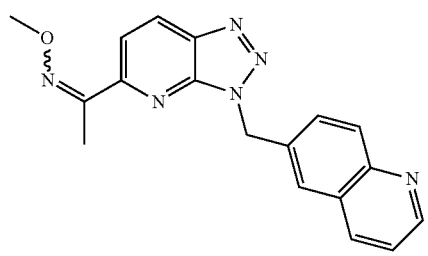 [SMILES: CON=C(C)c1ccc2nnn(Cc3ccc4ncccc4c3)c2n1] |
| Ex 218 | 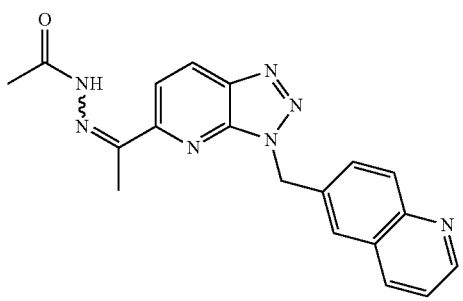 [SMILES: CC(=O)NN=C(C)c1ccc2nnn(Cc3ccc4ncccc4c3)c2n1] |
| Ex 219 | 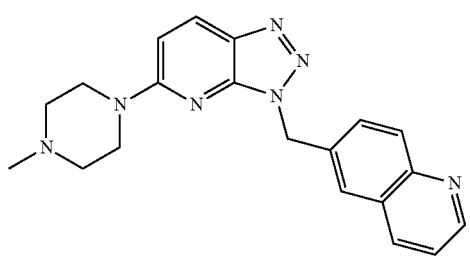 [SMILES: CN1CCN(c2ccc3nnn(Cc4ccc5ncccc5c4)c3n2)CC1] |

-continued

| Compound | Structure |
|---|---|
| Ex 220 | (structure) |
| Ex 221 | (structure) |
| Ex 222 | (structure) |
| Ex 223 | (structure) |
| Ex 224 | (structure) |
| Ex 225 | (structure) |

| Compound | Structure |
|---|---|
| Ex 226 | 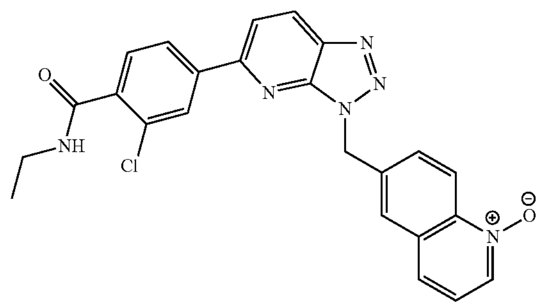 |
| Ex 227 | 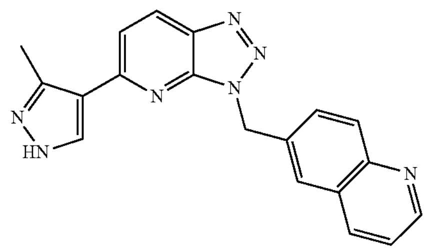 [SMILES: Cc1n[nH]cc1-c1ccc2nnn(Cc3ccc4ncccc4c3)c2n1] |

Yet another embodiment of the present invention is a method for treating a proliferative disease via modulation of a protein kinase (such as c-Met) by administering to a patient in need of such treatment an effective amount of at least one compound of formula (I), (I-A), (IA-1), (II), (II-A), (III), (IIIA), (IIIB), (IV), (IVA) or (IVB) as defined above.

Yet another embodiment of the present invention is a method for treating a proliferative disease via modulation of a protein kinase (such as c-Met) by administering to a patient in need of such treatment an effective amount of at least one compound of formula (I), (I-A), (IA-1), (II), (II-A), (III), (IIIA), (IIIB), (IV), (IVA) or (IVB) as defined above, in combination (simultaneously or sequentially) with at least one other anti-cancer agent. In a preferred embodiment, the proliferative disease is cancer.

More particularly, the compounds of formula (I), (I-A), (IA-1), (II), (II-A), (III), (IIIA), (IIIB), (IV), (IVA) or (IVB) and pharmaceutically acceptable esters or salts thereof can be administered for the treatment, prevention and/or amelioration of c-Met, RON, EGFR or KDR kinase associated diseases or disorders, including but not limited to, cancer and other proliferative diseases or disorders.

The compounds of formula (I), (I-A), (IA-1), (II), (II-A), (III), (IIIA), (IIIB), (IV), (IVA) or (IVB) are useful in the treatment of a variety of cancers, including, but not limited to, the following:

- carcinoma, including that of the bladder, breast, colon, kidney, liver, lung, including small cell lung cancer, esophagus, gall bladder, ovary, pancreas, stomach, cervix, thyroid, prostate, and skin, including squamous cell carcinoma;
- hematopoietic tumors of lymphoid lineage, including leukemia, acute lymphocytic leukemia, acute lymphoblastic leukemia, B-cell lymphoma, T-cell lymphoma, Hodgkin's lymphoma, non-Hodgkins lymphoma, hairy cell lymphoma and Burkett's lymphoma;
- hematopoietic tumors of myeloid lineage, including acute and chronic myelogenous leukemias, myelodysplastic syndrome and promyelocyte leukemia;
- tumors of mesenchymal origin, including fibrosarcoma and rhabdomyosarcoma;
- tumors of the central and peripheral nervous system, including astrocytoma, neuroblastoma, glioma and schwannomas; and
- other tumors, including melanoma, seminoma, teratocarcinoma, osteosarcoma, xenoderoma pigmentosum, keratoctanthoma, thyroid follicular cancer and Kaposi's sarcoma.

Due to the key role of protein kinases in the regulation of cellular proliferation in general, inhibitors could act as reversible cytostatic agents which may be useful in the treatment of any disease process which features abnormal cellular proliferation, e.g., benign prostatic hyperplasia, familial adenomatosis polyposis, neurofibromatosis, atherosclerosis, pulmonary fibrosis, arthritis, psoriasis, glomerulonephritis, restenosis following angioplasty or vascular surgery, hypertrophic scar formation, inflammatory bowel disease, transplantation rejection, endotoxic shock, and fungal infections.

The compounds of the present invention as modulators of apoptosis, are useful in the treatment of cancer (including but not limited to those types mentioned herein above), viral infections (including but not limited to herpevirus, poxvirus, Epstein-Barr virus, Sindbis virus and adenovirus), prevention of AIDS development in HIV-infected individuals, autoimmune diseases (including but not limited to systemic lupus, erythematosus, autoimmune mediated glomerulonephritis, rheumatoid arthritis, psoriasis, inflammatory bowel disease, and autoimmune diabetes mellitus), neurodegenerative disorders (including but not limited to Alzheimer's disease. AIDS-related dementia, Parkinson's disease, amyotrophic lateral sclerosis, retinitis pigmentosa, spinal muscular atrophy and cerebellar degeneration), myelodysplastic syndromes, aplastic anemia, ischemic injury associated with myocardial infarctions, stroke and reperfusion injury, arrhythmia, atherosclerosis, toxin-induced or alcohol related liver diseases, hematological diseases (including but not limited to chronic anemia and aplastic anemia), degenerative diseases of the musculoskeletal system (including but not limited to osteoporosis and arthritis) aspirin-sensitive rhinosinusitis, cystic fibrosis, multiple sclerosis, kidney diseases and cancer pain.

The compounds of present invention can modulate the level of cellular RNA and DNA synthesis. These agents are therefore useful in the treatment of viral infections (including but not limited to HIV) human papilloma virus, herpesvirus, poxvirus, Epstein-Barr virus, Sindbis virus and adenovirus).

The compounds of the present invention are useful in the chemoprevention of cancer. Chemoprevention is defined as inhibiting the development of invasive cancer by either blocking the initiating mutagenic event or by blocking the progression of pre-malignant cells that have already suffered an insult or inhibiting tumor relapse. The compounds are also useful in inhibiting tumor angiogenesis and metastasis. One embodiment of the invention is a method of inhibiting tumor angiogenesis or metastasis in a patient in need thereof by administering an effective amount of one or more compounds of the present invention.

Another embodiment of the present invention is a method of treating an immune system-related disease (e.g., an autoimmune disease), a disease or disorder invoking inflammation (e.g., asthma, chronic obstructive pulmonary disease, rheumatoid arthritis, inflammatory bowel disease, glomerulonephritis, neuroinflammatory diseases, multiple sclerosis, uveitis and disorders of the immune system), cancer or other proliferative disease, a hepatic disease or disorder, a renal disease or disorder. The method includes administering an effective amount of one or more compounds of the present invention.

Examples of immune disorders include psoriasis, rheumatoid arthritis, vasculitis, inflammatory bowel disease, dermatitis, osteoarthritis, asthma, inflammatory muscle disease, allergic rhinitis, vaginitis, interstitial cystitis, scleroderma, osteoporosis, eczema, allogeneic or xenogeneic transplantation (organ, bone marrow, stem cells and other cells and tissues) graft rejection, graft-versus-host disease, lupus erythematosus, inflammatory disease, type I diabetes, pulmonary fibrosis, dermatomyositis, Sjogren's syndrome, thyroiditis (e.g., Hashimoto's and autoimmune thyroiditis), myasthenia gravis, autoimmune hemolytic anemia, multiple sclerosis, cystic fibrosis, chronic relapsing hepatitis, primary biliary cirrhosis, allergic conjunctivitis and atopic dermatitis.

In one embodiment, the compounds described herein are used as immunosuppressants to prevent transplant graft rejections, allogeneic or xenogeneic transplantation rejection (organ, bone marrow, stem cells, other cells and tissues), and graft-versus-host disease. In other embodiments, transplant graft rejections result from tissue or organ transplants. In further embodiments, graft-versus-host disease results from bone marrow or stem cell transplantation. One embodiment, is a method of preventing or decreasing the risk of transplant graft rejection, allogeneic or xenogeneic transplantation rejection (organ, bone marrow, stem cells, other cells and tissues), or graft-versus-host disease by administering an effective amount of one or more compounds of the present invention.

The compounds of the present invention are also useful in combination (administered together or sequentially) with known anti-cancer treatments such as radiation therapy or with cytostatic or cytotoxic or anticancer agents, such as for example, but not limited to, DNA interactive agents, such as cisplatin or doxorubicin; topoisomerase II inhibitors, such as etoposide; topoisomerase I inhibitors such as CPT-11 or topotecan; tubulin interacting agents, such as paclitaxel, docetaxel or the epothilones (for example ixabepilone), either naturally occurring or synthetic; hormonal agents, such as tamoxifen; thymidilate synthase inhibitors, such as 5-fluorouracil; and anti-metabolites, such as methotrexate, other tyrosine kinase inhibitors such as Iressa and OSI-774; angiogenesis inhibitors; EGF inhibitors; VEGF inhibitors; CDK inhibitors; SRC inhibitors; c-Kit inhibitors; Her1/2 inhibitors and monoclonal antibodies directed against growth factor receptors such as erbitux (EGF) and herceptin (Her2) and other protein kinase modulators as well.

The compounds of the present invention are also useful in combination (administered together or sequentially) with one or more steroidal anti-inflammatory drugs, non-steroidal anti-inflammatory drugs (NSAIDs) or Immune Selective Anti-Inflammatory Derivatives (ImSAIDs), The invention further provides a pharmaceutical composition comprising one or more compounds of the present invention (such as a compound having formula (I), (I-A), (IA-1), (II), (II-A), (III), (IIIA), (IIIB), (IV), (IVA) or (IVB)) together with a pharmaceutically acceptable carrier. The pharmaceutical composition may further comprise one or more of the active ingredients identified above, such as other anti-cancer agents. In one embodiment, the pharmaceutical composition includes a therapeutically effective amount of one or more compounds of formula (I), (I-A), (IA-1), (II), (II-A), (III), (IIIA), (IIIB), (IV), (IVA) or (IVB).

Yet another embodiment is a method of treating leukemia in a patient in need thereof by administering a therapeutically effective amount of a compound of the present invention. For example, the compounds of the present invention are effective for treating carcinoma of the bladder, carcinoma of the breast, carcinoma of the colon, carcinoma of the kidney, carcinoma of the liver, carcinoma of the lung, small cell lung cancer, esophageal cancer, gall bladder cancer, ovarian cancer, pancreatic cancer, stomach cancer, cervical cancer, thyroid cancer, prostate cancer, skin cancer, squamous cell carcinoma; cholangiocarcinoma cancer, tumors of mesenchymal origin, fibrosarcoma, rhabdomyosarcoma; tumors of the central and peripheral nervous system, astrocytoma, neuroblastoma, glioma, schwannoma; melanoma, seminoma, teratocarcinoma, osteosarcoma, xenoderoma pigmentosum, keratoctanthoma, thyroid follicular cancer and Kaposi's sarcoma, synovial sarcoma, rhabdomyosarcoma, MFH/fibrosarcoma, leiomyosarcoma, multiple myeloma, lymphoma, glioblastoma, astrocytoma, melanoma, mesothelioma, Wilm's tumor, hematopoietic tumors of lymphoid lineage, leukemia, acute lymphocytic leukemia, acute lymphoblastic leukemia, B-cell lymphoma, T-cell lymphoma, Hodgkin's lymphoma, non-Hodgkins lymphoma, hairy cell lymphoma and Burkett's lymphoma; hematopoietic tumors of myeloid lineage, acute myelogenous leukemias, chronic myelogenous leukemias, myelodysplastic syndrome, promyelocyte leukemia.

Yet another embodiment is a pharmaceutical composition comprising one or more compounds having formula (I), (I-A), (IA-1), (II), (II-A), (III), (IIIA), (IIIB), (IV), (IVA) or (IVB) together with a pharmaceutically acceptable carrier.

DETAIL DESCRIPTION

As used herein the following definition shall apply unless otherwise indicated. Further many of the groups defined herein can be optionally substituted. The listing of substituents in the definition is exemplary and is not to be construed to limit the substituents defined elsewhere in the specification.

The term 'alkyl' refers to a straight or branched hydrocarbon chain radical consisting solely of carbon and hydrogen atoms, containing no unsaturation, having from one to eight carbon atoms, and which is attached to the rest of the molecule by a single bond, e.g., methyl, ethyl, n-propyl, 1-methylethyl (isopropyl), n-butyl, n-pentyl, and 1,1-dimethylethyl (t-butyl).

The term substituted or unsubstituted ($C_{1-4}$)alkyl refers to an alkyl group as defined above having up to 4 carbon atoms, and the term substituted or unsubstituted ($C_{1-6}$)alkyl refers to an alkyl group as defined above having up to 6 carbon atoms.

The term "alkenyl" refers to an aliphatic hydrocarbon group containing a carbon-carbon double bond and which may be a straight or branched or branched chain having about 2 to about 10 carbon atoms, e.g., ethenyl, 1-propenyl, 2-propenyl (allyl), iso-propenyl, 2-methyl-1-propenyl, 1-butenyl, and 2-butenyl, The term substituted or unsubstituted ($C_{1-6}$)alkenyl refers to an alkenyl group as defined above having up to 4 carbon atoms.

The term "alkynyl" refers to a straight or branched chain hydrocarbyl radicals having at least one carbon-carbon triple bond, and having in the range of about 2 up to 12 carbon atoms (with radicals having in the range of about 2 up to 10 carbon atoms presently being preferred) e.g., ethynyl, propynyl, and butynyl.

The term substituted or unsubstituted ($C_{1-6}$) alkynyl refers to an alkynyl group as defined above having up to 4 carbon atoms.

The term "alkoxy" denotes an alkyl group as defined above attached via an oxygen linkage to the rest of the molecule. Representative examples of these groups are —$OCH_3$ and —$OC_2H_5$. The term "substituted alkoxy" refers to an alkoxy group where the alkyl constituent is substituted (i.e., —O-(substituted alkyl) wherein the term "substituted alkyl" is the same as defined above for "alkyl". For example "alkoxy" refers to the group —O-alkyl, including from 1 to 8 carbon atoms of a straight, branched, cyclic configuration and combinations thereof attached to the parent structure through oxygen. Examples include methoxy, ethoxy, propoxy, isopropoxy, cyclopropyloxy, and cyclohexyloxy.

The term "cycloalkyl" denotes a non-aromatic mono or multicyclic ring system of about 3 to 12 carbon atoms such as cyclopropyl, cyclobutyl, cyclopentyl, and cyclohexyl. Examples of multicyclic cycloalkyl groups include perhydronapththyl, adamantyl and norbornyl groups, bridged cyclic groups, and sprirobicyclic groups, e.g., spiro (4,4) non-2-yl.

The term "$C_{3-8}$ cycloalkyl" refers to an cycloalkyl group as defined above having up to 6 atoms.

The term "cycloalkylalkyl" refers to a cyclic ring-containing radical containing in the range of about 3 up to 8 carbon atoms directly attached to an alkyl group which are then attached to the main structure at any carbon from alkyl group that results in the creation of a stable structure such as cyclopropylmethyl, cyclobutylethyl and cyclopentylethyl.

The term "$C_{3-6}$ cycloalkylalkyl" refers to an cycloalkylalkyl group as defined above having up to 6 atoms.

The term "cycloalkenyl" refers to cyclic ring-containing radicals containing in the range of about 3 up to 8 carbon atoms with at least one carbon-carbon double bond such as cyclopropenyl, cyclobutenyl and cyclopentenyl. The term "cycloalkenylalkyl" refers to a cycloalkenyl group directly attached to an alkyl group which are then attached to the main structure at any carbon from alkyl group that results in the creation of a stable structure The term "$C_{3-6}$ cycloalkenyl" refers to an cycloalkenyl group as defined above having up to 6 atoms.

The term "aryl" refers to aromatic radicals having in the range of 6 up to 20 carbon atoms such as phenyl, naphthyl, tetrahydronapthyl, indanyl and biphenyl.

The term "arylalkyl" refers to an aryl group as defined above directly bonded to an alkyl group as defined above, e.g., —$CH_2C_6H_5$ and —$C_2H_5C_6H_5$.

The term "heterocyclic ring" refers to a non-aromatic 3 to 15 member ring radical which, consists of carbon atoms and at least one heteroatom selected from the group consisting of nitrogen, phosphorus, oxygen and sulfur. For purposes of this invention, the heterocyclic ring radical may be a mono-, bi-, tri- or tetracyclic ring system, which may include fused, bridged or spiro ring systems, and the nitrogen, phosphorus, carbon, oxygen or sulfur atoms in the heterocyclic ring radical may be optionally oxidized to various oxidation states. In addition, the nitrogen atom may be optionally quaternized. The heterocyclic ring radical may be attached to the main structure at any heteroatom or carbon atom that results in the creation of a stable structure.

The term "heterocyclyl" refers to a heterocylic ring radical as defined above. The heterocyclyl ring radical may be attached to the main structure at any heteroatom or carbon atom that results in the creation of a stable structure.

The term "heterocyclylalkyl" refers to a heterocylic ring radical as defined above directly bonded to an alkyl group. The heterocyclylalkyl radical may be attached to the main structure at carbon atom in the alkyl group that results in the creation of a stable structure. Examples of such heterocycloalkyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl.

The term "heteroaryl" refers to an optionally substituted 5 to 14 member aromatic ring having one or more heteroatoms selected from N, O, and S as ring atoms. The heteroaryl may be a mono-, bi- or tricyclic ring system. Examples of such "heterocyclic ring" or "heteroaryl" radicals include, but are not limited to, oxazolyl, thiazolyl, imidazolyl, pyrrolyl, furanyl, pyridinyl, pyrimidinyl, pyrazinyl, benzofuranyl, indolyl, benzothiazolyl, benzoxazolyl, carbazolyl quinolyl, isoquinolyl, azetidinyl, acridinyl, benzodioxolyl, benzodioxanyl, benzofuranyl, carbazolyl, cinnolinyl, dioxolanyl indolizinyl, naphthyridinyl, perhydroazepinyl, phenazinyl, phenothiazinyl, phenoxazinyl, phthalazinyl, pteridinyl, purinyl, quinazolinyl, quinoxalinyl, tetrazoyl, tetrahydroisoquinolyl, piperidinyl, piperazinyl, 2-oxopiperazinyl, 2-oxopiperidinyl, 2-oxopyrrolidinyl, 2-oxoazepinyl, azepinyl, 4-piperidonyl, pyrrolidinyl, pyridazinyl, oxazolinyl, oxazolidinyl, triazolyl, indanyl, isoxazolyl, isoxazolidinyl, morpholinyl, thiazolinyl, thiazolidinyl, isothiazolyl, quinuclidinyl, isothiazolidinyl, isoindolyl, indolinyl, isoindolinyl, octahydroindolyl, octahydroisoindolyl, decahydroisoquinolyl, benzimidazolyl, thiadiazolyl, benzopyranyl, tetrahydrofuryl, tetrahydropyranyl, thienyl, benzothienyl, thiamorpholinyl, thiamorpholinyl sulfoxide, thiamorpholinyl, sulfone, dioxaphospholanyl, oxadiazolyl, chromanyl, and isochromanyl, The heteroaryl ring radical may be attached to the main structure at any heteroatom or carbon atom that results in the creation of a stable structure. The term "substituted heteroaryl" also includes ring systems substituted with one or more oxide (—O—) substituents, such as pyridinyl N-oxides.

The term "heteroarylalkyl" refers to heteroaryl ring radical as defined above directly bonded to an alkyl group. The heteroarylalkyl radical may be attached to the main structure at any carbon atom from alkyl group that results in the creation of a stable structure.

The term "heterocyclylalkyl" refers to a heterocylic ring radical as defined above directly bonded to an alkyl group. The heterocyclylalkyl radical may be attached to the main structure at carbon atom in the alkyl group that results in the creation of a stable structure.

The term "cyclic ring" refers to a cyclic ring containing 3-10 carbon atoms.

The term "substituted" unless otherwise specified, refers to substitution with any one or any combination of the following substituents and may be the same or different which one or more are selected from the groups such as hydrogen, hydroxy, halogen, carboxyl, cyano, nitro, oxo (=O) thio(=S), substituted or unsubstituted alkyl, substituted or unsubstituted alkoxy, substituted or unsubstituted alkenyl, substituted or unsubstituted alkynyl, substituted or unsubstituted cycloalkyl, substituted or unsubstituted cycloalkenyl, substituted or unsubstituted cycloalkylalkyl, substituted or unsubstituted cycloalkenylalkyl, substituted or unsubstituted heterocycyl, substituted or unsubstituted heterocyclyalkyl, substituted or unsubstituted aryl, substituted or unsubstituted arylalkyl, substituted or unsubstituted heteroaryl, substituted or unsubstituted heteroarylalkyl, —COOR', —C(O)R', —C(S)R', —C(O)NR'R", —C(O)ONR'R", —NR'R", —NR'CONR'R", —N(R')SOR", —N(R')SO$_2$R", —(=N—N(R')R"), —NR'C(O)OR", —NR'R", —NR'C(O)R"—, —NR'C(S)R"—NR'C(S)NR"R"', —SONR'R", —SO$_2$NR'R"—, —OR', —OR'C(O)NR"R"', —OR'C(O)OR"—, —OC(O)R', —OC(O)NR'R", —R'NR"C(O)R"', —R'OR", —R'C(O)OR", —R'C(O)NR"R"', —R'C(O)R", —R'OC(O)R", —SR', —SOR', —SO$_2$R', —SO$_2$R', —ONO$_2$ wherein R', R" and R"' in each of the above groups can be hydrogen, hydrogen, hydroxy, halogen, carboxyl, cyano, nitro, oxo (=O), thio(=S), imino (=NR'), substituted or unsubstituted alkyl, substituted or unsubstituted alkoxy, substituted or unsubstituted alkenyl, substituted or unsubstituted alkynyl, substituted or unsubstituted cycloalkyl, substituted or unsubstituted cycloalkenyl, substituted or unsubstituted cycloalkylalkyl, substituted or unsubstituted cycloalkenyl alkyl, substituted or unsubstituted heterocycyl, substituted or unsubstituted heterocyclyalkyl, substituted or unsubstituted aryl, substituted or unsubstituted arylalkyl, substituted or unsubstituted heteroaryl, substituted or unsubstituted heteroarylalkyl, or any two of R', R" and R"' may be joined to form a substituted or unsubstituted saturated or unsaturated 3-10 membered ring, which may optionally include heteroatoms which may be the same or different and are selected from O, NR$^X$ or S or form oxo (=O), thio(=S) or imino (=NR'). Substitution or the combinations of substituents envisioned by this invention are preferably those that result in the formation of a stable or chemically feasible compound. The term stable as used herein refers to the compounds or the structure that are not substantially altered when subjected to conditions to allow for their isolation, production, detection and preferably their recovery, purification and incorporation into a pharmaceutical composition.

The term "halo", "halide", or, alternatively, "halogen" means fluoro, chloro, bromo or iodo. The terms "haloalkyl," "haloalkenyl," "haloalkynyl" and "haloalkoxy" include alkyl, alkenyl, alkynyl and alkoxy structures that are substituted with one or more halo groups or with combinations thereof. For example, the terms "fluoroalkyl" and "fluoroalkoxy" include haloalkyl and haloalkoxy groups, respectively, in which the halo is fluorine.

The term "protecting group" or "PG" refers to a substituent that is employed to block or protect a particular functionality. Other functional groups on the compound may remain reactive. For example, an "amino-protecting group" is a substituent attached to an amino group that blocks or protects the amino functionality in the compound. Suitable amino-protecting groups include, but are not limned to, acetyl, trifluoroacetyl, tert-butoxycarbonyl (BOC), benzyloxycarbonyl (CBz) and 9-fluorenylmethylenoxycarbonyl (Fmoc). Similarly, a "hydroxy-protecting group" refers to a substituent of a hydroxy group that blocks or protects the hydroxy functionality. Suitable hydroxy-protecting groups include, but are not limited to, acetyl and silyl. A "carboxy-protecting group" refers to a substituent of the carboxy group that blocks or protects the carboxy functionality. Suitable carboxy-protecting groups include, but are not limited to, —CH2CH2SO2Ph, cyanoethyl 2-(trimethylsilyl)ethyl, 2-(trimethylsilyl) ethoxymethyl, -2-(p-toluenesulfonyl)ethyl, 2-(p-nitrophenylsulfenyl)ethyl 2-(diphenylphosphino)-ethyl, and nitroethyl. For a general description of protecting groups and their use, see T. W. Greene, Protective Groups in Organic Synthesis, John Wiley & Sons, New York, 1991.

The term "stereoisomer" refers to compounds, which have identical chemical composition, but differ with regard to arrangement of the atoms and the groups in space. These include enantiomers, diastereomers, geometrical isomers, atropisomer or conformational isomers.

All the stereoisomers or compounds described herein are within the scope of this invention. Racemic mixtures are also encompassed within the scope of this invention. Therefore, single stereochemical isomers as well enantiomeric, diastereoisomeric and geometric (or conformational) mixtures of the present compounds fall within the scope of the invention.

Certain of the compounds described herein contain one or more asymmetric centers and can thus give rise to enantiomers, diastereomers, and other stereoisomers forms that can be defined, in terms of absolute stereochemistry, as (R)- or (S)-. The present chemical entities, pharmaceutical compositions and methods are meant to include all such possible isomers, including racemic mixtures, optically pure forms and intermediate mixtures. For the instance the non-limiting example of intermediate mixtures include a mixture of isomers in a ratio of 10:90, 13:87, 17:83, 20:80, or 22:78. Optically active (R)- and (S)-isomers can be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers.

The term "tautomers" refers to compounds, which are characterized by relatively easy interconversion of isomeric forms in equilibrium. These isomers are intended to be covered by this invention. "Tautomers" are structurally distinct isomers that interconvert, by tautomerization. "Tautomerization" is a form of isomerization and includes prototropic or proton-shift tautomerization, which is considered a subset of acid-base chemistry. "Prototropic tautomerization" or "proton-shift tautomerization" involves the migration of a proton accompanied by changes in bond order, often the interchange of a single bond with an adjacent double bond. Where tautomerization is possible (e.g. in solution), a chemical equilibrium of tautomers can be reached. An example of tautomerization is keto-enol tautomerization. A specific example of keto-enol tautomerization is the inter/conversion of pentane-2,4-dione and 4-hydroxypent-3-en-2-one tautomers. Another example of tautomerization is phenol-keto tautomerization.

A specific example of phenol-keto tautomerization is the interconversion of pyridin-4-ol and pyridin-4(1H)-one tautomers.

A "leaving group or atom" is any group or atom that will, under the reaction conditions, cleave from the starting material, thus promoting reaction at a specified site. Suitable examples of such groups unless otherwise specified are halogen atoms and mesyloxy, p-nitrobenzensulphonyloxy and tosyloxy groups.

The term "prodrug" refers to a compound, which is an inactive precursor of a compound, converted into its active form in the body by normal metabolic processes. Prodrug design is discussed generally in Hardma, et al. (Eds.), Goodman and Gilman's The Pharmacological Basis of Therapeutics, 9th ed., pp. 11-16 (1996). A thorough discussion is provided in Higuchi, et al., Prodrugs as Novel Delivery Systems, Vol. 14, ASCD Symposium Series, and in Roche (ed.), Bioreversible Carriers in Drug Design, American Pharmaceutical Association and Pergamon Press (1987). To illustrate, prodrugs can be converted into a pharmacologically active form through hydrolysis of, for example, an ester or amide linkage, thereby introducing or exposing a functional group on the resultant product. The prodrugs can be designed to react with an endogenous compound to form a water-soluble conjugate that further enhances the pharmacological properties of the compound, for example, increased circulatory half-life. Alternatively, prodrugs can be designed to undergo covalent modification on a functional group with, for example, glucuronic acid, sulfate, glutathione, amino acids, or acetate. The resulting conjugate can be inactivated and excreted in the urine, or rendered more potent than the parent compound. High molecular weight conjugates also can be excreted into the bile, subjected to enzymatic cleavage, and released back into the circulation, thereby effectively increasing the biological half-life of the originally administered compound.

The term "ester" refers to a compound, which is formed by reaction between an acid and an alcohol with elimination of water. An ester can be represented by the general formula RCOOR'.

These prodrugs and esters are intended to be covered within the scope of this invention.

Additionally the instant invention also includes the compounds which differ only in the presence of one or more isotopically enriched atoms for example replacement of hydrogen with deuterium or tritium, or the replacement of a carbon by or $^{13}C$- or $^{14}C$-enriched carbon.

The compounds of the present invention may also contain unnatural proportions of atomic isotopes at one or more of atoms that constitute such compounds. For example, the compounds may be radiolabeled with radioactive isotopes, such as for example tritium ($^{3}H$), iodine-125 ($^{125}I$) or carbon-14 ($^{14}C$). All isotopic variations of the compounds of the present invention, whether radioactive or not, are encompassed within the scope of the present invention.

Pharmaceutically acceptable salts forming part of this invention include salts derived from inorganic bases such as Li, Na, K, Ca, Mg, Fe, Cu, Zn, and Mn; salts of organic bases such as N,N'-diacetylethylenediamine, glucamine, triethylamine, choline, hydroxide, dicyclohexylamine, metformin, benzylamine, trialkylamine, and thiamine; chiral bases such as alkylphenylamine, glycinol, and phenyl glycinol; salts of natural amino acids such as glycine, alanine, valine, leucine, isoleucine, norleucine, tyrosine, cystine, cysteine, methionine, proline, hydroxy proline, histidine, omithine, lysine, arginine, and serine; quaternary ammonium salts of the compounds of invention with alkyl halides, alkyl sulphates such as MeI and $(Me)_2SO_4$; non-natural amino acids such as D-isomers or substituted amino acids; guanidine; and substituted guanidine wherein the substituents are selected front nitro, amino, alkyl, alkenyl, alkynyl, ammonium or substituted ammonium salts and aluminum salts. Salts may include acid addition salts where appropriate which are sulphates, nitrates, phosphates, perchlorates, borates, hydrohalides, acetates, tartrates, maleates, citrates, fumarates, succinates, palmoates, methanesulphonates, benzoates, salicylates, benzenesulfonates, ascorbates, glycerophosphates, and ketoglutarates.

When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range may vary from, for example, between 1% and 15% of the stated number or numerical range. The term "comprising" (and related terms such as "comprise" or "comprises" or "having" or "including") includes those embodiments, for example, an embodiment of any composition of matter, composition, method, or process, or the like, that "consist of" or "consist essentially of" the described features.

The following abbreviations and terms have the indicated meanings throughout: HGFR is hepatocyte growth factor receptor; AIDS=Acquired Immuno Deficiency Syndrome; HIV=Human Immunodeficiency Virus; MeI=Methyl Iodide; $POCl_3$=Phosphorous Oxychloride; KCNS=Potassium IsoThiocyanate; TLC=Thin Layer Chromatography; MeOH=Methanol; and $CHCl_3$=Chloroform.

Abbreviations used herein have their conventional meaning within the chemical and biological arts.

The term "cell proliferation" refers to a phenomenon by which the cell number has changed as a result of division. This term also encompasses cell growth by which the cell morphology has changed (e.g., increased in size) consistent with a proliferative signal.

The term "co-administration," "administered in combination with," and their grammatical equivalents, as used herein, encompasses administration of two or more agents to an animal so that both agents and/or their metabolites are present in the animal at the same time. Co-administration includes simultaneous administration in separate compositions, administration at different times in separate compositions, or administration in a composition in which both agents are present.

The term "effective amount" or "therapeutically effective amount" refers to that amount, of a compound described herein that is sufficient to effect the intended application including but not limited to disease treatment, as defined below. The therapeutically effective amount may vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g. reduction of platelet adhesion and/or cell migration. The specific dose will vary depending on the particular compounds chosen, the dosing regimen to be followed, whether it is administered in combination with other compounds, timing of administration, the tissue to which it is administered, and the physical delivery system in which it is carried.

As used herein, "treatment," "treating," or "ameliorating" are used interchangeably. These terms refers to an approach for obtaining beneficial or desired results including but not limited to therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

A "therapeutic effect," as that term is used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

The terra "subject" or "patient" refers to an animal, such as a mammal, for example a human. The methods described herein can be useful in both human therapeutics and veterinary applications. In some embodiments, the patient is a mammal, and in some embodiments, the patient is human.

"Radiation therapy" means exposing a patient, using routine methods and compositions known to the practitioner, to radiation emitters such as alpha-particle emitting radionuclides (e.g., actinium and thorium radionuclides), low linear energy transfer (LET) radiation emitters (i.e. beta emitters), conversion electron emitters (e.g. strontium-89 and samarium-153-EDTMP, or high-energy radiation, including without limitation x-rays, gamma rays, and neutrons.

"Signal transduction" is a process during which stimulatory or inhibitory signals are transmitted into and within a cell to elicit an intracellular response. A modulator of a signal transduction pathway refers to a compound which modulates the activity of one or more cellular proteins mapped to the same specific signal transduction pathway. A modulator may augment (agonist) or suppress (antagonist) the activity of a signaling molecule.

The term "selective inhibition" or "selectively inhibit" as applied to a biologically active agent refers to the agent's ability to selectively reduce the target signaling activity as compared to off-target signaling activity, via direct or indirect interaction with the target.

The term "pharmaceutically acceptable carrier" or "pharmaceutically acceptable excipient" includes, but is not limited to, any and all solvents, dispersion media, coatings, antibacterial and antifungal agents, isotonic and absorption delaying agents, one or more suitable diluents, fillers, salts, disintegrants, binders, lubricants, glidants, wetting agents, controlled release matrices, colorants/flavoring, carriers, excipients, buffers, stabilizers, solubilizers, and combinations thereof. Except insofar as any conventional media or agent is incompatible with the active ingredient, its use. In the therapeutic compositions of the invention is contemplated. Supplementary active ingredients can also be incorporated into the compositions.

Inhibition of c-met kinase may be of therapeutic benefit in treatment of various conditions, e.g., conditions characterized by an inflammatory response including but not limited to autoimmune diseases, allergic diseases, and arthritic diseases.

"Inflammatory response" as used herein is characterized by redness, heat, swelling and pain (i.e., inflammation) and typically involves tissue injury or destruction. An inflammatory response is usually a localized, protective response elicited by injury or destruction of tissues, which serves to destroy, dilute or wall off (sequester) both the injurious agent and the injured tissue. Inflammatory responses are notably associated with the influx of leukocytes and/or leukocyte (e.g., neutrophil) chemolaxis. Inflammatory responses may result from infection with pathogenic organisms and viruses, noninfectious means such as trauma or reperfusion following myocardial infarction or stroke, immune responses to foreign antigens, and autoimmune diseases. Inflammatory responses amenable to treatment with the methods and compounds according to the invention encompass conditions associated with reactions of the specific defense system as well as conditions associated with reactions of the non-specific defense system.

The therapeutic methods of the invention include methods for the amelioration of conditions associated with inflammatory cell activation. "Inflammatory cell activation" refers to the induction by a stimulus (including but not limited to, cytokines, antigens or auto-antibodies) of a proliferative cellular response, the production of soluble mediators (including but not limited to cytokines, oxygen radicals, enzymes, prostanoids, or vasoactive amines), or cell surface expression of new or increased numbers of mediators (including but not limited to, major histocompatibility antigens or cell adhesion molecules) in inflammatory cells (including but not limited to monocytes, macrophages, T lymphocytes, B lymphocytes, granulocytes (polymorphonuclear leukocytes including neutrophils, basophils, and eosinophils) mast cells, dendritic cells, Langerhans cells, and endothelial cells). It will be appreciated by persons skilled in the art that the activation of one or a combination of these phenotypes in these cells can contribute to the initiation, perpetuation, or exacerbation of an inflammatory condition.

"Autoimmune disease" as used herein refers to any group of disorders in which tissue injury is associated with humoral or cell-mediated responses to the body's own constituents. "Transplant rejection" as used herein refers-to any immune response directed against grafted tissue (including organs or cells (e.g., bone marrow), characterized by a loss of function of the grafted and surrounding tissues, pain, swelling, leukocytosis, and thrombocytopenia). "Allergic disease" as used herein refers to any symptoms, tissue damage, or loss of tissue function resulting from allergy. "Arthritic disease" as used herein refers to any disease that is characterized by inflammatory lesions of the joints attributable to a variety of etiologies. "Dermatitis" as used herein refers to any of a large family of diseases of the skin that are characterized by inflammation of the skin attributable to a variety of etiologies.

The relative efficacies of compounds as inhibitors of an enzyme activity (or other biological activity) can be established by determining the concentrations at which each compound inhibits the activity to a predefined extent and then comparing the results. Typically, the preferred determination is the concentration that inhibits 50% of the activity in a biochemical assay, i.e., the 50% inhibitory concentration or "IC50". IC50 determinations can be accomplished using conventional techniques known in the art. In general, an IC50 can be determined by measuring the activity of a given enzyme in the presence of a range of concentrations of the inhibitor under study. The experimentally obtained values of enzyme activity then are plotted against the inhibitor concentrations used. The concentration of the inhibitor that shows 50% enzyme activity (as compared to the activity in the absence of any inhibitor) is taken as the IC50 value. Analogously, other inhibitory concentrations can be defined through appropriate determinations of activity. For example, in some settings it can be desirable to establish a 90% inhibitory concentration, i.e., IC90, etc.

Accordingly, a c-met selective inhibitor alternatively can be understood to refer to a compound that exhibits a 50% inhibitory concentration (IC50) with respect to c-met kinase, that is at least 10-fold, in another aspect at least 20-fold, and in another aspect at least 30-fold, lower than the IC50 value with respect to any or all of the other class receptor tyrosine kinase (RTK) family members. In an alternative embodiment of the invention, the term c-met kinase selective inhibitor can be understood to refer to a compound that exhibits an IC50 with respect to c-met kinase that is at least 50-fold, in another aspect at least 100-fold, in an additional aspect at least 200-fold, and in yet another aspect at least 500-fold, lower than the IC50 with respect to any or all of the other RTK family members. A c-met kinase selective inhibitor is typically administered in an amount such that it selectively inhibits c-met activity, as described above.

The methods of the invention may be applied to cell populations in vivo or ex vivo, "In vivo" means within a living individual, as within an animal or human or in a subject's body. In this context, the methods of the invention may be used therapeutically or prophylactically in an individual. "Ex vivo" or "In vitro" means outside of a living individual. Examples of ex vivo cell populations include in vitro cell cultures and biological samples including but not limited to fluid or tissue samples obtained from individuals. Such samples may be obtained by methods known in the art. Exemplary biological fluid samples include blood, cerebrospinal fluid, urine, and saliva. Exemplary tissue samples include tumors and biopsies thereof, in this context, the invention may be used for a variety of purposes, including therapeutic and experimental purposes. For example, the invention may be used ex vivo or in vitro to determine the optimal schedule and/or dosing of administration of a c-met kinase selective inhibitor for a given indication, cell type, individual, and other parameters. Information gleaned from such use may be used for experimental or diagnostic purposes or in the clinic to set protocols for in vivo treatment. Other ex vivo uses for which the invention may be suited are described below or will become apparent to those skilled in the art.

Pharmaceutical Compositions

The invention provides a pharmaceutical composition comprising one or more compounds of the present invention. The pharmaceutical composition may include one or more additional active ingredients as described herein. The pharmaceutical composition may be administered for any of the disorders described herein In some embodiments, the invention provides pharmaceutical compositions for treating diseases or conditions related to an undesirable, over-active, harmful or deleterious immune response in a mammal. Such undesirable immune response can be associated with or result in, e.g., asthma, emphysema, bronchitis, psoriasis, allergy, anaphylaxsis, auto-immune diseases, rhuematoid arthritis, graft versus host disease, and lupus erythematosus. The pharmaceutical compositions of the present invention can be used to treat other respiratory diseases including but not limited to diseases affecting the lobes of lung, pleural cavity, bronchial tubes, trachea, upper respiratory tract, or the nerves and muscle for breathing.

In some embodiments, the invention provides pharmaceutical compositions for the treatment of disorders such as hyperproliferative disorder including but not limited to cancer such as acute myeloid leukemia, thymus, brain, lung, squamous cell, skin, eye, retinoblastoma, intraocular melanoma, oral cavity and oropharyngeal, bladder, gastric, stomach, pancreatic, bladder, breast, cervical, head, neck, renal, kidney, liver, ovarian, prostate, colorectal, esophageal, testicular, gynecological, thyroid, CNS, PNS, AIDS related (e.g. Lymphoma and Kaposi's Sarcoma) or Viral-Induced cancer. In some embodiments, the pharmaceutical composition is for the treatment of a non-cancerous hyperproliferative disorder such as benign hyperplasia of the skin (e.g., psoriasis), restenosis, or prostate (e.g., benign prostatic hypertrophy (BPH)).

The invention also relates to a composition for treating a disease related to vasculogenesis or angiogenesis in a mammal which can manifest as tumor angiogenesis, chronic inflammatory disease such as rheumatoid arthritis, inflammatory bowel disease, atherosclerosis, skin diseases such as psoriasis, eczema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

The invention also provides compositions for the treatment of liver diseases (including diabetes), pancreatitis or kidney disease (including proliferative glomerulonephritis and diabetes-induced renal disease) or pain in a mammal.

The invention further provides a composition for the prevention of blastocyte implantation in a mammal.

The subject pharmaceutical compositions are typically formulated to provide a therapeutically effective amount of a compound of the present invention as the active ingredient, or a pharmaceutically acceptable salt, ester, or prodrug thereof. Whom desired, the pharmaceutical compositions contain a compound of the present invention as the active ingredient or a pharmaceutically acceptable salt and/or coordination complex thereof, and one or more pharmaceutically acceptable excipients, carriers, such as inert solid diluents and fillers, diluents, including sterile aqueous solution and various organic solvents, permeation enhancers, solubilizers and adjuvants.

The subject pharmaceutical compositions can be administered alone or in combination with one or more other agents, which are also typically administered in the form of pharmaceutical compositions. Where desired, the subject compounds and other agent(s) may be mixed into a preparation or both components may be formulated into separate preparations to use them in combination separately or at the same time.

Methods include administration of an inhibitor by itself, or in combination as described herein, and in each case optionally including one or more suitable diluents, fillers, salts, disintegrants, binders, lubricants, glidants, wetting agents, controlled release matrices, colorants/flavoring, carriers, excipients, buffers, stabilizers, solubilizers, and combinations thereof.

Preparations of various pharmaceutical compositions are known in the art. See, e.g., Anderson, Philip O.; Knoben, James E.; Troutman, William G, eds., Handbook of Clinical Drug Data, Tenth Edition, McGraw-Hill, 2002; Pratt and Taylor, eds., Principles of Drug Action, Third Edition, Churchill Livingston, New York, 1990; Katzung, ed., Basic and Clinical Pharmacology, Ninth Edition, McGraw Hill, 2003; Goodman and Oilman, eds., The Pharmacological Basis of Therapeutics, Tenth Edition, McGraw Hill, 2001; Remingtons Pharmaceutical Sciences, 20th Ed., Lippincott Williams & Wilkins., 2000; Martindale, The Extra Pharmacopoeia, Thirty-Second Edition (The Pharmaceutical Press, London, 1999), all of which are incorporated by reference herein in their entirety.

The compounds or pharmaceutical composition of the present invention can be administered by any route that enables delivery of the compounds to the site of action, such as oral routes, intraduodenal routes, parenteral injection (including intravenous, intraarterial, subcutaneous, intramuscular, intravascular, intraperitoneal or infusion), topical administration (e.g. transdermal application), rectal administration, via local delivery by catheter or stent or through inhalation. The compounds can also be administered intraadiposally or intrathecally.

The compositions can be administered in solid, semi-solid, liquid or gaseous form, or may be in dried powder, such as lyophilized form. The pharmaceutical compositions can be packaged in forms convenient for delivery, including, for example, solid dosage forms such as capsules, sachets, cachets, gelatins, papers, tablets, capsules, suppositories, pellets, pills, troches, and lozenges. The type of packaging will generally depend on the desired route of administration. Implantable sustained release formulations are also contemplated, as are transdermal formulations.

Routes of Administration

In the methods according to the invention, the inhibitor compounds may be administered by various routes. For example, pharmaceutical compositions may be for injection, or for oral, nasal, transdermal or other forms of administration, including, e.g., by intravenous, intradermal, intramuscular, intramammary, intraperitoneal, intrathecal, intraocular, retrobulbar, intrapulmonary (e.g., aerosolized drugs) or subcutaneous injection (including depot administration for long term release e.g., embedded-under the-splenic capsule, brain, or in the cornea); by sublingual, anal, or vaginal administration, or by surgical implantation, e.g., embedded under the splenic capsule, brain, or in the cornea. The treatment may consist of a single dose or a plurality of doses over a period of time. In general, the methods of the invention involve administering effective amounts of a modulator of the invention together with one or more pharmaceutically acceptable diluents, preservatives, solubilizers, emulsifiers, adjuvants and/or carriers, as described above.

The subject pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, and adjuvants.

In one aspect, the invention provides methods for oral administration of a pharmaceutical composition of the invention. Oral solid dosage forms are described generally in Remington's Pharmaceutical Sciences, supra at Chapter 89. Solid dosage forms include tablets, capsules, pills, troches or lozenges, and cachets or pellets. Also, liposomal or proteinoid encapsulation may be used to formulate the compositions (as, for example, proteinoid microspheres reported in U.S. Pat. No. 4,925,673). Liposomal encapsulation may include liposomes that are derivatized with various polymers (e.g., U.S. Pat. No. 5,013,556). The formulation may include a compound of the invention and inert ingredients which protect against degradation in the stomach and which permit release of the biologically active material in the intestine.

Toxicity and therapeutic efficacy of the met kinase compounds can be determined by standard pharmaceutical procedures in cell cultures or experimental animals, e.g., for determining the LD50 (the dose lethal to 50% of the population) and the ED50 (the dose therapeutically effective in 50% of the population). Additionally, this information can be determined in cell cultures or experimental animals additionally treated with other therapies including but not limited to radiation, chemotherapeutic agents, photodynamic therapies, radiofrequency ablation, anti-angiogenic agents, and combinations thereof.

The amount of the compound administered will be dependent on the mammal being treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to 7 g/day, preferably about 0.05 to about 2.5 g/day. In some instances, dosage levels below the lower limit of the aforesaid range may be more than adequate, while in other cases still larger doses may be employed without causing any harmful side effect, e.g. by dividing such larger doses into several small doses for administration throughout the day.

In some embodiments, a compound of the invention is administered in a single dose. Typically, such administration will be by injection, e.g., intravenous injection, in order to introduce the agent quickly. However, other routes may be used as appropriate. A single dose of a compound of the invention may also be used for treatment of an acute condition.

In practice of the methods of the invention, the pharmaceutical compositions are generally provided in doses ranging from 1 pg compound/kg body weight to 1000 mg/kg, 0.1 mg/kg to 100 mg/kg, 0.1 mg/kg to 50 mg/kg, and 1 to 20 mg/kg, given in daily doses or in equivalent doses at longer or shorter intervals, e.g., every other day, twice weekly, weekly, or twice or three times daily. The inhibitor compositions may be administered by an initial bolus followed by a continuous infusion to maintain therapeutic circulating levels of drug product. Those of ordinary skill in the art will readily optimize effective dosages and administration regimens as determined by good medical practice and the clinical condition of the individual to be treated. The frequency of dosing will depend on the pharmacokinetic parameters of the agents and the route of administration. The optimal pharmaceutical formulation will be determined by one skilled in the art depending upon the route of administration and desired dosage [see, for example, Remington's Pharmaceutical Sciences, pp. 1435-1712, the disclosure of which is hereby incorporated by reference]. Such formulations may influence the physical state, stability, rate of in vivo release, and rate of in vivo clearance of the administered agents. Depending on the route of administration, a suitable dose may be calculated according to body weight, body surface area, or organ size. Further refinement of the calculations necessary to determine the appropriate dosage for treatment involving each of the above mentioned formulations is routinely made by those of ordinary skill in the art without undue experimentation, especially in light of the dosage information and assays disclosed herein, as well as the pharmacokinetic data observed in human clinical trials. Appropriate dosages may be ascertained by using established assays for determining blood level dosages in conjunction with an appropriate physician considering various factors which modify the action of drugs, e.g., the drug's specific activity, the severity of the indication, and the responsiveness of the individual, the age, condition, body weight, sex and diet of the individual, the time of administration and other clinical factors. As studies are conducted, former information will emerge regarding the appropriate dosage levels and duration of treatment for various diseases and conditions capable of being treated with the methods of the invention.

In some embodiments, a compound of the invention is administered in multiple doses. Dosing may be about once, twice, three times, four times, five times, six times, or more than six times per day. Dosing may be about once a month, once every two weeks, once a week, or once every other day. In another embodiment a compound of the invention and another agent are administered together about once per day to about 6 times per day. In another embodiment the administration of a compound of the invention and an agent continues for less than about 7 days. In yet another embodiment the administration continues for more than about 6, 10, 14, 28 days, two months, six months, or one year. In some cases, continuous dosing is achieved and maintained as long as necessary.

Administration of the agents of the invention may continue as long as necessary. In some embodiments, an agent of the invention is administered for more than 1, 2, 3, 4, 5, 6, 7, 14, or 28 days. In some embodiments, an agent of the invention is administered for less than 28, 14, 7, 6, 5, 4, 3, 2, or 1 day. In some embodiments, an agent of the invention is administered chronically on an ongoing basis, e.g., for the treatment of chronic effects.

An effective amount of a compound of the invention may be administered in either single or multiple doses by any of the accepted modes of administration of agents having similar utilities, including rectal, buccal, intranasal and transdermal routes, by intraarterial injection, intravenously, intraperitoneally, parenterally, intramuscularly, subcutaneously, orally, topically, or as an inhalant.

The compounds of the invention may be administered in dosages. It is known in the art that due to intersubject variability in compound pharmacokinetics, individualization of dosing regimen is necessary for optimal therapy. Dosing for a compound of the invention may be found by routine experimentation in light of the instant disclosure.

When a compound of the invention, is administered in a composition that comprises one or more agents, and the agent has a shorter half-life than the compound of the invention unit dose forms of the agent and the compound of the invention may be adjusted accordingly.

The inhibitors of the invention may be covalently or non-covalently associated with a carrier molecule including but not limited to a linear polymer (e.g., polyethylene glycol, polylysine, dextran, etc.), a branched-chain polymer (see U.S. Pat. Nos. 4,289,872 and 5,229,490; PCT Publication No. WO 93/21259), a lipid, a cholesterol group (such as a steroid), or a carbohydrate or oligosaccharide. Specific examples of carriers for use in the pharmaceutical compositions of the invention include carbohydrate-based polymers such as trehalose, mannitol, xylitol sucrose, lactose, sorbitol, dextrans such as cyclodextran, cellulose, and cellulose derivatives. Also, the use of liposomes, microcapsules or microspheres, inclusion complexes, or other types of earners is contemplated.

Other carriers include one or more water soluble polymer attachments such as polyoxyethlene glycol, or polypropylene glycol as described U.S. Pat. Nos. 4,640,835, 4,496,689, 4,301,144, 4,670,417, 4,791,192 and 4,179,337. Still other useful carrier polymers known in the art include monomethoxy-polyethylene glycol, poly-(N-vinyl pyrrolidine)-polyethylene glycol, propylene glycol homopolymers, a polypropylene oxidelethylene oxide co-polymer, polyoxyethlated polyols (e.g., glycerol) and polyvinyl alcohol, as well as mixtures of these polymers.

Derivitization with bifunctional agents is useful for cross-linking a compound of the invention to a support matrix or to a carrier. One such carrier is polyethylene glycol (PEG). The PEG group may be of any convenient molecular weight and may be straight chain or branched. The average molecular weight of the PEG can range from about 2 kDa to about 100 kDa, in another aspect from about 5 kDa to about 50 kDa, and in a further aspect from about 5 kDa to about 10 kDa. The PEG groups will generally be attached to the compounds of the invention via acylation, reductive alkylation, Michael addition, thiol alkylation or other chemoselective conjugation/ligation methods through a reactive group on the PEG moiety (e.g., an aldehyde, amino, ester, thiol, ci-haloacetyl, maleimido or hydrazino group) to a reactive group on the target inhibitor compound (e.g., an aldehyde, amino, ester, thiol, a-haloacetyl, maleimido or hydrazine group). Cross-linking agents can include, e.g., esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl)dithiolpropiomidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 may be employed for inhibitor immobilization.

Method of Treatment

The invention also provides methods of using the compounds or pharmaceutical compositions of the present invention to treat disease conditions, including but not limited to diseases associated with malfunctioning of c-met kinase and family.

The treatment methods provided herein comprise administering to the subject a therapeutically effective amount of a compound of the invention. In one embodiment, the present invention provides a method of treating an inflammation disorder, including autoimmune diseases in a mammal. The method comprises administering to said mammal a therapeutically effective amount of a compound of the present invention.

The disorders, diseases, or conditions treatable with a compound provided herein, include, but are not limited to,
- inflammatory or allergic diseases, including systemic anaphylaxis and hypersensitivity disorders, atopic dermatitis, urticaria, drug allergies, insect sting allergies, food allergies (including celiac disease and the like), anaphylaxis, serum sickness, drug reactions, insect venom allergies, hypersensitivity pneumonitis, angioedema, erythema multiforme, Stevens-Johnson syndrome, atopic keratoconjunctivitis, venereal keratoconjunctivitis, giant papillary conjunctivitis, and mastocytosis;
- inflammatory bowel diseases, including Crohn's disease, ulcerative colitis, ileitis, enteritis, and necrotizing enterocolitis;
- vasculitis, and Behcet's syndrome;
- psoriasis and inflammatory dermatoses, including dermatitis, eczema, allergic contact dermatitis, viral cutaneous pathologies including those derived from human papillomavirus, HIV or RLV infection, bacterial, flugal, and other parasital cutaneous pathologies, and cutaneous lupus erythematosus;

asthma and respiratory allergic diseases, including allergic asthma, exercise induced asthma, allergic rhinitis, otitis media, hypersensitivity lung diseases, chronic obstructive pulmonary disease and other respiratory problems;

autoimmune diseases and inflammatory conditions, including but are not limited to acute disseminated encephalomyelitis (ADEM). Addison's disease, antiphospholipid antibody syndrome (APS), aplastic anemia, autoimmune hepatitis, coeliac disease, Crohn's disease. Diabetes mellitus (type 1), Goodpasture's syndrome, Graves' disease, Guillain-Barre syndrome (GBS). Reynaud's syndrome, Hashimoto's disease, lupus erythematosus, systemic lupus erythematosus (SLE), multiple sclerosis, myasthenia gravis, opsoclonus myoclonus syndrome (OMS), optic neuritis, Ord's thyroiditis, oemphigus, polyarthritis, primary biliary cirrhosis, psoriasis, rheumatoid arthritis, psoriatic arthritis, gouty arthritis, spondylitis, reactive arthritis, chronic or acute glomerulonephritis, lupus nephritis, Reiter's syndrome, Takayasu's arteritis, temporal arteritis (also known as "giant cell arteritis"), warm autoimmune hemolytic anemia, Wegener's granulomatosis, alopecia universalis, Chagas' disease, chronic fatigue syndrome, dysautonomia, endometriosis, hydradenitis suppurativa, interstitial cystitis, neuromyotonia, sarcoidosis, scleroderma, ulcerative colitis, connective tissue disease, autoimmune pulmonary inflammation, autoimmune thyroiditis, autoimmune inflammatory eye disease, vitiligo, and vulvodynia. Other disorders include bone-resorption disorders and thrombosis;

tissue or organ transplant rejection disorders including but not limited to graft rejection (including allograft rejection and graft-v-host disease (GVHD)), e.g., skin graft rejection, solid organ transplant rejection, bone marrow transplant rejection;

fever;

cardiovascular disorders, including acute heart failure, hypotension, hypertension, angina pectoris, myocardial infarction, cardiomyopathy, congestive heart failure, atherosclerosis, coronary artery disease, restenosis, and vascular stenosis;

cerebrovascular disorders, including traumatic brain injury, stroke, ischemic reperfusion injury and aneurysm;

cancers of the breast, skin, prostate, cervix, uterus, ovary, testes, bladder, lung, liver, larynx, oral cavity, colon and gastrointestinal tract (e.g., esophagus, stomach, pancreas), brain, thyroid, blood, and lymphatic system;

fibrosis, connective tissue disease, and sarcoidosis;

genital and reproductive conditions, including erectile dysfunction;

gastrointestinal disorders, including gastritis, ulcers, nausea, pancreatitis, and vomiting;

neurologic disorders, including Alzheimer's disease;

sleep disorders, including insomnia, narcolepsy, sleep apnea syndrome, and Pickwick Syndrome;

pain, myalgias due to infection;

renal disorders;

ocular disorders, including glaucoma;

infectious diseases, including HIV;

sepsis; septic shock; endotoxic shock; gram negative sepsis; gram positive sepsis; toxic shock syndrome; multiple organ injury syndrome secondary to septicemia, trauma, or hemorrhage;

pulmonary or respiratory conditions including but not limited to asthma, chronic bronchitis, allergic rhinitis, adult respiratory distress syndrome (ARDS), severe acute respiratory syndrome (SARS), chronic pulmonary inflammatory diseases (e.g., chronic obstructive pulmonary disease), silicosis, pulmonary sarcoidosis, pleurisy, alveolitis, vasculitis, pneumonia, bronchiectasis, hereditary emphysema, and pulmonary oxygen toxicity;

ischemic-reperfusion injury, e.g., of the myocardium, brain, or extremities;

fibrosis including but not limited to cystic fibrosis; keloid formation or scar tissue formation;

central or peripheral nervous system inflammatory conditions including but not limited to meningitis (e.g., acute purulent meningitis), encephalitis, and brain or spinal cord injury due to minor trauma;

Sjorgren's syndrome; diseases involving leukocyte diapedesis; alcoholic hepatitis; bacterial pneumonia; community acquired pneumonia (CAP); Pneumocystis carinii pneumonia (PCP); antigen-antibody complex mediated diseases; hypovolemic shock; acute and delayed hypersensitivity; disease states due to leukocyte dyscrasia and metastasis; thermal injury; granulocyte transfusion associated syndromes; cytokine-induced toxicity; stroke; pancreatitis; myocardial infarction, respiratory syncytial virus (RSV) infection; and spinal cord injury.

In certain embodiments, the cancer or cancers treatable with the methods provided herein includes, but is or are not limited to, leukemias, including, but not limited to, acute leukemia, acute lymphocytic leukemia, acute myelocytic leukemias such as myeloblasts, promyelocyte, myelomonoeytic, monocytic, erythroleukemia leukemias and myeiodysplastic syndrome or a symptom thereof (such as anemia, thrombocytopenia, neutropenia, bicytopenia or pancytopenia), refractory anemia (RA), RA with ringed sideroblasts (RARS), RA with excess blasts (RAEB), RAEB in transformation (RAEB-T), preleukemia, and chronic myelomonoeytic leukemia (CMML);

chronic leukemias, including, but not limited to, chronic myelocytic (granulocytic) leukemia, chronic lymphocytic leukemia, and hairy cell leukemia;

polycythemia vera;

lymphomas, including, but not limited to, Hodgkin's disease and non-Hodgkin's disease;

multiple myelomas, including, but not limited to, smoldering multiple myeloma, nonsecretory myeloma, osteosclerotic myeloma, plasma cell leukemia, solitary plasmacytoma, and extramedullary plasmacytoma;

Waldenstrom's macroglobulinemia;

monoclonal gammopathy of undetermined significance;

benign monoclonal gammopathy;

heavy chain disease;

bone and connective tissue sarcomas, including, but not limited to, bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosareoma, metastatic cancers, neurilemmoma, rhabdomyosarcoma, and synovial sarcoma;

brain tumors, including, but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, and primary brain lymphoma;

breast cancer, including, but not limned to, adenocarcinoma, lobular (small cell) carcinoma, intradductal carcinoma, medullary breast cancer, mucinous breast cancer, tubular breast cancer, papillary breast cancer, primary cancers, Paget's disease, and inflammatory breast cancer;

adrenal cancer, including, but not limited to, pheochromocytom and adrenocortical carcinoma;

thyroid cancer, including, but not limited to, papillary or follicular thyroid cancer, medullary thyroid cancer, and anaplastic thyroid cancer;

pancreatic cancer, including, but not limited to, insulinoma, gastrinoma, glucagonoma, vipoma, somatostatin-secreting tumor, and carcinoid or islet cell tumor;

pituitary cancer, including, but limited to, Cushing's disease, prolactin-secreting tumor, acromegaly, and diabetes insipidus;

eye cancer, including, but not limited, to ocular melanoma such as iris melanoma, choroidal melanoma, and cilliary body melanoma, and retinoblastoma;

vaginal cancer, including, but not limited to, squamous cell carcinoma, adenocarcinoma, and melanoma;

vulvar cancer, including, but not limited to, squamous cell carcinoma, melanoma, adenocarcinoma, basal cell carcinoma, sarcoma, and Paget's disease;

cervical cancers, including, but not limited to, squamous cell carcinoma, and adenocarcinoma;

uterine cancer, including, but not limited to, endometrial carcinoma and uterine sarcoma;

ovarian cancer, including, but not limited to, ovarian epithelial carcinoma, borderline tumor, germ cell tumor, and stromal tumor;

esophageal cancer, including, but not limited to, squamous cancer, adenocarcinoma, adenoid cystic carcinoma, mucoepidermoid carcinoma, adenosquamous carcinoma, sarcoma, melanoma, plasmacytoma, verrucous carcinoma, and oat cell (small cell) carcinoma;

stomach cancer, including, but not limited to, adenocarcinoma, fungating (polypoid), ulcerating, superficial spreading, diffusely spreading, malignant lymphoma, liposarcoma, fibrosarcoma, and carcinosarcoma;

colon cancer;
rectal cancer;
liver cancer, including, but not limited to, hepatocellular carcinoma and hepatoblastoma;

gallbladder cancer, including, but not limited to, adenocarcinoma;

cholangiocarcinomas, including, but not limited to, papillary, nodular, and diffuse;

lung cancer, including, but not limited to, non-small cell lung cancer, squamous cell carcinoma (epidermoid carcinoma), adenocarcinoma, large-cell carcinoma, and small-cell lung cancer;

testicular cancer, including, but not limited to, germinal tumor, seminoma, anaplastic, classic (typical), spermatocyte, nonseminoma, embryonal carcinoma, teratoma, carcinoma, and choriocarcinoma (yolk-sac tumor);

prostate cancer, including, but not limited to, adenocarcinoma, leiomyosarcoma, and rhabdomyosarcoma;

penal cancer;

oral cancer, including, but not limited to, squamous cell carcinoma;

basal cancer;

salivary gland cancer, including, but not limited to, adenocarcinoma, mucoepidermoid carcinoma, and adenoid-cystic carcinoma;

pharynx cancer, including, but not limited to, squamous cell cancer and verrucous;

skin cancer, including, but not limited to, basal cell carcinoma, squamous cell carcinoma and melanoma, superficial spreading melanoma, nodular melanoma, lentigo malignant melanoma, and acral lentiginous melanoma;

kidney cancer, including, but not limited to, renal cell cancer, adenocarcinoma, hypernephroma, fibrosarcoma, and transitional cell cancer (renal pelvis and/or uterer);

Wilms' tumor;

bladder cancer, including, but not limited to, transitional cell carcinoma, squamous cell cancer, adenocarcinoma, and carcinosarcoma; and other cancer, including, not limited to, myxosarcoma, osteogenic sarcoma, endotheliosarcoma, lymphangio-endotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma, and papillary adenocarcinomas See Fishman et al., 1985, Medicine, 2d Ed., J. B. Lippincott Co., Philadelphia and Murphy et al., 1997, Informed Decisions: The Complete Book of Cancer Diagnosis, Treatment, and Recovery, Viking Penguin, Penguin Books U.S.A., Inc., United States of America.

It will be appreciated that the treatment methods of the invention are useful in the fields of human medicine and veterinary medicine. Thus, the individual to be treated may be a mammal, preferably human, or other animals. For veterinary purposes, individuals include but are not limited to farm animals including cows, sheep, pigs, horses, and goats; companion animals such as dogs and cats; exotic and/or zoo animals; laboratory animals including mice, rats, rabbits, guinea pigs, and hamsters; and poultry such as chickens, turkeys, ducks, and geese.

In another embodiment, the compounds described herein are used for the treatment of cancer such as acute myeloid leukemia, thymus, brain, lung, squamous cell, skin, eye, retinoblastoma, intraocular melanoma, oral cavity and oropharyngeal, bladder, gastric, stomach, pancreatic, bladder, breast, cervical, head, neck, renal, kidney, liver, ovarian, prostate, colorectal, esophageal, testicular, gynecological, thyroid, CNS, PNS, AIDS-related (e.g. Lymphoma and Kaposi's Sarcoma) or viral-induced cancer. In some embodiments, said method relates to the treatment of a non-cancerous hyperproliferative disorder such as benign hyperplasia of the skin (e.g., psoriasis), restenosis, or prostate (e.g., benign prostatic hypertrophy (BPH)).

The invention also relates to a method of treating diseases related to vasculogenesis or angiogenesis in a mammal that comprises administering to said mammal a therapeutically effective amount of a compound of the present invention. In some embodiments, said method is for treating a disease selected from the group consisting of tumor angiogenesis, chronic inflammatory disease such as rheumatoid arthritis, atherosclerosis, inflammatory bowel disease, skin diseases such as psoriasis, eczema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

Patients that can be treated with compounds of the present invention, according to the methods of this invention include, for example, patients that have been diagnosed as having psoriasis; restenosis; atherosclerosis; BPH; breast cancer such as a ductal carcinoma in duct tissue in a mammary gland, medullary carcinomas, colloid carcinomas, tubular carcinomas, and inflammatory breast cancer; ovarian cancer, including epithelial ovarian tumors such as adenocarcinoma in the ovary and an adenocarcinoma that has migrated from the ovary into the abdominal cavity; uterine cancer; cervical cancer such as adenocarcinoma in the cervix epithelial including squamous cell carcinoma and adenocarcinomas; prostate cancer, such as a prostate cancer selected from the following: an adenocarcinoma or an adenocarcinoma that has migrated to the bone; pancreatic cancer such as epitheloid carcinoma in the pancreatic duct tissue and an adenocarcinoma in a pancreatic duct; bladder cancer such as a transitional cell carcinoma in urinary bladder, urothelial carcinomas (transitional cell carcinomas), tumors in the urothelial cells that line the bladder, squamous cell carcinomas, adenocarcinomas, and small cell cancers; leukemia such as acute myeloid leukemia (AML), acute lymphocytic leukemia, chronic lymphocytic leukemia, chronic myeloid leukemia, hairy cell leukemia, myelodysplasia, myeloproliferative disorders, acute myelogenous leukemia (AML), chronic myelogenous leukemia (CML), mastocytosis, chronic lymphocytic leukemia (CLL), multiple myeloma (MM), and myelodysplastic syndrome (MDS); bone cancer; lung cancer such as non-small cell lung cancer (NSCLC), which is divided into squamous cell carcinomas, adenocarcinomas, and large cell undifferentiated carcinomas, and small cell lung cancer; skin cancer such as basal cell carcinoma, melanoma, squamous cell carcinoma and actinic keratosis, which is a skin condition that sometimes develops into squamous cell carcinoma; eye retinoblastoma; cutaneous or intraocular (eye) melanoma; primary liver cancer (cancer that begins in the liver); kidney cancer; thyroid cancer such as papillary, follicular, medullary and anaplastic; AIDS-related lymphoma such as diffuse large B-cell lymphoma, B-cell immunoblastic lymphoma and small non-cleaved cell lymphoma; Kaposi's Sarcoma; viral-induced cancers including hepatitis B virus (HBV), hepatitis C virus (HCV), and hepatocellular carcinoma; human lymphotrophic virus-type 1 (HTLV-I) and adult T-cell leukemia/lymphoma; and human papilloma virus (HPV) and cervical cancer; central nervous system cancers (CNS) such as primary brain tumor, which includes gliomas (astrocytoma, anaplastic astrocytoma, or glioblastoma multiforme), Oligodendroglioma, Ependymoma, Meningioma, Lymphoma, Schwannoma, and Medulloblastoma; peripheral nervous system (PNS) cancers such as acoustic neuromas and malignant peripheral nerve sheath tumor (MPNST) including neurofibromas and schwannomas, malignant fibrous cytoma, malignant fibrous histiocytoma, malignant meningioma, malignant mesothelioma, and malignant mixed Müllerian tumor; oral cavity and oropharyngeal cancer such as, hypopharyngeal cancer, laryngeal cancer, nasopharyngeal cancer, and oropharyngeal cancer; stomach cancer such as lymphomas, gastric stromal tumors, and carcinoid tumors; testicular cancer such as germ cell tumors (GCTs), which include seminomas and nonseminomas, and gonadal stromal tumors, which include Leydig cell tumors and Sertoli cell tumors; thymus cancer such as to thymomas, thymic carcinomas, Hodgkin disease, non-Hodgkin lymphomas carcinoids or carcinoid tumors; rectal cancer; and colon cancer.

The invention also relates to a method of treating diabetes in a mammal that comprises administering to said mammal a therapeutically effective amount of a compound of the present invention.

In addition, the compounds described herein may be used to treat acne.

In addition, the compounds described herein may be used for the treatment of arteriosclerosis, including atherosclerosis. Arteriosclerosis is a general term describing any hardening of medium or large arteries. Atherosclerosis is a hardening of an artery specifically due to an atheromatous plaque.

Further the compounds described herein may be used for the treatment of glomerulonephritis. Glomerulonephritis is a primary or secondary autoimmune renal disease characterized by inflammation of the glomeruli. It may be asymptomatic, or present with hematuria, and/or proteinuria. There are many recognized types, divided in acute, subacute or chronic glomerulonephritis. Causes are infectious (bacterial, viral or parasitic pathogens), autoimmune or paraneoplastic.

Additionally, the compounds described herein may be used for the treatment of bursitis, lupus, acute disseminated encephalomyelitis (ADEM), addison's disease, antiphospholipid antibody syndrome (APS), aplastic anemia, autoimmune hepatitis, coeliac disease, Crohn's disease, diabetes mellitus (type 1), goodpasture's syndrome, graves' disease, guillain-barre syndrome (GBS), hashimoto's disease, inflammatory bowel disease, lupus erythematosus, myasthenia gravis, opsoclonus myoclonus syndrome (OMS), optic neuritis, ord's thyroiditiSjOstheoarthritis, uveoretinitis, pemphigus, polyarthritis, primary biliary cirrhosis, reiter's syndrome, takayasu's arteritis, temporal arteritis, warm autoimmune hemolytic anemia, Wegener's granulomatosis, alopecia universalis, chagas' disease, chronic fatigue syndrome, dysautonomia, endometriosis, hydradenitis suppurativa, interstitial cystitis, neuromyotonia, sarcoidosis, scleroderma, ulcerative colitis, vitiligo, vulvodynia, appendicitis, arteritis, arthritis, blepharitis, bronchiolitis, bronchitis, cervicitis, cholangitis, cholecystitis, chorioamnionitis, colitis, conjunctivitis, cystitis, dacryoadenitis, demiatomyositis, endocarditis, endometritis, enteritis, enterocolitis, epicondylitis, epididymitis, fasciitis, fibrositis, gastritis, gastroenteritis, gingivitis, hepatitis, hydradenitis, ileitis, iritis, laryngitis, mastitis, meningitis, myelitis, myocarditis, myositis, nephritis, omphalitis, oophoritis, orchitis, osteitis, otitis, pancreatitis, parotitis, pericarditis, peritonitis, pharyngitis, pleuritis, phlebitis, pneumonitis, proctitis, prostatitis, pyelonephritis, rhinitis, salpingitis, sinusitis, stomatitis, synovitis, tendonitis, tonsillitis, uveitis, vaginitis, vasculitis, or vulvitis.

The invention also relates to a method of treating a cardiovascular disease in a mammal that comprises administering to said mammal a therapeutically effective amount of a compound of the present invention. Examples of cardiovascular conditions include, but are not limited to, atherosclerosis, restenosis, vascular occlusion and carotid obstructive disease.

In another aspect, the present invention provides methods of disrupting the function of a leukocyte or disrupting a function of an osteoclast. The method includes contacting the leukocyte or the osteoclast with a function disrupting amount of a compound of the invention.

In another aspect of the present invention, methods are provided for treating ophthalmic disease by administering one or more of the subject compounds or pharmaceutical compositions to the eye of a subject.

The invention further provides methods of modulating kinase activity by contacting a kinase with an amount of a compound of the invention sufficient to modulate the activity of the kinase. Modulate can be inhibiting or activating kinase activity. In some embodiments, the invention provides methods of inhibiting kinase activity by contacting a kinase with an amount of a compound of the invention sufficient to inhibit the activity of the kinase. In some embodiments, the invention provides methods of inhibiting kinase activity in a solution by contacting said solution with an amount of a compound of the invention sufficient to inhibit the activity of the kinase in said solution. In some embodiments, the invention provides methods of inhibiting kinase activity in a cell by contacting said cell with an amount of a compound of the invention sufficient to inhibit the activity of the kinase in said cell. In some embodiments, the invention provides methods of inhibiting kinase activity in a tissue by contacting said tissue with an amount of a compound of the invention sufficient to inhibit the activity of the kinase in said tissue. In some embodiments, the invention provides methods of inhibiting kinase activity in an organism by contacting said organism with an amount of a compound of the invention sufficient to inhibit the activity of the kinase in said organism. In some embodiments, the invention provides methods of inhibiting kinase activity in an animal by contacting said animal with an amount of a compound of the invention sufficient to inhibit the activity of the kinase in said animal. In some embodiments, the invention provides methods of inhibiting kinase activity in a mammal by contacting said mammal with an amount of a compound of the invention sufficient to inhibit the activity of the kinase in said mammal. In some embodiments, the invention provides methods of inhibiting kinase activity in a human by contacting said human with an amount of a compound of the invention sufficient to inhibit the activity of the kinase in said human. In some embodiments, the % of kinase activity after contacting a kinase with a compound of the invention is less than 1, 5, 10, 20, 30, 40, 50, 60, 70, 80, 90, 95, or 99% of the kinase activity in the absence of said contacting step.

In some embodiments, the kinase is a pretein kinase, more particularly a non-receptor or receptor tyrosine protein kinase. In some embodiments, the kinase is selected from the group consisting of C-met including mutants if any; AbI, VEGFR, Ephrin receptor B4 (EphB4); TEK receptor tyrosine kinase (HE2); FMS-related tyrosine kinase 3 (FLT-3); Platelet derived growth factor receptor (PDGFR); RET; ATM; ATR; hSmg-1; Hck; Src; Epidermal growth factor receptor (EGFR); KIT; Inulin Receptor (IR) and IGFR.

The invention further provides methods of modulating c-met kinase activity by contacting a c-met kinase with an amount of a compound of the invention sufficient to modulate the activity of the c-met kinase. Modulate can be inhibiting or activating c-met kinase activity. In some embodiments, the invention provides methods of inhibiting c-met kinase activity by contacting a c-met kinase with an amount of a compound of the invention sufficient to inhibit the activity of the c-met kinase, in some embodiments, the invention provides methods of inhibiting c-met kinase activity. Such inhibition can take place in solution, in a cell expressing one or more c-met kinase, in a tissue comprising a cell expressing one or more c-met kinases, or in an organism expressing one or more c-met kinase. In some embodiments, the invention provides methods of inhibiting c-met kinase activity in an animal (including mammal such as humans) by contacting said animal with an amount of a compound of the invention sufficient to inhibit the activity of the c-met kinase in said animal.

Combination Treatment

The present invention also provides methods for combination therapies in which an agent known to modulate other pathways, or other components of the same pathway, or even overlapping sets of target enzymes are used in combination with a compound of the present invention. In one aspect, such therapy includes but is not limited to the combination of the subject compound with chemotherapeutic agents, therapeutic antibodies, and radiation treatment, to provide a synergistic or additive therapeutic effect.

For treatment of autoimmune diseases, the subject compounds or pharmaceutical compositions can be used in combination with commonly prescribed drugs including but not limited to Enbrel®, Remicade®, Humira®, Avonex®, and Rebif®. For treatment of respiratory diseases, the subject compounds or pharmaceutical compositions can be administered in combination with commonly prescribed drugs including but not limited to Xolair®, Advair®, Singulair®, and Spiriva®.

The compounds of the invention may be formulated or administered in conjunction with other agents that act to relieve the symptoms of inflammatory conditions such as encephalomyelitis, asthma, and the other diseases described herein. These agents include non-steroidal anti-inflammatory drugs (NSAIDs), e.g., acetylsalicylic acid; ibuprofen; naproxen; indomethacin; nabumetone; tolmetin; etc. Corticosteroids are used to reduce inflammation and suppress activity of the immune system. The most commonly prescribed drug of this type is Prednisone, Chloroquine (Aralen) or hydroxychloroquine (Plaquenil) may also be very useful in some individuals with lupus. They are most often prescribed for skin and joint symptoms of lupus. Azathioprine (Imuran) and cyclophosphamide (Cytoxan) suppress inflammation and tend to suppress the immune system. Other agents, e.g. methotrexate and cyclosporin are used to control the symptoms of lupus. Anticoagulants are employed to prevent blood from clotting rapidly. They range from aspirin at very low dose which prevents platelets from sticking to heparin/coumadin.

In another one aspect, this invention also relates to a pharmaceutical composition for inhibiting abnormal cell growth in a mammal which comprises an amount of a compound of the present invention, in combination with an amount of an anti-cancer agent (e.g., a chemotherapeutic agent). Many chemotherapeutics are presently known in the art and can be used in combination with the compounds of the invention.

In some embodiments, the chemotherapeutic is selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens. Non-limiting examples are chemotherapeutic agents, cytotoxic agents, and non-peptide small molecules such as Gleevec (Imatinib Mesylate), Velcade (bortezomib), Iressa (gefitinib), Sprycel (Dasatinib), and Adriamycin as well as a host of chemotherapeutic agents. Non-limiting examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlomaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, iomustine, nimustine, ranimustine; antibiotics such as aclacinomysins, actinomycin, authramycin, azaserine, bleomycins, cactinomycin, calicheamicin, carabicin, carminomycin, carzinophilin, Casodex™, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, pκ)tfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfornithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK.R™; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel (TAXOL™, Bristol-Myers Squibb Oncology, Princeton, N.J.) and docetaxel (TAXOTERE™, Rhone-Poulenc Rorer, Antony, France); retinoic acid; esperamicins; capecitabine; and pharmaceutically acceptable salts, acids or derivatives of any of the above. Also included as suitable chemotherapeutic cell conditioners are anti-hormonal agents that act to regulate or inhibit hormone action on tumors such as anti-estrogens including for example tamoxifen (Zolvadex™), raloxifene, aromatase inhibiting 4(5)-imidazoles, 4-hydroxy tamoxifen, trioxifene, keoxifene, LY 117018, onapristone, and toremifene (Fareston); and anti-androgens such as flutamide, nilutamide, bicalutamide (Casodex), leuprolide, and goserelin (Zoladex); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; camptothecin-11 (CPT-11); topoisomerase inhibitor RFS 2000; difluoromethylornithine (DMFO). 17α-Ethlnylestradiol, Diethylstilbestrol, Testosterone, Prednisone, Fluoxymesterone, Megesirolacetate, Methylprednisolone, Methyl-testosterone, Prednisolone, Triamcinolone, chlorotrianisene, Hydroxyprogesterone, Aminoglutethimide, Medroxyprogesteroneacetate, matrix metalloproteinase inhibitors, EGPR inhibitors, Pan Her inhibitors, VEGF inhibitors, including as anti-VEGF antibodies such as Avastin, and small molecules such as ZD6474 and SU6668, vatalanib, BAY-43-9006, SU11248, CF-547632, and CEP-7055. Anti-Her2 antibodies (such as Herceptin from Genentech) may also be utilized. Suitable EGFR inhibitors include gefitinib, erlotinib, and cetuxtmab. Pan Her inhibitors include canertinib, EKB-569, and GW-572016. Further suitable anticancer agents include, but are not limited to, Src inhibitors, MEK-1 kinase inhibitors, MAFK kinase inhibitors, PI3 kinase inhibitors, and PDGF inhibitors, such as imatinib. Also included are anti-angiogenic and antivascular agents which, by interrupting blood flow to solid tumors, render cancer cells quiescent by depriving them of nutrition. Castration which also renders androgen dependent carcinomas non-proliferative, may also be utilized. Also included are IGE1R inhibitors, inhibitors of non-receptor and receptor tyrosine kinases, and inhibitors of integrin signalling. Additional anticancer agents include microtubule-stabilizing agents 7-O-methythiomethylpaclitaxel (disclosed in U.S. Pat. No. 5,646,176). 4-desacety-4-methylcarbonatepaclitaxel, 3'-tert-butyl-3'-N-tert-butyloxycarbonyl-4-desacetyl-3'-dephenyl-3'-N-debenzoyl-4-O-methoxycarbonyl-paclitaxel (disclosed in U.S. Ser. No. 09/712,352 filed on Nov. 14, 2000), C-4 methyl carbonate paciltaxel, epothilone A, epothilone B, epothilone C, epothilone D, desoxyepothilone A, desoxyepothilone B, [1S-[1*,3R*(E),7R*,10S*,11R*,12R*,16S*]]-7-11-dihydroxy-8,8,10,12,16-entamethyl-3-[1-methyl-2-(2-methyl-4-thiazolyl)ethenyl]-4-aza-17 oxabicyclo [14.1.0]heptadecane-5,9-dione (disclosed in WO 99/02514), [1S-[1R*,3R*(E),7R*,10S*,11R*,12R*,16S*]]-3-[2-[2-(aminomethyl)-4-thiazolyl]-1-methyl ethenyl]-7,11-dihydroxy-8,8,10,12,16-pentamethyl-4-17-dioxabicyclo[14.1.0]-heptadecane-5,9-dione (as disclosed in U.S. Pat. No. 6,262,094) and derivatives thereof; and microtubule-disruptor agents. Also suitable are CDK inhibitors, an antiproliferative cell cycle inhibitor, epidophyllotoxin; an antineoplastic enzyme; biological response modifiers; growth inhibitors; antihormonal therapeutic agents; leucovorin; tegafur; and haematopoietic growth factors.

Additional cytotoxic agents include, hexamethyl melamine, idatrexate, L-asparaginase, camptothecin, topotecan, pyridobenzoindole derivatives, interferons, and interleukins. Where desired, the compounds or pharmaceutical composition of the present invention can be used in combination with commonly prescribed anti-cancer drugs such as Herceptin®, Avastin®, Erbitux®, Rituxan®, Taxol®, Armimidex®, Taxotere®, and Velcade®.

This invention further relates to a method for using the compounds or pharmaceutical composition in combination with radiation therapy in inhibiting abnormal cell growth or treating the hyperproliferative disorder in the mammal. Techniques for administering radiation therapy are known in the art, and these techniques can be used in the combination therapy described herein. The administration of the compound of the invention in this combination therapy can be determined as described herein.

Radiation therapy can be administered through one of several methods, or a combination of methods, including without limitation external-beam therapy, internal radiation therapy, implant radiation, stereotactic radiosurgery, systemic radiation therapy, radiotherapy and permanent or temporary interstitial brachytherapy. The term "brachytherapy," as used herein, refers to radiation therapy delivered by a spatially confined radioactive material inserted into the body at or near a tumor or other proliferative tissue disease site. The term is intended without limitation to include exposure to radioactive isotopes e.g., At-211, I-131, I-125, Y-90, Re-186, Re-188, Sm-153, Bi-212, P-32, and radioactive isotopes of Lu). Suitable radiation sources for use as a cell conditioner of the present invention include both solids and liquids. By way of non-limiting example, the radiation source can be a radionuclide, such as I-125, I-131, Yb-169, Ir-192 as a solid source, I-125 as a solid source, or other radionuclides that emit photons, beta particles, gamma radiation, or other therapeutic rays. The radioactive material can also be a fluid made from any 5 solution of radionuclides), e.g., a solution of I-125 or I-131, or a radioactive fluid can be produced using a slurry of a suitable fluid containing small particles of solid radionuclides, such as Au-198, Y-90. Moreover, the radionuclide(s) can be embodied in a gel or radioactive micro spheres.

Without being limited by any theory, the compounds of the present invention can render abnormal cells more sensitive to treatment with radiation for purposes of killing and/or inhibiting the growth of such cells. Accordingly, this invention further relates to a method for sensitizing abnormal cells in a mammal to treatment with radiation which comprises administering to the mammal an amount of a compound of the present invention, which amount is effective is sensitizing abnormal cells to treatment with radiation.

The compounds or pharmaceutical compositions of the present invention can be used in combination with an amount of one or more substances selected from anti-angiogenesis agents, signal transduction inhibitors, and antiproliferative agents.

Anti-angiogenesis agents, such as MMP-2 (matrix-metalloprotienase 2) inhibitors, MMP-9 (matrix-metalloprotienase 9) inhibitors, and COX-H (cyclooxygenase 11) inhibitors, can be used in conjunction with a compound of the present invention and pharmaceutical compositions described herein. Examples of useful COX-II inhibitors include CELEBREX™ (alecoxib), valdecoxib, and rofecoxib. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931,788 (published Jul. 28, 1999), WO 90/05719 (published May 31, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain Patent Application No. 9912961.1 (filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780, 386 (published Jun. 25, 1997), all of which are incorporated herein in their entireties by reference. Preferred MMP-2 and MMP-9 inhibitors are those that have little or no activity inhibiting MMP-I, More preferred, are those that selectively inhibit MMP-2 and/or AMP-9 relative to the other matrix-metalloproteinases (i.e., MAP-1, MMP-3, MMP-4, MMP-5, MMP-6, MMP-7, MMP-8, MMP-10, MMP-11, MMP-12, and MMP-13). Some specific examples of MMP inhibitors useful in the present invention are AG-3340, RO 32-3555, and RS 13-0830.

The invention also relates to a method of and to a pharmaceutical composition of treating a cardiovascular disease in a mammal which comprises an amount of a compound of the present invention, or an isotopically-labeled derivative thereof, and an amount of one or more therapeutic agents use for the treatment of cardiovascular diseases.

Examples for use in cardiovascular disease applications are anti-thrombotic agents, e.g., prostacyclin and salicylates, thrombolytic agents, e.g., streptokinase, urokinase, tissue plasminogen activator (TPA) and anisoylated plasminogen-streptokinase activator complex (APSAC), anti-platelets agents, e.g., acetyl-salicylic acid (ASA) and clopidrogel, vasodilating agents, e.g., nitrates, calcium channel blocking drugs, antiproliferative agents, e.g., colchicine and alkylating agents, intercalating agents, growth modulating factors such as interleukins, transformation growth factor-beta and congeners of platelet derived growth factor, monoclonal antibodies directed against growth factors, anti-inflammatory agents, both steroidal and non-steroidal, and other agents that can modulate vessel tone, function, arteriosclerosis, and the healing response to vessel or organ injury post intervention. Antibiotics can also be included in combinations or coatings comprised by the invention. Moreover, a coating can be used to effect therapeutic delivery locally within the vessel wall. By incorporation of the active agent in a swellable polymer, the active agent will be released upon swelling of the polymer.

Other exemplary therapeutic agents useful for a combination therapy include but are not limited to agents as described above, radiation therapy, hormone antagonists, hormones and their releasing factors, thyroid and antithyroid drugs, estrogens and progestins, androgens, adrenocorticotropic hormone; adrenocortical steroids and their synthetic analogs; inhibitors of the synthesis and actions of adrenocortical hormones, insulin, oral hypoglycemic agents, and the pharmacology of the endocrine pancreas, agents affecting calcification and bone turnover; calcium, phosphate, parathyroid hormone, vitamin D, calcitonin, vitamins such as water-soluble vitamins, vitamin B complex, ascorbic acid, fat-soluble vitamins, vitamins A, K, and E, growth factors, cytokines, chemokines, muscarinic receptor agonists and antagonists; anticholinesterase agents; agents acting at the neuromuscular junction and/or autonomic ganglia; catecholamines, sympathomimetic drugs, and adrenergic receptor agonists or antagonists; and 5-hydroxytryptamine (5-HT, serotonin) receptor agonists and antagonists.

Therapeutic agents can also include agents for pain and inflammation such as histamine and histamine antagonists, bradykinin and bradykinin antagonists, 5-hydroxytryptamine (serotonin), lipid substances that are generated by biotransformation of the products of the selective hydrolysis of membrane phospholipids, eicosanoids, prostaglandins, thromboxanes, leukotrienes, aspirin, nonsteroidal anti-inflammatory agents, analgesic-antipyretic agents, agents that inhibit the synthesis of prostaglandins and thromboxanes, selective inhibitors of the inducible cyclooxygenase, selective inhibitors of the inducible cyclooxygenase-2, autacoids, paracrine hormones, somatostatin, gastrin, cytokines that mediate interactions involved in hummoral and cellular immune responses, lipid-derived autacoids, eicosanoids, β-adrenergic agonists, ipratropium, glucocorticoids, methylxanthines, sodium channel blockers, opioid receptor agonists, calcium channel blockers, membrane stabilizers and leukotriene inhibitors.

Additional therapeutic agents contemplated herein include diuretics, vasopressin, agents affecting the renal conservation of water, rennin, angiotensin, agents useful in the treatment of myocardial ischemia, anti-hypertensive agents, angiotensin converting enzyme inhibitors, β-adrenergic receptor antagonists, agents for the treatment of hypercholesterolemia, and agents for the treatment of dyslipidemia.

Other therapeutic agents contemplated include drugs used for control of gastric acidity, agents for the treatment of peptic ulcers, agents for the treatment of gastroesophageal reflux disease, prokinetic agents, antiemetics, agents used in irritable bowel syndrome, agents used for diarrhea, agents used for constipation, agents used for inflammatory bowel disease, agents used for biliary disease, agents used for pancreatic disease. Therapeutic agents used to treat protozoan infections, drugs used to treat Malaria, Amebiasis, Giardiasis, Trichomoniasis, Trypanosomiasis, and/or Leishmaniasis, and/or drugs used in the chemotherapy of helminthiasis. Other therapeutic agents include antimicrobial agents, sulfonamides, trimethoprim-sulfamethoxazole quinoiones, and agents for urinary tract infections, penicillins, cephalosporins, and other. β-Lactam antibiotics, an agent comprising an aminoglycoside, protein synthesis inhibitors, drugs used in the chemotherapy of tuberculosis, mycobacterium avium complex disease, and leprosy, antifungal agents, antiviral agents including nonretroviral agents and antiretroviral agents.

Examples of therapeutic antibodies that can be combined with a subject compound include but are not limited to anti-receptor tyrosine kinase antibodies (cetuximab, panitumumab, trastuzumab), anti CD20 antibodies (rituximab, tositumomab), and other antibodies such as alemtuzumab, bevacizumab, and gemtuzumab.

Moreover, therapeutic agents used for immunomodulation, such as immunomodulators, immunosuppressive agents, tolerogens, and immunostimulants are contemplated by the methods herein. In addition, therapeutic agents acting on the blood and the blood-forming organs, hematopoietic agents, growth factors, minerals, and vitamins, anticoagulant, thrombolytic, and antiplatelet drugs.

Further therapeutic agents that can be combined with a subject compound may be found in Goodman and Gilman's "The Pharmacological Basis of Therapeutics" Tenth Edition edited by Hardman, Limbird and Gilman or the Physician's Desk Reference, both of which are incorporated herein by reference in their entirety.

The compounds described herein can be used in combination with the agents disclosed herein or other suitable agents, depending on the condition being treated. Hence, in some embodiments the compounds of the invention will be co-administered with other agents as described above. When used in combination therapy, the compounds described herein may be administered with the second agent simultaneously or separately. This administration in combination can include simultaneous administration of the two agents in the same dosage form, simultaneous administration in separate dosage forms, and separate administration. That is, a compound described herein and any of the agents described above can be formulated together in the same dosage form and administered simultaneously. Alternatively, a compound of the present invention and any of the agents described above can be simultaneously administered, wherein both the agents are present in separate formulations. In another alternative, a compound of the present invention can be administered just followed by and any of the agents described above, or vice versa. In the separate administration protocol, a compound of the present invention and any of the agents described above may be administered a few minutes apart, or a few hours apart, or a few days apart.

The methods in accordance with the invention may include administering a c-met kinase selective inhibitor with one or more other agents that either enhance the activity of the inhibitor or compliment its activity or use in treatment. Such additional factors and/or agents may produce an augmented or even synergistic effect when administered with a c-met kinase selective inhibitor, or minimize side effects.

In one embodiment, the methods of the invention may include administering formulations comprising a c-met kinase selective inhibitor of the invention with a particular cytokine, lymphokine, other hematopoietic factor, thrombolytic or antithrombotic factor, or anti-inflammatory agent before, during, or after administration of the c-met kinase inhibitor. One of ordinary skill can easily determine if a particular cytokine, lymphokine, hematopoietic factor, thrombolytic of anti-thrombotic factor, and/or anti-inflammatory agent enhances or compliments the activity or use of the c-met kinase inhibitors in treatment.

More specifically, and without limitation, the methods of the invention may comprise administering a c-met kinase selective inhibitor with one or more of TNF, IL-1, IL-2, IL-3, IL4, IL-5, IL-6, IL-7, IL-8, IL-9, IL-10, IL-11, IL-12, IL-13, IL14, IL-15, IL-16, IL-17, IL-18, IFN, G-CSF, Meg-CSF, GM-CSF, thrombopoietin, stem cell factor, and erythropoietin. Compositions in accordance with the invention may also include other known angiopoietins such as Ang-2, Ang4, and Ang-Y, growth Factors such as bone morphogenic protein-1, bone morphogenic protein-2, bone morphogenic protein-3, bone morphogenic protein-4, bone morphogenic protein-5, bone morphogenic protein-6, bone morphogenic protein-7, bone morphogenic protein-8, bone morphogenic protein-9, bone morphogenic protein-10, bone morphogenic protein-11, bone morphogenic protein-12, bone morphogenic protein-13, bone morphogenic protein-14, bone morphogenic protein-15, bone morphogenic protein receptor IA, bone morphogenic protein receptor IB, brain derived neurotrophic factor, ciliary neutrophil factor, ciliary neutrophic factor receptor a, cytokine-induced neutrophil chemotactic factor 1, cytokine-induced neutrophil chemotactic factor 2 alpha, cytokine-induced neutrophil chemotactic factor 2 beta, beta endothelial cell growth factor, endothelin I, epidermal growth factor, epithelial-derived neutrophil attractant, fibroblast growth factor 4, fibroblast growth factor 5, fibroblast growth factor 6, fibroblast growth factor 7, fibroblast growth factor 8, fibroblast growth factor 8b, fibroblast growth factor 8c, fibroblast growth factor 9, fibroblast growth factor 10, fibroblast growth factor acidic, fibroblast growth factor basic, glial cell line-derived neutrophic factor receptor al, glial cell line-derived neutrophic factor receptor a2, growth related protein, growth related protein a, growth related protein .beta., growth related protein .gamma., heparin binding epidermal growth factor, hepatocyte growth factor, hepatocyte growth factor receptor, insulin-like growth factor 1, insulin-like growth factor receptor, insulin-like growth factor II, Insulin-like growth factor binding protein, keratinocyte growth factor, leukemia inhibitory factor, leukemia inhibitory factor receptor alpha, nerve growth factor, nerve growth factor receptor, neurotrophin-3, neurptrophin-4, placenta growth factor, placenta growth factor 2, platelet derived endothelial cell growth factor, platelet derived growth factor, platelet derived growth factor A chain, platelet derived growth factor AA, platelet derived growth factor AB, platelet derived growth factor B chain, platelet derived growth factor BB, platelet derived growth factor receptor a, platelet derived growth factor receptor beta, pre-B cell growth stimulating factor, stem cell factor, stem cell factor receptor, transforming growth factor alpha, transforming growth factor beta, transforming growth factor beta 1, transforming growth factor beta 1.2, transforming growth factor beta 2, transforming growth factor beta 3, transforming growth factor beta 5, latent transforming growth factor beta 1, transforming growth factor beta binding protein I, transforming growth factor beta binding protein II, transforming growth factor beta binding protein III, tumor necrosis factor receptor type I, tumor necrosis factor receptor type II, urokinase-type plasminogen activator receptor, and chimeric proteins and biologically or immunologically active fragments thereof.

The following general methodology described herein provides the manner and process of making and using the compound of the present invention and are illustrative rather than limiting. Further modification of provided methodology and additionally new methods may also be devised in order to achieve and serve the purpose of the invention. Accordingly, it should be understood that there may be other embodiments which fall within the spirit and scope of the invention as defined by the specification hereto.

Representative compounds of the present invention include those specified above in Table 1 and pharmaceutically acceptable salts thereof. The present invention also includes the intermediate compounds discussed in the examples and elsewhere in the specification as well as their salts. The present invention should not be construed to be limited to them.

General Method of Preparation of Compounds of the Invention

The compounds of the present invention may be prepared by the following processes. Unless otherwise indicated, the variables (e.g. $Cy^1$, $R^2$, $L_2$, X, and $Cy^2$) when used in the below formulae are to be understood to present those groups described above in relation to formula (I).

Scheme 1:

This scheme provides a method for the preparation of the compound of formula (IA) wherein $L_2$ is —$CR^aR^b$—, X is $CR^1$ or N and the other variables such as $Cy^1$, $R^2$, and $Cy^2$ are the same as described above in relation to formula (I).

microwaves in the presence of $R^1COOH$ wherein $R^1$ is H or a $C_1$-$C_4$ alkyl group. The compound of formula (4) can be coupled with a boronic acid of formula $Cy^1$-$B(OR)_2$ (wherein R=H) or its ester (wherein R=alkyl) in the presence of a transition metal catalyst such as tetrakis(triphenylphospine) palladium(0) and a suitable base such as potassium carbonate to give the desired compounds of formula (IA) wherein $L_2$ is —$CR^aR^b$—, X is $CR^1$ or N and the other variables such as $Cy^1$, $R^2$ and $Cy^2$ are the same as described above in relation to formula (I)

Alternatively, the compound of formula (2) may be coupled with a boronic acid of formula $Cy^1$-$B(OR)_2$ (wherein R=H) or its ester (wherein R=alkyl) in the presence of a catalyst such as tetrakis(triphenylphosphine)palladium(0) and a suitable base such as potassium carbonate to give a compound of formula (5). The compound of formula (5) can then be converted to a compound of formula (6) by reducing

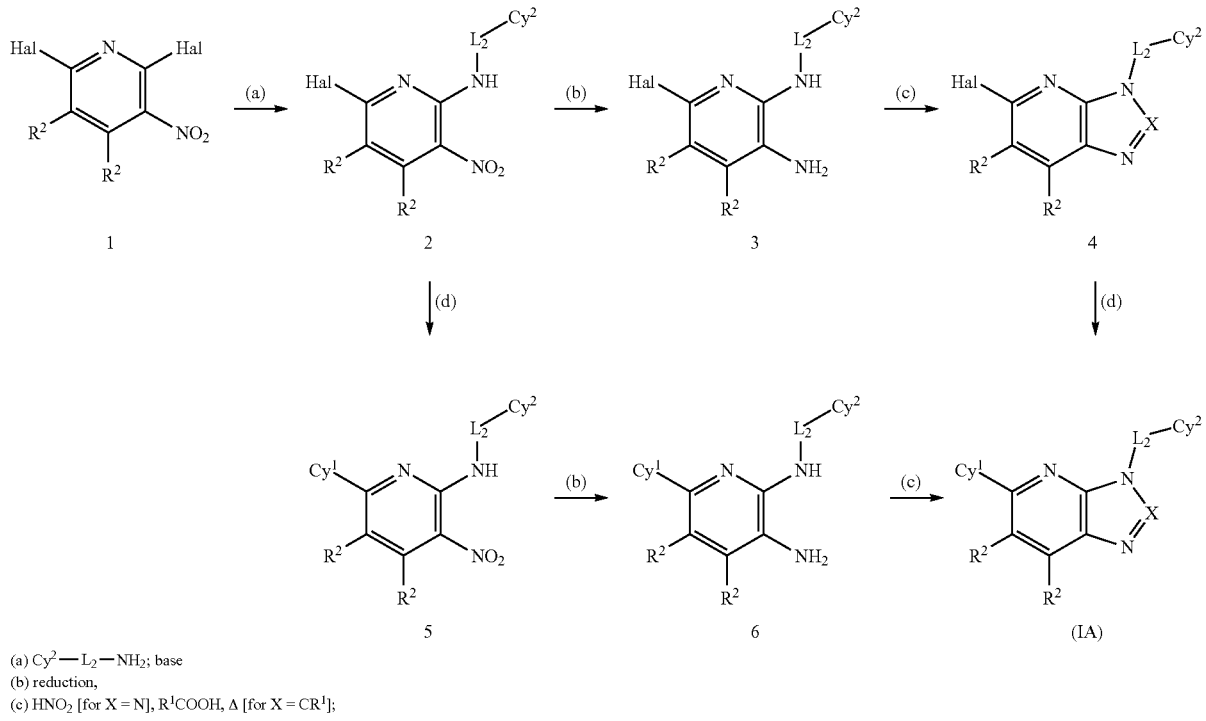

Scheme 1

(a) $Cy^2$—$L_2$—$NH_2$; base
(b) reduction,
(c) $HNO_2$ [for X = N], $R^1COOH$, Δ [for X = $CR^1$];
(d) $Cy^1$—$B(OR)_2$, base, transition metal catalyst.

The compound of formula (1) wherein Hal represents a halogen and $R^2$ is the same as described above in relation to formula (I) can be coupled with a compound of formula $Cy^2$-$L_2$-$NH_2$ in the presence of a suitable base, such as sodium or potassium carbonate, to give a compound of formula (2) wherein $L_2$ is —$CR^aR^b$—. The compound of formula (2) can then be converted to a compound of formula (3) by reducing with a metal such as iron, or a metal halide such as stannous chloride and an acid (such as acetic acid, hydrochloric acid or ammonium chloride). The compound of formula (3) can then be cyclised to a compound of formula (4) wherein X=N using nitrous acid, generated in situ by reacting an alkali metal nitrite such as sodium nitrite with an acid such as acetic acid or hydrochloric acid. The compound of formula (3) can also be cyclised to form a compound of formula (4) wherein X=$CR^1$, by heating or irradiating with with a metal such as iron, or a metal halide such as stannous chloride and an acid such as acetic acid, hydrochloric acid or ammonium chloride. The compound of formula (6) can then be cyclised to a compound of formula (IA) wherein X=N using nitrous acid, generated in situ by reacting an alkali metal nitrite such as sodium nitrite with an acid such as acetic acid or hydrochloric acid. The compound of formula (6) can also be cyclised to a compound of formula (IA) wherein X=$CR^1$, by heating or irradiating with microwaves in the presence of $R^1COOH$ wherein $R^1$ is H or a $C_1$-$C_4$ alkyl group.

Scheme 2:

This scheme provides a method for the preparation of a compound of formula (IA-1) wherein D is substituted or unsubstituted monocyclic aryl or substituted or unsubstituted monocyclic heteroaryl and the other variables such as $L_2$, $R^2$, X, and $Cy^2$ are the same as described above in relation to formula (IA-1):

Scheme 2

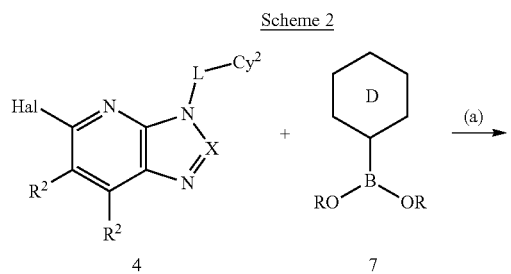

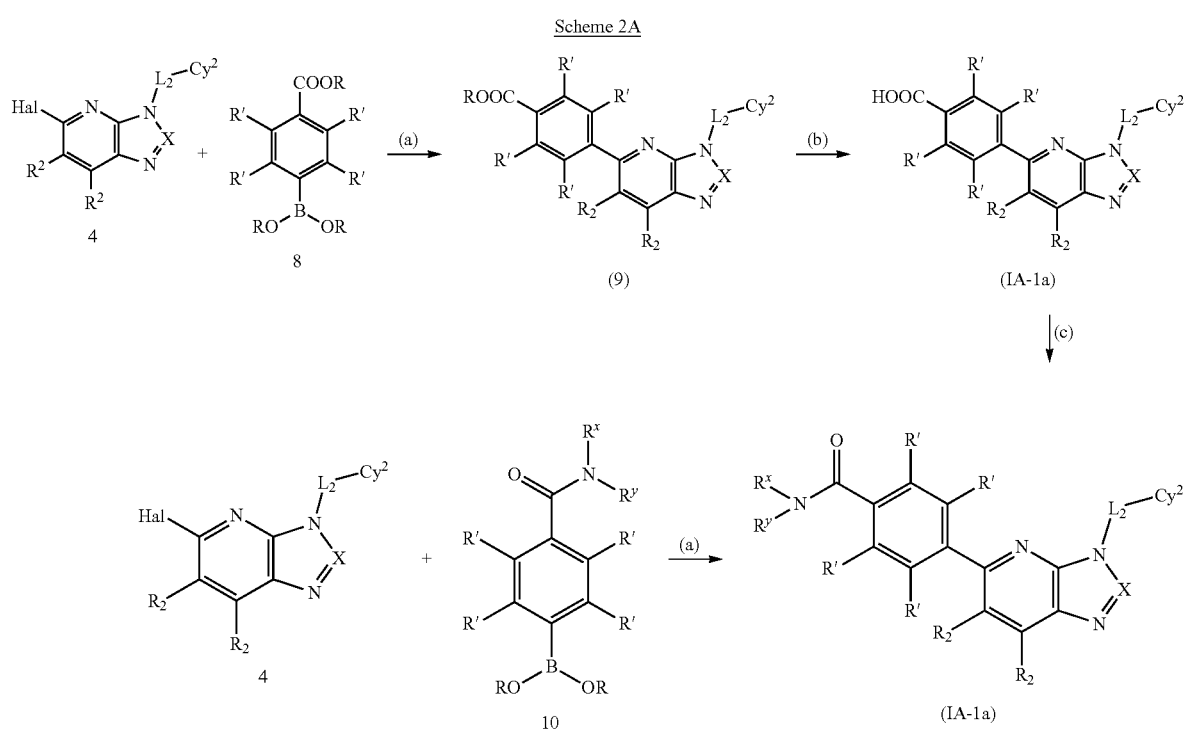

Scheme 2A (a) base, transition metal catalyst;
(b) Hydrolysis;
(c) amide coupling wih R$^x$R$^y$NH -continued

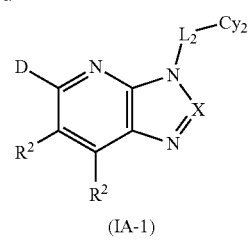

(IA-1)

(a) base, transition metal catalyst

A compound of formula (4) can be coupled with a boronic acid of formula 7 (wherein R=H) or its ester (wherein R=alkyl) in the presence of a transition metal catalyst such as tetrakis(triphenylphosphine)palladium(0) and a suitable base such as potassium carbonate to give compound of formula (IA-1).

Schemes 2A and 2B provide a non-limiting specific illustration covering some of the embodiments of the compound of formula (IA-1).

Scheme 2A:

This scheme provides a method for the preparation of a compound of formula (IA-1) wherein D is a substituted phenyl. In particular the phenyl ring is substituted with a group of formula COOR$^a$ (referred to as a compound of formula (IA-1a)) or CONR$^x$R$^y$ (referred to as a compound of formula (IA-1b)) wherein R$^x$ and R$^y$ are the same as described herein. Optionally the phenyl ring is further substituted with one or more R' wherein each R' is independently hydrogen, halogen or substituted or unsubstituted alkyl.

The compound of formula (4) can be coupled with a boronic acid of formula 8 (wherein R=H) or its ester (wherein R=alkyl) in the presence of a transition metal catalyst such as tetrakis(triphenylphosphine)palladium(0) and a suitable base such as potassium carbonate to give the compound of formula (9). The compound of formula (9) can be hydrolysed in the presence of an alkali metal hydroxide such as lithium hydroxide to give the compound of formula (IA-1a). The compound of formula (IA-1a) can be converted into a compound of formula (IA-1a) by reacting it with an amine of the formula R$^x$R$^y$NH in the presence of an amide coupling reagent such as N-(3-dimethylaminopropyl)-N'-ethylcarbodiimide hydrochloride (EDC.HCl), (benzotriazollyl)oxytris(dimethylamino)phosphonium hexafluorophosphate (BOP) or any other amide coupling reagent known in the art. Alternatively the conversion can be effected by reacting the compound of formula (IA-1a) with a halogenating agent such as thionyl chloride and subsequently reacting the resultant acid halide with an amine of the formula R^xR^yNH in the presence of a suitable base such as a trialkylamine. The compounds of formula (IA-1b) can also be obtained by reacting the compound of formula 4 with a boronic acid of formula 10 (wherein R=H) or its ester (wherein R=alkyl).

Scheme 2B:

This scheme provides a method for the preparation of compound of formula (IA-1) wherein D is a pyrazole (referred to as compound of formula (IA-1c) or substituted Pyrazole referred to as compound of formula (IA-1d). In particular the pyrazole ring is substituted with substituted or unsubstituted alkyl. Optionally the said pyrazole ring is further substituted with one or more of R'; wherein R' is hydrogen, halogen or substituted or unsubstituted alkyl.

Illustrative Examples for Scheme 2A

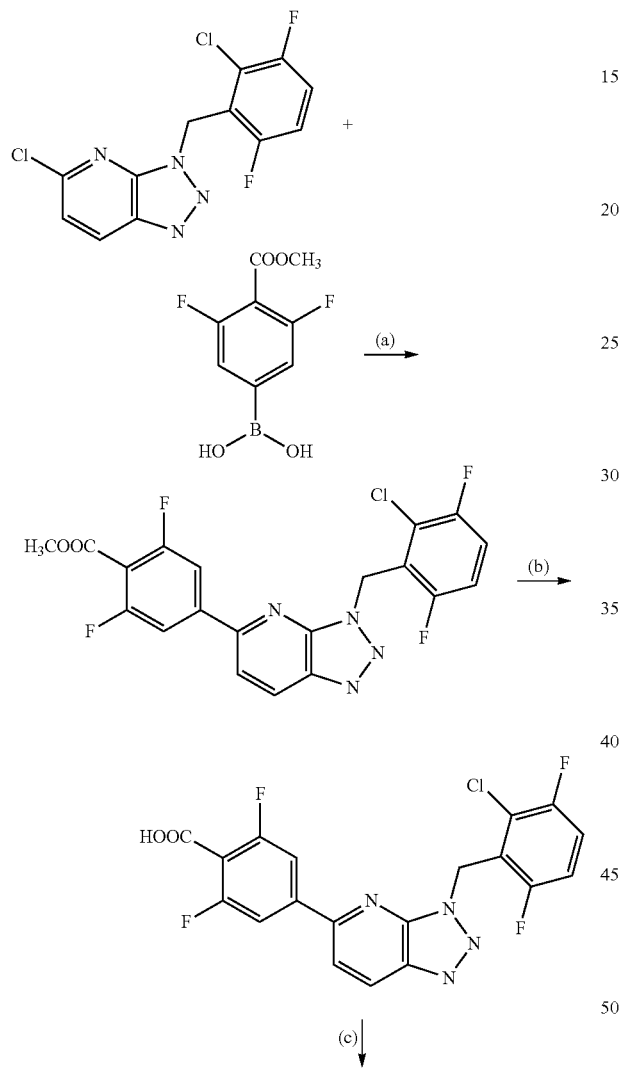

(a) base, transition metal catalyst;
(b) Hydrolysis;
(c) amide coupling wih EtNH₂

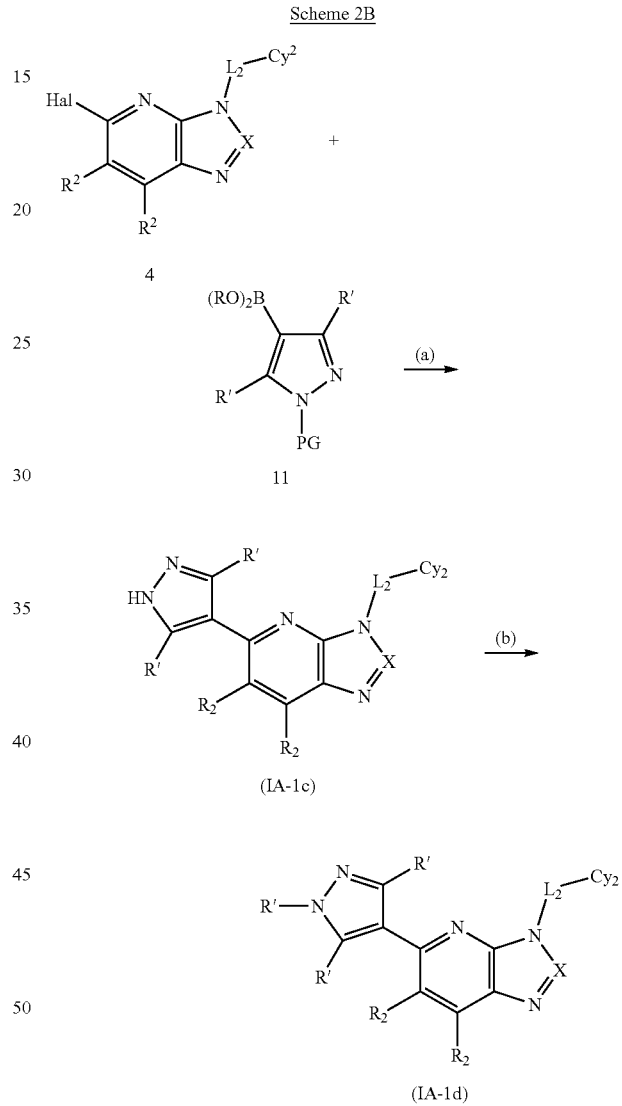

(a) base, transition metal catalyst;
(b) base, R'—X

The compound of formula (4) can be coupled with a boronic acid of formula 11 (wherein R=H) or its ester (wherein R=alkyl) in the presence of a transition metal catalyst such as tetrakis(triphenylphosphine)palladium(0) and a suitable base such as potassium carbonate to give compound of formula (IA-1c). The compound of formula (IA-1c) can be alkylated with an alkyl halide of formula R'X wherein R' is substituted or unsubstituted alkyl in the presence of a suitable base such as a metal hydride to give the compound of formula (IA-1d).

Illustrative Examples for Scheme 2B

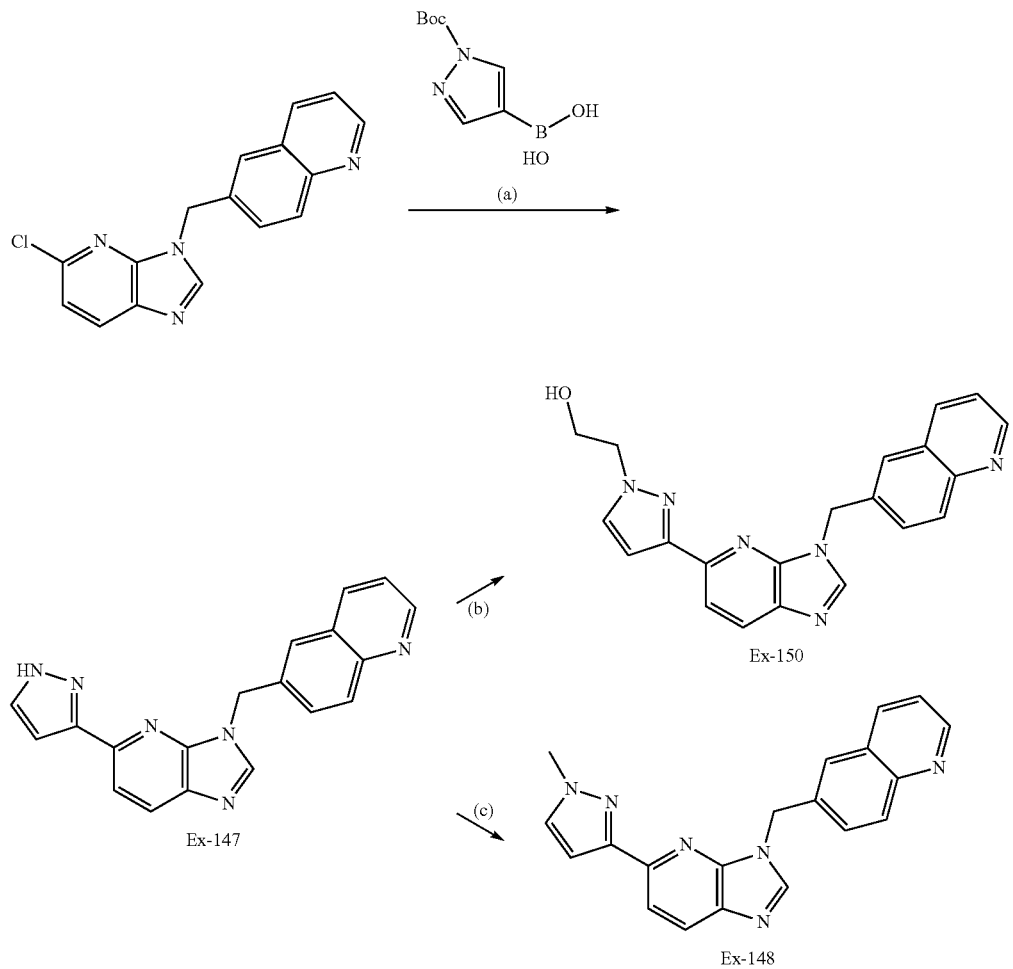

(a) base, palladium catalyst;
(b) i. PgO—CH₂CH₂—Cl, base ii. Deprotection;
(c) CH₃I, base Scheme 3:

This scheme provides a method for the preparation of the compound of formula (II) and (IIA) wherein A is —OR$^c$ or R$^c$R—N—, L$_2$ is —CR$^a$R$^b$—, X is CR$^1$ or N and the other variables such as R$^2$, and Cy$^2$ are the same as described above in relation to formula (II) and (IIA).

Scheme 3

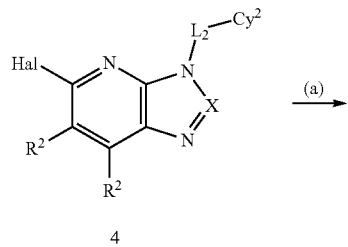

4

-continued

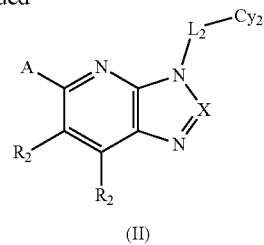

(II)

(a) AH base or base, transition metal catalyst, phosphine ligand

The compound of formula (4) can be reacted with a nucleophilic compound of formula AH wherein A is —OR$^c$ or R$^c$R—N, in the presence of a base such as an alkali metal fluoride, alkali metal carbonate or an alkali metal alkoxide to give a compound of formula (II). Optionally this reaction may be carried out in the presence of a transition metal catalyst such as palladium acetate and a phosphine ligand such as triphenyl phosphine.

Illustrative Examples for Scheme 3

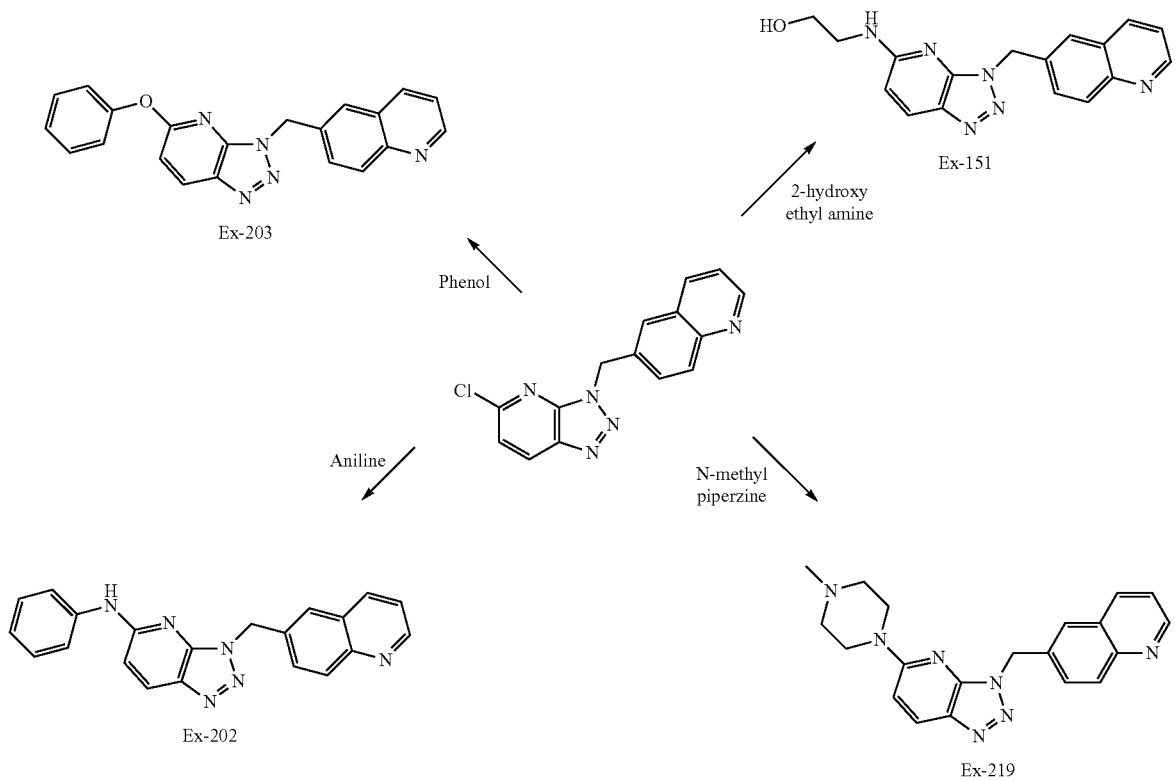

Scheme 4:

This scheme provides a method for the preparation of a compound of formula (III) wherein $L_2$ is —$CR^aR^b$—, X is $CR^1$ or N, U is C—$CR^3$, V is N, W is O or $NR^4$ and the other variables such as $R^5$, $R^2$, and $Cy^2$ are the same as described above in relation to formula (III).

Scheme 4

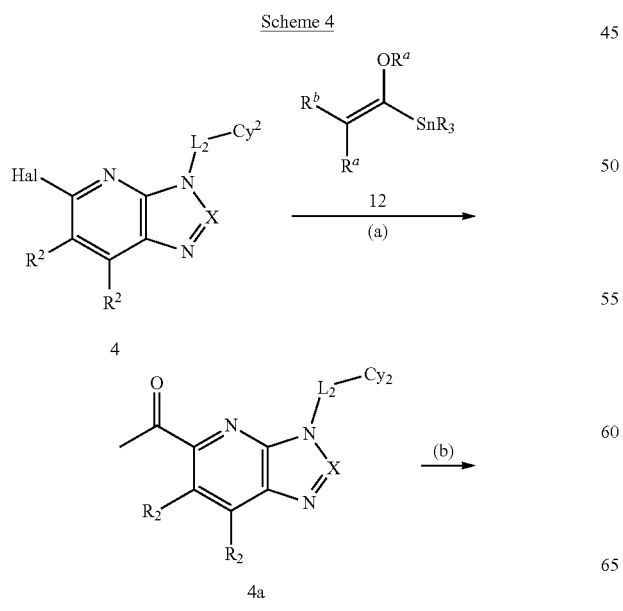

(a) transition metal catalyst;
(b) $R^5$—W—$NH_2$

-continued

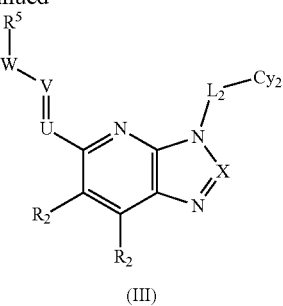

(III)

The compound of formula (4) can be reacted with a tin compound of formula 12 wherein $R^a$ and $R^b$ are (optionally $R^a$ and $R^b$ and can also be alkyl or aryl) in the presence of a transition metal catalyst such as tris(dibenzylidineacetone)palladium (0) and optionally in the presence of a ligand such as triphenylphosphine to give the compound of formula (4a). The compound of formula (4a) can be reacted with the compound of formula $R^5$—W—$NH_2$ or $R^5_2NCO$ wherein $R^5$ is as defined herein above and W is O, S or $NR^4$ to give the desired compound of formula (III).

Illustrative Examples for Scheme 4

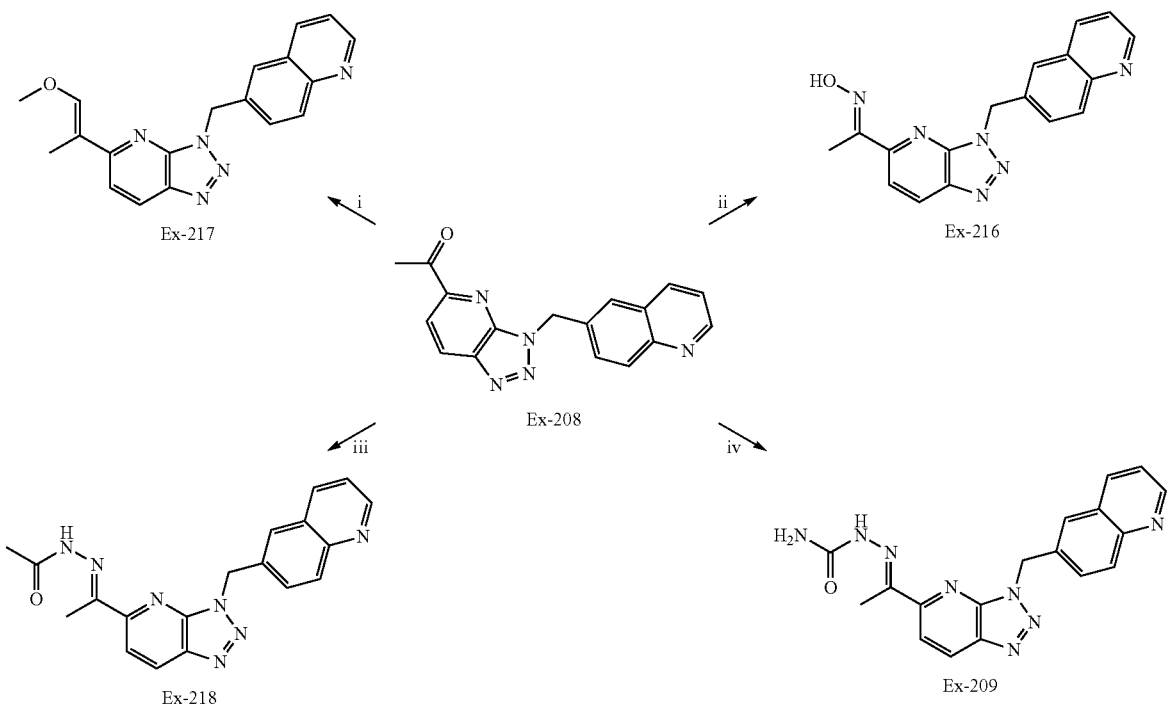

i. Methoxylamine hydrochloride,
ii. Hydroxyiamine hydrochloride,
iii. Acetyl hydrazide,
iv. Semicarbazide Similar methodologies with certain modifications as known to those skilled in the art can be used to synthesize compounds of formula (I), (IA), (IA-1) (II), (IIA), (III), (IIIA), (IIIB) and (IV) wherein all the variables are to be understood to present those groups described above in relation to formula (I), (IA), (IA-1) (II), (IIA), (III), (IIIA), (IIIB) and (IV) using suitable intermediates and reagents.

Experimental

Unless otherwise mentioned, work-up implies distribution of reaction mixture between the aqueous and organic phases indicated within parenthesis, separation and drying over $Na_2SO_4$ of the organic layer and evaporating the solvent to give a residue. Unless otherwise stated, purification implies column chromatography using silica gel as the stationary phase and a mixture of petroleum ether (boiling at 60-80° C.) and ethyl acetate or dichloromethane and methanol of suitable polarity as the mobile phases. RT implies ambient temperature (25-28° C.).

Intermediate 1: Quinolin-6-ylmethanamine

Step 1: Quinoline-6-carboxylic acid

To a mixture of 4-aminobenzoic acid (1.75 g, 1.28 mol), 4-nitrophenol (88.75 g, 0.64 mol) and sulphuric acid (1.2 lit.), glycerol (234.8 g, 2.55 mol) was added dropwise at 135° C. After 48 h, the reaction mixture was cooled to 0° C. and the pH adjusted to 3-5 with 10% sodium hydroxide solution. The resulting precipitate was collected by filtration and washed with water and dried under vacuum to afford the title compound as a black solid (125 g. 56%).

Step 2: Methyl quinoline-6-carboxylate

To a solution of quinoline-6-carboxylic acid (183 g, 1.06 mol) in methanol (1 lit.), thionyl chloride (150.7 g, 1.2 mol) was added dropwise at 0° C. and then stirred at 65° C. for 12 h. The reaction mixture was concentrated and to the residue dichloromethane and aqueous sodium carbonate solutions were added. The organic layer was dried with sodium sulphate and concentrated to afford the title compound as a brown solid (150 g, 75%).

Step 3: Quinoline-6-carboxamide

To a solution of methyl quinoline-6-carboxylate (148 g, 0.79 mol) in methanol (600 ml.), aqueous ammonia (800 ml) was added and then stirred at 45° C. for 12 h. The reaction mixture was concentrated to afford the title compound as a dark red solid (120 g, 88%).

Step 4: Quinoline-6-carbonitrile

To a solution of quinoline-6-carboxamide (177 g, 1.03 mol) in chloroform (1.5 lit.) and triethylamine (520.15 g, 5.15 mol), trifluoroacetic anhydride (540.34 g, 2.57 mol) was added dropwise below 10° C. After 1.5 h, the pH was adjusted to 7 with sodium bicarbonate solution and extracted with dichloromethane. The organic layer was dried with sodium sulphate and concentrated to afford the title compound as a brown solid (96 g, 59%).

Step 5: Quinolin-6-ylmethanamine

To a solution of quinoline-6-carbonitrile (96 g, 0.62 mol) in saturated ammonia in methanol (1 lit.), Raney-Ni (10 g) was added and the mixture was stirred at 1 atm of $H_2$ at RT for 16 h. The reaction mixture was filtered and the filtrate was concentrated under vacuum to afford the title compound as a brown oil (80 g, 82%). $^1$H-NMR (δ ppm. DMSO-$d_6$, 400 MHz): δ8.83 (dd, J=4.2, 1.7 Hz, 1H), 8.29 (d, J=8.2, 4.2 Hz, 1H), 3.90 (s, 2H).

Intermediate 2: 2-(quinolin-6-yl)propan-2-amine

Step 1: 2-(quinolin-6-yl)propan-2-ol

To an ice-cold solution of methylmagnesium iodide prepared from magnesium (0.454 g, 18.69 mmol) and methyliodide (1.16 ml, 18.69 mmol) in diethyl ether (15 ml), methyl quinoline-6-carboxylate (0.50 g, 2.67 mmol) in diethyl ether (5 ml) was added and warmed to room temperature. After 12 h, the reaction mixture was cooled to 0° C., quenched with dil. 6N HCl and extracted with ethyl acetate. The organic layer was dried over sodium sulphate and concentrated under reduced pressure and column chromatographed with ethyl acetate: petroleum ether to afford the title compound as a yellow liquid brown oil (0.41 g, 84%), $^1$H-NMR (δ ppm. DMSO-$d_6$, 400 MHz): 8.83 (dd, J=4.2, 1.7 Hz, 1H), 8.34 (dd, J=8.2, 1.1 Hz, 1H), 8.00 (d, J=1.9 Hz, 1H), 7.95 (d, J=8.8 Hz, 1H), 7.88 (dd, J=8.9, 2.0 Hz, 1H), 7.50 (q, J=4.1 Hz, 1H), 5.23 (s, 1H), 1.51 (s, 6H).

Step 2: 6-(2-azidopropan-2-yl)quinoline 2-(Quinolin-6-yl)propan-2-ol (0.50 g, 2.67 mmol) and sodium azide (1.73 g, 26.70 mmol) were added successively to ice-cold trifluoroacetic acid (20 ml) and warmed to room temperature. After 12 h, the reaction mixture was cooled to 0° C., quenched with water and basified with sodium hydroxide solution and extracted with ethyl acetate. The organic layer was dried over sodium sulphate and concentrated under reduced pressure to afford the title compound as brown liquid (0.340 g, 60%). $^1$H-NMR (δ ppm, DMSO-$d_6$, 400 MHz): δ8.90 (dd J=4.1, 1.6 Hz, 1H), 8.41 (d, J=7.6 Hz, 1H), 8.06 (d, J=2.1 Hz, 1H), 8.04 (d, J=9.0 Hz, 1H), 7.88 (dd, J=8.1, 2.2 Hz, 1H), 7.56 (q, J=4.2 Hz, 1H), 1.71 (s, 6H).

Step 3: 2-(quinolin-6-yl)propan-2-amine

To 6-(2-azidopropan-2-yl)quinoline (0.100 g. 2.67 mmol) in ethanol (3 ml), palladium on carbon (10 mg, 10% w/w) was added and stirred under a hydrogen atmosphere using hydrogen filled balloon. After 6 h, the reaction mass was filtered through celite, washed with methanol and concentrated to afford the title compound as brown liquid (0.079 g, 90%). $^1$H-NMR (δ ppm, DMSO-$d_6$, 400 MHz): δ8.82 (dd J=4.2, 1.6 Hz, 1H), 8.31 (d, J=8.9 Hz, 1H), 8.02 (d, J=1.9 Hz, 1H), 7.99 (dd, J=8.9, 2.1 Hz, 1H), 7.93 (d, J=8.9 Hz, 1H), 7.49 (q, J=4.2 Hz, 1H), 2.06 (s, 2H),1.46 (s, 6H).

Intermediate 3: (7-fluoroquinolin-6-yl)methanamine

Step 1: 6-Bromo-7-fluoroquinoline

To a mixture of 4-bromo-2-fluoroaniline (10 g, 52.62 mmol), ferrous sulphate (3.33 g, 11.97 mmol) and glycerol (15.78 ml), con.sulphuric acid (9.15 ml) was added slowly and the reaction mixture was heated to 140° C. After 12 h, the reaction mixture was cooled to 0° C. and the pH adjusted to 10-12 with 10% sodium hydroxide solution. The reaction mixture was filtered through celite, washed with ethyl acetate and layers were separated. The organic layer was washed with brine solution, dried over sodium sulphate and concentrated. The crude product was purified by column chromatography with ethyl acetate: petroleum ether to afford the title compound as a white solid (4.9 g, 44%). $^1$H-NMR (δ ppm, CDCl$_3$, 400 MHz): 8.96 (dd, J=4.3, 2.7 Hz, 1H), 8.15 (m, 2H), 7.81 (d, J=9.5 Hz, 1H), 7.42 (dd, J=8.3, 4.3 Hz, 1H).

Step 2: 7-Fluoroquinoline-6-carbonitrile

To a solution of 6-bromo-7-fluoroquinoline (4.90 g, 22.12 mmol) in dimethylacetamide (38 ml), potassium ferrocyanide (2.65 g, 4.86 mmol) and sodium carbonate (2.34 g, 22.12 mmol). The system was purged with nitrogen for 15 min. Palladium acetate (0.248 g, 1.10 mmol) was added under nitrogen and heated to 120° C. After 3 h, the reaction mixture was filtered through celite, washed with ethyl acetate. The organic layer was washed with brine solution, dried over sodium sulphate and concentrated. The crude product was purified by column chromatography with ethyl acetate: petroleum ether to afford the title compound as a white solid (3.2 g, 86%). $^1$H-NMR (δ ppm. CDCl$_3$, 400 MHz): 9.05 (dd, J=4.1, 2.9 Hz, 1H), 8.25 (m, 2H), 7.90 (d, J=10.0 Hz, 1H), 7.53 (dd, J=8.3, 4.3 Hz, 1H).

Step 3: (7-Fluoroquinolin-6-yl) methanamine

To 7-fluoroquinoline-6-carbonitrile (1.00 g, 5.813 mmol), methanol saturated with ammonia (13.5 ml) and Raney-Ni (1.27 g) were added and hydrogenated at 50-60 psi for 4 h. The reaction mixture was filtered and concentrated to afford the title compound as a brown oil (0.80 g, 78%), $^1$H-NMR (δ ppm, DMSO-$d_6$, 400 MHz): 8.85 (d, J=2.3 Hz, 1H), 8.35 (d$_6$8.0 Hz, 1H), 8.06 (d, J=9.5 Hz, 1H), 7.68 (d, J=11.8 Hz, 1H), 7.49 (t, J=3.8 Hz, 1H), 3.92 is, 2H), 1.90 (brs, 2H)

Intermediate 4: 6-Chloro-3-nitro-N-(quinolin-6-ylmethyl)pyridin-2-amine

To a solution of 2,6-Dichloro-3-nitropyridine (1.62 g, 8.42 mmol) in ethanol (30 ml), sodium carbonate (2.34 g. 22.12 mmol) was added at RT and cooled to 0° C. followed by the addition of intermediate 1 (2 g. 12.64 mmol) in ethanol (20 ml) the mixture was stirred at RT for 12 h. The reaction mixture was poured into 25 ml of water and extracted with ethyl acetate, washed with brine solution, dried over sodium sulphate and concentrated. The crude product was purified by column chromatography with dichloromethane:methanol to afford the title compound as a yellow solid (2.0 g, 50%). $^1$H-NMR (δ ppm, DMSO-$d_6$, 400 MHz): δ9.35 (t, J=6.0 Hz, 1H), 8.85 (dd, J=4.0, 1.4 Hz, 1H), 8.46 (d, J=8.5 Hz, 1H), 8.31 (d, J=7.8 Hz, 1H), 7.98 (d, J=8.7 Hz, 1H), 7.88 (s, 1H), 7.79 (dd, J=8.7, 1.6 Hz, 1H), 7.50 (dd, J=8.3, 4.2 Hz, 1H), 6.80 (d, J=8.6 Hz, 1H), 4.92 (d, J=6.1 Hz. 2H).

Intermediate 5: 6-chloro-N-(4-fluorobenzyl)-3-nitropyridin-2-amine

The title compound was obtained as a yellow solid (2.1 g, 70%) by using a procedure that is similar to the one described for intermediate 4 from 2,6-Dichloro-3-nitropyridine (2.05 g, 10.65 mmol), 4-Fluorobenzylamine (2.0 g, 15.98 mmol), ethanol (50 ml) and sodium carbonate (2.94 g, 27.80 mmol). $^1$H-NMR (δ ppm, DMSO-$d_6$, 400 MHz): δ 9.21 (t, J=5.9 Hz, 1H), 8.43 (d. J=8.6 Hz, 1H), 7.43 (m, 2H), 7.15 (m, 2H), 6.79 (d, J=8.6 Hz, 1H), 4.68 (d, J=6.1 Hz, 2H).

Intermediate 6: 6-chloro-N-(2-chloro-3,6-difluorobenzyl)-3-nitropyridin-2-amine

The title compound was obtained as a yellow solid (1.14 g, 61%) by using a procedure that is similar to the one described for intermediate 4 from 2,6-Dichloro-3-nitropyridine (0.724 g, 3.75 mmol), 2-chloro-3,6-difluorobenzylamine (1.0 g, 5.63 mmol), ethanol (25 ml) and sodium carbonate (2.94 g, 27.80 mmol). $^1$H-NMR ($\delta$ ppm, DMSO-$d_6$, 400 MHz): $\delta$8.94 (t, J=5.5 Hz, 1H), 8.41 (d, J=8.6 Hz, 1H), 7.44 (dt, J=9.0, 4.7 Hz, 1H), 7.34 (dt, 9.3, 4.3 Hz, 1H), 6.81 (d, J=8.6 Hz, 1H), 4.86 (d, J=5.5 Hz, 2H).

Intermediate 7: 6-chloro-3-nitro-N-(2-(quinolin-6-yl)propan-2-yl)pyridin-2-amine The title compound was obtained as a yellow solid (0.860 g, 47%) by using a procedure that is similar to the one described for intermediate 4 from 2,6-Dichloro-3-nitropyridine (1.55 g, 8.05 mmol). Intermediate 2 (1.0 g. 5.36 mmol), ethanol (35 ml) and sodium carbonate (2.34 g, 22.12 mmol). $^1$H-NMR ($\delta$ ppm, DMSO-$d_6$, 400 MHz): $\delta$8.84 (dd, J=4.2, 1.7 Hz, 1H), 8.76 (s, 1H), 8.42 (d, J=8.6 Hz, 1H), 8.33 (d, J=7.3 Hz, 1H), 8.00 (d, J=1.9 Hz, 1H), 7.91 (d, J=8.9 Hz, 1H), 7.85 (dd, J=8.9, 2.1 Hz, 1H), 7.49 (q, J=4.2 Hz, 1H), 6.70 (d, J=8.6 Hz, 1H), 1.89 (s, 6H).

Intermediate 8: 6-chloro-N-((7-fluoroquinolin-6-yl)methyl)-3-nitropyridin-2-amine The title compound was obtained as a yellow solid (0.750 g, 50%) by using a procedure that is similar to the one described for intermediate 4 from 2,6-dichloro-3-nitropyridine (1.31 g, 6.81 mmol), Intermediate 3 (0.80 g, 4.54 mmol), ethanol (15 ml) and sodium carbonate (0.838 g. 7.90 mmol). $^1$H-NMR ($\delta$ ppm, DMSO-$d_6$, 400 MHz): 9.27 (t, J=5.7 Hz, 1H), 8.87 (d, J=2.8 Hz, 1H), 8.49 (d, J=8.5 Hz, 1H), 8.34 (d, J=8.0 Hz, 1H), 7.96 (d, J=8.4 Hz, 1H), 7.78 (d, J=7.7 Hz, 1H), 7.49 (dd, J=8.3, 4.2 Hz. 1H), 6.83 (d, J=8.6 Hz, 1H), 4.95 (d, J=5.9 Hz, 2H).

Intermediate 9: 6-chloro-N2-(quinolin-6-ylmethyl)pyridine-2,3-diamine

Stannous chloride (0.258 g, 1.143 mmol) and conc. HCl (3 ml) were added to intermediate 4 (0.180 g, 0.571 mmol) at RT and stirred for 1 h. After 1 h stannous chloride (0.258 g, 1.143 mmol) and conc. HCl (2 ml) were added and maintained for 1 h. The reaction mixture was poured into ice water and the pH was adjusted to ca. (approx) 8 with sodium bicarbonate solution, extracted with ethyl acetate, washed with brine, dried over anhydrous sodium sulphate and concentrated to afford the title compound as a yellow solid (0.150 g, 92%). $^1$H-NMR ($\delta$ ppm, DMSO-$d_6$, 400 MHz): $\delta$8.85 (dd, J=4.2, 1.6 Hz, 1H), 8.32 (d, J=7.9 Hz, 1H), 7.98 (d, J=8.7 Hz, 1H), 7.86 (s, 1H), 7.76 (dd, J=8.7, 1.8 Hz, 1H), 7.51 (dd, J=8.3, 4.2 Hz, 1H), 6.73 (d, J=7.8 Hz. 1H), 6.59 (t, J=5.6 Hz, 1H), 6.38 (d, J=7.7 Hz, 1H). 4.92 (s, 2H), 4.70 (s, 2H).

Intermediate 10: 6-chloro-N2-(4-fluorobenzyl)pyridine-2,3-diamine

The title compound was obtained as a yellow solid (1.3 g, 99%) by using a procedure that is similar to the one described for intermediate 9 from intermediate 5 (1.5 g, 5.33 mmol), stannous chloride (4.09 g, 18.13 mmol) and conc. HCl (11.5 ml). $^1$H-NMR ($\delta$ ppm. DMSO-$d_6$, 400 MHz): $\delta$7.38 (m, 2H), 7.15 (m, 2H), 6.71 (d, J=7.8 Hz, 1H), 6.43 (t, J=5.9 Hz, 1H), 6.37 (d, J=7.8 Hz, 1H), 4.87 (s, 2H), 4.47 (d, J=5.6 Hz, 2H).

Intermediate 11: 6-chloro-N2-(2-chloro-3,6-difluorobenzyl)pyridine-2,3-diamine

Iron powder (2.0 g, 35.81 mmol) was added to a solution of the intermediate 6 (1.0 g, 2.99 mmol) in methanol (10 ml) and conc. HCl (1.5 ml) were added at RT and refluxed for 5 h. The reaction mixture was filtered through celite and concentrated. Ice water was added to the residue and the pH was adjusted to ca, 8 with sodium bicarbonate solution, extracted with ethyl acetate, washed with brine, dried over anhydrous sodium sulphate and concentrated to afford the title compound as a yellow solid (0.67 g, 74%). $^1$H-NMR ($\delta$ ppm, DMSO-$d_6$, 400 MHz): $\delta$7.47 (dt, J=9.0, 4.8 Hz, 1H), 7.34 (dt, J=9.1, 4.3 Hz, 1H), 6.69 (d, J=7.7 Hz, 1H), 6.40 (d, J=7.7 Hz, 1H), 6.13 (t, J=4.4 Hz, 1H), 4.89 (s, 2H), 4.55 (d J=3.5 Hz, 2H).

Intermediate 12: 6-chloro-N2-(2-(quinolin-6-yl)propan-2-yl)pyridine-2,3-diamine

Acetic acid (30 ml) was added at RT to a mixture of intermediate 7 (2.0 g, 5.83 mmol) and iron powder (1.6 g, 29.17 mmol) and stirred for 12 h. The reaction mixture was basified with sodium bicarbonate solution, extracted with ethyl acetate, washed with brine, dried over anhydrous sodium sulphate and concentrated to afford the title compound as a brown solid (1.42 g, 77%). $^1$H-NMR ($\delta$ ppm, DMSO-$d_6$, 400 MHz): $\delta$8.80 (d, J=2.7 Hz, 1H), 8.30 (d, J=8.0 Hz, 1H), 7.92 (s, 1H), 7.89 (d, J=8.0 Hz, 1H), 7.76 (d, J=8.8 Hz, 1H), 7.46 (q, J=4.2 Hz, 1H), 6.66 (d, J=7.7 Hz, 1H), 6.20 (d, J=7.7 Hz, 1H), 6.04 (s, 1H), 5.02 (s, 2H), 1.79 (s, 6H).

Intermediate 13: 6-Chloro-N2-((7-fluoroquinolin-6-yl)methyl)pyridine-2,3-diamine The title compound was obtained as a yellow solid (0.550 g, 74%) by using a procedure that is similar to the one described for intermediate 9 from intermediate 8 (0.750 g, 2.25 mmol), stannous chloride (2.28 g, 10.14 mmol) and conc. HCl (13 ml). $^1$H-NMR ($\delta$ ppm, DMSO-$d_6$, 400 MHz): $\delta$8.87 (d, J=3.0 Hz, 1H), 8.36 (d, J=8.2 Hz, 1H), 7.97 (d, J=8.3 Hz, 1H). 7.77 (d, J=11.6 Hz, 1H), 7.50 (dd, J=8.2, 4.1 Hz, 1H), 6.74 (d, J=8.5 Hz, 1H), 6.54 (t, J=5.0 Hz, 1H), 6.39 (d, J=7.8 Hz, 1H), 4.94 (s, 2H), 4.72 (d, J=5.3 Hz, 2H).

Intermediate 14: 6-((5-chloro-3H-[1,2,3]triazolo[4,5-b]pyridin-3-yl)methyl)quinoline Intermediate 9 (0.220 g, 0.772 mmol) was dissolved in acetic acid (1.3 ml) and cooled to 5° C. Sodium nitrite (0.063 g, 0.927 mmol) in 0.35 ml water was added slowly followed by sulphuric acid (0.09 ml). The reaction mixture was warmed to RT and stirred for 30 mm. The reaction mixture was poured into ice water and pH adjusted to ca. 8 with sodium bicarbonate solution, extracted with ethyl acetate, washed with brine, dried over sodium sulphate and concentrated to afford the title compound as a brown solid (0.220 g. 96%). $^1$H-NMR ($\delta$ ppm, DMSO-$d_6$, 400 MHz): $\delta$8.88 (s, 1H), 8.69 (d, J=8.6 Hz, 1H), 8.35 (d, J=8.1 Hz, 1H), 8.01 (d, J=8.6 Hz, 1H), 7.90 (s, 1H), 7.74 (d, J=8.5 Hz, 1H), 7.61 (d, J=8.5 Hz. 1H), 7.53 (dd, J=8.0, 4.0 Hz, 1H), 6.12 (s, 2H).

Intermediate 15: 5-chloro-3-(4-fluorobenzyl)-3H-[1,2,3]triazolo[4,5-b]pyridine The title compound was obtained as a brown solid (1.0 g, 76%) by using a procedure that is similar to the one described for intermediate 14 from intermediate 10 (1.3 g, 5.17 mmol), acetic acid (9 ml), sodium nitrite (0.428 g, 6.20 mmol), water (2.4 ml) and sulphuric acid (0.58 ml). $^1$H-NMR (δ ppm, DMSO-$d_6$, 400 MHz): δ8.66 (d, J=8.7 Hz, 1H), 7.60 (d, J=8.6 Hz. 1H), 7.43 (m, 2H), 7.20 (m, 2H), 5.90 (s, 2H).

Intermediate 16: 5-chloro-3-(2-chloro-3,6-difluorobenzyl)-3H-[1,2,3]triazolo[4,5-b]pyridine The title compound was obtained as a brown solid (0.66 g, 98%) by using a procedure that is similar to the one described for intermediate 14 from intermediate 11 (0.65 g, 2.13 mmol), acetic acid (4 ml), sodium nitrite (0.177 g, 2.56 mmol), water (0.93 ml) and sulphuric acid (0.58 ml), $^1$H-NMR (δ ppm, DMSO-$d^6$, 400 MHz): δ8.66 (d, J=8.7 Hz, 1H), 7.61 (d, J=8.8 Hz, 1H), 7.60 (dt, J=9.0, 4.9 Hz, 1H), 7.45 (dt, J=9.2, 4.2 Hz, 1H), 5.98 (s, 2H).

Intermediate 17: 6-(2-(2-(5-chloro-3H-[1,2,3]triazolo[4,5-b]pyridin-3-yl)propan-2-yl)quinoline The title compound was obtained as a brown solid (1.1 g, 91%) by using a procedure that is similar to the one described tor intermediate 14 from intermediate 12 (1.20 g, 3.83 mmol), acetic acid (7.2 ml), sodium nitrite (0.317 g, 4.604 mmol), water (2.8 ml) and sulphuric acid (0.5 ml). $^1$H-NMR (δ ppm, CDCl$_3$, 400 MHz); δ8.88 (dd, J=4.2, 1.5 Hz, 1H), 8.29 (d, J=8.6 Hz, 1H), 8.12 (d, J=7.8 Hz, 1H), 8.10 (d, J=8.9 Hz, 1H), 7.70 (d, J=2.1 Hz, 1H), 7.48 (dd, J=8.9, 2.2 Hz, 1H), 7.41 (q, J=4.2 Hz, 1H), 7.25 (m,1H), 2.44 (s, 6H), Mass: 323.76 (M$^+$).

Intermediate 18: 6-((5-Chloro-3H-[1,2,3]triazolo[4,5-b]pyridin-3-yl)methyl)-7-fluoroquinoline The title compound was obtained as a brown solid (0.345 g, 62%) by using a procedure that is similar to the one described for intermediate 14 from intermediate 13 (0.540 g, 1.78 mmol), acetic acid (3.1 ml), sodium nitrite (0.148 g, 2.13 mmol), water (0.8 ml) and sulphuric add (0.2 ml). $^1$H-NMR (δ ppm, CDCl$_3$, 400 MHz); δ 8.91 (d, J=2.9 Hz, 1H), 8.36 (d, J=8.6 Hz, 1H), 8.08 (d, J=8.1 Hz, 1H) 7.80 (d, J=11.0 Hz, 1H), 7.70 (d, J=7.8 Hz, 1H), 7.40 (m, 2H), 6.11 (s, 2H).

Intermediate 19: 2-(2-fluoro-4-(4,4,5,5-tetramethyl-1,3,2-dioxaborolan-2-yl)phenyl)propan-2-ol

Step 1: 1-(4-bromo-2-fluorophenyl)ethanol

A solution of 4-bromo-2-fluorobenzaldehyde (5 g, 24.62 mmol) in diethyl ether (10 ml) was added to an ice-cold solution of methylmagnesium iodide prepared from magnesium (1.7 g, 73.88 mmol) and methyliodide (4.58 ml, 73.88 mmol) in diethyl ether (50 ml). The mixture was warmed stirred at RT, for 12 h, and cooled to 0° C., quenched with dil. 6N HCl and extracted with ethyl acetate. The organic layer was dried over sodium sulphate and concentrated under reduced pressure to afford the title compound as red colour liquid (5 g, 94%), $^1$H-NMR (δ ppm, CDCl$_3$, 400 MHz): δ7.40 (t, J=8.2 Hz, 1H), 7.30 (dd, J=8.3. 1.7 Hz, 1H), 7.21 (dd, J=9.9, 1.9 Hz, 1H), 5.17 (q, J=6.4 Hz, 1H), 1.49 (d, J=6.5 Hz, 3H).

Step 2: 1-(4-bromo-2-fluorophenyl)ethanone

To a solution of intermediate 19 (step 1) (5.0 g, 22.82 mmol) in DMF (25 ml), pyridinium dichromate (12.8 g, 34.23 mmol) was added at room temperature. After 12 h, the reaction mixture was quenched with water, diluted with ethyl acetate and filtered through celite. The organic layer was washed with brine solution and dried over sodium sulphate and concentrated under reduced pressure to afford the title compound as a red colour liquid (4.1 g, 84%). $^1$H-NMR (δ ppm, DMSO-$d_6$, 400 MHz): δ7.76 J=8.3 Hz, 1H), 7.73 (dd, J=10.8, 1.8 Hz, 1H), 7.55 (dd, J=5.2, 1.8 Hz, 1H), 2.55 (s, 3H).

Step 3: 2-(4-bromo-2-fluorophenyl)propan-2-ol

A procedure similar to the one described in step 1 was followed to get the crude product from magnesium (0.33 g, 73.88 mmol), methyliodide (0.856 ml, 13.69 mmol), diethyl ether (10 ml) and the intermediate from step 2 (1 g, 4.56 mmol) in diethyl ether (10 ml). Purification by column chromatography with ethyl acetate: petroleum ether gave the title compound as a yellow liquid (0.5 g, 47% yield). $^1$H-NMR (δ ppm, CDCl$_3$, 400 MHz): δ7.48 (t, J=8.6 Hz, 1H), 7.27 (m, 1H), 7.21 (dd, J=11.3, 1.9 Hz, 1H), 2.04 (s, 1H), 1.60 (s, 6H).

Step 4: 2-(2-fluoro-4-(4,4,5,5-tetramethyl-1,3,2-dioxaboralan-2-yl)phenyl) propan-2-ol Potassium acetate (0.404 g, 4.11 mmol) and bis(pinacolato)diboron (0.575 g, 2.26 mmol) were added to a solution of the intermediate from step 3 (0.4800 g, 2.05 mmol) in dioxane (16 ml), and the solution was degassed for 30 min. [1,1'-bis (diphenylphosphino) ferrocene]dichloro palladium(II). CH$_2$Cl$_2$ (0.084 g, 0.102 mmol) was added under nitrogen atmosphere and heated to 80° C., After 12 h, the reaction mixture was filtered through celite and concentrated. The crude product was purified by column chromatography with ethyl acetate: petroleum ether to afford the title compound as a colourless oil (0.450 g, 61%). $^1$H-NMR (δ ppm, CDCl$_3$, 400 MHz): δ7.55 (s, 1H), 7.54 (d, J=4.8 Hz, 1H), 7.46 (d, J=12.6 Hz, 1H), 2.13 (d, J=3.5 Hz, 1H), 1.63 (d, J=5.5 Hz, 6H). 1.33 (s, 12H),

Intermediate 20: 2-(3-fluoro-4-isopropoxyphenyl)-4,4,5,5-tetramethyl-1,3,2-dioxaborolane

Step 1: 4-bromo-2-fluoro-1-isopropoxybenzene

To a solution of 4-bromo-3-fluorophenol (1.0 g, 52.35 mmol) in THF (100 ml), isopropyl alcohol (4.8 ml, 62.62 mmol) and triphenylphosphine (20.6 g, 78.52 mmol) were added and heated to 45° C. followed by diisopropylazodicarboxylate (15.4 ml, 78.52 mmol). The mixture was refluxed for 1b, concentrated and the residue was purified by column chromatography with ethyl acetate; petroleum ether to afford the title compound as a colourless liquid (13.1 g, 99%) which was used without purification in the next step.

Step 2: 2-(3-fluoro-4-isopropoxyphenyl)-4,4,5,5-tetramethyl-1,3,2-dioxaborolane The title compound was obtained as a yellow oil (13.9 g, 99%) by using the procedure described in step 4 for intermediate 19 from the product of step 1 (12.5 g g, 53.60 mmol), bis(pinacolato)diboron (15 g, 58.96 mmol), potassium acetate (10.52 g, 107.2 mmol), dioxane (125 ml) and [1,1'- bis(diphenylphosphino)ferrocene]dichloro palladium(II).CH$_2$Cl$_2$ (4.4 g, 5.36 mmol) which was used without purification in the next step.

Intermediate 21: 2-Methyl-4-(4,4,5,5-tetramethyl-1,3,2-dioxaborolan-2-yl)benzamide The title compound was obtained as a brown solid (0.600 g, 70%) by using the procedure described in step 4 for intermediate 19 from 4-bromo-2-methylbenzamide (0.700 g, 3.27 mmol), bis(pinacolato)diboron (0.913 g, 3.59 mmol), potassium acetate (0.96 g, 9.81 mmol), dioxane (12 ml) and [1,1'-bis(diphenylphosphino)ferrocene]dichloro palladium(II).CH$_2$Cl$_2$ (0.080 g, 0.098 mmol) which was used without characterisation in the next step.

Intermediate 22: 2-Chloro-5-(4,4,5,5-tetramethyl-1,3,2-dioxaborolan-2-yl)benzamide The title compound was obtained as a brown solid (0.75 g, 69%) by using the procedure described in step 4 for intermediate 19 from 5-bromo-2-chlorobenzamide (0.800 g, 3.83 mmol), bis(pinacolato)diboron (1.07 g, 4.21 mmol), potassium acetate (1.12 g, 11.49 mmol), dioxane (10.5 ml) and [1,1'-bis(diphenylphosphino)ferrocene]dichloro palladium (II). CH$_2$Cl$_2$ (0.083 g, 0.102 mmol) which was used without characterisation in the next step.

Intermediate 23: 3-amino-N,N-dimethylpropanamide trifluoroacetate

To a solution of N-boc-3-aminopropanoic acid (0.150 g, 0.793 mmol) in DMF (1.5 ml), N-Ethyldiisopropylamine (0.205 g, 1.58 mmol) and HATU (0.301 g, 0.793 mmol) were added and stirred for 5 min. Dimethylamine hydrochloride (0.065 g, 0.793 mmol) was added at RT and the reaction mixture was stirred for 12 h, Water was added to the reaction mixture and extracted with ethyl acetate, dried over sodium sulphate and concentrated under reduced pressure. The crude product was purified by column chromatography with methanol; dichloromethane to afford tert-butyl 3-(dimethylamino)-3-oxopropylcarbamate. Trifluoroacetic acid (1 ml) was added to the product obtained, stirred for 2 h and concentrated to afford title compound as the trifluoroacetate salt (0.090 g, 40%).

Intermediate 24: 2-amino-N,N-dimethylacetamide trifluoroacetate

Tert-butyl 2-(dimethylamino)-2-oxoethylcarbamate (0.120 g, 69%) was obtained by using the procedure described under intermediate 23 from N-boc-glycine (0.150 g, 0.856 mmol), DMF (1.5 ml), N-Ethyldiisopropylamine (0.221 g, 1.70 mmol), HATU (0.325 g, 0.856 mmol) and dimethylamine hydrochloride (0.069 g, 0.856 mmol). The product was dissolved in dichloromethane (1 ml), trifluoroacetic acid (0.5 ml) was added, stirred for 2 h and concentrated to give the title compound as the trifluoroacetate salt (0.100 g, 46%).

Intermediate 25: 2-amino-1-(pyrrolidin-1-yl)ethanone trifluoroacetate

Tert-butyl 2-oxo-2-(pyrrolidin-1-yl)ethylcarbamate (0.120 g, 61%) was prepared by using the procedure described under intermediate 23 from N-boc-glycine (0.150 g, 0.856 mmol), DMF (1.5 ml), N-Ethyldiisopropylamine (0.110 g, 0.856 mmol), HATU (0.325 g, 0.856 mmol) and pyrrolidine (0.061 g, 0.856 mmol). The product was dissolved in dichloromethane (1 ml), trifluoroacetic acid (0.5 ml) was added, stirred for 2 h and concentrated to give the title compound as the trifluoroacetate salt (0.100 g, 41%).

Intermediate 26: 3-amino-1-(pyrrolidin-1-yl)propan-1-one trifluoroacetate

Tert-butyl 2-oxo-2-(pyrrolidin-1-yl)propylcarbamate (0.080 g, 40%) was prepared by using the procedure described under intermediate 23 from N-boc-3-aminopropionic acid (0.150 g, 0.793 mmol), DMF (1.5 ml), N-Ethyldiisopropylamine (0.205 g, 1.58 mmol), HATU (0.301 g, 0.793 mmol) and pyrrolidine (0.056 g, 0.793 mmol). Trifluoroacetic acid (1 ml) was added to the product, stirred for 2 h and concentrated to give the title compound as the trifluoroacetate salt (0.080 g, 40%).

Intermediate 27: 3-amino-1-(piperidin-1-yl)propan-1-one trifluoroacetate

Tert-butyl 2-oxo-2-(piperidin-1-yl)propylcarbamate was prepared by using the procedure described under intermediate 23 from N-boc-3-aminopropionic acid (0.250 g, 1.32 mmol), DMF (2.5 ml), N-Ethyldiisopropylamine (0.171 g, 1.32 mmol), HATU (0.503 g, 1.32 mmol) and piperidine (0.225 g, 2.64 mmol). Trifluoroacetic acid (1 ml) was added to the product, stirred for 2 h and concentrated to give the title compound as the trifluoroacetate salt (0.120 g, 34%).

Intermediate 28: 3-amino-1-morpholinopropan-1-one trifluoroacetate

Tert-butyl 3-morpholino-3-oxopropylcarbamate was prepared by using the procedure described under intermediate 23 from N-boc-3-aminopropionic acid (0.250 g, 1.32 mmol), DMF (2.5 ml), N-Ethyldiisopropylamine (0.171 g, 1.32 mmol) and HATU (0.503 g, 1.32 mmol) and morpholine (0.230 g, 2.64 mmol). Trifluoroacetic acid (1 ml) was added to the product, stirred for 2 h and concentrated to give the title compound as the trifluoroacetate salt (0.120 g, 33%).

Intermediate 29: 6-((5-chloro-3H-imidazo[4,5-b]pyridin-3-yl)methyl)quinoline Intermediate 9 (0.200 g, 0.702 mmol) was dissolved in formic acid (1.0 ml) and heated to 300° C. and stirred for 12 h. The reaction mixture was poured into ice water and pH adjusted to 7-8 with sodium bicarbonate solution, extracted with ethyl acetate, washed with brine, dried over sodium sulphate and concentrated to afford the title compound as yellowish brown solid (0.200 g, 97% yield). $^1$H-NMR (δ ppm, DMSO-d$_6$, 400 MHz): δ8.88 (dd, J=4.0, 1.3 Hz, 1H), 8.70 (s, 1H), 8.33 (d, J=8.2 Hz, 1H), 8.19 (d, J=8.3 Hz, 1H), 8.01 (d, J=8.8 Hz, 1H), 7.81 (s, 1H), 7.73 (dd, J=8.7, 1.7 Hz, 1H), 7.52 (dd, J=8.3, 2.2 Hz, 1H), 7.37 (d, J=8.4 Hz, 1H), 5.69 (s, 2H).

Intermediate 30: 6-chloro-3-nitro-N-(1-(quinolin-6-yl)ethyl)pyridin-2-amine

The title compound was obtained as a yellow solid (0.785 g, 50%) by using a procedure that is similar to the one described for Intermediate 4 from 2,6-Dichloro-3-nitropyridine (0.924 g, 4.78 mmol), 1-(quinolin-6-yl)ethanamine (1.25 g, 7.25 mmol), ethanol (7 ml) and sodium carbonate (1.32 g, 12.54 mmol). $^1$H-NMR (δ ppm, DMSO-d$_6$; 400 MHz): δ8.86 (dd, J=4.2, 1.7 Hz, 1H), 8.78 (d, J=7.5 Hz, 1H), 8.44 (d, J=8.6 Hz, 1H), 8.33 (dd, J=8.3, 1.0 Hz, 1H), 7.99 (m, 2H), 7.89 (dd, J=8.8, 1.9 Hz, 1H), 7.51 (q, J=4.2 Hz, 1H), 6.80 (d, J=7.5 Hz, 1H), 5.57 (quintet, J=7.1 Hz, 1H). 1.69 (d, J=7.0 Hz, 3H).

Intermediate 31: 6-(m-pyrazol-4-yl)-N2-(1-(quinolin-6-yl)ethyl)pyridine-2,3-diamine To a solution of intermediate 30 (0.20 g, 0.608 mmol) and 1-tert-butoxycarbonyl-1H-pyrazole-4-boronic acid pinacol ester (0.229 g, 0.778 mmol) in dioxane (4 ml), potassium carbonate (0.279 g, 2.02 mmol) and water (0.8 ml) were added and degassed for 30 min. Tetrakis(triphenylphosphine) palladium(0) (0.055 g, 0.047 mmol) was added under nitrogen at RT and the reaction mixture was refluxed for 12 h. The solvent was evaporated completely and to the residue water was added and extracted with ethyl acetate, dried over sodium sulphate and concentrated under reduced pressure to afford the crude pyrazole compound as a yellow solid (0.219 g). To a solution of this intermediate in conc. HCl (3 ml), stannous chloride (0.750 g, 18.13 mmol) was added at RT and stirred for 5 h. The reaction mixture was poured into ice water and pH adjusted to 7-8 with sodium bicarbonate solution, extracted with ethyl acetate, washed with brine, dried over anhydrous sodium sulphate and concentrated to afford the title compound as yellow solid (0.194 g, 97%) which was used as such for the next step.

Intermediate 32: 6-chloro-N-((5,7-difluoroquinolin-6-yl)methyl)-3-nitropyridin-2-amine Step 1: 2-(5,7-difluoroquinolin-6-yl)acetic acid A mixture of 4-amino-2,6-difluorophenylacetic acid (3.2 g, 17.1 mmol), ferrous sulphate (1.04 g, 3.76 mmol), nitrobenzene (1.05 ml, 10.26 mmol) and conc. H$_2$SO$_4$ in glycerol (5.2 ml) was heated at 150° C. for 16 h. The mixture was cooled to RT, methanol (28 ml) was added followed by aq. 6N NaOH (28 ml) and heated at 110° C. for 3 h. After cooling to RT, the mixture was acidified with conc. HCl to pH 3.0. The precipitate formed was filtered, washed with water and dried under vacuum. The precipitate was refluxed with methanol, filtered under hot conditions and the filtrate was evaporated to give the title compound 11 g, 25%) as a brown solid, $^1$H-NMR (δ ppm, DMSO-d$_6$, 400 MHz): δ12.72 (bs, 1H), 8.98 (d, J=3.1 Hz, 1H): 8.47 (d, J=8.4, 1H); 7.71 (d, J=9.7, 1H); 7.62 (dd, J=8.4, 4.1, 2H); 3.85 (s, 2H).

Step 2: (5,7-difluoroquinolin-6-yl)methanamine

Diphenyl phosphoryl azide (0.5 ml, 2.32 mmol), triethylamine (0.34 ml, 2.43 mmol) and tert-butanol (1.3 ml, 13.78 mmol) were added to a solution of the product from step 1 (0.5 g, 2.24 mmol) in dioxan (6.5 ml) and heated at 110° C. for 4 h. The mixture was cooled to RT and distributed between ethyl acetate and aq, 10% citric acid. The organic layer was separated, dried over Na$_2$SO$_4$ and concentrated to leave a brown residue which was dissolved in dioxane (5 ml) and dichloromethane (1.5 ml) and treated with ether saturated with HCl (10 ml) and stirred at RT overnight. After removing the solvents completely, aq, NaHCO$_3$ was added to the residue and extracted into ethyl acetate, the organic layer dried over Na$_2$SO$_4$ and the solvent was removed. Purification of the residue by column chromatography gave the title compound as a mixture containing ca. 35 mol % of 1,3-bis((5,7-difluoroquinolin-6-yl)methyl)urea, which was used as such in the next step. $^1$H-NMR (δ ppm, DMSO-d$_6$, 400 MHz): δ8.95 (d, J=3.8 Hz, 2H); 8.45 (dd, J=7.5, 5.2, 2H): 7.65 (d, J=10.9, 2H); 7.59 (dd, J=8.29, 4.2, 2H); 6.50 (t, J=5.6, 1H), 4.44 (d, J=5.6, 2H); 3.90 (s, 2H).

Step 3: 6-chloro-N-((5,7-difluoroquinolin-6-yl)methyl)-3-nitropyridin-2-amine

The title compound was obtained as a yellow solid (0.050 g, 5%) by using a procedure that is similar to the one described for intermediate 4 from 2,6-Dichloro-3-nitropyridine (1.40 g, 7.73 mmol), (5,7-difluoroquinolin-6-yl)methanamine (1.00 g, 5.15 mmol), ethanol (10 ml) and sodium carbonate (0.97 g, 9.22 mmol). $^1$H-NMR (δ ppm. DMSO-d$_6$, 400 MHz): δ9.09 (t, J=5.1 Hz, 1H), 8.96 (d, J=3.7 Hz, 1H), 8.49 (d, J=8.4 Hz, 1H), 8.41 (d, J=8.5 Hz, 1H), 7.68 (d, J=11.0 Hz, 1H), 7.61 (dd, J=8.4, 4.2 Hz, 1H), 6.79 (d, J=8.5 Hz, 1H), 4.97 (d, J=5.5 Hz, 2H).

Intermediate 33: 6-chloro-N2-((5,7-difluoroquinolin-6-yl)methyl)pyridine-2,3-diamine The title compound was obtained as a brown solid (0.080 g, 73%) by using a procedure that is similar to the one described for intermediate 9 from intermediate 32 (0.12 g, 0.342 mmol), stannous chloride (0.347 g, 1.54 mmol) and cone, HCl (2 ml) which was used as such for the next step.

Intermediate 34: 6-((5-chloro-3H-[1,2,3]triazolo[4,5-b]pyridin-3-yl)methyl)-5,7-difluoroquinoline The title compound was obtained as a brown solid (0.068 g, 83%) by using a procedure that is similar to the one described for intermediate 14 from intermediate 33 (0.080 g, 0.249 mmol), acetic acid (0.4 ml), sodium nitrite (0.020 g, 0.299 mmol), water (0.2 ml) and sulphuric acid (0.1 ml), $^1$H-NMR (δ ppm, CDCl$_3$, 400 MHz): δ8.98 (d, J=2.7 Hz, 1H), 8.43 (d, J=8.2 Hz, 1H), 8.32 (d, J=8.6 Hz, 1H), 7.65 (d, J=10.4 Hz, 1H), 7.48 (dd, J=8.5, 4.3 Hz, 1H), 6.10 (s, 2H), 7.39 (d, J=8.6 Hz, 1H).

Intermediate 35: 2-chloro-4-(4,4,5,5-tetramethyl-1,3,2-dioxaborolan-2-yl)benzamide The title compound was obtained as a brown solid (0.75 g, 69%) by using the procedure described in step 4 for intermediate 19 from 4-bromo-2-chlorobenzamide (0.500 g, 2.13 mmol), bis(pinacolato)diboron (0.595 g, 2.34 mmol), potassium acetate (0.627 g, 6.39 mmol), dioxane (3.6 ml) and [1,1'-bis(diphenylphosphino)ferrocene]dichloro palladium (II), CH$_2$Cl$_2$ (0.052 g, 0.063 mmol). $^1$H-NMR (δ ppm, DMSO-d$_6$, 400 MHz): δ7.91 (s, 1H), 7.89 (m, 1H), 7.61 (m, 2H), 7.44 (d, J=7.6 Hz, 1H), 1.14 (s, 12H).

Intermediate 36: N-(benzo[d]thiazol-6-ylmethyl)-6-chloro-3-nitropyridin-2-amine

The title compound was obtained as a yellow solid (0.460 g, 9%) by using a procedure that is similar to the one described for intermediate 4 from 2,6-Dichloro-3-nitropyridine (4.75 g, 24.66 mmol), benzo[d]thiazol-6-ylmethanamine (2.70 g, 16.44 mmol), ethanol (50 ml) and sodium carbonate (3.03 g, 28.60 mmol) which was used as such for the next step,

Intermediate 37: N2-(benzo[d]thiazol-6-ylmethyl)-6-chloropyridine-2,3-diamine The title compound was obtained as a yellow solid (0.360 g, 88%) by using a procedure that is similar to the one described for intermediate 9 from intermediate 36 (0.450 g, 1.40 mmol), stannous chloride (1.42 g, 6.31 mmol) and conc. HCl (7.5 ml) which was used as such for the next step.

Intermediate 38: 6-((5-chloro-3H-[1,2,3]triazolo[4,5-b]pyridin-3-yl)methyl)benzo[d]thiazole The title compound was obtained as a brown solid (0.068 g, 83%) by using a procedure that is similar to the one described for intermediate 14 from intermediate 37 (0.350 g, 0.249 mmol), acetic acid (1.75 ml), sodium nitrite (0.099 g, 1.44 mmol), water (0.8 ml) and sulphuric acid (0.4 ml). $^1$H-NMR (δ ppm, CDCl$_3$, 400 MHz): δ8.99 (s, 1H), 8.32 (d, J=8.5 Hz, 1H), 8.11 (d, J=8.4 Hz, 1H), 8.07 (s, 1H), 7.66 (d, J=8.4 Hz, 1H), 7.36 (d, J=8.5 Hz, 1H), 6.00 (s, 2H).

Intermediate 39: 6-chloro-N2-(1-quinolin-6-yl)ethyl)pyridine-2,3-diamine

The title compound was obtained as a pale brown solid (0.600 g. 74%) by using a procedure that is similar to the one described for intermediate 9 from intermediate 39 (0.900 g, 2.72 mmol), stannous chloride (2.77 g, 12.28 mmol) and conc. HCl (1.5 ml) which is used without purification for next step.

Intermediate 40: 6-(1-(5-chloro-3H-[1,2,3]triazolo[4,5-b]pyridin-3-yl)ethyl)quinoline The title compound was obtained as a brown solid (0.500 g, 84%) by using a procedure that is similar to the one described for intermediate 14 from intermediate 39 (0.575 g, 1.91 mmol), acetic acid (3.5 ml), sodium nitrite (0.159 g, 2.30 mmol), water (1 ml) and sulphuric acid (0.3 ml), $^1$H-NMR (δ ppm, CDCl$_3$, 400 MHz): δ8.90 (dd, J=4.0, 2.7 Hz, 1H), 8.31 (d, J=8.6 Hz, 1H), 8.15 (d, J=8.2 Hz, 1H), 8.09 (d, J=8.8 Hz, 1H), 7.93 (s, 1H), 7.89 (dd, J=8.8, 1.9 Hz, 1H), 7.42 (dd, J=8.3, 4.1 Hz, 1H), 7.34 (d, J=8.6 Hz, 1H), 6.50 (q, J=7.1 Hz, 1H), 2.29 (d, J=7.2 Hz, 3H).

Intermediate 41: 4-bromo-2-(trifluoromethyl)benzamide

Thionyl chloride (10 ml) was added to 4-bromo-3-(trifluoromethyl)benzoic acid (1.0 g, 3.71 mmol, prepared as described by Hattori et. al. in *Bioorg. Med. Chem.* 2007, 15, 2198,) and refluxed for 3 h. Excess thionyl chloride was removed under reduced pressure and the residue was cooled to 0° C. Aqueous 25% ammonia (7 ml) was added and stirred for 15 min. The precipitate formed was washed with sodium bicarbonate solution and vacuum dried to afford title compound as a brown solid (0.500 g, 50%) which is used as such for next step.

Intermediate 42: 4-(4,4,5,5-tetramethyl-1,3,2-dioxaborolan-2-yl)-2-(trifluoromethyl)benzamide The title compound was obtained as a brown solid (0.30 g, 50%) by using the procedure described in step 4 for intermediate 19 from intermediate 41 (0.500 g. 1.86 mmol), bis(pinacolato)diboron (0.705 g, 2.77 mmol), potassium acetate (0.743 g, 7.57 mmol). dioxane (4.6 ml) and [1,1'-bis(diphenylphosphino)ferrocene]dichloro palladium(II).CH$_2$Cl$_2$ (0.061 g, 0.067 mmol) which was used without purification for the next step.

EXAMPLES

Example 1

6-((5-(4-Methoxyphenyl)-3H-[1,2,3]triazolo[4,5-b]pyridin-3-yl)methyl)quinoline To a solution of intermediate 14 (0.120 g, 0.405 mmol) and 4-methoxyphenylboronic acid (0.078 g, 0.519 mmol) in dioxane (2.4 ml), potassium carbonate (0.186 g, 1.35 mmol) and water (0.5 ml) were added and degassed for 30 min. tetrakis (triphenylphospine)palladium(0) (0.037 g, 0.032 mmol) was added under nitrogen at RT and the reaction mixture was refluxed for 12 h. The solvent was evaporated completely and water was added to the residue and extracted with ethyl acetate, dried over sodium sulphate and concentrated under reduced pressure. The crude product was purified by column chromatography with methanol: dichloromethane to afford the title compound as a yellow solid (0.084 g. 56%), M.P.: 144-146° C. $^1$H-NMR (δ ppm, DMSO-d$_6$, 400 MHz): 8.88 (d, J=2.6 Hz, 1H), 8.58 (d, J=8.7 Hz, 1H), 8.37 (d, J=8.1 Hz, 1H), 8.22 (d, J=8.9 Hz, 2H), 8.06 (d, J=8.7 Hz, 1H), 8.02 (m, 2H), 7.83 (dd, J=8.8, 1.5 Hz, 1H), 7.55 (dd, J=8.4, 4.2 Hz, 1H), 7.10 (d, J=8.8 Hz, 2H), 6.18 (s, 2H), 3.83 (s, 3H). MS (m/z): 367.95 (M$^+$).

Example 2

6-((5-(3-Methoxyphenyl)-3H-[1,2,3]triazolo[4,5-b]pyridin-3-yl)methyl)quinoline The title compound was prepared by following the procedure described for example 1 using intermediate 14 (0.120 g, 0.405 mmol), 3-methoxyphenylboronic acid (0.078 g, 0.519 mmol), potassium carbonate (0.186 g, 1.35 mmol), dioxane (2.4 ml), water (0.5 ml) and tetrakis(triphenylphosphine)palladium(0) (0.037 g, 0.032 mmol). Yellow solid (0.080 g, 53%). M.P.: 133-135° C. $^1$H-NMR (δ ppm, DMSO-d$_6$, 400 MHz): 8.88 (dd, J=4.0, 1.1 Hz, 1H), 8.64 (d, J=8.9 Hz, 1H), 8.36 (d, J=8.4 Hz, 1H), 8.13 (d, J=8.7 Hz, 1H), 8.02 (s, 1H), 7.99 (d, J=10.2 Hz, 1H), 7.83 (m, 2H), 7.74 (s, 1H), 7.53 (dd, J=8.3, 4.2 Hz, 1H), 7.47 (t, J=8.0 Hz, 1H), 7.10 (dd, J=8.2, 2.4 Hz, 1H), 6.21 (s, 2H), 3.83 (s, 3H), MS (m/z): 368.02 (M$^+$).

Example 3

3-(3-(quinolin-6-ylmethyl)-3H-[1,2,3]triazolo[4,5-b]pyridin-5-yl)benzaldehyde The title compound was prepared by following the procedure described for example 1 using intermediate 14 (0.140 g, 0.473 mmol), 3-formylphenylboronic acid (0.098 g, 0.605 mmol), potassium carbonate (0.217 g, 1.57 mmol), dioxane (2.8 ml), water (0.6 ml) and Tetrakis(triphenylphosphine)palladium(0) (0.043 g, 0.032 mmol) to give the title compound quantitatively.

Example 4

(3-(3-(quinolin-6-ylmethyl)-3H-[1,2,3]triazolo[4,5-b]pyridin-5-yl)phenyl)methanol Sodium borohydride (0.018 g, 0.493 mmol) was added to a solution of example 3 (0.180 g, 0.493 mmol) in methanol (4 ml), cooled to 0° C., and stirred 1 h. Ice-cold water was added to the mixture, extracted with ethyl acetate, washed with brine, dried over sodium sulphate and concentrated. The crude product was purified by column chromatography with methanol: dichloromethane to afford the title compound as a yellow solid (0.044 g, 24%). M.P. 191-193° C. $^1$H-NMR (δ ppm, DMSO-$d_6$, 400 MHz): 8.88 (dd. J=4.2, 1.7 Hz, 1H), 8.63 (d, J=8.7 Hz, 1H), 8.38 (d, J=8.3 Hz, 1H), 8.21 (d, J=8.3 Hz, 2H), 8.12 (d, J=8.8 Hz, 1H), 8.02 (s, 1H), 8.02 (d, J=8.8 Hz, 1H), 7.83 (dd, J=8.7, 2.0 Hz, 1H), 7.53 (m, 3H), 6.20 (s, 2H), 5.30 (t, J=5.7 Hz, 1H), 4.58 (d, J=5.4 Hz, 2H). MS (m/z): 368.37 ($M^{30}$+1).

Example 5

4-(3-(quinolin-6-ylmethyl)-3H-[1,2,3]triazolo[4,5-b]pyridin-5-yl)benzaldehyde The title compound was prepared by following the procedure described for example 1 using intermediate 14 (0.140 g, 0.473 mmol), 4-formylphenylboronic acid (0.098 g, 0.605 mmol), potassium carbonate (0.217 g. 1.57 mmol), dioxane (2.8 ml), water (0.5 ml) and tetrakis(triphenylphosphine)palladium(0) (0.043 g, 0.037 mmol). Brown solid (0.100 g, 58%), $^1$H-NMR (δ ppm, DMSO-$d_6$, 400 MHz): 10.10 (s, 1H), 8.88 (dd, J=4.2, 1.7 Hz, 1H), 8.74 (d, J=8.7 Hz, 1H), 8.48 (d, J=8.3 Hz, 2H). 8.39 (dd, J=8.4, 1.0 Hz, 1H), 8.25 (d, J=8.7 Hz, Hz, 1H), 8.08 (d, J=8.5 Hz, 2H), 8.04 (d, J=1.7 Hz, 1H), 8.02 (d, J=8.7 Hz, 1H), 7.84 (dd, J=8.7, 2.0 Hz, 1H), 7.51 (q, J=4.3 Hz, 1H), 6.23 (s, 2H).

Example 6

(4-(3-(quinolin-6-ylmethyl)-3H-[1,2,3]triazolo[4,5-b]pyridin-5-yl)phenyl)methanol To a solution of example 5 (0.180 g, 0.493 mmol) in methanol (4 ml) cooled to 0° C., sodium borohydride (0.018 g, 0.493 mmol) was added and stirred for 1 h. The reaction was quenched by the addition of ice-cold water, extracted with ethyl acetate, washed with brine, dried over sodium sulphate and concentrated. The crude product was purified by column chromatography with methanol: dichloromethane to afford the title compound as a yellow solid (0.070 g, 39%). M.P.: 187-189° C. $^1$H-NMR (δ ppm, DMSO-$d_6$, 400 MHz): 8.88 (dd, J=4.2, 1.7 Hz, 1H), 8.63 (d, J=8.7 Hz, 1H), 8.38 (d, J=8.3 Hz, 1H), 8.22 (d, J=8.3 Hz, 2H), 8.12 (d, J=8.7 Hz, 1H), 8.02 (s, 1H), 8.02 (d, J=8.4 Hz, 1H), 7.83 (dd, J=8.7, 2.0 Hz, 1H), 7.53 (dd, J=8.3, 4.2 Hz, 1H), 7.49 (d, J=8.4 Hz, 2H), 6.20 (s, 2H), 5.32 (t, J=5.7 Hz, 1H), 4.58 (d, J=5.7 Hz, 2H). MS (m/z): 367.88 ($M^+$).

Example 7

Methyl-4-(3-(quinolin-6-ylmethyl)-3H-[1,2,3]triazolo[4,5-b]pyridin-5-yl)benzoate The title compound was prepared by following the procedure described for example 1 using intermediate 14 (0.130 g, 0.439 mmol), 4-methoxycarbonylphenylboronic acid (0.100 g, 0.562 mmol), potassium carbonate (0.202 g, 1.46 mmol), dioxane (2.6 ml), water (0.5 ml) and tetrakis(triphenylphosphine)palladium(0) (0.040 g, 0.035 mmol). Off-white solid (0.100 g, 57%). $^1$H-NMR (δ ppm, DMSO-$d_6$, 400 MHz): 8.88 (dd, J=4.2, 1.8 Hz, 1H), 8.72 (d, J=8.7 Hz, 1H), 8.39 (m, 3H), 8.21 (d, J=8.8 Hz, 1H), 8.12 (d, J=8.6 Hz, 2H), 8.02 (s, 1H), 8.02 (d, J=8.8 Hz, 1H), 7.84 (dd, J=8.6, 2.0 Hz, 1H), 7.53 (dd, J=8.3, 4.2 Hz, 1H), 6.23 (s, 2H), 3.89 (s, 3H).

Example 8

4-(3-(quinolin-6-ylmethyl)-3H-[1,2,3]triazolo[4,5-b]pyridin-5-yl)benzoic acid To a solution of Example 7 (0.095 g. 0.240 mmol) in methanol (1.4 ml), lithium hydroxide (0.028 g, 1.20 mmol) in water (0.36 ml) was added and stirred at RT. After 12 h, the pH was adjusted to (approx) 7.5 using 0.5N HCl and the solid precipitated was filtered, washed with ethyl acetate and petroleum ether and dried under vacuum to afford the title compound as an off-white solid (0.070 g, 76%). M.P.: 245-247° C. $^1$H-NMR (δ ppm, DMSO-$d_6$, 400 MHz): 13.18 (s, 1H), 8.88 (dd, J=4.1, 1.7 Hz, 1H), 8.71 (d, J=8.7 Hz, 1H), 8.39 (d, J=1.1 Hz, 1H), 8.36 (d, J=8.5 Hz, 2H), 8.21 (d, J=8.7 Hz, 1H), 8.10 (d, J=8.5 Hz, 2H), 8.03 (d, J=9.2 Hz, 2H), 7.84 (dd, J=8.7, 2.0 Hz, 1H), 7.53 (dd. J=8.4, 4.2 Hz, 1H), 6.22 (s, 2H). MS (m/z): 381.88 ($M^+$).

Example 9

N-Methyl-4-(3-quinolin-6-ylmethyl)-3H-[1,2,3]triazolo[4,5-b]pyridin-5-yl)benzamide To Example 8 (0.050 g, 0.131 mmol) was refluxed with thionyl chloride (2 ml) for 3 h. Thionyl chloride was evaporated and the residue was cooled to 0° C. and an ethanolic 50% methylamine (1 ml) was added and stirred for 15 min. The precipitate formed was dissolved in dichloromethane, washed with sodium bicarbonate solution dried over sodium sulphate and concentrated to afford the title compound as an off-white solid (0.020 g, 39%). M.P.: 220-222° C. $^1$H-NMR (δ ppm, DMSO-$d_6$, 400 MHz): 8.88 (dd, J=4.2, 1.7 Hz, 1H), 8.69 (d, J=8.7 Hz, 1H), 8.57 (q, J=4.5 Hz, 1H), 8.38 (d, J=1.6 Hz, 1H) 8.33 (d, J=8.5 Hz, 2H), 8.20 (d, J=8.8 Hz, 1H), 8.03 (m, 4H), 7.84 (dd, J=8.7, 1.6 Hz, 1H), 7.53 (dd, J=8.3, 4.1 Hz, 1H), 6.22 (s, 2H), 2.81, (d, J=4.5 Hz, 3H), MS (m/z): 394.97 ($M^+$).

Example 10

4-(3-(4-Fluorobenzyl)-3H-[1,2,3]triazolo[4,5-b]pyridin-5-yl)benzaldehyde

The title compound was prepared by following the procedure described for example 1 using intermediate 15 (0.100 g, 0.380 mmol), 4-formylphenylboronic acid (0.073 g, 0.487 mmol), potassium carbonate (0.175 g, 1.26 mmol), dioxane (2.3 ml), water (0.5 ml) and tetrakis(triphenylphosphine)palladium(0) (0.035 g, 0.030 mmol). Brown solid (0.095 g, 68%). $^1$H-NMR (δ ppm, DMSO-$d_6$, 400 MHz): 10.11 (s, 1H), 8.72 (d, J=8.7 Hz, 1H), 8.48 (d, J=8.3 Hz, 2H), 8.24 (d, J=8.7 Hz, 1H), 8.10 (d, J=8.4 Hz, 2H), 7.55 (m, 2H), 7.22 (m, 2H), 6.01 (s, 2H).

Example 11

(4-(3-(Fluorobenzyl)-3H-[1,2,3]triazolo[4,5-b]pyridin-5-yl)phenyl)methanol

To a solution of example 10 (0.095 g, 0.259 mmol) in methanol (2 ml) cooled to 0° C., sodium borohydride (0.010 g, 0.259 mmol) was added and stirred for 1 h. The reaction was quenched by the addition of ice-cold water, extracted with ethyl acetate, washed with brine, dried over sodium sulphate and concentrated. The crude product was purified by column chromatography with methanol: dichloromethane to afford the title compound as an off-white solid (0.040 g, 46%). M.P.: 210-213° C., $^1$H-NMR (δ ppm, DMSO-d$_6$, 400 MHz): 8.61 (d, J=8.7 Hz, 1H), 8.22 (d, J=8.3 Hz, 2H), 8.11 (d, J=8.8 Hz, 1H), 7.53 (m, 4H), 7.21 (m, 2H), 5.98 (s, 2H), 5.32 (t, J=5.8 Hz, 1H), 4.59 (d, J=5.7 Hz, 2H). MS (m/z): 335.05 (M$^+$+1).

Example 12

Methyl-2-fluoro-4-(4-(quinolin-6-ylmethyl)-3H-[1,2,3]triazolo[4,5-b]pyridin-5-yl)benzoate The title compound was prepared by following the procedure described for example 1 using intermediate 14 (0.300 g, 1.01 mmol), 3-fluoro-4-methoxycarbonylphenylboronic acid (0.257 g, 1.29 mmol), potassium carbonate (0.466 g, 13.37 mmol), dioxane (6 ml), water (1.2 ml) and tetrakis(triphenylphosphine)palladium(0) (0.093 g, 0.081 mmol). Brown colour solid (0.300 g, 71%). $^1$H-NMR (δ ppm, DMSO-d$_6$, 400 MHz): 8.88 (dd, J=4.2, 1.8 Hz, 1H), 8.74 (d, J=8.7 Hz, 1H), 8.38 (dd, J=8.4, 1.0 Hz, 1H), 8.27 (d, J=8.8 Hz, 1H), 8.24 (s, 1H). 8.22 (m, 1H). 8.07-8.00 (m, 3H), 7.83 (dd, J=8.7, 2.0 Hz, 1H), 7.63 (m, 1H), 6.24 (s, 2H), 3.89 (s, 3H).

Example 13

2-Fluoro-4-(4-(quinolin-6-ylmethyl)-3H-[1,2,3]triazolo[4,5-b]pyridin-5-yl)benzoic acid To a solution of Example 12 (0.230 g, 0.556 mmol) in methanol (3.5 ml), lithium hydroxide (0.132 g, 5.56 mmol) in water (0.9 ml) was added and stirred at RT. After 12 h, the pH was adjusted to 7-7.5 using 0.5N HCl and the solid precipitated was filtered, washed with ethyl acetate and petroleum ether and dried under vacuum to afford the title compound as pale brown solid (0.130 g, 61%). M.P.: 254-257° C. $^1$H-NMR (δ ppm. DMSO-d$_6$, 400 MHz): 13.43 (s, 1H), 8.88 (dd, J=4.2, 1.7 Hz, 1H), 8.73 (d, J=8.8 Hz, 1H), 8.38 (d, J=7.5 Hz, 1H), 8.25 (d, J=8.8 Hz, 1H), 8.19 (m, 2H), 8.04 (m, 3H), 7.83 (dd, J=8.8, 2.0 Hz, 1H), 7.53 (dd, J=8.4, 4.2 Hz, 1H), 6.23 (s, 2H), MS (m/z): 400.01 (M$^+$+1).

Example 14

2-Fluoro-N-methyl-4-(3-(quinolin-6-ylmethyl)-3H-[1,2,3]triazolo[4,5-b]pyridin-5-yl)benzamide To Example 13 (0.045 g, 0.112 mmol), thionyl chloride (3 ml) was added and refluxed for 3 h. The excess thionyl chloride was removed under reduced pressure and the residue was cooled to 0° C. Methylamine in ethanol (50% solution, 3 ml) was added and stirred for 1.5 min. The precipitate formed was dissolved in dichloromethane, washed with sodium bicarbonate solution dried over sodium sulphate and concentrated to afford title compound as pale brown solid (0.015 g, 32%). M.P.: 212-214° C. $^1$H-NMR (δ ppm, DMSO-d$_6$ 400 MHz): 8.88 (dd, J=4.2, 1.7 Hz, 1H), 8.72 (d, J=8.7 Hz, 1H), 8.37 (m, 2H), 8.23 (d, J=8.8 Hz, 1H), 8.18 (m, 2H), 8.04 (d, J=1.7 Hz, 1H), 8.02 (d, J=8.7 Hz, 1H), 7.83 (dd, J=8.8, 2.0 Hz, 1H), 7.80 (t, J=8.1 Hz, 1H), 7.53 (dd, J=8.3, 4.1 Hz, 1H), 6.23 (s, 2H), 2.80 (d, J=4.6 Hz, 3H), MS (m/z): 412.96 (M$^+$).

Example 12

2-Fluoro-4-(3-(quinolin-6-ylmethyl)-3H-[1,2,3]triazolo[4,5-b]pyridin-5-yl)benzamide To Example 13 (0.045 g, 0.112 mmol), thionyl chloride (3 ml) was added and refluxed for 3 h. The excess thionyl chloride was removed under reduced pressure and the residue was cooled to 0° C. Aqueous ammonia (25% solution, 3 ml) was added and stirred for 15 min. The precipitate formed was dissolved in dichloromethane, washed with sodium bicarbonate solution dried over sodium sulphate and concentrated to afford title compound as off-white solid (0.025 g, 56%). M.P.: 198-200° C. $^1$H-NMR (δ ppm, DMSO-d$_6$, 400 MHz): 8.88 (dd, J=4.2, 1.7 Hz, 1H), 8.72 (d, J=8.7 Hz, 1H), 8.38 (dd, J=8.5, 1.0 Hz, 1H). 8.23 (d, J=8.7 Hz, 1H), 8.17 (m, 2H), 8.04 (d, J=1.6 Hz, 1H), 8.02 (d, J=8.7 Hz, 1H), 7.84 (m, 3H), 7.74 (br s, 1H), 7.54 (dd, J=8.3, 4.2 Hz, 1H), 6.23 (s, 2H), MS (m/z): 398.89 (M$^+$).

Example 16

(2-Fluoro-4-(3-(quinolin-6-ylmethyl)-3H-[1,2,3]triazolo[4,5-b]pyridin-5-yl)phenyl)methanol To a solution of Example 12 (0.130 g, 0.314 mmol) in THF (1.3 ml) cooled to 0° C., DIBAL-H (25% in toluene, 0.84 ml, 1.25 mmol) was added, stirred at RT for 3 h. The reaction mixture was poured in ice-cold water and extracted with ethyl acetate, washed with brine, dried over sodium sulphate and concentrated. The crude product was purified by column chromatography with methanol:dichloromethane to afford the title compound as pale yellow solid (0.030 g, 25%), M.P.: 202-204° C. $^1$H-NMR (δ ppm, DMSO-d$_6$, 400 MHz): 8.88 (dd, J=4.1, 1.6 Hz, 1H), 8.67 (d, J=8.7 Hz, 1H), 8.38 (d, J=8.4 Hz, 1H), 8.18 (d, J=8.7 Hz, 1H), 8.12 (dd, J=8.0, 1.5 Hz, 1H), 8.04 (m, 3H), 7.83 (dd, J=8.7, 1.9 Hz, 1H), 7.65 (t, J=7.9 Hz, 1H), 7.53 (dd, J=8.3, 4.2 Hz, 1H), 6.22 (s, 2H), 5.41 (t, J=5.8 Hz, 1H), 4.62 (d, J=5.6 Hz, 2H). MS (m/z): 386.01 (M$^+$+1).

Example 17

Methyl-4-(3-(2-chloro-3,6-difluorobenzyl)-3H-[1,2,3]triazolo[4,5-b]pyridin-5-yl)-2-fluorobenzoate The title compound was prepared by following the procedure described for example 1 using intermediate 16 (0.300 g, 0.951 mmol), 3-fluoro-4-methoxycarbonyl phenylboronic acid (0.241 g, 1.21 mmol), potassium phosphate (0.606 g, 2.856 mmol), toluene (10 ml), and Tetrakis(triphenylphosphine) palladium(0) (0.088 g, 0.076 mmol). Brown colour solid (0.380 g, 92%). $^1$H-NMR (δ ppm, DMSO-d$_6$, 400 MHz): 8.71 (d, J=8.7 Hz, 1H), 8.25 (d, J=8.7 Hz. 1H), 8.17 (s, 1H), 8.15 (d, J=7.2 Hz, 1H), 8.06 (t, J=8.0 Hz. 1H), 7.53 (dt, J=8.9, 5.2 Hz, 1H), 7.46 (dt, J=9.1, 4.2 Hz, 1H), 6.13 (s, 2H), 3.89 (s, 3H).

Example 18

4-(3-(2-Chloro-3,6-difluorobenzyl)-3H-[1,2,3]triazolo[4,5-b]pyridin-5-yl)-2-fluorobenzoic acid To a solution of Example 17 (0.300 g, 0.725 mmol) in methanol (1 ml), THF (2 ml), sodium hydroxide (0.150 g, 3.75 mmol) in water (1 ml) was added and stirred at RT. After 12 h, the pH was adjusted to 7-7.5 using 0.5N HCl and the solid precipitated was filtered, washed with ethyl acetate and petroleum ether and dried under vacuum to afford the title compound as a pale brown solid (0.120 g, 41%). M.P.: 211-213° C. $^1$H-NMR (δ ppm, DMSO-$d_6$, 400 MHz): 8.65 (d, J=8.8 Hz, 1H), 8.18 (d, J=8.8 Hz, 1H), 8.02 (m, 2H), 7.83 (t, J=7.4 Hz, 1H). 7.60 (dt, J=9.1, 4.8 Hz, 1H), 7.46 (dt, J=9.0, 4.0 Hz, 1H), 6.11 (s, 2H), MS (m/z): 418.70 ($M^+$).

Example 19

4-(3-(2-Chloro-3,6-difluorobenzyl)-3H-[1,2,3]triazolo[4,5-b]pyridin-5-yl)-2-fluoro-N-methylbenzamide To Example 18 (0.100 g, 0.250 mmol), thionyl chloride (2 ml) was added and refluxed for 3 h. The excess thionyl chloride was removed under reduced pressure and the residue was cooled to 0° C. Methylamine in ethanol (50% solution, 3 ml) was added and stirred for 15 min. The precipitate formed was filtered and washed with petroleum ether and to afford title compound as pale brown solid (0.030 g, 27%). M.P.: 213-215° C. $^1$H-NMR (δ ppm, DMSO-$d_6$, 400 MHz): 8.69 (d, J=8.8 Hz, 1H), 8.36 (br s, 1H), 8.22 (d. J=8.8 Hz, 1H), 8.12 (d, J=7.4 Hz, 1H), 8.10 (d, J=11.2 Hz, 1H), 7.80 (t, J=7.8 Hz, 1H), 7.61 (dt, J=8.8, 4.7 Hz, 1H), 7.45 (dt, J=9.2, 4.3 Hz, 1H), 6.13 (s, 2H), 2.80 (d, J=4.3 Hz, 3H). MS (m/z): 431.80 ($M^+$).

Example 20

N-(2-Hydroxyethyl)-4-(3-(quinolin-6-ylmethyl)-3H-[1,2,3]triazolo[4,5-b]pyridin-5-yl)benzamide To Example 8 (0.090 g, 0.235 mmol), thionyl chloride (3 ml) was added and refluxed for 3 h. The excess thionyl chloride was removed under reduced pressure and the residue was cooled to 0° C. Ethanolamine (5 ml) was added and stirred for 1 h. The precipitate formed was filtered and washed with petroleum ether and to afford title compound as an off-white solid (0.022 g, 22%). M.P.: >260° C. $^1$H-NMR (δ ppm, DMSO-$d_6$, 400 MHz): 8.88 (d, J=2.9 Hz, 1H), 8.69 (d, J=8.8 Hz, 1H), 8.57 (t, J=5.4 Hz, 1H), 8.38 (d, J=8.7 Hz, 1H), 8.34 (d, J=8.3 Hz, 2H), 8.21 (d, J=8.7 Hz, 1H), 8.03 (m, 4H), 7.84 (d, J=8.8 Hz, 1H), 7.53 (dd, J=8.3, 4.2 Hz, 1H), 6.22 (s, 2H), 4.76 (t, J=5.3 Hz, 1H), 3.53 (q, J=6.0 Hz, 2H), 3.36 (t, J=6.04.3 Hz, 2H).

Example 21

4-(3-(quinolin-6-ylmethyl)-3H-[1,2,3]triazolo[4,5-b]pyridin-5-yl)benzamide

To Example 8 (0.050 g, 0.131 mmol), thionyl chloride (1 ml) was added and refluxed for 3 h. The excess thionyl chloride was removed under reduced pressure and the residue was cooled to 0° C. Aqueous ammonia (25% solution, 3 ml) was added and stirred for 15 min. The precipitate formed was filtered, washed with petroleum ether and dried to afford title compound as a yellow solid (0.020 g, 40%). M.P.: 229-231° C. $^1$H-NMR (δ ppm, DMSO-$d_6$, 400 MHz): 8.88 (dd, J=4.1, 1.5 Hz, 1H), 8.69 (d, J=8.7 Hz, 1H), 8.38 (dd, J=7.4 Hz, 1H), 8.33 (d, J=8.3 Hz, 2H), 8.21 (d, J=8.9 Hz, 1H), 8.09 (s, 1H), 8.04-8.00 (m, 4H), 7.84 (dd, J=8.8, 1.9 Hz, 1H), 7.53 (dd, J=8.4, 4.2 Hz, 1H), 7.48 (s, 1H), 6.22 (s, 2H), MS (m/z): 380.90 ($M^++1$).

Example 22

Lithium 4-(3-(quinolin-6-ylmethyl)-3H-[1,2,3]triazolo[4,5-b]pyridin-5-yl)benzoate To Example 8 (0.010 g, 0.026 mmol), in methanol, lithium hydroxide (1.09 mg) was and stirred at RT for 12 h. The reaction mixture was concentrated completely to afford title compound as a yellow solid (0.010 g, 98%). M.P.: >280° C. $^1$H-NMR (δ ppm, DMSO-$d_6$, 400 MHz): 8.88 (d. J=2.7 Hz, 1H), 8.61 (d, J=8.7 Hz, 1H), 8.38 (d, J=8.1 Hz, 1H), 8.13 (m, 3H), 8.03 (s, 1H), 8.02 (d, J=8.9 Hz, 1H), 7.97 (d, J=8.1 Hz, 2H), 7.83 (d, J=7.3 Hz, 1H), 7.53 (dd, J=8.2, 4.1 Hz, 1H), 6.20 (s, 2H).

Example 23

6-((5-(3-(trifluoromethoxy)phenyl)-3H-[1,2,3]triazolo[4,5-b]pyridin-3-yl)methyl)quinoline To a solution of intermediate 14 (0.120 g, 0.405 mmol) and 3-trifluoromethoxyphenyl boronic acid (0.107 g, 0.519 mmol) in dioxane (2.4 ml), potassium carbonate (0.186 g, 1.35 mmol) and water (0.5 ml) were added and degassed for 30 min. Tetrakis triphenylphosphine palladium(0) (0.037 g, 0.032 mmol) was added under nitrogen at RT and the reaction mixture was refluxed for 12 h. The solvent was evaporated completely and to the residue water was added and extracted with ethyl acetate, dried over sodium sulphate and concentrated under reduced pressure. The crude product was purified by column chromatography with methanol:dichloromethane to afford the title compound as grey solid (0.090 g, 53%), M.P.: 140-142° C. $^1$H-NMR (δ ppm. DMSO-$d_6$, 400 MHz): 8.88 (dd, J=4.1, 1.6 Hz, 1H), 8.71 (d, J=8.7 Hz, 1H), 8.35 (d, J=7.9 Hz, 1H), 8.29 (d, J=8.0 Hz, 1H), 8.21 (d, J=8.8 Hz, 1H), 8.19 (s, 1H), 8.03 (s, 1H), 8.01 (d, J=8.7 Hz, 1H), 7.83 (dd, J=8.7, 1.9 Hz, 1H), 7.71 (t, J=8.1 Hz, 1H), 7.53 (dd, J=8.3, 4.1 Hz, 2H), 6.22 (s, 2H). MS (m/z): 421.92 ($M^+$).

Example 24

3-(3-(quinolin-6-ylmethyl)-3H-[1,2,3]triazolo[4,5-b]pyridin-5-yl)phenol

To a solution of example 2 (0.110 g, 0.299 mmol) in dichloromethane (1 ml), $BBr_3$ (1M in dichloromethane, 0.82 ml) was added at 0° C. and the reaction mixture was warmed to RT and stirred for 1 h. The reaction mixture was quenched with 1.5N HCl solution and extracted with dichloromethane. The organic layer was dried over sodium sulphate and concentrated. The crude product was purified by column chromatography with methanol:dichloromethane to afford the title compound as an off-white solid (0.030 g, 28%), M.P.: 255-257° C. $^1$H-NMR (δ ppm, DMSO-$d_6$, 400 MHz): 9.70 (s, 1H), 8.88 (dd, J=4.1, 2.6 Hz, 1H), 8.62 (d, J=8.7 Hz, 1H), 8.37 (d, J=8.0 Hz, 1H), 8.04 (m, 3H), 7.83 (dd, J=8.7, 1.8 Hz, 1H), 7.64 (s, 1H), 7.64 (d, J=8.6 Hz, 1H), 7.53 (dd, J=8.3, 4.2 Hz, 1H), 7.35 (t, J=7.9 Hz, 1H), 6.92 (dd. J=7.9, 1.4 Hz, 1H), 6.19 (s, 2H). MS (m/z): 354.02 ($M^+$).

Example 25

6-((5-(3-difluoromethoxy)phenyl)-3H-[1,2,3]triazolo[4,5-b]pyridin-3-yl)methyl)quinoline To a solution of intermediate 14 (0.100 g, 0.405 mmol) and 3-difluoromethoxyphenyl boronic acid (0.081 g, 0.438 mmol) in dioxane (3 ml), potassium carbonate (0.155 g, 1.12 mmol) and water (0.5 ml) were added and degassed for 30 min, Tetrakis triphenylphosphine palladium(0) (0.031 g, 0.032 mmol) was added under nitrogen at RT and the reaction mixture was refluxed for 12 h. The solvent was evaporated completely and to the residue water was added and extracted with ethyl acetate, dried over sodium sulphate and concentrated under reduced pressure. The crude product was purified by column chromatography with methanol:dichloromethane to afford the title compound as an off-white solid (0.046 g, 29%). M.P.: 122-125° C. $^1$H-NMR (δ ppm, DMSO-$d_6$, 400 MHz): 8.88 (dd, J=4.1, 1.6 Hz, 1H), 8.69 (d, J=8.7 Hz, 1H), 8.36 (d, J=8.5 Hz, 1H), 8.18 (d, J=8.8 Hz, 1H), 8.13 (d, J=7.9 Hz, 1H), 8.03 (m, 3H), 7.84 (dd, J=8.7, 1.5 Hz, 1H), 7.63 (t, J=8.0 Hz, 1H), 7.53 (dd, J=8.3, 4.2 Hz, 1H), 7.36 (s, 1H), 7.34 (dd, J=8.1, 2.2 Hz, 1H), 6.22 (s, 2H), MS (m/z): 403.79 (M$^+$).

Example 26

(4-methylpiperazin-1-yl)(4-(3-(quinolin-6-ylmethyl)-3H-[1,2,3]triazolo[4,5-b]pyridin-5-yl)phenyl)methanone To a solution of example 8 (0.100 g, 0.262 mmol) in DMF (1 ml) HOBT (0.042 g, 0.314 mmol), EDC-HCl (0.125 g, 0.655 mmol) and triethylamine (0.1 ml, 0.786 mmol) were added and stirred for 5 min. 4-Methylpiperazine (0.023 g, 0.235 mmol) was added at RT and the reaction mixture was stirred for 12 h. To the reaction mixture water was added and extracted with ethyl acetate, dried over sodium sulphate and concentrated under reduced pressure. The crude product was purified by column chromatography with methanol:dichloromethane to afford the title compound as a yellow solid (0.020 g, 1.7%). M.P.: 156-158° C. $^1$H-NMR (δ ppm, DMSO-$d_6$, 400 MHz): 8.88 (dd, J=4.1, 1.6 Hz, 1H), 8.69 (d, J=8.8 Hz, 1H), 8.36 (d, J=7.6 Hz, 1H), 8.31 (d, J=8.3 Hz, 2H), 8.17 (d, J=8.7 Hz, 1H), 8.02 (dd, J=5.1, 3.6 Hz, 2H), 7.83 (dd, J=8.8, 1.8 Hz, 1H), 7.56 (d, J=8.4 Hz, 2H), 7.52 (dd, J=8.2, 4.1 Hz, 1H), 6.21 (s, 2H), 3.63 (s, 2H), 3.30 (s, 2H), 2.36 (s, 4H), 2.19 (s, 3H).

Example 27

N-(2-dimethylamino)ethyl-4-(3-(quinolin-6-ylmethyl)-3H-[1,2,3]triazolo[4,5-b]pyridin-5-yl)benzamide To a solution of example 8 (0.200 g, 0.524 mmol) in DMF (1 ml), HOBT (0.084 g, 0.629 mmol), EDC-HCl (0.250 g, 1.31 mmol) and triethylamine (0.2 ml, 1.57 mmol) were added and stirred for 5 min. 2-N,N-Dimethylethylamine (0.046 g, 0.524 mmol) was added at RT and the reaction mixture was stirred for 12 h. To the reaction mixture water was added and extracted with ethyl acetate, dried over sodium sulphate and concentrated under reduced pressure. The crude product was purified by column chromatography with methanol:dichloromethane to afford the title compound as a yellow solid (0.100 g, 42%). M.P.: 122-125° C. $^1$H-NMR (δ ppm, DMSO-$d_6$, 400 MHz); 8.88 (dd, J=4.1, 1.5 Hz, 1H), 8.69 (d, J=8.8 Hz, 1H), 8.54 (t, J=5.4 Hz, 1H), 8.38 (d, J=8.3 Hz, 1H), 8.33 (d, J=8.3 Hz, 1H), 8.20 (d, J=8.7 Hz, 1H), 8.03-7.98 (m, 4H), 7.84 (dd, J=8.7, 1.7 Hz, 1H), 7.53 (dd, J=8.3, 4.2 Hz, 1H), 6.22 (s, 2H), 3.41 (q, J=6.6 Hz, 2H), 2.47 (m, 2H), 2.20 (s, 6H).

Example 28

4-(3-(quinolin-6-ylmethyl)-3H-[1,2,3]triazolo[4,5-b]pyridin-5-yl)-N-(tetrahydro-2H-pyran-4-yl)benzamide To a solution of example 8 (0.200 g, 0.524 mmol) in DMF (1 ml) HOBT (0.084 g, 0.629 mmol), EDC-HCl (0.250 g, 1.31 mmol) and methylamine (0.2 ml, 1.57 mmol) were added and stirred for 5 min, 4-Aminotetrahydropyran (0.106 g, 1.04 mmol) was added at RT and the reaction mixture was stirred for 12 h. To the reaction mixture water was added and extracted with ethyl acetate, dried over sodium sulphate and concentrated under reduced pressure. The crude product was purified by column chromatography with methanol:dichloromethane to afford the title compound as an off-white solid (0.050 g, 20%.). M.P.: 202-205° C., $^1$H-NMR (δ ppm, DMSO-$d_6$, 400 MHz): 8.88 (dd, J=4.1, 1.6 Hz, 1H), 8.69 (d, J=8.8 Hz, 1H), 8.44 (d, J=7.5 Hz, 1H), 8.38 (d, J=7.7 Hz, 1H), 8.33 (d, J=8.5 Hz, 2H), 8.20 (d, J=8.8 Hz, 1H), 8.03-7.99 (m, 4H), 7.85 (dd, J=8.7, 1.9 Hz, 1H), 7.53 (dd, J=8.3, 4.2 Hz, 1H), 6.22 (s, 2H), 4.04 (m, 1H), 3.89 (d, J=9.7 Hz, 2H), 3.39 (t, J=10.0 Hz. 2H), 1.78 (d, J=10.5 Hz, 2H), 1.63 (m, 2H).

Example 29 tert-Butyl 4-(4-(3-(quinolin-6-ylmethyl)-3H-[1,2,3]triazolo[4,5-b]pyridin-5-yl)benzamido)piperidine-1-carboxylate To a solution of example 8 (0.200 g, 0.524 mmol) in DMF (1 ml), HOBT (0.084 g, 0.629 mmol), EDC-HCl (0.250 g, 1.31 mmol) and triethylamine (0.2 ml, 1.57 mmol) were added and stirred for 5 min, 1-Boc-4-aminopiperidine (0.210 g, 1.04 mmol) was added at RT and the reaction mixture was stirred for 12 h. To the reaction mixture water was added and extracted with ethyl acetate, dried over sodium sulphate and concentrated under reduced pressure. The crude product was purified by column chromatography with methanol:dichloromethane to afford the title compound as an off-white solid (0.125 g. 42%). $^1$H-NMR (δ ppm, DMSO-$d_6$, 400 MHz): 8.88 (dd, J=4.1, 1.6 Hz, 1H), 8.69 (d, J=8.7 Hz, 1H), 8.40 (d, J=7.8 Hz, 1H), 8.38 (d, J=8.5 Hz, 1H), 8.33 (d, J=8.5 Hz, 2H), 8.20 (d, J=8.7 Hz, 1H), 8.03-7.99 (m, 4H), 7.84 (dd, J=8.7, 1.8 Hz, 1H), 7.53 (dd, J=8.3, 4.1 Hz, 1H), 6.22 (s, 2H). 3.99 (m, 3H), 2.87 (m, 2H), (d, J=9.9 Hz, 2H), 1.45-1.37 (m, 1H).

Example 30

N-(Piperidin-4-yl)-4-(3-(quinolin-6-ylmethyl)-3H-[1,2,3]triazolo[4,5-b]pyridin-5-yl)benzamide hydrochloride To a solution of example 29 (0.125 g, 0.222 mmol) in THF (1 ml), ether saturated with HCl (1.5 ml) was added at 0° C. and stirred for 15 min. The precipitate formed was washed with ether and dried under vacuum to afford the title compound as light yellow solid (0.105 g. 95%). M.P.: 220-224° C. $^1$H-NMR (δ ppm, DMSO-$d_6$, 400 MHz): 9.14 (d, J=3.6 Hz, 1H), 8.90 (m, 3H), 8.72 (d, J=8.7 Hz, 1H), 8.67 (d, J=7.4 Hz, 1H), 8.33 (d, J=8.5 Hz, 2H), 8.28 (m, 3H), 8.11 (dd, J=8.7, 1.5 Hz, 1H), 8.05 (d, J=8.5 Hz, 2H), 7.89 (dd, J=8.3, 4.8 Hz, 1H), 6.29 (s, 2H), 4.11 (m, 1H), 3.59 (m, 1H), 3.34 (m, 1H), 3.01 (m, 2H), 1.99 (m, 2H), 1.85 (m, 2H).

Example 31

N-(2-(dimethylamino)ethyl-2-fluoro-4-(3-(quinolin-6-ylmethyl)-3H-[1,2,3]triazolo[4,5-b]pyridin-5-yl)benzamide To a solution of example 13 (0.150 g, 0.375 mmol) in DMF (1.5 ml), HOBT (0.068 g, 0.454 mmol), EDC-HCl (0.180 g, 0.941 mmol) and triethylamine (0.15 ml, 1.09 mmol) were added and stirred for 5 min, 2-N,N-Dimethylethylamine (0.123 g, 1.39 mmol) was added at RT and the reaction mixture was stirred for 12 h. To the reaction mixture water was added and extracted with ethyl acetate, dried over sodium sulphate and concentrated under reduced pressure. The crude product was purified by column chromatography with methanol:dichloromethane to afford the title compound as a yellow solid (0.029 g, 17%). M.P.: 122-125° C. $^1$H-NMR (δ ppm, DMSO-$d_6$, 400 MHz): 8.88 (d, J=2.8 Hz, 1H), 8.72 (d, J=8.7 Hz, 1H), 8.37 (d, J=8.3 Hz, 1H), 8.29 (br s, 1H), 8.23 (d, J=8.8 Hz, 1H), 8.18 (m, 2H), 8.04 (s, 1H), 8.02 (d, J=8.8 Hz, 1H), 7.84 (m, 2H), 7.53 (dd, J=8.3, 4.1 Hz, 1H), 6.23 (s, 2H), 3.39 (m, 4H), 2.49 (s, 6H).

Example 32

(S)-(2-(pyrrolidin-1-ylmethyl)pyrrolidin-1-yl)(4-(3-(quinolin-6-ylmethyl)-3H-[1,2,3]triazolo[4,5-b]pyridin-5-yl)phenyl)methanone hydrochloride To a solution of example 8 (0.100 g, 0.262 mmol) in DMF (1 ml), HOBT (0.042 g, 0.314 mmol), EDC-HCl (0.125 g, 0.655 mmol) and triethylamine (0.3 ml, 2.35 mmol) were added and stirred for 5 min. (s)-1-(pyrrolidin-2-ylmethyl)pyrrolidine (0.120 g, 0.783 mmol) was added at RT and the reaction mixture was stirred for 12 h. To the reaction mixture water was added and extracted with ethyl acetate, dried over sodium sulphate and concentrated under reduced pressure. The crude product was purified by column chromatography with methanol:dichloromethane to afford the free base as a yellow solid (0.060 g). The free base was dissolved in THF (5 ml), ether saturated with HCl (2 ml) was added at 0° C. and stirred for 15 min. The precipitate formed was washed with ether and dried under vacuum to afford the title compound as a light yellow solid (0.040 g, 27%). M.P.: 120-122° C. $^1$H-NMR (δ ppm, DMSO-$d_6$, 400 MHz): 10.00 (s, 1H). 9.09 (s, 1H), 8.77 (m, 1H), 8.72 (d, J=8.7 Hz, 1H), 8.33 (d, J=8.2 Hz, 2H), 8.22 (m, 3H), 8.04 (d, J=9.0 Hz, 1H), 7.80 (m, 1H), 7.74 (d, J=8.0 Hz, 2H), 6.28 (s, 2H), 3.75-3.30 (m, 9H), 2.18-1.90 (m, 8H).

Example 33

(4-(2-hydroxyethyl)piperazin-1-yl)(4-(3-(quinolin-6-ylmethyl)-3H-[1,2,3]triazolo[4,5-b]pyridin-5-yl)phenyl)methanone To a solution of example 8 (0.150 g, 0.393 mmol) in DMF (1 ml), HOBT (0.063 g, 0.471 mmol), EDC-HCl (0.187 g, 0.983 mmol) and triethylamine (0.16 ml, 1.17 mmol) were added and stirred for 5 min. (2-(piperazin-1-yl)ethanol (0.046 g, 0.353 mmol) was added at RT and the reaction mixture was stirred for 12 h. To the reaction mixture water was added and extracted with ethyl acetate, dried over sodium sulphate and concentrated under reduced pressure. The crude product was purified by column chromatography with methanol:dichloromethane to afford the title compound as a yellow solid (0.025 g, 13%). M.P.: 158-160° C. $^1$H-NMR (δ ppm, DMSO-$d_6$, 400 MHz): 8.88 (d, J=2.7 Hz, 1H), 8.67 (d, J=8.7 Hz, 1H), 8.38 (d, J=7.8 Hz, 1H), 8.31 (d, J=8.2 Hz, 2H), 8.17 (d, J=8.8 Hz, 1H), 8.02 (t, J=4.2 Hz, 2H), 7.83 (dd, J=8.7, 1.6 Hz, 1H), 7.56 (d, J=8.4 Hz, 2H), 7.52 (dd, J=8.3, 4.2 Hz, 1H), 6.24 (s, 2H), 4.44 (t, J=5.3 Hz, 1H), 3.62 (m, 2H), 3.51 (q, J=6.0 Hz, 2H), 2.42 (m, 8H).

Example 34

(R)-(3-hydroxypyrrolidin-1-yl)(4-(3-(quinolin-6-ylmethyl)-3H-[1,2,3]triazolo[4,5-b]pyridin-5-yl)phenyl)methanone hydrochloride To a solution of example 8 (0.150 g, 0.393 mmol) in DMF (1 ml), HOBT (0.063 g, 0.471 mmol), EDC-HCl (0.187 g, 0.983 mmol) and triethylamine (0.16 ml, 1.17 mmol) were added and stirred for 5 min, (R)-pyrrolidin-3-ol (0.030 g, 0.353 mmol) was added at RT and the reaction mixture was stirred for 12 h. To the reaction mixture water was added and extracted with ethyl acetate, dried over sodium sulphate and concentrated under reduced pressure. The crude product was purified by column chromatography with methanol:dichloromethane to afford the amide as a yellow solid (0.015 g). The amide was dissolved in THF (2 ml), ether saturated with HCl (2 ml) was added at 0° C. and stirred for 15 min. The precipitate formed was washed with ether and dried under vacuum to afford the title compound as a yellow solid (0.017 g, 10%), M.P.: 120-122° C. $^1$H-NMR (δ ppm, DMSO-$d_6$, 400 MHz): 8.87 (d, J=2.9 Hz, 1H), 8.68 (d, J=8.7 Hz, 1H), 8.38 (d, J=8.2 Hz, 1H), 8.30 (d, J=8.2 Hz, 2H), 8.17 (d, J=8.8 Hz, 1H), 8.02 (d, J=8.3 Hz, 2H), 7.83 (d, J=8.7 Hz, 1H), 7.69 (m, 2H), 7.52 (dd, J=8.2, 4.1 Hz, 1H), 6.21 (s, 2H), 3.61 (m, 3H), 3.44 (m, 1H), 1.95-1.80 (m, 4H).

Example 35

N-(2-(piperidin-1-yl)ethyl)-4-(3-(quinolin-6-ylmethyl)-3H-[1,2,3]triazolo[4,5-b]pyridin-5-yl)benzamide To a solution of example 8 (0.120 g, 0.314 mmol) in DMF (0.7 ml), N-ethyldiisopropylamine (0.041 g, 0.314 mmol) and HATU (0.119 g, 0.314 mmol) were added and stirred for 5 min. (2-(piperidin-1-yl)ethanamine (0.040 g, 0.314 mmol) was added at RT and the reaction mixture was stirred for 12 h. To the reaction mixture water was added and extracted with ethyl acetate, dried over sodium sulphate and concentrated under reduced pressure. The crude product was purified by column chromatography with methanol:dichloromethane to afford the title compound as a yellow solid (0.080 g, 52%). M.P.: 104-107° C., $^1$H-NMR (δ ppm, DMSO-$d_6$, 400 MHz): 8.88 (dd, J=4.1, 1.6 Hz, 1H), 8.70 (d, J=8.7 Hz, 1H), 8.62 (bs, 1H), 8.38 (m, 3H), 8.21 (d, J=8.8 Hz, 1H), 8.03-7.98 (m, 4H), 7.84 (dd, J=8.7, 1.9 Hz, 1H), 7.53 (dd, J=8.3, 4.2 Hz, 1H), 6.22 (s, 2H), 3.48 (bs, 2H), 2.48 (m, 6H), 1.54 (m, 6H).

Example 36

N-(2-morpholinoethyl)-4-(3-(quinolin-6-ylmethyl)-3H-[1,2,3]triazolo[4,5-b]pyridin-5-yl)benzamide The title compound was prepared by following the procedure described for example 35 using 2-morpholinoethane amine (0.040 g, 0.314 mmol) Instead of (2-(piperidin-1-yl)ethanamine Yellow solid (0.070 g, 45%). M.P.: 146-149° C. $^1$H-NMR (δ ppm, DMSO-$d_6$, 400 MHz): 8.88 (dd, J=4.2, 1.6 Hz, 1H), 8.70 (d, J=8.7 Hz, 1H), 8.54 (t, J=4.5 Hz, 1H), 8.38

(d, J=8.5 Hz, 1H), 8.34 (d, J=8.5 Hz, 2H), 8.20 (d, J=8.8 Hz, 1H), 8.03-7.98 (m, 4H), 7.84 (dd. J=8.8, 2.0 Hz, 1H), 7.53 (dd, J=8.3, 4.2 Hz, 1H), 6.22 (s, 2H), 3.57 (t, J=4.4 Hz, 4H), 3.41 (m, 2H), 2.46 (m, 6H).

Example 37

N-(2-pyrrolidin-1-yl)ethyl)-4-(3-(quinolin-6-ylmethyl)-3H-[1,2,3]triazolo[4,5-b]pyridin-5-yl)benzamide The title compound was prepared by following the procedure described for example 35 using 2-(pyrrolidin-1-yl)ethanamine (0.036 g, 0.314 mmol) instead of (2-(piperidin-1-yl) ethanamine. Yellow solid (0.065 g, 43%). M.P.: 135-137° C. $^1$H-NMR (δ ppm. DMSO-$d_6$, 400 MHz): 8.88 (dd, J=4.2, 1.7 Hz, 1H), 8.70 (d, J=8.7 Hz, 1H), 8.58 (m, 1H), 8.38 (d, J=7.5 Hz, 1H), 8.34 (d, J=8.4 Hz, 2H), 8.21 (d, J=8.8 Hz, 1H), 8.03 (d, J=3.5 Hz, 2H), 8.00 (d, J=8.3 Hz, 2H), 7.84 (dd, J=8.7, 2.0 Hz, 1H), 7.53 (dd, J=8.3, 4.2 Hz, 1H), 6.22 (s, 2H), 3.41 (d, J=5.4 Hz, 2H), 2.49 (m, 6H), 1.68 (s, 4H).

Example 38

(4-(pyrrolidin-1-yl)piperidin-1-yl)(4-(3-(quinolin-6-ylmethyl)-3H-[1,2,3]triazolo[4,5-b]pyridin-5-yl) phenyl)methanone To a solution of example 8 (0.100 g, 0.262 mmol) in 1:1 DMF/dichlormethane mixture (1.0 ml), BOP (0.121 g, 0.275 mmol) and triethylamine (0.1 ml, 0.786 mmol) were added and stirred for 30 min, 4-(pyrrolidin-1-yl)piperidine (0.044 g, 0.288 mmol) was added at RT and the reaction mixture was stirred for 12 h. To the reaction mixture water was added and extracted with ethyl acetate, dried over sodium sulphate and concentrated under reduced pressure. The crude product was purified by column chromatography with methanol:dichloromethane to afford the title compound as a yellow solid (0.017 g. 12%), M.P.: 132-135° C., $^1$H-NMR (δ ppm, DMSO-$d_6$, 400 MHz): 8.88 (dd, J=4.2, 1.6 Hz, 1H), 8.71 (d, J=8.7 Hz, 1H), 8.38 (d, J=8.1 Hz, 1H), 8.33 (d, J=8.2 Hz, 2H), 8.19 (d, J=8.8 Hz, 1H), 8.03 (d, J=8.9 Hz, 1H), 8.00 (s, 1H). 7.83 (dd, J=8.7, 1.9 Hz, 1H), 7.57 (d, J=8.2 Hz, 2H), 7.53 (dd, J=8.4, 4.2 Hz, 1H), 6.22 (s, 2H), 3.49-3.10 (m, 9H), 2.07-1.53 (m, 8H).

Example 39

N-(3-dimethylamino)propyl)-4-(3-(quinolin-6-ylmethyl)-3H-[1,2,3]triazolo[4,5-b]pyridin-5-yl)benzamide The title compound was prepared by following the procedure described for example 35 using 3-N,N-dimethylaminopropylamine (0.026 g, 0.262 mmol) instead of (2-(piperidin-1-yl)ethanamine Yellow solid (0.035 g, 29%). M.P.: 132-135° C. $^1$H-NMR (δ ppm, DMSO-$d_6$, 400 MHz): δ8.88 (dd, J=4.1, 1.6 Hz, 1H), 8.70 (d, J=8.8 Hz, 1H), 8.66 (t, J=5.8 Hz, 1H), 8.38 (d, J=8.3 Hz, 1H), 8.33 (d, J=8.4 Hz, 2H), 8.20 (d, J=8.8 Hz, 1H), 8.03-7.97 (m, 4H), 7.84 (dd, J=8.7, 1,9 Hz, 1H), 7.53 (dd, J=8.3, 4.2 Hz, 1H), 6.22 (s, 2H), 3.30 (m, 2H), 2.30 (t, J=7.0 Hz, 2H), 2.14 (s, 6H), 1.68 (t, J=7.0 Hz, 2H).

Example 40

N,N-Bis(2-methoxyethyl)-4-(3-(quinolin-6-ylmethyl)-3H-[1,2,3]triazolo[4,5-b]pyridin-5-yl)benzamide hydrochloride To a solution of example 8 (0.150 g, 0.393 mmol) in DMF (1 ml), HOBT (0.063 g, 0.471 mmol), EDC-HCl (0.187 g, 0.983 mmol) and diethyl amine (0.16 ml, 1.17 mmol) were added and stirred for 5 min, Bis(2-methoxyethyl)amine (0.104 g, 0.786 mmol) was added at RT and the reaction mixture was stirred for 12 h. To the reaction mixture water was added and extracted with ethyl acetate, dried over sodium sulphate and concentrated under reduced pressure. The crude product was purified by column chromatography with methanol:dichloromethane to afford the amide as a yellow solid (0.04 g). The amide was dissolved in THF (2 ml), ether saturated with HCl (2 ml) was added at 0° C. and stirred for 15 min. The precipitate formed was washed with ether and dried under vacuum to afford the title compound as a yellow solid (0.035 g, 17%). M.P.: 126-129° C. $^1$H-NMR (δ ppm, DMSO-$d_6$, 400 MHz): 9.07 (m, 1H), 8.74 (m, 1H), 8.70 (d, J=8.7 Hz, 1H), 8.29 (d, J=8.3 Hz, 2H), 8.19 (m, 3H), 8.02 (m, 1H), 7.78 (m, 1H), 7.53 (d, J=8.2 Hz, 2H), 6.27 (s, 2H), 3.64 (bs, 2H), 3.58 (br.s, 2H), 3.41 (br.s, 4H), 3.30 (s, 3H), 3.16 (s, 3H).

Example 41

(2-Fluoro-4-(3-(quinolin-6-ylmethyl)-3H-[1,2,3] triazolo[4,5-b]pyridin-5-yl)phenyl)methanol hydrochloride Example 16 (0.050 g, 0.129 mmol) was dissolved in THF (3 ml) and methanol (3 ml), ether saturated with HCl (3 ml) was added at 0° C. and stirred for 15 min. The precipitate formed was washed with ether and dried under vacuum to afford the title compound as an off-white solid (0.040 g, 74%). M.P.: 190-192° C. $^1$H-NMR (δ ppm, DMSO-$d_6$, 400 MHz): 9.14 (d, J=3.6 Hz, 1H), 8.88 (d, J=8.1 Hz, 1H), 8.68 (d, J=8.7 Hz, 1H), 8.24 (s, 1H), 8.24 (d, J=8.6 Hz, 1H), 8.18 (d, J=8.8 Hz, 1H), 8.11 (m, 2H), 8.03 (dd, J=11.7, 1.5 Hz, 1H), 7.87 (dd, J=8.1, 4.8 Hz, 1H), 7.65 (t, J=7.9 Hz, 1H), 6.29 (s, 2H), 5.86 (s, 1H), 4.61 (s, 2H).

Example 42

6-((5-(3-Fluoro-4-(methoxymethyl)phenyl)-3H-[1,2,3]triazolo[4,5-b]pyridin-3-yl)methyl)quinoline Sodium hydride (0.010 g, 0.259 mmol) was added at 0° C. to a solution of example 16 (0.100 g, 0.259 mmol) in DMF (1 ml) and stirred for 30 min. Methyl iodide (0.073 g, 0.518 mmol) was added and the reaction mixture was warmed to RT. After 12 h, the reaction mixture was poured into ice-cold water and extracted with ethyl acetate, washed with brine, dried over sodium sulphate and concentrated. The crude product was purified by column chromatography with methanol:dichloromethane to afford the title compound as an off-white solid (0.033 g, 32%). M.P.: 200-201° C. $^1$H-NMR (δ ppm, DMSO-$d_6$, 400 MHz): 8.88 (dd, J=4.2, 1.7 Hz, 1H), 8.68 (d, J=8.8 Hz, 1H), 8.37 (d, J=8.4 Hz, 1H), 8.18 (d, J=8.8 Hz, 1H), 8.11-8.00 (m, 4H), 7.83 (dd, J=8.7, 1.9 Hz, 1H), 7.61 (t, J=7.7 Hz, 1H), 7.53 (dd, J=8.4, 4.2 Hz, 1H), 6.22 (s, 2H), 4.53 (s, 2H), 3.33 (s, 3H).

Example 43

N-ethyl-2-fluoro-4-(3-(quinolin-6-ylmethyl)-3H-[1,2,3]triazolo[4,5-b]pyridin-5-yl)benzamide To a solution of example 13 (0.100 g, 0.250 mmol) In DMF (0.7 ml), N-ethyldiisopropylamine (0.064 g, 0.50 mmol) and HATU (0.095 g, 0.250 mmol) were added and stirred for 5 min. Ethylamine hydrochloride (0.020 g, 0.250 mmol) was added at RT and the reaction mixture was stirred for 12 h. Water was added to the reaction mixture and extracted with ethyl acetate, dried over sodium sulphate and concentrated under reduced pressure. The crude product was purified by column chromatography with methanol:dichloromethane to afford the title compound as a yellow solid (0.070 g, 66%). M.P.: 207-209° C. $^1$H-NMR ($\delta$ ppm, DMSO-d$_6$, 400 MHz): 8.88 (dd, J=4.2, 1.7 Hz, 1H), 8.71 (d, J=8.7 Hz, 1H), 8.41 (m, 1H), 8.37 (d, J=7.6 Hz, 1H), 8.23 (d, J=8.8 Hz, 1H), 8.17 (m, 2H), 8.04 (s, 1H), 8.02 (d, J=8.8 Hz, 1H), 7.84 (dd, J=8.7, 1.9 Hz, 1H), 7.77 (t, J=7.9 Hz, 1H), 7.54 (dd, J=8.3, 4.1 Hz, 1H), 6.23 (s, 2H), 3.29 (m, 2H), 1.4 (t, J=7.2 Hz. 3H).

Example 44

2-Fluoro-N-(2-(pyrrolidin-1-yl)ethyl)-4-(3-(quinolin-6-ylmethyl)-3H-[1,2,3]triazolo[4,5-b]pyridin-5-yl)benzamide The title compound was prepared by following the procedure described for example 43 using (2-(piperidin-1-yl)ethanamine (0.028 g, 0.250 mmol) instead of ethylamine hydrochloride. Yellow solid (0.015 g, 12%), M.P.: 183-186° C. $^1$H-NMR ($\delta$ ppm, DMSO-d$_6$, 400 MHz): 8.89 (dd, J=4.0, 1.5 Hz, 1H), 8.74 (d, J=8.7 Hz, 1H), 8.59 (m, 1H), 8.37 (d, J=7.7 Hz, 1H), 8.25-8.19 (m, 3H), 8.03 (s, 1H), 8.02 (d, J=8.7 Hz, 1H), 7.90 (t, J=8.0 Hz, 1H), 7.84 (dd, J=8.7, 1.8 Hz, 1H), 7.54 (dd, J=8.4, 4.2 Hz, 1H), 6.24 (s, 2H), 3.62 (m, 4H), 3.06-2.89 (m, 4H), 1.89-1.86 (m, 4H).

Example 45

N-cyclohexyl-2-fluoro-4-(3-(quinolin-6-ylmethyl)-3H-[1,2,3]triazolo[4,5-b]pyridin-5-yl)benzamide The title compound was prepared by following the procedure described for example 43 using cyclohexylamine (0.025 g, 0.250 mmol) instead of ethylamine hydrochloride. Yellow solid (0.050 g, 41%). M.P.: 172-175° C. MS (m/z): 481.21 (M$^+$+1).

Example 46

N-Cyclopropyl-2-fluoro-4-(3-(quinolin-6-ylmethyl)-3H-[1,2,3]triazolo[4,5-b]pyridin-5-yl)benzamide The title compound was prepared by following the procedure described for example 43 using cyclopropylamine (0.014 g. 0.250 mmol) instead of ethylamine hydrochloride. Off-white solid (0.015 g, 14%), M.P.: 193-195° C. $^1$H-NMR ($\delta$ ppm, DMSO-d$_6$ 400 MHz): 8.88 (dd, J=4.1, 1.6 Hz, 1H), 8.71 (d, J=8.7 Hz, 1H), 8.48 (d, J=3.8 Hz, 1H), 8.37 (d, J=7.3 Hz, 1H), 8.23 (d, J=8.8 Hz, 1H), 8.16 (m, 2H), 8.04 (s, 1H), 8.02 (d, J=8.7 Hz, 1H), 7.83 (dd, J=8.7, 2.0 Hz, 1H), 7.72 (t, J=8.0 Hz, 1H), 7.54 (dd, J=8.4, 4.2 Hz, 1H), 6.23 (s, 2H), 2.87 (m, 1H), 0.70 (m, 2H), 0.57 (m, 2H).

Example 47

2-Fluoro-N-(pyridin-4-yl)-4-(3-quinolin-6-ylmethyl)-3H-[1,2,3]triazolo[4,5-b]pyridin-5-yl)benzamide The title compound was prepared by following the procedure described for example 43 using 4-aminopyridine (0.023 g, 0.250 mmol) instead of ethylamine hydrochloride. Yellow solid (0.050 g, 42%). M.P.: 217-219° C. MS (m/z); 476.17 (M$^+$+1).

Example 48

N-Benzyl-2-fluoro-4-(3-(quinolin-6-ylmethyl)-3H-[1,2,3]triazolo[4,5-b]pyridin-5-yl)benzamide The title compound was prepared by following the procedure described for example 43 using benzylamine (0.023 g, 0.250 mmol) instead of ethylamine hydrochloride. Pale green solid (0.040 g, 32%). M.P.: 163-165° C. MS (m/z): 489.19 (M$^+$+1).

Example 49

2-Fluoro-N,N-dimethyl-4-(3-(quinolin-6-ylmethyl)-3H-[1,2,3]triazolo[4,5-b]pyridin-5-yl)benzamide The title compound was prepared by following the procedure described for example 43 using dimethylamine hydrochloride (0.020 g, 0.250 mmol) instead of ethylamine hydrochloride. Pale brown solid (0.020 g, 18%). M.P.: 163-165° C. MS (m/z): 426.96 (M$^+$+1).

Example 50

Methyl-2-(2-fluoro-4-(3-(quinolin-6-ylmethyl)-3H-[1,2,3]triazolo[4,5-b]pyridin-5-yl)benzamido)acetate To glycine (0.100 g. 1.133 mmol) in methanol (4 ml), thionyl chloride (0.9 ml) was added and refluxed for 1 h. The solvent was removed and the residue was dissolved in DMF (2 ml). To this solution example 13 (0.150 g, 0.375 mmol), N-ethyldiisopropylamine (0.097 g. 0.751 mmol) and HATU (0.0142 g, 0.375 mmol) were added at RT and the reaction mixture was stirred for 12 h. To the reaction mixture water was added and extracted with ethyl acetate, dried over sodium sulphate and concentrated under reduced pressure. The crude product was purified by column chromatography with methanol:dichloromethane to afford the title compound as a yellow solid (0.055 g, 31%). $^1$H-NMR ($\delta$ ppm. CDCl$_3$, 400 MHz): $\delta$8.92 (dd, J=4.2, 1.6 Hz, 1H), 8.48 (d, J=8.6 Hz. 1H), 8.27 (t, J=8.4 Hz, 1H), 8.16 (d, J=8.8 Hz, 1H), 8.10 (d, J=8.7 Hz, 1H), 8.00 (m, 3H), 7.88 (m, 2H), 7.43 (dd, J=8.4, 4.2 Hz, 1H), 7.36 (m, 1H), 6.16 (s, 2H), 4.32 (d, J=4.7 Hz, 2H), 3.83 (s, 3H).

Example 51

2-(2-Fluoro-4-(3-(quinolin-6-ylmethyl)-3H-[1,2,3]triazolo[4,5-b]pyridin-5-yl)benzamido)acetic acid To a solution of Example 50 (0.055 g, 0.113 mmol) in methanol (0.5 ml), lithium hydroxide (0.045 g, 1.05 mmol) in water (0.5 ml) was added and stirred at RT. After 12 h, pH was adjusted to ca. 7 using 0.5N HCl and the solid precipitated was filtered, washed with ethyl acetate and petroleum ether and dried under vacuum to afford the title compound as a pale green solid (0.050 g, 96%). M.P.: 252-254° C. ¹H-NMR (δ ppm. DMSO-$d_6$, 400 MHz): 12.70 (s, 1H), 9.01 (d, J=3.9 Hz, 1H) 8.73 (d, J=8.7 Hz, 1H), 8.64 (m, 2H), 8.25 (d, J=8.8 Hz, 1H), 8.20 (m, 4H), 7.97 (d, J=8.9 Hz, 1H), 7.86 (t, J=8.1 Hz, 1H), 7.71 (dd, J=7.8, 4.2 Hz, 1H) 6.27 (s, 2H), 3.96 (d, J=5.8 Hz, 2H), MS (m/z): 456.85 (M⁺).

Example 52

2-Fluoro-4-(3-quinolin-6-ylmethyl)-3H-[1,2,3]triazolo[4,5-b]pyridin-5-yl)-N-(1H-1,2,4-triazol-3-yl)benzamide The title compound was prepared by following the procedure described for example 43 using 3-amino-1,2,4-triazole (0.021 g, 0.250 mmol) instead of ethylamine hydrochloride. Off-white solid (0.010 g, 9%). M.P.: 265-267° C. ¹H-NMR (δ ppm, DMSO-$d_6$, 400 MHz): 13.70 (s, 1H), 12.10 (s, 1H), 8.87 (m, 1H), 8.74 (d, J=8.5 Hz, 1H), 8.38 (d, J=8.3 Hz, 1H), 8.27-8.22 (m, 3H), 8.05 (m, 2H), 7.89-7.79 (m, 3H), 7.54 (q, J=4.2 Hz, 1H), 6.25 (s, 2H), MS (m/z): 465.95 (M⁺).

Example 53

Methyl 3-(3-(quinolin-6-ylmethyl)-3H-[1,2,3]triazolo[4,5-b]pyridin-5-yl)benzoate The title compound was prepared by following the procedure described for example 1 using intermediate 14 (0.250 g, 0.845 mmol), 3-methoxycarbonylphenylboronic acid (0.190 g, 1.056 mmol), potassium acetate (0.276 g, 2.81 mmol), dioxane (5 ml) and tetrakis(triphenylphosphine)palladium(0) (0.078 g, 0.067 mmol). Brown solid (0.190 g, 56%).

Example 54

3-(3-(quinolin-6-ylmethyl)-3H-[1,2,3]triazolo[4,5-b]pyridin-5-yl)benzoic acid

To a solution of example 53 (0.190 g, 0.480 mmol) in methanol (2.7 ml), lithium hydroxide (0.201 g, 4.80 mmol) in water (0.75 ml) was added and stirred at RT. After 12 h, the pH was adjusted to 7-7.5 using 0.5N HCl and the solid precipitated was filtered, washed with ethyl acetate and petroleum ether and dried under vacuum to afford the title compound as brown solid (0.070 g, 38%). ¹H-NMR (δ ppm, DMSO-$d_6$, 400 MHz): 13.39 (s, 1H), 8.87 (d, J=2.6 Hz, 1H), 8.77 (s, 1H), 8.68 (d, J=8.7 Hz, 1H), 8.39 (m, 2H), 8.16 (d, J=8.7 Hz, 1H), 8.07 (m, 3H). 7.85 (dd, J=8.7, 1.5 Hz, 1H), 7.66 (t, J=7.8 Hz, 1H), 7.52 (dd, J=8.3, 4.1 Hz, 1H), 6.22 (s, 2H).

Example 55

N-Methyl-3-(3-(quinolin-6-ylmethyl)-3H-[1,2,3]triazolo[4,5-b]pyridin-5-yl)benzamide To example 54 (0.070 g, 0.183 mmol), thionyl chloride (3 ml) was added and refluxed for 3 h. The excess thionyl chloride was removed under reduced pressure and the residue was cooled to 0° C. Methyl amine in ethanol (50% solution, 5 ml) was added and stirred for 15 min. The precipitate formed was washed with sodium bicarbonate solution and dried under vacuum to afford the title compound as pale brown solid (0.050 g, 69%) M.P.: 215-217° C. MS (m/z): 359.04 (M⁺+1).

Example 56

6-((5-(3-Fluorophenyl)-3H-[1,2,3]triazolo[4,5-b]pyridin-3-yl)methyl)quinoline

The title compound was prepared by following the procedure described for example 1 using intermediate 14 (0.100 g, 0.338 mmol), 3-fluorophenylboronic acid (0.059 g, 0.422 mmol), potassium carbonate (0.156 g, 0.027 mmol), dioxane (2 ml), water (0.5 ml) and tetrakis(triphenylphosphine)palladium(0) (0.031 g, 0.067 mmol) in microwave oven (100 W, 100° C.) for 20 min. Yellow solid (0.040 g, 30%). M.P.: 145-147° C. MS (m/z): 356.05 (M⁺+1).

Example 57

Methyl 3-(2-fluoro-4-(3-(quinolin-6-ylmethyl)-3H-[1,2,3]triazolo[4,5-b]pyridin-5-yl)phenylamino)propanoate To 2-aminopropionic acid (0.100 g, 1.122 mmol) in methanol (4 ml), thionyl chloride (0.9 ml) was added and refluxed for 1 h. Solvents were removed and residue was dissolved in DMF (2 ml). To this solution example 13 (0.150 g, 0.375 mmol), N-ethyldiisopropylamine (0.097 g, 0.751 mmol) and HATU (0.0142 g, 0.375 mmol) were added at RT and the reaction mixture was stirred for 12 h. To the reaction mixture water was added and extracted with ethyl acetate, dried over sodium sulphate and concentrated under reduced pressure. The crude product was purified by column chromatography with methanol:dichloromethane to afford the title compound as a yellow solid (0.078 g, 44%).

Example 58

3-(2-Fluoro-4-(3-(quinolin-6-ylmethyl)-3H-[1,2,3]triazolo[4,5-b]pyridin-5-yl)phenylamino)propanoic acid To a solution of example 57 (0.080 g, 0.165 mmol) in methanol (0.8 ml), lithium hydroxide (0.064 g, 1.54 mmol) in water (0.8 ml) was added and stirred at RT. After 12 h, pH was adjusted to ca. 7.5 using 0.5N HCl and the solid precipitated was filtered, washed with ethyl acetate and petroleum ether and dried under vacuum to afford the title compound as pale green solid (0.075 g, 68%). M.P.: 132-135° C.

Example 59

2-Fluoro-N-methoxy-N-methyl-4-(3-quinolin-6-ylmethyl)-3H-[1,2,3]triazolo[4,5-b]pyridin-5-yl)benzamide hydrochloride The title compound was prepared by following the procedure described for example 43 using N,O-dimethylhydroxylamine hydrochloride (0.025 g, 0.250 mmol) instead of Ethylamine hydrochloride. Yellow solid (0.055 g, 46%). M.P.: 201-202° C. MS (m/z): 443.20 (M⁺+1-HCl).

Example 60

N-tert-butyl-2-fluoro-4-(3-(quinolin-6-ylmethyl)-3H-[1,2,3]triazolo[4,5-b]pyridin-5-yl)benzamide The title compound was prepared by following the procedure described for example 43 using tert-butylamine (0.018 g, 0.250 mmol) instead of ethylamine hydrochloride. Yellow solid (0.050 g, 44%). M.P.: 210-212° C. MS (m/z): 455.10 (M⁺+1).

Example 61

N-Allyl-2-fluoro-4-(3-(quinolin-6-ylmethyl)-3H-[1,2,3]triazolo[4,5-b]pyridin-5-yl)benzamide The title compound was prepared by following the procedure described for example 43 using allylamine (0.018 g, 0.250 mmol) instead of ethylamine hydrochloride. Yellow solid (0.033 g, 29%), M.P.: 162-164° C. MS (m/z): 438.93 (M⁺).

Example 62

2-Fluoro-N-methoxy-4-(3-(quinolin-6-ylmethyl)-3H-[1,2,3]triazolo[4,5-b]pyridin-5-yl)benzamide The title compound was prepared by following the procedure described for example 43 using methoxylamine hydrochloride (0.0208 g, 0.250 mmol) instead of ethylamine hydrochloride. Yellow solid (0.055 g, 51%). MP.: 197-199° C. MS (m/z): 429.06 (M⁺).

Example 63

N-(4-(3-(quinolin-6-ylmethyl)-3H-[1,2,3]triazolo[4,5-b]pyridin-5-yl)phenylacetamide The title compound was prepared by following tire procedure described for example 1 using intermediate 14 (0.100 g, 0.338 mmol), 4-acetamidophenylboronic acid (0.076 g, 0.422 mmol), potassium carbonate (0.156 g, 0.027 mmol), dioxane (2 ml), water (0.5 ml) and tetrakis(triphenylphosphine)palladium(O) (0.031 g, 0.067 mmol) in microwave oven (100 W, 100° C.) for 20 min. Brown solid (0.090 g, 67%). M.P.: 220-223° C. MS (m/z); 394.83 (M⁺1).

Example 64

4-(3-(quinolin-6-ylmethyl)-3H-[1,2,3]triazolo[4,5-b]pyridin-5-yl)aniline

To a solution of example 63 (0.060 g, 0.152 mmol) in ethanol (1 ml) was added con. HCl (0.5 ml) and refluxed for 2 h. The reaction mixture was cooled, basified with sodium bicarbonate solution, extracted with ethyl acetate, dried over sodium sulphate and concentrated under reduced pressure to afford the title compound as a brown solid (0.030 g, 42%). M.P.: 190-193° C. MS (m/z); 353.18 (M⁺+1).

Example 65

6-((5-(3,4-Dimethoxyphenyl)-3H-[1,2,3]triazolo[4,5-b]pyridin-3-yl)methyl)quinoline The title compound was prepared by following the procedure described for example 1 using intermediate 14 (0.100 g, 0.338 mmol), 3,4-dimethoxyphenylboronic acid (0.076 g, 0.422 mmol), potassium carbonate (0.156 g, 0.027 mmol), dioxane (2 ml), water (0.5 ml) and tetrakis(triphenylphosphine)palladium(0) (0.031 g, 0.067 mmol) in microwave oven (100 W, 100° C.) for 20 min. Brown solid (0.090 g, 67%). M.P.: 149-152° C. MS (m/z); 397.77 (M⁺).

Example 66

6-((5-(3-Fluoro-4-methoxyphenyl)-3H-[1,2,3]triazolo[4,5-b]pyridin-3-yl)methyl)quinoline The title compound was prepared by following the procedure described for example 1 using intermediate 14 (0.100 g, 0.338 mmol), 3-fluoro-4-methoxyphenylboronic acid (0.074 g, 0.439 mmol), potassium carbonate (0.156 g, 0.027 mmol), dioxane (2 ml), water (0.5 ml) and tetrakis(triphenylphosphine)palladium(0) (0.031 g, 0.067 mmol) in microwave oven (100 W, 100° C.) for 20 min. Pale green solid (0.060 g, 46%), M.P.; 187-190° C. MS (m/z): 385.873 (M⁺).

Example 67

6-((5-(4-Fluorophenyl)-3H-[1,2,3]triazolo[4,5-b]pyridin-3-yl)methyl)quinoline

The title compound was prepared by following the procedure described for example 1 using intermediate 14 (0.100 g, 0.338 mmol), 4-fluorophenylboronic acid (0.059 g, 0.422 mmol), potassium carbonate (0.156 g, 0.027 mmol), dioxane (2 ml), water (0.5 ml) and tetrakis(triphenylphosphine)palladium(0) (0.031 g, 0.067 mmol) in microwave oven (100 W, 100° C.) for 20 min. Yellow solid (0.060 g, 50%). M.P.: 153-156° C. MS (m/z); 355.98 (M⁺).

Example 68

6-((5-(2-Fluorophenyl)-3H-[1,2,3]triazolo[4,5-b]pyridin-3-yl)methyl)quinoline

The title compound was prepared by following the procedure described for example 1 using intermediate 14 (0.100 g, 0.338 mmol), 2-fluorophenylboronic acid (0.059 g, 0.422 mmol), potassium carbonate (0.156 g, 0.027 mmol), dioxane (2 ml), water (0.5 ml) and tetrakis(triphenylphosphine)palladium(0) (0.031 g, 0.067 mmol) in microwave oven (100 W, 100° C.) for 20 min. Yellow solid (0.050 g. 41%), M.P.: 164-166° C. MS (m/z): 355.84 (M⁺).

Example 69

N-(3-(3-(quinolin-6-ylmethyl)-3H-[1,2,3]triazolo[4,5-b]pyridin-5-yl)phenyl)acetamide The title compound was prepared by following the procedure described for example 1 using intermediate 14 (0.100 g, 0.338 mmol), 4-acetamidophenylboronic acid (0.078 g, 0.439 mmol), potassium carbonate (0.156 g, 0.027 mmol), dioxane (2 ml), water (0.5 ml) and tetrakis(triphenylphosphine)palladium(0) (0.031 g, 0.067 mmol) in microwave oven (100 W, 100° C.) for 20 min. Pale green solid (0.065 g, 49%). M.P.: 198-201° C. MS (m/z): 395.11 (M⁺+1).

Example 70

6-((5-(3-(2,2,2-Trifluoroethoxy)phenyl)-3H-[1,2,3]triazolo[4,5-b]pyridin-3-yl)methyl)quinoline The title compound was prepared by following the procedure described for example 1 using intermediate 14 (0.100 g, 0.338 mmol), 3-trifluoroethoxyphenylboronic acid (0.096 g, 0.439 mmol), potassium carbonate (0.156 g, 0.027 mmol), dioxane (2 ml), water (0.5 ml) and tetrakis(triphenylphosphine)palladium(0) (0.031 g, 0.067 mmol) in microwave

Example 71

3-(3-(quinolin-6-ylmethyl)-3H-[1,2,3]triazolo[4,5-b]pyridin-5-yl)aniline

To a solution of example 69 (0.045 g, 0.152 mmol) in ethanol (1 ml), con. HCl (0.5 ml) was added and refluxed for 2 h. The reaction mixture was cooled, basified with sodium bicarbonate solution, extracted with ethyl acetate, dried over sodium sulphate and concentrated under reduced pressure to afford the title compound as brown solid (0.028 g, 70%). M.P.: 187-189° C. MS (m/z): 352.90 (M+).

Example 72

N-(3-dimethylamino)propyl-2-fluoro-4-(3-(quinolin-6-ylmethyl)-3H-[1,2,3]triazolo[4,5-b]pyridin-5-yl)benzamide The title compound was prepared by following the procedure described for example 43 using 3-N,N-Dimethylaminopropylamine (0.026 g, 0.262 mmol) instead of ethylamine hydrochloride. Off-white solid (0.063 g, 54%). M.P.: 148-150° C. MS (m/z): 483.92 (M+).

Example 73

N-Ethyl-2-fluoro-4-(3-(quinolin-6-ylmethyl)-3H-[1,2,3]triazolo[4,5-b]pyridin-5-yl)benzamide hydrochloride The example 43 (0.050 g, 0.117 mmol) was dissolved in THF (1 ml), ether saturated with HCl (1 ml) was added at 0° C. and stirred for 15 min. The precipitate ionised was washed with ether and dried under vacuum to afford the title compound as an off-white solid (0.052 g. 95%). M.P.: 236-238° C. $^1$H-NMR ($\delta$ ppm, DMSO-d$_6$, 400 MHz): 9.07 (m, 1H), 8.73 (m, 2H), 8.41 (m, 1H), 8.24 (d, J=8.8 Hz, 1H), 8.19-8.13 (m. 4H), 8.02 (d, J=7.4 Hz, 1H), 7.80 (m, 2H), 6.29 (s, 2H), 3.23 (m, 2H), 1.14 (t, J=7.2 Hz, 3H).

Example 74

2-Fluoro-4-(3-(quinolin-6-ylmethyl)-3H-[1,2,3]triazolo[4,5-b]pyridin-5-yl)benzamide hydrochloride The example 15 (0.040 g, 0.100 mmol) was dissolved in THF (1 ml), ether saturated with HCl (1 ml) was added at 0° C. and stirred for 15 min. The precipitate formed was washed with ether and dried under vacuum to afford the title compound as an off-white solid (0.043 g, 96%), M.P.: 165-1688° C. $^1$H-NMR ($\delta$ ppm, DMSO-d$_6$, 400 MHz): $\delta$9.10 (m, 1H), 8.79 (m, 1H), 8.73 (d, J=8.8 Hz, 1H), 8.24-8.13 (m, 4H), 8.05 (d, J=8.7 Hz, 1H), 7.83 (m, 3H), 7.74 (s, 1H), 6.29 (s, 2H).

Example 75

6-((5-(3-Fluoro-4-isopropoxyphenyl)-3H-[1,2,3]triazolo[4,5-g]pyridin-3-yl)methyl)quinoline The title compound was prepared by following the procedure described for example 1 using intermediate 14 (0.100 g, 0.338 mmol), 3-fluoro-4-isopropoxyphenylboronic acid pinacol ester (0.113 g, 0.439 mmol), potassium carbonate (0.156 g. 0.027 mmol), dioxane (2 ml), water (0.5 ml) and tetrakis(triphenylphosphine)palladium(0) (0.031 g, 0.067 mmol) in microwave oven (100 W, 100° C.) for 30 min. Brown solid (0.095 g, 68%). M.P.: 128-130° C. MS (m/z): 413.92 (M+).

Example 76

N-(3-(dimethylamino)-3-oxopropyl)-2-fluoro-4-(3-(quinolin-6-ylmethyl)-3H-[1,2,3]triazolo[4,5-b]pyridin-5-yl)benzamide The title compound was prepared by following the procedure described for example 43 using intermediate 23 (0.075 g, 0.326 mmol) instead of Ethylamine hydrochloride. Off-white solid (0.075 g. 60%). M.P.: 163-165° C. $^1$H-NMR ($\delta$ ppm. DMSO-d$_6$, 400 MHz): 8.91 (dd, J=4.2, 1.6 Hz, 1H), 8.46 (d, J=8.7 Hz, 1H), 8.21 (d, J=7.9 Hz, 1H), 8.17 (d, J=9.3 Hz, 1H), 8.10 (d, J=8.7 Hz, 1H), 7.97-7.83 (m, 5H), 7.78 (m, 1H), 7.43 (dd, J=8.3, 4.2 Hz, 1H), 6.15 (s, 2H), 3.84 (q, J=5.4 Hz, 1H), 2.68 (t, J=5.5 Hz, 2H), 3.01 (s, 3H), 2.98 (s, 3H).MS (m/z): 498.41 (M++1).

Example 77

N-(2-(dimethylamino)-2-oxoethyl)-2-fluoro-4-(3-(quinolin-6-ylmethyl)-3H-[1,2,3]triazolo[4,5-b]pyridin-5-yl)benzamide The title compound was prepared by following the procedure described for example 43 using intermediate 24 (0.050 g, 0.280 mmol) instead of Ethylamine hydrochloride. Off-white solid (0.085 g, 70%). M.P.: 177-179° C. MS (m/z): 483.85 (M+).

Example 78

2-Fluoro-N-(2-oxo-2-(pyrrolidin-1-yl)ethyl)-4-(3-(quinolin-6-ylmethyl)-3H-[1,2,3]triazolo[4,5-b]pyridin-5-yl)benzamide The title compound was prepared by following the procedure described for example 43 using intermediate 25 (0.096 g, 0.396 mmol) instead of Ethylamine hydrochloride. Off-white solid (0.085 g. 66%). M.P.: 175-177° C. $^1$H-NMR ($\delta$ ppm. DMSO-d$_6$, 400 MHz): 8.91 (dd, J=4.1, 1.5 Hz, 1H), 8.47 (d, J=8.6 Hz, 1H), 8.22 (d, J=8.0 Hz, 1H), 8.17 (d, J=8.4 Hz, 1H), 8.10 (d, J=8.7 Hz, 1H), 7.98 (m, 4H), 7.87 (dd, J=8.7, 3.2 Hz, 2H), 7.43 (dd, J=8.3, 4.2 Hz, 1H), 6.15 (s, 2H), 4.25 (d, J=3.5 Hz, 2H), 3.58 (t, J=5.9 Hz, 2H), 3.48 (t, J=5.8 Hz, 2H), 2.06 (q, J=6.9 Hz, 2H), 1.94 (q, J=6.8 Hz, 2H), MS (m/z): 509.96 (M+).

Example 79

6-((5-(4-(Cyclopropylmethoxy)-3-fluorophenyl)-3H-[1,2,3]triazolo[4,5-b]pyridin-3-yl)methyl)quinoline The title compound was prepared by following the procedure described for example 1 using intermediate 14 (0.100 g, 0.338 mmol), 2-(4-(cyclopropylmethoxy)-3-fluorophenyl)-4,4,5,5-tetramethyl-1,3,2-dioxaborolane (0.123 g, 0.422 mmol), potassium carbonate (0.156 g, 0.027 mmol), dioxane (2 ml), water (0.5 ml) and tetrakis(triphenylphosphine)palladium(0) (0.031 g, 0.067 mmol) in microwave oven (100 W, 100° C.) for 30 min. Off-white solid (0.040 g, 28%), M.P.: 160-162° C. MS (m/z): 425.89 (M+).

Example 80

6-((5-(3-Fluoro-4-isobutoxyphenyl)-3H-[1,2,3]triazolo[4,5-b]pyridin-3-yl)methylquinoline The title compound was prepared by following the procedure described for example 1 using intermediate 14 (0.100 g, 0.338 mmol), 4-isobutyloxy-3-fluorophenyl boronic acid pinacol ester (0.122 g, 0.422 mmol), potassium carbonate (0.156 g, 0.027 mmol), dioxane (2 ml), water (0.5 ml) and tetrakis(triphenylphosphine)palladium(0)(0.031 g, 0.067 mmol) in microwave oven (100 W, 100° C.) for 30 min. Pale brown solid (0.065 g. 45%). M.P.: 115-157° C. MS (m/z): 428.13 (M++1).

Example 81

3-(2-Fluoro-4-(3-(quinolin-6-ylmethyl)-3H-[1,2,3]triazolo[4,5-b]pyridin-5-yl)phenoxy)-N,N-dimethylpropan-1-amine The title compound was prepared by following the procedure described for example 1 using intermediate 14 (0.100 g, 0.338 mmol), 3-(2-fluoro-4-(4,4,5,5-tetramethyl-1,3,2-dioxaborolan-2-yl)phenoxy)-N,N-dimethylpropan-1-amine (0.137 g, 0.422 mmol), potassium carbonate (0.156 g, 0.027 mmol), dioxane (2 ml), water (0.5 ml) and tetrakis(triphenylphosphine)palladium(0) (0.031 g, 0.067 mmol) in microwave oven (100 W, 100° C.) for 30 min. Pale brown solid (0.055 g. 45%). M.P.: 102-105° C. MS (m/z): 457.18 (M++1).

Example 82

Methyl 2-fluoro-4-(3-(2-(quinolin-6-yl)propan-2-yl)-3H-[1,2,3]triazolo[4,5-b]pyridin-5-yl)benzoate The title compound was prepared by following the procedure described for example 1 using intermediate 17 (0.600 g, 1.841 mmol), 3-fluoro-4-methoxycarbonyl phenylboronic acid (0.459 g, 2.30 mmol), potassium acetate (0.585 g, 5.965 mmol), dioxane (12 ml) and tetrakis(triphenylphosphine)palladium(0) (0.170 g, 0.147 mmol). Off-white solid (0.705 g, 87%). $^1$H-NMR (δ ppm, DMSO-$d_6$, 400 MHz): 8.90 (dd, J=4.2, 1.5 Hz, 1H), 8.44 (d, J=8.7 Hz, 1H), 8.18 (d, J=7.8 Hz, 1H), 8.00 (d, J=9.0 Hz, 1H), 7.92 (m, 2H), 7.75 (d, J=8.7 Hz, 1H), 7.69-7.60 (m, 3H), 7.41 (m, 1H), 3.93 (s, 3H), 2.50 (s, 6H).

Example 83

2-Fluoro-4-(3-(2-(quinolin-6-yl)propan-2-yl)-3H-[1,2,3]triazolo[4,5-b]pyridin-5-yl)benzoic acid To a solution of Example 82 (0.700 g, 1.60 mmol) in methanol (3.7 ml), lithium hydroxide (0.626 g, 14.94 mmol) in water (3.7 ml) and THF (14 ml) were added and stirred at RT. After 12 h, the pH was adjusted to 7-7.5 using 0.5N HCl and the solid precipitated was filtered, washed with ethyl acetate and petroleum ether and dried under vacuum to afford the title compound as an off-white solid (0.485 g, 71%) MS (m/z): 472.99 (M+).

Example 84

2-Fluoro-4-(3-(2-(quinolin-6-yl)propan-2-yl)-3H-[1,2,3]triazolo[4,5-b]pyridin-5-yl)benzamide To Example 83 (0.050 g, 0.116 mmol), thionyl chloride (1 ml) was added and refluxed for 3 h. The excess thionyl chloride was removed under reduced pressure and the residue was cooled to 0° C. Aqueous ammonia (25% solution, 3 ml) was added and stirred for 15 min. The precipitate formed was washed with sodium bicarbonate solution and vacuum dried to afford title compound as brown solid (0.025 g, 50%). M.P.: 127-130° C. $^1$H-NMR (δ ppm, DMSO-$d_6$, 400 MHz): 8.87 (d, J=2.5 Hz, 1H), 8.67 (d, J=8.9 Hz, 1H), 8.42 (d, J=7.9 Hz, 1H), 8.11 (d, J=8.9 Hz, 1H), 8.09 (s, 1H), 7.91 (d, J=8.8 Hz, 1H), 7.79 (d, J=8.3 Hz, 1H), 7.71-7.61 (m, 4H), 7.75 (m, 2H), 2.48 (s, 6H).

Example 85

6-((5-(3-Fluoro-4-(tetrahydro-2H-pyran-4-yloxy)phenyl)-3H-[1,2,3]triazolo[4,5-b]pyridin-3-yl)methyl)quinoline The title compound was prepared by following the procedure described for example 1 using intermediate 14 (0.100 g, 0.338 mmol), 2-(3-fluoro-4-(tetrahydro-2H-pyran-4-yloxy)phenyl)-4,4,5,5-tetramethyl-1,3,2-dioxaborolane (0.109 g. 0.422 mmol), potassium carbonate (0.156 g, 0.027 mmol), dioxane (2 ml), water (0.5 ml) and Tetrakis(triphenylphosphine)palladium(0) (0.031 g, 0.067 mmol) in microwave oven (100 W, 100° C.) for 30 mm. Pale brown solid (0.055 g, 35%). M.P.: 165-167° C., MS (m/z): 455.85 (M+).

Example 86

6-((5-(3-Fluoro-4-(2-methoxyethoxy)phenyl)-3H-[1,2,3]triazolo[4,5-b]pyridin-3-yl)methyl)quinoline The title compound was prepared by following the procedure described for example 1 using intermediate 14 (0.100 g, 0.338 mmol), 2-(3-fluoro-4-(2-methoxyethoxy)phenyl)-4,4,5,5-tetramethyl-1,3,2-dioxaborolane (0.125 g, 0.422 mmol), potassium carbonate (0.156 g, 0.027 mmol), dioxane (2 ml), water (0.5 ml) and tetrakis(triphenylphosphine)palladium(0) (0.031 g, 0.067 mmol) in microwave oven (100 W, 100° C.) for 30 min. Pale yellow solid (0.060 g, 41%). M.P.: 122-124 C. MS (m/z): 430.02 (M++1).

Example 87

2-Fluoro-N-propyl-4-(3-(quinolin-6-ylmethyl)-3H-[1,2,3]triazolo[4,5-b]pyridin-5-yl)benzamide The title compound was prepared by following the procedure described for example 43 using propylamine (0.015 g, 0.250 mmol) instead of ethylamine hydrochloride. Pale yellow solid (0.070 g, 63%). M.P.: 157-159° C. MS (m/z): 440.87 (M+).

Example 88

6-((5-(4-(Cyclopropylcarbamoyl)-3-fluorophenyl)-3H-[1,2,3]triazolo[4,5-b]pyridin-3-yl)methyl)quinoline 1-oxide To a solution of example 46 (0.080 g, 0.182 mmol) in dichloromethane (1 ml), m-chloroperbenzoic acid (0.044 g, 0.255 mmol) was added and stirred at RT for 12 h. The reaction mixture was quenched with sodium sulphite solution, washed with saturated potassium carbonate solution and concentrated. The crude product was chromatographed using methanol:dichloromethane to afford the title compound as a pale yellow solid (0.025 g, 30%). M.P.: 89-92° C. $^1$H-NMR (δ ppm, DMSO-$d_6$, 400 MHz): 8.88 (dd, J=4.1, 1.6 Hz, 1H), 8.75 (d, J=9.0 Hz, 1H), 8.51 (m, 2H) 8.28 (t, J=8.1 Hz, 1H), 7.98-7.86 (m, 5H), 7.71 (d, J=8.5 Hz, 1H), 7.32 (dd, J=8.5, 6.1 Hz, 1H), 6.89 (d, J=11.8 Hz, 1H), 6.15 (s, 2H), 2.99 (m, 1H), 0.94 (m, 2H), 0.69 (m, 2H).

Example 89

N-Cyclopropyl-2-fluoro-4-(3-(quinolin-6-ylmethyl)-3H-[1,2,3]triazolo[4,5-b]pyridin-5-yl)benzamide hydrochloride The example 46 (0.045 g, 0.102 mmol) was dissolved in THF (1 ml), ether saturated with HCl (1 ml) was added at 0° C. and stirred for 15 min. The precipitate formed was washed with ether and dried under vacuum to afford the title compound as an off-white solid (0.046 g, 95%). M.P.: 105-107° C. MS (m/z): 439.12 (M$^+$+1-HCl).

Example 90

N-(Cyclopropylmethyl)-2-fluoro-4-(3-(quinolin-6-ylmethyl)-3H-[1,2,3]triazolo[4,5-b]pyridin-5-yl)benzamide The title compound was prepared by following the procedure described for example 43 using cyclopropylmethylamine (0.018 g, 0.250 mmol) instead of ethylamine hydrochloride. Off-white solid (0.085 g, 75%). M.P.: 120-122° C. MS (m/z): 452.91 (M$^+$).

Example 91

N-Butyl-2-fluoro-4-(3-(quinolin-6-ylmethyl)-3H-[1,2,3]triazolo[4,5-b]pyridin-5-yl)benzamide The title compound was prepared by following the procedure described for example 43 using n-butylamine (0.019 g, 0.250 mmol) instead of ethylamine hydrochloride. Off-white solid (0.064 g, 56%). M.P.: 100-102° C. MS (m/z): 455.08 (M$^+$).

Example 92

2-Fluoro-N-(furan-2-ylmethyl)-4-(3-(quinolin-6-ylmethyl)-3H-[1,2,3]triazolo[4,5-b]pyridin-5-yl)benzamide The title compound was prepared by following the procedure described for example 43 using furfurylamine (0.024 g, 0.250 mmol) instead of ethylamine hydrochloride. Brown solid (0.060 g, 50%). M.P.: 144-147° C. MS (m/z): 479.02 (M$^+$).

Example 93

2-Fluoro-4-(3-(quinolin-6-ylmethyl)-3H-[1,2,3]triazolo[4,5-b]pyridin-5-yl)-N-(2,2,2-trifluoroethyl)benzamide The title compound was prepared by following the procedure described for example 43 using 2,2,2-trifluoroethylamine (0.024 g. 0.250 mmol) instead of ethylamine hydrochloride. Pale yellow solid (0.060 g, 50%). M.P.: 194-196° C., MS (m/z): 481.12 (M$^+$).

Example 94

2-Fluoro-N-(2-methoxyethyl)-4-(3-(quinolin-6-ylmethyl)-3H-[1,2,3]triazolo[4,5-b]pyridin-5-yl)benzamide The title compound was prepared by following the procedure described for example 43 using 2-methoxyethylamine (0.019 g, 0.250 mmol) instead of ethylamine hydrochloride. Pale green solid (0.060 g, 52%). M.P.: 162-164° C. MS (m/z): 456.83 (M$^+$).

Example 95

N-Isopropyl-4-(3-(quinolin-6-ylmethyl)-3H-[1,2,3]triazolo[4,5-b]pyridin-5-yl)benzenesulfonamide The title compound was prepared by following the procedure described for example 1 using intermediate 14 (0.102 g, 0.338 mmol), 4-(N-isopropylsulfamoyl)phenylboronic acid (0.102 g, 0.422 mmol), potassium carbonate (0.156 g, 0.027 mmol), dioxane (2 ml), water (0.5 ml) and tetrakis(triphenylphosphine)palladium(0) (0.031 g, 0.067 mmol) in microwave oven (100 W, 100° C.) for 30 min. Green solid (0.050 g, 30%). M.P.: 154-156° C. MS (m/z): 458.79 (M$^+$).

Example 96

N,N-Dimethyl-3-(3-(quinolin-6-ylmethyl)-3H-[1,2,3]triazolo[4,5-b]pyridin-5-yl)aniline The title compound was prepared by following the procedure described for example 1 using intermediate 14 (0.302 g, 0.338 mmol), 3-(dimethylamino) phenylboronic acid (0.072 g, 0.422 mmol), potassium carbonate (0.156 g, 0.027 mmol), dioxane (2 ml), water (0.5 ml) and tetrakis(triphenylphosphine)palladium(0) (0.031 g, 0.067 mmol) in microwave oven (100 W, 100° C.) for 30 min. Green solid (0.041) g, 31%). M.P.: 124-126° C. MS (m/z): 380.88 (M$^+$).

Example 97

2-Fluoro-N-isobutyl-4-(3-(quinolin-6-ylmethyl)-3H-[1,2,3]triazolo[4,5-b]pyridin-5-yl)benzamide The title compound was prepared by following the procedure described for example 43 using isobutylamine (0.018 g, 0.250 mmol) instead of ethylamine hydrochloride. Off-white solid (0.050 g, 44%). M.P.: 158-160° C. MS (m/z): 455.01 (M$^+$).

Example 98

N-Cyclopentyl-2-fluoro-4-(3-(quinolin-6-ylmethyl)-3H-[1,2,3]triazolo[4,5-b]pyridin-5-yl)benzamide The title compound was prepared by following the procedure described for example 43 using cyclopentylamine (0.021 g. 0.250 mmol) instead of ethylamine hydrochloride. Pale green solid (0.040 g, 34%). M.P.: 166-168° C. MS (m/z): 467.12 (M$^+$+1).

Example 99

2-Fluoro-N-isopropyl-4-(3-(quinolin-6-ylmethyl)-3H-[1,2,3]triazolo[4,5-b]pyridin-5-yl)benzamide The title compound was prepared by following the procedure described for example 43 using isopropylamine (0.029 g, 0.500 mmol) instead of ethylamine hydrochloride. Off-white solid (0.060 g, 54%). M.P.: 177-179° C. MS (m/z): 440.87 (M$^+$).

Example 100

Methyl 2-chloro-4-(3-(quinolin-6-ylmethyl)-3H-[1,2,3]triazolo[4,5-b]pyridin-5-yl)benzoate The title compound was prepared by following the procedure described for example 1 using intermediate 14 (1.00 g, 3.07 mmol), 3-chloro-4-methoxycarbonylphenylboronic acid (0.825 g, 3.84 mmol), potassium acetate (0.976 g, 9.945 mmol), dioxane (20 ml) and tetrakis(triphenylphosphine)palladium(0) (0.284 g. 0.246 mmol). Reddish brown solid (1.00 g, 71%). $^1$H-NMR (δ ppm, DMSO-d$_6$, 400 MHz): 8.92 (dd, J=4.2, 1.6 Hz, 1H), 8.48 (d, J=8.6 Hz, 1H), 8.24 (d, J=1.3 Hz, 1H), 8.17 (d, J=8.3 Hz, 1H), 8.10 (d, J=11.8 Hz, 1H), 8.04 (m, 3H), 7.87 (m, 2H), 7.43 (q, J=4.2 Hz, 1H), 6.15 (s, 2H), 3.98 (s, 3H).

Example 101

2-Chloro-4-(3-(quinolin-6-ylmethyl)-3H-[1,2,3]triazolo[4,5-b]pyridin-5-yl)benzoic acid To a solution of Example 100 (1.00 g, 2.18 mmol) in methanol (5 ml), lithium hydroxide (0.856 g, 20.40 mmol) in water (5 ml) and THF (19 ml) were added and stirred at RT. After 12 h, pH was adjusted to 7-7.5 using 0.5N HCl and the solid precipitated was filtered, washed with ethyl acetate and petroleum ether and dried under vacuum to afford the title compound as an off-white solid (0.900 g, 93%).

Example 102

2-Chloro-N-propyl-4-(3-(quinolin-6-ylmethyl)-3H-[1,2,3]triazolo[4,5-b]pyridin-5-yl)benzamide The title compound was prepared by following the procedure described for example 43 by replacing the example 13 with example 101 (0.100 g, 0.240 mmol) and using propylamine (0.028 g, 0.480 mmol) instead of ethylamine hydrochloride. Brown solid (0.043 g, 39%). M.P.: 128-130° C. MS (m/z): 456.83 (M$^+$+1).

Example 103

2-Fluoro-N-methyl-4-(3-(2-(quinolin-6-yl)propan-2-yl)-3H-[1,2,3]triazolo[4,5-b]pyridin-5-yl)benzamide To Example 83 (0.100 g, 0.234 mmol), thionyl chloride (3 ml) was added and refluxed for 3 h. The excess thionyl chloride was removed under reduced pressure and the residue was cooled to 0° C. Methylamine in ethanol (50% solution, 5 ml) was added and stirred for 15 min. The precipitate formed was filtered, washed with sodium bicarbonate solution, dried over sodium sulphate and concentrated to afford title compound as a yellow solid (0.028 g, 27%). M.P.: 171-173° C. MS (m/z): 440.94 (M$^+$).

Example 104

N-Cyclobutyl-2-fluoro-4-(3-(quinolin-6-ylmethyl)-3H-[1,2,3]triazolo[4,5-b]pyridin-5-yl)benzamide The title compound was prepared by following the procedure described for example 43 by using cyclobutylamine (0.035 g, 0.500 mmol) instead of ethylamine hydrochloride. Off-white solid (0.050 g, 44%). M.P.: 171-174° C. MS (m/z): 452.91 (M$^+$).

Example 105

2-Fluoro-N-propyl-4-(3-(2-(quinolin-6-yl)propan-2-yl)-3H-[1,2,3]triazolo[4,5-b]pyridin-5-yl)benzamide The title compound was prepared by following the procedure described for example 43 by replacing the example 13 with example 83 (0.100 g, 0.234 mmol) and using propylamine (0.027 g, 0.468 mmol) instead of ethylamine hydrochloride. Pale green solid (0.050 g, 47%). M.P.: 162-164° C. MS (m/z): 468.94 (M$^+$).

Example 106

N-Cyclopropyl-2-fluoro-4-(3-(2-(quinolin-6-yl)propan-2-yl)-3H-[1,2,3]triazolo[4,5-b]pyridin-5-yl)benzamide The title compound was prepared by following the procedure described for example 43 by replacing the example 13 with example 83 (0.080 g, 0.187 mmol) and using cyclopropylamine (0.021 g, 0.374 mmol) instead of ethylamine hydrochloride. Pale green solid (0.015 g, 17%). M.P.: 156-159° C. MS (m/z): 466.98 (M$^+$).

Example 107

N-Ethyl-2-fluoro-4-(3-(2-(quinolin-6-yl)propan-2-yl)-3H-[1,2,3]triazolo[4,5-b]pyridin-5-yl)benzamide The title compound was prepared by following the procedure described for example 43 by replacing the example 13 with example 83 (0.080 g, 0.187 mmol) and ethylamine hydrochloride (0.015 g, 0.187 mmol). Pale green solid (0.015 g, 17%). M.P.: 132-135° C. MS (m/z): 454.94 (M$^+$).

Example 108

2-Chloro-4-(3-(2-(quinolin-6-ylmethyl-3H-[1,2,3]triazolo[4,5-b]pyridin-5-yl)benzamide To Example 101 (0.100 g. 0.240 mmol), thionyl chloride (3 ml) was added and refluxed for 3 h. The excess thionyl chloride was removed under reduced pressure and the residue was cooled to 0° C. Aqueous 25% ammonia (4 ml) was added and stirred for 15 min. The precipitate formed was washed with sodium bicarbonate solution and vacuum dried to afford title compound as a brown solid (0.060 g, 60%). M.P.: 212-215° C. $^1$H-NMR (δ ppm, DMSO-d$_6$, 400 MHz): 8.88 (dd, J=4.1, 2.6 Hz, 1H). 8.70 (d, J=8.7 Hz, 1H). 8.37 (d, J=8.3 Hz, 1H), 8.31 (s, 1H), 8.24 (d, J=8.1 Hz, 1H), 8.21 (d, J=8.8 Hz, 1H), 8.04 (m, 3H), 7.83 (dd, J=8.7, 1.6 Hz, 1H), 7.69 (s, 1H), 7.61 (d, J=8.0 Hz, 1H), 7.53 (dd, J=8.3, 4.2 Hz, 1H), 6.23 (s, 2H), MS (m/z): 415.11 (M$^+$).

Example 109

2-Chloro-N-methyl-4-(3-(2-(quinolin-6-ylmethyl)-3H-[1,2,3]triazolo[4,5-b]pyridin-5-yl)benzamide To Example 101 (0.100 g, 0.240 mmol), thionyl chloride 13 ml) was added and refluxed for 3 h. The excess thionyl chloride was removed under reduced pressure and the residue was cooled to 0° C. Methylamine in ethanol (50% solution, 4 ml) was added and stirred for 15 min. The precipitate formed was filtered, washed with sodium bicarbonate solution and diethyl ether and vacuum dried to afford title compound as pale brown solid (0.060 g, 58%). M.P.: 227-230° C. MS (m/z): 429.04 (M$^+$+1).

Example 110

2-Fluoro-N-methoxy-4-(3-(quinolin-6-ylmethyl)-3H-[1,2,3]triazolo[4,5-b]pyridin-5-yl)benzamide hydrochloride The example 62 (0.040 g, 0.093 mmol) was dissolved in THF (1 ml), ether saturated with HCl (1 ml) was added at 0° C. and stirred for 15 min. The precipitate formed was washed with ether and dried under vacuum to afford the title compound as an off-white solid (0.030 g, 69%), M.P.: 145-147° C. MS (m/z): 429.46 (M$^+$+1-HCl).

Example 111

2-Fluoro-4-(3-(2-(quinolin-6-ylmethyl)-3H-[1,2,3]triazolo[4,5-b]pyridin-5-yl)-N-(thiazol-2-yl)benzamide The title compound was prepared by following the procedure described for example 43 by using 2-aminothiazole (0.050 g, 0.500 mmol) instead of ethylamine hydrochloride. Pale brown solid (0.016 g, 13%). M.P.: 204-206° C., MS (m/z): 481.89 (M$^+$).

Example 112

N-(3-Aminopropyl)-2-fluoro-4-(3-(2-(quinolin-6-ylmethyl)-3H-[1,2,3]triazolo[4,5-b]pyridin-5-yl)benzamide To a solution of example 13 (0.150 g, 0.375 mmol) in DMF (1 ml) N-ethyldiisopropylamine (0.048 g, 0.375 mmol) and HATU (0.143 g, 0.375 mmol) were added and stirred for 5 min. N-boc-1,3-diaminopropane (0.130 g, 0.751 mmol) was added at RT and the reaction mixture was stirred for 12 h. To the reaction mixture water was added and extracted with ethyl acetate, dried over sodium sulphate and concentrated under reduced pressure. The crude product was purified by column chromatography with methanol:dichloromethane to afford N-boc-protected amide (0.200 g). The amide was dissolved in dichlomethane (1 ml) and trifluoroacetic acid (0.5 ml) was added and stirred at RT for 1 h. The reaction mixture was quenched with sodium bicarbonate solution, extracted with dicloromethane, dried over sodium sulphate and concentrated to afford the title compound as a pale brown solid (0.160 g, 93%). M.P.: 292-294° C. MS (m/z): 456.270 (M$^+$).

Example 113

2-Chloro-N-cyclopropyl-4-(3-(quinolin-6-ylmethyl)-3H-[1,2,3]triazolo[4,5-b]pyridin-5-yl)benzamide The title compound was prepared by following the procedure described for example 43 by replacing the example 13 with example 101 (0.100 g, 0.240 mmol) and using cyclopropylamine (0.028 g, 0.480 mmol) instead of ethylamine hydrochloride. Off-white solid (0.047 g, 43%). M.P.: 197-199° C. MS (m/z): 455.08 (M$^+$).

Example 114

2-Fluoro-N-(3-oxo-3-(pyrrolidin-1-yl)propyl)-4-(3-(quinolin-6-ylmethyl)-3H-[1,2,3]triazolo[4,5-b]pyridin-5-yl)benzamide The title compound was prepared by following the procedure described for example 43 using intermediate 26 (0.080 g, 0.312 mmol) instead of ethylamine hydrochloride. Off-white solid (0.075 g, 57%). M.P.: 151-153° C. MS (m/z): 524.24 (M$^+$).

Example 115

2-Fluoro-N-hydroxy-4-(3-(quinolin-6-ylmethyl)-3H-[1,2,3]triazolo[4,5-b]pyridin-5-yl)benzamide The title compound was prepared by following the procedure described for example 43 by using hydroxylamine hydrochloride (0.035 g, 0.500 mmol) instead of ethylamine hydrochloride. Off-white solid (0.010 g, 9%), M.P.: 180-182° C. MS (m/z): 415.31 (M$^+$+1).

Example 116

N-Isopropyl-4-(3-(quinolin-6-ylmethyl)-3H-[1,2,3]triazolo[4,5-b]pyridin-5-yl)benzamide The title compound was prepared by following the procedure described for example 43 by using example 8 (0.100 g, 0.262 mmol) and isopropylamine (0.031 g, 0.524 mmol) instead of ethylamine hydrochloride. Off-white solid (0.080 g, 12%). M.P.: 181-183° C., MS (m/z): 423.37 (M$^+$+1).

Example 117

2-Fluoro-N-(3-oxo-3-(piperidin-1-yl)propyl)-4-(3-(quinolin-6-ylmethyl)-3H-[1,2,3]triazolo[4,5-b]pyridin-5-yl)benzamide The title compound was prepared by following the procedure described for example 43 using intermediate 27 (0.135 g, 0.500 mmol) instead of ethylamine hydrochloride. Off-white solid (0.025 g, 19%). M.P.: 109-111° C. MS (m/z): 538.03 (M$^+$).

Example 118

1-Ethyl-3-(4-(3-(4-(quinolin-6-ylmethyl)-3H-[1,2,3]triazolo[4,5-b]pyridin-5-yl)phenyl)urea The title compound was prepared by following the procedure described for example 1 using intermediate 14 (0.102 g, 0.338 mmol). 4-(3-ethylureido)phenylboronic acid (0.123 g, 0.422 mmol), potassium carbonate (0.156 g, 0.027 mmol), dioxane (2 ml), water (0.5 ml) and tetrakis(triphenylphosphine)palladium(0) (0.031 g, 0.067 mmol) in microwave oven (100 W, 100° C.) for 30 min. Brown solid (0.060 g, 42%). M.P.: 193-196° C. MS (m/z): 424.28 (M$^+$+1).

Example 119

2-Chloro-N-ethyl-4-(3-(quinolin-6-ylmethyl)-3H-[1,2,3]triazolo[4,5-b]pyridin-5-yl)benzamide The title compound was prepared by following the procedure described for example 43 by replacing the example 13 with example 101 (0.100 g, 0.240 mmol) and ethylamine hydrochloride. Off-white solid (0.050 g, 47%). M.P.: 187-190° C. $^1$H-NMR (δ ppm, DMSO-d$_6$, 400 MHz): 8.88 (dd, J=4.1, 1.4 Hz, 1H). 8.70 (d, J=8.7 Hz, 1H), 8.51 (d, J=5.4 Hz, 1H), 8.37 (d, J=8.3 Hz, 1H), 8.31 (s, 1H), 8.25 (d, J=8.0 Hz, 1H), 8.21 (d, J=8.0 Hz, 1H), 8.04 (s, 1H), 8.01 (d, J=8.7 Hz, 1H), 7.82 (d, J=8.7 Hz, 1H), 7.58 (d, J=8.0 Hz, 1H), 7.53 (dd, J=8.3, 4.2 Hz, 1H), 6.23 (s, 2H), 3.30 (m, 2H), 1.14 (t, J=7.2 Hz, 3H), MS (m/z): 443.04 (M$^+$).

Example 120

2-Fluoro-N-(3-morpholino-3-oxopropyl)-4-(3-(quinolin-6-ylmethyl)-3H-[1,2,3]triazolo[4,5-b]pyridin-5-yl)benzamide The title compound was prepared by following the procedure described for example 43 using intermediate 28 (0.136 g, 0.500 mmol) instead of ethylamine hydrochloride. Pale yellow solid (0.025 g, 19%). M.P.: 212-215° C. MS (m/z): 540.13 (M$^+$+1).

Example 121

N-(3-(dimethylamino)propyl)-2-fluoro-4-(3-(2-(quinolin-6-ylmethyl)propan-2-yl)-3H-[1,2,3]triazolo[4,5-b]pyridin-5-yl)benzamide dihydrochloride Ether saturated with HCl (1 ml) was added at 0° C. to a solution of example 72 (0.040 g, 0.082 mmol) in THF (1 ml), and stirred for 15 min. The precipitate formed was washed with ether and dried under vacuum to afford the title compound as an off-white solid (0.040 g, 88%). M.P.: 137-140° C. MS (m/z): 483.54 (M$^+$–2HCl).

Example 122

2-chloro-4-(3-(quinolin-6-ylmethyl)-3H-[1,2,3]triazolo[4,5-b]pyridin-5-yl)-N-(1H-1,2,4-triazol-3-yl)benzamide The title compound was prepared by following the procedure described for example 43 by replacing example 13 with example 101 (0.100 g, 0.240 mmol) and 3-amino-1,2,4-triazole (0.040 g, 0.480 mmol) instead of ethylamine hydrochloride. Pale green solid (0.015 g, 13%). M.P.: 286-288° C. $^1$H-NMR (δ ppm, DMSO-d$_6$, 400 MHz): 8.88 (d, J=3.7 Hz, 1H), 8.74 (d, J=8.7 Hz, 1H), 8.40-8.32 (m, 3H), 8.26 (d, J=8.7 Hz, 1H), 8.05 (s, 1H), 8.02 (d, J=8.7 Hz, 1H), 7.87-7.82 (m, 4H), 7.54 (s, 1H), 7.53 (dd. J=8.4, 4.2 Hz, 1H), 6.24 (s, 2H), MS (m/z): 482.03 (M$^+$).

Example 123

2-Chloro-4-(3-(quinolin-6-ylmethyl)-3H-[1,2,3]triazolo[4,5-b]pyridin-5-yl)benzamide hydrochloride Example 108 (0.150 g, 0.360 mmol) was dissolved in THF (1 ml), ether saturated with HCl (1 ml) was added at 0° C. and stirred for 15 min. The precipitate formed was washed with ether and dried under vacuum to afford the title compound as an off-white solid (0.060 g, 46%). M.P.: 273-275° C.

Example 124

2-Fluoro-N-(3-piperidin-1-yl)propyl)-4-(3-(quinolin-6-ylmethyl)-3H-[1,2,3]triazolo[4,5-b]pyridin-5-yl)benzamide The title compound was prepared by following the procedure described for example 43 using 3-(piperidin-1-yl)propan-1-amine (0.086 g, 0.500 mmol) instead of ethylamine hydrochloride. Off-white solid (0.040 g, 30%). M.P.: 135-137° C. MS (m/z): 524.52 (M$^+$+1).

Example 125

N-(3-Aminopropyl)-2-fluoro-4-(3-(quinolin-6-ylmethyl)-3H-[1,2,3]triazolo[4,5-b]pyridin-5-yl)benzamide dihydrochloride Example 112 (0.130 g, 0.287 mmol) was dissolved in THF (2 ml), ether saturated with HCl (1 ml) was added at 0° C. and stirred for 15 min. The precipitate formed was washed with ether and dried under vacuum to afford the title compound as an off-white-solid (0.090 g, 64%). M.P.: 290-293° C.

Example 126

2-Chloro-N-(3-(dimethylamino)propyl)-4-(3-(quinolin-6-ylmethyl)-3H-[1,2,3]triazolo[4,5-b]pyridin-5-yl)benzamide dihydrochloride The title compound was prepared by following the procedure described for example 43 by replacing example 13 with example 101 (0.150 g, 0.360 mmol) and 3-N,N-dimethylaminopropylamine (0.072 g, 0.720 mmol) instead of ethylamine hydrochloride and hydrochloride salt formation with ether saturated with HCl (2 ml). Pale yellow solid (0.045 g, 22%). M.P.: 185-187° C. $^1$H-NMR (δ ppm, DMSO-d$_6$, 400 MHz): 10.11 (br.s, 1H), 9.06 (d, J=4.4 Hz, 1H), 8.73 (d, J=8.8 Hz, 1H), 8.71 (m, 2H), 8.33 (s, 1H), 8.27 (m, 2H), 8.17 (m, 2H), 8.00 (d, J=8.7 Hz, 1H). 7.79 (dd, J=8.1, 4.1 Hz, 1H), 7.64 (d, J=8.0 Hz, 1H), 6.28 (s, 2H), 3.34 (q, J=6.5 Hz, 2H), 3.13 (m, 2H), 2.76 (s, 3H), 2.75 (s, 3H), 1.93 (m, 2H).

Example 127

2-Fluoro-4-(3-(quinolin-6-ylmethyl)-3H-[1,2,3]triazolo[4,5-b]pyridin-5-yl)-N-(1H-1,2,4-triazol-3-yl)benzamide hydrochloride The example 52 (0.026 g, 0.055 mmol) was dissolved in THF (1 ml), ether saturated with HCl (0.5 ml) was added at 0° C. and stirred for 15 min. The precipitate formed was washed with ether and dried under vacuum to afford the title compound as an off-white solid (0.024 g, 87%). M.P.: 274-276° C. $^1$H-NMR (δ ppm, DMSO-d$_6$, 400 MHz): δ11.74 (br s, 1H), 9.06 (d, J=4.1 Hz, 1H), 8.79 (m, 2H), 8.79 (m, 2H), 8.35-8.12 (m, 6H), 8.02 (m, 2H), 7.87 (m, 1H), 7.78 (dd, J=8.0, 4.7 Hz, 1H), 6.30 (s, 2H).

Example 128

Methyl 2,6-difluoro-4-(3-(quinolin-6-ylmethyl)-3H-[1,2,3]triazolo[4,5-b]pyridin-5-yl)benzoate The title compound was prepared by following the procedure described for example 1 using intermediate 14 (1.15 g, 3.91 mmol), 3,5-difluoro-4-methoxycarbonyl phenylboronic acid (prepared according to Krzysztof Durka, et al in Eur. J, Org, Chem. 2009, 4325-4332, 1.10 g, 5.09 mmol), potassium acetate (1.276 g, 13.03 mmol), dioxane (20) and tetrakis (triphenylphosphine)palladium(0) (0.361 g, 0.31346 mmol). Brown solid (0.620 g, 37%), $^1$H-NMR ($\delta$ ppm, DMSO-d$_6$, 400 MHz): 8.91 (d, J=2.9 Hz, 1H), 8.49 (d, J=8.6 Hz, 1H), 8.17 (d, J=8.2 Hz, 1H), 8.10 (d, J=8.7 Hz, 1H), 7.97 (s, 1H), 7.86 (dd, J=8.8, 1.4 Hz, 1H), 7.81 (d, J=8.6 Hz, 1H), 7.74 (d, J=9.1 Hz, 2H), 7.43 (dd, J=8.4, 4.2 Hz, 1H), 6.15 (s, 2H), 3.99 (s, 3H).

Example 129

2,6-Difluoro-4-(3-(quinolin-6-ylmethyl)-3H-[1,2,3] triazolo[4,5-b]pyridin-5-yl)benzoic acid To a solution of Example 128 (0.70 g, 1.62 mmol) in methanol (3.8 ml), lithium hydroxide (0.635 g, 15.13 mmol) in water (3.8 ml) and THF (14.3 ml) were added and stirred at RT. After 12 h, pH was adjusted to ca. 7 using 0.5N HCl and the solid precipitated was filtered, washed with ethyl acetate and petroleum ether and dried under vacuum to afford the title compound as pale brown solid (0.50 g, 74%).

Example 130

2,6-Difluoro-4-(3-(quinolin-6-ylmethyl)-3H-[1,2,3] triazolo[4,5-b]pyridin-5-yl)benzamide The title compound was prepared by following the procedure described for example 102 using Example 129 (0.500 g, 1.19 mmol), thionyl chloride (10 ml) and aqueous 25% ammonia (7 ml). Off-white solid (0.400 g, 81%). M.P.: 272-275° C. $^1$H-NMR ($\delta$ ppm, DMSO-d$_6$, 400 MHz); 8.88 (d, J=3.9 Hz, 1H), 8.74 (d, J=8.8 Hz, 1H), 8.37 (d, J=7.8 Hz, 1H), 8.25 (d, J=8.9 Hz, 1H), 8.20 (s, 1H), 8.07 (m, 3H), 8.01 (d, J=8.5 Hz, 1H), 7.93 (s, 1H), 7.83 (d, J=6.8 Hz, 1H), 7.53 (dd, J=8.6, 4.4 Hz, 1H), 6.24 (s, 2H).

Example 131

Methyl 2-chloro-4-(3-((7-fluoroquinolin-6-yl)methyl-3H-[1,2,3]triazolo[4,5-b]pyridin-5-yl)benzoate The title compound was prepared by following the procedure described for example 1 using intermediate 18 (0.345 g, 1.091 mmol), 3-chloro-4-methoxycarbonylphenylboronic acid (0.295 g, 1.37 mmol), potassium acetate (0.359 g, 3.65 mmol), dioxane (8 ml) and tetrakis(triphenylphosphine)palladium(0) (0.101 g, 0.087 mmol). Off-white solid (0.277 g, 56%). $^1$H-NMR ($\delta$ ppm, DMSO-d$_6$, 400 MHz); 8.91 (d, J=3.3 Hz, 1H), 8.50 (d, J=8.6 Hz, 1H), 8.23 (s, 1H), 8.10 (d, J=8.2 Hz, 1H), 8.03 (d, J=6.9 Hz, 1H). 7.98 (d, J=8.1 Hz, 1H), 7.87 (m, 3H), 7.38 (dd, J=8.3, 4.2 Hz, 1H), 6.22 (s, 2H), 3.97 (s, 3H).

Example 132

2-Chloro-4-(3-((7-fluoroquinolin-6-yl)methyl)-3H-[1,2,3]triazolo[4,5-b]pyridin-5-yl)benzoic acid To a solution of Example 131 (0.185 g, 0.412 mmol) in methanol (2 ml), lithium hydroxide (0.161 g, 3.84 mmol) in water (2 ml), THF (4 ml) were added and stirred at RT. After 12 h, pH was adjusted to ca. 7 using 0.5N HCl and the solid precipitated was filtered, washed with ethyl acetate and petroleum ether and dried under vacuum to afford the title compound as a pale brown solid (0.150 g, 84%).

Example 133

2-Chloro-N-ethyl-4-(3-((7-fluoroquinolin-6-yl)methyl-3H-[1,2,3]triazolo[4,5-b]pyridin-5-yl)benzamide The title compound was prepared by following the procedure described for example 43 replacing the example 13 with example 132 (0.100 g, 0.230 mmol) and ethylamine hydrochloride. Off-white solid (0.020 g, 19%). M.P.: 197-199° C. $^1$H-NMR ($\delta$ ppm, DMSO-d$_6$, 400 MHz): 8.92 (dd, J=4.2, 2.8 Hz, 1H), 8.70 (d, J=8.7 Hz, 1H), 8.51 (t, J=5.4 Hz, 1H), 8.44 (d, J=8.0 Hz, 1H), 8.28 (d, J=1.4 Hz, 1H), 8.22 (m, 3H), 7.83 (d, J=11.4 Hz, 1H), 7.56 (m, 2H), 6.26 (s, 2H), 3.28 (m, 2H), 1.14 (t, J=7.2 Hz, 3H).

Example 134

2-Chloro-4-(3-((7-fluoroquinolin-6-yl)methyl)-3H-[1,2,3]triazolo[4,5-b]pyridin-5-yl)benzamide The title compound was prepared by following the procedure described for example 102 using Example 132 (0.050 g, 0.115 mmol), thionyl chloride (2 ml) and aqueous 25% ammonia (2 ml). Brown solid (0.015 g, 30%). M.P.: 202-204° C., $^1$H-NMR ($\delta$ ppm, DMSO-d$_6$, 400 MHz): 8.92 (d, J=4.1 Hz, 1H), 8.70 (d, J=8.6 Hz, 1H), 8.44 (d, J=8.0 Hz, 1H). 8.27 (s, 1H), 8.22 (m, 3H), 7.96 (s, 1H) 7.83 (d, J=11.5 Hz, 1H), 7.68 (s, 1H), 7.60 (d, J=8.0 Hz, 1H), 7.55 (dd, J=8.4, 4.3 Hz, 1H), 6.26 (s, 2H).

Example 135

Methyl 2-fluoro-4-(3-((7-fluoroquinolin-6-yl)methyl)-3H-[1,2,3]triazolo[4,5-b]pyridin-5-yl)benzoate The title compound was prepared by following the procedure described for example 1 using intermediate 18 (0.350 g, 1.15 mmol), 3-fluoro-4-methoxycarbonyl phenylboronic acid (0.276 g, 1.39 mmol), potassium acetate (0.365 g, 3.71 mmol), dioxane (8 ml) and tetrakis(triphenylphosphine)palladium(0) (0.103 g, 0.089 mmol). Pale brown solid (0.350 g, 70%). M.P.: 213-215° C.

Example 136

2-Fluoro-4-(3-((7-fluoroquinolin-6-yl)methyl)-3H-[1,2,3]triazolo[4,5-b]pyridin-5-yl)benzoic acid To a solution of Example 135 (0.240 g, 0.605 mmol) in methanol (3 ml), lithium hydroxide (0.237 g, 5.64 mmol) in water (3 ml), THF (6 ml) were added and stirred at RT. After 12 h, pH was adjusted to ca 7 using 0.5N HCl and the solid precipitated was filtered, washed with ethyl acetate and petroleum ether and dried under vacuum to afford the title compound as pale brown solid (0.110 g, 44%).

Example 137

2-Fluoro-4-(3-((7-fluoroquinolin-6-yl)methyl-3H-[1, 2,3]triazolo[4,5-b]pyridin-5-yl)benzamide The title compound was prepared by following the procedure described for example 102 using Example 136 (0.080 g, 0.191 mmol), thionyl chloride (2 ml) and aqueous 25% ammonia (2 ml). Pale brown solid (0.060 g, 75%). M.P.: 206-208° C. $^1$H-NMR (δ ppm, DMSO-d$_6$, 400 MHz): 8.92 (d, J=3.2 Hz, 1H), 8.71 (d, J=8.7 Hz, 1H), 8.44 (d, J=8.4 Hz, 1H), 8.23 (t, J=9.2 Hz, 2H), 8.19 (m, 2H), 7.83-7.73 (m, 4H), 7.54 (dd, J=8.2, 4.0 Hz, 1H), 6.26 (s, 2H).

Example 138

3-(3-Quinolin-6-ylmethyl)-3H-[1,2,3]triazolo[4,5-b]pyridin-5-yl)benzamide

The title compound was prepared by following the procedure described for example 102 using Example 54 (0.100 g, 0.262 mmol), thionyl chloride (4 ml) and aqueous 25% ammonia (4 ml). Brown solid (0.040 g, 40%). M.P.: 263-265° C.

Example 139

2,6-Difluoro-4-(3-(quinolin-6-ylmethyl)-3H-[1,2,3]triazolo[4,5-b]pyridin-5-yl)benzamide hydrochloride Example 130 (0.040 g, 0.096 mmol) was dissolved in THF (1 ml), ether saturated with HCl (1 ml) was added at 0° C. and stirred for 15 min. The precipitate formed was washed with ether and dried under vacuum to afford the title compound as a brown solid (0.027 g, 43%). M.P.: 272-275° C. $^1$H-NMR (δ ppm, DMSO-d$_6$, 400 MHz): 9.02 (d, J=3.2 Hz, 1H), 8.74 (d, J=8.8 Hz, 1H), 8.63 (d, J=7.6 Hz, 1H), 8.26 (d, J=8.7 Hz, 1H), 8.20 (d, J=13.6 Hz, 2H), 8.11 (m, 3H), 7.96 (m, 2H), 7.72 (dd, J=8.3, 4.6 Hz, 1H), 6.28 (s, 2H).

Example 140

2-Chloro-4-(3-((7-fluoroquinolin-6-yl)methyl)-3H-[1,2,3]triazolo[4,5-b]pyridin-5-yl)benzamide hydrochloride The example 134 (0.035 g, 0.080 mmol) was dissolved in THF (2 ml), ether saturated with HCl (2 ml) was added at 0° C. and stirred for 15 min. The precipitate formed was washed with ether and dried under vacuum to afford the title compound as a pale yellow solid (0.022 g. 59%). M.P.: 269-272° C.

Example 141

2-Fluoro-4-(3-((7-fluoroquinolin-6-yl)methyl)-3H-[1,2,3]triazolo[4,5-b]pyridin-5-yl)benzamide hydrochloride Example 137 (0.080 g, 0.192 mmol) was dissolved in THF (2 ml), ether saturated with HCl (2 ml) was added at 0° C. and stirred for 15 min. The precipitate formed was filtered, washed with ether and dried under vacuum to afford the title compound as a pale-brown solid (0.070 g, 80%). M.P.: 258-260° C.

Example 142

2-Methyl-4-(3-(quinolin-6-ylmethyl)-3H-[1,2,3]triazolo[4,5-b]pyridin-5-yl)benzamide The title compound was prepared by following the procedure described for example 1 using intermediate 14 (0.100 g. 0.338 mmol), intermediate 21 (0.109 g, 0.422 mmol), potassium carbonate (0.155 g. 1.12 mmol), DMF (8 ml), water (0.5 ml) and tetrakis(triphenylphosphine) palladium(0) (0.031 g, 0.027 mmol). Pale green solid (0.045 g, 34%), M.P.: 235-237° C. $^1$H-NMR (δ ppm, DMSO-d$_6$, 400 MHz): 8.88 (d, J=2.9 Hz, 1H), 8.66 (d, J=8.7 Hz, 1H), 8.38 (d, J=8.0 Hz, 1H), 8.15 (d, J=8.7 Hz, 1H), 8.07-8.00 (m, 4H), 7.83 (m, 2H), 7.54 (m, 2H), 7.45 (s, 1H), 6.21 (s, 2H), 2.46 (s, 3H).

Example 143

6-((5-(1H-Pyrazol-4-yl)-3H-[1,2,3]triazolo[4,5-b]pyridin-3-yl)methyl)quinoline

The title compound was obtained as a yellow solid (0.065 g, 29%) by following the procedure described for example 1 using intermediate 14 (0.20 g, 0.676 mmol), tert-butyl 4-(4,4,5,5-tetramethyl-1,3,2-dioxaborolan-2-yl)-1H-pyrazole-1-carboxylate (0.254 g, 0.856 mmol), potassium carbonate (0.310 g, 2.25 mmol), dioxane (4 ml), water (0.8 ml) and tetrakis(triphenylphosphine)palladium(0) (0.062 g, 0.054 mmol). $^1$H-NMR (δ ppm, DMSO-d$_6$, 400 MHz): 13.25 (s, 1H), 8.88 (dd, J=4.1, 1.4 Hz, 1H), 8.55 (s, 1H), 8.50 (d, J=8.7 Hz, 1H), 8.38 (d, J=8.1, Hz, 1H), 8.23 (s, 1H). 8.01 (d, J=9.0, Hz, 2H), 7.85 (t, J=8.6, 2H), 7.53 (dd, J=8.3, 4.2 Hz, 1H), 6.11 (s, 2H), MS (m/z): 328.12 (M$^+$+1)).

Example 144

6-(6-(1-Methyl-1H-pyrazol-4-yl)-3H-[1,2,3]triazolo[4,5-b]pyridin-3-yl)methyl)quinoline Sodium hydride (0.014 g, 0.596 mmol) was added to a solution of example 143 (0.130 g, 0.397 mmol) in DMF (3 ml) at 0° C. and stirred for 30 mm. To this solution methyl iodide (0.113 g, 0.794 mmol) was added and the reaction mixture was warmed to RT. After 3 h, the reaction mixture was poured into ice water and extracted with ethyl acetate, washed with brine, dried over sodium sulphate and concentrated. The crude product was purified by column chromatography with methanol:dichloromethane to afford the title compound as an off-white solid (0.080 g, 59%). $^1$H-NMR (δ ppm, DMSO-d$_6$, 400 MHz): 8.88 (d, J=2.8 Hz, 1H), 8.51 (s, 1H), 8.49 (s, 1H), 8.38 (d, J=7.9 Hz, 1H), 8.18 (s, 1H), 8.01 (d, J=8.8 Hz, 2H), 7.82 (t, J=9.6 Hz, 2H), 7.53 (dd, J=8.3, 4.1 Hz, 1H), 6.10 (s, 2H), 3.91 (s, 3H), MS (m/z):: 341.98 (M$^+$+1).

Example 145

6-((5-(1-(2-(Tetrahydro-2H-pyran-2-yloxy)ethyl-1H-pyrazol-4-yl)-3H-[1,2,3]triazolo[4,5-b]pyridin-3-yl)methyl)quinoline To a solution of example 143 (0.250 g, 0.763 mmol) in DMF (10 ml), cesium carbonate (0.496 g, 1.52 mmol) was added and stirred for 15 min, 2-(2-bromoethoxy)tetrahydro-2H-pyran (0.638 g, 3.04 mmol) and tetrabutylammonium iodide (0.20 g, 2.16 mmol) were added and heated to 80-85° C. for 12 h. The reaction was quenched by the addition of water, extracted with ethyl acetate, washed with brine, dried over sodium sulphate and concentrated. The crude product was purified by column chromatography with methanol:dichloromethane to afford the title compound as a yellow solid (0.195 g, 56%). $^1$H-NMR (δ ppm, DMSO-d$_6$, 400 MHz): 8.88 (dd, J=4.1, 1.6 Hz, 1H), 8.52 (s, 1H), 8.51 (d, J=8.8 Hz, 1H), 8.37 (dd, J=8.4, 1.3 Hz, 1H), 8.22 (s, 1H), 8.01 (d, J=9.0 Hz, 2H), 7.82 (dd, J=8.7, 2.7 Hz, 2H), 7.53 (dd, J=8.3, 4.2 Hz, 1H), 6.11 (s, 2H), 4.54 (t, J=2.9 Hz, 1H), 4.37 (m, 2H), 3.99 (m, 1H), 3.73 (m, 1H), 3.55 (m, 1H), 1.63-1.30 (m, 6H).

Example 146

2-(4-(3-(Quinolin-6-ylmethyl)-3H-[1,2,3]triazolo[4,5-b]pyridin-5-yl)-1H-pyrazol-1-yl)ethanol To a solution of example 145 (0.190 g, 0.417 mmol) in methanol (2 ml) and water (2 ml), camphor sulphonic acid (0.968 g, 4.17 mmol) was added and stirred for 1 h. The reaction was poured into ice water and the pH was adjusted to ca 8 with sodium bicarbonate solution, extracted with ethyl acetate, washed with brine, dried over sodium sulphate and concentrated. The crude product was purified by recrystallisation from isopropanol to afford the title compound as a light yellow solid (0.059 g, 38%). M.P.: 179-178° C. $^1$H-NMR (δ ppm, DMSO-$d_6$, 400 MHz): 8.88 (dd, J=4.2, 1.6 Hz, 1H), 8.51 (d, J=8.7 Hz, 1H), 8.49 (s, 1H), 8.38 (dd, J=8.3, 1.3 Hz, 1H), 8.20 (s, 1H), 8.01 (d, J=8.0 Hz, 2H), 7.82 (dd, J=8.7, 1.7 Hz, 2H), 7.53 (dd, J=8.3, 4.1 Hz, 1H), 6.11 (s, 2H), 4.96 (t, J=5.3 Hz, 1H), 4.22 (t, J=5.5 Hz, 2H), 3.79 (dd, J=10.8, 5.4 Hz. 2H), MS (m/z): 372.08 (M$^+$+1).

Example 147

6-((5-(1H-Pyrazol-4-yl)-3H-imidazo[4,5-b]pyridin-3-yl)quinoline

The title compound was prepared as a yellow solid (0.110 g, 49%) by following the procedure described for example 1 using intermediate 29 (0.20 g, 0.678 mmol), tert-butyl 4-(4,4,5,5-tetramethyl-4,3,2-dioxaborolan-2-yl)-1H-pyrazole-1-carboxylate (0.255 g, 0.868 mmol), potassium carbonate (0.310 g, 2.24 mmol), dioxane (4 ml), water (0.8 ml) and tetrakis(triphenylphosphine)palladium(0) (0.062 g, 0.054 mmol). M.P.: 214-216° C., $^1$H-NMR (δ ppm, DMSO-$d_6$, 400 MHz): 13.02 (s, 1H), 8.86 (dd, J=4.2, 1.7 Hz, 1H), 8.56 (s, 1H), 8.35 (dd, J=8.2, 1.1 Hz, 2H), 8.10 (s, 1H), 8.04-7.98 (m, 3H), 7.85 (dd, J=8.8, 1.9 Hz, 1H), 7.61 (d, J=8.3 Hz, 1H), 7.52 (dd, J=8.3, 4.2 Hz, 1H), 5.69 (s, 2H), MS (m/z); 326.86 (M+).

Example 148

6-((6-(1-Methyl-1H-pyrazol-4-yl)-3H-imidazo[4,5-b]pyridin-3-yl)methyl)quinoline

The title compound was prepared as an off-white solid (0.022 g, 27%) by following the procedure described for example 144 using example 147 (0.080 g, 0.246 mmol), sodium hydride (0.014 g, 0.367 mmol), methyl iodide (0.069 g, 0.49 mmol) and DMF (2 ml). M.P.: 150-152° C. $^1$H-NMR (δ ppm, DMSO-$d_6$, 400 MHz): 8.86 (s, 1H), 8.56 (s, 1H), 8.35 (d, J=8.1 Hz, 1H), 8.29 (s, 1H), 8.04 (m, 4H), 7.84 (d, J=8.8 Hz, 1H), 7.56 (d, J=8.3 Hz, 1H), 7.52 (dd, J=7.8, 4.2 Hz, 1H), 5.69 (s, 2H), 3.88 (s, 3H), MS (m/z): 341.14 (M$^+$+1).

Example 149

6-((5-(1-(2-(Tetrahydro-2H-pyran-2-yloxy)ethyl)-1H-pyrazol-4-yl)-3H-[4,5-b]pyridin-3-yl)methyl)quinoline The title compound was prepared as a yellow solid (0.300 g, 86%) by following the procedure described for example 145 using example 147 (0.250 g, 0.766 mmol), 2-(2-bromoethoxy)tetrahydro-2H-pyran (0.640 g, 3.06 mmol), cesium carbonate (0.746 g, 2.29 mmol), tetrabutylammonium iodide (0.20 g, 0.54 mmol) and DMF (10 ml).

Example 150

2-(4-(3-(Quinolin-6-ylmethyl)-3H-imidazo[4,5-b]pyridin-5-yl)-1H-pyrazol-1-yl)ethanol The title compound was prepared by following the procedure described for example 146 using example 149 (0.200 g, 0.44 mmol), camphor sulphonic acid (1.02 g, 4.40 mmol), methanol (2 ml) and water (2 ml). Yellow solid (0.09 g, 55%). M.P.: 160-163° C. $^1$H-NMR (δ ppm, DMSO-$d_6$, 400 MHz): 8.86 (dd, J=4.0, 1.4 Hz, 1H), 8.55 (s, 1H), 8.35 (d, J=7.9 Hz, 1H), 8.30 (s, 1H), 8.05 (m, 4H), 7.84 (dd, J=8.7, 1.7 Hz, 1H), 7.57 (d, J=8.3 Hz, 1H), 7.52 (dd, J=8.4, 4.2 Hz, 1H), 5.69 (s, 2H), 4.94 (t, J=5.2 Hz, 1H), 4.19 (t, J=5.6 Hz, 2H), 3.77 (t, J=5.4 Hz, 2H), MS (m/z): 370.89 (M+).

Example 151

2-(3-(Quinolin-6-ylmethyl)-3H-[1,2,3]triazolo[4,5-b]pyridin-5-ylamino)ethanol

To a solution of intermediate 14 (0.100 g, 0.338 mmol) and 2-aminoethanol (0.041 g, 0.67 mmol) in ethanol (2.5 ml), sodium carbonate (0.071 g, 0.676 mmol) was added and heated to reflux. After 12 h, the reaction was quenched by the addition of ice water, extracted with ethyl acetate, washed with brine, dried over sodium sulphate and concentrated. The crude product was purified by column chromatography with methanol:dichloromethane to afford the title compound as a yellow solid (0.060 g, 55%), M.P.: 184-186° C. $^1$H-NMR (δ ppm, DMSO-$d_6$, 400 MHz): 8.88 (dd, J=4.1, 1.6 Hz, 1H), 8.35 (dd, J=8.3, 0.9 Hz, 1H), 7.99 (d, J=8.7 Hz, 1H), 7.95 (d, J=8.9 Hz, 1H), 7.92 (s, 1H), 7.76 (dd, J=8.7, 2.0 Hz, 1H), 7.55 (t, J=4.5 Hz, 1H), 7.53 (dd, J=8.3, 4.2 Hz, 1H), 6.64 (d, J=9.1 Hz, 1H), 5.82 (s, 2H), 4.73 (t, J=5.4 Hz, 1H), 3.58 (q, J=5.9 Hz, 2H), 3.45 (q, J=5.6 Hz, 2H), MS (m/z): 321.19 (M$^+$+1).

Example 152

6-((5-(1H-Imidazol-1-yl)-3H-[1,2,3]triazolo[4,5-b]pyridin-3-yl)methyl)quinoline

To a solution of intermediate 14 (0.100 g, 0.338 mmol) and imidazole (0.100 g, 1.46 mmol) in DMF (3 ml), cesium fluoride (0.056 g, 0.368 mmol) was added and heated to 130° C. After 12 h, the reaction was quenched by the addition of ice water, extracted with ethyl acetate, washed with brine, dried over sodium sulphate and concentrated. The crude product was purified by column chromatography with methanol:dichloromethane to afford the title compound as light brown solid (0.023 g, 21%), M.P.: 227-230° C., $^1$H-NMR (δ ppm, DMSO-$d_6$, 400 MHz): 8.88 (dd, J=4.2, 1.7 Hz, 1H), 8.80 (d, J=8.9 Hz, 1H), 8.76 (s, 1H), 8.39 (dd, J=8.4, 0.9 Hz, 1H), 8.14 (s, 1H), 8.06 (d, J=1.6 Hz, 1H), 8.02 (d, J=8.7 Hz, 1H), 7.98 (d, J=9.0 Hz, 1H), 7.84 (dd, J=8.7, 2.0 Hz, 1H), 7.53 (dd, J=8.3, 4.2 Hz, 1H), 7.18 (s, 1H), 6.15 (s, 2H). MS (m/z):: 327.91 (M+).

Example 153

6-((5-(1-Propyl-1H-pyrazol-4-yl)-3H-[1,2,3]triazolo[4,5-b]pyridin-3-yl)methyl)quinoline To a solution of Example 143 (0.100 g, 0.305 mmol) in DMF (4 ml), cesium carbonate (0.297 g, 0.913 mmol), tetrabutylammonium iodide (0.078 g, 0.213 mmol) and 1-bromopropane (0.150 g, 1.22 mmol) were added and heated to 65° C. After 12 h, the reaction mixture was poured into ice water and extracted with ethyl acetate, washed with brine, dried over sodium sulphate and concentrated. The crude product was purified by column chromatography with methanol:dichloromethane to afford the title compound as a greenish-yellow solid (0.045 g, 40%). M.P.: 128-430° C. $^1$H-NMR (δ ppm, DMSO-d$_6$, 400 MHz): 8.88 (dd, J=4.1, 1.6 Hz, 1H), 8.53 (s, 1H), 8.51 (d, J=8.8 Hz, 1H), 8.38 (dd, J=8.4, 1.8 Hz, 1H), 8.19 (s, 1H), 8.01 (d, J=8.3 Hz, 1H), 7.99 (s, 1H). 7.82 (m, 2H), 7.53 (q, J=4.2 Hz, 1H), 6.11 (s, 2H), 4.11 (t, J=6.9 Hz, 2H), 1.85 (m, 2H), 0.86 (t, J=7.3 Hz, 3H). MS (m/z): 370.33 (M$^+$+1).

Example 154

Ethyl-2-(4-(3-(quinolin-6-ylmethyl)-3H-[1,2,3]triazolo[4,5-b]pyridin-5-yl)-1H-pyrazol-1-yl)acetate To a solution of example 143 (0.250 g, 0.763 mmol) in DMF (3 ml) cooled to 0° C., sodium hydride (0.0365 g, 0.916 mmol) was added and stirred for 30 min., ethyl bromoacetate (0.153 g, 0.916 mmol) were added and warmed to RT. After 12 h, the reaction mixture was poured into ice water and extracted with ethyl acetate, washed with brine, dried over sodium sulphate and concentrated. The crude product was purified by column chromatography with methanol:dichloromethane to afford the title compound as a yellow solid (0.225 g, 80%).

Example 155

2-(4-(3-(Quinolin-6-ylmethyl)-3H-[1,2,3]triazolo[4,5-b]pyridin-5-yl)-1H-pyrazol-1-yl)acetic acid To a solution of Example 154 (0.085 g, 0.218 mmol) in methanol (1.4 ml), lithium hydroxide (0.026 g, 1.09 mmol) in water (0.36 ml) was added and stirred at RT. After 12 h, the pH was adjusted to 7-7.5 using 0.5N HCl and the solid precipitated was filtered, washed with ethyl acetate and petroleum ether and dried under to afford the title compound as a yellow solid (0.034 g, 38%). M.P.: >270° C. $^1$H-NMR (δ ppm, DMSO-d$_6$, 400 MHz): 8.87 (d, J=2.7 Hz, 1H), 8.47 (d, J=8.7 Hz, 1H), 8.39 (m, 2H), 8.08 (s, 1H), 8.00 (s. 1H), 7.99 (d, J=7.1 Hz, 1H), 7.82 (t, J=8.9 Hz, 2H), 7.52 (q, J=4.1 Hz, 1H), 6.10 (s, 2H), 4.48 (s, 2H), MS (m/z): 385.87 (M+).

Example 156 tert-Butyl 4-(4-((3-(quinolin-6-ylmethyl)-3H-[1,2,3]triazolo[4,5-b]pyridin-5-yl)-1H-pyrazol-1-yl)piperidine-1-carboxylate To a solution of example 143 (0.100 g, 0.305 mmol) in DMF (2 ml) was cooled to 0° C., sodium hydride (0.0146 g, 0.366 mmol) was added and stirred for 30 min., tert-butyl 4-(methylsulfonyloxy)piperidine-1-carboxylate (0.093 g, 0.336 mmol) were added and heated to 80° C. After 12 h, the reaction mixture was poured into ice water and extracted with ethyl acetate, washed with brine, dried over sodium sulphate and concentrated. The crude product, was purified by column chromatography with methanol:dichloromethane to afford the title compound as a yellow solid (0.066 g, 42%). $^1$H-NMR (δ ppm, DMSO-d$_6$, 400 MHz): 8.88 (d, J=2.7 Hz, 1H), 8.60 (s, 1H), 8.52 (d, J=8.7 Hz, 1H), 8.30 (d, J=8.0 Hz, 1H), 8.21 (s, 1H), 8.01 (s, 1H), 8.01 (d, J=7.5 Hz, 1H), 7.82 (d, J=8.6 Hz, 2H), 7.53 (q, J=4.1 Hz, 1H), 6.11 (s, 2H), 4.46 (m, 1H), 4.12 (m, 2H), 2.91 (m, 2H), 2.06 (m, 2H), 1.87 (m, 2H), 1.41 (s, 9H).

Example 157

6-((5-(1-(Piperidin-4-yl)-1H-pyrazol-4-yl)-3H-[1,2,3]triazolo[4,5-b]pyridin-3-yl)methyl)quinoline To a solution of example 156 (0.063 g, 0.123 mmol) in dichloromethane (1 ml) was cooled to 0° C., TFA (0.356 g, 2.47 mmol) was added and warmed to RT. After 12 h, the reaction mixture was poured in ice water and pH was adjusted to 10-11 with 10% NaOH solution and extracted with ethyl acetate, washed with brine, dried over sodium sulphate and concentrated to afford the title compound as an off-white solid (0.021 g, 42%), M.P.: 188-191° C. $^1$H-NMR (δ ppm, DMSO-d$_6$, 400 MHz): 8.88 (dd, J=4.2, 1.6 Hz, 1H), 8.55 (s, 1H), 8.51 (d, J=8.6 Hz, 1H), 8.38 (d, J=7.8 Hz, 1H), 8.20 (s, 1H), 8.01 (s, 1H), 8.01 (m, 2H), 7.82 (m, 2H), 7.53 (q, J=4.2 Hz, 1H), 6.11 (s, 2H), 4.29 (m, 1H), 3.07 (m, 2H), 2.63 (m, 2H), 1.99 (m, 2H),1.56 (m, 2H), MS (m/z): 41.1.28 (M$^+$+1).

Example 158

(R)-1-(3-(Quinolin-6-ylmethyl)-3H-[1,2,3]triazolo[4,5-b]pyridin-5-yl)pyrrolidin-3-ol The title compound was prepared by following the procedure described for example 152 using intermediate 14 (0.100 g, 0.338 mmol), (R)-3-hydroxypyrrolidine (0.044 g, 0.507 mmol), cesium fluoride (0.102 g, 0.676 mmoles) and DMF (3 ml). Brown solid (0.040 g, 34%). M.P.: 167-169° C. $^1$H-NMR (δ ppm, DMSO-d$_6$, 400 MHz): 8.88 (dd, J=4.2, 1.7 Hz, 1H), 8.36 (dd, J=8.4, 1.0 Hz, 1H), 8.11 (d, J=7.9 Hz, 1H), 7.99 (d, J=8.6 Hz, 1H), 7.93 (d, J=1.5 Hz, 1H), 7.77 (dd, J=8.7, 2.0 Hz, 1H), 7.53 (q. J=4.2 Hz, 1H), 6.66 (d, J=9.2 Hz, 1H), 5.86 (s, 2H), 5.01 (s, 1H), 4.40 (s, 1H), 3.60 (m, 4H), 2.04-1.92 (m, 2H). MS (m/z): 346.95 (M+).

Example 159

3-(4-Fluorobenzyl)-5-(1H-pyrazol-4-yl)-3H-[1,2,3]triazolo[4,5-b]pyridine

The title compound was prepared by following the procedure described for example 1 using intermediate 15 (0.500 g, 1.90 mmol), text-butyl 4-(4,4,5,5-tetramethyl-1,3,2-dioxaborolan-2-yl)-1H-pyrazole-1-carboxylate (0.716 g, 2.43 mmol), potassium carbonate (0.874 g, 6.33 mmol), dioxane (11 ml), water (2.2 ml) and tetrakis(triphenylphosphine)palladium(0) (0.175 g, 0.152 mmol). Yellow solid (0.270 g. 48%). $^1$H-NMR (δ ppm, DMSO-d$_6$, 400 MHz): 13.26 (s, 1H), 8.55 (s, 1H), 8.48 (d, J=8.7 Hz, 1H), 8.23 (s, 1H), 7.84 (d, J=8.7 Hz, 1H), 7.53 (dd, J=8.5, 6.4 Hz, 2H), 7.18 (t, J=8.9 Hz, 2H), 5.89 (s, 2H).

Example 160

3-(4-Fluorobenzyl)-5-(1-(2-(tetrahydro-2H-pyran-2-yloxy)ethyl)-1H-pyrazol-4-yl)-3H-[1,2,3]triazolo[4,5-b]pyridine The title compound was prepared by following the procedure described for example 145 using example 159 (0.270 g, 0.917 mmol), 2-(2-bromoethoxy)tetrahydro-2H-pyran (0.766 g, 3.66 mmol), cesium carbonate (0.894 g, 2.75 mmol), tetrabutylammonium iodide (0.237 g, 0.624 mmol) and DMF (12 ml). Brown solid (0.150 g, 38%). $^1$H-NMR (δ ppm, DMSO-d$_6$, 400 MHz): 8.52 (s, 1H), 8.49 (d. J=8.6 Hz, 1H), 8.21 (s, 1H), 7.80 (d, J=8.6 Hz, 1H), 7.50 (m, 2H), 7.20 (m, 2H), 5.89 (s, 2H), 4.56 (t, J=3.4 Hz, 1H), 4.38 (m, 2H), 3.98 (m, 1H), 3.80 (m, 1H), 3.57 (m, 1H), 3.38 (m, 1H), 1.66-1.05 (m, 6H).

Example 161

2-(4-(3-(4-Fluorobenzyl)-3H-[1,2,3]triazolo[4,5-b]pyridin-5-yl)-1H-pyrazol-1-yl)ethanol The title compound was prepared by following the procedure described for example 145 using example 160 (0.150 g, 0.355 mmol), camphor sulphonic acid (0.824 g, 3.55 mmol), methanol (2 ml) and water (2 ml). Brown solid (0.070 g, 58%). M.P.: 204-206° C. $^1$H-NMR (δ ppm, DMSO-d$_6$, 400 MHz): 8.49 (s, 1H), 8.49 (d, J=Hz, 1H), 8.20 (s, 1H), 7.80 (d, J=8.7 Hz, 1H), 7.51 (dd, J=8.7, 5.5 Hz, 2H), 7.20 (t, J=8.9 Hz, 2H), 5.89 (s, 2H), 4.96 (t, J=5.3 Hz, 1H), 4.23 (t, J=5.5 Hz, 2H), 3.80 (q, J=5.4 Hz, 2H), MS (m/z): 339.25 (M$^+$+1).

Example 162

6-(1-(5-(1H-Pyrazol-4-yl)-3H-[1,2,3]triazolo[4,5-b]pyridin-3-yl)ethyl)quinoline

The title compound was prepared by following the procedure described for intermediate 14 using intermediate 31 (0.290 g, 0.877 mmol), acetic acid (1.8 ml), sodium nitrite (0.072 g. 1.05 mmol) and water (0.4 ml). Brown solid (0.250 g, 84%). $^1$H-NMR (δ ppm, DMSO-d$_6$, 400 MHz): 13.25 (s, 1H), 8.87 (dd, J=4.0, 1.4 Hz, 1H), 8.48 (d, J=8.7 Hz, 1H), 8.39 (d, J=7.6 Hz, 1H), 8.09 (d, J=1.5 Hz, 1H), 8.00 (d, J=8.8 Hz, 1H), 7.88 (dd, J=8.8, 1.9 Hz, 1H), 7.82 (d, J=8.7 Hz, 1H), 7.64-7.46 (m, 3H), 6.60 (q, J=7.1 Hz, 1H), 2.22 (d, J=7.1 Hz, 3H).

Example 163

6-(1-(5-(1-(2-(Tetrahydro-2H-pyran-2-yloxy)-pyran-2-yloxy)ethyl)-1H-pyrazol-4-yl)-3H-[1,2,3]triazolo[4,5-b]pyridin-3-yl)ethyl)quinoline The title compound was prepared by following the procedure described for example 145 using example 162 (0.190 g, 0.556 mmol), 2-(2-bromoethoxy)tetrahydro-2H-pyran (0.465 g, 2.22 mmol), cesium carbonate (0.550 g, 1.69 mmol), tetrabutylammonium iodide (0.143 g, 0.387 mmol) and DMF (7 ml). Yellow solid (0.138 g, 46%). $^1$H-NMR (δ ppm, DMSO-d$_6$, 400 MHz): 8.87 (dd, J=4.1, 1.6 Hz, 1H), 8.50 (s, 1H), 8.49 (d. J=8.7 Hz, 1H), 8.38 (d, J=8.1 Hz, 1H), 8.19 (s, 1H), 8.06 (s, 1H), 7.99 (d, J=8.7 Hz, 1H), 7.86 (d, J=8.7 Hz, 1H), 7.78 (d, J=8.7 Hz, 1H), 7.52 (q, J=4.2 Hz, 1H), 6.59 (q, J=7.0 Hz, 1H), 4.53 (t, J=3.0 Hz, 1H), 4.48 (m, 2H), 3.99 (m, 1H), 3.78 (m, 1H), 3.56 (m, 1H), 2.23 (d, J=7.2 Hz, 3H), 1.59-1.20 (m, 7H).

Example 164

2-(4-(3-(1-(Quinolin-6-yl)ethyl)-3H-[1,2,3]triazolo[4,5-b]pyridin-5-yl)-1H-pyrazol-1-yl)ethanol The title compound was prepared by following the procedure described for example 146 using example 163 (0.130 g, 0.276 mmol), camphor sulphonic acid (0.643 g. 2.76 mmol), methanol (2 ml) and water (2 ml). Yellow solid (0.030 g, 28%). M.P.: 188-191° C. $^1$H-NMR (δ ppm, DMSO-d$_6$, 400 MHz): 8.87 (d, J=2.6 Hz, 1H), 8.48 (d, J=8.7 Hz, 1H), 8.47 (s, 1H). 8.39 (d, J=8.1 Hz, 1H), 8.18 (s, 1H), 8.08 (dd, J=0.7 Hz, 1H), 8.00 (d, J=8.7 Hz, 1H), 7.87 (dd, J=8.8, 1.9 Hz, 1H), 7.79 (d, J=8.7 Hz, 1H), 7.52 (q, J=4.2 Hz, 1H), 6.60 (q, J=6.8 Hz, 1H), 4.97 (t, J=5.4 Hz, 1H), 4.21 (t, J=5.4 Hz, 2H), 3.78 (q, J=5.4 Hz, 2H), 2.22 (d, J=7.2 Hz, 3H), MS (m/z): 385.87 (M+).

Example 165

2-(4-(3-(2-Chloro-3,6-difluorobenzyl)-3H-[1,2,3]triazolo[4,5-b]pyridin-5-yl)-1H-pyrazol-1-yl)ethanol To a solution of Example 213 (0.160 g, 0.461 mmol) in DMF (7 ml), cesium carbonate (0.449 g, 1.38 mmol) was added and stirred for 15 min. 2-(2-bromoethoxy)tetrahydro-2H-pyran (0.385 g, 1.84 mmol) and tetrabutylammonium iodide (0.137 g, 0.368 mmol) were added and heated to 80-85° C. for 12 h. The reaction was quenched by the addition of water, extracted with ethyl acetate, washed with brine, dried over sodium sulphate and concentrated to give the crude product (0.220 g). To a solution of above crude product (0.210 g, 0.442 mmol) in methanol (2 ml) and water 12 ml), camphor sulphonic acid (1.027 g, 4.42 mmol) was added and stirred for 1 h. The reaction was poured into ice water and the pH was adjusted to ca. 8 by sodium bicarbonate solution, extracted with ethyl acetate, washed with brine, dried over sodium sulphate and concentrated to afford the title compound as a yellow solid (0.045 g, 26%). M.P.: 143-145° C. $^1$H-NMR (δ ppm, DMSO-d$_6$, 400 MHz): 8.47 (d, J=8.7 Hz, 1H), 8.43 (s, 1H), 8.11 (s, 1H), 7.79 (d, J=8.7 Hz, 1H), 7.61 (dt, J=9.1, 4.8 Hz, 1H), 7.45 (dt, J=9.2, 4.3 Hz, 1H), 6.01 (s, 2H), 4.99 (t, J=5.2 Hz, 1H), 4.22 (t, J=5.3 Hz, 2H), 3.79 (q, J=5.2 Hz, 2H), MS (m/z):: 390.70 (M+).

Example 166 tert-butyl-4-(4-(3-(2-chloro-3,6-difluorobenzyl)-3H-[1,2,3]triazolo[4,5-b]pyridin-5-yl)-1H-pyrazol-1-yl)piperidine-1-carboxylate The title compound was prepared as a yellow solid (0.250 g, 41%) by following the procedure described for example 156 using example 213 (0.400 g, 1.15 mmol), sodium hydride (0.060 g, 1.49 mmol), text-butyl 4-(methylsulfonyloxy)piperidine-1-carboxylate (0.400 g, 1.43 mmol) and DMF (2 ml).

Example 167

3-(2-Chloro-3,6-difluorobenzyl)-5-(1-(piperidin-4-yl)-1H-pyrazol-4-yl)-3H-[1,2,3]triazolo[4,5-b]pyridine hydrochloride To a solution of Example 166 (0.240 g, 0.453 mmol) in dichloromethane (3 ml) cooled to 0° C., (0.1 ml) was added and warmed to RT. After 2 h, the reaction mixture was poured in ice water and pH was adjusted to call with 10% NaOH solution and extracted with ethyl acetate, washed with brine, dried over sodium sulphate and concentrated. The residue was dissolved in THF (1 ml), ether saturated with HCl (1 ml) was added at 0° C. and stirred for 15 min. The precipitate formed was filtered and washed with ether and dried under vacuum to afford the title compound as an off-white solid (0.090 g, 43%). M.P.: 85-87° C. $^1$H-NMR (δ ppm, DMSO-d$_6$, 400 MHz); 8.48 (d, J=1.5 Hz, 1H), 8.45 (s, 1H), 8.09 (s, 1H), 7.79 (d, J=8.7 Hz, 1H), 7.60 (dt, J=13.8, 4.8 Hz, 1H), 7.45 (dt, J=13.4, 4.2 Hz, 1H), 6.01 (s, 2H), 4.29 (m, 1H), 3.07 (d, J=12.4 Hz, 2H), 2.63 (m, 2H), 1.98 (m, 2H), 1.85 (m, 2H). MS (m/z):: 429.69 (M$^+$–HCl).

Example 168

6-((5-(3-Methyl-1H-indazol-6-yl)-3H-[1,2,3]triazolo[4,5-b]pyridin-3-yl)methyl)quinoline The title compound was prepared as a yellow solid (0.030 g, 15%) by Suzuki coupling of tert-butyl 3-methyl-6-(4,4,5,5-tetramethyl-1,3,2-dioxaborolan-2-yl)-1H-indazole-1-carboxylate (0.227 g, 0.634 mmol) with intermediate 14 (0.150 g, 0.507 mmol) following the procedure described for example 1 using potassium carbonate (0.233 g, 1.68 mmol), dioxan (3 ml), water (0.6 ml) and tetrakis(triphenylphosphine)palladium(0) (0.046 g, 0.04052 mmol) followed by deprotection of the carbamate as described under 157. M.P.: 136-137° C. $^1$H-NMR (δ ppm, DMSO-d$_6$, 400 MHz): 12.90 (s, 1H), 8.88 (d, J=3.1 Hz, 1H), 8.66 (d, J=8.8 Hz, 1H), 8.38 (d, J=8.5 Hz, 1H), 8.30 (s, 1H), 8.21 (d, J=8.6 Hz, 1H), 8.04 (d, J=8.4 Hz, 1H), 8.02 (s, 1H), 7.98 (d, J=8.4 Hz, 1H), 7.85 (d, J=8.5 Hz, 2H), 7.53 (q, J=4.2 Hz, 1H), 6.25 (s, 3H).

Example 169

6-((5-(1H-Indol-5-yl)-3H-[1,2,3]triazolo[4,5-b]pyridin-3-yl)methyl)quinoline

The title compound was prepared by following the procedure described for example 1 using intermediate 14 (0.150 g, 0.507 mmol), 6-(4,4,5,5-tetramethyl-1,3,2-dioxaborolan-2-yl)-1H-indole (0.154 g, 0.634 mmol), potassium carbonate (0.233 g, 1.68 mmol), dioxane (3 ml), water (0.6 ml) and tetrakis(triphenylphosphine)palladium(0) (0.046 g, 0.04052 mmol). Light green solid (0.025 g, 13%). M.P.: 120-122° C. $^1$H-NMR (δ ppm, DMSO-d$_6$, 400 MHz): 11.30 (s, 1H), 8.88 (dd, J=4.2, 1.6 Hz, 1H), 8.56 (d, J=8.8 Hz, 1H), 8.45 (s, 1H), 8.39 (d, J=8.3 Hz, 1H), 8.13 (d, J=8.9 Hz, 1H), 8.04 (m, 3H), 7.84 (dd, J=8.8, 1.8 Hz, 1H), 7.53 (m, 2H), 7.42 (t, J=2.7 Hz, 1H), 6.56 (s, 1H), 6.20 (s, 2H).

Example 170

6-((5-(1H-Indol-6-yl)-3H-[1,2,3]triazolo[4,5-b]pyridin-3-yl)methyl)quinoline

The title compound was obtained as an off-white solid (0.015 g, 8%) by following the procedure described for example 1 using intermediate 14 (0.150 g, 0.507 mmol), 1H-indole-6-yl boronic acid (0.102 g, 0.634 mmol), potassium carbonate (0.233 g, 1.68 mmol), dioxane (3 ml), water (0.6 ml) and tetrakis(triphenylphosphine)palladium(0) (0.046 g, 0.04052 mmol). M.P.: 143-145° C. $^1$H-NMR (δ ppm, DMSO-d$_6$, 400 MHz): 11.38 (s, 1H), 8.88 (dd, J=4.0, 1.5 Hz, 1H), 8.58 (d, J=8.8 Hz, 1H), 8.38 (d, J=8.7 Hz, 1H), 8.31 (s, 1H), 8.13 (d, J=8.8 Hz, 1H), 8.04 (m, 2H), 7.92 (dd, J=8.4, 1.4 Hz, 1H), 7.86 (dd, J=8.8, 1.9 Hz, 1H), 7.68 (d, J=8.4 Hz, 1H), 7.54 (q, J=4.2 Hz, 1H), 7.49 (d, J=2.6 Hz, 1H), 6.49 (s, 1H), 6.20 (s, 2H).

Example 171

6-((5-(2-Chloropyridin-4-yl)-3H-[1,2,3]triazolo[4,5-b]pyridin-3-yl)methyl)quinoline The title compound was prepared as an off-white solid (0.020 g, 11%) by following the procedure described for example 1 using intermediate 14 (0.150 g, 0.507 mmol), 2-chloropyridine-4-boronic acid (0.099 g, 0.634 mmol), potassium carbonate (0.233 g, 1.68 mmol), dioxane (3 ml), water (0.6 ml) and tetrakis(triphenylphosphine)palladium(0) (0.046 g, 0.04052 mmol). M.P.: 197-199° C. $^1$H-NMR (δ ppm, DMSO-d$_6$, 400 MHz): 8.88 (dd, J=4.1, 1.5 Hz, 1H), 8.79 (d, J=8.7 Hz, 1H), 8.61 (d, J=5.2 Hz, 1H), 8.37 (d, J=8.4 Hz, 1H), 8.32 (d, J=8.8 Hz, 1H), 8.30 (s, 1H), 8.25 (dd, J=5.2, 1.5 Hz, 1H), 8.04 (s, 1H), 8.02 (d, J=8.7 Hz, 1H), 7.83 (dd, J=8.7, 1.9 Hz, 1H), 7.54 (q, J=4.2 Hz, 1H), 6.25 (s, 2H).

Example 172

6-((5-(3-Methyl-1H-indazol-5-yl)-3H-[1,2,3]triazolo[4,5-b]pyridin-3-yl)methyl)quinoline The title compound was prepared as a yellow solid (0.050 g, 25%) by following the procedure described for example 1 using intermediate 14 (0.150 g, 0.507 mmol), tert-butyl 3-methyl-6-(4,4,5,5-tetramethyl-1,3,2-dioxaborolan-2-yl)-3-methyl-1H-indazole-1-carboxylate (0.227 g, 0.634 mmol), potassium carbonate (0.233 g, 1.68 mmol), dioxane (3 ml), water (0.6 ml) and tetrakis(triphenylphosphine)palladium(0) (0.046 g, 0.04052 mmol) followed by the procedure described in example 157, M.P.: 246-249° C. $^1$H-NMR (δ ppm, DMSO-d$_6$, 400 MHz): 12.82 (s, 1H), 8.88 (d, J=2.6 Hz, 1H), 8.62 (d, J=8.8 Hz, 1H), 8.59 (s, 1H), 8.38 (d. J=8.3 Hz, 1H), 8.30 (d, J=9.1 Hz, 1H), 8.23 (d, J=8.8 Hz, 1H), 8.03 (s, 1H), 8.01 (d, J=9.9 Hz, 1H), 7.84 (dd, J=8.6, 1.5 Hz, 1H), 7.59 (d, J=8.8 Hz, 1H), 7.53 (q, J=4.2 Hz, 1H), 6.21 (s, 2H), 2.56 (s, 3H).

Example 173

6-((5-(Pyridin-3-yl)-3H-[1,2,3]triazolo[4,5-b]pyridin-3-yl)methyl)quinoline

The title compound was prepared by following the procedure described for example 1 using intermediate 14 (0.150 g, 0.507 mmol), pyridine-3-boronic acid (0.079 g, 0.649 mmol), potassium carbonate (0.233 g, 1.68 mmol), dioxane (3 ml), water (0.6 ml) and tetrakis(triphenylphosphine)palladium(0) (0.046 g, 0.04052 mmol) followed by the procedure described in example 157. Yellow solid (0.040 g, 24%). M.P.: 208-210° C. $^1$H-NMR (δ ppm, DMSO-d$_6$, 400 MHz): 8.88 (dd, J=4.1, 1.7 Hz, 1H), 8.77 (m, 3H), 8.38 (dd, J=8.4, 0.9 Hz, 1H), 8.26 (d, J=8.7 Hz, 1H), 8.21 (m, 2H), 8.04 (d, J=1.5 Hz, 1H), 8.02 (d, J=8.7 Hz, 1H), 7.85 (dd. J=8.7, 2.0 Hz, 1H), 7.53 (q, J=4.2 Hz, 1H), 6.24 (s, 2H).

Example 174

(S)-6-((5-(1-(Pyrrolidin-3-yl)-1H-pyrazol-4-yl)-3H-[1,2,3]triazolo[4,5-b]pyridin-3-yl)methyl)quinoline The title compound was prepared by alkylation of example 143 (0.300 g, 0.916 mmol) with (R)-tert-butyl(methylsulfonyloxy)pyrrolidine-1-carboxylate (0.291 g, 1.09 mmol) following the procedure described under example 156 using sodium hydride (0.026 g, 1.09 mmol) and DMF (6 ml) followed by deprotection of the carbamate using the procedure described for 157. Yellow solid (0.100 g, 44%). $^1$H-NMR (δ ppm, DMSO-d$_6$, 400 MHz): 8.88 (dd, J=4.1, 1.4 Hz, 1H), 8.59 (s, 1H), 8.52 (d, J=8.8 Hz, 1H), 8.37 (d, J=8.2 Hz, 1H), 8.22 (s, 1H), 8.01 (d, J=8.8 Hz, 1H), 7.99 (s, 1H), 7.82 (m, 2H), 7.53 (dd, J=8.3, 4.2 Hz, 1H), 6.11 (s, 2H), 4.98 (m, 1H), 3.26-2.96 (m, 5H), 2.28-2.11 (m, 2H).

Example 1.75

(S)-6-((5-(1-(Pyrrolidin-3-yl)-1H-pyrazol-4-yl)-3H-[1,2,3]triazolo[4,5-b]pyridin-3-yl)methyl)quinoline hydrochloride Example 174 (0.100 g, 0.25 mmol), was dissolved in THF (1 ml), ether saturated with HCl (1 ml) was added at 0° C. and stirred for 15 min. The precipitate formed was washed with ether and dried under vacuum to afford the title compound as a yellow solid (0.070 g, 65%). M.P.: 117-121° C. $^1$H-NMR (δ ppm, DMSO-$d_6$, 400 MHz): 9.58 (s, 1H), 9.45 (s, 1H), 9.12 (d, J=3.7 Hz, 1H), 8.87 (d, J=8.1 Hz, 1H), 8.73 (s, 1H), 8.56 (d, J=8.7 Hz, 1H), 8.30 (s, 1H), 8.25 (d, J=8.7 Hz, 1H), 8.21 (s, 1H), 8.07 (d, J=8.8 Hz, 1H), 7.85 (d, J=8.7 Hz, 2H), 6.18 (s, 2H), 5.27 (t, J=3.3 Hz, 1H), 3.69-3.34 (m, 4H), 2.43-2.30 (s, 2H).

Example 176

4-(2-(4-(3-(Quinolin-6-ylmethyl)-3H-[1,2,3]triazolo[4,5-b]pyridin-5-yl)-1H-pyrazol-1-yl)ethyl)morpholine hydrochloride The title compound was prepared by following the procedure described for example 156 using example 143 (0.150 g, 0.458 mmol), sodium hydride (0.022 g, 0.55 mmol), (4-(2-chloroethyl)morpholine (0.115 g, 1.00 mmol) and DMF (3 ml) followed by using the procedure described for 175, Yellow solid (0.080 g, 36%). M.P.: 118-120° C. $^1$H-NMR (δ ppm, DMSO-$d_6$, 400 MHz): 11.08 (s, 1H), 9.06 (d, J=3.7 Hz, 1H), 8.74 (d, J=8.3 Hz, 1H), 8.65 (s, 1H), 8.57 (d, J=8.6 Hz, 1H), 8.31 (s, 1H), 8.18 (d, J=8.8 Hz, 1H), 8.13 (s, 1H), 7.99 (d, J=8.8 Hz, 1H), 7.85 (d, J=8.7 Hz, 1H), 7.78 (dd, J=7.7, 4.4 Hz, 1H), 6.16 (s, 2H), 4.72 (t, J=6.6 Hz, 1H). 3.97 (br.s, 2H), 3.77 (t, J=11.5 Hz, 2H), 3.65 (t, J=11.5 Hz, 2H), 3.42 (d, J=11.6 Hz, 2H), 3.17 (m, 2H).

Example 177

6-((5-(1-(Tetrahydro-2H-pyran-4-yl)-1H-pyrazol-4-yl)-3H-[1,2,3]triazolo[4,5-b]pyridin-3-yl)methyl)quinoline The title compound was prepared as a yellow solid (0.130 g, 52%) by following the procedure described for example 156 using example 143 (0.200 g, 0.610 mmol), cesium carbonate (0.596 g, 1.83 mmol), tetrahydro-2H-pyran-4-yl methanesulfonate (0.220 g, 1.22 mmol) and DMF (6 ml). M.P.: 182-184° C. $^1$H-NMR (δ ppm, DMSO-$d_6$, 400 MHz): 8.88 (dd, J=4.2, 1.7 Hz, 1H), 8.59 (s, 1H), 8.51 (d, J=8.8 Hz, 1H), 8.38 (d, J=8.2 Hz, 1H), 8.21 (s, 1H), 8.01 (m, 2H), 7.82 (m, 2H), 7.53 (dd, J=8.3, 4.1 Hz, 1H), 6.11 (s, 2H), 4.52 (m, 1H), 3.99 (m, 2H), 3.51 (dt, J=11.2, 3.0 Hz, 2H), 2.02 (m, 4H).

Example 178

6-((5-(1-(2-Hydroxyethyl)-1H-pyrazol-4-yl)-3H-[1,2,3]triazolo[4,5-b]pyridin-3-yl)methyl)quinoline 1-oxide: T To a solution of example 146 (0.100 g, 0.269 mmol) in acetic acid (1 ml), hydrogen peroxide solution (50%, 1 ml) and heated to 100° C. After 12 h, the mixture was concentrated, extracted with chloroform, washed with brine, dried over sodium sulphate and concentrated. The crude product was purified by column chromatography using dichloromethane: methanol to afford the title compound as an off-white solid (0.015 g, 14%), M.P.: 222-224° C. $^1$H-NMR (δ ppm, DMSO-$d_6$, 400 MHz): 8.58-8.48 (m, 4H), 8.19 (s, 1H), 8.08 (s, 1H), 7.93 (d, J=8.5 Hz, 1H), 7.85 (dd, J=9.0, 1.8 Hz, 1H), 7.82 (d, J=8.8 Hz, 1H), 7.47 (dd, J=8.4, 6.0 Hz, 1H), 6.12 (s, 2H), 4.95 (t, J=5.2 Hz, 1H), 4.22 (t, J=5.5 Hz, 2H), 3.77 (q, J=5.5 Hz, 2H).

Example 179

6-((5-(1,3-dimethyl-1H-indazol-6-yl)-3H-[1,2,3]triazolo[4,5-b]pyridin-3-yl)methyl)quinoline The title compound was prepared by following the procedure described for example 1 using intermediate 14 (0.100 g, 0.338 mmol), 1,3-dimethyl-6-(4,4,5,5-tetramethyl-1,3,2-dioxaborolan-2-yl)-1H-indazole (0.0117 g, 0.432 mmol), potassium carbonate (0.146 g, 1.05 mmol), dioxane (3 ml), water (0.6 ml) and tetrakis(triphenylphosphine)palladium(0). (0.061 g, 45%) Yellow solid (0.061 g, 45%), M.P.: 159-163° C. $^1$H-NMR (δ ppm, DMSO-$d_6$, 400 MHz): 8.88 (dd, J=4.0, 1.6 Hz, 1H), 8.69 (d, J=8.8 Hz, 1H), 8.41 (s, 1H), 8.38 (d, J=8.0 Hz, 1H), 8.30 (d, J=8.8 Hz, 1H), 8.05-8.01 (m, 3H), 7.85 (m, 2H), 7.54 (dd, J=8.3, 4.1 Hz, 1H), 6.24 (s, 2H).

Example 180

5-(3-(Quinolin-6-ylmethyl)-3H-[1,2,3]triazolo[4,5-b]pyridin-5-yl)pyrimidin-2-amine The title compound was prepared by following the procedure described for example 1 using intermediate 14 (0.100 g, 0.338 mmol), 2-amino-5-pyrimidineboronic acid (0.058 g, 0.422 mmol), potassium carbonate (0.156 g, 0.027 mmol), dioxane (2 ml), water (0.5 ml) and tetrakis(triphenylphosphine)palladium(0) (0.031 g, 0.067 mmol) under microwave irradiation (100 W, 100° C.) for 20 min. Yellow solid (0.020 g, 16%). M.P.: 244-246° C. MS (m/z): 354.72 (M+).

Example 181 tert-Butyl 3-ethyl-6-(3-(quinolin-6-ylmethyl)-3H-[1,2,3]triazolo[4,5-b]pyridin-5-yl)-1H-indazole-1-carboxylate The title compound was prepared by following the procedure described for example 1 using intermediate 14 (0.100 g, 0.338 mmol), tert-butyl 3-ethyl-6-(4,4,5,5-tetramethyl-1,3,2-dioxaborolan-2-yl)-1H-indazole-1-carboxylate (0.157 g, 0.422 mmol), potassium carbonate (0.156 g, 0.027 mmol), dioxane (2 ml), wafer (0.5 ml) and tetrakis(triphenylphosphine)palladium(0) (0.031 g, 0.067 mmol) under microwave irradiation (100 W, 100° C.) for 20 min. Off-white solid (0.070 g. 51%). M.P.: 185-188° C. $^1$H-NMR (δ ppm, DMSO-$d_6$, 400 MHz): 8.93 (s, 1H), 8.91 (dd, J=4.2, 1.5 Hz, 1H), 8.47 (d, J=8.7 Hz, 1H), 8.20 (d, J=8.3 Hz, 1H), 8.11 (m, 2H), 7.98 (s, 1H), 7.96 (d, J=8.7 Hz, 1H), 7.90 (dd, J=8.8, 1.8 Hz, 1H), 7.83 (d, J=8.3 Hz, 1H), 7.41 (dd, J=8.3, 4.3 Hz, 1H), 6.16 (s, 2H), 3.10 (q, J=7.6 Hz, 2H), 1.74 (s, 9H), 1.48 (t, J=7.6 Hz, 3H).

Example 182

4-(3-(Quinolin-6-ylmethyl)-3H-[1,2,3]triazolo[4,5-b]pyridin-5-yl)thiophene-2-carbaldehyde The title compound was prepared by following the procedure described for example 1 using intermediate 14 (0.100 g, 0.338 mmol), 2-formylthiophene-4-boronic acid (0.032 g, 0.422 mmol), potassium carbonate (0.156 g, 0.027 mmol), dioxane (2 ml), water (0.5 ml) and tetrakis(triphenylphosphine)palladium(0) (0.031 g, 0.067 mmol) under microwave irradiation (100 W, 100° C.) for 20 min. Brown solid (0.060 g, 7%). M.P.: 195-197° C. MS (m/z): 372.08 (M+).

Example 183

6-((5-(2-Methoxypyrimidin-5-yl)-3H-[1,2,3]triazolo[4,5-b]pyridin-3-yl)methyl)quinoline The title compound was prepared by following the procedure described for example 1 using intermediate 14 (0.100 g, 0.338 mmol), 2-methoxypyrimidine-5-boronic acid (0.065 g, 0.422 mmol), potassium carbonate (0.156 g, 0.027 mmol), dioxane (2 ml), water (0.5 ml) and tetrakis(triphenylphosphine)palladium(0) (0.031 g. 0.067 mmol) under microwave irradiation (100 W, 100° C.) for 20 min. Yellow solid (0.060 g, 48%). M.P.: 201-203° C. MS (m/z): 369.98 (M+).

Example 184

6-((5-Benzo[d][1,3]dioxol-5-yl)-3H-[1,2,3]triazolo[4,5-b]pyridin-3-yl)methyl)quinoline The title compound was prepared by following the procedure described for example 1 using intermediate 14 (0.100 g, 0.338 mmol), benzo[d][1,3]dioxol-5-ylboronic acid (0.056 g, 0.422 mmol), potassium carbonate (0.156 g, 0.027 mmol). dioxane (2 ml), water (0.5 ml) and tetrakis(triphenylphosphine)palladium(0) (0.031 g, 0.067 mmol) under microwave irradiation (100 W, 100° C.) for 20 min. Off-white solid (0.070 g, 54%). M.P.: 179-181° C. MS (m/z): 382.16 (M++1).

Example 185

6-((5-(2,3-Dihydrobenzofuran-5-yl)-3H-[1,2,3]triazolo[4,5-b]pyridin-3-yl)methyl)quinoline The title compound was prepared by following the procedure described for example 1 using intermediate 14 (0.100 g, 0.338 mmol), 2,3-dihydrobenzofuran-5-ylboronic acid (0.055 g, 0.422 mmol), potassium carbonate (0.156 g, 0.027 mmol), dioxane (2 ml), water (0.5 ml) and tetrakis(triphenylphosphine)palladium(0) (0.031 g. 0.067 mmol) under microwave irradiation (100 W, 100° C.) for 20 min. Pale brown solid (0.065 g, 50%). MS (m/z): 379.92 (M+).

Example 186

5-(3-(Quinolin-6-ylmethyl)-3H-[1,2,3]triazolo[4,5-b]pyridin-5-yl)pyridin-2-amine The title compound was prepared by following the procedure described for example 1 using intermediate 14 (0.100 g, 0.338 mmol), 5-(4,4,5,5-tetramethyl-1,3,2-dioxaborolan-2-yl)pyridin-2-amine (0.096 g, 0.439 mmol), potassium carbonate (0.156 g, 0.027 mmol), dioxane (2 ml), water (0.5 ml) and tetrakis(triphenylphosphine)palladium(0) (0.031 g, 0.067 mmol) under microwave irradiation (100 W, 100° C.) for 20 min. Yellow solid (0.050 g, 42%). M.P.: 194-197° C. MS (m/z): 353.95 (M+).

Example 187

6-((5-(1-(2-fluoroethyl)-1H-pyrazol-4-yl)-3H-[1,2,3]triazolo[4,5-b]pyridin-3-yl)methyl)quinoline Methane sulphonyl chloride (0.069 g, 0.605 mmol) was added at 0° C. to a solution of example 146 (0.150 g, 0.403 mmol) and triethylamine (0.122 g. 1.21 mmol) in dichloromethane (3 ml) and warmed to RT. After 1 h, the mixture was diluted and washed with sodium bicarbonate solution, washed with brine, dried over sodium sulphate and concentrated. To the residue, cesium fluoride (0.270 g, 1.77 mmol) and tert-butanol (2 ml) were added and heated to 70° C. for 12 h. The reaction mixture was poured in water, extracted with ethyl acetate, washed with brine, dried over sodium sulphate and concentrated. The crude product was purified by column chromatography using dichloromethane:methanol to afford the title compound as an off-white solid (0.015 g, 10%). M.P.: 168-170° C. $^1$H-NMR (δ ppm, DMSO-$d_6$, 400 MHz): 8.88 (dd, J=4.2, 1.7 Hz, 1H), 8.57 (s, 1H), 8.53 (d, J=8.7 Hz, 1H), 8.37 (d, J=7.4 Hz, 1H), 8.26 (s, 1H), 8.01 (d, J=8.1 Hz, 1H), 7.99 (s, 1H), 7.83 (m, 2H), 7.53 (dd, J=8.3, 4.2 Hz, 1H), 6.11 (s, 2H), 4.88 (dt, J=47.1, 4.5 Hz, 2H), 4.56 (dt, J=27.7, 4.8 Hz, 2H) MS (m/z):: 374.1 (M++1).

Example 188

(4-(3-(Quinolin-6-ylmethyl)-3H-[1,2,3]triazolo[4,5-b]pyridin-5-yl)thiophen-2-yl)methanol The title compound was prepared by following the procedure described for example 1 using intermediate 14 (0.100 g, 0.338 mmol), (4-(4,4,5,5-tetramethyl-1,3,2-dioxaborolan-2-yl)thiophen-2-yl)methanol (0.066 g, 0.475 mmol), potassium carbonate (0.156 g, 0.027 mmol), dioxane 12 ml), water (0.5 ml) and tetrakis(triphenylphosphine) palladium(0) (0.031 g, 0.067 mmol) under microwave irradiation (100 W, 100° C.) for 20 min. Yellow solid (0.080 g, 63%). M.P.: 188-191° C., MS (m/z): 373.95 (M+).

Example 189

6-(2-(5-(1-(2-(Tetrahydro-2H-pyran-2-yloxy)ethyl)-1H-pyrazol-4-yl)-3H-[1,2,3]triazolo[4,5-b]pyridin-3-yl)propan-2-yl)quinoline The title compound was prepared by following the procedure described for example 1 using intermediate 17 (0.100 g, 0.307 mmol), 1-(2-(tetrahydro-2H-pyran-2-yloxy)ethyl)-4-(4,4,5,5-tetramethyl-1,2,3-dioxaborolan-2-yl)-1H-pyrazole (0.126 g, 0.394 mmol), potassium carbonate (0.133 g, 0.963 mmol), dioxane (2.5 ml), water (0.5 ml) and tetrakis(triphenylphosphine)palladium(0) (0.028 g, 0.024 mmol). Yellow liquid (0.065 g, 44%). $^1$H-NMR (δ ppm, DMSO-$d_6$, 400 MHz): 8.85 (d, J=2.8 Hz, 1H), 8.47 (d, J=8.7 Hz, 1H), 8.37 (d, J=7.9 Hz, 1H), 8.22 (s, 1H), 7.95 (d, J=1.7 Hz, 1H), 7.90 (s, 1H), 7.88 (d, J=7.3 Hz, 1H), 7.69 (d, J=8.7 Hz, 1H), 7.53 (m, 1H), 4.46 (m, 1H), 4.27 (m, 2H), 3.88 (m, 1H), 3.69 (m, 1H), 3.47 (m, 1H), 3.26 (m, 1H), 1.63-1.30 (m, 6H).

Example 190

2-(4-(3-(2-(Quinolin-6-yl)propan-2-yl)-3H-[1,2,3]triazolo[4,5-b]pyridin-5-yl)-1H-pyrazol-1-yl)ethanol The title compound was prepared by following the procedure described for example 146 from example 189 (0.050 g. 0.104 mmol), camphor sulphonic acid (0.121 g, 0.521 mmol), methanol (0.5 ml) and water (0.5 ml). Brown solid (0.031 g, 74%). M.P.: 95-98° C. $^1$H-NMR (δ ppm, DMSO-$d_6$, 400 MHz): 8.85 (d, J=2.8 Hz, 1H). 8.46 (d, J=8.7 Hz, 1H), 8.40 (d, J=7.9 Hz, 1H), 8.22 (s, 1H), 8.00 (d, J=1.8 Hz, 1H), 7.91 (d, J=8.9 Hz, 1H), 7.85 (s, 1H), 7.68 (d, J=8.7 Hz, 1H), 7.53 (m, 2H), 4.87 (t, J=5.3 Hz, 1H), 4.11 (t, J=5.4 Hz, 2H), 3.70 (q, J=5.4 Hz, 2H), 2.46 (s, 6H).

Example 191

6-((5-(3-ethyl-1H-indazol-6-yl)-3H-[1,2,3]triazolo[4,5-b]pyridin-3-yl)methyl)quinoline To a solution of Example 181 (0.050 g, 0.099 mmol) in dichloromethane (1 ml) cooled to 0° C., TFA (0.5 ml) was added and warmed to RT. After 2 h, the reaction mixture was poured in ice water and pH was adjusted to ca. 11 with 10% NaOH solution and extracted with ethyl acetate, washed with brine, dried over sodium sulphate and concentrated to afford the title compound as a yellow solid (0.023 g, 61%). M.P.: 211-213° C. MS (m/z): 406.08 (M$^+$).

Example 192

6-(2-(5-(1H-Pyrazol-4-yl)-3H-[1,2,3]triazolo[4,5-b]pyridin-3-yl)propan-2-yl)quinoline The title compound was prepared by following the procedure described for example 1 using intermediate 17 (0.20 g. 0.615 mmol), tert-butyl 4-(4,4,5,5-tetramethyl-1,3,2-dioxaborolan-2-yl)-1H-pyrazole-1-carboxylate (0.231 g, 0.788 mmol), potassium carbonate (0.266 g, 1.92 mmol), dioxane (5 ml), water (1 ml) and tetrakis(triphenylphosphine)palladium(0) (0.057 g, 0.049 mmol). Yellow solid (0.075 g, 34%). M.P.: 218-220° C. $^1$H-NMR (δ ppm, DMSO-$d_6$, 400 MHz): 13.02 (s, 1H), 8.86 (dd, J=4.2, 1.7 Hz, 1H), 8.56 (s, 1H), 8.35 (dd, J=8.2, 1.1 Hz, 2H), 8.10 (s, 1H), 8.04-7.98 (m, 3H), 7.85 (dd, J=8.8, 1.9 Hz, 1H), 7.61 (d, J=8.3 Hz, 1H), 7.52 (dd, J=8.3, 4.2 Hz, 1H), 5.69 (s, 2H), MS (m/z): 359.89 (M$^+$).

Example 193

6-((5-(4-Methylthiophen-2-yl)-3H-[1,2,3]triazolo[4,5-b]pyridin-3-yl)methyl)quinoline The title compound was prepared by following the procedure described for example 1 using intermediate 14 (0.100 g, 0.338 mmol), 4-methyl-2-thiopheneboronic acid (0.061 g, 0.432 mmol), potassium carbonate (0.146 g, 1.058 mmol), dioxane (2.5 ml), water (0.5 ml) and tetrakis(triphenylphosphine)palladium(0) (0.031 g, 0.027 mmol) under microwave irradiation (100 W, 100° C.) for 20 min. Brown solid (0.048 g, 40%). M.P.: 153-156° C. MS (m/z): 357.85 (M+).

Example 194

6-((6-(6-Methylthiophen-2-yl)-3H-[1,2,3]triazolo[4,5-b]pyridin-3-yl)methyl)quinoline The title compound was prepared by following the procedure described for example 1 using intermediate 14 (0.100 g, 0.338 mmol), 5-methyl-2-thiopheneboronic acid (0.060 g, 0.422 mmol), potassium carbonate (0.156 g, 1.12 mmol), dioxane (2.5 ml), water (0.5 ml) and tetrakis(triphenylphosphine)palladium(0) (0.031 g, 0.027 mmol) under microwave irradiation (100 W, 100° C.) for 20 min. Off-white solid (0.035 g, 29%), M.P.: 154-156° C. MS (m/z): 357.85 (M+).

Example 195

4-(5-(3-(Quinolin-6-ylmethyl)-3H-[1,2,3]triazolo[4,5-b]pyridin-5-yl)pyridin-2-yl)morpholine The title compound was prepared by following the procedure described for example 1 using intermediate 14 (0.100 g, 0.338 mmol), 6-morpholinopyridine-3-boronic acid (0.088 g, 0.422 mmol), potassium carbonate (0.156 g, 1.12 mmol), dioxane (2.5 ml), water (0.5 ml) and tetrakis(triphenylphosphine)palladium(0) (0.031 g. 0.027 mmol) under microwave irradiation (100 W, 100° C.) for 20 min, Yellow solid (0.045 g, 31%). M.P.: 183-185° C. MS (m/z): 423.93 (M+).

Example 196

6-((5-(6-(Piperidin-1-yl)pyridin-3-yl)-3H-[1,2,3]triazolo[4,5-b]pyridin-3-yl)methyl)quinoline The title compound was prepared by following the procedure described for example 1 using intermediate 14 (0.100 g, 0.338 mmol), 2-(piperidin-1-yl)-5-(4,4,5,5-tetramethyl-1,3,2-dioxaborolan-2-yl)pyridine (0.122 g, 0.422 mmol), potassium carbonate (0.156 g, 1.12 mmol), dioxane (2.5 ml), water (0.5 ml) and tetrakis (triphenylphosphine)palladium(0) (0.031 g. 0.027 mmol) under microwave irradiation (100 W, 100° C.) for 20 min. Brown solid (0.090 g, 63%). M.P.: 133-135° C. MS (m/z): 422.18 (M$^+$+1).

Example 197

6-((5-(1-Ethyl-1H-pyrazol-4-yl)-3H-[1,2,3]triazolo[4,5-b]pyridin-3-yl)methyl)quinoline The title compound was prepared by following the procedure described for example 144 from example 143 (0.130 g, 0.397 mmol), sodium hydride (0.014 g, 0.596 mmol), ethyl iodide (0.123 g, 0.794 mmol) and DMF (3 ml). Yellow solid (0.065 g, 46%), M.P.: 132-134° C. MS (m/z): 356.03 (M$^+$+1).

Example 198

6-((6-(1-Isopropyl-1H-pyrazol-4-yl)-3H-[1,2,3]triazolo[4,5-b]pyridin-3-yl)methyl)quinoline The title compound was prepared by following the procedure described for example 144 from example 143 (0.130 g, 0.397 mmol), sodium hydride (0.014 g, 0.596 mmol), 2-bromopropane (0.097 g, 0.794 mmol) and DMF (3 ml). Off-white solid (0.050 g, 34%). M.P.: 126-128° C. MS (m/z): 370.24 (M$^+$+1).

Example 199

6-((5-(1-Isobutyl-1H-pyrazol-4-yl)-3H-[1,2,3]triazolo[4,5-b]pyridin-3-yl)methyl)quinoline The title compound was prepared by following the procedure described for example 144 from example 143 (0.130 g, 0.397 mmol), sodium hydride (0.014 g, 0.596 mmol), 1-bromo-2-methylpropane (0.108 g, 0.794 mmol) and DMF (3 ml). Pale green solid (0.070 g, 46%). M.P.: 150-163° C. MS (m/z): 384.10 (M$^+$+1).

Example 200

1-(Pyrrolidin-1-yl)-2-(4-(3-(quinolin-6-ylmethyl)-3H-[1,2,3]triazolo[4,5-b]pyridin-5-yl)-1H-pyrazol-1-yl)ethanone To a solution of example 155 (0.056 g, 0.145 mmol) in DMF (0.5 ml) N-ethyldiisopropylamine (0.018 g, 0.145 mmol) and HATU (0.055 g, 0.1.45 mmol) were added and stirred for 5 min. Pyrrolidine (0.020 g, 0.290 mmol) was added at RT and the reaction mixture was stirred for 12 h. To the reaction mixture water was added and extracted with ethyl acetate, dried over sodium sulphate and concentrated under reduced pressure. The crude product was purified by column chromatography with methanol:dichloromethane to afford the title compound as a yellow solid (0.010 g, 16%). M.P.: 136-138° C. $^1$H-NMR (δ ppm, DMSO-d$_6$, 400 MHz): 8.87 (dd, J=2.7 Hz, 1H), 8.52 (d, J=8.7 Hz, 1H), 8.45 (s, 1H), 8.37 (d, J=7.7 Hz, 1H), 8.20 (s, 1H), 8.01 (d, J=8.6 Hz, 1H), 7.99 (s, 1H), 7.83 (m, 2H), 7.52 (dd, J=8.3, 4.2 Hz, 1H), 6.11 (s, 2H), 5.11 (s, 2H), 3.52 (t, J=6.7 Hz, 2H), 3.33 (m, 2H), 1.93-1.77 (m, 4H).

Example 201

6-((5-(1-(2-Methoxyethyl)-1H-pyrazol-4-yl)-3H-[1,2,3]triazolo[4,5-b]pyridin-3-yl)methyl)quinoline The title compound was prepared by following the procedure described for example 144 from example 143 (0.130 g, 0.397 mmol), sodium hydride (0.014 g, 0.596 mmol), 2-bromoethyl methyl ether (0.110 g, 0.794 mmol) and DMF (3 ml). Pale yellow solid (0.050 g, 33%). M.P.: 162-164° C. $^1$H-NMR (δ ppm, CDCl$_3$, 400 MHz): 8.90 (d, J=3.5 Hz, 1H), 8.30 (d, J=8.6 Hz, 1H), 8.13 (m, 4H), 7.89 (s, 1H), 7.86 (d, J=8.9 Hz, 1H), 7.54 (d, J=8.7 Hz, 1H), 7.41 (dd, J=8.3, 4.2 Hz, 1H), 6.07 (s, 2H), 4.38 (t, J=5.0 Hz, 2H), 3.81 (t, J=5.1 Hz, 2H), 3.36 (s, 3H).

Example 202

N-Phenyl-3-(quinolin-6-ylmethyl)-3H-[1,2,3]triazolo[4,5-b]pyridin-5-amine

To a solution of intermediate 14 (0.10 g, 0.338 mmol) and aniline (0.047 g, 0.507 mmol) in o-xylene (0.8 ml), sodium tert-butoxide (0.038 g, 0.405 mmol), triphenylphosphine (0.008 g, 0.033 mmol) and palladium acetate (0.003 g, 0.169 mmol) were added and degassed for 30 min. and the reaction mixture was heated to 120° C. for 4 h. The reaction mixture was filtered through celite and washed with ethyl acetate, dried over sodium sulphate and concentrated under reduced pressure. The crude product was purified by column chromatography with methanol:dichloromethane to afford the title compound as a brown solid (0.030 g, 25%), M.P.: 237-239° C. $^1$H-NMR (δ ppm, DMSO-d$_6$, 400 MHz): 9.72 (s, 1H), 8.87 (d, J=3.9 Hz, 1H), 8.36 (d, J=8.6 Hz, 1H), 8.19 (d, J=9.0 Hz, 1H), 8.00 (s, 1H), 7.98 (d, J=8.1 Hz, 1H), 7.73 (m, 3H), 7.53 (dd, J=8.0, 4.2 Hz, 1H), 7.26 (m, 2H), 6.96 (t, J=7.4 Hz, 1H), 6.90 (d, J=9.0 Hz, 1H), 5.98 (s, 2H).

Example 203

6-((5-Phenoxy-3H-[1,2,3]triazolo[4,5-b]pyridin-3-yl)methyl)quinoline

To a solution of intermediate 14 (0.10 g, 0.338 mmol) and phenol (0.031 g, 0.338 mmol) in N-methyl pyrrolidone (0.7 ml), potassium tert-butoxide (0.045 g, 0.405 mmol) was added and the reaction mixture was heated to 80° C. for 12 h. The reaction mixture was quenched with water, extracted with ethyl acetate, dried over sodium sulphate and concentrated under reduced pressure. The crude product was purified by column chromatography with methanol:dichloromethane to afford the title compound as an off-white solid (0.040 g, 33%). M.P.: 225-227° C. $^1$H-NMR (δ ppm, DMSO-d$_6$, 400 MHz): 8.91 (d, J=2.9 Hz, 1H), 8.29 (d, J=8.8 Hz, 1H), 8.07 (d, J=8.1 Hz, 1H), 8.01 (d, J=8.7 Hz, 1H), 7.76 (s, 1H), 7.67 (dd, J=8.6, 1.4 Hz, 1H), 7.47 (m, 3H), 7.33 (t, J=7.4 Hz, 1H), 7.16 (d, J=8.0 Hz, 1H), 6.98 (d, J=8.9 Hz, 1H), 5.80 (s, 2H).

Example 204

Methyl-2-fluoro-5-(3-(quinolin-6-ylmethyl)-3H-[1,2,3]triazolo[4,5-b]pyridin-5-yl)benzoate The title compound was prepared by following the procedure described for example 1 using intermediate 14 (0.250 g, 0.845 mmol), 4-fluoro-3-methoxycarbonylphenylboronic acid pinacol ester (0.294 g, 0.422 mmol), potassium acetate (0.276 g, 2.81 mmol), dioxane (4 ml) and tetrakis(triphenylphosphine)palladium(0) (0.050 g, 0.042 mmol). Off-white solid (0.080 g, 23%).

Example 205

2-Fluoro-5-(3-(quinolin-6-ylmethyl)-3H-[1,2,3]triazolo[4,5-b]pyridin-5-yl)benzoic acid To a solution of Example 204 (0.080 g, 0.193 mmol) in methanol (1 ml), lithium hydroxide (0.075 g, 1.80 mmol) in water (1 ml) and THF (2 ml) were added and stirred at RT. After 12 h, pH was adjusted to ca. 7 using 0.5N HCl and the solid precipitated was filtered, washed with ethyl acetate and petroleum ether and dried under vacuum to afford the title compound as an off-white solid (0.060 g, 78%). The acid was used without further purification in the next step.

Example 206

2-Fluoro-5-(3-(quinolin-6-ylmethyl)-3H-[1,2,3]triazolo[4,5-b]pyridin-5-yl)benzamide To Example 205 (0.060 g, 0.149 mmol), thionyl chloride (0.8 ml) was added and refluxed for 3 h. The excess thionyl chloride was removed; aqueous 25% ammonia (0.8 ml) was added to the residue at 0° C. and stirred for 15 min. The precipitate formed was washed with sodium bicarbonate solution and vacuum dried to afford title compound as an off-white solid (0.020 g, 34%), M.P.: 262-264° C. $^1$H-NMR (δ ppm, DMSO-d$_6$, 400 MHz): 8.87 (d, J=2.7 Hz, 1H), 8.68 (d, J=8.7 Hz, 1H), 8.50 (d, J=6.7 Hz, 1H), 8.39 (d, J=8.1 Hz, 2H), 8.17 (d, J=8.7 Hz, 1H), 8.04 (s, 1H), 8.02 (d, J=8.6 Hz, 1H), 7.89 (s, 1H), 7.83 (d, J=8.7 Hz, 1H), 7.78 (s, 1H), 7.53 (dd, J=8.2, 3.9 Hz, 1H), 7.49 (d, J=9.7 Hz, 1H), 6.21 (s, 2H).

Example 207

2-Chloro-4-(3-((5,7-difluoroquinolin-6-yl)methyl)-3H-[1,2,3]triazolo[4,5-b]pyridin-5-yl)benzamide The title compound was prepared by following the procedure described for example 1 using intermediate 34 (0.065 g, 0.196 mmol), intermediate 35 (0.070 g, 0.245 mmol), potassium carbonate (0.090 g, 0.654 mmol), dioxane (2 ml), water (0.3 ml) and tetrakis(triphenylphosphine)palladium(0) (0.018 g, 0.015 mmol) under microwave irradiation (100 W, 100° C.) for 30 mm. Brown solid (0.020 g. 23%), M.P.: 216-219° C., $^1$H-NMR (δ ppm, DMSO-$d_6$, 400 MHz): 9.01 (d, J=2.9 Hz, 1H), 8.67 (d, J=8.7 Hz, 1H), 8.59 (d, J=8.5 Hz, 1H). 8.26 (s, 1H), 8.20 (d, J=8.6 Hz, 1H), 8.18 (s, 1H), 7.96 (s, 1H), 7.77 (d, J=10.9 Hz, 1H), 7.69 (s, 1H), 7.67 (dd, J=8.6, 4.3 Hz, 1H), 7.59 (d, J=8.0 Hz, 1H), 7.59 (d, J=8.0 Hz, 1H), 6.26 (s, 2H).

Example 208

1-(3-(Quinolin-6-ylmethyl)-3H-[1,2,3]triazolo[4,5-b]pyridin-5-yl)ethanone

The title compound was prepared by following the procedure described for example 1 using intermediate 14 (0.200 g, 0.676 mmol), 1-ethoxyvinyl tri(n-butyl)stannane (0.244 g, 0.676 mmol), triphenylphosphine (0.0284 g, 0.054 mmol), toluene (3.8 ml) and tris(dibenzilidineacetone) palladium(0) (0.028 g. 0.027 mmol) followed by acid hydrolysis. Brown solid (0.080 g, 39%). $^1$H-NMR, (δ ppm, CDCl$_3$, 400 MHz): 8.92 (d, J=3.0 Hz, 1H), 8.49 (d, J=8.5 Hz, 1H), 8.15 (m, 3H), 7.94 (s, 1H), 7.87 (d, J=8.6 Hz, 1H), 7.43 (dd, J=8.3, 4.2 Hz, 1H), 6.15 (s, 2H), 2.82 (s, 3H).

Example 209

2-(1-(3-(Quinolin-6-ylmethyl)-3H-[1,2,3]triazolo[4,5-b]pyridin-5-yl)ethylidene)hydrzainecarboxamide To a solution of example 208 (0.070 g, 0.230 mmol) In ethanol (2 ml), sodium acetate (0.018 g, 0.230 mmol) and semicarbazide hydrochloride (0.026 g, 0.230 mmol) were added and stirred at RT for 12 h. The reaction mixture was concentrated and the residue was washed with bicarbonate solution, dichloromethane and dried under vacuum to afford the title compound as a yellow solid (0.040 g, 48%). M.P.: 249-250° C. $^1$H-NMR, (δ ppm, DMSO-$d_6$, 400 MHz): 9.70 (s, 1H), 8.88 (d, J=2.8 Hz, 1H), 8.54 (d, J=8.9 Hz, 1H), 8.45 (d, J=8.9 Hz, 1H), 8.37 (d, J=8.2 Hz, 1H), 8.01 (s, 1H), 7.99 (d, J=8.6 Hz, 1H), 7.81 (dd, J=8.6, 1.3 Hz, 1H), 7.53 (dd, J=8.2, 4.1 Hz, 1H), 6.78 (br s, 2H), 6.14 (s, 2H), 2.35 (s, 3H).

Example 210

4-(3-(Benzo[d]thiazol-6-ylmethyl)-3H-[1,2,3]triazolo[4,5-b]pyridin-5-yl)-2-chlorobenzamide The title compound was prepared by following the procedure described for example 1 using intermediate 38 (0.150 g. 0.496 mmol), intermediate 35 (0.174 g. 0.620 mmol), potassium carbonate (0.228 g, 1.65 mmol), dioxane (3 ml), water (1 ml) and tetrakis(triphenylphosphine)palladium(0) (0.045 g, 0.039 mmol) under microwave irradiation (100 W, 100° C.) for 30 mm. Yellow solid (0.090 g, 43%). M.P.: 238-240° C. $^1$H-NMR (δ ppm, DMSO-$d_6$, 400 MHz): 9.38 (s, 1H), 8.69 (d, J=8.7 Hz, 1H), 8.32 (s, 1H), 8.27 (s, 1H), 8.25 (d, J=8.2 Hz, 1H), 8.21 (d, J=8.8 Hz, 1H), 8.08 (d, J=8.4 Hz, 1H), 7.97 (s, 1H), 7.69 (s, 1H), 7.64 (m, 2H), 6.18 (s, 2H).

Example 211

2-(2-Fluoro-4-(3-(quinolin-6-ylmethyl)-3H-[1,2,3]triazolo[4,5-b]pyridin-5-yl)phenyl)propan-2-ol The title compound was prepared by following the procedure described for example 1 using intermediate 14 (0.150 g, 0.507 mmol), intermediate 19 (0.177 g, 0.634 mmol), potassium carbonate (0.233 g, 1.68 mmol), dioxane (3 ml), water (0.6 ml) and tetrakis(triphenylphosphine)palladium(0) (0.047 g, 0.040 mmol). Pale green solid (0.080 g, 38%). M.P.: 85-89° C. $^1$H-NMR (δ ppm, DMSO-$d_6$, 400 MHz): 9.59 (s, 1H), 8.88 (d, J=2.7 Hz, 1H), 8.67 (d, J=8.7 Hz, 1H), 8.37 (d, J=7.7 Hz, 1H), 8.15 (m, 4H), 7.83 (m, 2H), 7.53 (dd, J=8.1, 4.0 Hz, 1H), 6.21 (s, 2H), 5.38 (s, 1H), 1.51 (s, 6H).

Example 212

2-Chloro-5-(3-(quinolin-6-ylmethyl)-3H-[1,2,3]triazolo[4,5-b]pyridin-5-yl)benzamide The title compound was obtained as an off-white solid (0.065 g, 46%) by following the procedure described for example 1 using intermediate 14 (0.100 g, 0.338 mmol), intermediate 22 (0.118 g, 0.422 mmol), potassium carbonate (0.155 g, 1.12 mmol), DMF (8 ml), water (0.5 ml) and tetrakis (triphenylphosphine)palladium(0) (0.031 g, 0.027 mmol). M.P.: 241-244° C. $^1$H-NMR (δ ppm, DMSO-$d_6$, 400 MHz): 8.88 (dd, J=4.0, 2.6 Hz, 1H), 8.69 (d, J=8.7 Hz, 1H), 8.36 (d, J=8.2 Hz, 1H), 8.29 (s, 1H), 8.26 (dd, J=11.6, 1.5 Hz, 1H), 8.20 (d, J=8.8 Hz, 1H), 8.03 (m, 3H), 7.83 (dd, J=8.7, 1.6 Hz, 1H), 7.73 (s, 1H), 7.67 (d, J=8.3 Hz, 1H), 7.53 (dd, J=8.3, 4.2 Hz, 1H), 6.22 (s, 2H).

Example 213

3-(2-Chloro-3,6-difluorobenzyl)-5-(1H-pyrazol-4-yl)-3H-[1,2,3]triazolo[4,5-b]pyridine The title compound was prepared by following the procedure described for example 1 using intermediate 16 (0.180 g, 0.571 mmol), tert-butyl 4-(4,4,5,5-tetramethyl-1,3,2-dioxaborolan-2-yl)-1H-pyrazole-1-calboxylate (0.215 g, 0.731 mmol), potassium carbonate (0.260 g, 1.88 mmol), dioxane (3.5 ml), water (0.8 ml) and tetrakis(triphenylphosphine)palladium(0) (0.052 g, 0.044 mmol). Yellow solid (0.165 g, 83%), $^1$H-NMR (δ ppm, DMSO-$d_6$, 400 MHz): 13.22 (s, 1H), 8.48 (d, J=8.7 Hz, 1H), 8.18 (s, 1H), 7.82 (d, J=8.7 Hz, 1H), 7.63-7.51 (m, 2H), 7.45 (dt, J=9.2, 4.2 Hz, 1H), 6.02 (s, 2H).

Example 214

2-Chloro-4-(3-(1-(quinolin-6-yl)ethyl)-3H-[1,2,3]triazolo[4,5-b]pyridin-5-yl)benzamide The title compound was prepared by following the procedure described for example 1 using intermediate 40 (0.450 g, 1.45 mmol), intermediate 35 (0.511 g, 1.81 mmol), potassium carbonate (0.668 g, 3.33 mmol), dioxane (5 ml), water (1.5 ml) and tetrakis(triphenylphosphine)palladium(0) (0.134 g, 0.116 mmol) under microwave irradiation (100 W, 100° C.)

for 45 min. Off-white solid (0.250 g, 40%). M.P.: 140-143° C. ¹H-NMR (δ ppm, DMSO-d₆, 400 MHz): 8.87 (dd, J=3.8, 2.7 Hz, 1H). 8.68 (d, J=8.7 Hz, 1H), 8.39 (d, J=8.2 Hz, 1H), 8.25 (s, 1H), 8.20 (m, 2H), 8.11 (s, 1H), 8.00 (d, J=8.9 Hz, 1H), 7.94 (s, 1H), 7.86 (d, J=8.6 Hz, 1H), 7.67 (s, 1H), 7.60 (d, J=8.0 Hz, 1H), 7.53 (dd, J=8.4, 4.2 Hz, 1H), 6.73 (q, J=6.7 Hz, 1H), 2.25 (d, J=7.0 Hz, 3H).

Example 215

2-Chloro-4-(3-(quinolin-6-ylmethyl)-3H-[1,2,3]triazolo[4,5-b]pyridin-5-yl)benzamide The title compound was prepared by following the procedure described for example 1 using intermediate 29 (0.150 g, 0.508 mmol), intermediate 35 (0.179 g, 0.636 mmol), potassium carbonate (0.234 g, 1.69 mmol), dioxan (3 ml), water (1 ml) and tetrakis(triphenylphosphine) palladium(0) (0.047 g, 0.040 mmol) and in microwave oven (100 W, 100° C.) for 45 min. Off-white solid (0.095 g, 45%). M.P.: 212-214° C. ¹H-NMR (δ ppm, DMSO-d₆, 400 MHz): 8.87 (dd, J=4.1, 2.8 Hz, 1H), 8.73 (s, 1H), 8.35 (d, J=8.5 Hz, 1H), 8.20 (s, 1H), 8.18 (d, J=7.6 Hz, 1H), 8.13 (d, J=8.1 Hz, 1H), 8.01 (m, 3H), 7.90 (s, 1H), 7.83 (d, J=8.7 Hz, 1H), 7.62 (s, 1H), 7.55 (d, J=8.0 Hz, 1H), 7.53 (dd, J=8.6, 4.5 Hz, 1H), 5.78 (s, 2H).

Example 216

1-(3-(Quinolin-6-ylmethyl)-3H-[1,2,3]triazolo[4,5-b]pyridin-5-yl)ethanone oxime

To a solution of example 208 (0.060 g, 0.197 mmol) in ethanol (1.3 ml), sodium acetate (0.016 g, 0.197 mmol) and hydroxylamine hydrochloride (0.013 g, 0.197 mmol) were added and stirred at RT for 12 h. The reaction mixture was concentrated and the residue was washed with bicarbonate solution, dichloromethane and dried under vacuum to afford the title compound as a ca. 9:1 mixture of two isomers. Off-white solid (0.030 g, 48%). M.P.: 259-261° C. ¹H-NMR (δ ppm, DMSO-d₆, 400 MHz): 11.95 (s, 0.9H), 11.28 (s, 0.1H), 8.88 (d, J=2.6 Hz, 1H), 8.74 (d, J=8.8 Hz, 0.1H), 8.61 (d, J=8.4 Hz, 0.1H), 8.52 (d, J=8.8 Hz, 0.9H), 8.36 (d, J=8.4 Hz, 0.9H), 8.00 (m, 3H), 7.81 (dd, J=8.4, 1.6 Hz, 1H), 7.53 (dd, J=8.3, 4.1 Hz, 1H), 6.24 (s, 0.2H), 6.15 (s, 1.8H), 2.74 (s, 0.3H), 2.30 (s, 2.7H).

Example 217

1-(3-(Quinolin-6-ylmethyl)-3H-[1,2,3]triazolo[4,5-b]pyridin-5-yl)ethanone O-methyl oxime The title compound was prepared as a ca. 9.5:0.5 mixture of two isomers by using a procedure similar to the one described for example 216 from example 208 (0.070 g, 0.230 mmol), ethanol (1.5 ml), sodium acetate (0.018 g, 0.230 mmol) and methoxylamine hydrochloride (0.019 g, 0.230 mmol). Off-white solid (0.020 g. 26%). M.P.: 155-157° C. ¹H-NMR (δ ppm. DMSO-d₆, 400 MHz): 8.88 (d, J=2.6 Hz, 1H), 8.61 (d, J=8.8 Hz, 0.05H), 8.55 (d, J=8.8 Hz, 0.95H), 8.36 (d, J=8.4 Hz, 1H), 8.02 (m, 3H), 7.81 (dd, J=8.8, 1.7 Hz, 1H), 7.53 (dd, J=8.3, 4.2 Hz, 1H), 6.16 (s, 2H), 4.01 (s, 2.85H), 3.79 (s, 0.15H), 2.32 (s, 2.85H), 2.24 (s, 0.15H).

Example 218

N'-(1-(3-(Quinolin-6-ylmethyl)-3H-[1,2,3]triazolo[4,5-b]pyridin-5-yl)ethylidene)acetohydrazide To a solution of example 208 (0.070 g, 0.230 mmol) in ethanol (1.3 ml), acetyl hydrazide (0.017 g, 0.230 mmol) was added refluxed for 4 h. The reaction mixture was concentrated and the residue was washed with water, ethyl acetate and dried under vacuum to afford the title compound as a ca. 1:1 mixture of two isomers. Pale yellow solid (0.035 g, 42%). M.P.: 249-251° C. ¹H-NMR (δ ppm, DMSO-d₆, 400 MHz): 10.79 (s, 0.5 H), 10.76 (s, 0.5H), 8.89 (d, J=2.9 Hz, 1H), 8.66 (d, J=8.7 Hz, 0.5H), 8.55 (d, J=8.8 Hz, 0.5H), 8.37 (m, 1.5H), 8.20 (d, J=9.0 Hz, 0.5H), 8.01 (m, 2H), 7.84 (dt, J=9.0. 1.8 Hz, 1H), 7.54 (dd, J=8.3, 4.2 Hz, 1H), 6.20 (s, 1H), 6.16 (s, 1H), 2.39 (s, 3H), 2.29 (s, 3H).

Example 219

6-((5-(4-Methylpiperazin-1-yl)-3H-[1,2,3]triazolo[4,5-b]pyridin-3-yl)methyl)quinoline The title compound was prepared by following the procedure described for example 152 using intermediate 14 (0.150 g, 0.507 mmol), N-methyl piperazine (0.076 g, 0.760 mmol), cesium fluoride (0.154 g, 1.01 mmol) and DMF (4.5 ml). Brown solid (0.023 g, 13%). M.P.: 131-133° C. ¹H-NMR (δ ppm, DMSO-d₆, 400 MHz): 8.87 (d, J=2.6 Hz, 1H), 8.35 (d, J=8.1 Hz, 1H), 8.15 (d, J=9.3 Hz, 1H), 7.99 (d, J=8.6 Hz, 1H), 7.93 (s, 1H), 7.74 (d, J=8.5 Hz, 1H), 7.53 (dd, J=8.0, 4.0 Hz, 1H), 7.05 (d, J=9.4 Hz, 1H), 5.89 (s, 2H), 3.68 (br.s, 4H), 2.42 (br.s, 4H), 2.22 (s, 3H).

Example 220

N'-(1-(3-(quinolin-6-ylmethyl)-3H-[1,2,3]triazolo[4,5-b]pyridin-5-yl)ethylidene)isonicotinohydrazide To a solution of example 208 (0.065 g, 0.214 mmol) in ethanol (1.5 ml), isonicotinic hydrazide (0.050 g, 0.428 mmol) was added refluxed for 12 h. The reaction mixture was concentrated and the residue was washed with water, ethyl acetate and dried under vacuum to afford the title compound as a single isomer and as a pale yellow solid (0.070 g, 77%). M.P.: 239-241° C. ¹H-NMR (δ ppm, DMSO-d₆, 400 MHz): 11.24 (s, 1H), 8.88 (dd, J=4.1, 2.5 Hz, 1H), 8.77 (s, 2H), 8.60 (brs, 1H), 8.37 (d, J=8.0 Hz, 2H), 8.02 (d, J=8.8 Hz, 2H), 7.82 (d, J=7.1 Hz, 2H), 7.71 (m, 1H), 7.54 (dd, J=8.3, 4.2 Hz, 1H), 6.18 (s, 2H), 2.55 (s, 3H).

Example 221

(−)-2-chloro-4-(3-(1-(quinolin-6-yl)ethyl)-3H-[1,2,3]triazolo[4,5-b]pyridin-5-yl)benzamide The isomer was obtained through preparative SFC separation of the racemic compound i.e., (±)-2-chloro-4-(3-(1-(quinolin-6-yl)ethyl)-3H-[1,2,3]triazolo[4,5-b]pyridin-5-yl) benzamide (0.24 g) on a CHIRALPAK IA column (250×30 mm; 5μ) using ethanol:CO₂ (35:65) as the mobile phase at a flow rate of 70 g/min. Off-white solid (0.095 g). e.e. 96.84%. Rt: 4.27 min (CHIRALPAK IA column (250×4.6 mm: 5μ) using ethanol: CO₂ (40:60) as the mobile phase at a flow rate of 3.0 ml/min.). MP: 202-203° C. [α]D²³:−427.30 (c=1, CHCl₃). ¹H-NMR (δ ppm, CDCl₃+DMSO-d₆ 300 MHz): 8.88 (d, J=3.2 Hz, 1H), 8.43 (d, J=8.6 Hz, 1H), 8.15 (d, J=6.1 Hz, 1H), 8.14 (s, 1H), 8.07 (d, J=8.7 Hz, 1H), 8.00 (d, J=8.4 Hz, 1H), 7.98 (s, 1H), 7.91 (m, 2H), 7.79 (d, J=8.6 Hz, 1H), 7.40 (dd, J=8.2, 4.2 Hz, 1H), 6.62 (q, J=6.9 Hz, 1H), 6.54 (s, 1H), 6.12 (s, 1H), 2.34 (d, J=7.1 Hz, 3H).

Example 222

(+)-2-chloro-4-(3-(1-(quinolin-6-yl)ethyl)-3H-[1,2,3]triazolo[4,5-b]pyridin-5-yl)benzamide The isomers was obtained through preparative SFC separation of the racemic compound i.e. (±)-2-chloro-4-(3-(1-(quinolin-6-yl)ethyl)-3H-[1,2,3]triazolo[4,5-b]pyridin-5-yl)benzamide (0.24 g) on a CHIRALPAK IA column (250×30 mm; 5μ) using ethanol:$CO_2$ (35:65) as the mobile phase at a flow rate of 70 g/min. Off-white solid (0.035 g). e.e. 96.21%. Rt: 4.82 min (CHIRALPAK IA column (250×4.6 mm; 5μ) using ethanol:$CO_2$ (40:60) as the mobile phase at a flow rate of 3.0 ml/min.). MP: 200-202° C. $^1$H-NMR (δ ppm, $CDCl_3$, 400 MHz): 8.90 (d, J=2.8 Hz, 1H), 8.46 (d, J=8.6 Hz, 1H), 8.16 (m, 2H). 8.10 (d, J=8.7 Hz, 1H), 8.13-7.95 (m, 3H), 7.92 (d, J=7.1 Hz, 1H), 7.81 (d, J=8.7 Hz, 1H), 7.42 (dd, J=8.2, 4.2 Hz, 1H), 6.64 (q, J=7.0 Hz, 1H), 6.43 (s, 1H), 5.87 (s, 1H), 2.36 (d, J=7.2 Hz, 3H).

Example 223

4-(3-(Quinolin-6-ylmethyl)-3H-[1,2,3]triazolo[4,5-b]pyridin-5-yl)-2-(trifluoromethyl)benzamide The title compound was prepared by following the procedure described for example 1 using intermediate 14 (0.200 g, 0.676 mmol), intermediate 42 (0.277 g, 0.879 mmol), potassium carbonate (0.311 g, 2.25 mmol), dioxane (4 ml), water (2 ml) and tetrakis(triphenylphosphine)palladium(0) (0.062 g, 0.054 mmol) in a microwave oven (100 W, 100° C.) for 45 min. Brown solid (0.035 g, 12%), M.P.: 230-232° C. $^1$H-NMR (δ ppm, DMSO-$d_6$, 400 MHz): 8.88 (d, J=2.9 Hz, 1H), 8.73 (d, J=8.7 Hz, 1H), 8.55 (d, J=5.5 Hz, 1H), 8.52 (s, 1H), 8.35 (d, J=8.1 Hz, 1H), 8.28 (d, J=8.8 Hz, 1H), 8.05 (m, 3H), 7.84 (dd, J=10.2, 1.4 Hz, 1H), 7.72 (d, J=8.6 Hz, 1H), 7.70 (s, 1H), 7.54 (dd, J=8.3, 4.3 Hz, 1H), 6.24 (s, 2H).

Example 224

6-((5-(4-carbamoyl-3-chlorophenyl)-3H-[1,2,3]triazolo[4,5-b]pyridin-3-yl)methyl)quinoline 1-oxide To a solution of example 108 (0.100 g, 0.241 mmol) in acetone (0.6 ml), oxone (0.74 g, 1.20 mmol) in water (2 ml) was added and heated under reflux for 20 h. The mixture was diluted with aqueous 10% sodium bicarbonate solution and extracted with dichloromethane, the organic layer dried over anhydrous sodium sulphate and concentrated. The crude product was purified by column chromatography with methanol:dichloromethane to afford the title compound (0.030 g, 29%) as a pale brown solid. M.P.: 182-183° C. $^1$H-NMR (δ ppm, DMSO-$d_6$, 400 MHz): 8.71 (d, J=8.8 Hz, 1H), 8.55 (d, J=6.1 Hz, 1H), 8.52 (d, J=9.1 Hz, 1H), 8.29 (s, 1H), 8.23 (m, 2H), 8.12 (s, 1H), 7.95-7.83 (m, 3H), 7.67 (s, 1H), 7.61 (d, J=7.9 Hz, 1H), 7.47 (dd, J=8.4, 6.2 Hz, 1H), 6.24 (s, 2H).

Example 225

2-chloro-N-ethyl-4-(3-(quinolin-6-yl)ethyl)-3H-[1,2,3]triazolo[4,5-b]pyridin-5-yl)benzamide hydrochloride Ether saturated with HCl (1 ml) was added at 0° C. to a solution of example 119 (0.020 g, 0.045 mmol) in THF (1 ml), and stirred for 15 min. The precipitate formed was filtered, washed with ether and dried under vacuum to afford the title compound as an off-white solid (0.012 g, 56%). M.P.: 151-153° C.

Example 226

6-((5-(4-carbamoyl-3-chlorophenyl)-3H-[1,2,3]triazolo[4,5-b]pyridin-3-yl)methyl)quinoline 1-oxide To a solution of example 119 (0.060 g, 0.135 mmol) in dichloromethane (1 ml), 3-chloroperbenzoic acid (0.46 g, 0.270 mmol) was added and stirred at RT for 12 h. The mixture was diluted with water, extracted with dichloromethane, the organic layer dried over sodium sulphate and concentrated. The crude product was purified by column chromatography with methanol:dichloromethane as the eluent to afford the title compound as a grey solid. (0.016 g, 26%). M.P.: 212-215° C. $^1$H-NMR (δ ppm, DMSO-$d_6$, 400 MHz): 8.71 (d, J=8.8 Hz, 1H), 8.68 (d, J=9.1 Hz, 1H), 8.56 (m, 2H), 8.30 (d, J=1.5 Hz, 1H), 8.24 (m, 2H), 8.12 (s, 1H), 7.93 (d, J=8.6 Hz, 1H), 7.86 (dd, J=9.1, 1.8 Hz, 1H), 7.57 (d, J=8.0 Hz, 1H), 7.48 (dd, J=8.4, 6.0 Hz, 1H), 6.20 (s, 2H), 3.28 (m, 2H), 1.14 (t, J=7.3 Hz, 3H).

Example 227

6-((5-(1H-pyrazol-4-yl)-3H-[1,2,3]triazolo[4,5-b]pyridin-3-yl)methyl)quinoline

The title compound was prepared by following the procedure described for example 1 using intermediate 14 (0.100 g, 0.338 mmol), text-butyl 3-methyl-4-(4,4,5,5-tetramethyl-1,3,2-dioxaborolan-2-yl)-1H-pyrazole-1-carboxylate (0.088 g, 0.422 mmol), potassium carbonate (0.155 g, 1.12 mmol), DMF (2 ml), water (0.5 ml) and tetrakis(triphenylphosphine)palladium(0) (0.031 g, 0.027 mmol) under microwave irradiation (100 W, 100° C.) for 45 mm. Brown solid (0.025 g, 23%). M.P.: 215-218° C., $^1$H-NMR (δ ppm, DMSO-$d_6$, 400 MHz): 12.94 (s, 1H), 8.88 (dd, J=4.1, 1.5 Hz, 1H), 8.47 (d, J=8.7 Hz, 1H), 8.36 (d, J=7.7 Hz, 1H), 8.13 (s, 1H), 8.00 (d, J=7.9 Hz, 1H), 8.00 (s, 1H), 7.79 (m, 2H), 7.53 (dd, J=8.3, 4.2 Hz, 1H), 6.11 (s, 2H), 2.56 (s, 3H).

Biological Assay

The pharmacological properties of the compounds of this invention may be confirmed by a number of pharmacological assays. The pharmacological assays which can be been carried out with the compounds according to the invention and/or their pharmaceutically acceptable salts are exemplified below.

1. MET Kinase Assay Protocol:
Colorimetric Determination of c-Met Kinase Activity The receptor tyrosine kinase c-Met is a heterodimeric transmembrane glycoprotein involved in several cellular processes that aid in tumor progression. Phosphorylation of the tyrosine residues in the c-Met kinase domain is critical for its activity and the resulting down-stream effects. The colorimetric assay allows detection of the phosphorylated form of a biotinylated peptide upon activation of human recombinant Met kinase.

MET Kinase Assay Protocol:

c-Met Kinase activity shall be determined using an HTScan® Met Kinase Assay Kit. (Cell Signalling Technology, Beverly, Mass.) with modifications. All incubations are carried out at room temperature. Briefly, 12.5 μl of a 4× reaction cocktail (DTT/Kinase buffer containing appropriate quantity of human Met kinase) is added to each well of a 96-well plate containing 12.5 μl pre-diluted compound of interest and incubated for 5 minutes. After the initial incubation, 25 µl/well of 2×ATP/biotinylated peptide is added and incubated for an additional 30 minutes. The reaction is terminated by the addition of 50 µl/well stop buffer (50 mM EDTA, pH 8.0). The reaction mixture (25 µl/well) is then transferred to a streptavidin coated plate (Ferkin Elmer, Cat#4009-0010) containing 75 µl dH$_2$O and incubated for 60 minutes. The plate is washed with 200 µl/well wash buffer (1×FBS, 0.05% Tween-20). After washing, 100 µl/well phospho-tyrosine mAb (1:1000 in wash buffer containing 1% BSA) is added and incubated for 60 minutes. After another round of washes, 100 µl/well europium labelled anti-mouse IgG (1:500 in wash buffer containing 1% BSA) is added and incubated for an additional 30 minutes. Following additional washes, 100 µl/well Delfia$^{(R)}$ enhancement solution (Ferkin Elmer, Cat#1244-105) is added and incubated for 45 minutes. Florescence is measured on a microplate reader (BMG Labtech., Germany) at 340 nm (excitation) and 615 nm (emission) for calculating % inhibition. Data generated can be analyzed further using Graphpad Prism (Graphpad software, San Diego Calif.) for determination of IC$_{50}$.

Results:

The results are as given below in Table 2 as % Inhibition of c-Met at 1 µM.

TABLE 2

| Cpd. | Inhibition | IC 50 |
|---|---|---|
| Ex 2 | A | +++ |
| Ex 6 | A | +++ |
| Ex 8 | A | +++ |
| Ex 9 | A | +++ |
| Ex 13 | A | +++ |
| Ex 14 | A | ++ |
| Ex 15 | A | +++ |
| Ex 16 | A | +++ |
| Ex 21 | B | + |
| Ex 52 | A | ++++ |
| Ex 108 | A | ++++ |
| Ex 119 | A | ++++ |
| Ex 130 | A | ++++ |
| Ex 134 | A | ++++ |
| Ex 137 | A | ++++ |
| Ex 221 | A | +++ |
| Ex 222 | B | + |

A = ≥75 to 100 and
B = ≥50-<75%;
++++ = ≤50 nm;
+++ = >50 to ≤100 nM;
++ = >100-≤250 and
+ = >251-≤1000 nM.

Inhibition of MKN-45 Proliferation

Cell proliferation assays were carried out using the high Met expressing human gastric adenocarcinoma cell line, MKN-45, according to the following schedule:

Day 1: Cells were plated in 96-well plates in complete growth medium.

Day 2: Compounds at desired concentrations were added.

Day 5: Cell viability was determined using the 3-[4,5-dimethylthiazol-2-yl]. 2,5-diphenyltetrazolium bromide (MTT) dye reduction test.

Results:

The results are as given below as % Inhibition of MKN-45 proliferation at 1 µM in Table 3, at 0.1 µM in Table 3A and as GI$_{50}$ values in Table 4.

TABLE 3

| Cpd. | % inhibition @ 1 uM |
|---|---|
| Ex 1 | C |
| Ex 18 | D |
| Ex 19 | D |
| Ex 22 | D |
| Ex 23 | D |
| Ex 24 | D |
| Ex 25 | D |
| Ex 47 | B |
| Ex 48 | A |
| Ex 49 | C |
| Ex 51 | D |
| Ex 56 | D |
| Ex 58 | D |
| Ex 59 | B |
| Ex 60 | D |
| Ex 61 | A |
| Ex 62 | A |
| Ex 63 | B |
| Ex 64 | C |
| Ex 65 | D |
| Ex 66 | C |
| Ex 67 | 13.83 |
| Ex 68 | D |
| Ex 69 | D |
| Ex 70 | D |
| Ex 71 | C |
| Ex 73 | B |
| Ex 74 | B |
| Ex 75 | D |
| Ex 76 | B |
| Ex 77 | B |
| Ex 78 | B |
| Ex 79 | B |
| Ex 80 | C |
| Ex 81 | A |
| Ex 84 | D |
| Ex 85 | A |
| Ex 86 | A |
| Ex 87 | D |
| Ex 88 | D |
| Ex 89 | D |
| Ex 90 | A |
| Ex 91 | B |
| Ex 92 | D |
| Ex 93 | C |
| Ex 94 | D |
| Ex 95 | B |
| Ex 96 | D |
| Ex 97 | C |
| Ex 98 | B |
| Ex 99 | B |
| Ex 102 | A |
| Ex 104 | A |
| Ex 105 | D |
| Ex 106 | A |
| Ex 110 | B |
| Ex 111 | A |
| Ex 114 | B |
| Ex 115 | A |
| Ex 116 | A |
| Ex 117 | A |
| Ex 118 | A |
| Ex 120 | C |
| Ex 121 | D |
| Ex 122 | D |
| Ex 124 | B |
| Ex 125 | D |
| Ex 127 | A |
| Ex 137 | B |
| Ex 138 | A |
| Ex 139 | D |
| Ex 140 | A |
| Ex 141 | A |
| Ex 147 | D |
| Ex 148 | D |
| Ex 150 | D |

TABLE 3-continued

| Cpd. | % inhibition @ 1 uM |
|---|---|
| Ex 151 | B |
| Ex 167 | C |
| Ex 180 | C |
| Ex 181 | A |
| Ex 182 | C |
| Ex 184 | D |
| Ex 185 | D |
| Ex 186 | D |
| Ex 190 | D |
| Ex 191 | C |
| Ex 192 | D |
| Ex 193 | B |
| Ex 194 | B |
| Ex 195 | B |
| Ex 196 | D |
| Ex 212 | C |
| Ex 225 | B |
| Ex 226 | D |
| Ex 227 | D |

D = <25%, C = ≥25-<50%, B = ≥50-<75%, A = ≥75 to 100%

TABLE 3A

| Cpd | Inhibition |
|---|---|
| Ex 47 | D |
| Ex 48 | D |
| Ex 49 | D |
| Ex 51 | D |
| Ex 52 | D |
| Ex 55 | D |
| Ex 56 | D |
| Ex 58 | D |
| Ex 59 | D |
| Ex 60 | D |
| Ex 61 | A |
| Ex 62 | A |
| Ex 63 | D |
| Ex 64 | D |
| Ex 65 | D |
| Ex 66 | D |
| Ex 67 | D |
| Ex 68 | D |
| Ex 69 | D |
| Ex 70 | D |
| Ex 71 | D |
| Ex 72 | D |
| Ex 73 | A |
| Ex 74 | B |
| Ex 75 | D |
| Ex 76 | A |
| Ex 77 | B |
| Ex 78 | B |
| Ex 79 | D |
| Ex 80 | D |
| Ex 81 | B |
| Ex 84 | D |
| Ex 85 | D |
| Ex 86 | D |
| Ex 87 | A |
| Ex 88 | D |
| Ex 89 | A |
| Ex 90 | B |
| Ex 91 | C |
| Ex 92 | D |
| Ex 93 | C |
| Ex 94 | B |
| Ex 95 | D |
| Ex 96 | D |
| Ex 97 | C |
| Ex 98 | C |

TABLE 3A-continued

| Cpd | Inhibition |
|---|---|
| Ex 99 | B |
| Ex 102 | B |
| Ex 103 | D |
| Ex 104 | B |
| Ex 105 | D |
| Ex 106 | D |
| Ex 107 | D |
| Ex 108 | B |
| Ex 109 | A |
| Ex 110 | B |
| Ex 111 | D |
| Ex 113 | A |
| Ex 114 | B |
| Ex 115 | D |
| Ex 116 | D |
| Ex 117 | B |
| Ex 118 | D |
| Ex 119 | A |
| Ex 120 | A |
| Ex 121 | A |
| Ex 122 | D |
| Ex 123 | B |
| Ex 124 | A |
| Ex 125 | D |
| Ex 126 | A |
| Ex 127 | A |
| Ex 130 | A |
| Ex 133 | A |
| Ex 134 | B |
| Ex 135 | D |
| Ex 137 | A |
| Ex 138 | C |
| Ex 139 | B |
| Ex 140 | A |
| Ex 141 | A |
| Ex 142 | A |
| Ex 180 | D |
| Ex 181 | D |
| Ex 182 | D |
| Ex 183 | D |
| Ex 184 | D |
| Ex 185 | D |
| Ex 186 | D |
| Ex 187 | A |
| Ex 188 | A |
| Ex 190 | D |
| Ex 191 | C |
| Ex 192 | D |
| Ex 193 | D |
| Ex 194 | D |
| Ex 195 | C |
| Ex 196 | D |
| Ex 197 | C |
| Ex 198 | D |
| Ex 199 | D |
| Ex 200 | D |
| Ex 201 | D |
| Ex 202 | D |
| Ex 203 | D |
| Ex 212 | A |
| Ex 206 | B |
| Ex 207 | A |
| Ex 209 | A |
| Ex 210 | A |
| Ex 214 | A |
| Ex 215 | D |
| Ex 216 | D |
| Ex 217 | B |
| Ex 218 | D |
| Ex 219 | D |
| Ex 220 | D |
| Ex 221 | B |
| Ex 222 | C |
| Ex 223 | A |
| Ex 224 | C |
| Ex 225 | A |

TABLE 3A-continued

| Cpd | Inhibition |
|---|---|
| Ex 226 | D |
| Ex 227 | C |

D = <25%,
C = ≥25-<50%,
B = ≥50-<75%,
A = ≥75 to 100%

TABLE 4

| Cpd | GI 50 (nM) | IC 50 (nM) |
|---|---|---|
| Ex 2 | E | — |
| Ex 4 | C | — |
| Ex 6 | C | — |
| Ex 8 | E | — |
| Ex 9 | B | B' |
| Ex 14 | B | B' |
| Ex 15 | B | B' |
| Ex 16 | A | A' |
| Ex 21 | C | — |
| Ex 22 | E | — |
| Ex 26 | D | — |
| Ex 27 | B | — |
| Ex 28 | C | — |
| Ex 30 | C | — |
| Ex 31 | C | — |
| Ex 32 | D | — |
| Ex 33 | C | — |
| Ex 34 | D | — |
| Ex 35 | B | — |
| Ex 36 | B | — |
| Ex 37 | A | — |
| Ex 38 | D | — |
| Ex 39 | B | — |
| Ex 40 | D | — |
| Ex 41 | B | — |
| Ex 43 | A | B' |
| Ex 44 | B | — |
| Ex 45 | B | — |
| Ex 46 | A | B' |
| Ex 52 | A | A' |
| Ex 55 | B | — |
| Ex 61 | A | — |
| Ex 62 | A | — |
| Ex 108 | A | A' |
| Ex 119 | A | A' |
| Ex 130 | A | A' |
| Ex 133 | A | — |
| Ex 134 | A | A' |
| Ex 137 | A | A' |
| Ex 142 | B | — |
| Ex 143 | B | — |
| Ex 144 | B | — |
| Ex 146 | B | B' |
| Ex 152 | C | — |
| Ex 157 | D | — |
| Ex 164 | B | B' |
| Ex 168 | C | — |
| Ex 169 | D | — |
| Ex 170 | D | — |
| Ex 171 | C | — |
| Ex 172 | D | — |
| Ex 173 | D | — |
| Ex 175 | C | — |
| Ex 176 | D | — |
| Ex 177 | D | — |
| Ex 179 | C | — |
| Ex 187 | A | — |
| Ex 188 | B | — |
| Ex 207 | A | — |
| Ex 209 | A | — |
| Ex 210 | A | — |
| Ex 211 | C | — |
| Ex 214 | A | — |
| Ex 221 | A | — |
| Ex 222 | C | — |

A = A' = ≤50;
B = B' = >50 to ≤150;
C = >150- ≤500;
D = >500-≤1000 &
E = >1000 in nM

Inhibition of c-Met Kinase Phosphorylation in MKN-45 Cells:

MKN45 cells are a prototype of "c-Met addicted" cells having constitutively activated c-Met kinase similar to that observed in sub-sects of gastric or hepatocellular cancer patients with dysregulated c-Met kinase activity. Inhibition of Met phosphorylation was determined using a cell based ELISA assay according to the following schedule:

Day 1: MKN-45 cells were plated in 96-well plates in complete growth medium.

Day 2: Inhibitors at the desired concentration were added to the plates and incubated for 1 h and lysed subsequently.

Lysates were transferred to NUNC Maxisorp plates coaled with anti-cMet receptor antibody. Phopho-tyrosine mAb and HRP-lined and -mouse IgG were used as primary and secondary antibodies respectively. Optical density was measured on a microplate reader (BMG Labtech, Germany) at 450 nM. Inhibition of c-Met phosphorylation in this cell line indicates a therapeutic potential for test compounds in patients diagnosed with cancers caused by aberrant c-Met kinase signalling.

Results:

The results are provided above in Table 4 as IC50 values.

Inhibition of c-Met kinase phosphorylation in NCI-H441 cells:

Inhibition of Met phosphorylation was determined using a cell based ELISA assay according to the following schedule:

Day 1: NCI-H441 cells were plated in 96-well plates in complete growth medium.

Day 2: Inhibitors at the desired concentration were added to the plates, incubated for 1 h and lysed subsequently. Lysates were transferred to NUNC Maxisorp plates coated with anti-cMet receptor antibody. Phopho-tyrosine mAb and HRP-lined anti-mouse IgG were used as primary and secondary antibodies respectively. Optical density was measured on a microplate reader (BMG Labtech., Germany) at 450 nM. The compounds potently inhibited c-Met kinase phosphorylation in NCI-H441, a non-small cell lung cancer derived cell line indicating a therapeutic potential in lung cancer patients with mutant kras.

Results:

The results are given below in Table 5 as IC50 values.

TABLE 5

| Cpd | IC 50 |
|---|---|
| Ex 146 | +++ |
| Ex 14 | ++ |
| Ex 15 | ++ |
| Ex 52 | + |
| Ex 108 | + |
| Ex 119 | + |
| Ex 139 | + |

TABLE 5-continued

| Cpd | IC 50 |
|---|---|
| Ex 134 | + |
| Ex 137 | + |

+ = ≤10;
++ = >10 to ≤50
+++ = >50-≤100 in nM

Inhibition of Akt Phosphorylation in MKN-45 or NCI-H441 Cells:

Akt is a serine-threonine kinase and a downstream marker regulated by c-Met kinase via the PI3K pathway. Once phosphorylated, Akt regulates several end processes including cell survival and growth. Cells were treated with 0-1.000 nM of test compounds, lysed, and the proteins separated on a 10% SDS-PAGE. Following separation, proteins were transferred onto a nitrocellulose membrane and detected by chemiluminescence after incubation with pAkt S473 mAb (primary) and rabbit anti-mouse Ab (secondary). Intensity of the bands was determined using ImageJ 1.42q (NIH, USA) and normalized to Actin (loading control). Results: The results are provided below as IC50 values in Table 6.

TABLE 6

AKT PHOSPHORYLATION

| Cpd | MNK-45 (IC50-nM) | NCI-H441 (IC50-nM) |
|---|---|---|
| Ex 146 | — | B |
| Ex 15 | D | A |
| Ex 52 | C | A |
| Ex 108 | A | A |
| Ex 119 | A | A |
| Ex 130 | C | B |
| Ex 134 | A | A |

A = ≤25;
B = >25 to ≤50,
C = >50-≤100,
D = >100-≤200 in nM,

6. Induction of Apoptosis in MKN-45 Cells:

Induction of Caspase 3 was measured fluorimetrically. Cells were incubated with desired concentrations of the compound for 24 h. After incubation, cells were harvested and counted. An equal number of viable cells per well ($0.3 \times 10^6$ cells) were used for determination of caspase-3 activity, increase in apoptosis manifested by an elevation in caspase-3 levels was determined using a Caspase-3 kit from Millipore. Data are expressed as a percent of the maximum response (100%), Compounds of the invention dose-dependently induced apoptosis in MKN-45 cells manifested by an increase in caspase-3 activity.

Results:

The results are provided below as percentage induction @3 µM in Table 7.

TABLE 7

| Cpd | Apoptosis in MNK-45 cells) |
|---|---|
| Ex 15 | A |
| Ex 52 | A |
| Ex 108 | A |
| Ex 119 | A |
| Ex 130 | B |
| Ex 134 | A |

B = ≤50,
A = > 50 to 100%

7. Inhibition of BGF-Induced Met Phosphorylation in MDA-MB-231 cells:

MDA-MB-231 is a breast cancer cell line having a high level of c-Met expression. Activation of Met kinase in these cells occurs only alter the addition of its natural ligand, Hepatocyte Growth Factor (HGF). Upon binding to the extracellular domain of the enzyme, it triggers phosphorylation of tyrosine residues and regulates several downstream events such as cell proliferation. Cell proliferation assays were carried out using the high Met expressing cell line (MDA-MB-231) according to the following schedule:

Day 1. Cells were plated in 96-well plates in complete growth medium.

Day 2: Media was replaced with starvation medium containing 0.04% BSA.

Day 3: Inhibitors at the desired concentrations and HGF (50 ng/ml) were added.

Day 5: Cell viability was determined using the 3-[4,5-dimethylthiazol-2-yl]-2,5-diphenyltetrazolium bromide (MIT) dye reduction test.

The compounds of the present invention tested potently inhibited HGF-induced Met phosphorylation in MDA-MB-231 cells thereby implicating their role in the modulation of the HGF/Met axis in breast cancer.

Results:

The results are provided below in Table 8 as IC50 values.

TABLE 8

| Cpd | HGF stimulated Met phosphorylation |
|---|---|
| Ex 15 | + |
| Ex 108 | + |
| Ex 119 | + |
| Ex 130 | + |
| Ex 134 | ++ |

+ = ≤10;
++ = > 10 to ≤50 nM

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as described above and the claims.

All publications and patent and/or patent applications cited in this application are herein incorporated by reference to the same extent as if each individual publication or patent application was specifically and individually indicated to be incorporated herein by reference.

The invention claimed is:
1. A compound of the formula

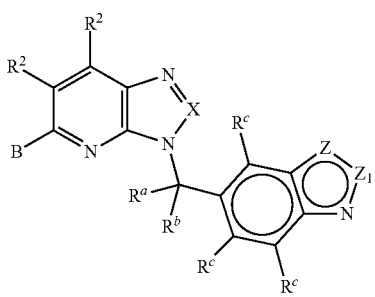

(IV)

or a tautomer, stereoisomer, enantiomer, diastereomer, or salt thereof, wherein

X is $CR^1$ or N;

B is selected from $Cy^1$, $-NR^cR^d$ or $-U=V-W-R^5$;

$Cy^1$ is selected from substituted or unsubstituted cycloalkyl, substituted or unsubstituted heterocyclic group, substituted or unsubstituted aryl, and substituted or unsubstituted heteroaryl;

wherein when X is N, $Cy^1$ is other than phenyl substituted with one to five substituents selected from halogen, substituted or unsubstituted alkyl, and $-CONR^xR^y$;

$R^1$ is selected from hydrogen, nitro, hydroxy, cyano, halogen, $-OR^a$, $-S(=O)_q-R^a$, $-NR^aR^b$, $-C(=Y)-R^a$, $-CR^aR^b-C(=Y)-R^a$, $-CR^aR^b-Y-CR^aR^b$, $-C(=Y)-NR^aR^b$, $-NR^a-C(=Y)-NR^aR^b$, $-S(=O)_q-NR^aR^b$, $-NR^a-S(=O)_q-NR^aR^b$, $-NR^a-NR^aR^b$, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-6}$ cycloalkyl, substituted or unsubstituted $C_{3-6}$ cycloalkylalkyl, substituted or unsubstituted $C_{3-6}$ cycloalkenyl;

$R^2$ is hydrogen, nitro, hydroxy, cyano, halogen, $-OR^a$, $-S(=O)_q-R^a$, $-NR^aR^b$, $-C(=O)-R^a$, or $-C(=O)-R^a$, wherein $R^a$ and $R^b$ in the $R^2$ group are independently hydrogen, hydroxy, or substituted or unsubstituted $C_{1-6}$ alkyl;

each occurrence of $R^a$ and $R^b$ may be same or different and are independently selected from hydrogen, halogen, or substituted or unsubstituted $(C_{1-6})$ alkyl, or both together with the carbon atom to which they are attached form a saturated 3 to 6 member cyclic ring which may optionally include heteroatoms which may be same or different and are selected from O, $NR^e$ or S;

$R^c$ and $R^d$ together with the nitrogen to which they are attached form a substituted or unsubstituted, saturated or unsaturated 3-10 member ring, which may optionally include one or more heteroatoms which may be same or different and are selected from O, $NR^e$ or S;

$R^e$ is selected from hydrogen, hydroxy, halogen, carboxyl, cyano, nitro, oxo (=O), thio (=S), substituted or unsubstituted alkyl, substituted or unsubstituted alkoxy, substituted or unsubstituted alkenyl, substituted or unsubstituted alkynyl, substituted or unsubstituted cycloalkyl, substituted or unsubstituted cycloalkylalkyl, substituted or unsubstituted cycloalkenyl, substituted or unsubstituted cycloalkenylalkyl, substituted or unsubstituted heterocyclic ring, substituted or unsubstituted heterocyclylalkyl ring, substituted or unsubstituted aryl, substituted or unsubstituted arylalkyl, substituted or unsubstituted heteroaryl, substituted or unsubstituted heteroarylalkyl, substituted or unsubstituted guanidine, $-COOR^x$, $-C(O)R^x$, $-C(S)R^x$, $-C(O)NR^xR^y$, $-C(O)ONR^xR^y$, $-NR^xCONR^yR^z$, $-N(R^x)SOR^y$, $-N(R^x)SO_2R^y$, $-(=N-N(R^x)R^y)$, $-NR^xC(O)OR^y$, $-NR^xR^y$, $-NR^xC(O)R^y-$, $-NR^xC(S)R^y$, $-NR^xC(S)NR^yR^z$, $-SONR^xR^y-$, $-SO_2NR^xR^y-$, $-OR^x$, $-OR^xC(O)NR^yR^z$, $-OR^xC(O)OR^y-$, $-OC(O)R^x$, $-OC(O)NR^xR^y$, $-R^xNR^yC(O)R^z$, $-R^xOR^y$, $-R^xC(O)OR^y$, $-R^xC(O)NR^yR^z$, $-R^xC(O)R^x$, $-R^xOC(O)R^y$, $-SR^x$, $-SOR^x$, $-SO_2R^x$, and $-ONO_2$;

each occurrence of $R^x$, $R^y$ and $R^z$ is independently hydrogen, substituted or unsubstituted amino, substituted or unsubstituted alkyl, substituted or unsubstituted alkoxy, substituted or unsubstituted alkenyl, substituted or unsubstituted alkynyl, substituted or unsubstituted cycloalkyl, substituted or unsubstituted cycloalkylalkyl, substituted or unsubstituted cycloalkenyl, substituted or unsubstituted cycloalkenylalkyl, substituted or unsubstituted heterocyclic ring, substituted or unsubstituted heterocyclylalkyl ring, substituted or unsubstituted aryl, substituted or unsubstituted arylalkyl, substituted or unsubstituted heteroaryl, and substituted or unsubstituted heteroarylalkyl, or any two of $R^x$, $R^y$ and $R^z$ which are directly bound to a common atom may be joined to form (i) an oxo (C=O), thio (C=S) or imino (C=NR') group (where R' is H or alkyl) or (ii) substituted or unsubstituted, saturated or unsaturated 3-10 membered ring, which may optionally include one or more heteroatoms which may be the same or different and are selected from O, NR' (where R' is H or alkyl) or S;

U and V are each independently selected from $CR^3$ or N;

W is selected from O, S, or $NR^4$;

each occurrence of $R^3$ is independently hydrogen, halogen, cyano (CN), $-OR^c$, $-S(=O)_q-R^c$, $-NR^cR^d$, substituted or unsubstituted alkyl, substituted or unsubstituted alkenyl, substituted or unsubstituted alkynyl, substituted or unsubstituted $C_{3-6}$ cycloalkyl, substituted or unsubstituted $C_{3-6}$ cycloalkylalkyl, or substituted or unsubstituted $C_{3-6}$ cycloalkenyl;

$R^4$ is selected from hydrogen, hydroxy, carboxyl, cyano, oxo (=O), thio (=S), substituted or unsubstituted alkyl, substituted or unsubstituted alkoxy, substituted or unsubstituted alkenyl, substituted or unsubstituted alkynyl, substituted or unsubstituted $C_{3-6}$ cycloalkyl, substituted or unsubstituted $C_{3-6}$ cycloalkylalkyl, and substituted or unsubstituted $C_{3-6}$ cycloalkenyl;

$R^5$ is selected from hydrogen, hydroxy, halogen, carboxyl, cyano, nitro, oxo (=O), thio (=S), substituted or unsubstituted alkyl, substituted or unsubstituted alkoxy, substituted or unsubstituted alkenyl, substituted or unsubstituted alkynyl, substituted or unsubstituted cycloalkyl, substituted or unsubstituted cycloalkylalkyl, substituted or unsubstituted cycloalkenyl, substituted or unsubstituted heterocyclic ring, substituted or unsubstituted heterocyclylalkyl, substituted or unsubstituted aryl, substituted or unsubstituted arylalkyl, substituted or unsubstituted heteroaryl, substituted or unsubstituted heteroarylalkyl, substituted or unsubstituted guanidine, $-COOR^x$, $-C(O)R^x$, $-C(S)R^x$, $-C(O)NR^xR^y$, $-C(O)ONR^xR^y$, $-NR^xR^z$, $-NR^xCONR^yR^z$, $-N(R^x)SOR^y$, $-N(R^x)SO_2R^y$, $-(=N-N(R^x)R^y)$, $-NR^xC(O)OR^y$, $-NR^xC(O)R^y-$, $-NR^xC(S)R^y-NR^xC(S)NR^yR^z$, $-SONR^xR^y-$, $-SO_2NR^xR^y-$, $-OR^x$, $-OR^xC(O)NR^yR^z$, $-OR^xC(O)OR^y-$, $-OC(O)R^x$, $-OC(O)NR^xR^y$, $-R^xNR^yC(O)R^z$, $-R^xOR^y$, $-R^xC$ (O)OR$^y$, —R$^x$C(O)NR$^y$R$^z$, —R$^x$C(O)R$^x$, —R$^x$OC(O)R$^y$, —SR$^x$, —SOR$^x$, —SO$_2$R$^x$, and —ONO$_2$; or when W is NR$^4$, R$^4$ and R$^5$ together with the nitrogen to which they are attached form a substituted or unsubstituted, saturated or unsaturated 3-10 member ring, which may optionally include one or more heteroatoms which may be same or different and are selected from O, NR$^e$ or S;

Z is selected from CR$^c$, S, O, NR$^c$, R$^c$C=CR$^c$, —N=CR$^c$—, —R$^c$C=N—;

Z$_1$ is selected from N, NR$^c$ or CR$^c$;

each occurrence of Y is independently selected from O, S, and NR$^a$;

each occurrence of n independently represents 0, 1, 2, 3 or 4;

each occurrence of q independently represents 0, 1 or 2 and

R$^c$ is absent or selected from hydrogen, hydroxy or halogen.

2. The compound of claim 1, wherein X is N.

3. The compound of claim 1, wherein each occurrence of R$^2$ is H.

4. The compound of claim 1, wherein each of R$^a$ and R$^b$ are same or different and selected from hydrogen, methyl or fluoro.

5. The compound of claim 4, wherein each of R$^a$ and R$^b$ is selected from hydrogen or methyl.

6. The compound of claim 1, wherein Z is CR$^c$, N, S, O, HC=CH—, —N=CH—.

7. The compound of claim 1, wherein Z$_1$ is CH or N.

8. The compound of claim 6, wherein Z is —HC=CH—, —S— or —O— and Z$_1$ is CH.

9. The compound of claim 8, wherein Z is —HC=CH— and Z$_1$ is CH.

10. The compound of claim 6, wherein Z is —S— and Z$_1$ is CH.

11. The compound of claim 1, wherein each occurrence of R$^c$ is hydrogen or fluoro.

12. The compound of claim 1, wherein B is Cy$^1$.

13. The compound of claim 12, wherein Cy$^1$ is selected from

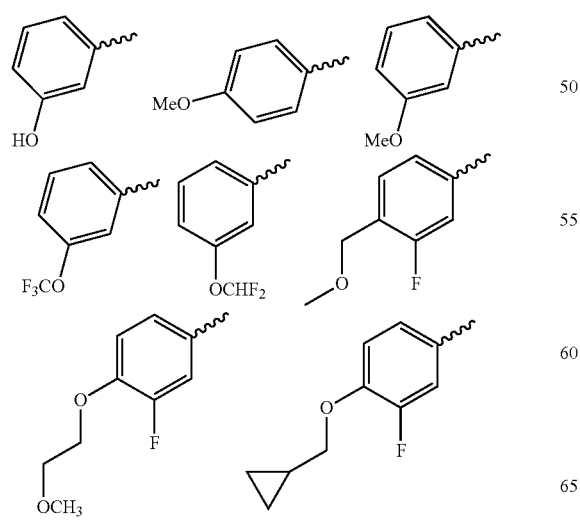

-continued

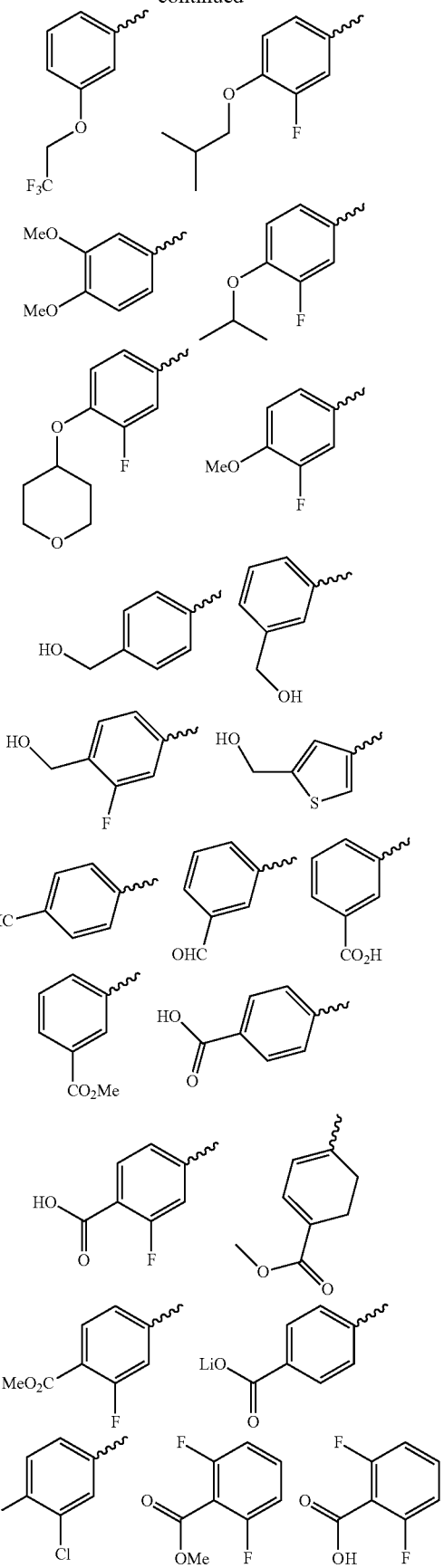

283
-continued
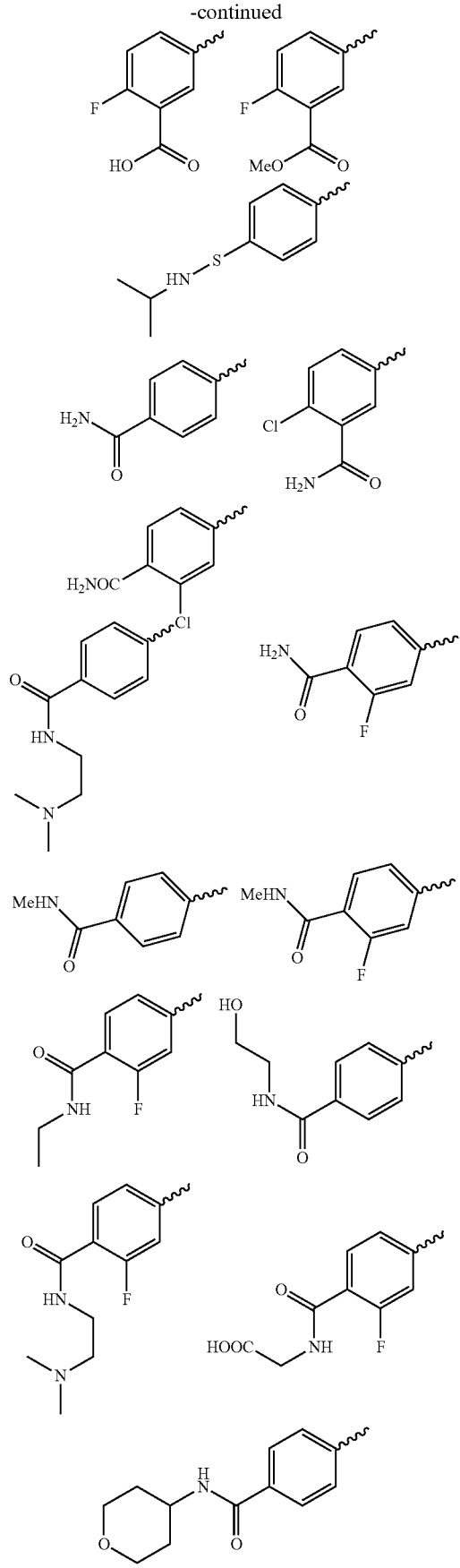
284
-continued
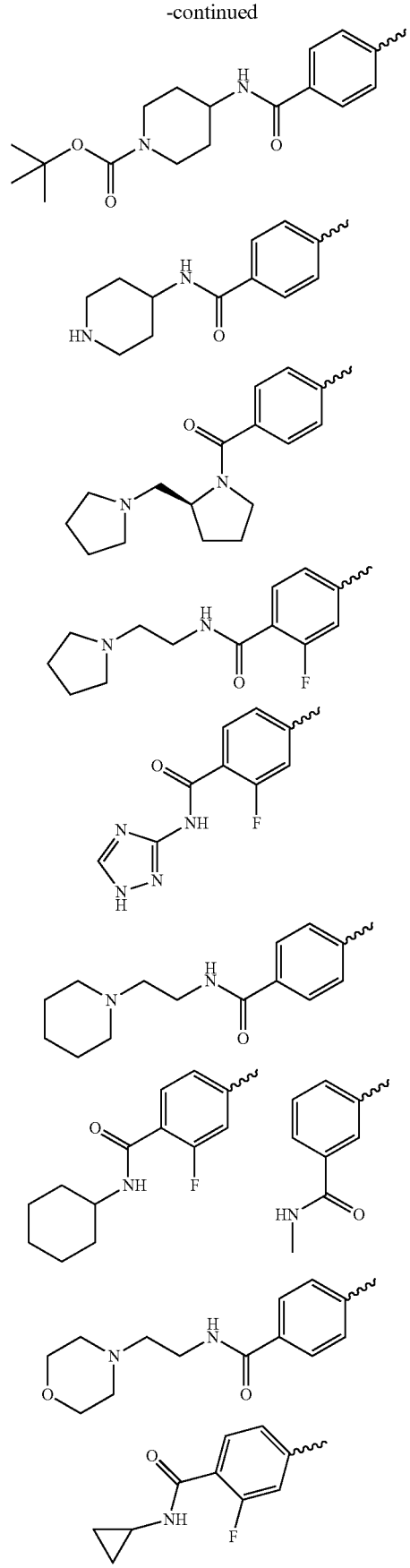

285
-continued
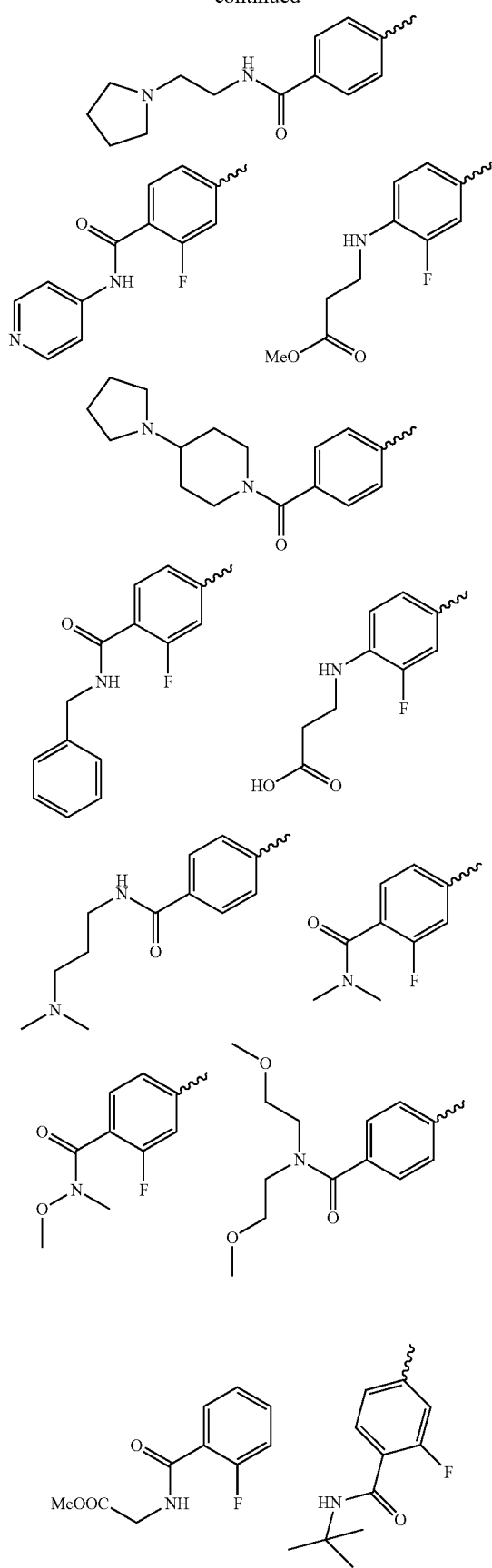
286
-continued
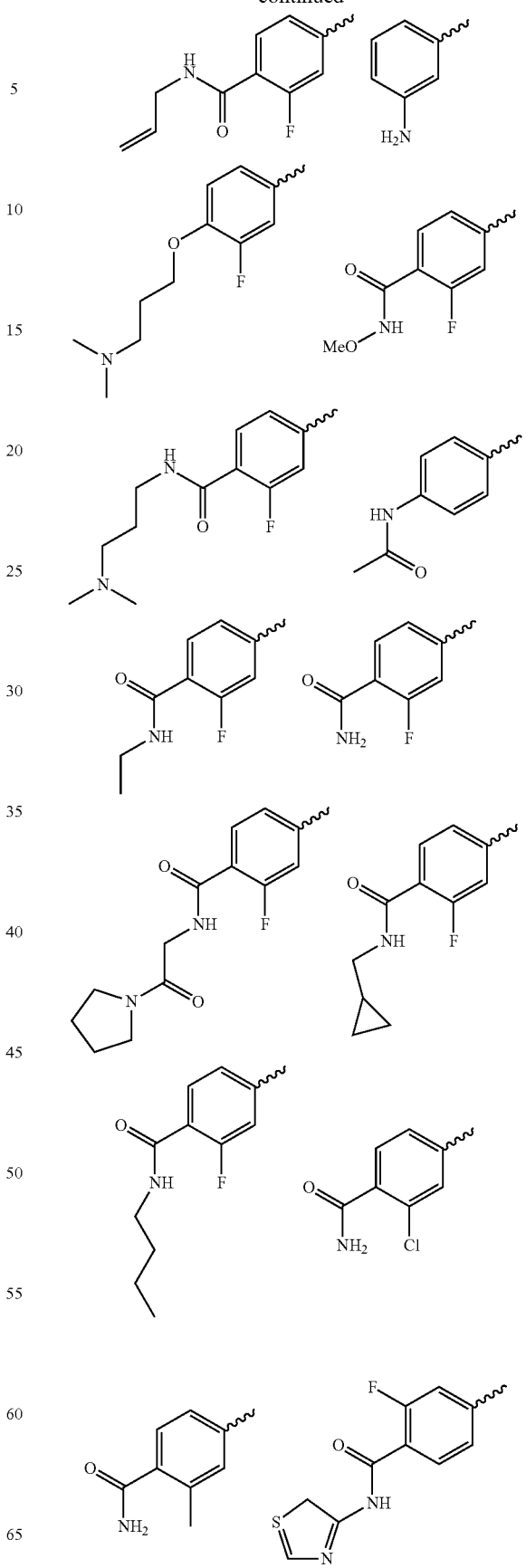

287
-continued
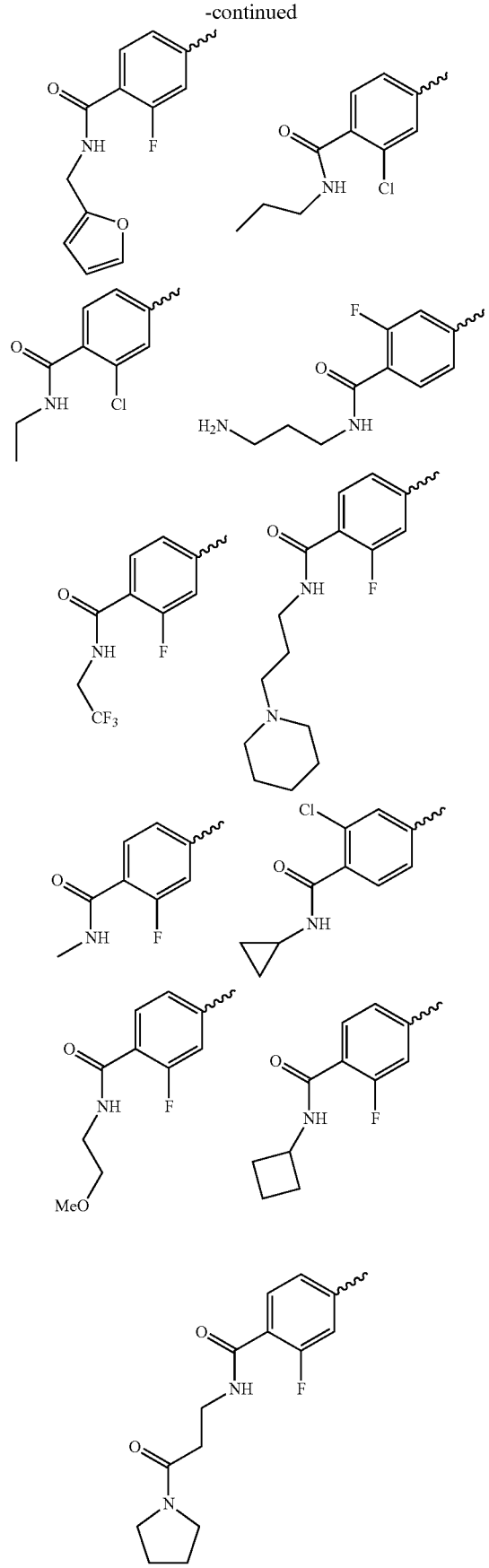
288
-continued
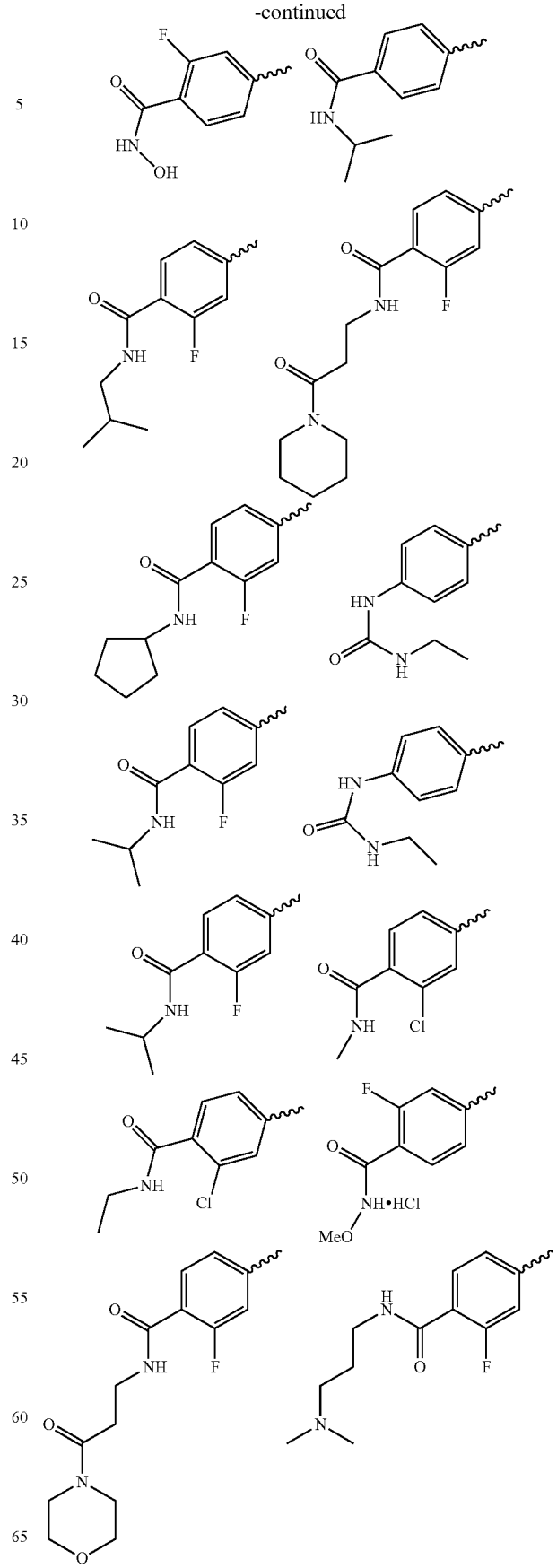

289
-continued
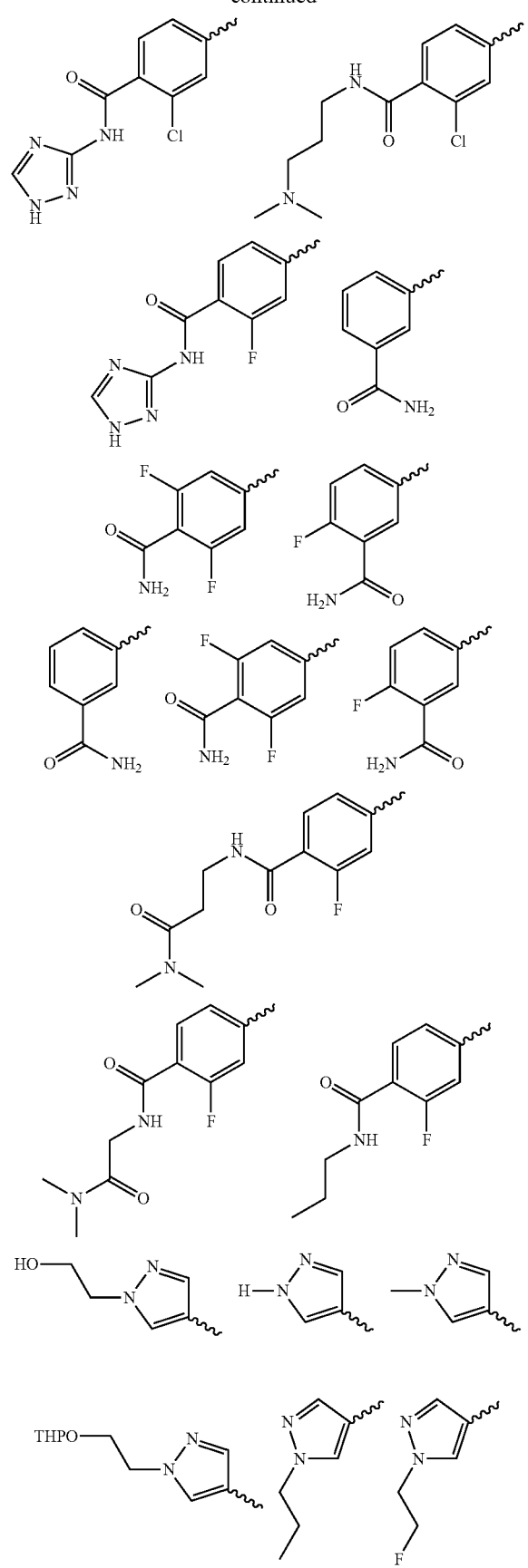
290
-continued
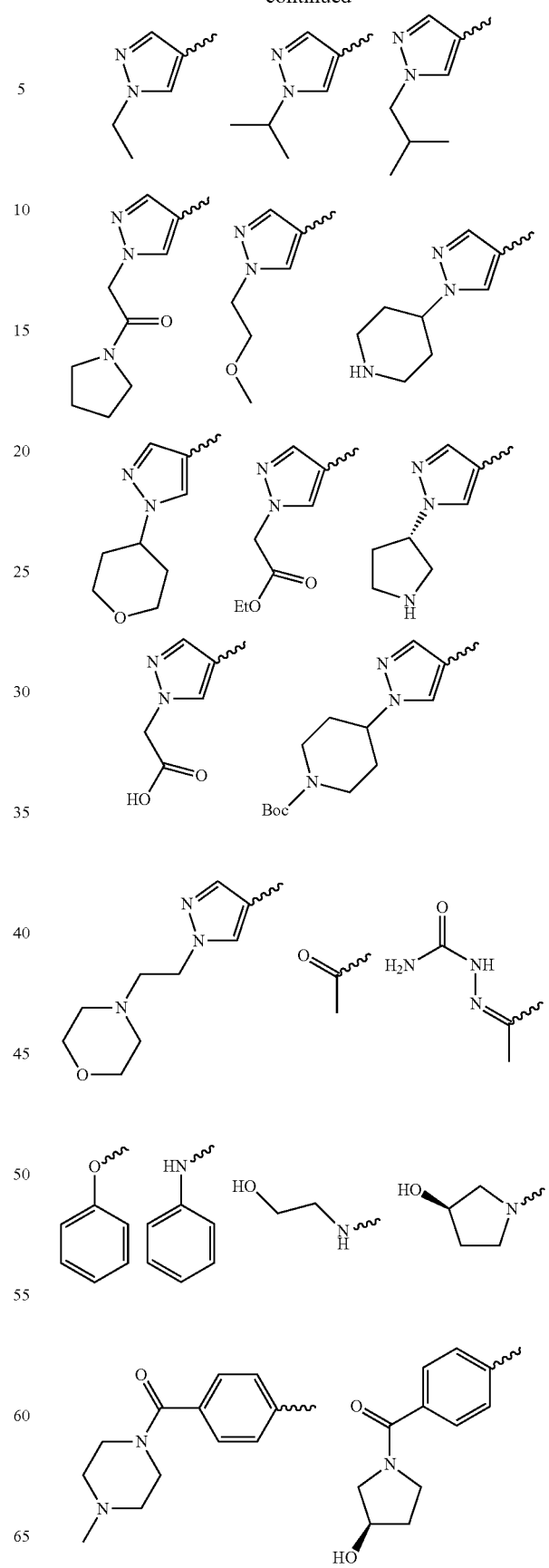

291
-continued
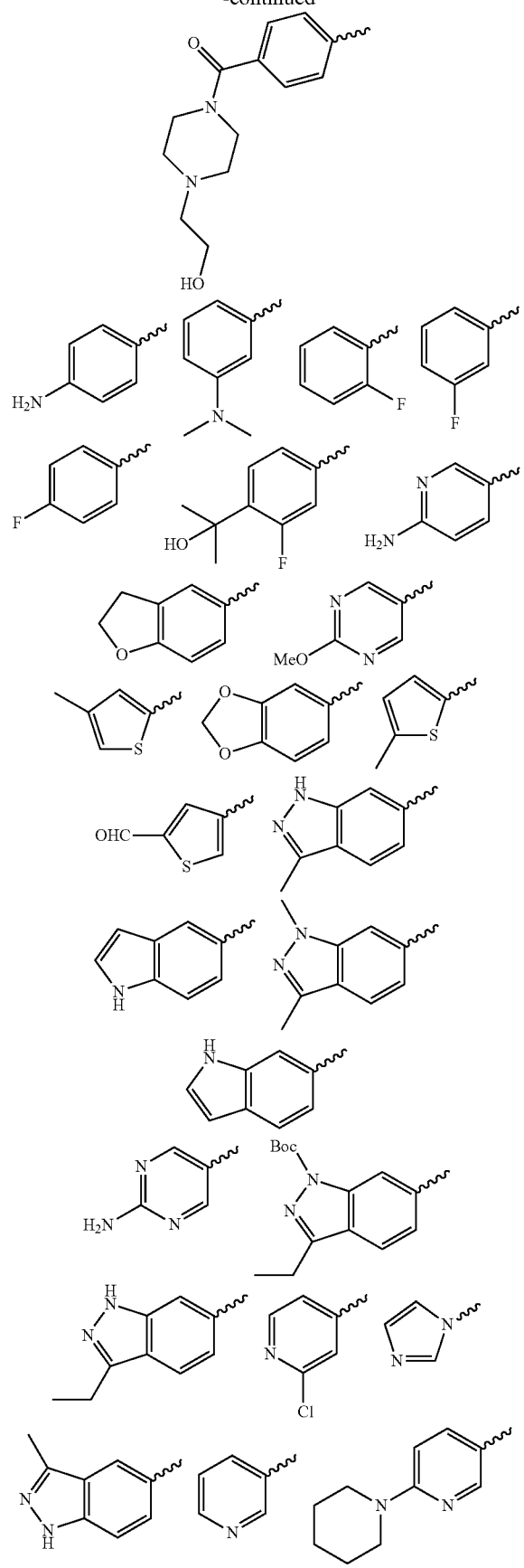
292
-continued
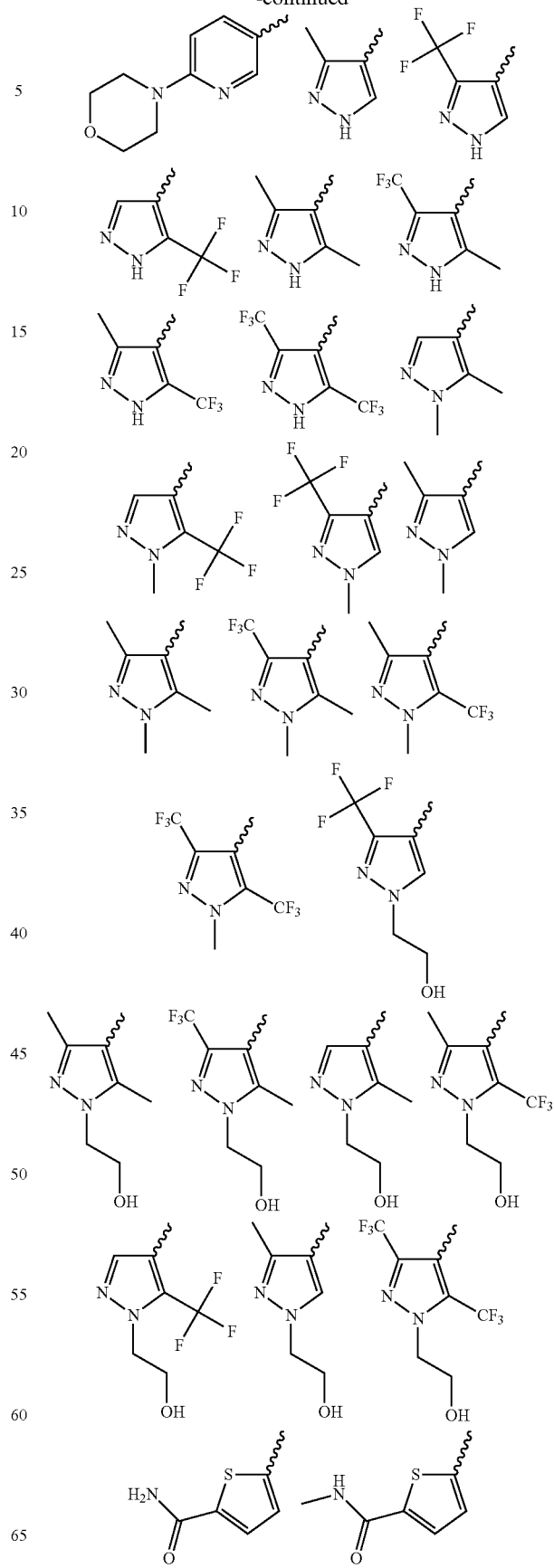

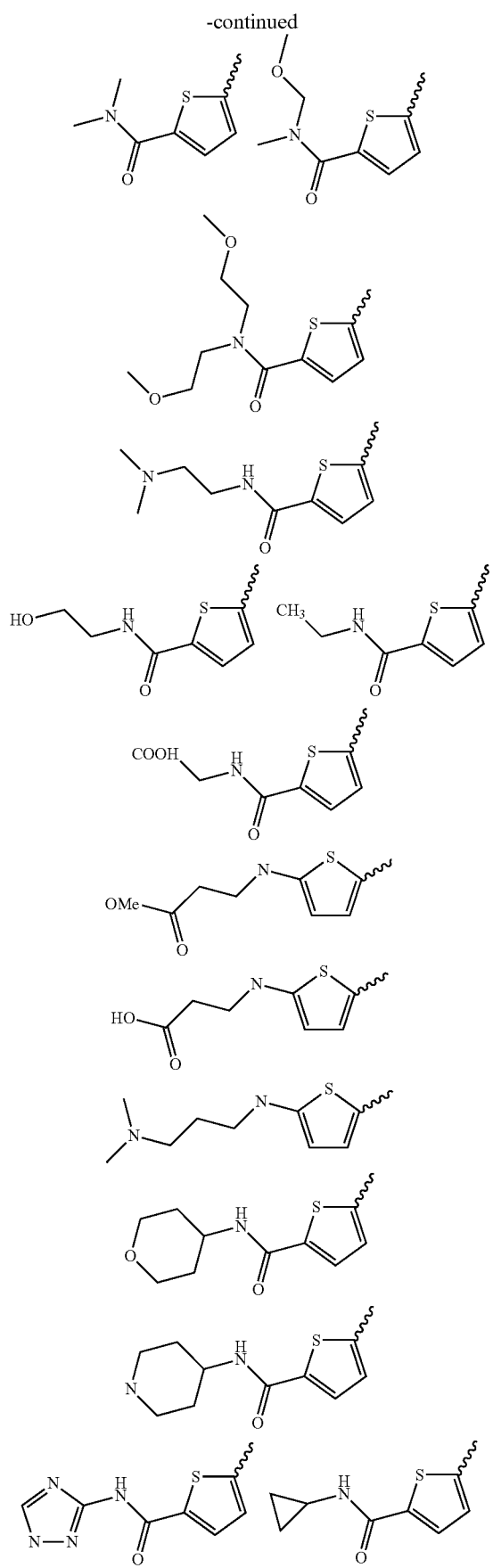
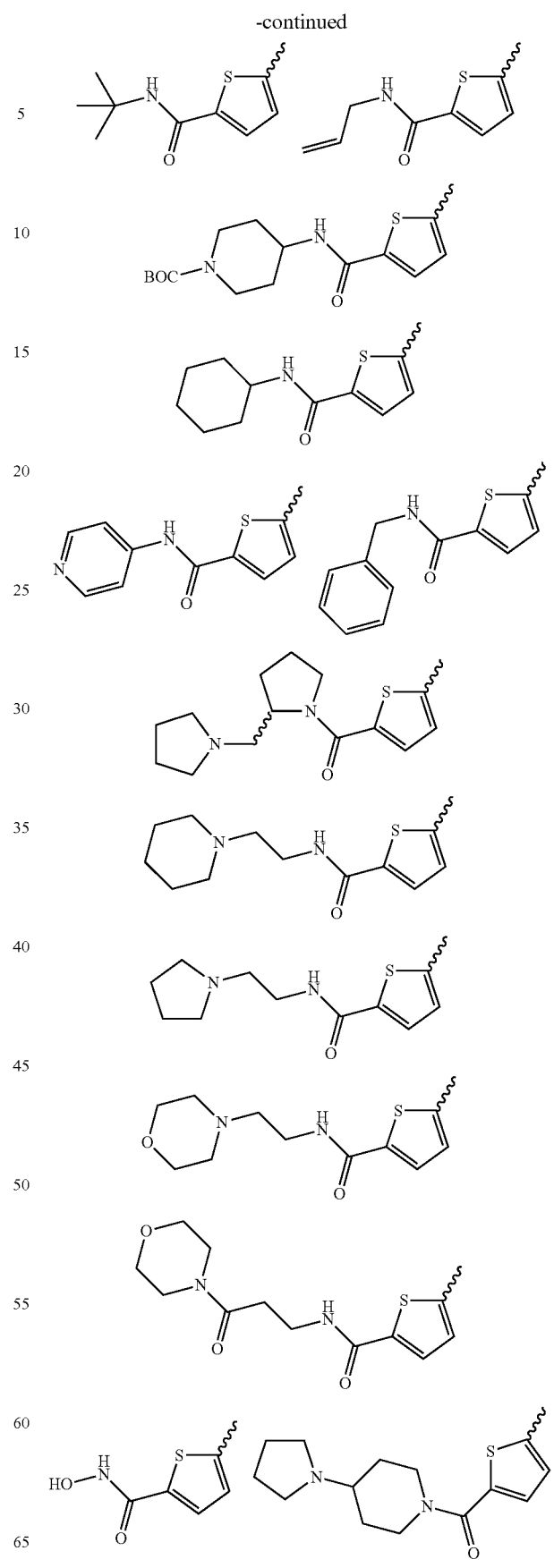

295
-continued
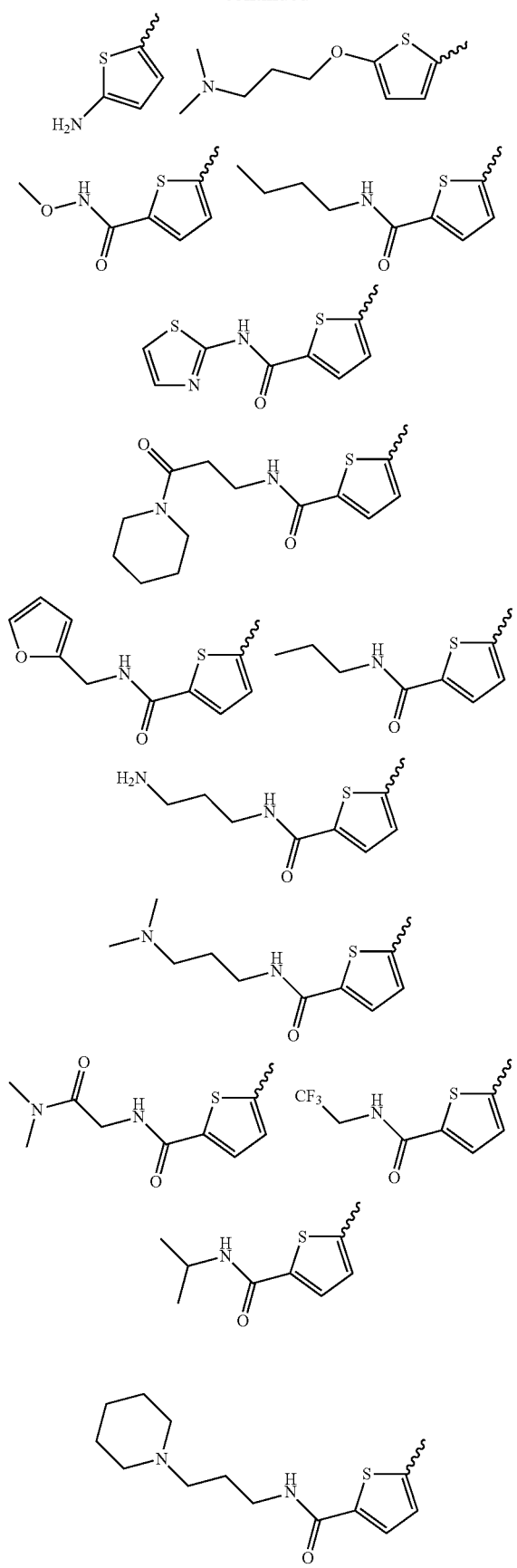
296
-continued
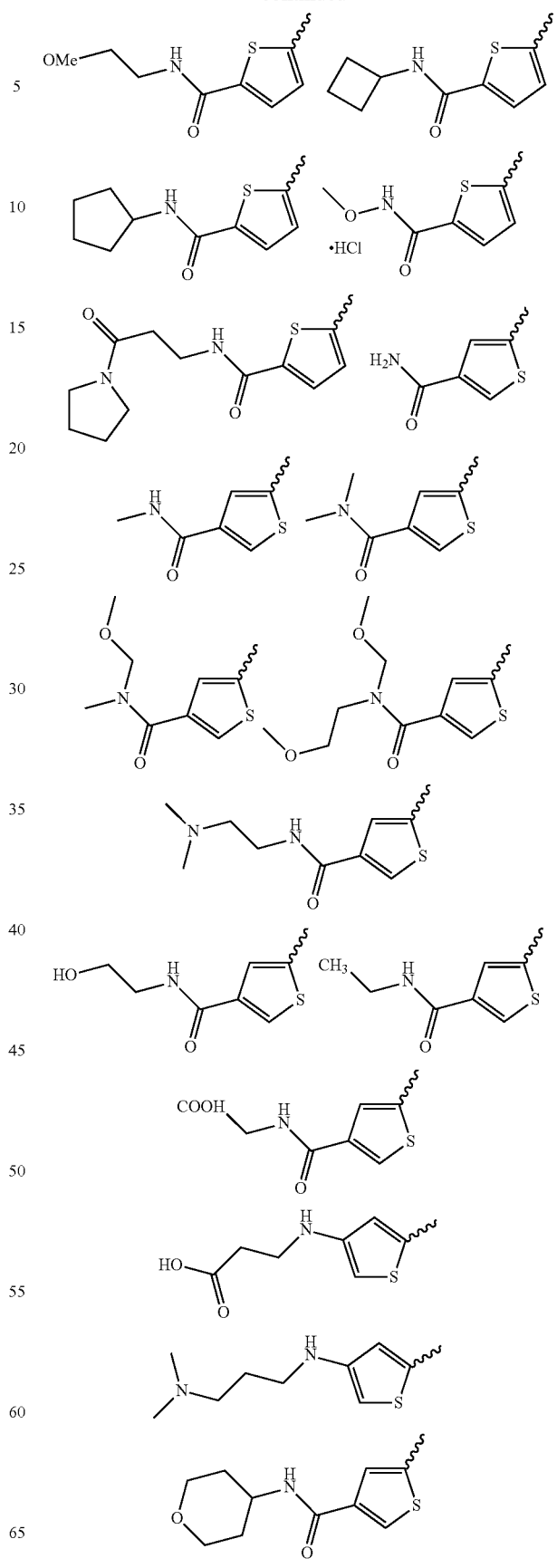

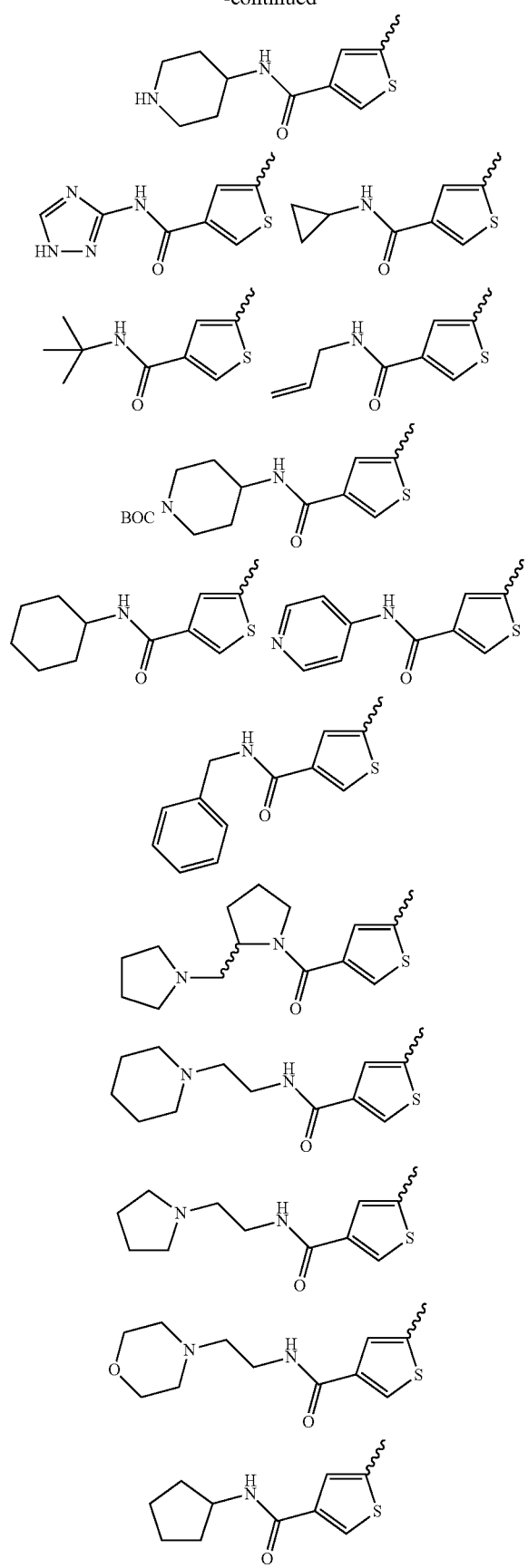
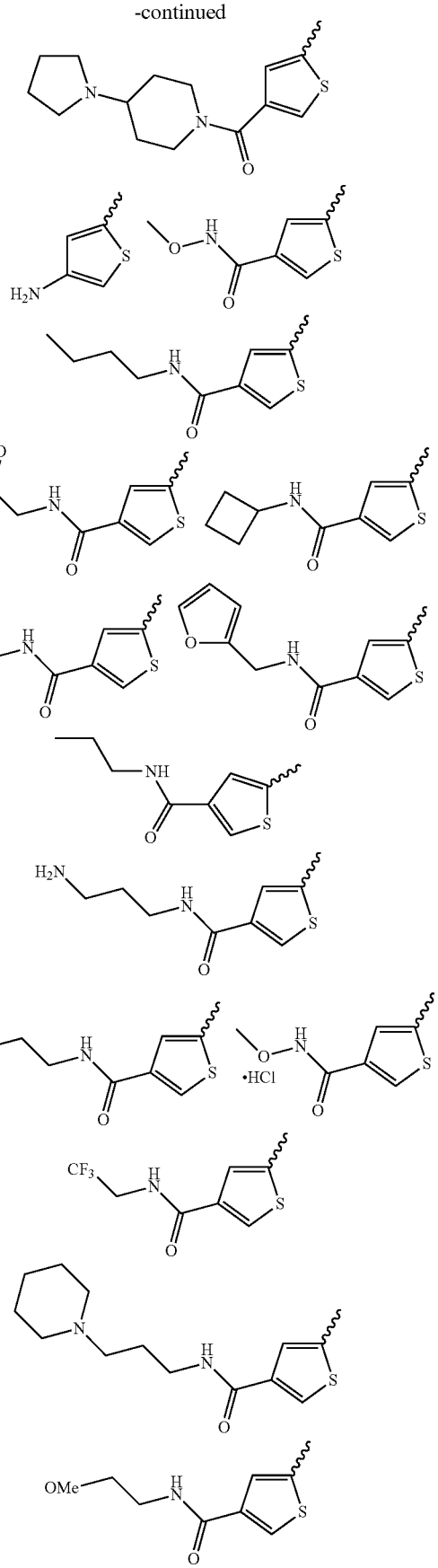

299
-continued
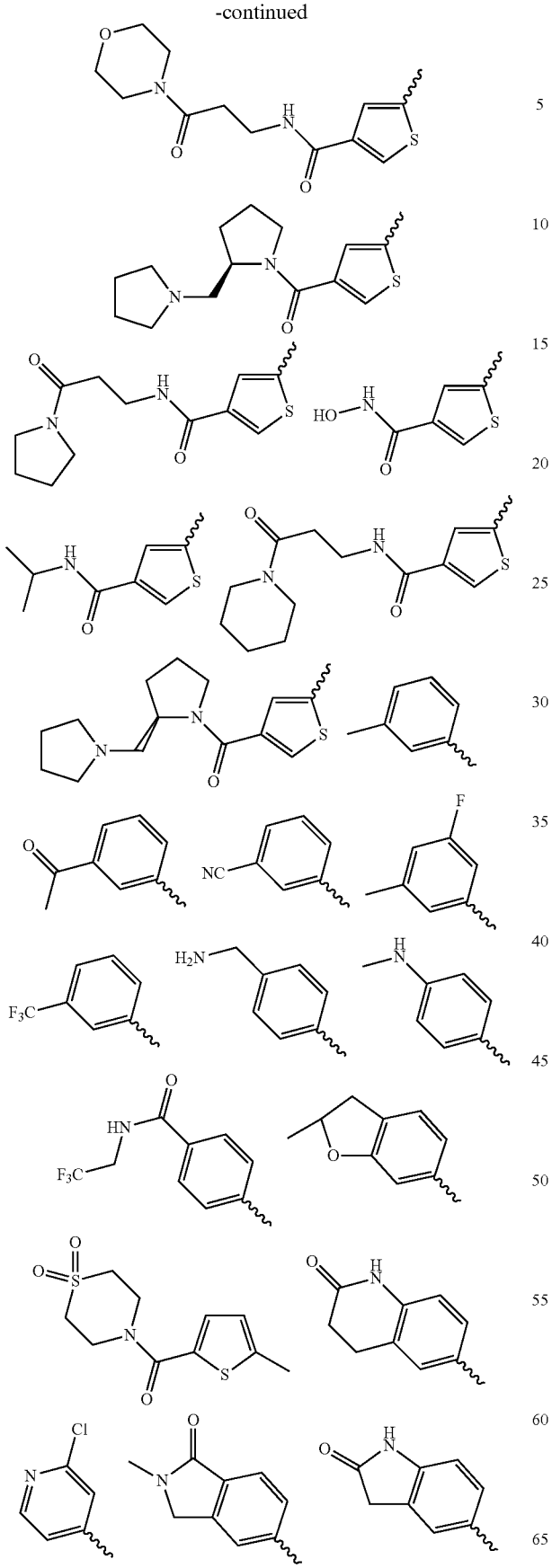
300
-continued
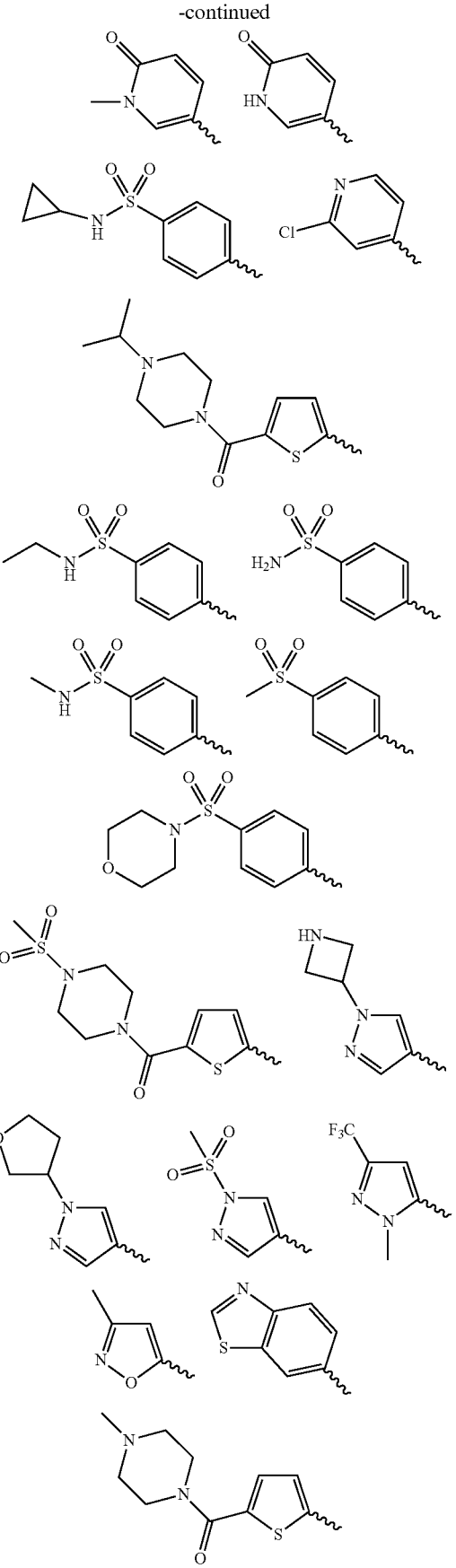

301
-continued
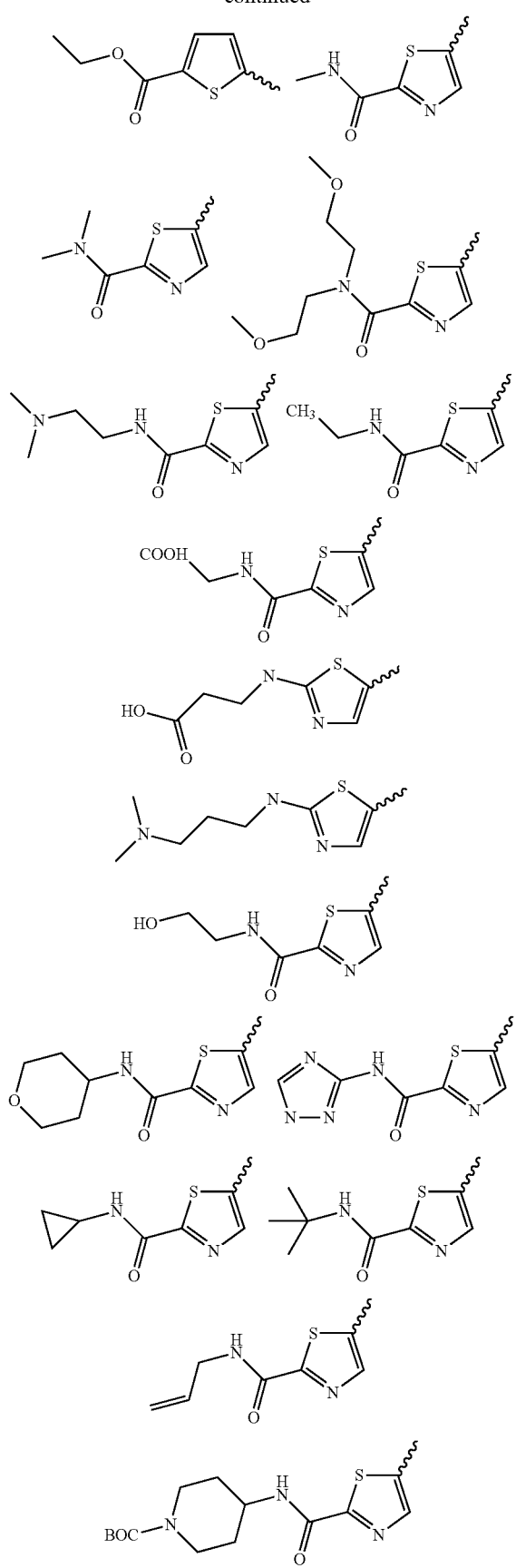
302
-continued
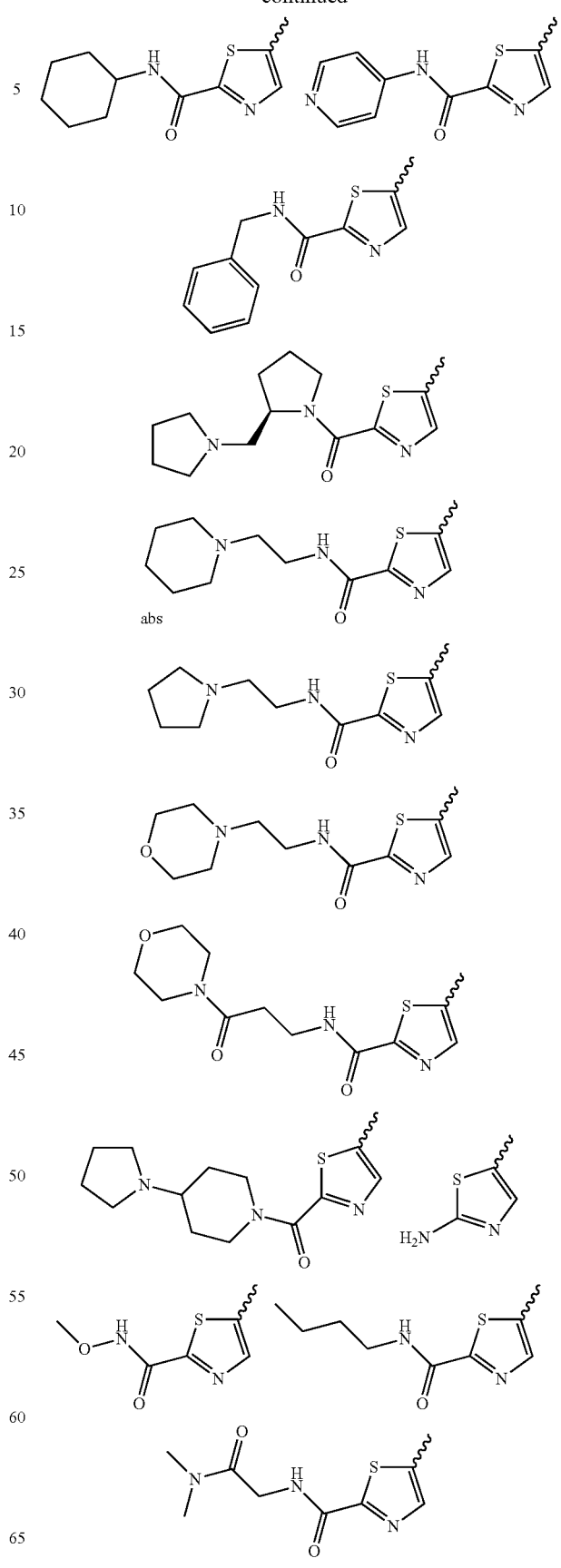

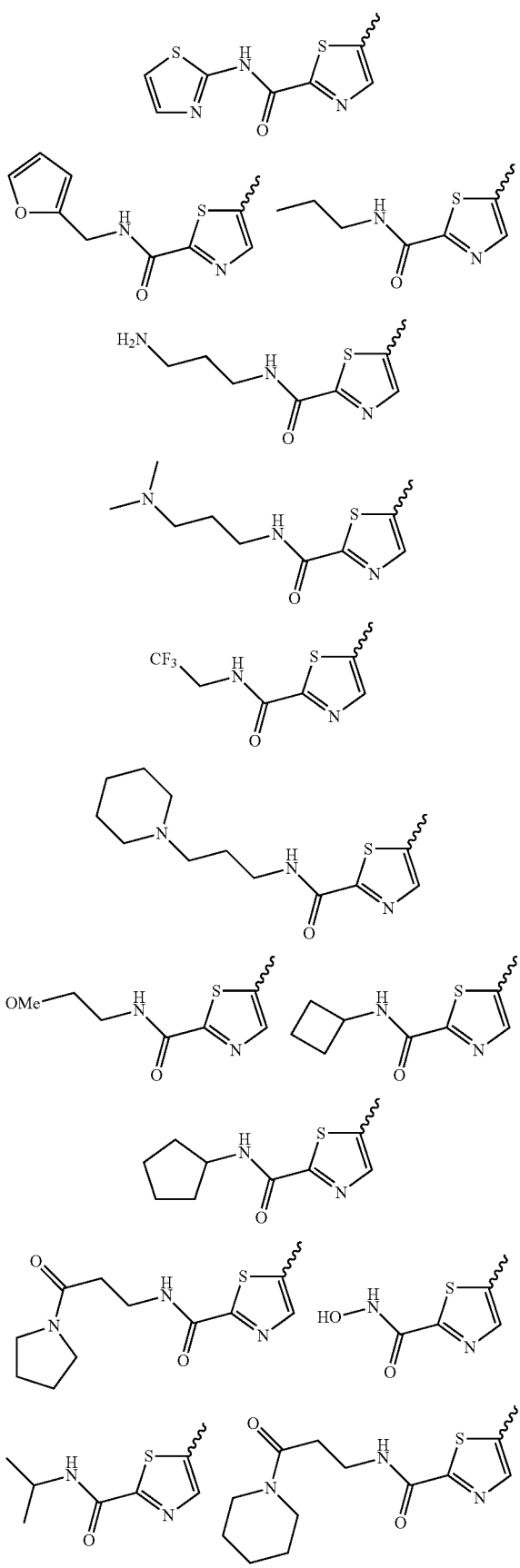

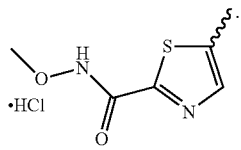

14. The compound of claim 1, wherein Cy¹ is substituted or unsubstituted monocyclic aryl or substituted or unsubstituted monocyclic heteroaryl.

15. The compound of claim 14, wherein Cy¹ is substituted monocyclic aryl.

16. The compound of claim 1, wherein B is NR$^c$R$^d$.

17. The compound of any one of claim 16, wherein NR$^c$R$^d$ is selected from

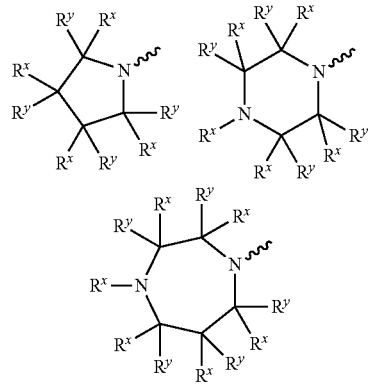

wherein each occurrence of R$^x$ and R$^y$ is independently selected from hydrogen, substituted or unsubstituted alkyl, substituted or unsubstituted alkoxy, or any two of R$^x$ and R$^y$ which are directly bound to a common atom may be joined to form an oxo (C=O), thio (C=S) or imino (C=NR') group (where R' is H or alkyl), or any two of R$^x$ and R$^y$ may be joined to form a substituted or unsubstituted, saturated or unsaturated 3-6 membered ring, which may optionally include heteroatoms which may be the same or different and are selected from O, NR' (where R' is H or alkyl) or S.

18. The compound of claim 1, wherein B is —U=V—W—R⁵.

19. A compound selected from
6-((5-(4-Methoxyphenyl)-3H-[1,2,3]triazolo[4,5-b]pyridin-3-yl)methyl)quinoline
6-((5-(3-Methoxyphenyl)-3H-[1,2,3]triazolo[4,5-b]pyridin-3-yl)methyl)quinoline
3-(3-(quinolin-6-ylmethyl)-3H-[1,2,3]triazolo[4,5-b]pyridin-5-yl)benzaldehyde
4-(3-(quinolin-6-ylmethyl)-3H-[1,2,3]triazolo[4,5-b]pyridin-5-yl)benzaldehyde
Methyl 4-(3-(quinolin-6-ylmethyl)-3H-[1,2,3]triazolo[4,5-b]pyridin-5-yl)benzoate
4-(3-(quinolin-6-ylmethyl)-3H-[1,2,3]triazolo[4,5-b]pyridin-5-yl)benzoic acid
Methyl 2-fluoro-4-(3-(quinolin-6-ylmethyl)-3H-[1,2,3]triazolo[4,5-b]pyridin-5-yl)benzoate
2-Fluoro-4-(3-(quinolin-6-ylmethyl)-3H-[1,2,3]triazolo[4,5-b]pyridin-5-yl)benzoic acid
Lithium 4-(3-(quinolin-6-ylmethyl)-3H-[1,2,3]triazolo[4,5-b]pyridin-5-yl)benzoate
6-((5-(3-(trifluoromethoxy)phenyl)-3H-[1,2,3]triazolo[4,5-b]pyridin-3-yl)methyl)quinoline 3-(3-(quinolin-6-ylmethyl)-3H-[1,2,3]triazolo[4,5-b]pyridin-5-yl)phenol
6-((5-(3-(difluoromethoxy)phenyl)-3H-[1,2,3]triazolo[4,5-b]pyridin-3-yl)methyl)quinoline
Methyl 3-(3-(quinolin-6-ylmethyl)-3H-[1,2,3]triazolo[4,5-b]pyridin-5-yl)benzoate
3-(3-(quinolin-6-ylmethyl)-3H-[1,2,3]triazolo[4,5-b]pyridin-5-yl)benzoic acid
Methyl 3-(2-fluoro-4-(3-(quinolin-6-ylmethyl)-3H-[1,2,3]triazolo[4,5-b]pyridin-5-yl)phenyl amino) propanoate
3-(2-Fluoro-4-(3-(quinolin-6-ylmethyl)-3H-[1,2,3]triazolo[4,5-b]pyridin-5-yl)phenylamino)propanoic acid
4-(3-(quinolin-6-ylmethyl)-3H-[1,2,3]triazolo[4,5-b]pyridin-5-yl)aniline
6-((5-(3,4-Dimethoxyphenyl)-3H-[1,2,3]triazolo[4,5-b]pyridin-3-yl)methyl)quinoline
6-((5-(3-Fluoro-4-methoxyphenyl)-3H-[1,2,3]triazolo[4,5-b]pyridin-3-yl)methyl)quinoline
6-((5-(3-(2,2,2-Trifluoroethoxy)phenyl)-3H-[1,2,3]triazolo[4,5-b]pyridin-3-yl)methyl) quinoline
3-(3-(quinolin-6-ylmethyl)-3H-[1,2,3]triazolo[4,5-b]pyridin-5-yl)aniline
6-((5-(3-Fluoro-4-isopropoxyphenyl)-3H-[1,2,3]triazolo[4,5-b]pyridin-3-yl)methyl)quinoline
6-((5-(4-(Cyclopropylmethoxy)-3-fluorophenyl)-3H-[1,2,3]triazolo[4,5-b]pyridin-3-yl)methyl) quinoline
6-((5-(3-Fluoro-4-isobutoxyphenyl)-3H-[1,2,3]triazolo[4,5-b]pyridin-3-yl)methyl)quinoline
3-(2-Fluoro-4-(3-(quinolin-6-ylmethyl)-3H-[1,2,3]triazolo[4,5-b]pyridin-5-yl)phenoxy)-N,N-dimethylpropan-1-amine
Methyl 2-fluoro-4-(3-(2-(quinolin-6-yl)propan-2-yl)-3H-[1,2,3]triazolo[4,5-b]pyridin-5-yl)benzoate
2-Fluoro-4-(3-(2-(quinolin-6-yl)propan-2-yl)-3H-[1,2,3]triazolo[4,5-b]pyridin-5-yl)benzoic acid
6-((5-(3-Fluoro-4-(tetrahydro-2H-pyran-4-yloxy)phenyl)-3H-[1,2,3]triazolo[4,5-b]pyridin-3-yl)methyl) quinoline
6-((5-(3-Fluoro-4-(2-methoxyethoxy)phenyl)-3H-[1,2,3]triazolo[4,5-b]pyridin-3-yl)methyl)quinoline
N-Isopropyl-4-(3-(quinolin-6-ylmethyl)-3H-[1,2,3]triazolo[4,5-b]pyridin-5-yl)benzenesulfonamide
N,N-Dimethyl-3-(3-(quinolin-6-ylmethyl)-3H-[1,2,3]triazolo[4,5-b]pyridin-5-yl) aniline
Methyl 2-chloro-4-(3-(quinolin-6-ylmethyl)-3H-[1,2,3]triazolo[4,5-b]pyridin-5-yl)benzoate
2-Chloro-4-(3-(quinolin-6-ylmethyl)-3H-[1,2,3]triazolo[4,5-b]pyridin-5-yl)benzoic acid
1-Ethyl-3-(4-(3-(quinolin-6-ylmethyl)-3H-[1,2,3]triazolo[4,5-b]pyridin-5-yl)phenyl)urea
Methyl 2,6-difluoro-4-(3-(quinolin-6-ylmethyl)-3H-[1,2,3]triazolo[4,5-b]pyridin-5-yl)benzoate
2,6-Difluoro-4-(3-(quinolin-6-ylmethyl)-3H-[1,2,3]triazolo[4,5-b]pyridin-5-yl)benzoic acid
Methyl 2-chloro-4-(3-((7-fluoroquinolin-6-yl)methyl)-3H-[1,2,3]triazolo[4,5-b]pyridin-5-yl)benzoate
2-Chloro-4-(3-((7-fluoroquinolin-6-yl)methyl)-3H-[1,2,3]triazolo[4,5-b]pyridin-5-yl)benzoic acid
Methyl 2-fluoro-4-(3-((7-fluoroquinolin-6-yl)methyl)-3H-[1,2,3]triazolo[4,5-b]pyridin-5-yl)benzoate
2-Fluoro-4-(3-((7-fluoroquinolin-6-yl)methyl)-3H-[1,2,3]triazolo[4,5-b]pyridin-5-yl)benzoic acid
Methyl 2-fluoro-5-(3-(quinolin-6-ylmethyl)-3H-[1,2,3]triazolo[4,5-b]pyridin-5-yl)benzoate
2-Fluoro-5-(3-(quinolin-6-ylmethyl)-3H-[1,2,3]triazolo[4,5-b]pyridin-5-yl)benzoic acid
and pharmaceutically acceptable salts thereof.

20. A compound selected from
6-((5-(1H-Pyrazol-4-yl)-3H-[1,2,3]triazolo[4,5-b]pyridin-3-yl)methyl)quinoline
6-((5-(1-Methyl-1H-pyrazol-4-yl)-3H-[1,2,3]triazolo[4,5-b]pyridin-3-yl)methyl)quinoline
6-((5-(1-(2-(Tetrahydro-2H-pyran-2-yloxy)ethyl)-1H-pyrazol-4-yl)-3H-[1,2,3]triazolo[4,5-b]pyridin-3-yl)methyl)quinoline
2-(4-(3-(Quinolin-6-ylmethyl)-3H-[1,2,3]triazolo[4,5-b]pyridin-5-yl)-1H-pyrazol-1-yl)ethanol
6-((5-(1H-Pyrazol-4-yl)-3H-imidazo[4,5-b]pyridin-3-yl)methyl)quinoline
6-((5-(1-Methyl-1H-pyrazol-4-yl)-3H-imidazo[4,5-b]pyridin-3-yl)methyl)quinoline
6-((5-(1-(2-(Tetrahydro-2H-pyran-2-yloxy)ethyl)-1H-pyrazol-4-yl)-3H-imidazo[4,5-b]pyridin-3-yl)methyl)quinoline
2-(4-(3-(Quinolin-6-ylmethyl)-3H-imidazo[4,5-b]pyridin-5-yl)-1H-pyrazol-1-yl)ethanol
6-((5-(1H-Imidazol-1-yl)-3H-[1,2,3]triazolo[4,5-b]pyridin-3-yl)methyl)quinoline
6-((5-(1-Propyl-1H-pyrazol-4-yl)-3H-[1,2,3]triazolo[4,5-b]pyridin-3-yl)methyl)quinoline
Ethyl 2-(4-(3-(quinolin-6-ylmethyl)-3H-[1,2,3]triazolo[4,5-b]pyridin-5-yl)-1H-pyrazol-1-yl)acetate
2-(4-(3-(Quinolin-6-ylmethyl)-3H-[1,2,3]triazolo[4,5-b]pyridin-5-yl)-1H-pyrazol-1-yl)acetic acid
tert-Butyl 4-(4-(3-(quinolin-6-ylmethyl)-3H-[1,2,3]triazolo[4,5-b]pyridin-5-yl)-1H-pyrazol-1-yl)piperidine-1-carboxylate
6-((5-(1-(Piperidin-4-yl)-1H-pyrazol-4-yl)-3H-[1,2,3]triazolo[4,5-b]pyridin-3-yl)methyl) quinoline
6-(1-(5-(1H-Pyrazol-4-yl)-3H-[1,2,3]triazolo[4,5-b]pyridin-3-yl)ethyl)quinoline
6-(1-(5-(1-(2-(Tetrahydro-2H-pyran-2-yloxy)ethyl)-1H-pyrazol-4-yl)-3H-[1,2,3]triazolo[4,5-b]pyridin-3-yl)ethyl)quinoline
2-(4-(3-(1-(Quinolin-6-yl)ethyl)-3H-[1,2,3]triazolo[4,5-b]pyridin-5-yl)-1H-pyrazol-1-yl)ethanol
6-((5-(3-Methyl-1H-indazol-6-yl)-3H-[1,2,3]triazolo[4,5-b]pyridin-3-yl)methyl)quinoline
6-((5-(1H-Indol-5-yl)-3H-[1,2,3]triazolo[4,5-b]pyridin-3-yl)methyl)quinoline
6-((5-(1H-Indol-6-yl)-3H-[1,2,3]triazolo[4,5-b]pyridin-3-yl)methyl)quinoline
6-((5-(2-Chloropyridin-4-yl)-3H-[1,2,3]triazolo[4,5-b]pyridin-3-yl)methyl)quinoline
6-((5-(3-Methyl-1H-indazol-5-yl)-3H-[1,2,3]triazolo[4,5-b]pyridin-3-yl)methyl)quinoline
6-((5-(Pyridin-3-yl)-3H-[1,2,3]triazolo[4,5-b]pyridin-3-yl)methyl)quinoline
(S)-6-((5-(1-(Pyrrolidin-3-yl)-1H-pyrazol-4-yl)-3H-[1,2,3]triazolo[4,5-b]pyridin-3-yl)methyl)quinoline
(S)-6-((5-(1-(Pyrrolidin-3-yl)-1H-pyrazol-4-yl)-3H-[1,2,3]triazolo[4,5-b]pyridin-3-yl)methyl)quinoline hydrochloride
4-(2-(4-(3-(Quinolin-6-ylmethyl)-3H-[1,2,3]triazolo[4,5-b]pyridin-5-yl)-1H-pyrazol-1-yl)ethyl)morpholine hydrochloride
6-((5-(1-(Tetrahydro-2H-pyran-4-yl)-1H-pyrazol-4-yl)-3H-[1,2,3]triazolo[4,5-b]pyridin-3-yl)methyl)quinoline
6-((5-(1-(2-Hydroxyethyl)-1H-pyrazol-4-yl)-3H-[1,2,3]triazolo[4,5-b]pyridin-3-yl)methyl)quinoline 1-oxide 6-((5-(1,3-Dimethyl-1H-indazol-6-yl)-3H-[1,2,3]triazolo[4,5-b]pyridin-3-yl)methyl) quinoline 5-(3-(Quinolin-6-ylmethyl)-3H-[1,2,3]triazolo[4,5-b]pyridin-5-yl)pyrimidin-2-amine tert-Butyl 3-ethyl-6-(3-(quinolin-6-ylmethyl)-3H-[1,2,3]triazolo[4,5-b]pyridin-5-yl)-1H-indazole-1-carboxylate 4-(3-(Quinolin-6-ylmethyl)-3H-[1,2,3]triazolo[4,5-b]pyridin-5-yl)thiophene-2-carbaldehyde 6-((5-(2-Methoxypyrimidin-5-yl)-3H-[1,2,3]triazolo[4,5-b]pyridin-3-yl)methyl)quinoline 6-((5-(Benzo[d][1,3]dioxol-5-yl)-3H-[1,2,3]triazolo[4,5-b]pyridin-3-yl)methyl)quinoline 6-((5-(2,3-Dihydrobenzofuran-5-yl)-3H-[1,2,3]triazolo[4,5-b]pyridin-3-yl)methyl)quinoline 5-(3-(Quinolin-6-ylmethyl)-3H-[1,2,3]triazolo[4,5-b]pyridin-5-yl)pyridin-2-amine 6-((5-(1-(2-fluoroethyl)-1H-pyrazol-4-yl)-3H-[1,2,3]triazolo[4,5-b]pyridin-3-yl)methyl) quinoline (4-(3-(Quinolin-6-ylmethyl)-3H-[1,2,3]triazolo[4,5-b]pyridin-5-yl)thiophen-2-yl)methanol 6-(2-(5-(1-(2-(Tetrahydro-2H-pyran-2-yloxy)ethyl)-1H-pyrazol-4-yl)-3H-[1,2,3]triazolo[4,5-b]pyridin-3-yl)propan-2-yl)quinoline 2-(4-(3-(2-(Quinolin-6-yl)propan-2-yl)-3H-[1,2,3]triazolo[4,5-b]pyridin-5-yl)-1H-pyrazol-1-yl)ethanol 6-((5-(3-ethyl-1H-indazol-6-yl)-3H-[1,2,3]triazolo[4,5-b]pyridin-3-yl)methyl)quinoline 6-(2-(5-(1H-Pyrazol-4-yl)-3H-[1,2,3]triazolo[4,5-b]pyridin-3-yl)propan-2-yl)quinoline 6-((5-(4-Methylthiophen-2-yl)-3H-[1,2,3]triazolo[4,5-b]pyridin-3-yl)methyl)quinoline 6-((5-(5-Methylthiophen-2-yl)-3H-[1,2,3]triazolo[4,5-b]pyridin-3-yl)methyl)quinoline 4-(5-(3-(Quinolin-6-ylmethyl)-3H-[1,2,3]triazolo[4,5-b]pyridin-5-yl)pyridin-2-yl) morpholine 6-((5-(6-(Piperidin-1-yl)pyridin-3-yl)-3H-[1,2,3]triazolo[4,5-b]pyridin-3-yl)methyl) quinoline 6-((5-(1-Ethyl-1H-pyrazol-4-yl)-3H-[1,2,3]triazolo[4,5-b]pyridin-3-yl)methyl)quinoline 6-((5-(1-Isopropyl-1H-pyrazol-4-yl)-3H-[1,2,3]triazolo[4,5-b]pyridin-3-yl)methyl)quinoline 6-((5-(1-Isobutyl-1H-pyrazol-4-yl)-3H-[1,2,3]triazolo[4,5-b]pyridin-3-yl)methyl)quinoline 1-(Pyrrolidin-1-yl)-2-(4-(3-(quinolin-6-ylmethyl)-3H-[1,2,3]triazolo[4,5-b]pyridin-5-yl)-1H-pyrazol-1-yl)ethanone 6-((5-(1-(2-Methoxyethyl)-1H-pyrazol-4-yl)-3H-[1,2,3]triazolo[4,5-b]pyridin-3-yl)methyl)quinoline 6-((5-(3-methyl-1H-pyrazol-4-yl)-3H-[1,2,3]triazolo[4,5-b]pyridin-3-yl)methyl)quinoline and pharmaceutically acceptable salts thereof.

21. A compound selected from 2-(3-(Quinolin-6-ylmethyl)-3H-[1,2,3]triazolo[4,5-b]pyridin-5-ylamino)ethanol N-Phenyl-3-(quinolin-6-ylmethyl)-3H-[1,2,3]triazolo[4,5-b]pyridin-5-amine 6-((5-Phenoxy-3H-[1,2,3]triazolo[4,5-b]pyridin-3-yl)methyl)quinoline 1-(3-(Quinolin-6-ylmethyl)-3H-[1,2,3]triazolo[4,5-b]pyridin-5-yl)ethanone and pharmaceutically acceptable salts thereof.

22. A compound selected from (R)-1-(3-(Quinolin-6-ylmethyl)-3H-[1,2,3]-triazolo[4,5-b]pyridin-5-yl)pyrrolidin-3-ol 6-((5-(4-Methylpiperazin-1-yl)-3H-[1,2,3]-triazolo[4,5-b]pyridin-3-yl)methyl)quinoline and pharmaceutically acceptable salts thereof.

23. A compound selected from 2-(1-(3-(Quinolin-6-ylmethyl)-3H-[1,2,3]-triazolo[4,5-b]pyridin-5-yl)ethylidene) hydrazinecarboxamide 1-(3-(Quinolin-6-ylmethyl)-3H-[1,2,3]-triazolo[4,5-b]pyridin-5-yl)ethanone oxime 1-(3-(Quinolin-6-ylmethyl)-3H-[1,2,3]-triazolo[4,5-b]pyridin-5-yl)ethanoneO-methyl oxime N'-(1-(3-(Quinolin-6-ylmethyl)-3H-[1,2,3]-triazolo[4,5-b]pyridin-5-yl)ethylidene)acetohydrazide N'-(1-(3-(quinolin-6-ylmethyl)-3H-[1,2,3]-triazolo[4,5-b]pyridin-5-yl)ethylidene)isonicotinohydrazide and pharmaceutically acceptable salts thereof.

24. A pharmaceutical composition, comprising a compound of claim 1 and a pharmaceutically acceptable carrier.

25. The pharmaceutical composition of claim 24, further comprising one or more additional therapeutic agents and mixtures thereof.

26. The pharmaceutical composition of claim 24, wherein the one or more additional therapeutic agent is an anti-cancer agent, anti-inflammatory agent, immunosuppressive agent, steroid, non-steroidal anti-inflammatory agent, antihistamine, analgesic, or a mixture thereof.

27. A method of inhibiting the HGF/c-Met kinase signaling pathway in a cell comprising contacting said cell with a compound of claim 1.

28. A method of inhibiting the proliferative activity of a cell comprising contacting said cell with a compound of claim 1.

* * * * *